US011098041B2

(12) United States Patent
Gaillard et al.

(10) Patent No.: US 11,098,041 B2
(45) Date of Patent: Aug. 24, 2021

(54) HETEROARYL COMPOUNDS AS BTK INHIBITORS AND USES THEREOF

(71) Applicant: Merck Patent GmbH, Darmstadt (DE)

(72) Inventors: Pascale Gaillard, Collonges sous Salève (FR); Jeyaprakashnarayanan Seenisamy, Karnataka (IN); Lesley Liu-Bujalski, Bedford, MA (US); Richard D. Caldwell, Brookline, MA (US); Justin Potnick, Acton, MA (US); Hui Qiu, Acton, MA (US); Constantin Neagu, Belmont, MA (US); Reinaldo Jones, Lowell, MA (US); Annie Cho Won, Somerville, MA (US); Andreas Goutopoulos, Boston, MA (US); Brian A. Sherer, Nashua, NH (US); Theresa L. Johnson, Salem, MA (US); Anna Gardberg, Arlington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/378,383

(22) Filed: Apr. 8, 2019

(65) Prior Publication Data
US 2019/0233417 A1 Aug. 1, 2019

Related U.S. Application Data

(62) Division of application No. 14/876,224, filed on Oct. 6, 2015, now Pat. No. 10,253,023.

(60) Provisional application No. 62/060,249, filed on Oct. 6, 2014.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ...... A61P 9/10; A61P 9/00; A61P 7/06; A61P 7/04; A61P 7/00; A61P 5/38; A61P 5/14; A61P 43/00; A61P 37/08; A61P 37/06; A61P 37/02; A61P 37/00; A61P 31/04; A61P 29/00; A61P 25/28; A61P 25/16; A61P 25/00; A61P 21/04; A61P 19/02; A61P 19/00; A61P 17/16; A61P 17/14; A61P 17/06; A61P 17/00; A61P 13/12; A61P 13/02; A61P 11/06; A61P 11/02; A61P 11/00; A61P 1/18; A61P 1/16; A61P 1/04; A61P 1/02; A61P 3/10; A61P 21/00; A61K 31/553; A61K 31/437; C07D 471/04; C07D 519/00
USPC ...................................................... 546/118
See application file for complete search history.

(56) References Cited

U.S. PATENT DOCUMENTS

2011/0201599 A1  8/2011  Bahceci et al.

FOREIGN PATENT DOCUMENTS

| EP | 2 487 180 | 8/2012 |
| WO | 03/057696 | 7/2003 |
| WO | 2007/040438 | 4/2004 |
| WO | 2012/175513 | 12/2012 |
| WO | 2013157021 A1 | 10/2013 |
| WO | 2013157022 A1 | 10/2013 |
| WO | 2015089327 A1 | 6/2015 |

OTHER PUBLICATIONS

Berge et al., "Pharmaceutical Salts," J. Pharmaceutical Sciences, Jan. 1977, vol. 66, No. 1, pp. 1-19.
Ellmeier et al., "Severe B Cell Deficiency in Mice Lacking the Tec Kinase Family Members Tec and Btk," J. Exp. Med. Dec. 4, 2000, 192(11):1611-1623.
Feldhahn et al., "Mimicry of a constitutively active pre-B cell receptor in acute lymphoblastic leukemia cells," J. Exp. Med., Jun. 6, 2005, 201(11):1837-1852.
Allan B. Foster, "Deuterium Isotope Effects in the Metabolism of Drugs and Xenobiotics: Implications for Drug Design," Advances in Drug Research, 1985, 14:1-40.
Gillette et al., "Theory for the Observed Isotope Effects on the Formation of Multiple Products by Different Kinetic Mechanisms of Cytochrome P450 Enzymes," 1994, 33(10):2927-2937.
Hanzlik et al., "Active Site Dynamics of Toluene Hydroxilation by Cytochrome P-450¹," J. Org. Chem., 1990, 55(13):3992-3997.
Horwood et al., "Bruton's Tyrosine Kinase is Required for Lipopolysaccharide-induced Tumor Necrosis Factor α Production," J. Exp. Med, Jun. 16, 2003, 197(12):1603-1611.
Tony Hunter, "A Thousand and One Protein Kinases," Cell, vol. 50, 823-829, 1987.
Islam et al., "The cellular phenotype conditions Btk for cell survival or apoptosis signaling," Immunological Reviews, 2000, 178:49-63.
Iwaki et al., "Btk Plays a Crucial Role in the Amplification of FcεRI-mediated Mast Cell Activation by Kit," Journal of Biological Chemistry vol. 280, No. 48, p. 40261-40270, Dec. 2, 2005.
Jansson et al., "Genes on the X chromosome affect development of collagen-induced arthritis in mice," Clin. Exp. Immunol., 1993, 94:459-465.
Jarman et al., "The deuterium isotope effect for the α-hydroxylation of tamoxifen by rat liver microsome accounts for the reduced genotoxicity of [D₅-ethyl]tamoxifen," Carcinogenesis vol. 16 No. 4 pp. 683-688, 1995.
Kawakami et al., "Functions of Bruton's tyrosine kinase in mast and B cells," Leukocyte Biology, vol. 65, Mar. 1999, pp. 286-290.
Khan et al., "Defective B Cell Development and Functions in Btk-Deficient Mice," Immunity, vol. 3, 283-299, Sep. 1995, pp. 283-299.
Lindvall et al., "Bruton's tyrosine kinase: cell biology, sequence conservation, mutation spectrum, siRNA modifications, and expression profiling," Immunological Reviews, 2005, 203:200-215.
Pan et al., "Discovery of Selective Irreversible Inhibitors for Bruton's Tyrosine Kinase," Chem. Med Chem., 2007, 2:58-61.

(Continued)

Primary Examiner — Taylor V Oh

(74) Attorney, Agent, or Firm — Kathryn M. Bishop; EMD Serono Research and Development Institute

(57) ABSTRACT

Imidazo pyridine compounds, and pharmaceutically acceptable compositions thereof are useful as BTK inhibitors.

10 Claims, No Drawings

(56) References Cited

OTHER PUBLICATIONS

Rastetter et al., "*Rituximab: Expanding Role in Therapy for Lymphomas and Autoimmune Diseases*," Annu. Rev. Med. 2004, 55:477-503.
Reider et al., "*Synthesis of (R)-Serine-2-d and Its Conversion to the Broad Spectrum Antibiotic Fludalanine*," J. Org. Chem., 1987, 52:3326-3334.
Rosen et al., "*The Primary immunodeficiencies*," New England Journal of Medicine, 1995, 333(7):431-440.
Song et al., "*Imidazopyridines as selective CYP3A4 inhibitors*," Bioorganic & Medicinal Chemistry Letters, 22 (2012)1611-1614.
Vassilev et al., "*Bruton's Tyrosine Kinase as an Inhibitor of the Fas/CD95 Death-inducing Signaling Complex*," Journal of Biological Chemistry, vol. 274, No. 3, Issue of Jan. 15, pp. 1646-1656, 1999.
Vihinen et al., "*Bruton Tyrosine Kinase (BTK) in X-Linked Agammaglobulinemia (XLA)*," Frontiers in Bioscience 5, d917-928, Dec. 1, 2000.
Yngve et al., "*Imidazopyridine-Based Inhibitors of Glycogen Synthase Kinase 3: Synthesis and Evaluation of Amide Isostere Replacements of the Carboxamide Scaffold*," Chemistry & Biodiversity, vol. 9 (2012)2442-2452.
Zhao et al., "*Pyrrolo[2,3-b]pyridine derivatives as potent Bruton's tyrosine kinase inhibitors*," Bioorganic & Medicinal Chemistry, 23 (2015)4344-4353.

HETEROARYL COMPOUNDS AS BTK INHIBITORS AND USES THEREOF

RELATED APPLICATION

This application is a divisional of U.S. application Ser. No. 14/876,224, filed on Oct. 6, 2015, which claims the benefit of U.S. Provisional Application No. 62/060,249, filed Oct. 6, 2014, both of which are incorporated in their entireties by reference.

TECHNICAL FIELD OF THE INVENTION

The present invention relates to imidazo pyridine compounds that are useful as inhibitors of Bruton's Tyrosine Kinase (BTK). The invention also provides pharmaceutically acceptable compositions comprising compounds of the present invention and methods of using said compositions in the treatment of various disorders.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling, they provide a target to modulate cellular function with small molecular kinase inhibitors and thus make good drug targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology, such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes. Also, BTK has been reported to play a role in apoptosis (Islam and Smith Immunol. Rev. 2000 178:49) and thus BTK inhibitors would be useful for the treatment of certain B-cell lymphomas and leukemias (Feldhahn et al. J. Exp. Med. 2005 201:1837).

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immune-compromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has demonstrated dose-dependent efficacy in a mouse arthritis model (Z. Pan et al., Chem. Med Chem. 2007 2:58-61).

BTK is also expressed by cells other than B-cells that may be involved in disease processes. BTK is key component of Fc-gamma signaling in myeloid cells. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 197:1603, 2003). Therefore TNF alpha mediated inflammation could be modulated by small molecular BTK inhibitors.

SUMMARY OF THE INVENTION

It has now been found that compounds of this invention, and pharmaceutically acceptable compositions thereof, are effective as inhibitors of BTK. Such compounds have general formula I:

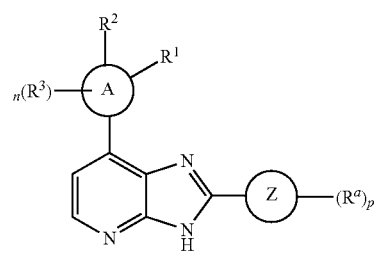

or a tautomer, or a pharmaceutically acceptable salt thereof, wherein each of $R^1$, $R^2$, $R^3$, $R^a$, Ring A, Ring Z, n, and p, is as defined and described in embodiments herein.

Compounds of the present invention, and pharmaceutically acceptable compositions thereof, are useful for treating a variety of diseases, disorders or conditions, associated with BTK. Such diseases, disorders, or conditions include those described herein.

DETAILED DESCRIPTION OF CERTAIN EMBODIMENTS

1. General Description of Compounds of the Invention

In certain aspects, the present invention provides for inhibitors of BTK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith. M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl). NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

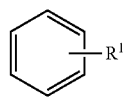

refers to at least

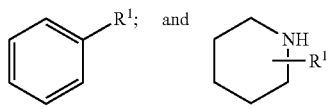

refers to at least

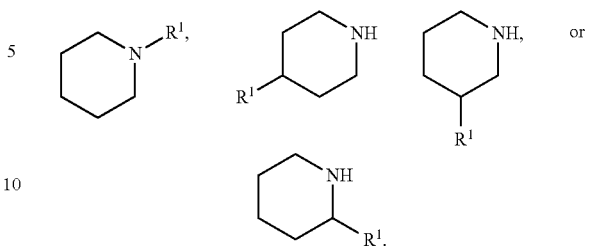

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen: —(CH$_2$)$_{0-4}$R°; —(CH$_2$)$_{0-4}$OR°; —O(CH$_2$)$_{0-4}$R, —O—(CH$_2$)$_{0-4}$C(O)OR°; —(CH$_2$)$_{0-4}$—CH(OR°)$_2$; —(CH$_2$)$_{0-4}$SR°; —(CH$_2$)$_{0-4}$Ph, which are optionally substituted with R°: —(CH$_2$)$_{0-4}$O(CH$_2$)$_{0-4}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR$_2$; —C(O)N(OR°)R°; —C(O)C(O)R°; —C(O)CH$_2$C(O)R°—C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_4$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR$_2$; —P(O)$_2$R°; —P(O)R°$_2$; —OP(O)R°; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$)$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR*, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH-aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH-alkenyl, —NHC(NH)NH— alkynyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl, —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the term "tautomer" means each of two or more isomers of a compound that exist together in equilibrium, and are readily interchanged by migration of an atom or group within the molecule. Tautomers are constitutional isomers of organic compounds that readily interconvert by a chemical reaction called tautomerization. This reaction commonly results in the formal migration of a hydrogen atom or proton, accompanied by a switch of a single bond and adjacent double bond. For example, see

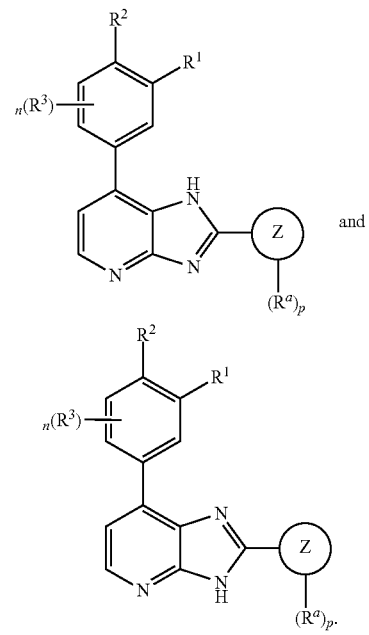

and

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 5 µM, less than about 1 µM, less than about 500 nM, less than about 100 nM, or less than about 10 nM.

The terms "measurable affinity" and "measurably inhibit," as used herein, means a measurable change in BTK activity between a sample comprising a compound of the present invention, or composition thereof, and BTK, and an equivalent sample comprising BTK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

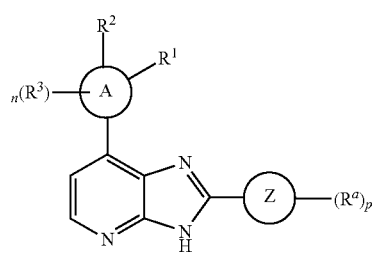

or a tautomer, or a pharmaceutically acceptable salt thereof, wherein:
Ring A is a 5-6 membered aryl or heteroaryl;
$R^1$ is H, halo, $(C(R^5)(R^5))_mNR_2$, $N(R^4)C(O)R$, $N(R^4)C(O)NR_2$, $N(R^4)CO_2R$, $N(R^4)S(O)_2R$, $N(R^4)S(O)R$, $N(R^4)(R^4)$, optionally substituted 3-7 membered heterocyclic ring having 1-4 heteroatoms independently selected from nitrogen, oxygen, or sulfur, or optionally substituted 5-6 membered monocyclic heteroaryl ring having 1-4 heteroatoms independently selected from nitrogen, oxygen, or sulfur, or $R^1$ is absent;
$R^2$ is H, $(C(R^5)(R^5))_mOR^4$, $(C(R^5)(R^5))_mN(R^4)COR$, $(C(R^5)(R^5))_mN(R^4)C(O)C(O)NR_2$, $(C(R^5)(R^5))_mN(R^4)(R^4)$, optionally substituted 3-7 membered heterocylic ring having 1-4 heteroatoms independently selected from nitrogen, oxygen, or sulfur, or optionally substituted 5-6 membered monocyclic heteroaryl ring having 1-4 heteroatoms independently selected from nitrogen, oxygen, or sulfur or $R^2$ is absent;

or $R^1$ and $R^2$ together with the atoms to which they are connected, form a fused 3-7 membered ring which is optionally substituted;

wherein $R^1$ and $R^2$ are both not H; and wherein $R^1$ and $R^2$ are both not absent;

each $R^3$ is independently halogen, $C_{1-6}$ aliphatic, $C_{5-10}$ to aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted:

each $R^4$ is independently —R, —$SO_2R$, —SOR, —C(O)R, —$CO_2R$, or —$C(O)N(R)_2$;

each $R^5$ is independently —R, halogen, —OR, —SR, —CN, —$NO_2$, —$SO_2R$, —SOR, —C(O)R, —$CO_2R$, —$C(O)N(R)_2$, —NRC(O)R, —$NRC(O)N(R)_2$, —$NRSO_2R$, or —$N(R)_2$;

each R is independently hydrogen, $C_{1-6}$ aliphatic, $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted; or two R groups on the same atom are taken together with the atom to which they are attached to form a $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, a 5-6 membered monocyclic heteroaryl ring having 1-4 heteroatoms independently selected from nitrogen, oxygen, or sulfur; a 10-15 membered fused aryl ring; a 6-15 membered saturated or partially unsaturated fused carbocyclic ring; a 10-15 membered fused heteroaryl ring; or a 6-15 membered saturated or partially unsaturated fused heterocyclic ring; each of which is optionally substituted;

Ring Z is $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted; or Ring Z is absent;

each $R^a$ is independently —R, halogen, —OR, —SR, —CN, —$NO_2$, —$SO_2R$, —SOR, —C(O)R, —$CO_2R$, —$C(O)N(R)_2$, —NRC(O)R, —$NRC(O)N(R)_2$, —$NRSO_2R$, or —$N(R)_2$;

m is 1, 2, or 3;
n is 0, 1, or 2; and
p is 0, 1, 2, or 3.

In certain embodiments, Ring A is phenyl, pyridine, pyrazine, pyrimidine, pyridazine, or triazine.

In certain embodiments, Ring A is phenyl. In certain embodiments, Ring A is pyridine.

In certain embodiments, Ring A is

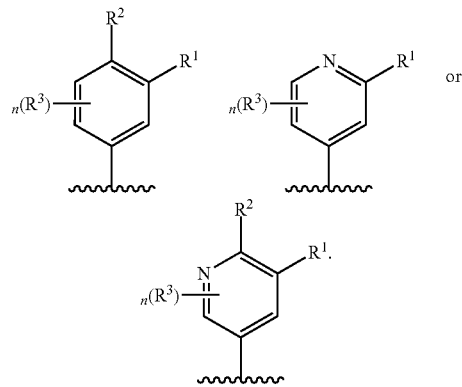

In certain embodiments, $R^1$ is H. In certain embodiments, $R^1$ is F, Cl, Br, or I. In certain embodiments, $R^1$ is F.

In certain embodiments, $R^1$ is $(C(R^5)(R^5))_mNR_2$, $N(R^4)C(O)R$, $N(R^4)C(O)NR_2$, $N(R^4)CO_2R$, $N(R^4)S(O)_2R$, $N(R^4)S(O)R$, $N(R^4)(R^4)$, optionally substituted 3-7 membered heterocylic ring having 1-4 heteroatoms independently selected from nitrogen, oxygen, or sulfur, or optionally substituted 5-6 membered monocyclic heteroaryl ring having 1-4 heteroatoms independently selected from nitrogen, oxygen, or sulfur.

In certain embodiments, $R^1$ is $(C(R^5)(R^5))_mNR_2$, $N(R^4)C(O)R$, $N(R^4)C(O)NR_2$, $N(R^4)(R^4)$, optionally substituted 3-7 membered heterocylic ring having 1-4 heteroatoms independently selected from nitrogen, oxygen, or sulfur, or optionally substituted 5-6 membered monocyclic heteroaryl ring having 1-4 heteroatoms independently selected from nitrogen, oxygen, or sulfur.

In certain embodiments, $R^1$ is $(C(R^5)(R^5))_mNR_2$. In certain embodiments, $R^1$ is $N(R^4)C(O)R$. In certain embodiments, $R^1$ is $N(R^4)C(O)NR_2$. In certain embodiments, $R^1$ is $N(R^4)(R^4)$. In certain embodiments. $R^1$ is optionally substituted 3-7 membered heterocylic ring having 1-4 heteroatoms independently selected from nitrogen, oxygen, or sulfur. In certain embodiments, $R^1$ is optionally substituted 5-6 membered monocyclic heteroaryl ring having 1-4 heteroatoms independently selected from nitrogen, oxygen, or sulfur.

In certain embodiments, $R^1$ is optionally substituted 3-7 membered heterocylic ring having 1-4 heteroatoms independently selected from nitrogen, oxygen, or sulfur, wherein the heterocyclic ring is further substituted by a fused ring.

In certain embodiments, $R^1$ is optionally substituted 5-6 membered monocyclic heteroaryl ring having 1-4 heteroatoms independently selected from nitrogen, oxygen, or sulfur, wherein the heteroaryl ring is further substituted by a fused ring.

In certain embodiments, $R^1$ is absent.

In certain embodiments, $R^1$ is selected from:

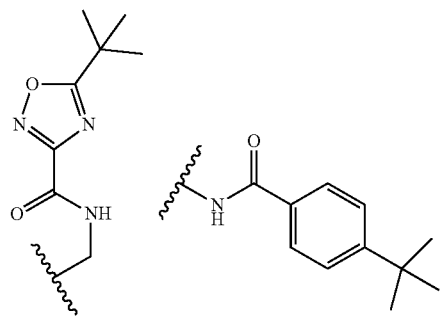

-continued

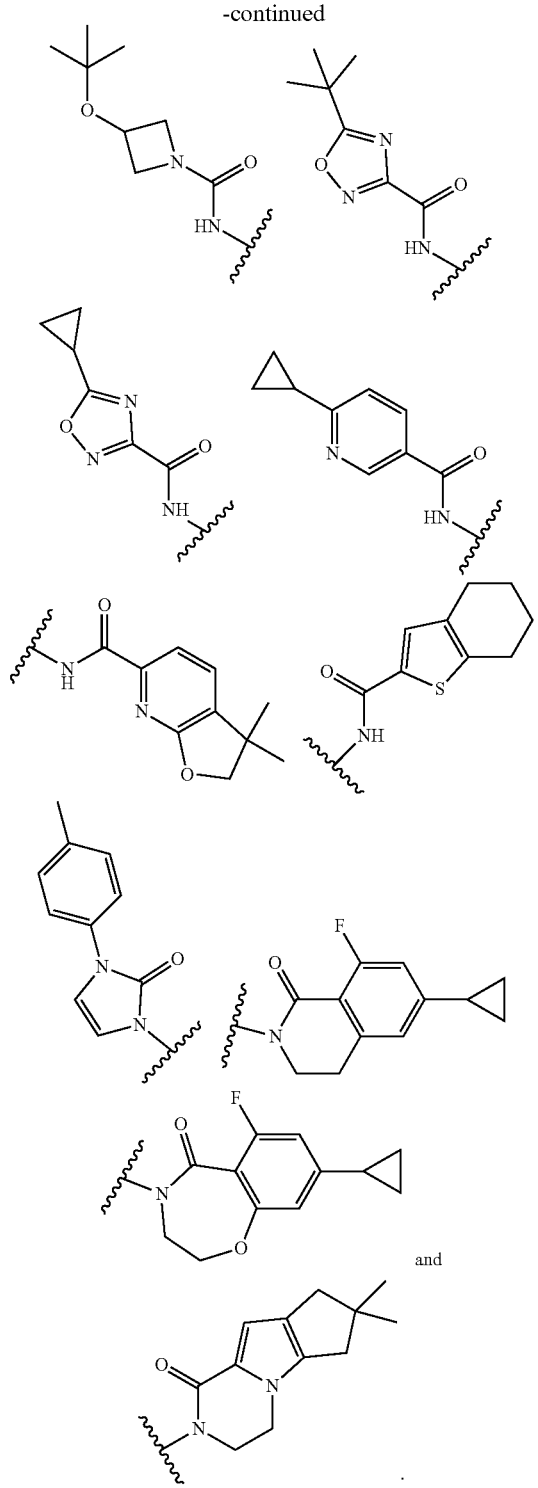

In certain embodiments, $R^2$ is hydrogen.

In certain embodiments, $R^2$ is $(C(R^5)(R^5))_m OR^4$, $(C(R^5)(R^5))_m N(R^4)COR$, $(C(R^5)(R^5))_m N(R^4)C(O)C(O)NR_2$, $(C(R^5)(R^5))_m N(R^4)(R^4)$, optionally substituted 3-7 membered heterocylic ring having 1-4 heteroatoms independently selected from nitrogen, oxygen, or sulfur, or optionally substituted 5-6 membered monocyclic heteroaryl ring having 1-4 heteroatoms independently selected from nitrogen, oxygen, or sulfur.

In certain embodiments, $R^2$ is $(C(R^5)(R^5))_m N(R^4)(R^4)$. In certain embodiments, $R^2$ is $(C(R^5)(R^5))_m OR^4$. In certain embodiments, $R^2$ is $(C(R^5)(R^5))_m N(R^4)COR$. In certain embodiments, $R^2$ is $(C(R^5)(R^5))_m N(R^4)C(C)C(O)NR_2$. In certain embodiments. $R^2$ is optionally substituted 3-7 membered heterocylic ring having 1-4 heteroatoms independently selected from nitrogen, oxygen, or sulfur. In certain embodiments, $R^2$ is optionally substituted 5-6 membered monocyclic heteroaryl ring having 1-4 heteroatoms independently selected from nitrogen, oxygen, or sulfur.

In certain embodiments, $R^2$ is $(CH_2)_m N(R^4)(R^4)$. In certain embodiments, $R^2$ is $(CH_2)_m OR^4$. In certain embodiments, $R^2$ is $(CH_2)_m N(R^4)COR$. In certain embodiments, $R^2$ is $(CH_2)_m N(R^4)C(O)C(O)NR_2$.

In certain embodiments, $R^2$ is —CH$_2$OH, —CH$_2$NH$_2$,

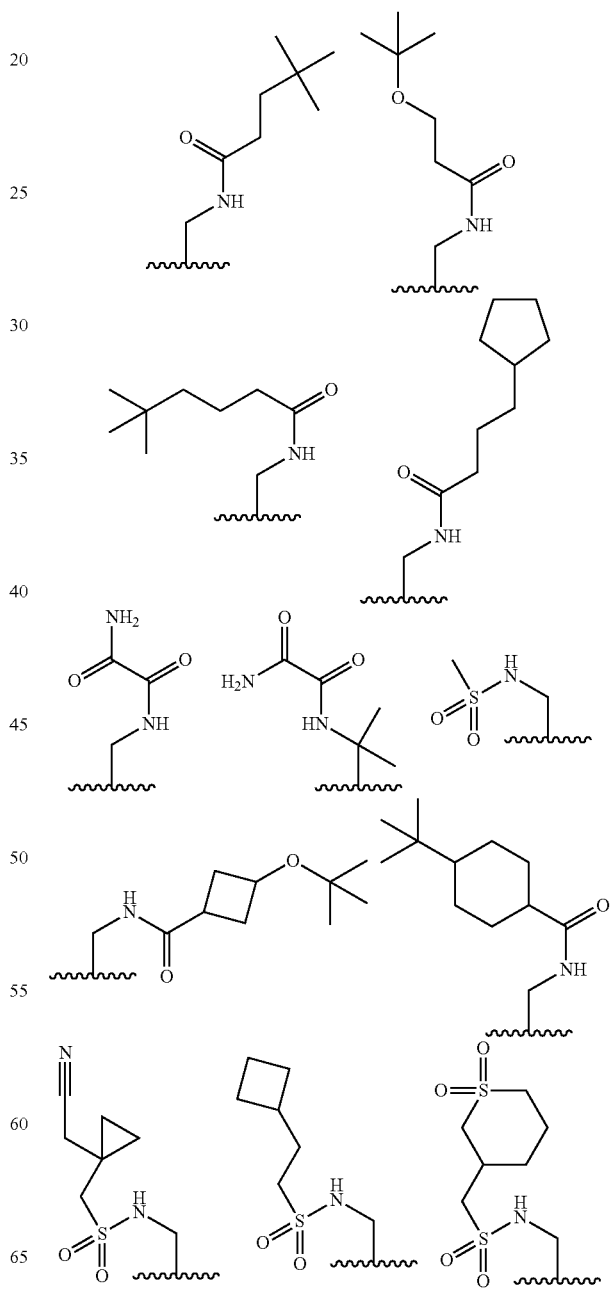

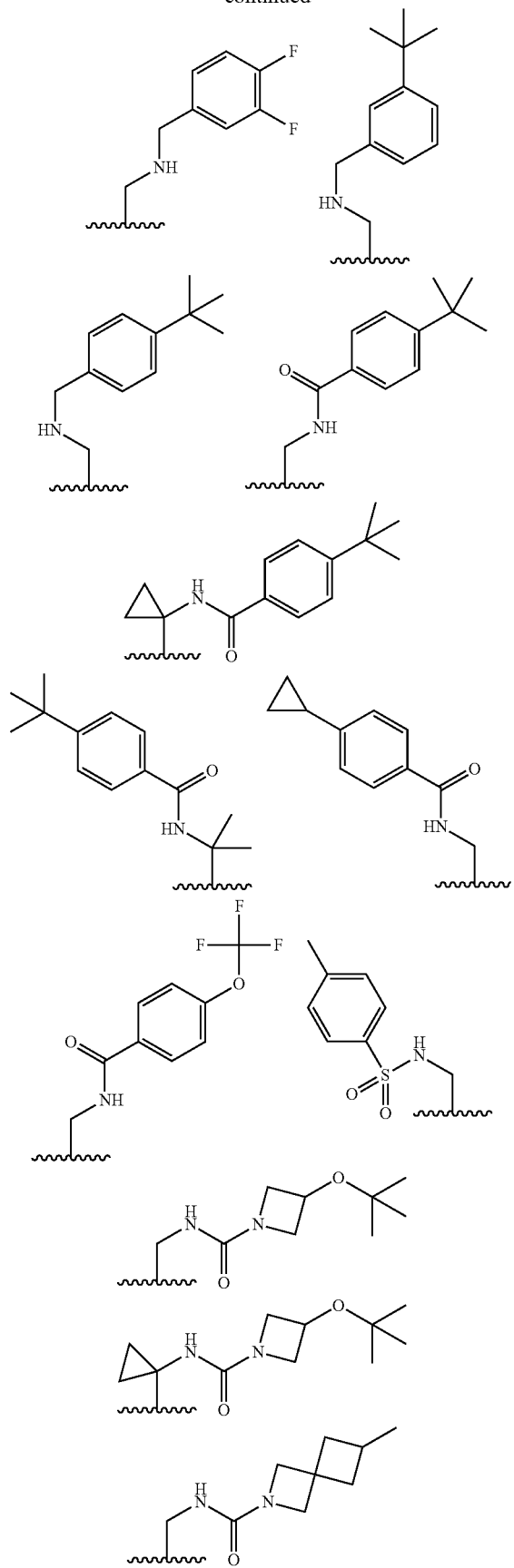
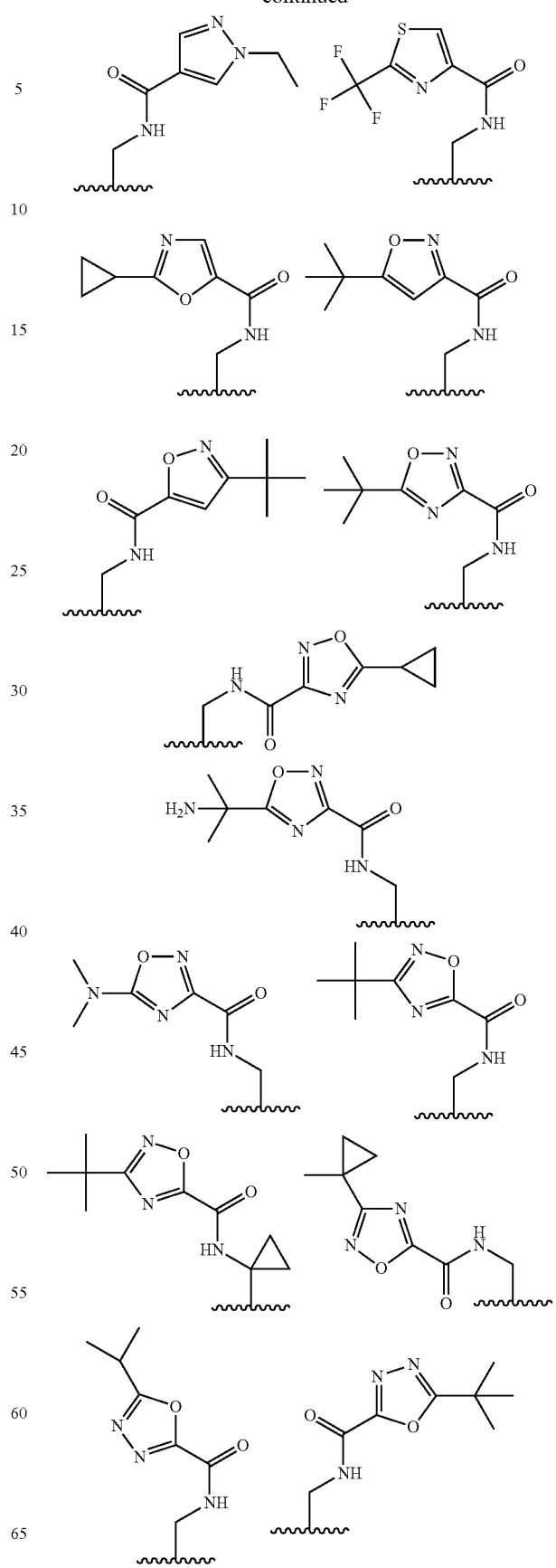

-continued

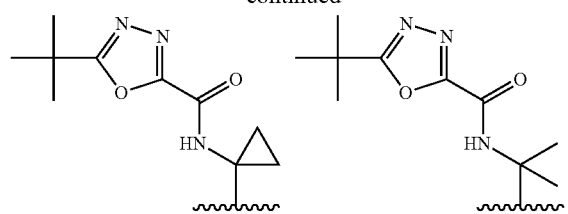
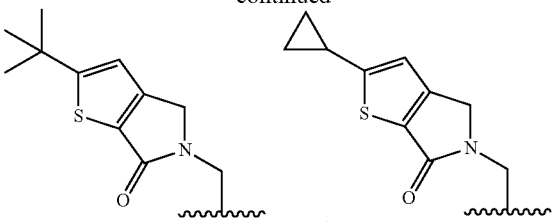

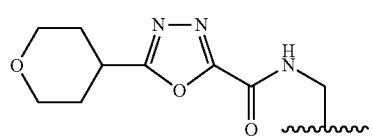
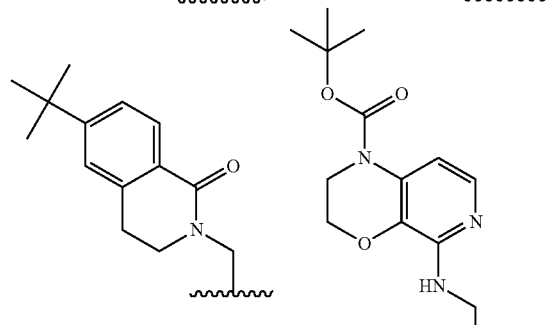

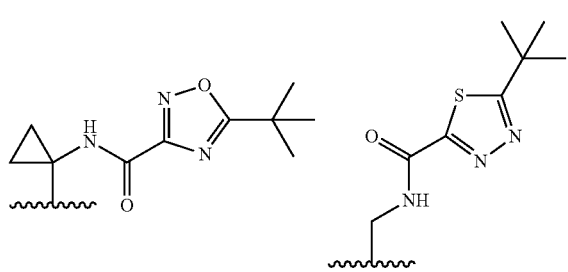
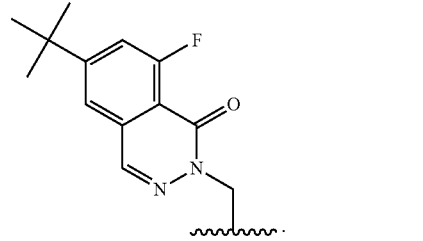

In certain embodiments, each $R^1$ and $R^2$ together form

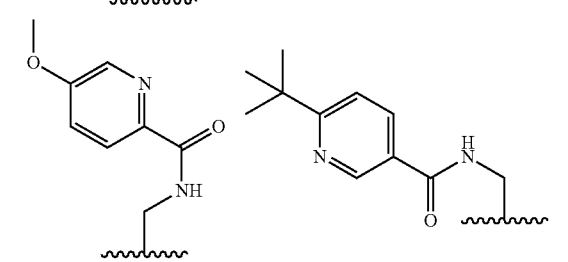
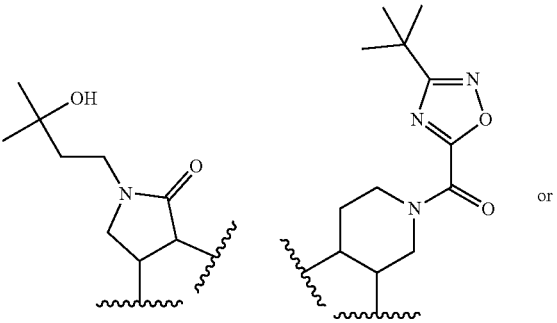

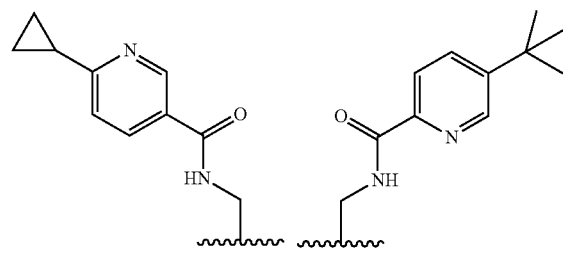

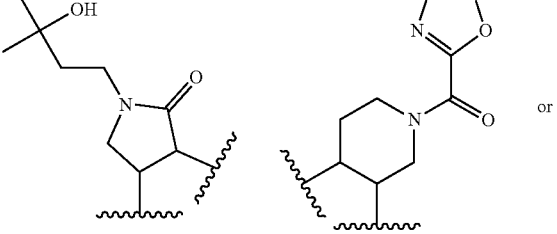

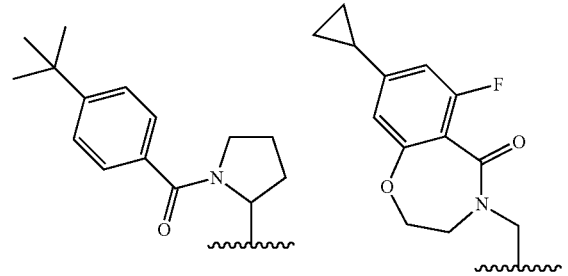
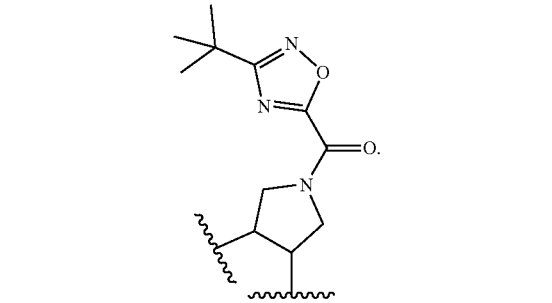

In certain embodiments, each $R^3$ is independently halogen. In certain embodiments, each $R^3$ is independently an optionally substituted $C_{1-6}$ aliphatic. In certain embodiments, each $R^3$ is independently an optionally substituted $C_{5-10}$ aryl. In certain embodiments, each $R^3$ is independently an optionally substituted a 3-8 membered saturated or partially unsaturated carbocyclic ring. In certain embodiments, each $R^3$ is independently an optionally substituted a 3-7 membered heterocyclic ring having 1-4 heteroatoms independently selected from nitrogen, oxygen, or sulfur. In certain embodiments, each $R^3$ is independently an optionally substituted or a 5-6 membered monocyclic heteroaryl ring having 1-4 heteroatoms independently selected from nitrogen, oxygen, or sulfur.

In certain embodiments, each $R^3$ is independently halogen or an optionally substituted $C_{1-6}$ aliphatic.

In certain embodiments, each $R^3$ is independently F, Cl, Br, I, methyl, ethyl, ethyl, propyl, i-propyl, butyl, s-butyl, t-butyl, straight or branched pentyl, or straight or branched hexyl; each of which is optionally substituted.

In certain embodiments, each $R^3$ is independently F, methyl, —$CF_3$, or —$CH_2OH$.

In certain embodiments, Ring Z is an optionally substituted $C_{5-10}$ aryl. In certain embodiments, Ring Z is an optionally substituted a 3-8 membered saturated or partially unsaturated carbocyclic ring. In certain embodiments. Ring Z is an optionally substituted a 3-7 membered heterocyclic ring having 1-4 heteroatoms independently selected from nitrogen, oxygen, or sulfur. In certain embodiments, Ring Z is an optionally substituted or a 5-6 membered monocyclic heteroaryl ring having 1-4 heteroatoms independently selected from nitrogen, oxygen, or sulfur.

In certain embodiments, Ring Z is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidine-one, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydropyridine, tetrahydropyran, 6H-1, 2,5-thiadiazinyl, 1,2,3-thiadiazolyl, 1,2,4-thiadiazolyl, 1,2, 5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, Ring Z is cyclopropyl, phenyl, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, piperidine-one, pyrimidinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydropyridine, tetrahydropyran, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, or 1,3,4-triazolyl; each of which is optionally substituted.

In certain embodiments, Ring Z is cyclopropyl, piperidine-one, phenyl, pyrazolyl, pyridinyl, tetrahydropyridine, or tetrahydropyran; each of which is optionally substituted.

In certain embodiments, Ring Z is

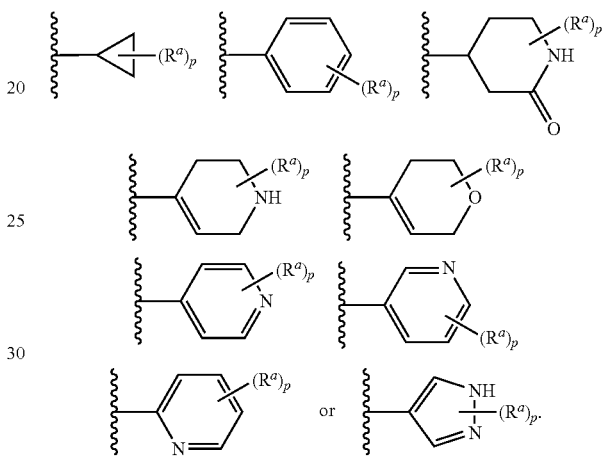

In certain embodiments, Ring Z is

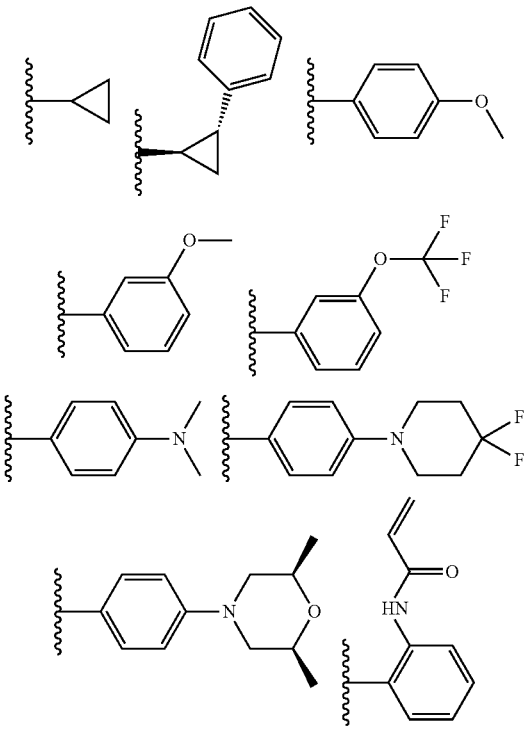

23
-continued
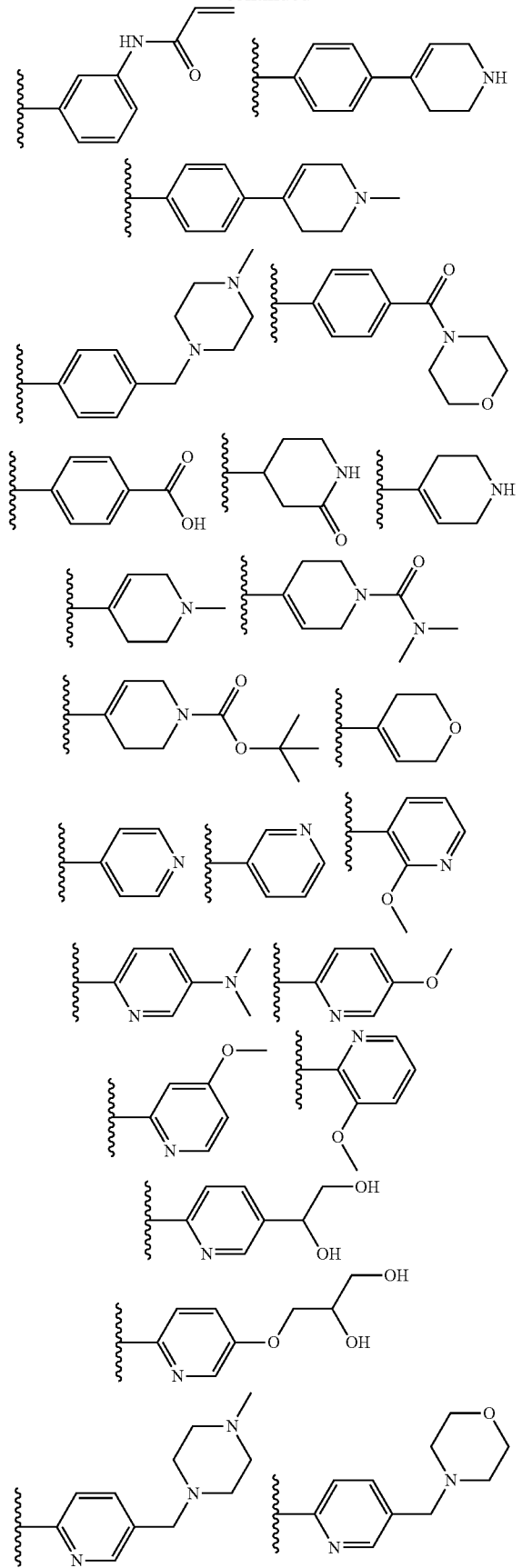
24
-continued
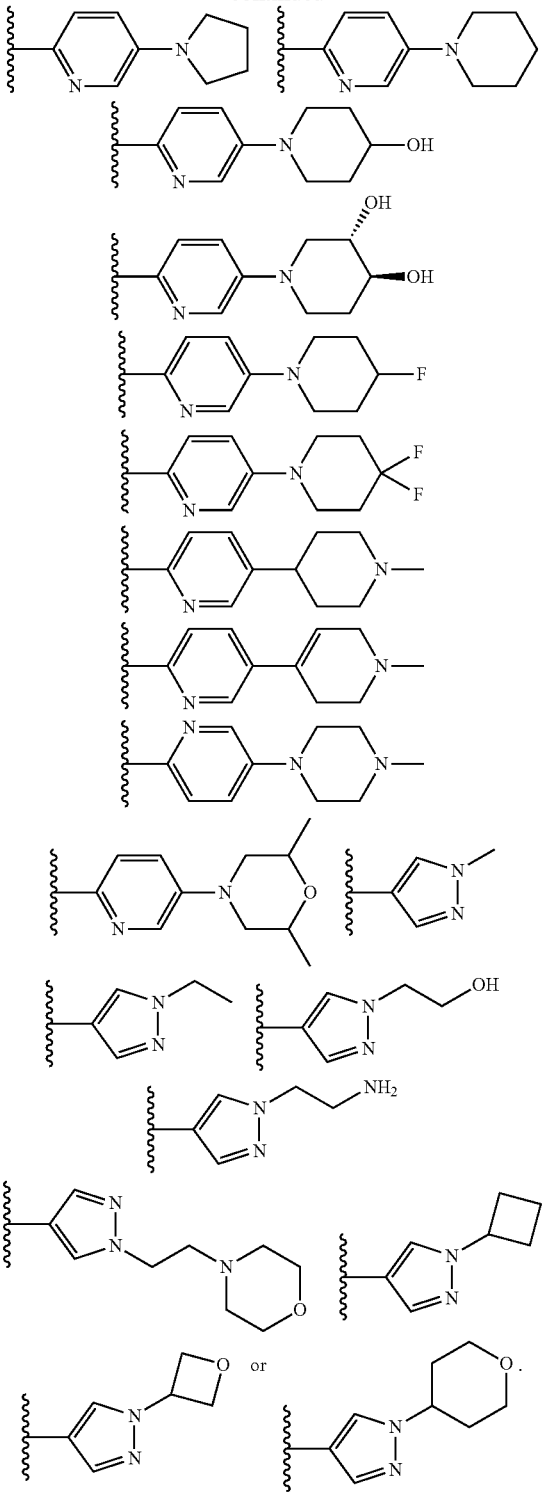
In certain embodiments, Ring Z is absent and $R^a$ is —$CF_3$, i-Pr, or i-Bu.
In certain embodiments, each of $R^1$, $R^2$, $R^3$, Ring Z, and n, is as defined above and described in embodiments, classes and subclasses above and herein, singly or in combination.
In certain embodiments, the present invention provides a compound of formula II,

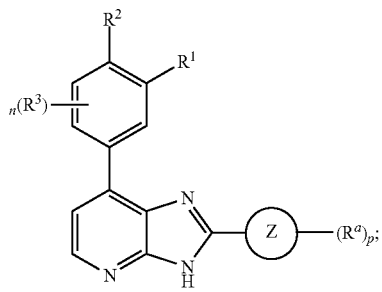

or a pharmaceutically acceptable salt thereof, wherein each of Ring Z, $R^1$, $R^2$, $R^3$, $R^a$, n, and p, is as defined above and described in embodiments, classes and subclasses above and herein, singly or in combination.

In certain embodiments, the present invention provides a compound of formula II-a,

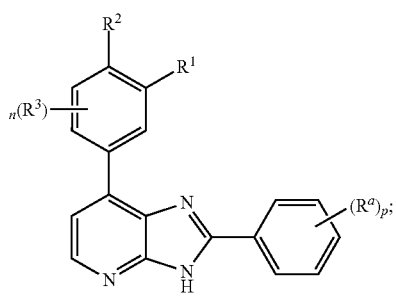

or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-b,

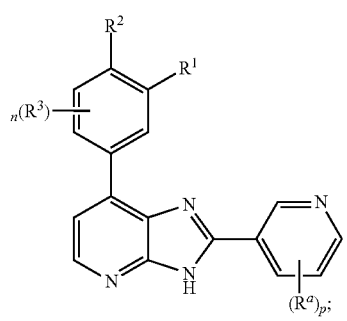

or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-c,

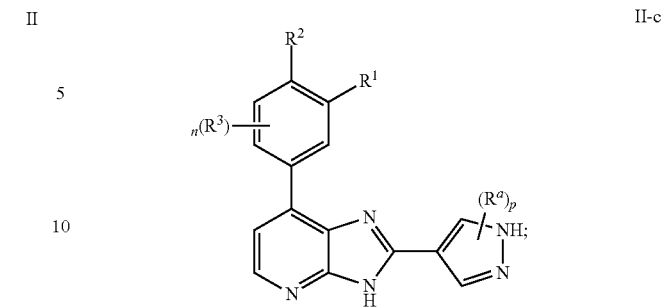

or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-d,

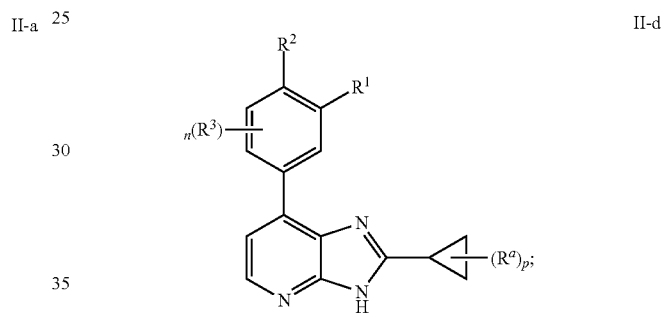

or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-e,

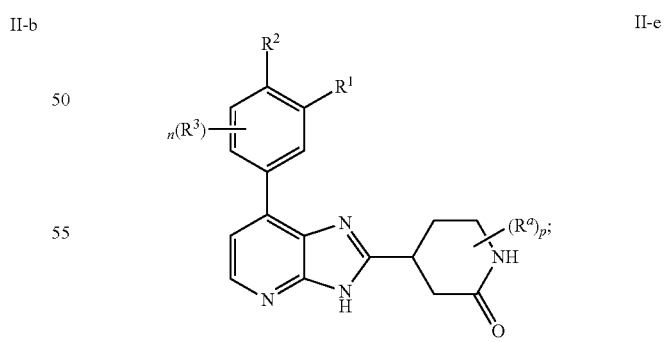

or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-f,

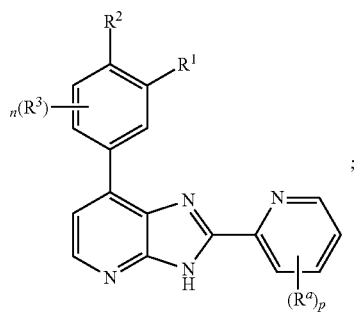

II-f or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-g,

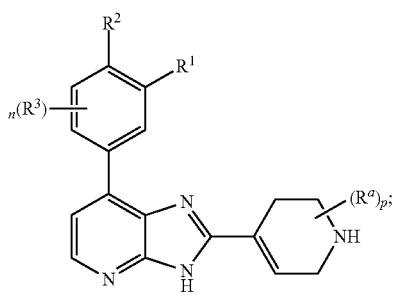

II-g or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-h,

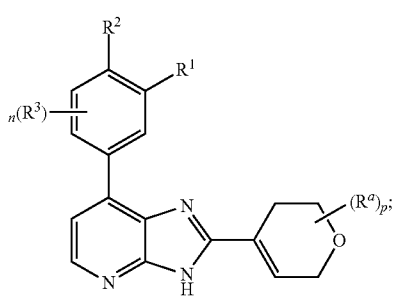

II-h or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula II-i,

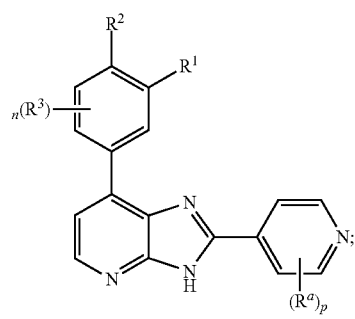

II-i or a pharmaceutically acceptable salt thereof, wherein each of $R^1$, $R^2$, $R^3$, $R^a$, n, and p, is as defined above and described in embodiments, classes and subclasses above and herein, singly or in combination.

In certain embodiments, the present invention provides a compound of formula III,

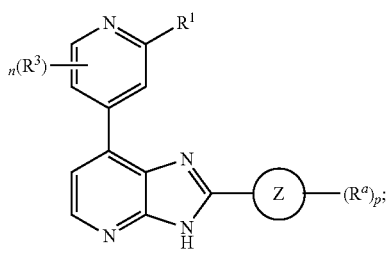

III or a pharmaceutically acceptable salt thereof, wherein each of Ring Z, $R^1$, $R^3$, $R^a$, n, and p, is as defined above and described in embodiments, classes and subclasses above and herein, singly or in combination.

In certain embodiments, the present invention provide a compound of formula III-a,

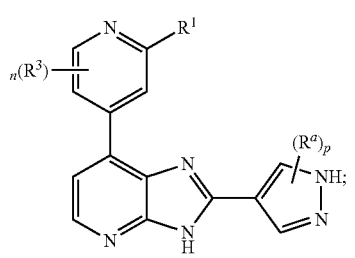

III-a or a pharmaceutically acceptable salt thereof, wherein each of $R^1$, $R^3$, $R^a$, n, and p, is as defined above and described in embodiments, classes and subclasses above and herein, singly or in combination.

In certain embodiments, the present invention provides a compound of formula III,

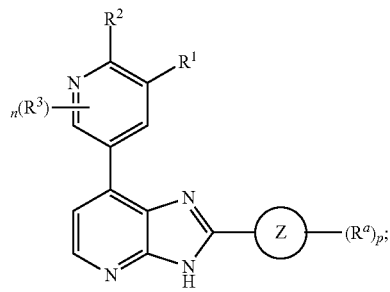

III

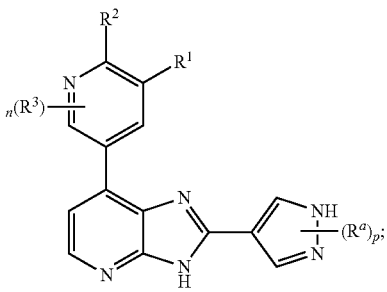

III-a or a pharmaceutically acceptable salt thereof, wherein each of Ring Z, R¹, R², R³, R$^a$, n, and p, is as defined above and described in embodiments, classes and subclasses above and herein, singly or in combination.

In certain embodiments, the present invention provides a compound of formula III-a, or a pharmaceutically acceptable salt thereof, wherein each of R¹, R², R³, R$^a$, n, and p, is as defined above and described in embodiments, classes and subclasses above and herein, singly or in combination.

In certain embodiments, the invention provides a compound selected from Table 1:

TABLE 1

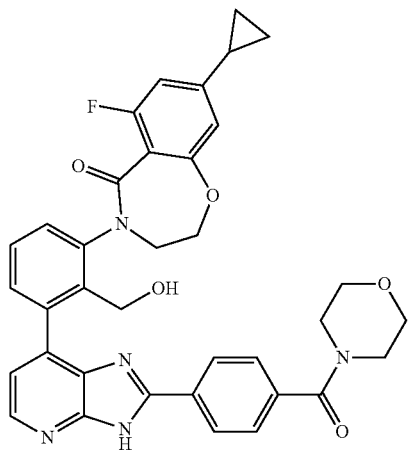 [SMILES: O=C(c1ccc(-c2nc3c(-c4cccc(N5CCOc6cc(C7CC7)cc(F)c6C5=O)c4CO)ccnc3[nH]2)cc1)N1CCOCC1]

1

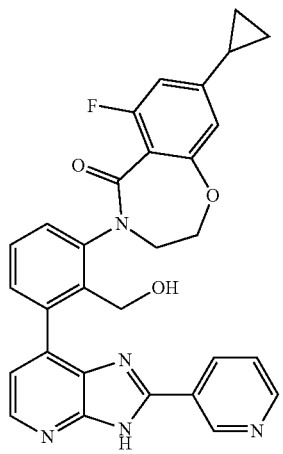 [SMILES: O=C1c2c(F)cc(C3CC3)cc2OCCN1c1cccc(-c2ccnc3[nH]c(-c4cccnc4)nc23)c1CO]

2

TABLE 1-continued
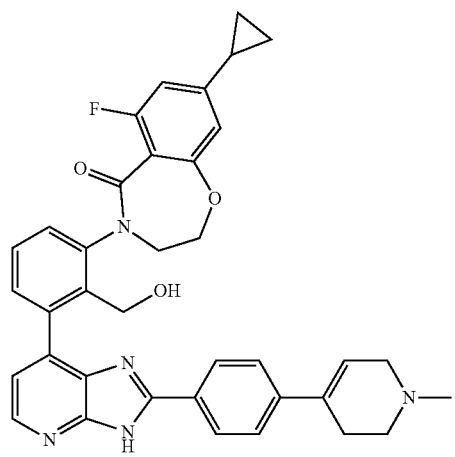 [SMILES: CN1CC=C(c2ccc(-c3nc4c(-c5cccc(N6CCOc7cc(C8CC8)cc(F)c7C6=O)c5CO)ccnc4[nH]3)cc2)CC1]
3
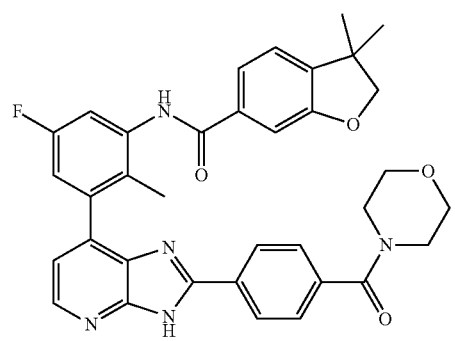 [SMILES: Cc1c(NC(=O)c2ccc3c(c2)OCC3(C)C)cc(F)cc1-c1ccnc2[nH]c(-c3ccc(C(=O)N4CCOCC4)cc3)nc12]
4
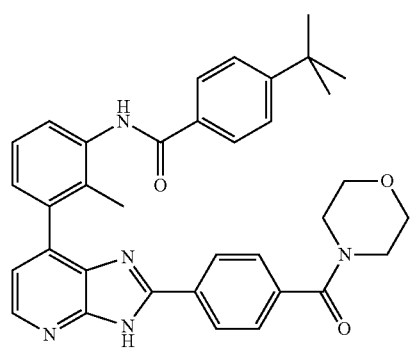 [SMILES: Cc1c(NC(=O)c2ccc(C(C)(C)C)cc2)cccc1-c1ccnc2[nH]c(-c3ccc(C(=O)N4CCOCC4)cc3)nc12]
5
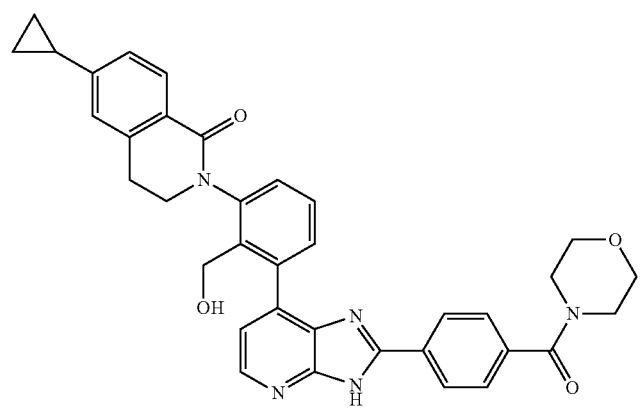 [SMILES: O=C(c1ccc(-c2nc3c(-c4cccc(N5CCc6cc(C7CC7)ccc6C5=O)c4CO)ccnc3[nH]2)cc1)N1CCOCC1]
6

TABLE 1-continued
| | |
|---|---|
| 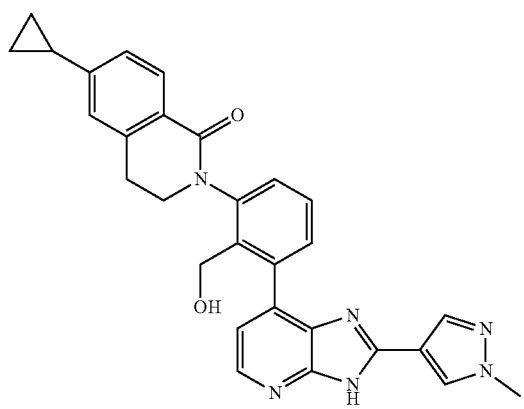 [SMILES: Cn1cc(-c2nc3c(-c4cccc(N5CCc6cc(C7CC7)ccc6C5=O)c4CO)ccnc3[nH]2)cn1] | 7 |
| 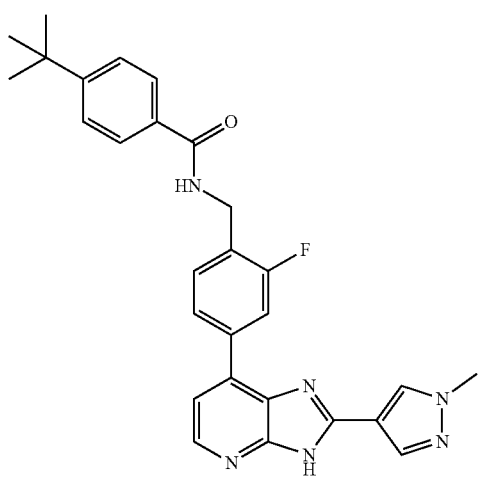 [SMILES: Cn1cc(-c2nc3c(-c4ccc(CNC(=O)c5ccc(C(C)(C)C)cc5)c(F)c4)ccnc3[nH]2)cn1] | 8 |
| 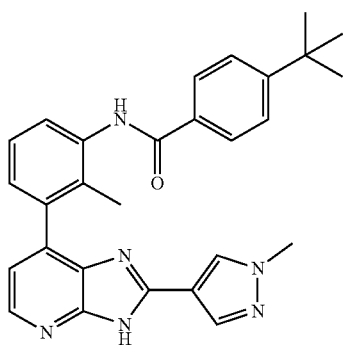 [SMILES: Cc1c(NC(=O)c2ccc(C(C)(C)C)cc2)cccc1-c1ccnc2[nH]c(-c3cnn(C)c3)nc12] | 9 |
| 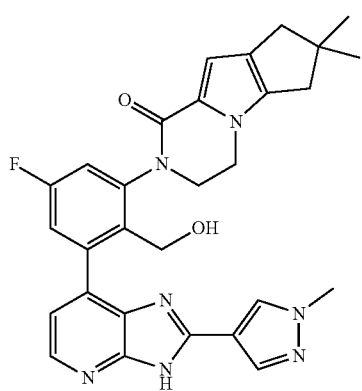 [SMILES: Cn1cc(-c2nc3c(-c4cc(F)cc(N5CCn6c(cc7c6CC(C)(C)C7)C5=O)c4CO)ccnc3[nH]2)cn1] | 10 |

TABLE 1-continued
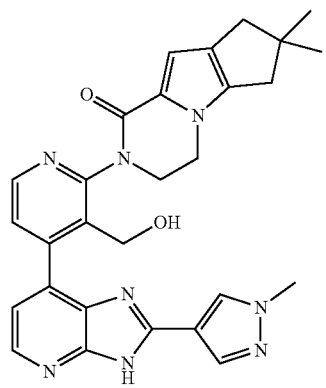 [SMILES: Cn1cc(-c2nc3c(-c4ccnc(N5CCn6c(cc7c6CC(C)(C)C7)C5=O)c4CO)ccnc3[nH]2)cn1]
11
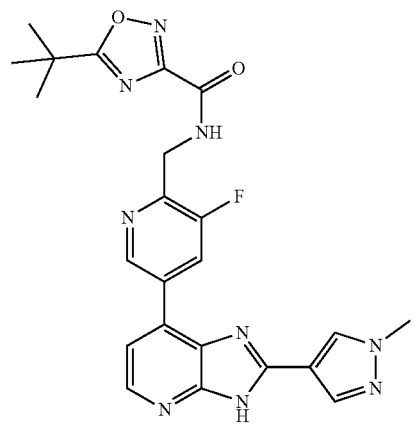 [SMILES: Cn1cc(-c2nc3c(-c4cnc(CNC(=O)c5noc(C(C)(C)C)n5)c(F)c4)ccnc3[nH]2)cn1]
12
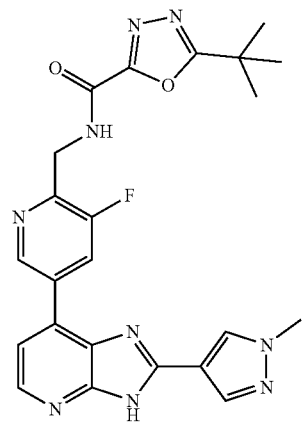 [SMILES: Cn1cc(-c2nc3c(-c4cnc(CNC(=O)c5nnc(C(C)(C)C)o5)c(F)c4)ccnc3[nH]2)cn1]
13
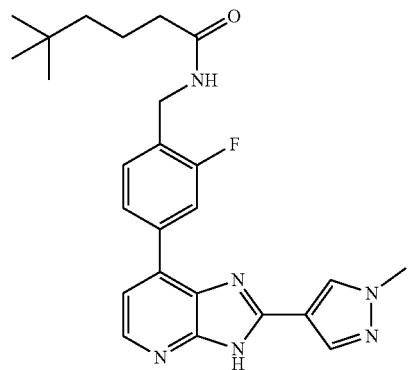 [SMILES: Cn1cc(-c2nc3c(-c4ccc(CNC(=O)CCCC(C)(C)C)c(F)c4)ccnc3[nH]2)cn1]
14

TABLE 1-continued
15
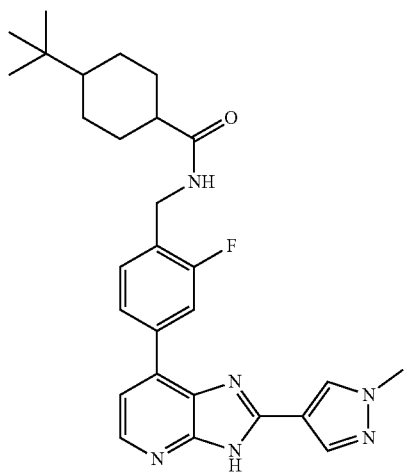 [SMILES: Cn1cc(-c2nc3c(-c4ccc(CNC(=O)C5CCC(C(C)(C)C)CC5)c(F)c4)ccnc3[nH]2)cn1]
16
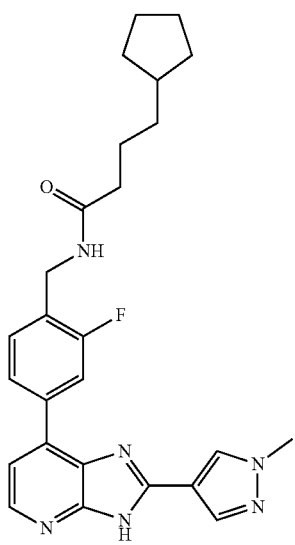 [SMILES: Cn1cc(-c2nc3c(-c4ccc(CNC(=O)CCCC5CCCC5)c(F)c4)ccnc3[nH]2)cn1]
17
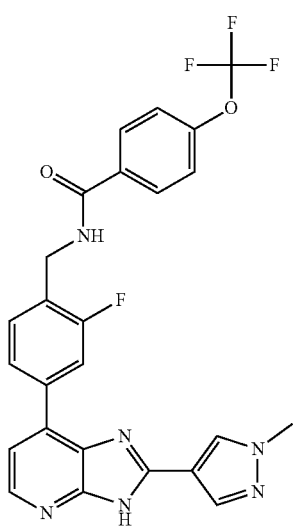 [SMILES: Cn1cc(-c2nc3c(-c4ccc(CNC(=O)c5ccc(OC(F)(F)F)cc5)c(F)c4)ccnc3[nH]2)cn1]

TABLE 1-continued
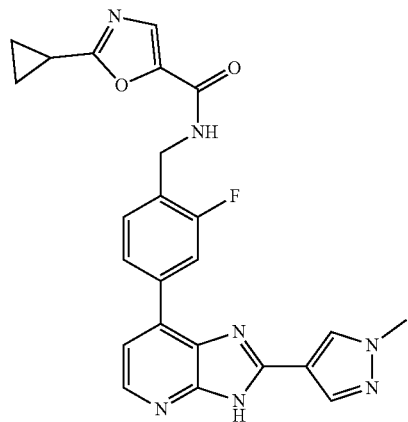 [SMILES: Cn1cc(-c2nc3c(-c4ccc(CNC(=O)c5cnc(C6CC6)o5)c(F)c4)ccnc3[nH]2)cn1]
18
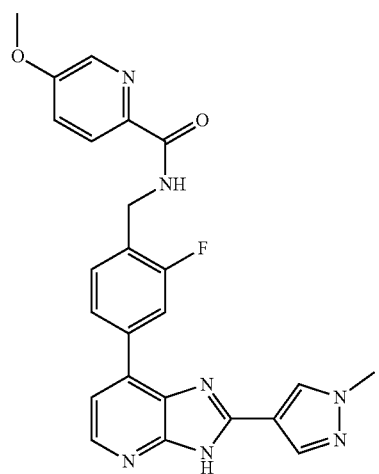 [SMILES: COc1ccc(C(=O)NCc2ccc(-c3ccnc4[nH]c(-c5cnn(C)c5)nc34)cc2F)nc1]
19
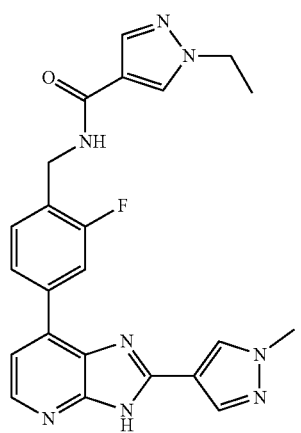 [SMILES: CCn1cc(C(=O)NCc2ccc(-c3ccnc4[nH]c(-c5cnn(C)c5)nc34)cc2F)cn1]
20

TABLE 1-continued
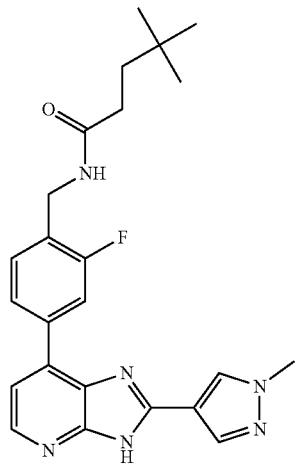 [SMILES: Cn1cc(-c2nc3c(-c4ccc(CNC(=O)CCC(C)(C)C)c(F)c4)ccnc3[nH]2)cn1]
21
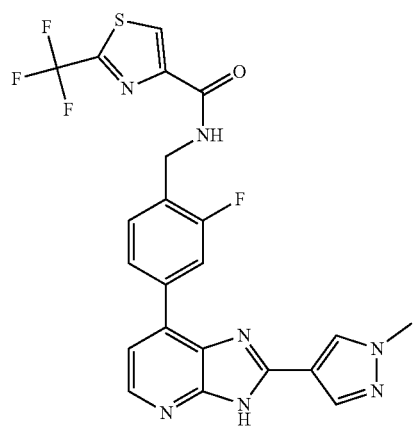 [SMILES: Cn1cc(-c2nc3c(-c4ccc(CNC(=O)c5csc(C(F)(F)F)n5)c(F)c4)ccnc3[nH]2)cn1]
22
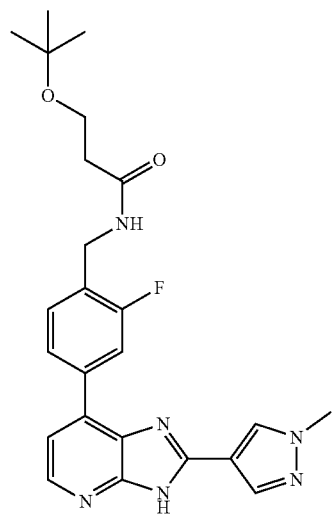 [SMILES: Cn1cc(-c2nc3c(-c4ccc(CNC(=O)CCOC(C)(C)C)c(F)c4)ccnc3[nH]2)cn1]
23

TABLE 1-continued
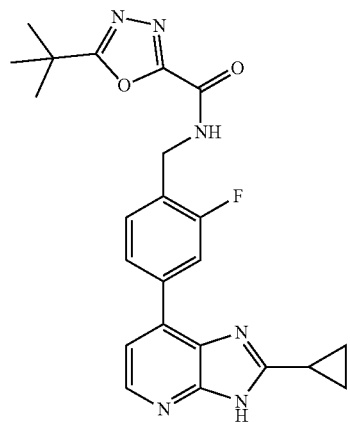 [SMILES: CC(C)(C)c1nnc(C(=O)NCc2ccc(-c3ccnc4[nH]c(C5CC5)nc34)cc2F)o1]
24
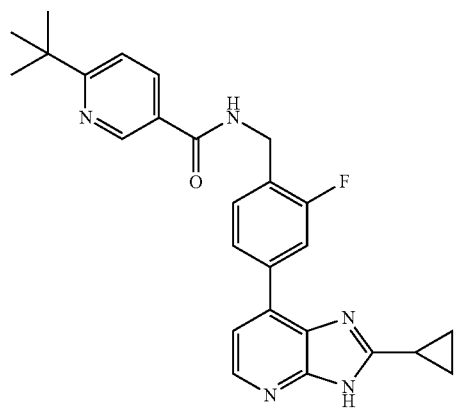 [SMILES: CC(C)(C)c1ccc(C(=O)NCc2ccc(-c3ccnc4[nH]c(C5CC5)nc34)cc2F)cn1]
25
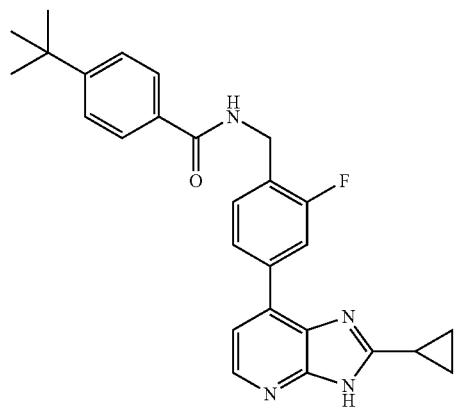 [SMILES: CC(C)(C)c1ccc(C(=O)NCc2ccc(-c3ccnc4[nH]c(C5CC5)nc34)cc2F)cc1]
26

TABLE 1-continued
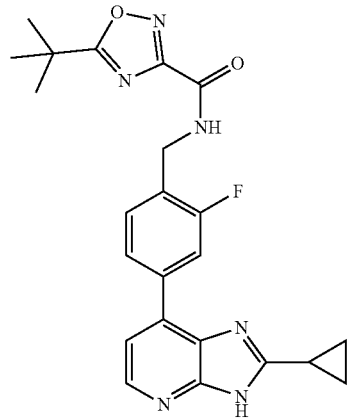 [SMILES: CC(C)(C)c1nc(C(=O)NCc2ccc(-c3ccnc4[nH]c(C5CC5)nc34)cc2F)no1]
27
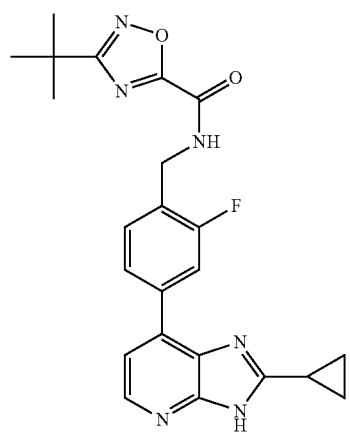 [SMILES: CC(C)(C)c1noc(C(=O)NCc2ccc(-c3ccnc4[nH]c(C5CC5)nc34)cc2F)n1]
28
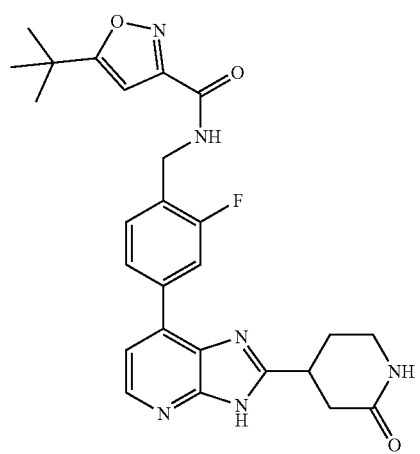 [SMILES: CC(C)(C)c1cc(C(=O)NCc2ccc(-c3ccnc4[nH]c(C5CCNC(=O)C5)nc34)cc2F)no1]
29

TABLE 1-continued
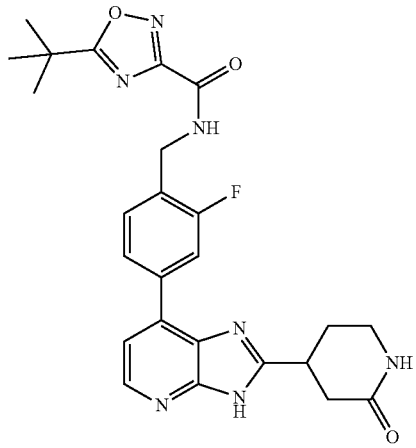 [SMILES: CC(C)(C)c1nc(C(=O)NCc2ccc(-c3ccnc4[nH]c(C5CCNC(=O)C5)nc34)cc2F)no1]
30
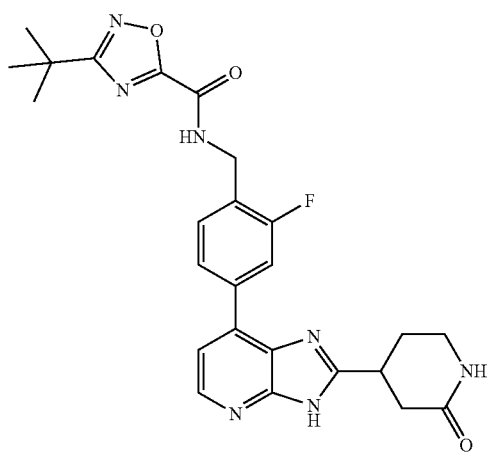 [SMILES: CC(C)(C)c1noc(C(=O)NCc2ccc(-c3ccnc4[nH]c(C5CCNC(=O)C5)nc34)cc2F)n1]
31
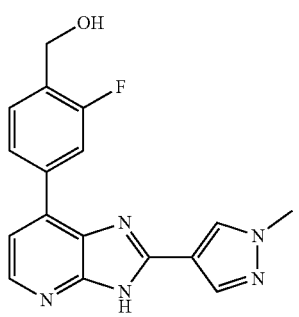 [SMILES: Cn1cc(-c2nc3c(-c4ccc(CO)c(F)c4)ccnc3[nH]2)cn1]
32

TABLE 1-continued
| | |
|---|---|
| 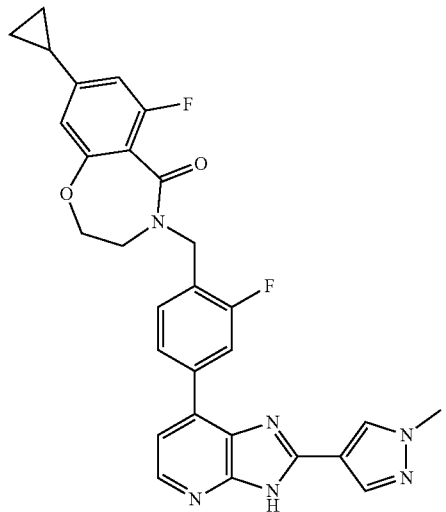 [SMILES: Cn1cc(-c2nc3c(-c4ccc(CN5CCOc6cc(C7CC7)cc(F)c6C5=O)c(F)c4)ccnc3[nH]2)cn1] | 34 |
| 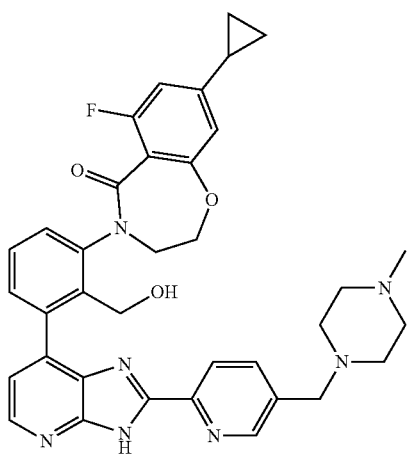 [SMILES: CN1CCN(Cc2ccc(-c3nc4c(-c5cccc(N6CCOc7cc(C8CC8)cc(F)c7C6=O)c5CO)ccnc4[nH]3)nc2)CC1] | 35 |
| 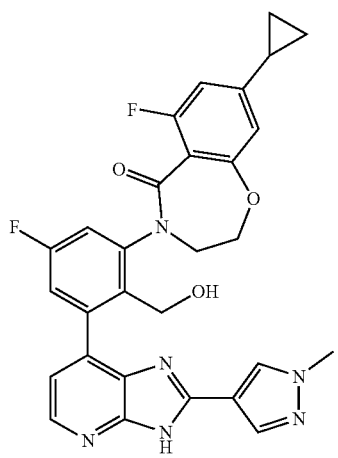 [SMILES: Cn1cc(-c2nc3c(-c4cc(F)cc(N5CCOc6cc(C7CC7)cc(F)c6C5=O)c4CO)ccnc3[nH]2)cn1] | 37 |

TABLE 1-continued
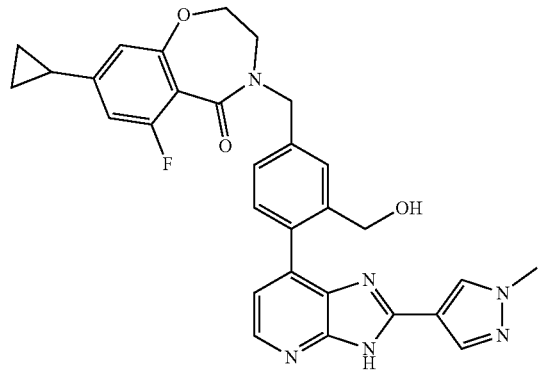 [SMILES: Cn1cc(-c2nc3c(-c4ccc(CN5CCOc6cc(C7CC7)cc(F)c6C5=O)cc4CO)ccnc3[nH]2)cn1]
38
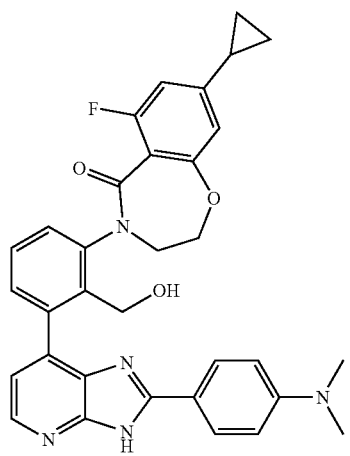 [SMILES: CN(C)c1ccc(-c2nc3c(-c4cccc(N5CCOc6cc(C7CC7)cc(F)c6C5=O)c4CO)ccnc3[nH]2)cc1]
39
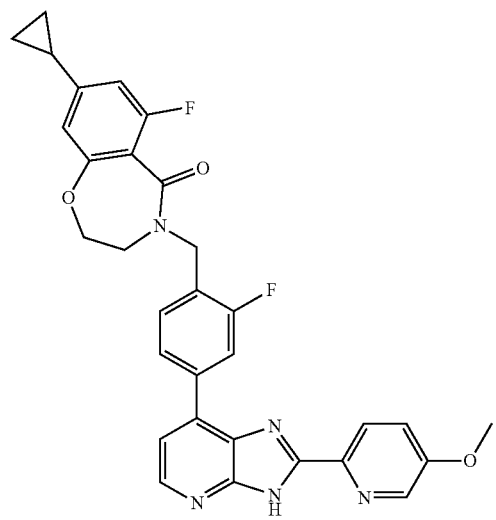 [SMILES: COc1ccc(-c2nc3c(-c4ccc(CN5CCOc6cc(C7CC7)cc(F)c6C5=O)c(F)c4)ccnc3[nH]2)nc1]
40

TABLE 1-continued
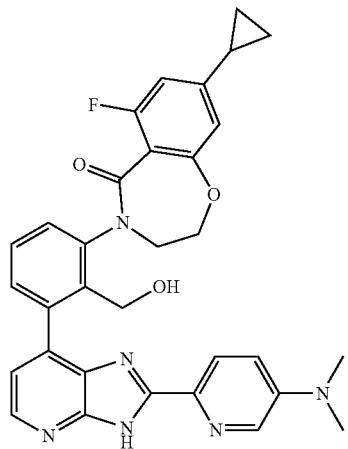
41
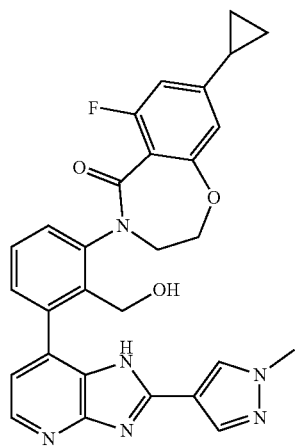 [SMILES: Cn1cc(-c2nc3nccc(-c4cccc(N5CCOc6cc(C7CC7)cc(F)c6C5=O)c4CO)c3[nH]2)cn1]
42
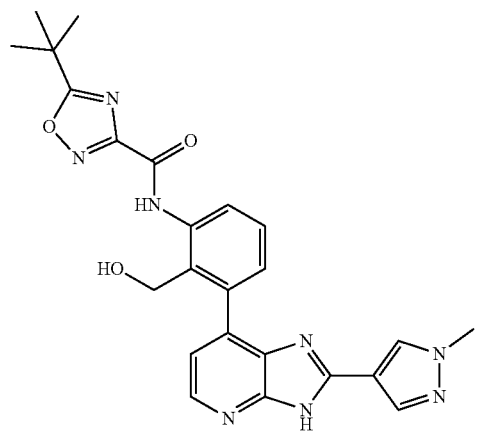 [SMILES: Cn1cc(-c2nc3c(-c4cccc(NC(=O)c5noc(C(C)(C)C)n5)c4CO)ccnc3[nH]2)cn1]
43

TABLE 1-continued
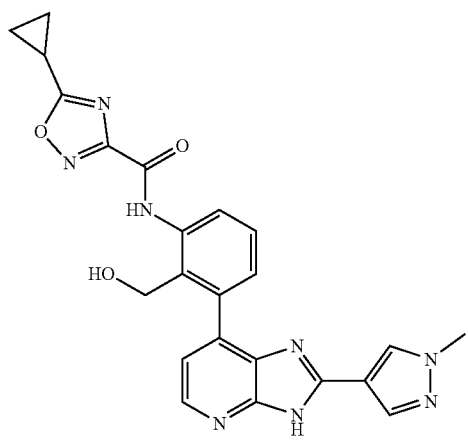 [SMILES: Cn1cc(-c2nc3c(-c4cccc(NC(=O)c5noc(C6CC6)n5)c4CO)ccnc3[nH]2)cn1]
44
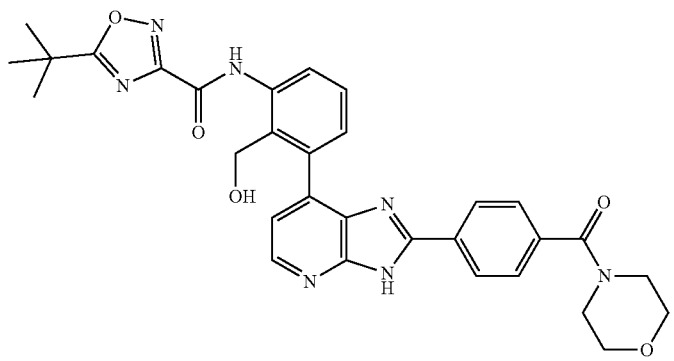 [SMILES: CC(C)(C)c1nc(C(=O)Nc2cccc(-c3ccnc4[nH]c(-c5ccc(C(=O)N6CCOCC6)cc5)nc34)c2CO)no1]
45
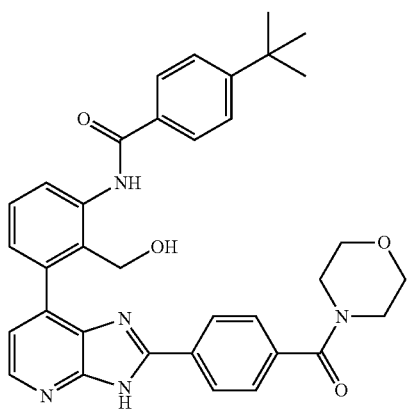 [SMILES: CC(C)(C)c1ccc(C(=O)Nc2cccc(-c3ccnc4[nH]c(-c5ccc(C(=O)N6CCOCC6)cc5)nc34)c2CO)cc1]
46
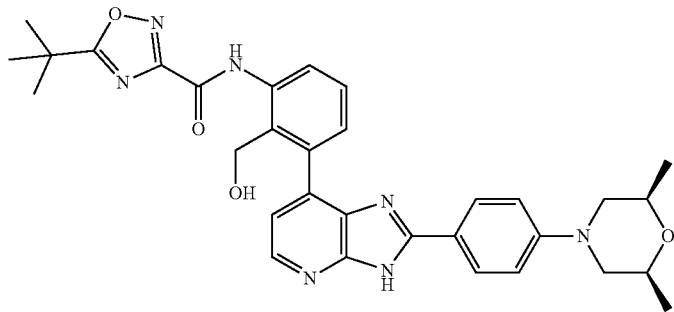 [SMILES: C[C@@H]1CN(c2ccc(-c3nc4c(-c5cccc(NC(=O)c6noc(C(C)(C)C)n6)c5CO)ccnc4[nH]3)cc2)C[C@H](C)O1]
47

TABLE 1-continued

| | |
|---|---|
| (structure) | 48 |
| (structure) | 49 |
| (structure) | 50 |
| (structure) | 51 |

TABLE 1-continued
| | |
|---|---|
| 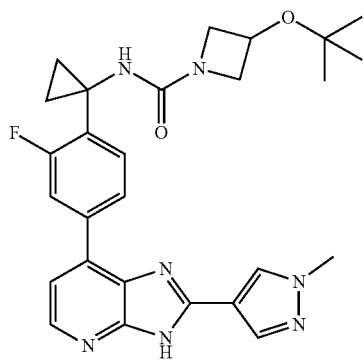 [SMILES: Cn1cc(-c2nc3c(-c4ccc(C5(NC(=O)N6CC(OC(C)(C)C)C6)CC5)c(F)c4)ccnc3[nH]2)cn1] | 52 |
| 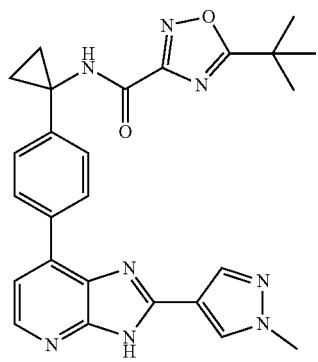 [SMILES: Cn1cc(-c2nc3c(-c4ccc(C5(NC(=O)c6noc(C(C)(C)C)n6)CC5)cc4)ccnc3[nH]2)cn1] | 53 |
| 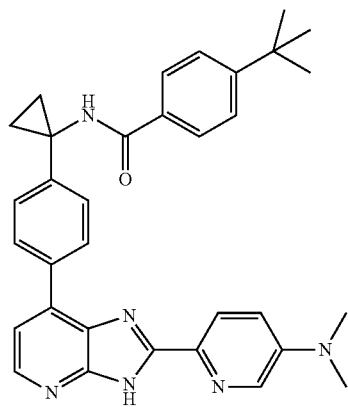 [SMILES: CN(C)c1ccc(-c2nc3c(-c4ccc(C5(NC(=O)c6ccc(C(C)(C)C)cc6)CC5)cc4)ccnc3[nH]2)nc1] | 54 |
| 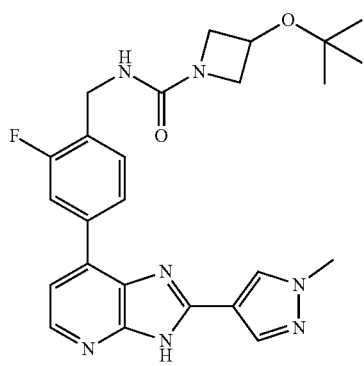 [SMILES: Cn1cc(-c2nc3c(-c4ccc(CNC(=O)N5CC(OC(C)(C)C)C5)c(F)c4)ccnc3[nH]2)cn1] | 55 |

TABLE 1-continued
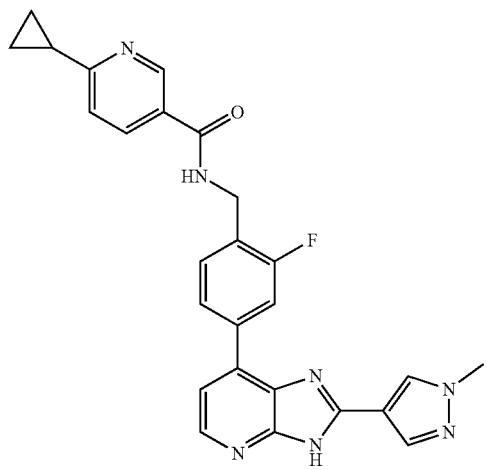 [SMILES: Cn1cc(-c2nc3c(-c4ccc(CNC(=O)c5ccc(C6CC6)nc5)c(F)c4)ccnc3[nH]2)cn1]
56
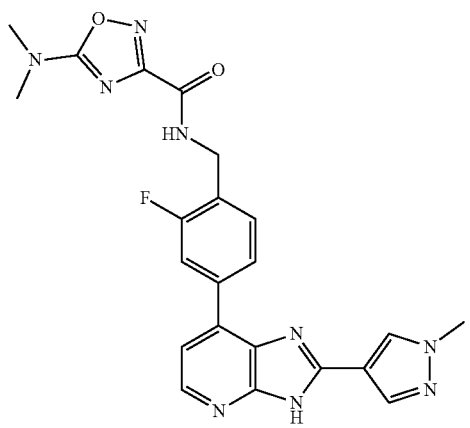
57
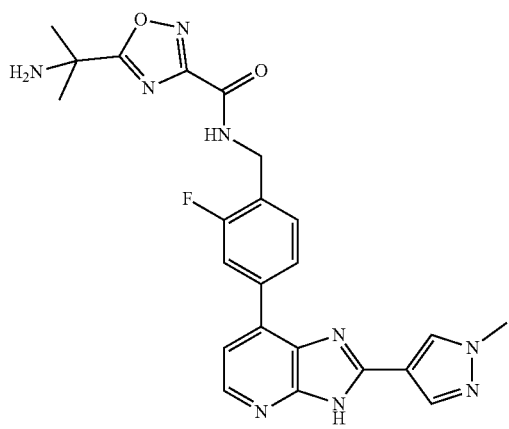 [SMILES: Cn1cc(-c2nc3c(-c4ccc(CNC(=O)c5noc(C(C)(C)N)n5)c(F)c4)ccnc3[nH]2)cn1]
58

TABLE 1-continued

| | |
|---|---|
| (structure) | 59 |
| (structure) | 60 |
| (structure) | 61 |
| (structure) | 62 |

TABLE 1-continued
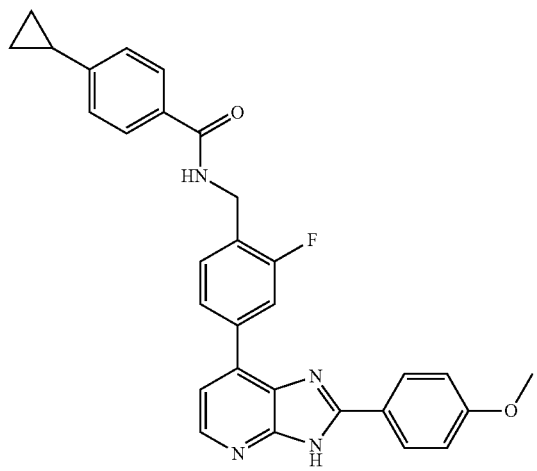 [SMILES: COc1ccc(-c2nc3c(-c4ccc(CNC(=O)c5ccc(C6CC6)cc5)c(F)c4)ccnc3[nH]2)cc1]
63
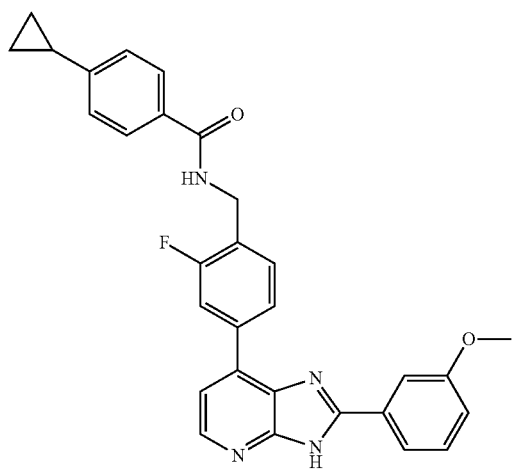 [SMILES: COc1cccc(-c2nc3c(-c4ccc(CNC(=O)c5ccc(C6CC6)cc5)c(F)c4)ccnc3[nH]2)c1]
64
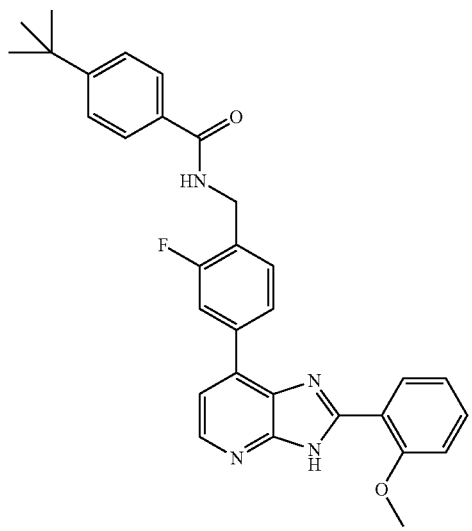 [SMILES: COc1ccccc1-c1nc2c(-c3ccc(CNC(=O)c4ccc(C(C)(C)C)cc4)c(F)c3)ccnc2[nH]1]
65

TABLE 1-continued
| | |
|---|---|
| 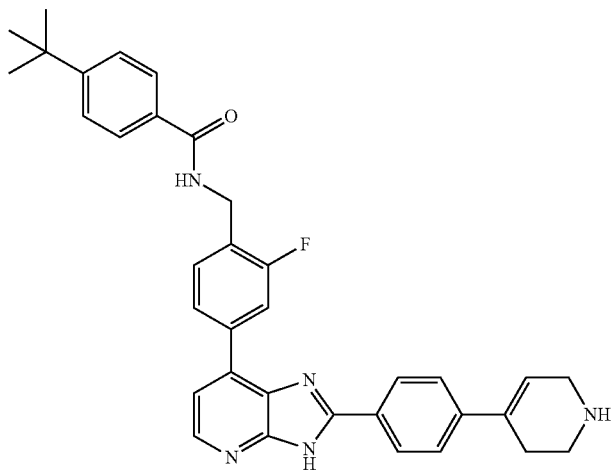 [SMILES: CC(C)(C)c1ccc(C(=O)NCc2ccc(-c3ccnc4[nH]c(-c5ccc(C6=CCNCC6)cc5)nc34)cc2F)cc1] | 66 |
| 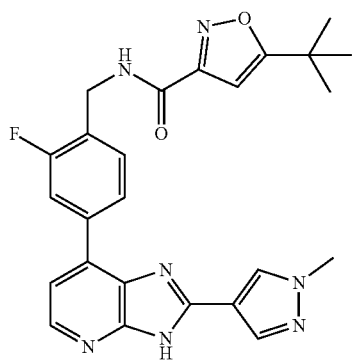 [SMILES: Cn1cc(-c2nc3c(-c4ccc(CNC(=O)c5cc(C(C)(C)C)on5)c(F)c4)ccnc3[nH]2)cn1] | 67 |
| 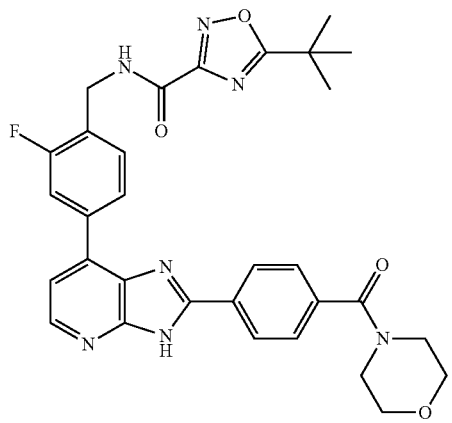 [SMILES: CC(C)(C)c1nc(C(=O)NCc2ccc(-c3ccnc4[nH]c(-c5ccc(C(=O)N6CCOCC6)cc5)nc34)cc2F)no1] | 68 |
| 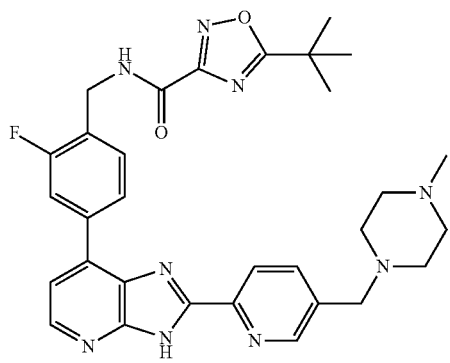 | 69 |

TABLE 1-continued
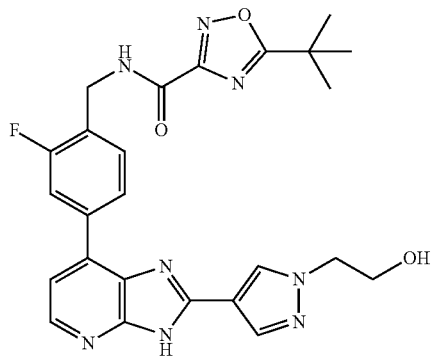 [SMILES: CC(C)(C)c1nc(C(=O)NCc2ccc(-c3ccnc4[nH]c(-c5cnn(CCO)c5)nc34)cc2F)no1]
70
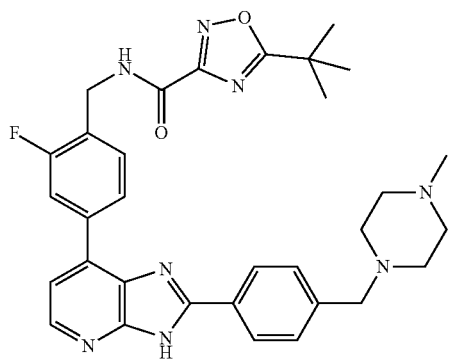 [SMILES: CN1CCN(Cc2ccc(-c3nc4c(-c5ccc(CNC(=O)c6noc(C(C)(C)C)n6)c(F)c5)ccnc4[nH]3)cc2)CC1]
71
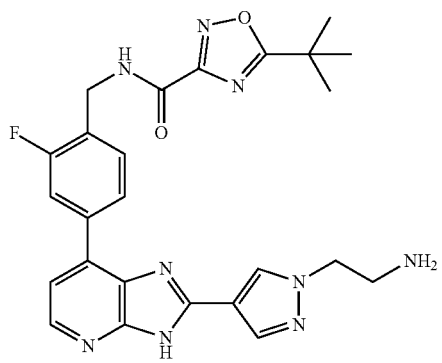 [SMILES: CC(C)(C)c1nc(C(=O)NCc2ccc(-c3ccnc4[nH]c(-c5cnn(CCN)c5)nc34)cc2F)no1]
72
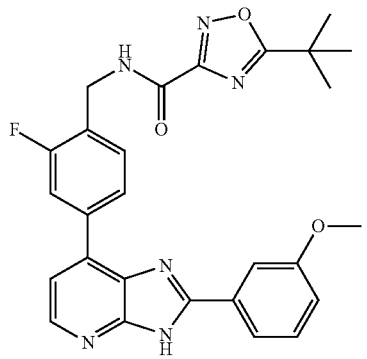
73

TABLE 1-continued
| | |
|---|---|
| 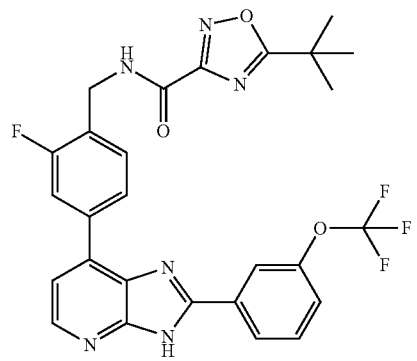 [SMILES: CC(C)(C)c1nc(C(=O)NCc2ccc(-c3ccnc4[nH]c(-c5cccc(OC(F)(F)F)c5)nc34)cc2F)no1] | 74 |
| 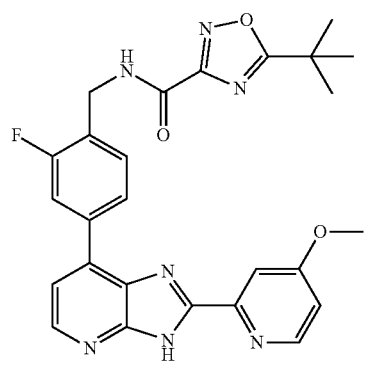 [SMILES: COc1ccnc(-c2nc3c(-c4ccc(CNC(=O)c5noc(C(C)(C)C)n5)c(F)c4)ccnc3[nH]2)c1] | 75 |
| 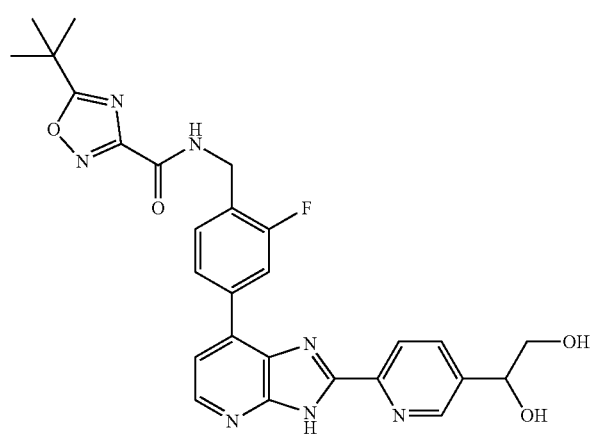 [SMILES: CC(C)(C)c1nc(C(=O)NCc2ccc(-c3ccnc4[nH]c(-c5ccc(C(O)CO)cn5)nc34)cc2F)no1] | 76 |
| 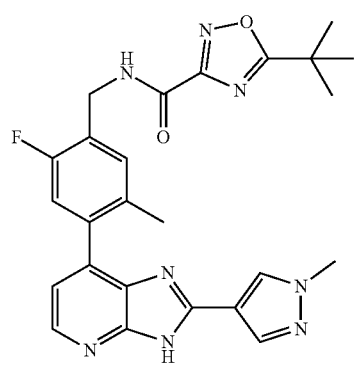 [SMILES: Cc1cc(CNC(=O)c2noc(C(C)(C)C)n2)c(F)cc1-c1ccnc2[nH]c(-c3cnn(C)c3)nc12] | 77 |

TABLE 1-continued
| | |
|---|---|
| 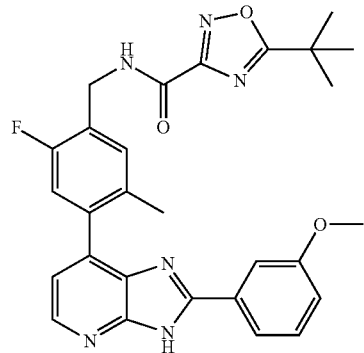 [SMILES: COc1cccc(-c2nc3c(-c4cc(F)c(CNC(=O)c5noc(C(C)(C)C)n5)cc4C)ccnc3[nH]2)c1] | 78 |
| 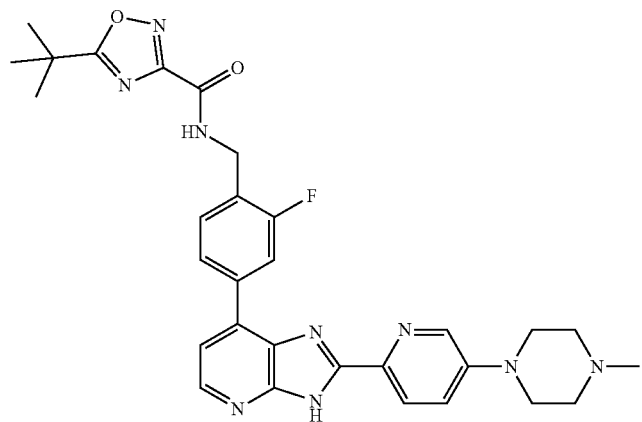 [SMILES: CN1CCN(c2ccc(-c3nc4c(-c5ccc(CNC(=O)c6noc(C(C)(C)C)n6)c(F)c5)ccnc4[nH]3)nc2)CC1] | 79 |
| 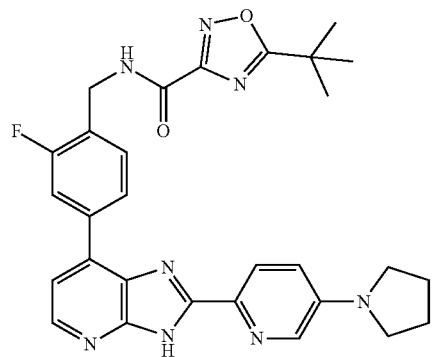 [SMILES: CC(C)(C)c1nc(C(=O)NCc2ccc(-c3ccnc4[nH]c(-c5ccc(N6CCCC6)cn5)nc34)cc2F)no1] | 80 |
| 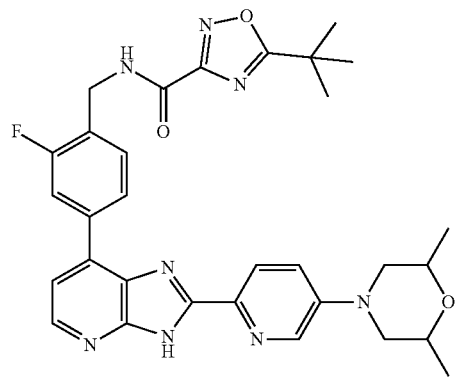 [SMILES: CC1CN(c2ccc(-c3nc4c(-c5ccc(CNC(=O)c6noc(C(C)(C)C)n6)c(F)c5)ccnc4[nH]3)nc2)CC(C)O1] | 81 |

TABLE 1-continued
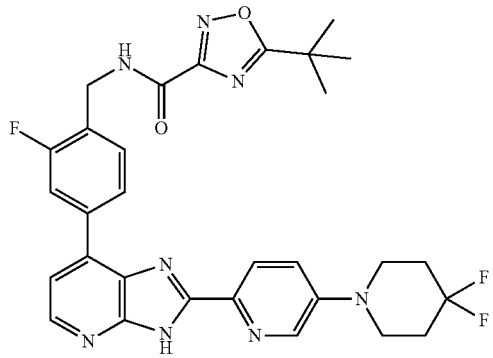 [SMILES: CC(C)(C)c1nc(C(=O)NCc2ccc(-c3ccnc4[nH]c(-c5ccc(N6CCC(F)(F)CC6)cn5)nc34)cc2F)no1]
82
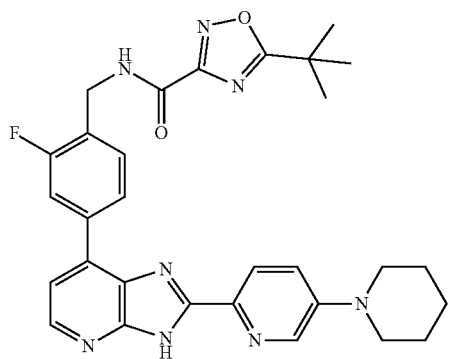
83
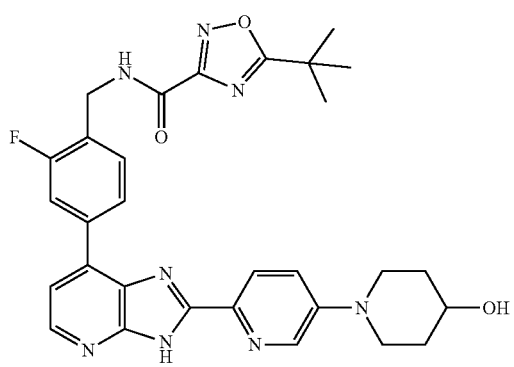 [SMILES: CC(C)(C)c1nc(C(=O)NCc2ccc(-c3ccnc4[nH]c(-c5ccc(N6CCC(O)CC6)cn5)nc34)cc2F)no1]
84
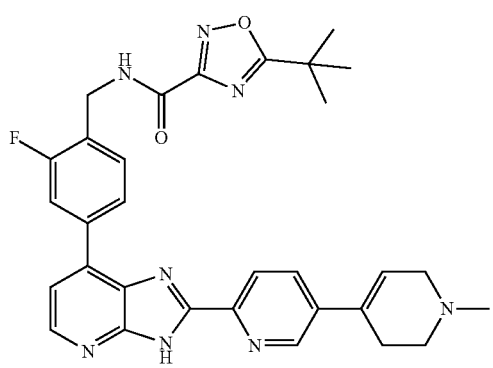 [SMILES: CN1CC=C(c2ccc(-c3nc4c(-c5ccc(CNC(=O)c6noc(C(C)(C)C)n6)c(F)c5)ccnc4[nH]3)nc2)CC1]
85

TABLE 1-continued
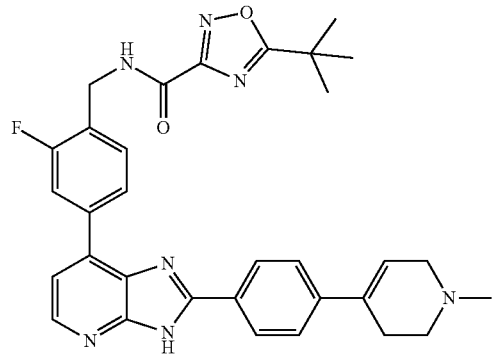 [SMILES: CN1CC=C(c2ccc(-c3nc4c(-c5ccc(CNC(=O)c6noc(C(C)(C)C)n6)c(F)c5)ccnc4[nH]3)cc2)CC1]
86
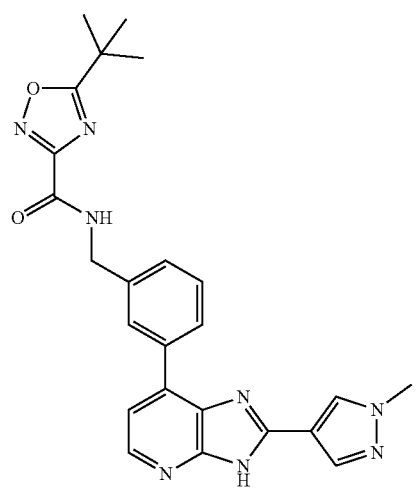 [SMILES: Cn1cc(-c2nc3c(-c4cccc(CNC(=O)c5noc(C(C)(C)C)n5)c4)ccnc3[nH]2)cn1]
87
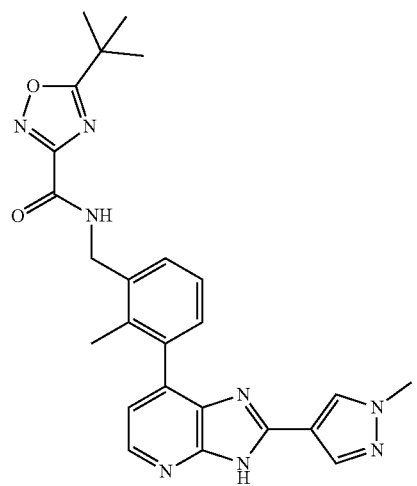 [SMILES: Cc1c(CNC(=O)c2noc(C(C)(C)C)n2)cccc1-c1ccnc2[nH]c(-c3cnn(C)c3)nc12]
88

TABLE 1-continued
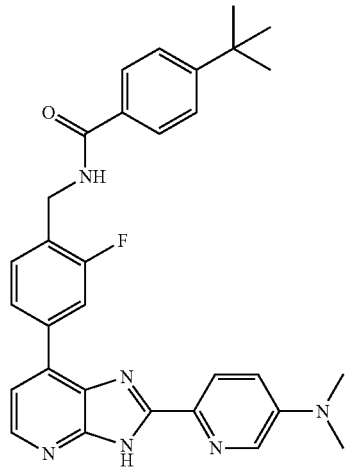 [SMILES: CN(C)c1ccc(-c2nc3c(-c4ccc(CNC(=O)c5ccc(C(C)(C)C)cc5)c(F)c4)ccnc3[nH]2)nc1]
89
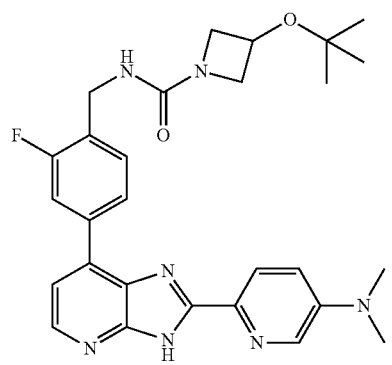 [SMILES: CN(C)c1ccc(-c2nc3c(-c4ccc(CNC(=O)N5CC(OC(C)(C)C)C5)c(F)c4)ccnc3[nH]2)nc1]
90
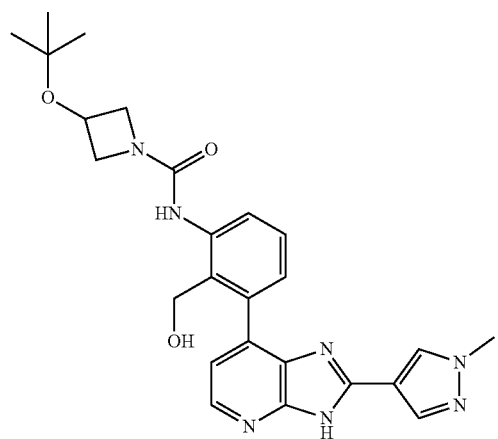 [SMILES: Cn1cc(-c2nc3c(-c4cccc(NC(=O)N5CC(OC(C)(C)C)C5)c4CO)ccnc3[nH]2)cn1]
91

TABLE 1-continued
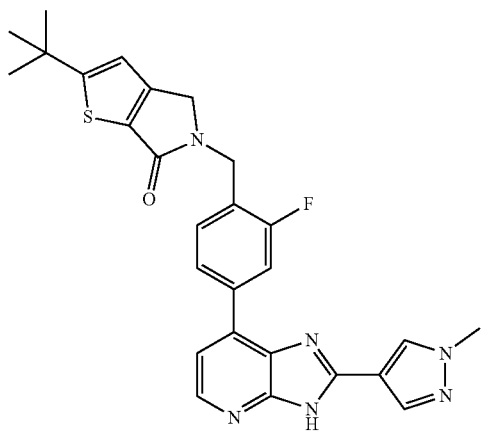 [SMILES: Cn1cc(-c2nc3c(-c4ccc(CN5Cc6cc(C(C)(C)C)sc6C5=O)c(F)c4)ccnc3[nH]2)cn1]
92
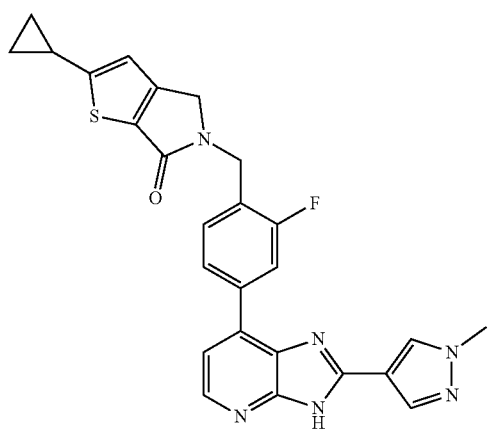 [SMILES: Cn1cc(-c2nc3c(-c4ccc(CN5Cc6cc(C7CC7)sc6C5=O)c(F)c4)ccnc3[nH]2)cn1]
93
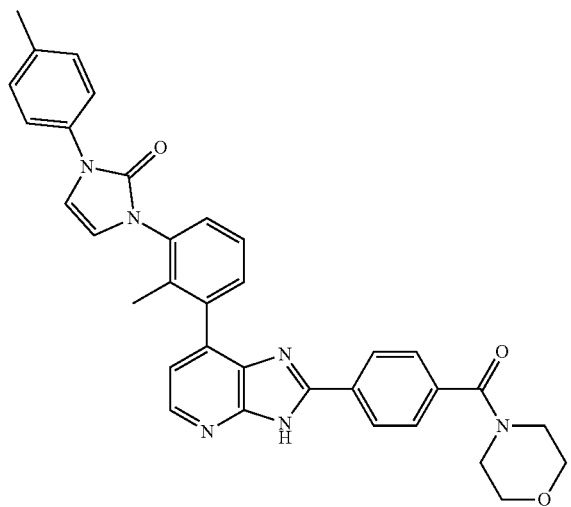 [SMILES: Cc1ccc(-n2ccn(-c3cccc(-c4ccnc5[nH]c(-c6ccc(C(=O)N7CCOCC7)cc6)nc45)c3C)c2=O)cc1]
95

TABLE 1-continued
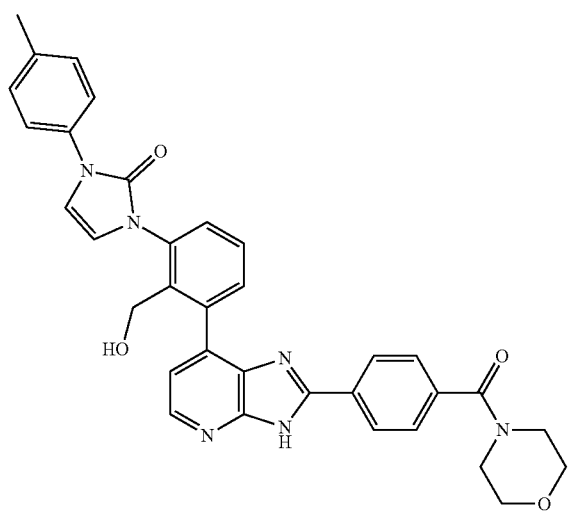 [SMILES: Cc1ccc(-n2ccn(-c3cccc(-c4ccnc5[nH]c(-c6ccc(C(=O)N7CCOCC7)cc6)nc45)c3CO)c2=O)cc1]
96
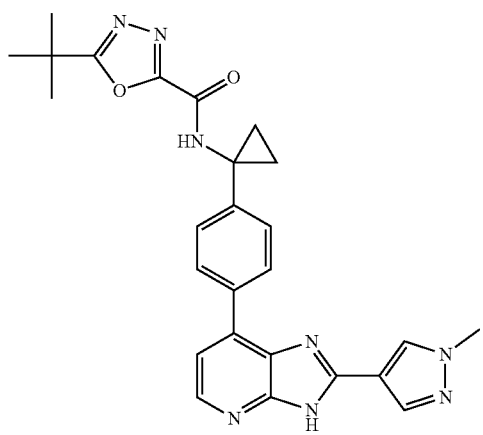 [SMILES: Cn1cc(-c2nc3c(-c4ccc(C5(NC(=O)c6nnc(C(C)(C)C)o6)CC5)cc4)ccnc3[nH]2)cn1]
97
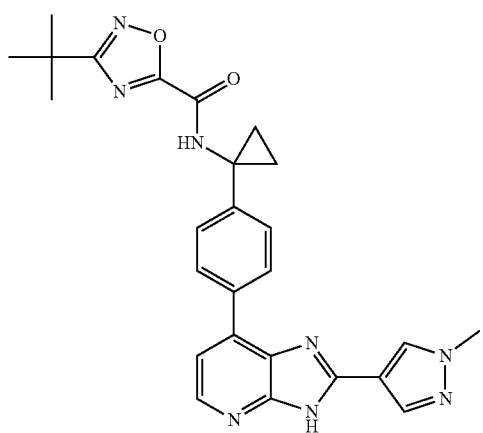 [SMILES: Cn1cc(-c2nc3c(-c4ccc(C5(NC(=O)c6nc(C(C)(C)C)no6)CC5)cc4)ccnc3[nH]2)cn1]
98

TABLE 1-continued
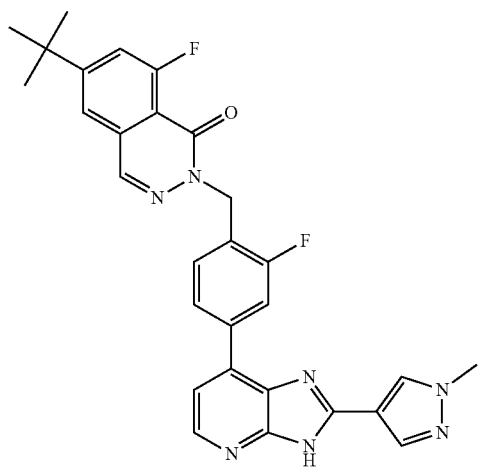 [SMILES: Cn1cc(-c2nc3c(-c4ccc(Cn5ncc6cc(C(C)(C)C)cc(F)c6c5=O)c(F)c4)ccnc3[nH]2)cn1]
99
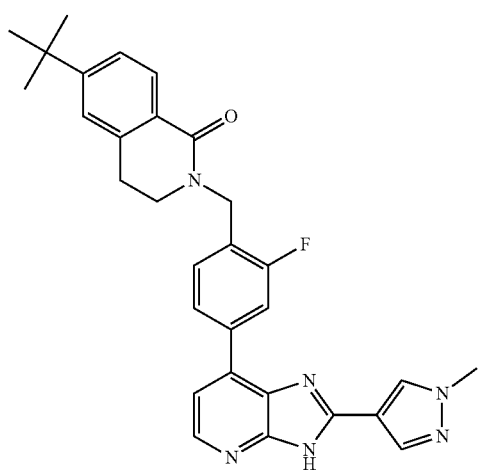 [SMILES: Cn1cc(-c2nc3c(-c4ccc(CN5CCc6cc(C(C)(C)C)ccc6C5=O)c(F)c4)ccnc3[nH]2)cn1]
100
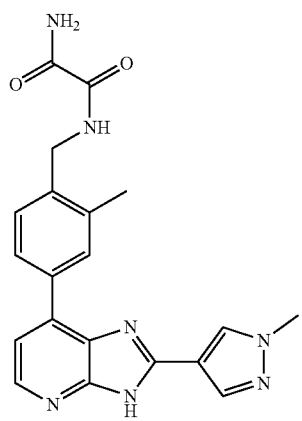 [SMILES: Cc1cc(-c2ccnc3[nH]c(-c4cnn(C)c4)nc23)ccc1CNC(=O)C(N)=O]
101

TABLE 1-continued
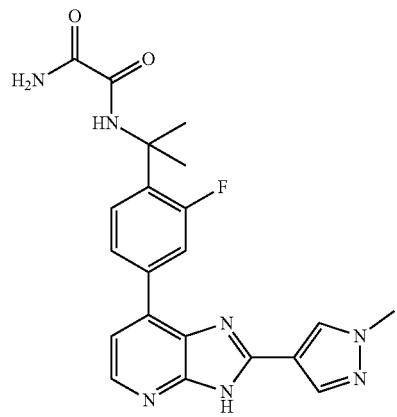 [SMILES: Cn1cc(-c2nc3c(-c4ccc(C(C)(C)NC(=O)C(N)=O)c(F)c4)ccnc3[nH]2)cn1]
102
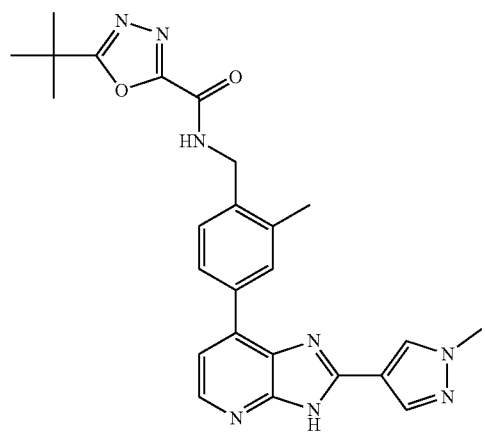 [SMILES: Cc1cc(-c2ccnc3[nH]c(-c4cnn(C)c4)nc23)ccc1CNC(=O)c1nnc(C(C)(C)C)o1]
103
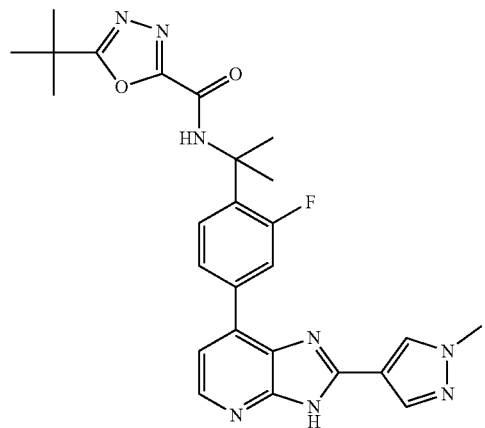 [SMILES: Cn1cc(-c2nc3c(-c4ccc(C(C)(C)NC(=O)c5nnc(C(C)(C)C)o5)c(F)c4)ccnc3[nH]2)cn1]
104

TABLE 1-continued
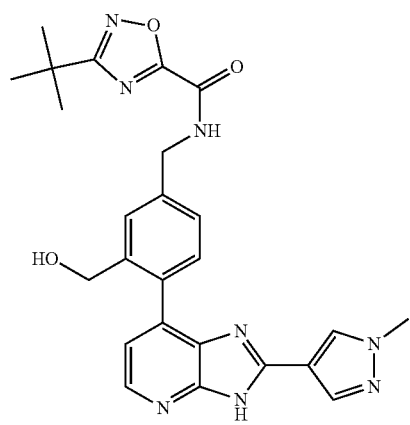 [SMILES: Cn1cc(-c2nc3c(-c4ccc(CNC(=O)c5nc(C(C)(C)C)no5)cc4CO)ccnc3[nH]2)cn1]
105
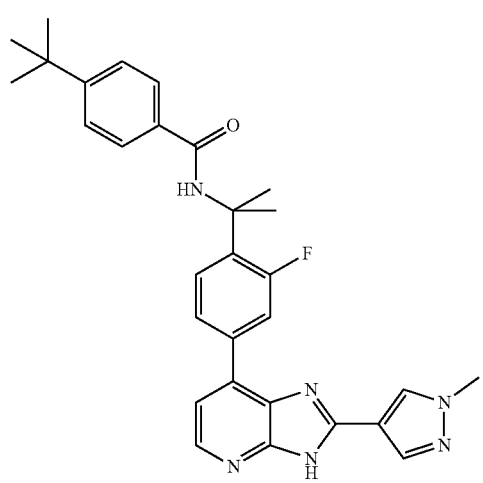 [SMILES: Cn1cc(-c2nc3c(-c4ccc(C(C)(C)NC(=O)c5ccc(C(C)(C)C)cc5)c(F)c4)ccnc3[nH]2)cn1]
106
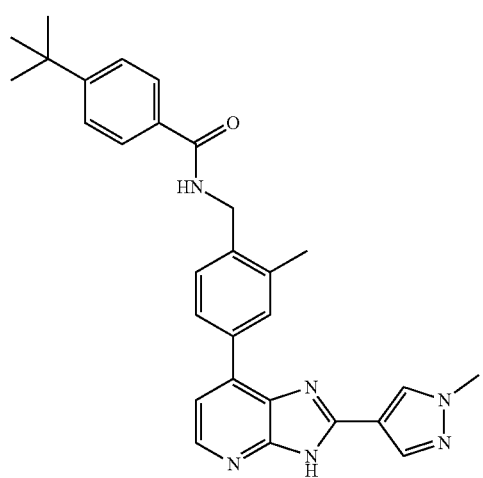 [SMILES: Cc1cc(-c2ccnc3[nH]c(-c4cnn(C)c4)nc23)ccc1CNC(=O)c1ccc(C(C)(C)C)cc1]
107

TABLE 1-continued
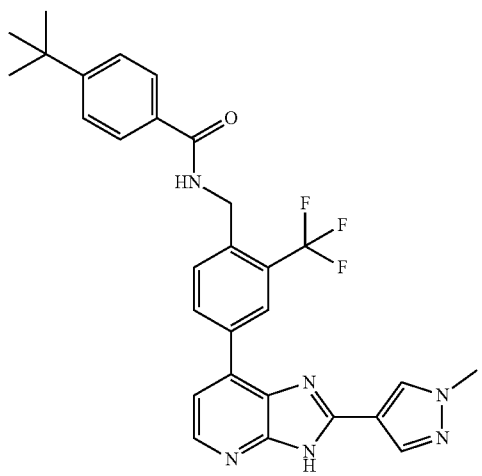 [SMILES: Cn1cc(-c2nc3c(-c4ccc(CNC(=O)c5ccc(C(C)(C)C)cc5)c(C(F)(F)F)c4)ccnc3[nH]2)cn1]
108
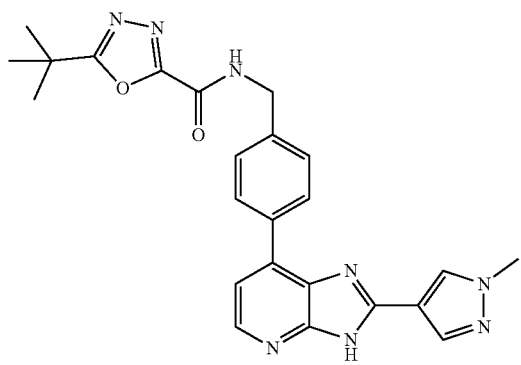 [SMILES: Cn1cc(-c2nc3c(-c4ccc(CNC(=O)c5nnc(C(C)(C)C)o5)cc4)ccnc3[nH]2)cn1]
109
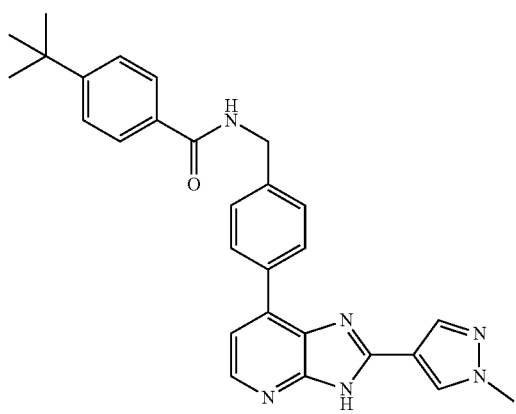 [SMILES: Cn1cc(-c2nc3c(-c4ccc(CNC(=O)c5ccc(C(C)(C)C)cc5)cc4)ccnc3[nH]2)cn1]
110

TABLE 1-continued
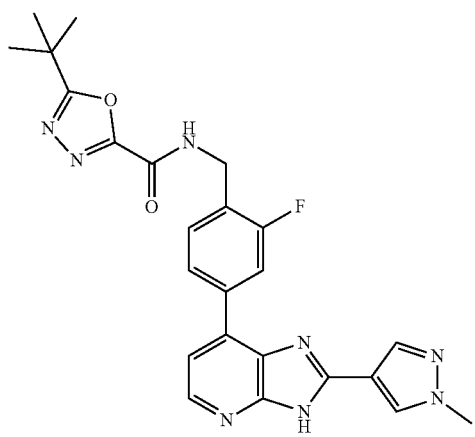 [SMILES: Cn1cc(-c2nc3c(-c4ccc(CNC(=O)c5nnc(C(C)(C)C)o5)c(F)c4)ccnc3[nH]2)cn1]
111
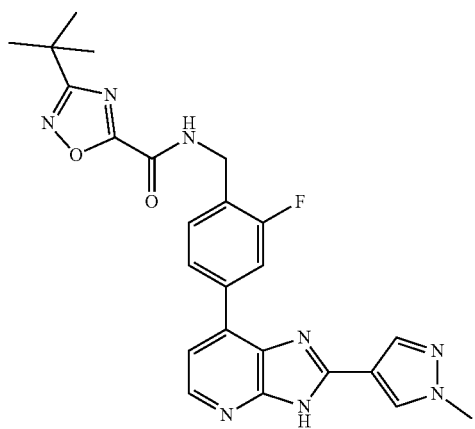 [SMILES: Cn1cc(-c2nc3c(-c4ccc(CNC(=O)c5nc(C(C)(C)C)no5)c(F)c4)ccnc3[nH]2)cn1]
112
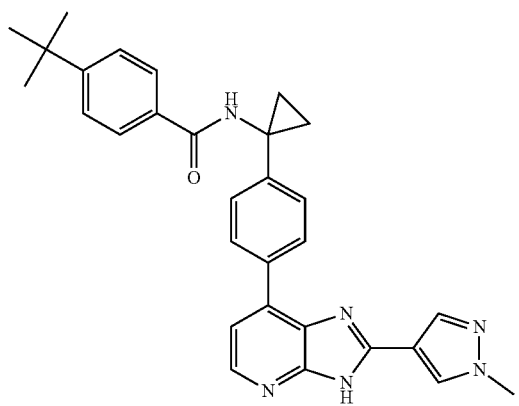 [SMILES: Cn1cc(-c2nc3c(-c4ccc(C5(NC(=O)c6ccc(C(C)(C)C)cc6)CC5)cc4)ccnc3[nH]2)cn1]
113

TABLE 1-continued
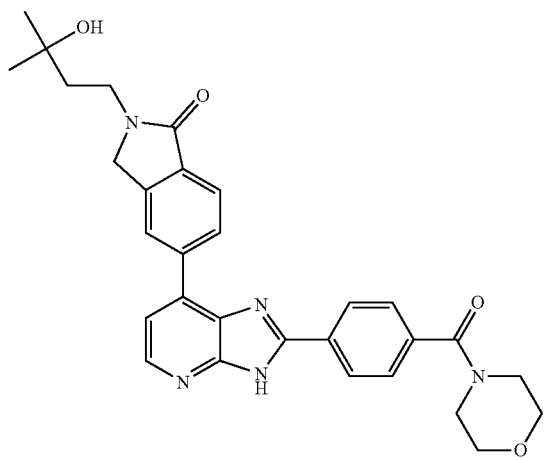 [SMILES: CC(C)(O)CCN1Cc2cc(-c3ccnc4[nH]c(-c5ccc(C(=O)N6CCOCC6)cc5)nc34)ccc2C1=O]
114
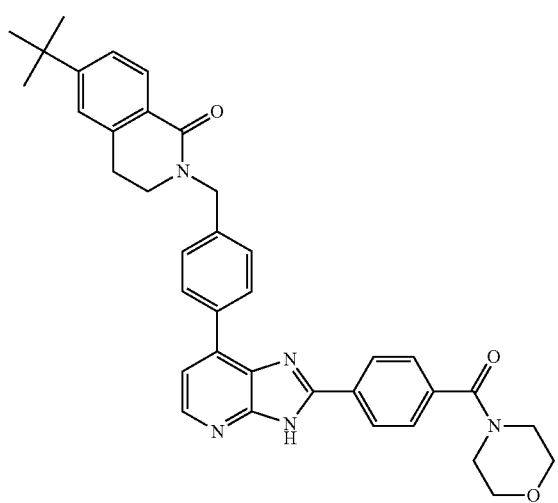 [SMILES: CC(C)(C)c1ccc2c(c1)CCN(Cc1ccc(-c3ccnc4[nH]c(-c5ccc(C(=O)N6CCOCC6)cc5)nc34)cc1)C2=O]
115
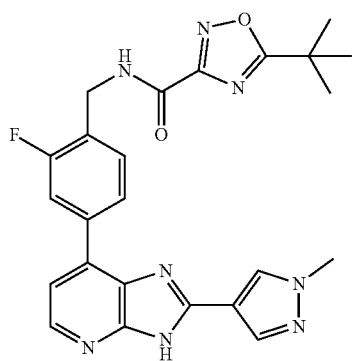 [SMILES: Cn1cc(-c2nc3c(-c4ccc(CNC(=O)c5noc(C(C)(C)C)n5)c(F)c4)ccnc3[nH]2)cn1]
116

TABLE 1-continued
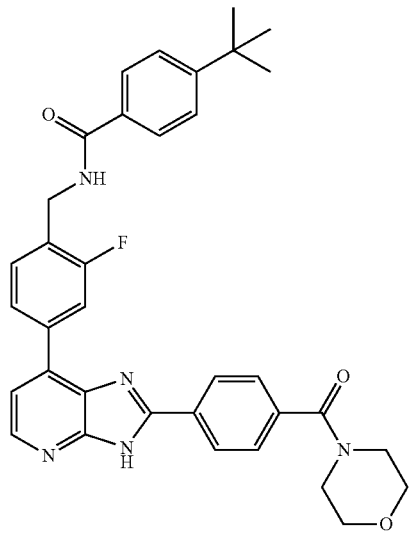 [SMILES: CC(C)(C)c1ccc(C(=O)NCc2ccc(-c3ccnc4[nH]c(-c5ccc(C(=O)N6CCOCC6)cc5)nc34)cc2F)cc1]
118
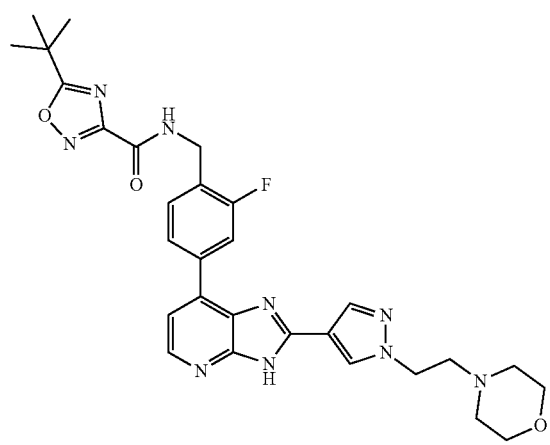 [SMILES: CC(C)(C)c1nc(C(=O)NCc2ccc(-c3ccnc4[nH]c(-c5cnn(CCN6CCOCC6)c5)nc34)cc2F)no1]
119
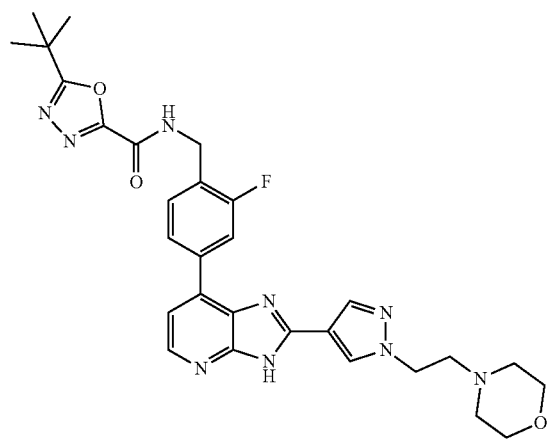 [SMILES: CC(C)(C)c1nnc(C(=O)NCc2ccc(-c3ccnc4[nH]c(-c5cnn(CCN6CCOCC6)c5)nc34)cc2F)o1]
120

TABLE 1-continued
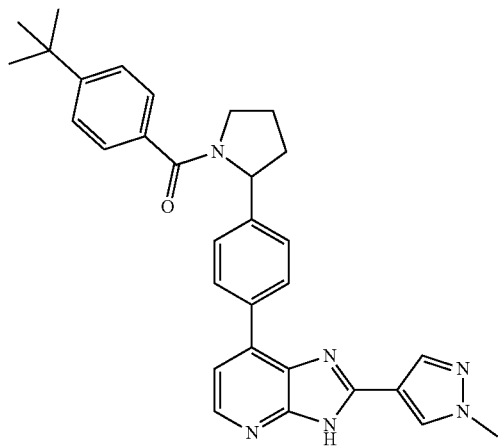 [SMILES: Cn1cc(-c2nc3c(-c4ccc(C5CCCN5C(=O)c5ccc(C(C)(C)C)cc5)cc4)ccnc3[nH]2)cn1]
121
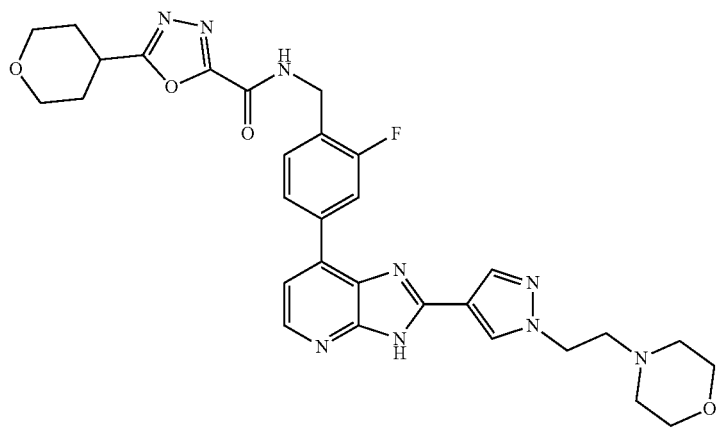 [SMILES: O=C(NCc1ccc(-c2ccnc3[nH]c(-c4cnn(CCN5CCOCC5)c4)nc23)cc1F)c1nnc(C2CCOCC2)o1]
122
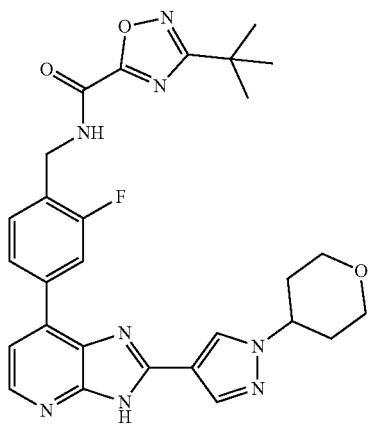 [SMILES: CC(C)(C)c1noc(C(=O)NCc2ccc(-c3ccnc4[nH]c(-c5cnn(C6CCOCC6)c5)nc34)cc2F)n1]
124

TABLE 1-continued
125
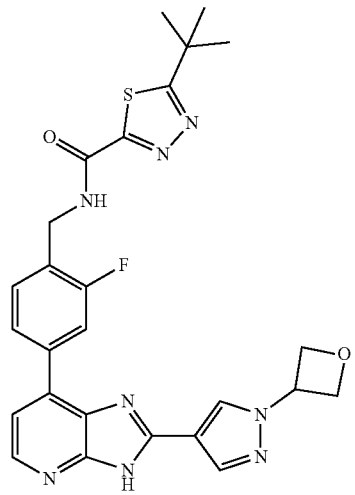 [SMILES: CC(C)(C)c1nnc(C(=O)NCc2ccc(-c3ccnc4[nH]c(-c5cnn(C6COC6)c5)nc34)cc2F)s1]
126
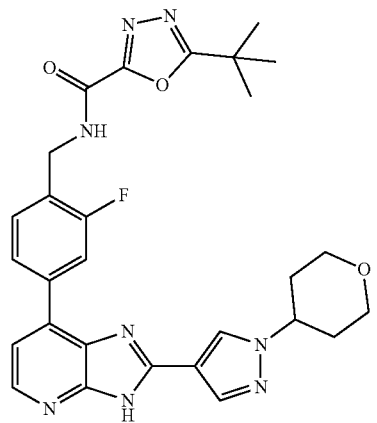 [SMILES: CC(C)(C)c1nnc(C(=O)NCc2ccc(-c3ccnc4[nH]c(-c5cnn(C6CCOCC6)c5)nc34)cc2F)o1]
127
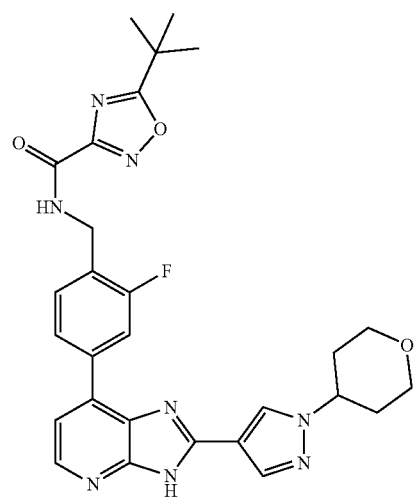 [SMILES: CC(C)(C)c1nc(C(=O)NCc2ccc(-c3ccnc4[nH]c(-c5cnn(C6CCOCC6)c5)nc34)cc2F)no1]

TABLE 1-continued
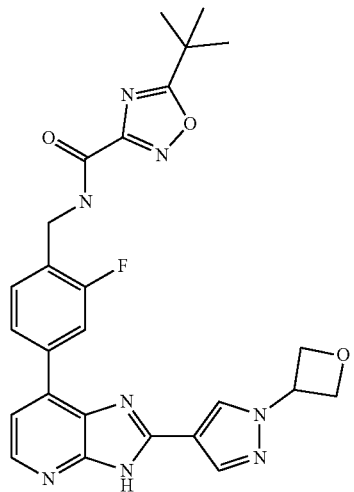 [SMILES: CC(C)(C)c1nc(C(=O)NCc2ccc(-c3ccnc4[nH]c(-c5cnn(C6COC6)c5)nc34)cc2F)no1]
129
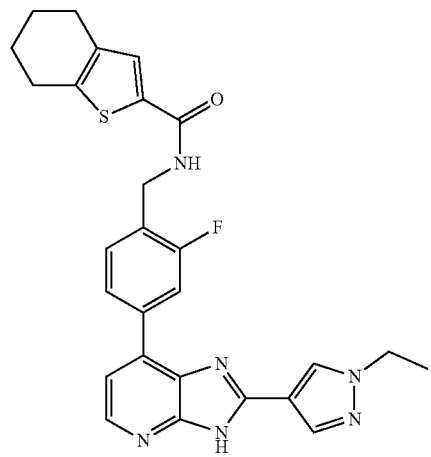 [SMILES: CCn1cc(-c2nc3c(-c4ccc(CNC(=O)c5cc6c(s5)CCCC6)c(F)c4)ccnc3[nH]2)cn1]
130
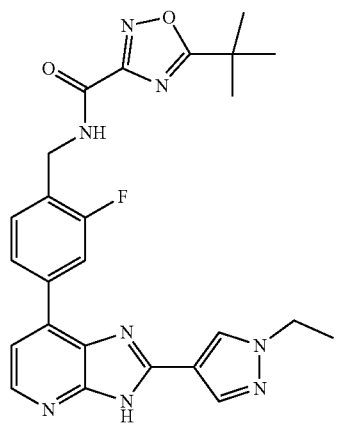 [SMILES: CCn1cc(-c2nc3c(-c4ccc(CNC(=O)c5noc(C(C)(C)C)n5)c(F)c4)ccnc3[nH]2)cn1]
131

TABLE 1-continued
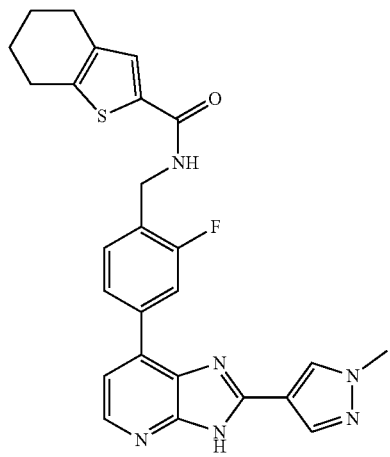 [SMILES: Cn1cc(-c2nc3c(-c4ccc(CNC(=O)c5cc6c(s5)CCCC6)c(F)c4)ccnc3[nH]2)cn1]
132
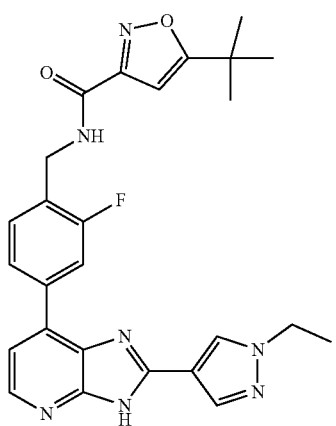 [SMILES: CCn1cc(-c2nc3c(-c4ccc(CNC(=O)c5cc(C(C)(C)C)on5)c(F)c4)ccnc3[nH]2)cn1]
133
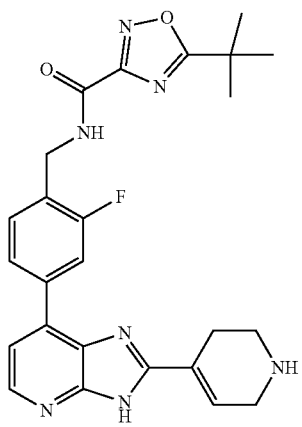
134

TABLE 1-continued
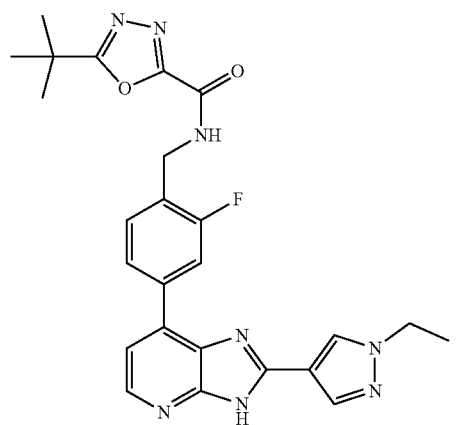 [SMILES: CCn1cc(-c2nc3c(-c4ccc(CNC(=O)c5nnc(C(C)(C)C)o5)c(F)c4)ccnc3[nH]2)cn1]
135
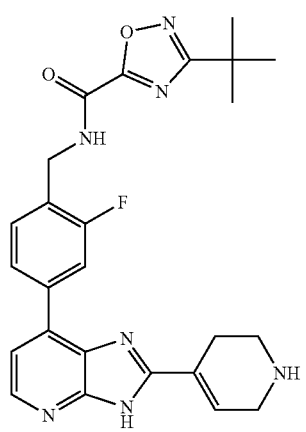 [SMILES: CC(C)(C)c1noc(C(=O)NCc2ccc(-c3ccnc4[nH]c(C5=CCNCC5)nc34)cc2F)n1]
136
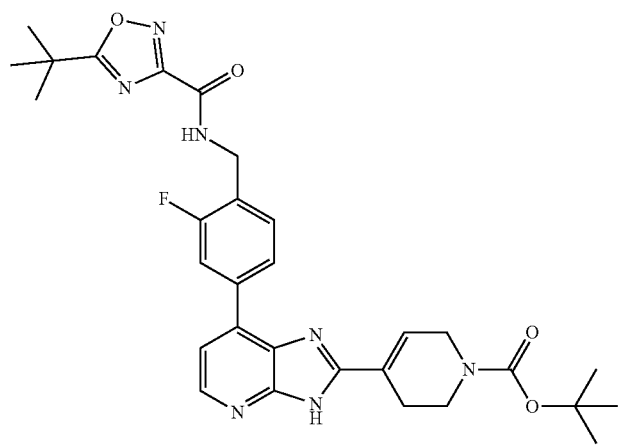 [SMILES: CC(C)(C)OC(=O)N1CC=C(c2nc3c(-c4ccc(CNC(=O)c5noc(C(C)(C)C)n5)c(F)c4)ccnc3[nH]2)CC1]
137

TABLE 1-continued
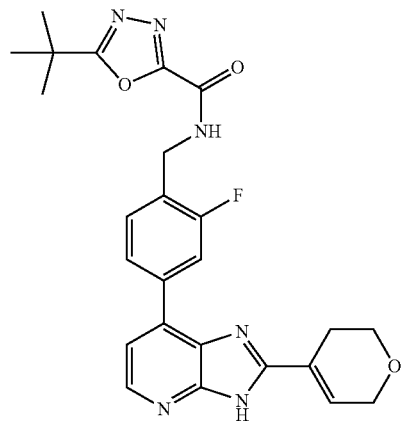 [SMILES: CC(C)(C)c1nnc(C(=O)NCc2ccc(-c3ccnc4[nH]c(C5=CCOCC5)nc34)cc2F)o1]
138
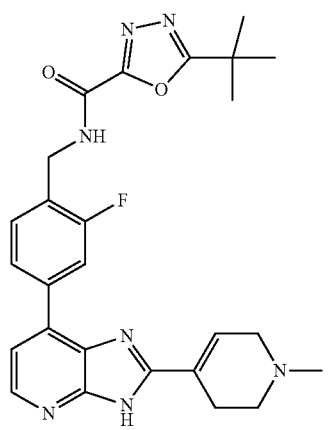 [SMILES: CN1CC=C(c2nc3c(-c4ccc(CNC(=O)c5nnc(C(C)(C)C)o5)c(F)c4)ccnc3[nH]2)CC1]
139
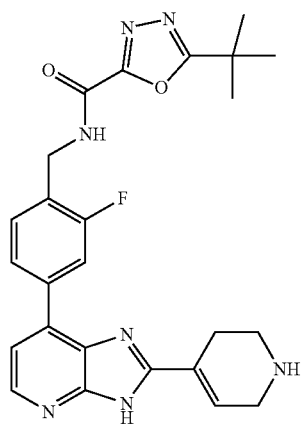 [SMILES: CC(C)(C)c1nnc(C(=O)NCc2ccc(-c3ccnc4[nH]c(C5=CCNCC5)nc34)cc2F)o1]
140

TABLE 1-continued
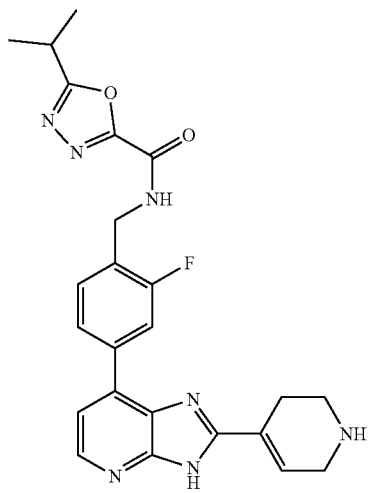 [SMILES: CC(C)c1nnc(C(=O)NCc2ccc(-c3ccnc4[nH]c(C5=CCNCC5)nc34)cc2F)o1]
142
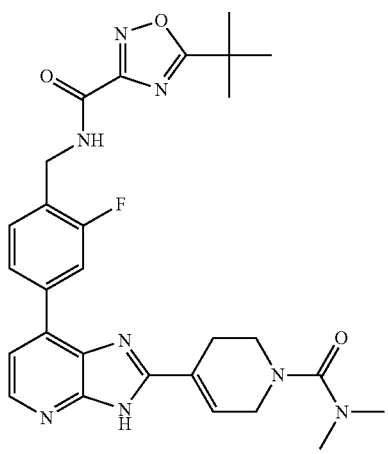 [SMILES: CN(C)C(=O)N1CC=C(c2nc3c(-c4ccc(CNC(=O)c5noc(C(C)(C)C)n5)c(F)c4)ccnc3[nH]2)CC1]
143
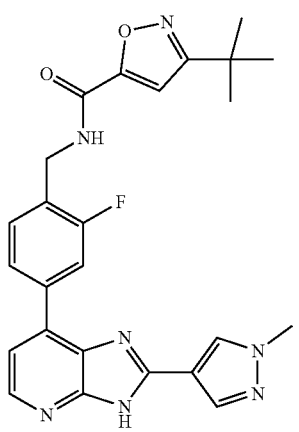 [SMILES: Cn1cc(-c2nc3c(-c4ccc(CNC(=O)c5cc(C(C)(C)C)no5)c(F)c4)ccnc3[nH]2)cn1]
144

TABLE 1-continued
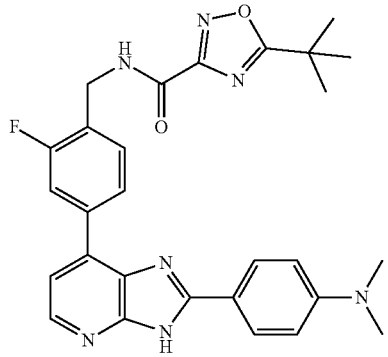
145
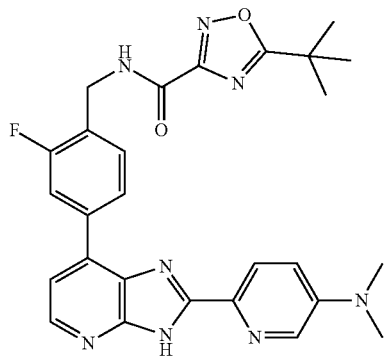 [SMILES: CN(C)c1ccc(-c2nc3c(-c4ccc(CNC(=O)c5noc(C(C)(C)C)n5)c(F)c4)ccnc3[nH]2)nc1]
146
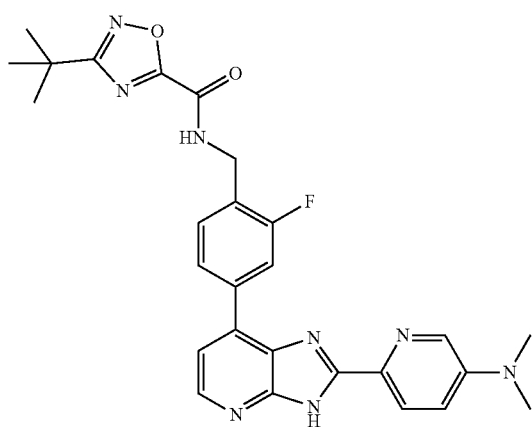 [SMILES: CN(C)c1ccc(-c2nc3c(-c4ccc(CNC(=O)c5nc(C(C)(C)C)no5)c(F)c4)ccnc3[nH]2)nc1]
148
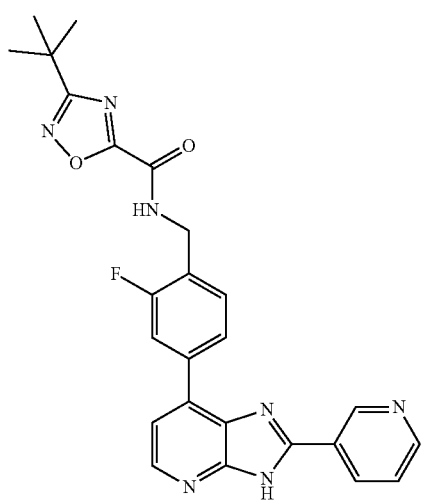 [SMILES: CC(C)(C)c1noc(C(=O)NCc2ccc(-c3ccnc4[nH]c(-c5cccnc5)nc34)cc2F)n1]
149

TABLE 1-continued
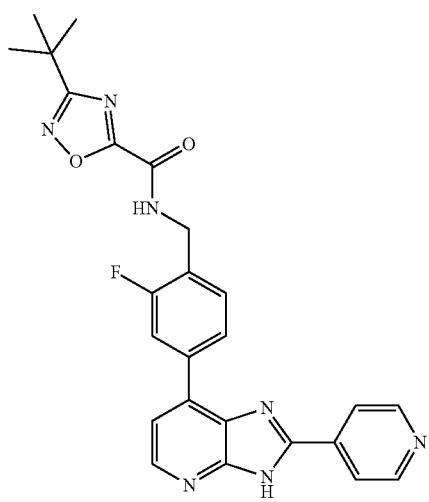 [SMILES: CC(C)(C)c1noc(C(=O)NCc2ccc(-c3ccnc4[nH]c(-c5ccncc5)nc34)cc2F)n1]
150
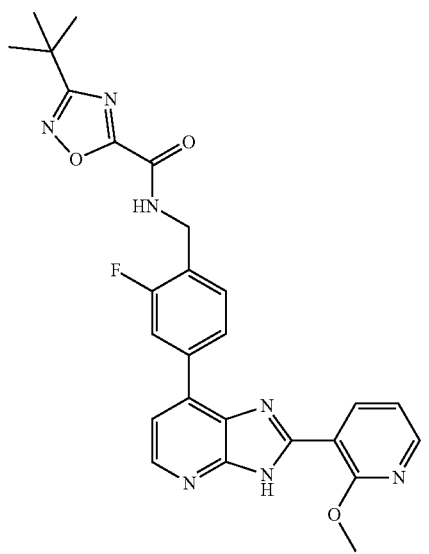 [SMILES: COc1ncccc1-c1nc2c(-c3ccc(CNC(=O)c4nc(C(C)(C)C)no4)c(F)c3)ccnc2[nH]1]
151
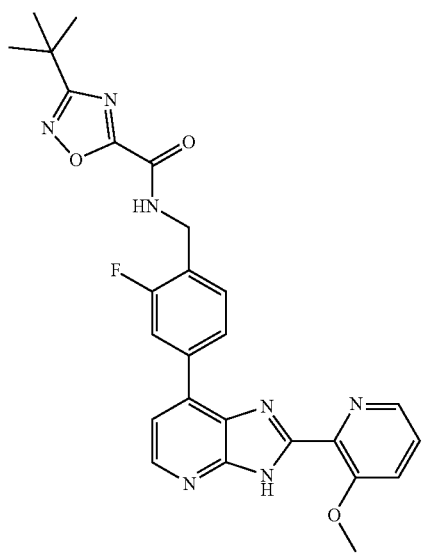 [SMILES: COc1cccnc1-c1nc2c(-c3ccc(CNC(=O)c4nc(C(C)(C)C)no4)c(F)c3)ccnc2[nH]1]
152

TABLE 1-continued
| | |
|---|---|
| 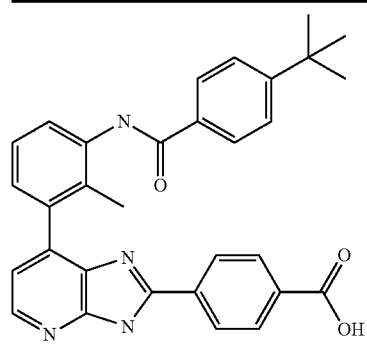 | 153 |
| 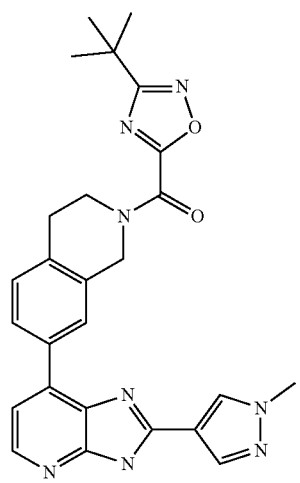 [SMILES: Cn1cc(-c2nc3c(-c4ccc5c(c4)CN(C(=O)c4nc(C(C)(C)C)no4)CC5)ccnc3[nH]2)cn1] | 155 |
| 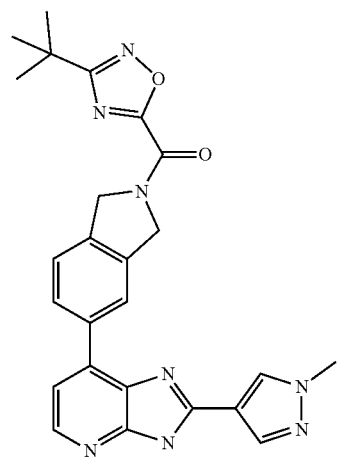 [SMILES: Cn1cc(-c2nc3c(-c4ccc5c(c4)CN(C(=O)c4nc(C(C)(C)C)no4)C5)ccnc3[nH]2)cn1] | 156 |
| 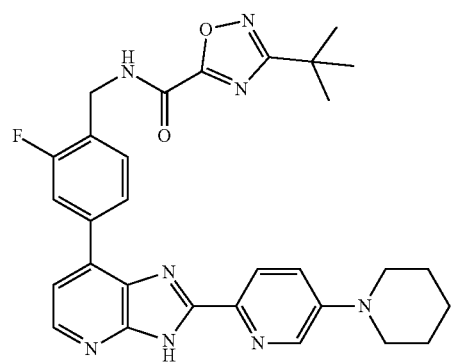 [SMILES: CC(C)(C)c1noc(C(=O)NCc2ccc(-c3ccnc4[nH]c(-c5ccc(N6CCCCC6)cn5)nc34)cc2F)n1] | 157 |

TABLE 1-continued
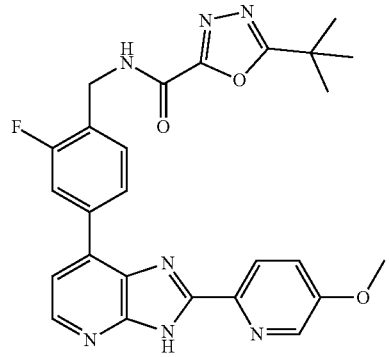 [SMILES: COc1ccc(-c2nc3c(-c4ccc(CNC(=O)c5nnc(C(C)(C)C)o5)c(F)c4)ccnc3[nH]2)nc1]
158
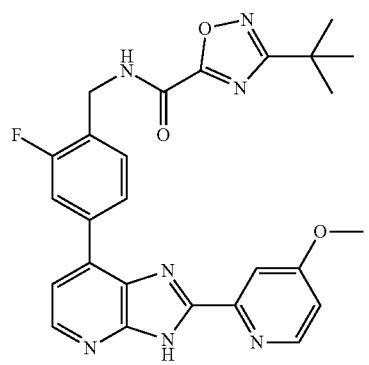 [SMILES: COc1ccnc(-c2nc3c(-c4ccc(CNC(=O)c5nc(C(C)(C)C)no5)c(F)c4)ccnc3[nH]2)c1]
159
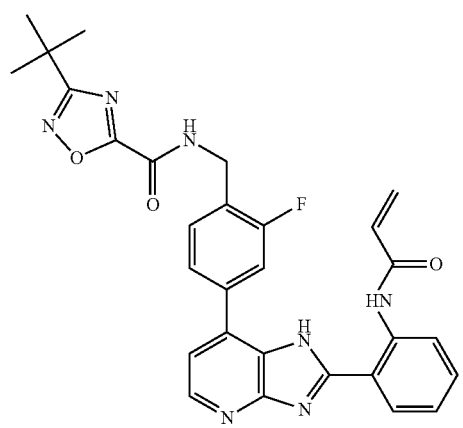 [SMILES: C=CC(=O)Nc1ccccc1-c1nc2nccc(-c3ccc(CNC(=O)c4nc(C(C)(C)C)no4)c(F)c3)c2[nH]1]
160
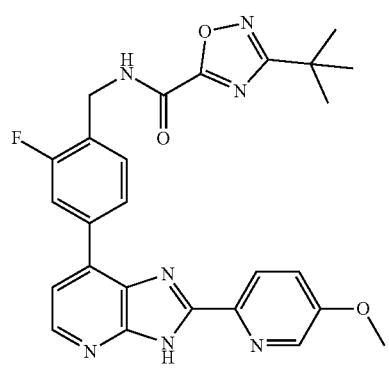 [SMILES: COc1ccc(-c2nc3c(-c4ccc(CNC(=O)c5nc(C(C)(C)C)no5)c(F)c4)ccnc3[nH]2)nc1]
161

TABLE 1-continued

| | |
|---|---|
| 162 | |
| 163 | |
| 164 | |
| 165 | |

TABLE 1-continued
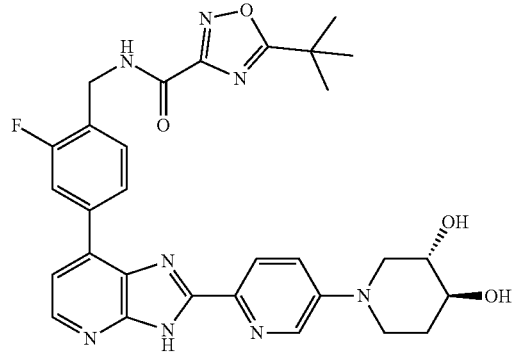 [SMILES: CC(C)(C)c1nc(C(=O)NCc2ccc(-c3ccnc4[nH]c(-c5ccc(N6CC[C@H](O)[C@@H](O)C6)cn5)nc34)cc2F)no1]
166
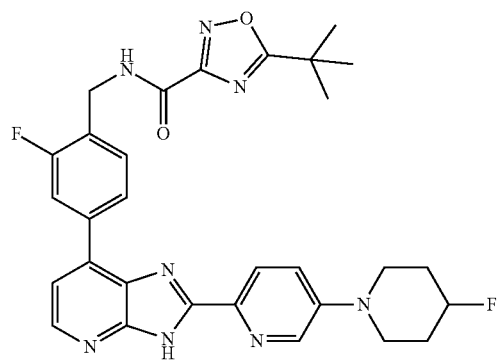 [SMILES: CC(C)(C)c1nc(C(=O)NCc2ccc(-c3ccnc4[nH]c(-c5ccc(N6CCC(F)CC6)cn5)nc34)cc2F)no1]
167
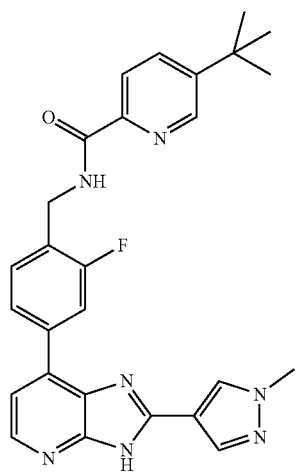 [SMILES: Cn1cc(-c2nc3c(-c4ccc(CNC(=O)c5ccc(C(C)(C)C)cn5)c(F)c4)ccnc3[nH]2)cn1]
168
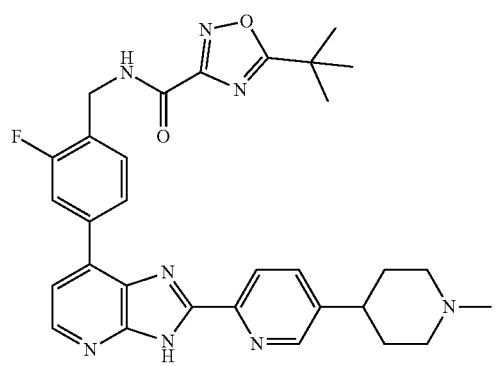 [SMILES: CN1CCC(c2ccc(-c3nc4c(-c5ccc(CNC(=O)c6noc(C(C)(C)C)n6)c(F)c5)ccnc4[nH]3)nc2)CC1]
169

TABLE 1-continued
170
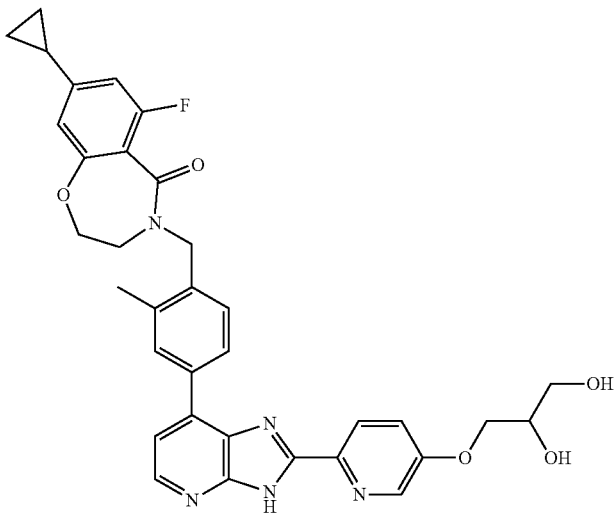 [SMILES: Cc1cc(-c2ccnc3[nH]c(-c4ccc(OCC(O)CO)cn4)nc23)ccc1CN1CCOc2cc(C3CC3)cc(F)c2C1=O]
171
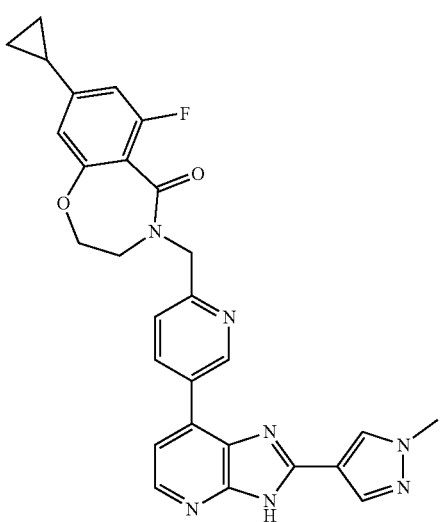 [SMILES: Cn1cc(-c2nc3c(-c4ccc(CN5CCOc6cc(C7CC7)cc(F)c6C5=O)nc4)ccnc3[nH]2)cn1]
172
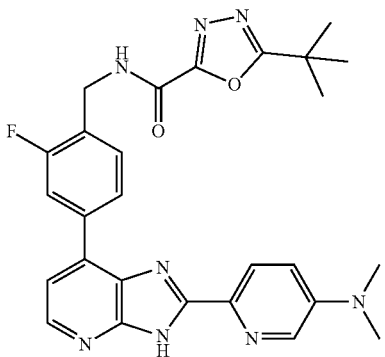 [SMILES: CN(C)c1ccc(-c2nc3c(-c4ccc(CNC(=O)c5nnc(C(C)(C)C)o5)c(F)c4)ccnc3[nH]2)nc1]

TABLE 1-continued
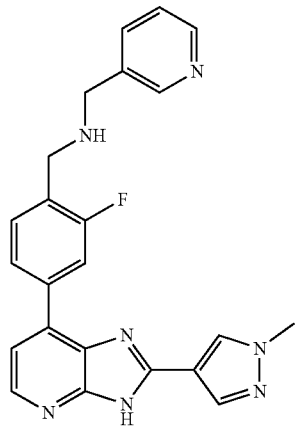 [SMILES: Cn1cc(-c2nc3c(-c4ccc(CNCc5cccnc5)c(F)c4)ccnc3[nH]2)cn1] 173
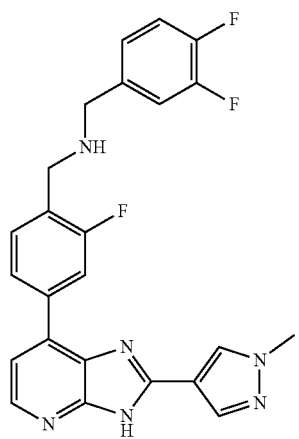 [SMILES: Cn1cc(-c2nc3c(-c4ccc(CNCc5ccc(F)c(F)c5)c(F)c4)ccnc3[nH]2)cn1] 174
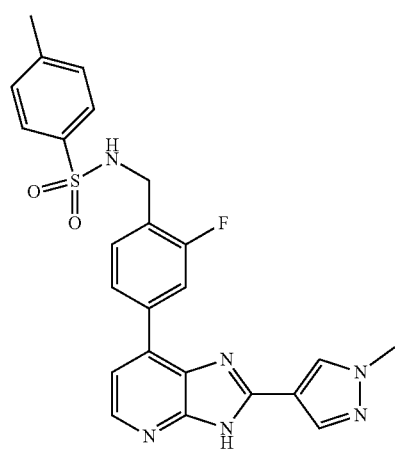 [SMILES: Cc1ccc(S(=O)(=O)NCc2ccc(-c3ccnc4[nH]c(-c5cnn(C)c5)nc34)cc2F)cc1] 175
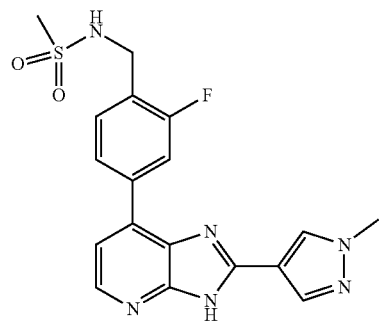 [SMILES: Cn1cc(-c2nc3c(-c4ccc(CNS(C)(=O)=O)c(F)c4)ccnc3[nH]2)cn1] 176

TABLE 1-continued
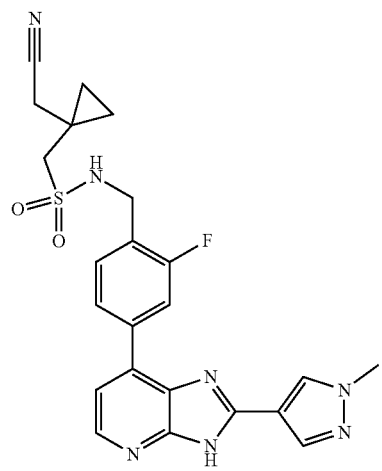 [SMILES: Cn1cc(-c2nc3c(-c4ccc(CNS(=O)(=O)CC5(CC#N)CC5)c(F)c4)ccnc3[nH]2)cn1]
177
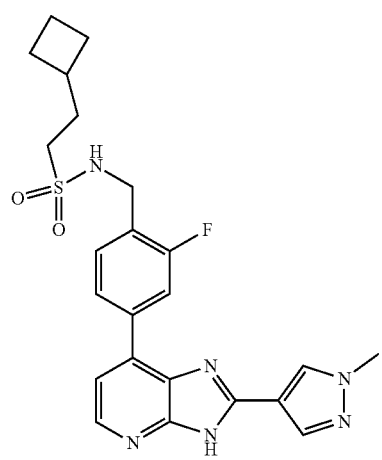 [SMILES: Cn1cc(-c2nc3c(-c4ccc(CNS(=O)(=O)CCC5CCC5)c(F)c4)ccnc3[nH]2)cn1]
178
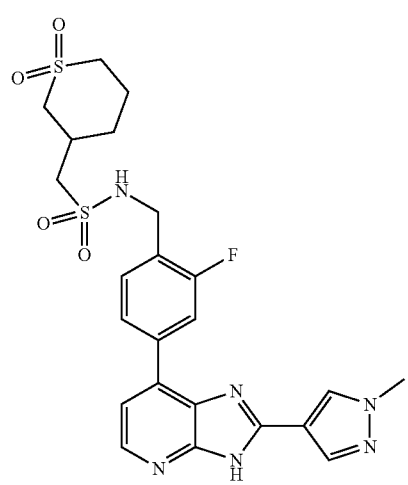 [SMILES: Cn1cc(-c2nc3c(-c4ccc(CNS(=O)(=O)CC5CCCS(=O)(=O)C5)c(F)c4)ccnc3[nH]2)cn1]
179

TABLE 1-continued
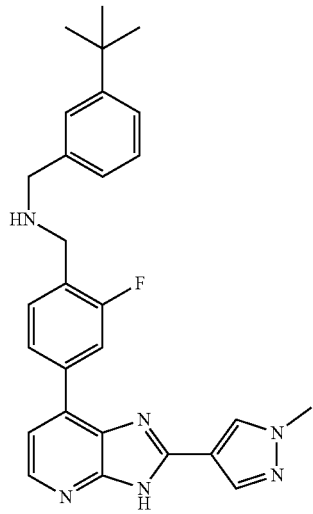 [SMILES: Cn1cc(-c2nc3c(-c4ccc(CNCc5cccc(C(C)(C)C)c5)c(F)c4)ccnc3[nH]2)cn1]
180
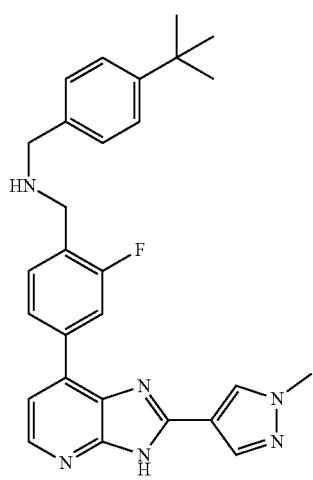 [SMILES: Cn1cc(-c2nc3c(-c4ccc(CNCc5ccc(C(C)(C)C)cc5)c(F)c4)ccnc3[nH]2)cn1]
181
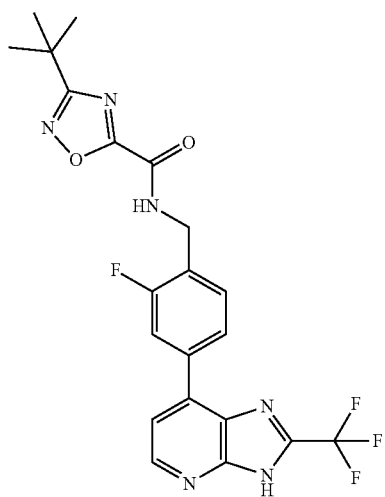 [SMILES: CC(C)(C)c1noc(C(=O)NCc2ccc(-c3ccnc4[nH]c(C(F)(F)F)nc34)cc2F)n1]
182

TABLE 1-continued
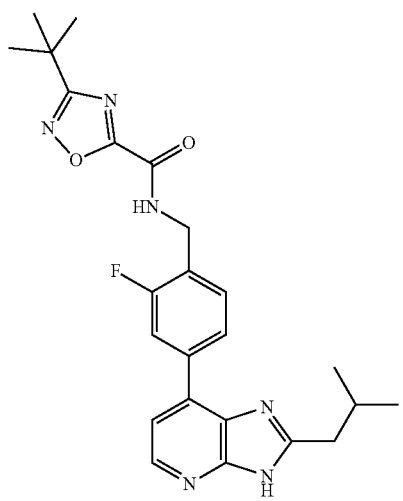 [SMILES: CC(C)Cc1nc2c(-c3ccc(CNC(=O)c4nc(C(C)(C)C)no4)c(F)c3)ccnc2[nH]1]
183
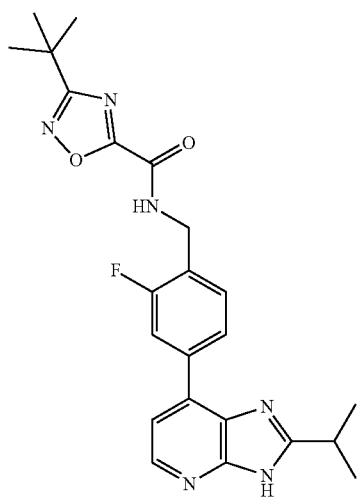 [SMILES: CC(C)c1nc2c(-c3ccc(CNC(=O)c4nc(C(C)(C)C)no4)c(F)c3)ccnc2[nH]1]
184
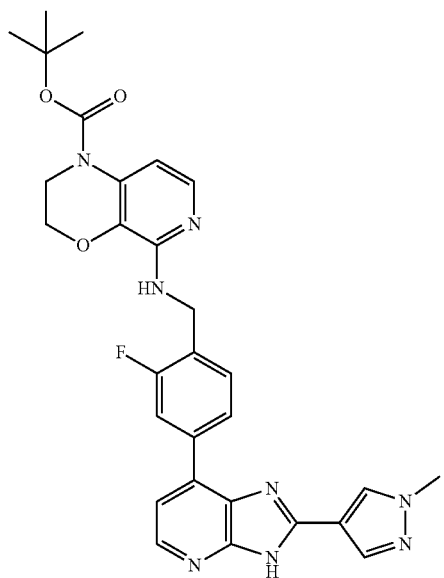 [SMILES: Cn1cc(-c2nc3c(-c4ccc(CNc5nccc6c5OCCN6C(=O)OC(C)(C)C)c(F)c4)ccnc3[nH]2)cn1]
185

TABLE 1-continued
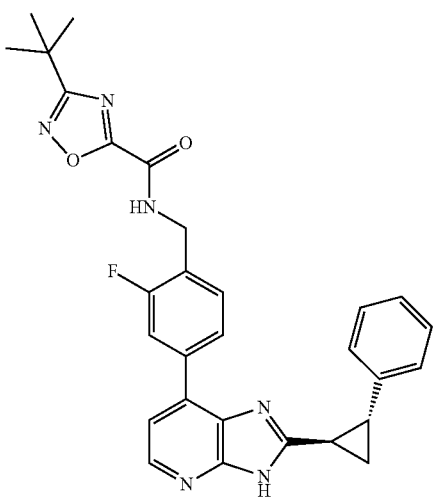 [SMILES: CC(C)(C)c1noc(C(=O)NCc2ccc(-c3ccnc4[nH]c([C@@H]5C[C@H]5c5ccccc5)nc34)cc2F)n1]
186
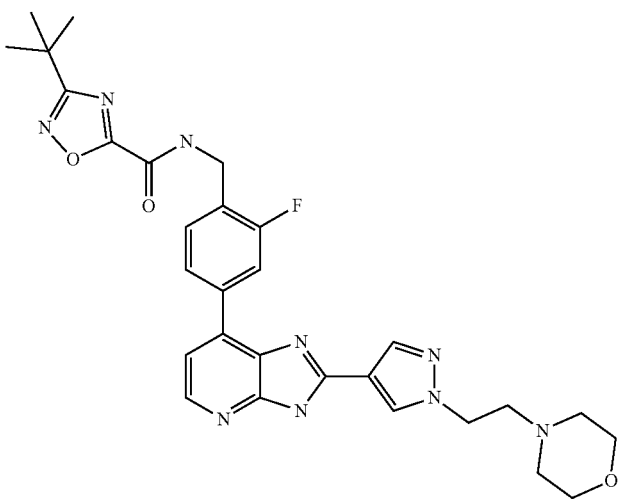 [SMILES: CC(C)(C)c1noc(C(=O)NCc2ccc(-c3ccnc4[nH]c(-c5cnn(CCN6CCOCC6)c5)nc34)cc2F)n1]
187
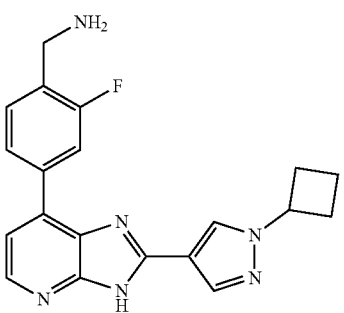 [SMILES: NCc1ccc(-c2ccnc3[nH]c(-c4cnn(C5CCC5)c4)nc23)cc1F]
188

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

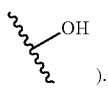

).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit BTK, or a mutant thereof, in a biological sample or in a patient. In certain embodiments, the amount of compound in compositions of this invention is such that is effective to measurably inhibit BTK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibiting BTK, or a mutant thereof, in a patient or in a biological sample comprising the step of administering to said patient or contacting said biological sample with a compound according to the invention.

In certain embodiments, the invention is directed to the use of compounds of the invention and/or physiologically acceptable salts thereof, for modulating or inhibiting a BTK enzyme. The term "modulation" denotes any change in BTK-mediated signal transduction, which is based on the action of the specific inventive compounds capable to interact with the BTK target in such a manner that makes recognition, binding and activating possible. The compounds are characterized by such a high affinity to BTK, which ensures a reliable binding of BTK. In certain embodiments, the substances are highly selective for BTK over most other kinases in order to guarantee an exclusive and directed recognition with the single BTK target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor (enzyme-inhibitor) interactions, and the like. Such association may also encompass the presence of other molecules such as peptides, proteins or nucleotide sequences. The present protein/ligand(enzyme-inhibitor)-interaction is characterized by high affinity, high selectivity and minimal or even lacking cross-reactivity to other target molecules to exclude unhealthy and harmful impacts to the treated subject.

In certain embodiments, the present invention relates to a method for inhibiting a BTK enzyme, with at least one compound of formula (I) according to the invention and/or physiologically acceptable salts thereof, under conditions such that said BTK enzyme is inhibited. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating a BTK enzyme is performed in-vitro. The prior teaching of the present specification concerning the compounds of formula (I), including any embodiments thereof, is valid and applicable without restrictions to the compounds according to formula (I) and their salts when used in the method for inhibiting BTK. The prior teaching of the present specification concerning the compounds of formula (I), including any embodiments thereof, is valid and applicable without restrictions to the compounds according to formula (I) and their salts when used in the method for inhibiting BTK.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc epsilon RI). BTK deficient murine mast cells have reduced degranulation and decreased production of proinflammatory cytokines following Fc epsilon RI cross-linking (Kawakami et al. Journal of Leukocyte Biology 65: 286-290).

Provided compounds are inhibitors of BTK and are therefore useful for treating one or more disorders associated with activity of BTK. Thus, in some embodiments, the present invention provides a method for treating a BTK-mediated disorder comprising the step of administering to a patient in need thereof a compound of the present invention, or pharmaceutically acceptable composition thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, systemic lupus erythematosus (SLE or lupus), lupus nephritis, vasculitis, idiopathic thrombocytopenic purpura (ITP), rheumatoid arthritis (RA), psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis (MS), systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome. Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, or vulvodynia. In certain embodiments, the disease or condition is systemic lupus erythematosus (SLE or lupus) or lupus nephritis. In certain embodiments, the disease or condition is RA. In certain embodiments, the disease or condition is MS.

In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method for treating or lessening the severity of one or more diseases and conditions associated with BTK, wherein the disease or condition is cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone. In certain embodiments, the cancer is colorectal cancer or pancreatic cancer.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder or cardiovascular disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. In certain embodiments, the present invention provides an anti-thrombotic agent because Btk is also involved in the activation of platelets.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease. In certain embodiments, the diabetes is type I diabetes.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma, Hodgkin's lymphoma, multiple myeloma, bone cancer, bone metastasis, osteoporosis, diabetes (e.g. type I diabetes), irritable bowel syndrome, Crohn's disease, lupus and renal transplant.

It is another object of the invention to provide a method for treating diseases that are caused, mediated and/or propagated by BTK activity, wherein at least one compound of formula (I) according to the invention and/or physiologically acceptable salts thereof is administered to a mammal in need of such treatment. In certain embodiments, the invention provides a method for treating lupus, wherein at least one compound of formula (I) according to the invention and/or physiologically acceptable salts thereof is administered to a mammal in need of such treatment. In certain embodiments, the compound is administered in an effective amount as defined above. In certain embodiments, the treatment is an oral administration.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit BTK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters: rabbits: horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing BTK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of BTK activity if expedient.

The invention also relates to the use of compounds according to formula (I) and/or physiologically acceptable salts thereof for the prophylactic or therapeutic treatment and/or monitoring of diseases that are caused, mediated and/or propagated by BTK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by BTK activity. In certain embodiments, the invention provides the use of a compound according to formula I or physiologically acceptable salts thereof, for the production of a medicament for the prophylactic or therapeutic treatment of a BTK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by BTK activity. Another preferred object of the invention concerns compounds of formula (I) according to the invention and/or physiologically acceptable salts thereof for use in the prophylactic or therapeutic treatment and/or monitoring of lupus. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of lupus.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with BTK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with BTK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib dnd/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; portimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumabt[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

[1] Prop. INN (Proposed International Nonproprietary Name);
[2] Rec. INN (Recommended International Nonproprietary Names);
[3] USAN (United States Adopted Name);
[4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder: the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting BTK activity in a biological sample comprising the step of contacting said biological sample with a compound of this invention, or a composition comprising said compound.

According to another embodiment, the invention relates to a method of inhibiting BTK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of BTK, including the evaluation of the many factors thought to influence, and be influenced by, the production of BTK and the interaction of BTK. The present compounds are also useful in the development of other compounds that interact with BTK since the present compounds provide important structure-activity relationship (SAR) information that facilitate that development. Compounds of the present invention that bind to BTK can be used as reagents for detecting BTK in living cells, fixed cells, in biological fluids, in tissue homogenates, in purified, natural biological materials, etc. For example, by labeling such compounds, one can identify cells expressing BTK. In addition, based on their ability to bind BTK, compounds of the present invention can be used in in-situ staining, FACS (fluorescence-activated cell sorting), sodium dodecyl sulfate polyacrylamide gel electrophoresis (SDS-PAGE). ELISA (enzyme-linked immunoadsorptive assay), etc., enzyme purification, or in purifying cells expressing BTK inside permeabilized cells. The compounds of the invention can also be utilized as commercial research reagents for various medical research and diagnostic uses. Such uses can include but are not limited to: use as a calibration standard for quantifying the activities of candidate BTK inhibitors in a variety of functional assays; use as blocking reagents in random compound screening, i.e. in looking for new families of BTK ligands, the compounds can be used to block recovery of the presently claimed BTK compounds; use in the co-crystallization with BTK enzyme, i.e. the compounds of the present invention will allow formation of crystals of the compound bound to BTK, enabling the determination of enzyme/compound structure by x-ray crystallography; other research and diagnostic applications, wherein BTK is preferably activated or such activation is conveniently calibrated against a known quantity of an BTKinhibitor, etc.; use in assays as probes for determining the expression of BTK in cells; and developing assays for detecting compounds which bind to the same site as the BTK binding ligands.

The compounds of the invention can be applied either themselves and/or in combination with physical measurements for diagnostics of treatment effectiveness. Pharmaceutical compositions containing said compounds and the use of said compounds to treat BTK-mediated conditions is a promising, novel approach for a broad spectrum of therapies causing a direct and immediate improvement in the state of health, whether in human or animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of BTK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds were prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Compound numbers utilized in the Examples below correspond to compound numbers set forth supra.

| | |
|---|---|
| ACN | acetonitrile |
| Aq. | Aqueous |
| BBFO | Broad band fluorine observation |
| BCR | B cell receptor |
| Boc | tert-butyloxycarbonyl |
| BrettPhos | 2-(Dicyclohexylphosphino)3,6-dimethoxy-2',4',6'-triisopropyl-1,1'-biphenyl |
| BTK | Bruton's tyrosine kinaes |
| C | cysteine |
| CN | nitrile |
| CV | column volume |
| Cy | cyclohexyl |
| δ | chemical shift |
| d | deuterium or doublet |
| dd | doublet of doublets |
| DCM | dichloromethane |
| DIEA, DIPEA | diIsopropylethylamine |
| DME | Dimethoxyethane |
| DMF | dimethylformamide |
| DMSO | dimethylsulfoxide |
| dppf | 1,1'-bis(diphenylphosphino)ferrocene |
| DTT | Dithiothreitol |
| ELISA | enzyme-linked immunosorbent assay |
| eq. | equivalent |
| ES | electrospray |
| Fc | fragment crystallizable |
| FITC | Fluorescein isothiocyanate |
| g | gas |
| h, hr | hour |
| $^1$H | proton |

| | |
|---|---|
| HAUT | N-[(Dimethylamino)-1H-1,2,3-triazolo-[4,5-b]pyridin-1-ylmethylene]-N-methylmethanaminium hexafluorophosphate N-oxide |
| HEPES | (4-(2-hydroxyethyl)-1-piperazineethanesulfonic acid |
| HOAt | 1-Hydroxy-7-azabenzotriazole |
| HPLC | high pressure liquid chromatography |
| $IC_{50}$ | half maximal inhibitory concentration |
| IL-1β | interleukin-1 beta |
| IR | infrared |
| J | coupling constant |
| K | kelvin |
| LC | liquid chromatography |
| LCK | lymphocyte-specific protein tyrosine kinase |
| LC-MS | Liquid chromatography coupled to mass spectrometry |
| LPS | lipopolysaccharide |
| m | Multiplet or meta |
| M | molecular ion |
| Me | methyl |
| MHz | Megahertz |
| min | minute |
| mL | milliliter |
| MS | mass spectrometry |
| m/z | mass-to-charge ratio |
| N | Normality (equivalent per liter) |
| NMM | N-methyl morpholine |
| NMR | nuclear magnetic resonance |
| ODS | octadecylsilyl |
| p | para |
| PBMC | Peripheral blood mononuclear cell |
| PBS | Phosphate buffered saline |
| Pet | petroleum |
| Ph | phenyl |
| PMA | phorbol myristate acetate |
| ppm | Parts per million |
| PSI | Pounds per square inch |
| PyBOP | (Benzotriazol-1-yloxy)tripyrrolidinophosphonium hexafluorophosphate |
| PyBroP | Bromotripyrrolidinophosphonium hexafluorophosphate |
| RBF | Round Bottom Flask |
| rpm | Revolutions per minute |
| RT | room temperature |
| RuPhos | 2-dicyclohexylphosphino-2',6'-diisopropoxybiphenyl |
| s | singlet |
| S | serine |
| Super-Hydride | lithium triethylborohydride |
| T3P | Propylphosphonic anhydride solution |
| TEA | triethylamine |
| TFA | trifluoroacetic acid |
| THF | tetrhydrofuran |
| TLC | thin layer chromatography |
| TSA | toluenesulfonic acid |
| TsOH | p-toluenesulfonic acid |
| UFLC | ultra fast liquid chromatography |
| URL | uniform resource locator |
| UV | ultraviolet |
| V | Volume |
| VT | Variable temperature |

General Conditions and Analytical Methods

All solvents used were commercially available and were used without further purification. Reactions were typically run using anhydrous solvents under an inert atmosphere of nitrogen unless otherwise noted.

NMR experiments were recorded on a Bruker Mercury Plus 400 NMR Spectrometer equipped with a Bruker 400 BBFO probe, or a Bruker Avance III 400 MHz. Deuterated solvents typically contained 0.03% to 0.05% v/v tetramethylsilane, which was used as the reference signal (set at δ 0.00 for both $^1$H and $^{13}$C). Chemical shifts (δ) are reported in ppm. Coupling constants are in units of Hertz (Hz). Splitting patterns describe apparent multiplicities and are designated as s (singlet), d (doublet), t (triplet), q (quartet), m (multiplet), or br (broad).

For examples 1-4 and examples 33-96, LC-MS analyses were performed on a SHIMADZU LC-MS machine consisting of an UFLC 20-AD system and LC-MS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in ACN) over 2.2 min with a total run time of 3.6 min. The column temperature was at 40° C. with the flow rate at 1.0 mL/min. The Diode Array Detector was scanned from 200-400 nm. The mass spectrometer was equipped with an electrospray ion source (ES) operated in a positive or negative mode. The mass spectrometer was scanned between m/z 90-900 with a scan time of 0.6 s.

For example 5. LC-MS analyses were performed using an XBridge C8 (50×4.6 mm, 3.5 μm) in positive mode. A gradient was applied, using buffer A (0.1% TFA in $H_2O$) and buffer B (0.1% TFA in acetonitrile) at a flow rate of 2.0 mL/min. HPLC was performed using the same conditions.

For all other examples, LC-MS spectra were obtained on Agilent 1200 Series mass spectrometers from Agilent technologies, using either Atmospheric Chemical Ionization (APCI) or Electrospray Ionization (ESI). Column: XBridge C8, 3.5 μm, 4.6×50 mm; Solvent A: water+0.1% TFA; Solvent B: CAN; Flow: 2 ml/min; Gradient: 0 min: 5% B, 8 min: 100% B, 8.1 min: 100% B, 8.5 min: 5% B, 10 min 5% B. HPLC data were obtained using Agilent 1100 series HPLC from Agilent technologies using XBridge column (C8, 3.5 μm, 4.6×50 mm). Mobile Phase A: water+0.1% TFA; Mobile Phase B: ACN; Flow: 2 ml/min; Gradient: 0 min: 5% Mobile Phase B, 8 min: 100% Mobile Phase B, 8.1 min: 100% Mobile Phase B, 8.5 min: 5% Mobile Phase B, 10 min 5% Mobile Phase B.

The microwave reactions were conducted using Biotage Initiator Microwave Synthesizer using standard protocols that are known in the art.

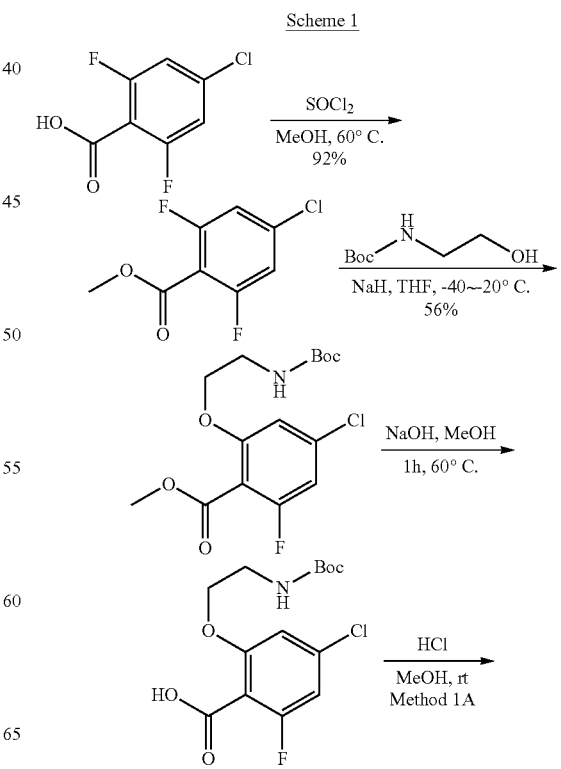

Scheme 1

-continued

-continued

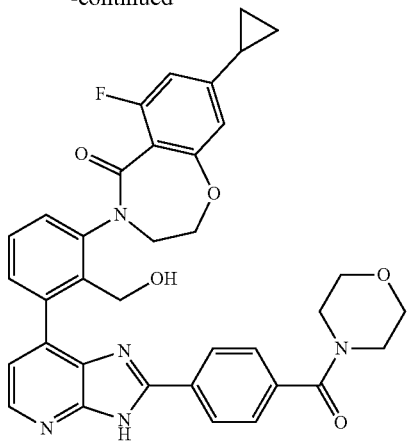

Example 1. 8-Cyclopropyl-6-fluoro-4-[2-(hydroxymethyl)-3-(2-[4-[(morpholin-4-yl)carbonyl]phenyl]-3H-imidazo [4,5-b]pyridin-7-yl)phenyl]-2,3,4,5-tetrahydro-1,4-benzoxazepin-5-one (1)

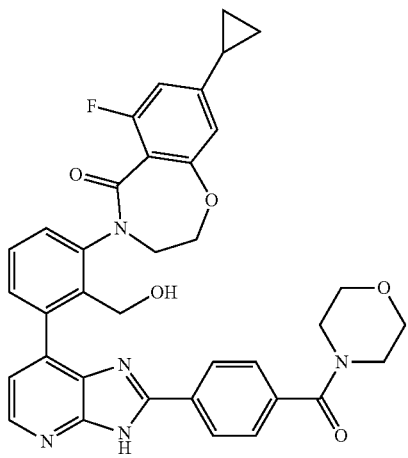 [SMILES: O=C(c1ccc(-c2nc3c(-c4cccc(N5CCOc6cc(C7CC7)cc(F)c6C5=O)c4CO)ccnc3[nH]2)cc1)N1CCOCC1]

Methyl 4-chloro-2,6-difluorobenzoate

In a 500-mL round bottom flask with magnetic stir bar, 4-chloro-2,6-difluorobenzoic acid (5.0 g, 25.97 mmol, 1.0 equiv) was dissolved in thionyl chloride (15.45 g, 129.84 mmol, 5.00 equiv) at room temperature. The resulting solution was stirred for 1 h at 60° C. After the reaction was done, the reaction mixture was concentrated under reduced pressure to give the acid chloride intermediate, which was then dissolved in DCM (10 mL). The prepared acid chloride solution was then added dropwise to methanol (100 mL) at 0° C. The resulting solution was stirred for another 30 min at room temperature. After the reaction was done, the reaction mixture was concentrated under reduced pressure to give methyl 4-chloro-2,6-difluorobenzoate (5 g, 92%) as yellow oil.

Methyl 2-(2-[[(tert-butoxy)carbonyl]amino]ethoxy)-4-chloro-6-fluorobenzoate

In a 100-mL round bottom flask with magnetic stir bar, tert-butyl N-(2-hydroxyethyl)carbamate (4.68 g, 29.04 mmol, 1.20 equiv) was dissolved in tetrahydrofuran (50 mL), to which was added sodium hydride (1.26 g, 31.46 mmol, 60%, 1.30 equiv) in portions at −40° C. The resulting suspension was stirred for 10 min and was added by methyl 4-chloro-2,6-difluorobenzoate (5.0 g, 24.2 mmol, 1.0 equiv) at −40° C. The reaction mixture was stirred for 30 min at −40° C., then slowly warmed up to −20° C. over 1 h period while stirring. When the reaction was done, it was quenched by the addition of 100 mL sat.NH$_4$Cl solution and the mixture was extracted with ethyl acetate (3×150 mL). The organic layers were combined, dried over sodium sulfate and concentrated under reduced pressure. The residue was purified in a silica gel column eluting with ethyl acetate in petroleum ether (1% to 10% gradient) to afford methyl 2-(2-[[(tert-butoxy)carbonyl]amino] ethoxy)-4-chloro-6-fluorobenzoate (5 g, 56%) as yellow oil. MS: m/z=248.0 [M+H−100]$^+$.

2-(2-[[(tert-Butoxy)carbonyl]amino]ethoxy)-4-chloro-6-fluorobenzoic acid

In a 250-mL round bottom flask with magnetic stir bar, methyl 2-(2-[[(tert-butoxy)carbonyl]amino]ethoxy)-4-chloro-6-fluorobenzoate (5.00 g, 14.38 mmol, 1.00 equiv) was dissolved in a mixture of methanol (50 mL) and water (30 mL) at room temperature. Then sodium hydroxide (2.88 g, 72.00 mmol, 5.01 equiv) was added slowly. The resulting solution was stirred for 1 h at 60° C. After the reaction was done, the reaction mixture was concentrated under reduced pressure. The pH value of the remaining solution was adjusted to 4 using citric acid solution (10% w/w) and the mixture was extracted with ethyl acetate (3×100 mL). The organic layers were combined, dried over sodium sulfate and concentrated under reduced pressure to afford 2-(2-[[(tert-butoxy)carbonyl]amino]ethoxy)-4-chloro-6-fluorobenzoic acid (4.3 g, crude) as yellow oil.

Method 1A:
8-Bromo-4-chloro-7-methylquinoline-3-carboxamide

In a 100-mL round bottom flask with magnetic stir bar, 2-(2-[[(tert-butoxy)carbonyl]amino]ethoxy)-4-chloro-6-fluorobenzoic acid (2 g, 5.99 mmol, 1.00 equiv) was dissolved in a solution of HCl in methanol (4N, 30 mL) at room temperature. The resulting mixture was stirred for 2 h at room temperature. After the reaction was done, the reaction mixture was concentrated under reduced pressure to afford 2-(2-aminoethoxy)-4-chloro-6-fluorobenzoic acid (1.6 g, crude) as white solid.

8-Chloro-6-fluoro-2,3,4,5-tetrahydro-1,4-benzoxazepin-5-one

In a 100-mL round bottom flask with magnetic stir bar. HATU (7.81 g, 20.55 mmol, 1.50 equiv) and NMM (3.88 g, 38.35 mmol, 2.80 equiv) were added to a solution of 2-(2-aminoethoxy)-4-chloro-6-fluorobenzoic acid (3.20 g, 13.70 mmol, 1.00 equiv) in N,N-dimethylformamide (50 mL) at room temperature. The resulting solution was stirred for 3 h at room temperature. After the reaction was done, the reaction mixture was concentrated under reduced pressure and the residue was purified in a silica gel column eluting with methanol in dichloromethane (1% to 10% gradient) to afford 8-chloro-6-fluoro-2,3,4,5-tetrahydro-1,4-benzoxazepin-5-one (2.3 g, 46% for three steps) as off-white solid. MS: m/z=216.0 [M+H]$^+$.

8-Cyclopropyl-6-fluoro-2,3,4,5-tetrahydro-1,4-benzoxazepin-5-one

In a 100-mL round bottom flask purged and maintained with an inert atmosphere of nitrogen, 8-chloro-6-fluoro-2,3,4,5-tetrahydro-1,4-benzoxazepin-5-one (3.4 g, 15.77 mmol, 1.00 equiv), cyclopropylboronic acid (4.06 g, 47.31 mmol, 3.00 equiv), PCy$_3$.HBF$_4$ (2.32 g, 6.31 mmol, 0.40 equiv), Pd(OAc)$_2$ (708 mg, 3.15 mmol, 0.20 equiv) and K$_3$PO$_4$ (10.04 g, 47.31 mmol, 3.00 equiv) were mixed in a mixture of toluene and water (10:1, 55 mL) at room temperature. The resulting mixture was stirred for 12 h at 90° C. After the reaction was done, the reaction mixture was diluted with water (50 mL) and extracted with ethyl acetate (3×150 mL). The organic layers were combined, dried over sodium sulfate and concentrated under reduced pressure. The residue was purified in a silica gel column eluting with ethyl acetate in petroleum ether (5% to 50% gradient) to afford 8-cyclopropyl-6-fluoro-2,3,4,5-tetrahydro-1,4-benzoxazepin-5-one (3.2 g, 87%) as yellow solid. MS: m/z=222.0 [M+H]$^+$.

Method 1B: 2-Bromo-6-(8-cyclopropyl-6-fluoro-5-oxo-2,3,4,5-tetrahydro-1,4-benzoxazepin-4-yl)benzaldehyde In a 100-mL round bottom flask purged and maintained with an inert atmosphere of nitrogen, 8-cyclopropyl-6-fluoro-2,3,4,5-tetrahydro-1,4-benzoxazepin-5-one (3.1 g, 14.01 mmol, 1.00 equiv), 2,6-dibromobenzaldehyde (11.11 g, 42.10 mmol, 3.00 equiv), CuI (533.2 mg, 2.80 mmol, 0.20 equiv), potassium carbonate (3.85 g, 27.86 mmol, 1.99 equiv) were mixed in N,N-dimethylformamide (30 mL) at room temperature. The resulting mixture was stirred for 12 h at 110° C. After cooling to RT, the reaction mixture was diluted with 100 mL H$_2$O and extracted with ethyl acetate (3×200 ml). The organic layers were combined and concentrated under reduced pressure. The residue was purified in a silica gel column eluting with ethyl acetate in petroleum ether (5% to 60% gradient) to afford 2-bromo-6-(8-cyclopropyl-6-fluoro-5-oxo-2,3,4,5-tetrahydro-1,4-benzoxazepin-4-yl)benzaldehyde (2 g 0.35%) as yellow solid. MS: m/z=404.0 [M+H]$^+$.

Method 1C: 4-[3-Bromo-2-(hydroxymethyl)phenyl]-8-cyclopropyl-6-fluoro-2,3,4,5-tetrahydro-1,4-benzoxazepin-5-one In a 100-mL round bottom flask with magnetic stir bar, to solution of 2-bromo-6-(8-cyclopropyl-6-fluoro-5-oxo-2,3,4,5-tetrahydro-1,4-benzoxazepin-4-yl)benzaldehyde (2 g, 4.95 mmol, 1.00 equiv) in tetrahydrofuran (30 mL) was added lithium triethylborohydride (1.58 g, 14.91 mmol, 3.01 equiv) in portions at room temperature. The resulting solution was stirred for 40 min at room temperature. When the reaction was done, it was quenched by 20 mL H$_2$O and the mixture was extracted with ethyl acetate (3×50 mL). The organic layers were combined, dried over sodium sulfate and concentrated under reduced pressure. The residue was purified in a silica gel column eluting with ethyl acetate in petroleum ether (5% to 60% gradient) to afford 4-[3-bromo-2-(hydroxymethyl)phenyl]-8-cyclopropyl-6-fluoro-2,3,4,5-tetrahydro-1,4-benzoxazepin-5-one (1.7 g, 85%) as yellow solid. MS: m/z=406.0 [M+H]$^+$.

Method 1D: [2-Bromo-6-(8-cyclopropyl-6-fluoro-5-oxo-2,3,4,5-tetrahydro-1,4-benzoxazepin-4-yl)phenyl]methyl acetate In a 100-mL round bottom flask with magnetic stir bar, 4-[3-bromo-2-(hydroxymethyl)phenyl]-8-cyclopropyl-6-fluoro-2,3,4,5-tetrahydro-1,4-benzoxazepin-5-one (1.7 g, 4.01 mmol, 1.00 equiv) and TEA (1.27 g, 12.54 mmol, 3.00 equiv) were dissolved in dichloromethane (20 mL) at room temperature. The mixture was cooled to 0° C. and was added by acetyl chloride (986 mg, 12.56 mmol, 3.00 equiv) dropwise. The resulting solution was then stirred for 3 h at room temperature. After the reaction was done, the reaction mixture was diluted with 20 mL H$_2$O and extracted with ethyl acetate (3×50 mL). The organic layers were combined and concentrated under reduced pressure to afford [2-bromo-6-(8-cyclopropyl-6-fluoro-5-oxo-2,3,4,5-tetrahydro-1,4-benzoxazepin-4-yl)phenyl]methyl acetate (1.67 g, 93%) as yellow solid. MS: m/z=447.9 [M+H]$^+$

Method 1E: [2-(8-Cyclopropyl-6-fluoro-5-oxo-2,345-tetrahydro-4-benzoxazepin-4-yl)-6-(tetramethyl-1,3,2-dioxaborolan-2-yl)phenyl]methyl acetate In a 30-mL sealed tube purged and maintained with an inert atmosphere of argon, [2-bromo-6-(8-cyclopropyl-6-fluoro-5-oxo-2,3,4,5-tetrahydro-1,4-benzoxazepin-4-yl)phenyl]methyl acetate (1.67 g, 3.57 mmol, 1.00 equiv), KOAc (733 mg, 7.47 mmol, 2.00 equiv), 4,4,5,5-tetramethyl-2-(tetramethyl-1,3,2-dioxaborolan-2-yl)-1,3,2-dioxaborolane (1.14 g, 4.49 mmol, 1.21 equiv), Pd(dppf)Cl$_2$.CH$_2$Cl$_2$ (305.6 mg, 0.37 mmol, 0.10 equiv) were mixed in DMSO (10 mL) at room temperature. The resulting mixture was stirred for 5 h at 100° C. After the reaction was done, the reaction mixture was diluted with 30 mL water and extracted with ethyl acetate (3×100 mL). The organic layers were combined, dried over sodium sulfate and concentrated under reduced pressure. The residue was purified in a silica gel column eluting with methanol in dichloromethane (1% to 6% gradient) to afford [2-(8-cyclopropyl-6-fluoro-5-oxo-2,3,4,5-tetrahydro-1,4-benzoxazepin-4-yl)-6-(tetramethyl-1,3,2-dioxaborolan-2-yl)phenyl]methyl acetate (2 g, crude) as yellow solid.

Method 1F: [2-(2-Amino-3-nitropyridin-4-yl)-6-(8-cyclopropyl-6-fluoro-5-oxo-2,3,4,5-tetrahydro-1,4-benzoxazepin-4-yl)phenyl]methyl acetate In a 100-mL round bottom flask purged and maintained with an inert atmosphere of nitrogen, [2-(8-cyclopropyl-6-fluoro-5-oxo-2,3,4,5-tetrahydro-1,4-benzoxazepin-4-yl)-6-(tetramethyl-1,3,2-dioxaborolan-2-yl)phenyl]methyl acetate (2 g, 2.58 mmol, 1.00 equiv) 4-chloro-3-nitropyridin-2-amine (773.3 mg, 4.46 mmol, 1.72 equiv), Pd(PPh$_3$)$_2$Cl$_2$ (283.6 mg, 0.40 mmol, 0.16 equiv) and sodium carbonate (856.5 mg, 8.08 mmol, 3.13 equiv) were mixed in a mixture of ethylene glycol dimethyl ether and water (5:1, 25 mL) at room temperature. The resulting solution was stirred for 1 h at 80° C. After the reaction was done, the reaction mixture was diluted with 30 mL water and extracted with ethyl acetate (3×100 mL). The organic layers were combined, dried over sodium sulfate and concentrated under reduced pressure. The residue was purified in a silica gel column eluting with methanol in dichloromethane (1% to 6% gradient) to afford [2-(2-amino-3-nitropyridin-4-yl)-6-(8-cyclopropyl-6-fluoro-5-oxo-2,3,4,5-tetrahydro-1,4-benzoxazepin-4-yl)phenyl]methyl acetate (900 mg, 47.6% for two steps) as yellow solid. MS: m/z=529.4 [M+Na]$^+$

Method 1G: [2-(8-Cyclopropyl-6-fluoro-5-oxo-2,3,4,5-tetrahydro-1,4-benzoxazepin-4-yl)-6-(2,3-diaminopyridin-4-yl)phenyl]methyl acetate In a 100-mL round bottom flask, [2-(2-amino-3-nitropyridin-4-yl)-6-(8-cyclopropyl-6-fluoro-5-oxo-2,3,4,5-tetrahydro-1,4-benzoxazepin-4-yl)phenyl]methyl acetate (500 mg, 0.98 mmol, 1.00 equiv) was dissolved in methanol (50 mL) at room temperature. Then palladium carbon (10%, 100 mg, 0.0089 mmol, 0.1 equiv) was added under nitrogen atmosphere. The reaction flask was vacuumed and flushed with hydrogen and the mixture was hydrogenated at room temperature for 3 hours under hydrogen atmosphere using a hydrogen balloon. After the reaction was done, the reaction mixture was filtered through a celite pad and the filtrate was concentrated under reduced pressure to afford [2-(8-cyclopropyl-6-fluoro-5-oxo-2,3,4,5-tetrahydro-1,4-benzoxazepin-4-yl)-6-(2,3-diaminopyridin-4-yl)phenyl]methyl acetate (470 mg, 100%) as yellow solid. MS: m/z=477.1 [M+H]$^+$.

4-[(Morpholin-4-yl)carbonyl]benzaldehyde

In a 250-mL round bottom flask, 4-formylbenzoic acid (1.50 g, 9.99 mmol, 1.00 equiv), 3H-[1,2,3]triazolo[4,5-b]pyridin-3-ol (1.49 g, 10.99 mmol, 1.10 equiv) and HATU (4.56 g, 11.99 mmol, 1.20 equiv) were mixed in dichloromethane (140 mL), to which were added DIEA (3.87 g, 29.9 mmol, 3.00 equiv) and morpholine (1.09 g, 12.5 mmol, 1.25 equiv) at room temperature. The resulting solution was stirred for 16 h at room temperature. After the reaction was done, the reaction mixture was concentrated under reduced pressure. The residue was purified in a silica gel column eluting with ethyl acetate in petroleum ether (5% to 3% gradient) to afford 4-[(morpholin-4-yl)carbonyl]benzaldehyde (1.5 g, 68%) as colorless oil. MS: m/z=477.1 [M+H]$^+$ Method 1H: [2-(8-Cyclopropyl-6-fluoro-5-oxo-2,3,4,5-tetrahydro-1,4-benzoxazepin-4-yl)-6-(2-[4-[(morpholin-4-yl)carbonyl]phenyl]-3H-imidazo[4,5-b]pyridin-7-yl)phenyl]methyl Acetate In a 8-mL vial purged and maintained with an inert atmosphere of nitrogen, [2-(8-cyclopropyl-6-fluoro-5-oxo-2,3,4,5-tetrahydro-1,4-benzoxazepin-4-yl)-6-(2,3-diaminopyridin-4-yl)phenyl]methyl acetate (200 mg, 0.42 mmol, 1.00 equiv) was dissolved in 5 mL N,N-dimethylformamide, to which were added 4-[(morpholin-4-yl)carbonyl]benzaldehyde (110.4 mg, 0.50 mmol, 1.20 equiv) and pTSA (93.9 mg, 0.55 mmol, 1.30 equiv) at room temperature. The resulting solution was stirred for 4 h at 80° C. After the reaction was done, the reaction mixture was concentrated under reduced pressure. The residue was purified by reverse flash chromatography with the following conditions: column, C18 silica gel; mobile phase, MeOH in water, 10% to 50% gradient in 10 min; detector, UV 254 nm. [2-(8-cyclopropyl-6-fluoro-5-oxo-2,3,4,5-tetrahydro-1,4-benzoxazepin-4-yl)-6-(2-[4-[(morpholin-4-yl)carbonyl]phenyl]-3H-imidazo[4,5-b]pyridin-7-yl)phenyl] methyl acetate (120 mg, 40%) was obtained as yellow solid.

Method 1I

8-Cyclopropyl-6-fluoro-4-[2-(hydroxymethyl)-3-(2-[4-[(morpholin-4-yl)carbonyl]phenyl]-3H-imidazo[4,5-b]pyridin-7-yl)phenyl]-2,3,4,5-tetrahydro-1,4-benzoxazepin-5-one (1)

In a 50 mL round bottom flask, [2-(8-cyclopropyl-6-fluoro-5-oxo-2,3,4,5-tetrahydro-1,4-benzoxazepin-4-yl)-6-(2-[4-[(morpholin-4-yl)carbonyl]phenyl]-3H-imidazo[4,5-b]pyridin-7-yl)phenyl]methyl acetate (100 mg, 0.15 mmol, 1.00 equiv) was dissolved in a mixture of methanol and water (3:1, 4 mL), to which LiOH (17.7 mg, 0.74 mmol, 4.99 equiv) was added at room temperature. The resulting solution was then stirred for 1 h at room temperature. After the reaction was done, the reaction mixture was concentrated under reduced pressure. The pH value of the remaining solution was adjusted to 7 using HCl solution (1 M) and the resulting solution was extracted with ethyl acetate (3×30 mL). The organic layers were combined, dried over sodium sulfate and concentrated under reduced pressure. The residue was purified by prep-HPLC using the following conditions: column, SunFire Prep C18 OBD Column, 19*150 mm 5 um 10 nm; mobile phase, acetonitrile in water (with 10 mM NH$_4$HCO$_3$), 43% to 50% gradient in 9 min; detector, UV 254 nm. 8-cyclopropyl-6-fluoro-4-[2-(hydroxymethyl)-3-(2-[4-[(morpholin-4-yl)carbonyl]phenyl]-3H-imidazo[4,5-b]pyridin-7-yl)phenyl]-2,3,4,5-tetrahydro-1,4-benzoxazepin-5-one (10 mg, 11%) was obtained as white solid. HPLC: 99.3% purity. MS: m/z=634.2 [M+H]$^+$. $^1$H NMR (400 MHz, CD$_3$OD): δ 8.50 (s, 1H), 8.26 (br s, 2H), 7.77-7.54 (m, 5H), 7.39 (d, J=5.1 Hz, 1H), 6.85-6.75 (m, 2H), 4.66-4.49 (m, 3H), 4.41-4.40 (m, 1H), 4.08-4.03 (m, 2H), 3.81-3.58 (m, 6H), 3.50-3.48 (m, 2H), 2.07-1.95 (m, 1H), 1.16-1.05 (m, 2H), 0.88-0.82 (m, 2H).

Example 2. 8-Cyclopropyl-6-fluoro-4-[2-(hydroxymethyl)-3-[2-(pyridin-3-yl)-3H-imidazo[4,5-b]pyridin-7-yl]phenyl]-2,3,4,5-tetrahydro-1,4-benzoxazepin-5-one (2)

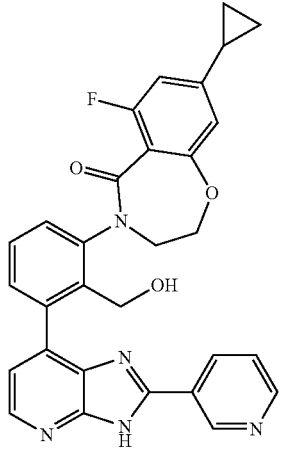 [SMILES: O=C1c2c(F)cc(C3CC3)cc2OCCN1c1cccc(-c2ccnc3[nH]c(-c4cccnc4)nc23)c1CO]

8-cyclopropyl-6-fluoro-4-[2-(hydroxymethyl)-3-[2-(pyridin-3-yl)-3H-imidazo[4,5-b]pyridin-7-yl]phenyl]-2,3,4,5-tetrahydro-1,4-benzoxazepin-5-one 4.9 mg (8%) was prepared from [2-(8-cyclopropyl-6-fluoro-5-oxo-2,3,4,5-tetrahydro-1,4-benzoxazepin-4-yl)-6-(2,3-diaminopyridin-4-yl)phenyl]methyl acetate, pyridine-3-carbaldehyde, LiOH using method 1H and 1I from Example 1. HPLC: 98.5% purity. MS: m/z=522.1 [M+H]$^+$. H-NMR (400 MHz, DMSO-d$_6$): δ 9.32 (s, 1H), 8.69-8.68 (m, 1H), 8.49-8.43 (m, 2H), 7.61-7.53 (m, 3H), 7.46 (d, J=8 Hz, 1H), 7.34 (d, J=4 Hz, 1H), 6.84-6.77 (m, 2H), 4.51-4.45 (m, 3H), 4.40-4.38 (m, 1H), 4.26-4.23 (m, 1H), 3.97-3.93 (m, 2H), 2.01-1.99 (m, 1H), 1.04-1.02 (m, 2H), 0.80-0.77 (m, 2H).

Scheme 2

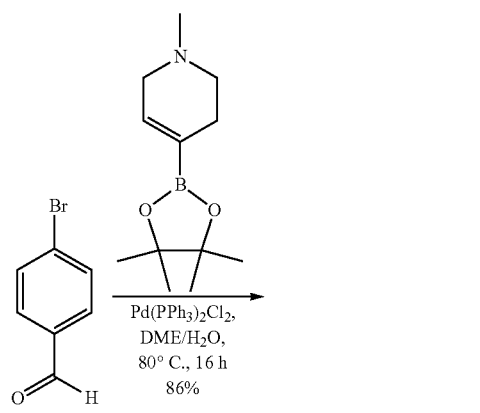

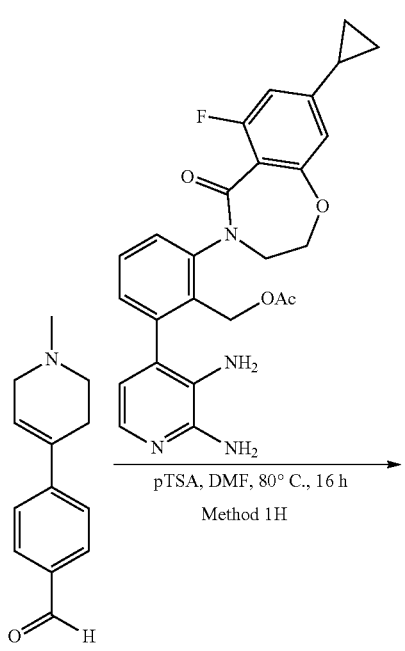

pTSA, DMF, 80° C., 16 h
Method 1H

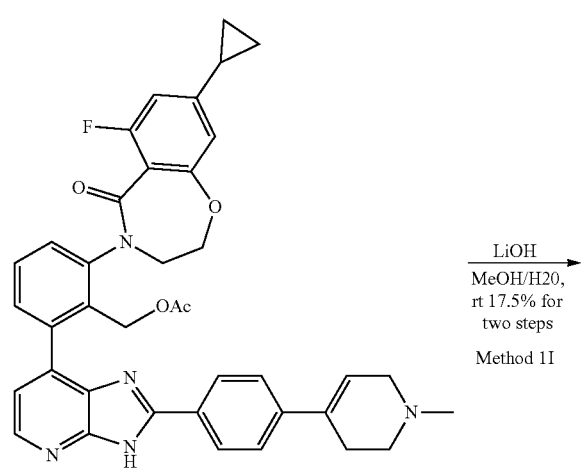

LiOH
MeOH/H2O,
rt 17.5% for two steps
Method 1I

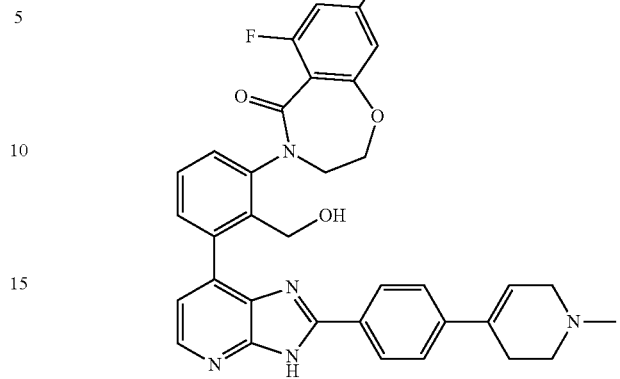

Example 3. 8-Cyclopropyl-6-fluoro-4-[2-(hydroxymethyl)-3-[2-[4-(1-methyl-1,2,3,6-tetrahydropyridin-4-yl)phenyl]-3H-imidazo[4,5-b]pyridin-7-yl]phenyl]-2,3,4,5-tetrahydro-1,4-benzoxazepin-5-one (3)

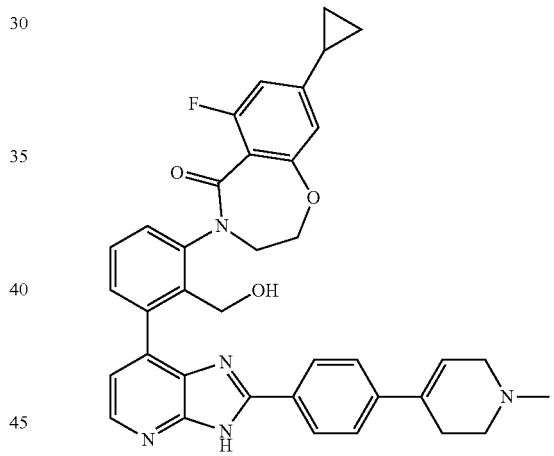

4-(1-Methyl-1,2,3,6-tetrahydropyridin-4-yl)benzaldehyde

In a 30 mL sealed tube purged and maintained with an inert atmosphere of argon, 4-bromobenzaldehyde (500 mg, 2.70 mmol, 1.00 equiv), 1-methyl-4-(tetramethyl-1,3,2-dioxaborolan-2-yl)-1,2,3,6-tetrahydropyridine (723.6 mg, 3.24 mmol, 1.20 equiv), Pd(PPh$_3$)$_2$Cl$_2$ (189.7 mg, 0.27 mmol, 0.10 equiv) and a solution of sodium carbonate (572.8 mg, 5.40 mmol, 2.00 equiv) were mixed in a mixture of ethylene glycol dimethyl ether/water (10:3, 13 mL) at room temperature. The resulting mixture was stirred for 16 h at 80° C. After the reaction was done, the reaction mixture was concentrated under reduced pressure. The residue was purified in a silica gel column eluting with ethyl acetate in (10% to 30% gradient) petroleum ether to afford 4-(1-methyl-1,2,3,6-tetrahydropyridin-4-yl)benzaldehyde (490 mg, 86%) as a yellow solid.

165

8-Cyclopropyl-6-fluoro-4-[2-(hydroxymethyl)-3-[2-[4-(1-methyl-1,2,3,6-tetrahydropyridin-4-yl)phenyl]-3H-imidazo[4,5-b]pyridin-7-yl]phenyl]-2,3,4,5-tetrahydro-1,4-benzoxazepin-5-one 8-cyclopropyl-6-fluoro-4-[2-(hydroxymethyl)-3-[2-[4-(1-methyl-1,2,3,6-tetrahydropyridin-4-yl) phenyl]-3H-imidazo[4,5-b]pyridin-7-yl]phenyl]-2,3,4,5-tetrahydro-1,4-benzoxazepin-5-one 25 mg (17.5% for two steps) was prepared from [2-(8-cyclopropyl-6-fluoro-5-oxo-2,3,4,5-tetrahydro-1,4-benzoxazepin-4-yl)-6-(2,3-diaminopyridin-4-yl)phenyl]methyl acetate and 4-(1-methyl-1,2,3,6-tetrahydropyridin-4-yl)benzaldehyde using method 1H and 1I. HPLC: 99.7% purity. MS: m/z=616.1 [M+H]$^+$. $^1$H NMR (400 MHz, DMSO-$d_6$): δ 8.46 (d, J=5.6 Hz, 1H), 8.15-8.05 (m, 2H), 7.71-7.53 (m, 5H), 7.35 (d, J=4.8 Hz, 1H), 6.83-6.73 (m, 2H), 6.32 (s, 1H), 4.65-4.32 (m, 4H), 4.05-3.85 (m, 2H), 3.26-3.20 (m, 2H), 2.81-2.75 (m, 2H), 2.66-2.60 (m, 2H), 2.42 (s, 3H), 2.01-1.92 (m, 1H), 1.10-1.05 (m, 2H), 0.84-0.80 (m, 2H).

Scheme 3

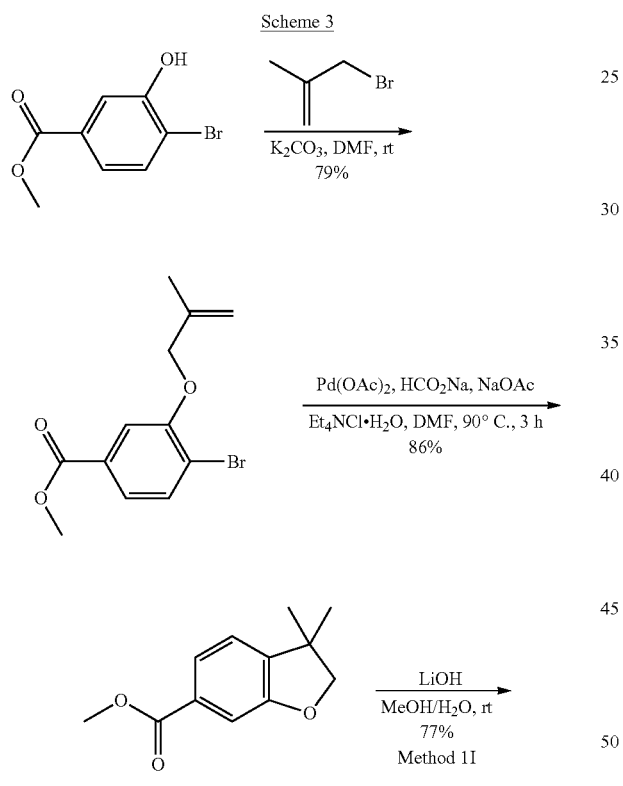

166

-continued

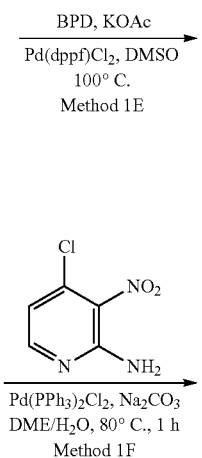

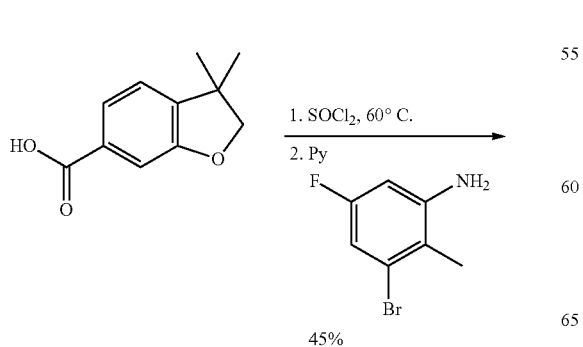

Example 4. N-[5-Fluoro-2-methyl-3-(2-[4-[(morpholin-4-yl)carbonyl]phenyl]-3H-imidazo[4,5-b]pyridin-7-yl) phenyl]-3,3-dimethyl-2,3-dihydro-1-benzofuran-6-carboxamide (4)

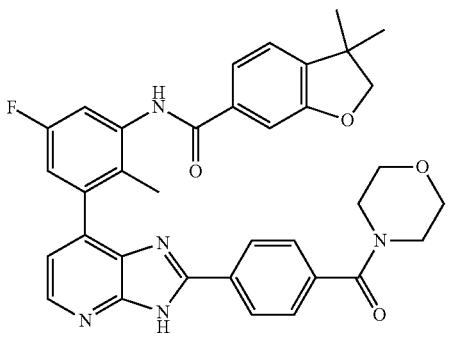 [SMILES: Cc1c(NC(=O)c2ccc3c(c2)OCC3(C)C)cc(F)cc1-c1ccnc2[nH]c(-c3ccc(C(=O)N4CCOCC4)cc3)nc12]

Methyl 4-bromo-3-[(2-methylprop-2-en-1-yl)oxy]benzoate

In a 250-mL round bottom flask, methyl 4-bromo-3-hydroxybenzoate (5.0 g, 21.64 mmol, 1.00 equiv) and 3-bromo-2-methylprop-1-ene (2.92 g, 21.63 mmol, 1.00 equiv) were dissolved in N,N-dimethylformamide (100 mL), to which was added potassium carbonate (4.49 g, 32.49 mmol, 1.50 equiv) at room temperature. The resulting solution was then stirred for 18 h at room temperature. After the reaction was done, the reaction mixture was diluted with a mixture of ethyl acetate (20 mL) and hexanes (80 mL). The insoluble solids in the mixture were filtered out and the filtrate was concentrated under reduced pressure. The residue was purified in a silica gel column eluting with ethyl acetate in petroleum ether (1% to 10% gradient) to afford methyl 4-bromo-3-[(2-methylprop-2-en-1-yl)oxy]benzoate (5.1 g, 79%) as colorless oil. MS: m/z=284.9 [M+H]$^+$.

Methyl 3,3-dimethyl-2,3-dihydro-1-benzofuran-6-carboxylate

In a 250-mL round bottom flask purged and maintained with an inert atmosphere of nitrogen, methyl 4-bromo-3-[(2-methylprop-2-en-1-yl)oxy]benzoate (6.900 g, 24.20 mmol, 1.00 equiv), sodium acetate (4.963 g, 60.50 mmol, 2.50 equiv), sodium formate (1.975 g, 29.04 mmol, 1.20 equiv), tetraethylazanium chloride hydrate (5.335 g, 29.04 mmol, 1.20 equiv) and Pd(OAc)$_2$ (543 mg, 2.42 mmol, 0.10 equiv) were mixed in N,N-dimethylformamide (150 mL) at room temperature. The resulting mixture was then stirred for 3 h at 90° C. After the reaction was done, the reaction mixture was cooled to room temperature, diluted with 600 mL ethyl acetate and washed with brine (5×150 mL). The organic layer was dried over sodium sulfate and concentrated under reduced pressure. The residue was purified in a silica gel column eluting with ethyl acetate in petroleum ether (1% to 20% gradient) to afford methyl 3,3-dimethyl-2,3-dihydro-1-benzofuran-6-carboxylate (4.5 g, 86%) as yellow oil. MS: m/z=206.9 [M+H]$^+$.

3,3-Dimethyl-2,3-dihydro-1-benzofuran-6-carboxylic acid 3,3-dimethyl-2,3-dihydro-1-benzofuran-6-carboxylic acid 399 mg (77%) was prepared from methyl 3,3-dimethyl-2,3-dihydro-1-benzofuran-6-carboxylate using Method 1I. MS: m/z=192.9 [M+H]$^+$.

N-(3-Bromo-5-fluoro-2-methylphenyl)-3,3-dimethyl-2,3-dihydro-1-benzofuran-6-carboxamide In a 50-mL round-bottom flask purged and maintained with an inert atmosphere of nitrogen, 3,3-dimethyl-2,3-dihydro-1-benzofuran-6-carboxylic acid (500 mg, 2.45 mmol, 1.00 equiv) was dissolved in thionyl chloride (5 mL) at room temperature. The resulting solution was stirred for 1 h at 60 (2. After the reaction was done, the reaction mixture was concentrated under reduced pressure to afford acid chloride intermediate (600 mg), which was used in next step without further purification. In a 50-mL round-bottom flask, the acid chloride (600 mg) prepared above was slowly added to a solution of 3-bromo-5-fluoro-2-methylaniline (637 mg, 3.31 mmol, 1.35 equiv) in pyridine (5 mL) at 0° C. The mixture was then stirred 2 h at room temperature. After the reaction was done, the reaction mixture was concentrated under reduced pressure. The residue was purified in a silica gel column eluting with methanol in dichloromethane (1% to 20% gradient) to afford N-(3-bromo-5-fluoro-2-methylphenyl)-3,3-dimethyl-2,3-dihydro-1-benzofuran-6-carboxamide (430 mg, 45%) as white solid. MS: m/z=379.8 [M+H]$^+$ N-[5-Fluoro-2-methyl-3-(2-[4-[(morpholin-4-yl)carbonyl]phenyl]-3H-imidazo[4,5-b]pyridin-7-yl)phenyl]-3,3-dimethyl-2,3-dihydro-1-benzofuran-6-carboxamide N-[5-fluoro-2-methyl-3-(2-[4-[(morpholin-4-yl)carbonyl]phenyl]-3H-imidazo[4,5-b]pyridin-7-yl)phenyl]-3,3-dimethyl-2,3-dihydro-1-benzofuran-6-carboxamide 20 mg (3.5% for 4 steps) was prepared from N-(3-bromo-5-fluoro-2-methylphenyl)-3,3-dimethyl-2,3-dihydro-1-benzofuran-6-carboxamide, 4-chloro-3-nitropyridin-2-amine, 4-[(morpholin-4-yl)carbonyl]benzaldehyde using Method 1E, 1F 1G and 1H. HPLC: 97.8% purity. MS: m/z=606.2 [M+H]$^+$. $^1$H-NMR (400 MHz, DMSO-d$_6$): δ 13.82 (br s, 1H), 9.96 (s, 1H), 8.51 (s, 1H), 8.30-8.29 (m, 2H), 7.57-7.55 (m, 3H), 7.38-7.35 (m, 3H), 7.15-7.13 (m, 2H), 4.28 (s, 2H), 3.55-3.45 (m, 6H), 3.31-3.30 (m, 2H), 2.06 (s, 3H), 1.32 (s, 6H).

Example 5. 4-(tert-butyl)-N-(2-methyl-3-(2-(4-(morpholine-4-carbonyl)phenyl)-3H-imidazo[4,5-b]pyridin-7-yl)phenyl)benzamide (5)

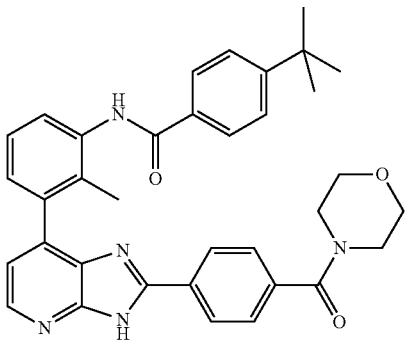 [SMILES: Cc1c(NC(=O)c2ccc(C(C)(C)C)cc2)cccc1-c1ccnc2[nH]c(-c3ccc(C(=O)N4CCOCC4)cc3)nc12]

4-chloro-3-nitropyridin-2-amine

A nitrating mixture (HNO$_3$:H$_2$SO$_4$, 5 mL) was added to 4-chloropyridin-2-amine (2.56 g, 20 mmol) at 0° C. and stirred for 16 h. After completion of the reaction, the mixture was diluted with water and ethyl acetate, extracted with ethyl acetate, washed with water, brine, dried over anhydrous Na$_2$SO$_4$, and then concentrated under reduced pressure. The resulting crude product was purified by flash chromatography to afford 4-chloro-3-nitropyridin-2-amine as a yellow solid (1.211 g, 35% yield). HPLC: 97.2% purity. MS: 74.0 [M+H]$^+$. $^1$H NMR: 400 MHz, DMSO-d6: δ 8.11 (d, J=5.24 Hz, 1H), 7.23 (s, 2H), 6.85 (d, −=5.24 Hz, 1H).

N-(3-(2-amino-3-nitropyridin-4-yl)-2-methylphenyl)-4-(tert-butyl)benzamide

A pressure tube was charged with 4-chloro-3-nitropyridin-2-amine (300 mg, 1.73 mmol), 4-(tert-butyl)-N-(2-methyl-3-(4,4,5,5-tetramethyl-1,3,2-dioxaborolan-2-yl)phenyl)benzamide (744, 1.89 mmol), DME (10 mL) and Na$_2$CO$_3$ (294 mg, 3.4 mmol) and then degassed for 10 min. Pd$_2$Cl$_2$(PPh$_3$)$_2$ (120 mg, 0.171 mmol) was then added and the reaction mixture was heated to 80° C. for 1 h. After completion of the reaction, the reaction was quenched by the addition of water, extracted with ethyl acetate, washed with water and brine, and then dried over anhydrous Na$_2$SO$_4$. The solvent was evaporated under reduced pressure to afford the crude compound, which was purified by flash chromatography to afford N-(3-(2-amino-3-nitropyridin-4-yl)-2-methylphenyl)-4-(tert-butyl)benzamide (0.400 g, 57% yield). HPLC: 86.8% purity. MS: 405.2 [M+H]$^+$

4-(tert-butyl)-N-(3-(2,3-diaminopyridin-4-yl)-2-methylphenyl)benzamide

A solution of 4-(tert-butyl)-N-(3-(2,3-diaminopyridin-4-yl)-2-methylphenyl)benzamide (50 mg, 0.124 mmol) in MeOH (10 mL) was reduced using an H-cube at 30° C. (flow rate=0.9 mL/min) and a 10% Pd/C cartridge. Upon completion of the reaction, the solvent was evaporated under reduced pressure to afford 4-(tert-butyl)-N-(3-(2,3-diaminopyridin-4-yl)-2-methylphenyl)benzamide as a pale yellow liquid (0.043 g, 93%). HPLC: 97.5% purity. MS: 375.3 [M+H]$^+$. $^1$H NMR: 400 MHz, DMSO-d6: δ 9.84 (s, 1H), 7.91-7.95 (m, 2H), 7.54 (dd, J=1.92, 6.64 Hz, 2H), 7.42 (d, J=7.04 Hz, 1H), 7.36 (d, J=5.16 Hz, 1H), 7.31 (t, J=7.76 Hz, 1H), 7.03 (dd, J=1.16, 7.46 Hz, 1H), 5.70 (s, 2H), 2.00 (s, 3H), 1.31 (s, 9H).

4-(tert-butyl)-N-(2-methyl-3-(2-(4-(morpholine-4-carbonyl)phenyl)-3H-imidazo[4,5-b]pyridin-7-yl)phenyl)benzamide To a solution of 4-(tert-butyl)-N-(3-(2,3-diaminopyridin-4-yl)-2-methylphenyl)benzamide and 4-(morpholine-4-carbonyl)benzaldehyde (85 mg, 0.227 mmol) in DMF (3 mL) was added pTSA (43 mg, 0.25 mmol) and heated to 85° C. for 12 h. After completion of the reaction, the reaction was quenched by addition of water, extracted with ethyl acetate, washed with water, brine, and then dried over anhydrous Na$_2$SO$_4$. The solvent was evaporated under reduced pressure. The resulting crude compound which was then purified by flash chromatography to afford 4-(tert-butyl)-N-(2-methyl-3-(2-(4-(morpholine-4-carbonyl)phenyl)-3H-imidazo[4,5-b]pyridin-7-yl)phenyl)benzamide as an off-white solid (17 mg, 13% yield). HPLC: 96.2% purity. MS: 574.3 [M+H]$^+$. $^1$H NMR (400 MHz, DMSO-d6): δ 9.95 (s, 1H), 8.35-8.46 (m, 1H), 8.25 (d, J=7.48 Hz, 2H), 7.96 (d, J=7.88 Hz, 2H), 7.47-7.61 (m, 6H), 7.28-7.39 (m, 2H), 7.17 (d, J=4.84 Hz, 1H), 3.61-0.00 (m, 6H), 3.32-0.00 (m, 2H), 2.11 (s, 3H), 1.32 (s, 9H).

Example 6. 6-Cyclopropyl-2-(2-hydroxymethyl-3-{2-[4-(morpholine-4-carbonyl)-phenyl]-3H-imidazo[4,5-b]pyridin-7-yl}-phenyl)-3,4-dihydro-2H-isoquinolin-1-one (6)

2-(6-cyclopropyl-1-oxo-3,4-dihydroisoquinolin-2(1H)-yl)-6-(4,4,5,5-tetramethyl-1,3,2-dioxaborolan-2-yl)benzyl acetate To a 20 mL reaction vial charged with a stir bar was added 2-bromo-6-(6-cyclopropyl-1-oxo-3,4-dihydroisoquinolin-2(1H)-yl)benzyl acetate (500.00 mg; 1.21 mmol; 1.00 eq.), bis(pinacolato)diboron (612.95 mg; 2.41 mmol; 2.00 eq.), tris(dibenzylideneacetone)dipalladium-chloroform adduct (124.92 mg; 0.12 mmol; 0.10 eq.), dicyclohexyl-(2',4',6'-triisopropyl-biphenyl-2-yl)-phosphane (115.07 mg; 0.24 mmol; 0.20 eq.), and potassium acetate (355.34 mg; 3.62 mmol; 3.00 eq.). The vial was sealed and flushed with argon. The reaction mixture was then treated with dioxane (10.00 ml; 117.36 mmol: 97.24 eq.) via syringe, degassed with argon, and heated to 65° C. overnight with stirring. Upon completion of the reaction (monitored by LC-MS), the reaction mixture was cooled to RT and filtered. The filtrate was concentrated under reduced pressure, then loaded on to a 25 g KP-sil samplet cartridge, and purified by flash chromatography using a Biotage system (KP-silica column; mobile phase 5%-50% EtOAc/hex 15 column volumes). The product fractions were concentrated under reduced pressure to afford 2-(6-cyclopropyl-1-oxo-3,4-dihydroisoquinolin-2(1H)-yl)-6-(4,4,5,5-tetramethyl-1,3,2-dioxaborolan-2-yl) benzyl acetate as a brown, waxy solid (729 mg, 131%). LC-MS analysis showed the presence of des-bromo starting material as an impurity. MS: [M+H]$^+$ 462.

2-(2-amino-3-nitropyridin-4-yl)-6-(6-cyclopropyl-1-oxo-3,4-dihydroisoquinolin-2(1H)-yl)benzyl acetate To a 30 mL reaction tube charged with a stir bar was added 2-amino-4-chloro-3-nitropyridine (250.00 mg; 1.44 mmol; 1.00 eq.), 2-(6-cyclopropyl-1-oxo-3,4-dihydroisoquinolin-2(1H)-yl)-6-(4,4,5,5-tetramethyl-1,3,2-dioxaborolan- 2-yl)benzyl acetate (731.02 mg; 1.58 mmol; 1.10 eq.), and 1,1'-bis(diphenylphosphino)ferrocene-palladium(ii)dichloride dichloromethane complex (117.63 mg; 0.14 mmol; 0.10 eq.). The tube was sealed and flushed with argon. To the reaction mixture was then added aqueous dibasic potassium phosphate (1M; 2.88 ml; 2.88 mmol; 2.00 eq.), aqueous sodium acetate (2.88 ml; 2.88 mmol; 2.00 eq.), and ACN (7.50 ml; 143.59 mmol; 99.69 eq.) via syringe. The reaction tube was degassed with argon and heated to 110° C. for 2 h. Upon completion of the reaction (as monitored by LC-MS), the reaction was quenched by the addition of water (10 mL), poured into a separatory funnel, and then extracted with EtOAc (3×10 mL). The organic phases were combined, washed with brine, dried over anhydrous $Na_2SO_4$, and concentrated under reduced pressure. The residue was loaded onto a 25 g samplet and subjected to flash chromatography on a Biotage system (KP-NH column; mobile phase 20-100% EtOAc/hexanes; 15 column volumes). The product fractions were concentrated under reduced pressure to afford 2-(2-amino-3-nitropyridin-4-yl)-6-(6-cyclopropyl-1-oxo-3,4-dihydroisoquinolin-2(1H)-yl)benzyl acetate as a yellow solid (353 mg, 52%). HPLC: 97% purity. MS: 473 [M+H]$^+$ 2-(6-cyclopropyl-1-oxo-3,4-dihydroisoquinolin-2(1H)-yl)-6-(2,3-diaminopyridin-4-yl)benzyl acetate 2-(2-amino-3-nitropyridin-4-yl)-6-(6-cyclopropyl-1-oxo-3,4-dihydroisoquinolin-2(1H)-yl)benzyl acetate (350.00 mg; 0.74 mmol; 1.00 eq.) was dissolved in methanol (30.00 ml; 740.59 mmol: 999.78 eq.) and subjected to hydrogenation on an H-Cube system (1 mL/min, 30° C., full hydrogen pressure) over a 10% Pd/C cartridge. Upon completion of the reaction (as monitored by LC-MS), the solution was concentrated under reduced pressure to afford 2-(6-cyclopropyl-1-oxo-3,4-dihydroisoquinolin-2(1H)-yl)-6-(2,3-diaminopyridin-4-yl)benzyl acetate as a brown, waxy solid (308 mg, 94%). The crude product was used in further reactions without further purification.

2-(6-cyclopropyl-1-oxo-3,4-dihydroisoquinolin-2(1H)-yl)-6-(2-(4-(morpholine-4-carbonyl)phenyl)-3H-imidazo[4,5-b]pyridin-7-yl)benzyl acetate To a 10 mL reaction tube charged with a stir bar was added a solution of 2-(6-cyclopropyl-1-oxo-3,4-dihydroisoquinolin-2(1H)-yl)-6-(2,3-diaminopyridin-4-yl)benzyl acetate (75.00 mg; 0.17 mmol; 1.00 eq.) and 4-(morpholine-4-carbonyl)-benzaldehyde (40.87 mg; 0.19 mmol; 1.10 eq.) in DMF (2.00 ml; 25.94 mmol; 153.04 eq.). To this mixture was then was added p-toluenesulfonic acid monohydrate (3.22 mg; 0.02 mmol; 0.10 eq.). The reaction mixture was heated to 85° C. for 12 h. Upon completion of the reaction (as monitored by LC-MS), the reaction was quenched by the addition of water (5 mL), and extracted with ethyl acetate (3×10 mL). The organic phases were combined, washed with sat. aq. $NaHCO_3$ and brine, dried over anhydrous $Na_2SO_4$, and concentrated under reduced pressure. The residue was dissolved residue and subjected to preparative HPLC (Interchim system; C-18 (10 μm) column, 30×150 mm), using mobile phase A (0.1% $NH_4OH$ in water) and mobile phase B ((0.1% $NH_4OH$ in acetonitrile). The method used 35% mobile phase B for min then a gradient from 35% to 95% mobile phase B over 10 min at flow rate of 60 mL/min. The product eluted with 59% mobile phase B. The product fractions were combined and concentrated to afford 2-(6-cyclopropyl-1-oxo-3,4-dihydroisoquinolin-2(1H)-yl)- 6-(2-(4-(morpholine-4-carbonyl)phenyl)-3H-imidazo[4,5-b]pyridin-7-yl)benzyl acetate as a white solid (37 mg, 34% yield).

6-Cyclopropyl-2-(2-hydroxymethyl-3-{2-[4-(morpholine-4-carbonyl)-phenyl]-3H-imidazo[4,5-b]pyridin-7-yl}-phenyl)-3,4-dihydro-2H-isoquinolin-1-one To a 10 mL reaction vial charged with a stir bar was added 2-(6-cyclopropyl-1-oxo-3,4-dihydroisoquinolin-2(1H)-yl)-6-(2-(4-(morpholine-4-carbonyl)phenyl)-3H-imidazo[4,5-b]pyridin-7-yl)benzyl acetate (37.00 mg; 0.06 mmol; 1.00 eq.), lithium hydroxide monohydrate (120.98 mg; 2.88 mmol; 50.00 eq.), isopropanol (1.00 ml; 13.06 mmol; 226.55 eq.), THF (1.00 ml; 12.34 mmol; 214.07 eq.), and water (0.50 ml; 27.75 mmol; 481.37 eq.). The reaction mixture heated to 30° C. with stirring for 2 h. Upon completion of the reaction (as monitored by LC-MS), the reaction mixture was partitioned between EtOAc and water and then extracted with EtOAc (3×10 mL). The organic phases were combined, dried over anhydrous magnesium sulfate, and concentrated under reduced pressure. The residue was loaded onto 10 g samplet and purified by flash chromatography using a Biotage system (KP-Silica column; mobile phase 2-20% MeOH/DCM). The product fractions were combined and concentrated to dryness to afford 6-cyclopropyl-2-(2-hydroxymethyl-3-{2-[4-(morpholine-4-carbonyl)-phenyl]-3H-imidazo[4,5-b]pyridin-7-yl}-phenyl)-3,4-dihydro-2H-isoquinolin-1-one as an off-white solid (27 mg, 78% yield). HPLC: 96% purity. MS: 600 [M+H]$^+$. $^1$H NMR (500 MHz, DMSO-d6) δ 13.96 (s, 1H), 8.45 (d, J=5.0 Hz, 1H), 8.22 (d, J=7.9 Hz, 2H), 7.79 (d, J=8.0 Hz, 1H), 7.60 (d, J=7.9 Hz, 2H), 7.57 (d, J=7.5 Hz, 1H), 7.52 (d, J=7.6 Hz, 1H), 7.49 (d, J=7.7 Hz, 1H), 7.39 (d, J=5.0 Hz, 1H), 7.09 (d, J=8.0 Hz, 1H), 7.08 (s, 1H), 5.53 (s, 1H), 4.42-4.28 (m, 1H), 4.23 (d, J=11.4 Hz, 1H), 4.08-3.88 (m, 2H), 3.64 (s, 6H), 3.36 (s, 2H), 3.30-3.19 (m, 1H), 3.06 (dt, J=16.0, 5.1 Hz, 1H), 2.00 (tt, J=8.7, 4.9 Hz, 1H), 1.09-0.97 (m, 2H), 0.77 (q, J=5.4 Hz, 2H).

Example 7. 6-cyclopropyl-2-(2-(hydroxymethyl)-3-(2-(1-methyl-1H-pyrazol-4-yl)-3H-imidazo[4,5-b]pyridin-7-yl)phenyl)-3,4-dihydroisoquinolin-1(2H)-one (7)

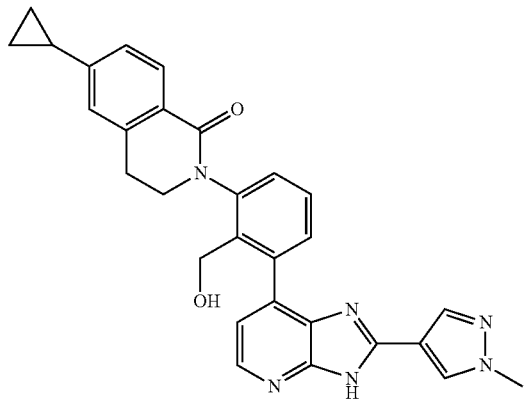 [SMILES: Cn1cc(-c2nc3c(-c4cccc(N5CCc6cc(C7CC7)ccc6C5=O)c4CO)ccnc3[nH]2)cn1]

2-(6-cyclopropyl-1-oxo-3,4-dihydroisoquinolin-2 (1H)-yl)-6-(2-(1-methyl-1H-pyrazol-4-yl)-3H-imidazo[4,5-b]pyridin-7-yl)benzyl acetate To a 10 mL reaction tube charged with a stir bar was added a solution of 2-(6-cyclopropyl-1-oxo-3,4-dihydroisoquinolin-2(1H)-yl)-6-(2,3-diaminopyridin-4-yl)benzyl acetate (75.00 mg; 0.17 mmol; 1.00 eq.) and 1-methyl-1H-pyrazole-4-carbaldehyde (18.66 µl; 0.19 mmol; 1.10 eq.) in DMF (2.00 ml; 25.94 mmol; 153.04 eq.). The reaction mixture was then treated with p-toluenesulfonic acid monohydrate (3.22 mg; 0.02 mmol; 0.10 eq.) and heated to 85° C. for 12 h. The reaction mixture was quenched by the addition of water (5 mL) and extracted with ethyl acetate (3×10 mL). The organic phases were combined, washed with saturated aq. NaHCO₃ and brine, dried over anhydrous sodium sulfate, and concentrated under reduced pressure. The resulting was dissolved in DMSO and subjected to preparative HPLC (Interchim system; C-18 column (10 µm); 30×150 mm; mobile phase A: 0.1% NH₄OH in water; mobile phase B: 0.1% NH₄OH in acetonitrile) using 35% mobile phase B for 1 min and then a gradient from 35% to 95% mobile phase B over 10 min at a flow rate of 60 mL/min. The product eluted with 60% mobile phase B. The product fractions were combined and concentrated to afford 2-(6-cyclopropyl-1-oxo-3,4-dihydroisoquinolin-2(1H)-yl)-6-(2-(1-methyl-1H-pyrazol-4-yl)-3H-imidazo[4,5-b]pyridin-7-yl)benzyl acetate as an off-white solid (30 mg, 33% yield).

6-cyclopropyl-2-(2-(hydroxymethyl)-3-(2-(1-methyl-1H-pyrazol-4-yl)-3H-imidazo[4,5-b]pyridin-7-yl)phenyl)-3,4-dihydroisoquinolin-1(2H)-one To a 10 mL reaction vial charged with a stir bar was added 2-(6-cyclopropyl-1-oxo-3,4-dihydroisoquinolin-2(1H)-yl)-6-(2-(1-methyl-1H-pyrazol-4-yl)-3H-imidazo[4,5-b]pyridin-7-yl)benzyl acetate (30.00 mg; 0.06 mmol; 1.00 eq.), lithium hydroxide monohydrate (118.19 mg; 2.82 mmol; 50.00 eq.), isopropanol (1.00 ml; 13.06 mmol; 231.90 eq.), THF (1.00 ml; 12.34 mmol; 219.13 eq.), and water (0.50 ml; 27.75 mmol: 492.73 eq.). The reaction mixture was heated to 30° C. with stirring for 2 h. The reaction mixture was partitioned between EtOAc and water and extracted with EtOAc (3×10 mL). The organic phases were combined, dried over magnesium sulfate, and concentrated under reduced pressure. The residue was loaded onto a 10 g samplet and subjected to flash chromatography on a Biotage system (KP-Silica column: 2-20% MeOH/DCM eluent). The product fractions were concentrated under reduced pressure to afford 6-cyclopropyl-2-(2-(hydroxymethyl)-3-(2-(1-methyl-1H-pyrazol-4-yl)-3H-imidazo[4,5-b]pyridin-7-yl)phenyl)-3,4-dihydroisoquinolin-1(2H)-one as an off-white solid (21 mg, 76% yield). HPLC: 94% purity. MS: 491 [M+H]⁺ ¹H NMR (500 MHz, DMSO-d6) δ 13.53 (s, 1H), 8.36 (s, 1H), 8.33 (d, J=5.0 Hz, 1H), 8.06 (s, 1H), 7.78 (d, J=7.9 Hz, 1H), 7.55 (t, J=7.7 Hz, 1H), 7.45 (d, J=7.4 Hz, 2H), 7.27 (d, J=5.2 Hz, 1H), 7.11-7.05 (m, 2H), 5.71 (s, 1H), 4.29 (t, J=9.5 Hz, 1H), 4.15 (d, J=11.6 Hz, 1H), 4.05-3.85 (m, 5H), 3.29-3.21 (m, 1H), 3.05 (dt, J=16.1, 5.1 Hz, 1H), 1.99 (ddd. J=13.4, 8.6, 4.9 Hz, 1H), 1.02 (dt, J=9.1, 3.1 Hz, 2H), 0.77 (td, J=5.9, 3.9 Hz, 2H).

Scheme 4

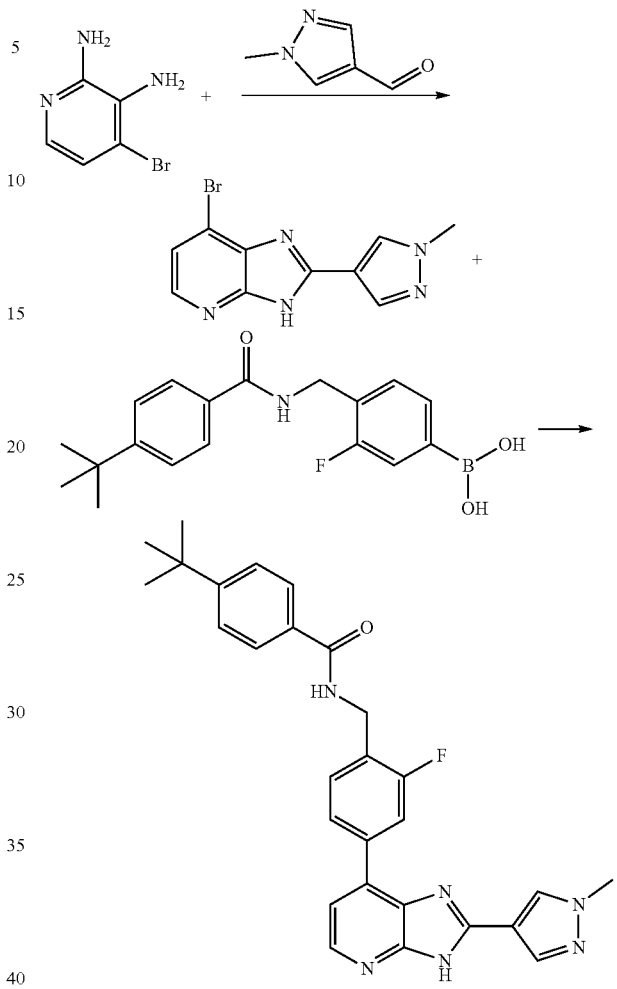

Example 8. 4-tert-Butyl-N-{2-fluoro-4-[2-(1-methyl-1H-pyrazol-4-yl)-3H-imidazo[4,5-b]pyridin-7-yl]-benzyl}-benzamide (8)

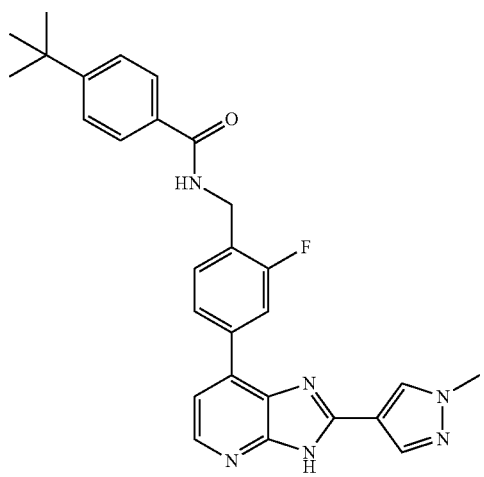 [SMILES: Cn1cc(-c2nc3c(-c4ccc(CNC(=O)c5ccc(C(C)(C)C)cc5)c(F)c4)ccnc3[nH]2)cn1]

7-Bromo-2-(1l-methyl-1H-pyrazol-4-yl)-3H-imidazo[4,5-b]pyridine

To a 10 mL reaction tube charged with a stir bar was added a solution of 2,3-diamino-4-bromopyridine (75.00 mg; 0.40 mmol; 1.00 eq.) and 1-methyl-1h-pyrazole-4-carbaldehyde (41.93 µl; 0.42 mmol; 1.05 eq.) in DMF (2.00 ml; 25.94 mmol; 65.03 eq.). The reaction mixture was then treated with p-toluenesulfonic acid monohydrate (7.59 mg; 0.04 mmol; 0.10 eq.) and heated to 85° C. for 12 h. Upon completion of the reaction, the mixture was poured into saturated aq. NaHCO3 (20 mL) and transferred to a separatory funnel. The product was extracted with ethyl acetate (3×10 mL), washed with saturated aq. NaHCO$_3$ and brine, dried over anhydrous Na2SO4, and concentrated under reduced pressure. The crude product was loaded onto a 10 g KP-NH samplet and purified on a Biotage system by flash chromatography (KP-NH column; 2-10% MeOH/CH2Cl2 over 15 column volumes). The product fractions were concentrated to afford 7-bromo-2-(1-methyl-1H-pyrazol-4-yl)-3H-imidazo[4,5-b]pyridine as a beige solid (68% yield). HPLC: 99% purity. MS: 279 [M+H]$^+$

[4-[[(4-tert-butylbenzoyl)amino]methyl]-3-fluoro-phenyl]boronic acid

To a 20 mL reaction vial was added 4-(aminomethyl)-3-fluorophenylboronic acid, hcl (500.00 mg; 2.43 mmol; 1.00 eq.) and sodium bicarbonate (511.18 mg; 6.09 mmol; 2.50 eq.). The mixture was suspended in water (0.80 ml; 44.41 mmol: 18.24 eq.) and THF (8.00 ml; 98.74 mmol; 40.57 eq.) and then cooled to 0° C. The reaction mixture was then treated with 4-tert-butyl-benzoyl chloride (0.49 ml; 2.68 mmol; 1.10 eq.) and allowed to slowly warm to ambient temperature with stirring overnight. Upon completion of the reaction (as monitored by LC-MS), the mixture was concentrated under reduced pressure, loaded onto a 50 g Biotage samplet, and subjected to flash chromatography on a Biotage column chromatography (50 g column, eluted with 20-70% EtOAc/Hexanes). The product fractions were collected, concentrated, and dried to afford [4-[[(4-tert-butylbenzoyl)amino]methyl]-3-fluoro-phenyl]boronic acid as a white solid (650 mg, 81% yield). HPLC: 99% purity. MS: 330 [M+H]$^+$

4-tert-Butyl-N-{2-fluoro-4-[2-(1-methyl-1H-pyrazol-4-yl)-3H-imidazo[4,5-b]pyridin-7-yl]-benzyl}-benzamide (8)

To a 5 mL reaction tube with charged with a stir bar was added 7-bromo-2-(1-methyl-1H-pyrazol-4-yl)-3H-imidazo[4,5-b]pyridine (35.00 mg: 0.13 mmol; 1.00 eq.), [4-[[(4-tert-butylbenzoyl)amino]methyl]-3-fluoro-phenyl]boronic acid (53.85 mg: 0.16 mmol; 1.30 eq.), and 1,1'-bis(diphenylphosphino)ferrocene-palladium(ii)dichloride dichloromethane complex (10.28 mg; 0.01 mmol; 0.10 eq.). The tube was sealed and flushed with argon. To the reaction mixture was added dibasic potassium phosphate solution (0.25 ml; 1M; 2.00 eq.), sodium acetate solution (0.25 ml; 0.25 mmol; 2.00 eq.), and ACN (1.50 ml; 28.72 mmol; 228.20 eq.) via syringe. The reaction tube was degassed with argon and heated to 110° C. for 2 h. Upon completion of the reaction (monitored by LC-MS), the mixture was loaded onto 25 g KP-Sil samplet and subjected to flash chromatography to afford 4-tert-butyl-N-{2-fluoro-4-[2-(1-methyl-1H-pyrazol-4-yl)-3H-imidazo[4,5-b]pyridin-7-yl]-benzyl}-benzamide as a brown solid (44 mg, 72% yield). HPLC: 99% purity. MS: 483 [M+H]$^+$. $^1$H NMR (500 MHz, DMSO-d6) δ 13.38 (s, 1H), 9.04 (t, J=5.8 Hz, 1H), 8.44 (s, 1H), 8.29-8.23 (m, 2H), 8.14 (d, J=10.4 Hz, 2H), 7.87 (d, J=8.2 Hz, 2H), 7.53-7.46 (m, 4H), 4.59 (d, J=5.8 Hz, 2H), 3.93 (s, 3H), 1.30 (s, 9H).

Example 9. 4-tert-Butyl-N-{2-methyl-3-[2-(1-methyl-1H-pyrazol-4-yl)-3H-imidazo[4,5-b]pyridin-7-yl]-phenyl}-benzamide (9)

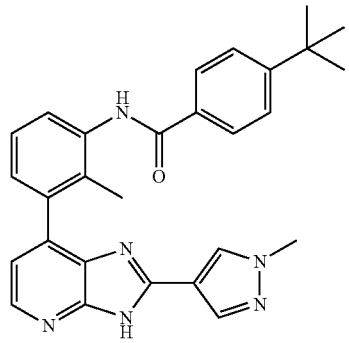 [SMILES: Cc1c(NC(=O)c2ccc(C(C)(C)C)cc2)cccc1-c1ccnc2[nH]c(-c3cnn(C)c3)nc12]

4-tert-Butyl-N-[2-methyl-3-(4,4,5,5-tetramethyl-[1,3,2]dioxaborolan-2-yl)-phenyl]-benzamide To a 20 mL reaction vial was added 2-methyl-3-(4,4,5,5-tetramethyl-[1,3,2]dioxaborolan-2-yl)-phenylamine (300.00 mg; 1.29 mmol; 1.00 eq.) and sodium bicarbonate (162.16 mg; 1.93 mmol; 1.50 eq.). The mixture was suspended in water (0.50 ml; 27.75 mmol; 21.57 eq.) and THF (5.00 ml; 61.71 mmol: 47.96 eq.), and then cooled to 0° C. The mixture was then treated with 4-tert-butyl-benzoyl chloride (0.28 ml; 1.54 mmol; 1.20 eq.) The reaction mixture was allowed to warm to ambient temperature while stirring overnight. Upon completion of the reaction (as monitored by LC-MS), the crude product was subjected to flash chromatography on a Biotage system ((25 g column, using 10-60% EtOAc/Hexanes). Product fractions were collected and concentrated to afford 4-tert-butyl-N-[2-methyl-3-(4,4,5,5-tetramethyl-[1,3,2]dioxaborolan-2-yl)-phenyl]-benzamide as a white solid (300 mg, 59% yield). HPLC: 99% purity. MS: 394 [M+H]$^+$.

4-tert-Butyl-N-{2-methyl-3-[2-(1-methyl-1H-pyrazol-4-yl)-3H-imidazo[4,5-b]pyridin-7-yl]-phenyl}-benzamide (9)

To a 5 mL reaction tube charged with a stir bar was added 7-bromo-2-(1-methyl-1H-pyrazol-4-yl)-3H-imidazo[4,5-b]pyridine (35.00 mg; 0.13 mmol; 1.00 eq.), 4-tert-butyl-N-[2-methyl-3-(4,4,5,5-tetramethyl-[1,3,2]dioxaborolan-2-yl)-phenyl]-benzamide (64.35 mg; 0.16 mmol; 1.30 eq.), and 1,1'-bis(diphenylphosphino)ferrocene-palladium(ii)dichloride dichloromethane complex (10.28 mg; 0.01 mmol; 0.10 eq.). The tube was sealed and flushed with argon. To the reaction mixture was added dibasic potassium phosphate (1 M solution, 2.00 eq.), sodium acetate (0.25 ml; 0.25 mmol; 2.00 eq.), and ACN (1.50 ml; 28.72 mmol: 228.20 eq.) via syringe. The reaction tube was degassed with argon and then heated to 110° C. for 2 h. Upon completion of the reaction (monitored by LC-MS), the reaction mixture was loaded onto a 25 g KP-Sil samplet and then subjected to flash chromatography to afford 4-tert-butyl-N-(2-methyl-3-[2-(1-methyl-1H-pyrazol-4-yl)-3H-imidazo[4,5-b]pyridin-7-yl]-phenyl)-benzamide as an off-white solid (30 mg, 51% yield). HPLC: 99% purity. MS: 465 [M+H]+. 1H NMR (500 MHz, DMSO-d6) δ 13.31 (s, 1H), 9.92 (s, 1H), 8.37 (s, 1H), 8.27 (d, J=5.0 Hz, 1H), 8.06 (s, 1H), 7.94 (d, J=8.2 Hz, 2H), 7.54 (d, J=8.2 Hz, 2H), 7.45 (d, J=7.8 Hz, 1H), 7.34 (t, J=7.8 Hz, 1H), 7.25 (d, J=7.5 Hz, 1H), 7.05 (d, J=5.0 Hz, 1H), 3.89 (s, 3H), 2.07 (s, 3H), 1.32 (s, 9H).

Example 10. 2-(5-fluoro-2-(hydroxymethyl)-3-(2-(1-methyl-1H-pyrazol-4-yl)-3H-imidazo[4,5-b]pyridin-7-yl)phenyl)-7,7-dimethyl-2,3,4,6,7,8-hexahydro-1H-cyclopenta[4,5]pyrrolo[1,2-a]pyrazin-1-one (10)

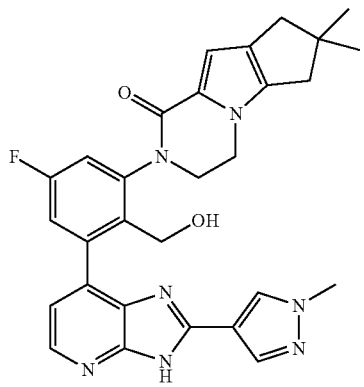 [SMILES: Cn1cc(-c2nc3c(-c4cc(F)cc(N5CCn6c(cc7c6CC(C)(C)C7)C5=O)c4CO)ccnc3[nH]2)cn1]

7-chloro-2-(1-methyl-1H-pyrazol-4-yl)-3H-imidazo[4,5-b]pyridine

To a solution of 4-chloropyridine-2,3-diamine (1.80 g, 12.5 mmol) in DMF (20 mL) was added TPSA (410 mg, 2.38 mmol) and 1-methyl-1H-pyrazole-4-carbaldehyde (1.38 g, 12.5 mmol). The mixture was stirred at 80° C. for 10 hrs. After LC-MS showed the reaction was completed, the reaction mixture was concentrated under reduced pressure to give a residue which was purified by preparative HPLC (neutral condition)s to give 7-chloro-2-(1-methyl-1H-pyrazol-4-yl)-3H-imidazo[4,5-b]pyridine (1.58 g, 53.9% yield) as a yellow solid. 1H NMR (400 MHz, DMSO-d6) δ: 8.49 (s, 1H), 8.22 (d, J=5.2 Hz, 1H), 8.17 (s, 1H), 7.36 (d, J=5.6 Hz, 1H), 3.95 (s, 3H).

2-(7,7-dimethyl-1-oxo-3,4,7,8-tetrahydro-1H-cyclopenta[4,5]pyrrolo[1,2-a]pyrazin-2(6H)-yl)-4-fluoro-6-(2-(1-methyl-1H-pyrazol-4-yl)-3H-imidazo[4,5-b]pyridin-7-yl)benzyl acetate The mixture of 2-(7,7-dimethyl-1-oxo-3,4,7,8-tetrahydro-1H-cyclopenta[4,5]pyrrolo[1,2-a]pyrazin-2(6H)-yl)-4-fluoro-6-(4,4,5,5-tetramethyl-1,3,2-dioxaborolan-2-yl)benzyl acetate (600 mg, 1.21 mmol), 7-chloro-2-(1-methyl-1H-pyrazol-4-yl)-3H-imidazo[4,5-b]pyridine (282 mg, 1.21 mmol), Pd (dppf)Cl2 (106 mg, 120 umol), NaOAc (297 mg, 3.63 mmol) and K3PO4 (768 mg, 3.63 mmol) in ACN (10 mL) and H2O (5 mL) was degassed and purged with N2 for 3 times, and then the mixture was stirred at 110° C. for 3 hrs under N2 atmosphere. After LC-MS showed the reaction was completed, the reaction mixture was filtered and the solvent was concentrated under reduced pressure to give 2-(7,7-dimethyl-1-oxo-3,4,7,8-tetrahydro-1H-cyclopenta[4,5]pyrrolo[1,2-a]pyrazin-2(6H)-yl)-4-fluoro-6-(2-(1-methyl-1H-pyrazol-4-yl)-3H-imidazo[4,5-b]pyridin-7-yl)benzyl acetate (300 mg, 43.6% yield) which was used for the next step without further purification.

2-(5-fluoro-2-(hydroxymethyl)-3-(2-(1-methyl-1H-pyrazol-4-yl)-3H-imidazo[4,5-b]pyridin-7-yl)phenyl)-7,7-dimethyl-2,3,4,6,7,8-hexahydro-1H-cyclopenta[4,5]pyrrolo[1,2-a]pyrazin-1-one To a solution of 2-(7,7-dimethyl-1-oxo-3,4,7,8-tetrahydro-1H-cyclopenta[4,5]pyrrolo[1,2-a]pyrazin-2(6H)-yl)-4-fluoro-6-(2-(1-methyl-1H-pyrazol-4-yl)-3H-imidazo[4,5-b]pyridin-7-yl)benzyl acetate (300 mg, 528 umol) in THF (10 mL) was added a solution of NaOH (21.1 mg, 528 umol) in H2O (3 mL). The mixture was stirred at 70° C. for 1 hour. After LC-MS showed the reaction was completed, the reaction mixture was concentrated under reduced pressure to give a residue which was purified by preparative HPLC (neutral conditions) to give 2-(5-fluoro-2-(hydroxymethyl)-3-(2-(1-methyl-1H-pyrazol-4-yl)-3H-imidazo[4,5-b]pyridin-7-yl)phenyl)-7,7-dimethyl-2,3,4,6,7,8-hexahydro-1H-cyclopenta[4,5]pyrrolo[1,2-a]pyrazin-1-one (36 mg, 12.9% yield) as a white solid. 1H NMR (400 MHz, DMSO-d6): δ: 8.38 (s, 1H), 8.34 (d, J=4.8 Hz, 1H), 8.07 (s, 1H), 7.45 (d, J=7.6 Hz, 1H), 7.32-7.35 (m, 2H), 6.50 (s, 1H), 4.01-4.27 (m, 6H), 3.92 (s, 3H), 2.56 (s, 2H), 2.41 (s, 2H), 1.21 (s, 6H).

Example 11. 2-(3-(hydroxymethyl)-4-(2-(1-methyl-1H-pyrazol-4-yl)-3H-imidazo[4,5-b]pyridin-7-yl)pyridin-2-yl)-7,7-dimethyl-2,3,4,6,7,8-hexahydro-1H-cyclopenta[4,5]pyrrolo[1,2-a]pyrazin-1-one (11)

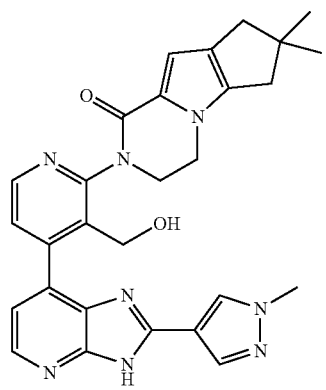 [SMILES: Cn1cc(-c2nc3c(-c4ccnc(N5CCn6c(cc7c6CC(C)(C)C7)C5=O)c4CO)ccnc3[nH]2)cn1]

(2-(7,7-dimethyl-1-oxo-3,4,7,8-tetrahydro-1H-cyclopenta[4,5]pyrrolo[1,2-a]pyrazin-2(6H)-yl)-4-(2-(1-methyl-1H-pyrazol-4-yl)-3H-imidazo[4,5-b]pyridin-7-yl)pyridin-3-yl)methyl acetate A mixture of (2-(7,7-dimethyl-1-oxo-3,4,7,8-tetrahydro-1H-cyclopenta[4,5]pyrrolo[1,2-a]pyrazin-2(6H)-yl)-4-(4,4,5,5-tetramethyl-1,3,2-dioxaborolan-2-yl)pyridin-3-yl)methyl acetate (900.0 mg, 1.88 mmol, 1.00 eq), 7-chloro-2-(1-methyl-1H-pyrazol-4-yl)-3H-imidazo[4,5-b]pyridine (438 mg, 1.88 mmol), Pd (dppf)Cl2 (1.10 g, 1.88 mmol), NaOAc (308 mg, 3.75 mmol) and K3PO4 (796 mg, 3.75 mmol) in dioxane (50 mL) was degassed and purged with N2 for 3 times, and then the mixture was stirred at 110° C. for 2.5 hrs under N₂ atmosphere. After LC-MS showed the reaction was completed, the reaction mixture was filtered and the solvent was concentrated under reduced pressure to give (2-(7,7-dimethyl-1-oxo-3,4,7,8-tetrahydro-1H-cyclopenta[4,5]pyrrolo[1,2-a]pyrazin-2(6H)-yl)-4-(2-(1-methyl-1H-pyrazol-4-yl)-3H-imidazo[4,5-b]pyridin-7-yl)pyridin-3-yl)methyl acetate (900 mg, 86.9% yield) as a red solid which was used for the next step without further purification.

2-(3-(hydroxymethyl)-4-(2-(1-methyl-1H-pyrazol-4-yl)-3H-imidazo[4,5-b]pyridin-7-yl)pyridin-2-yl)-7,7-dimethyl-2,3,4,6,7,8-hexahydro-1H-cyclopenta[4,5]pyrrolo[1,2-a]pyrazin-1-one To a solution of (2-(7,7-dimethyl-1-oxo-3,4,7,8-tetrahydro-1H-cyclopenta[4,5]pyrrolo[1,2-a]pyrazin-2(6H)-yl)-4-(2-(1-methyl-1H-pyrazol-4-yl)-3H-imidazo[4,5-b]pyridin-7-yl)pyridin-3-yl)methyl acetate (900 mg, 1.63 mmol) in THF (10 mL) was added a solution of NaOH (65.2 mg, 1.63 mmol) in H₂O (3 mL). The mixture was stirred at 70° C. for 2 hrs. After LC-MS showed the reaction was completed, the reaction mixture was concentrated under reduced pressure to give a residue, which was purified by preparative HPLC (neutral conditions) to give 2-(3-(hydroxymethyl)-4-(2-(1-methyl-1H-pyrazol-4-yl)-3H-imidazo[4,5-b]pyridin-7-yl)pyridin-2-yl)-7,7-dimethyl-2,3,4,6,7,8-hexahydro-1H-cyclopenta[4,5]pyrrolo[1,2-a]pyrazin-1-one (37.0 mg, 4.46% yield) as a white solid. ¹H NMR (400 MHz, DMSO-d6): δ 8.58 (d, J=5.2 Hz, 1H), 8.32-8.36 (m, 2H), 8.06 (s, 1H), 7.49 (d, J=4.8 Hz, 1H), 7.28 (d, J=5.2 Hz, 1H), 6.55 (s, 1H), 4.15-4.38 (m, 5H), 3.85-3.92 (m, 4H), 2.58 (d, J=6.0 Hz, 2H), 2.43 (s, 2H), 1.22 (s, 6H).

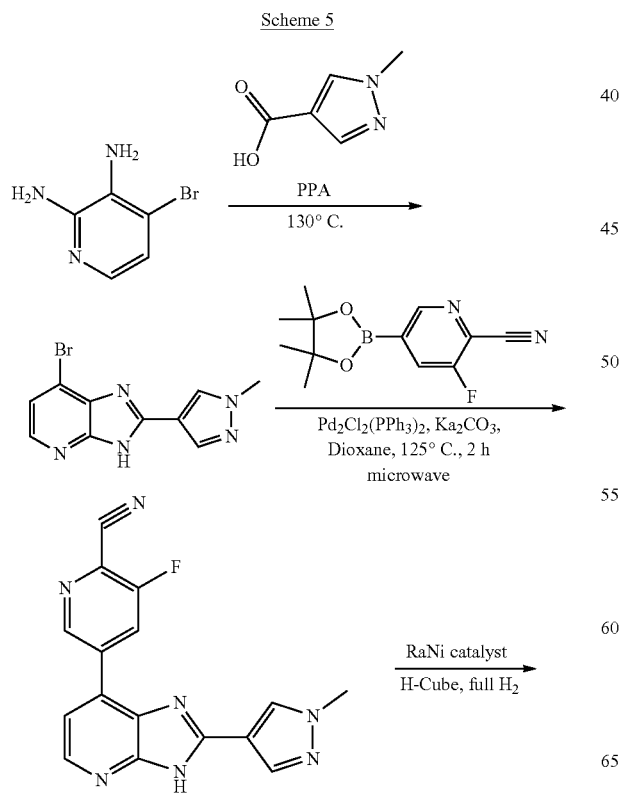

Scheme 5

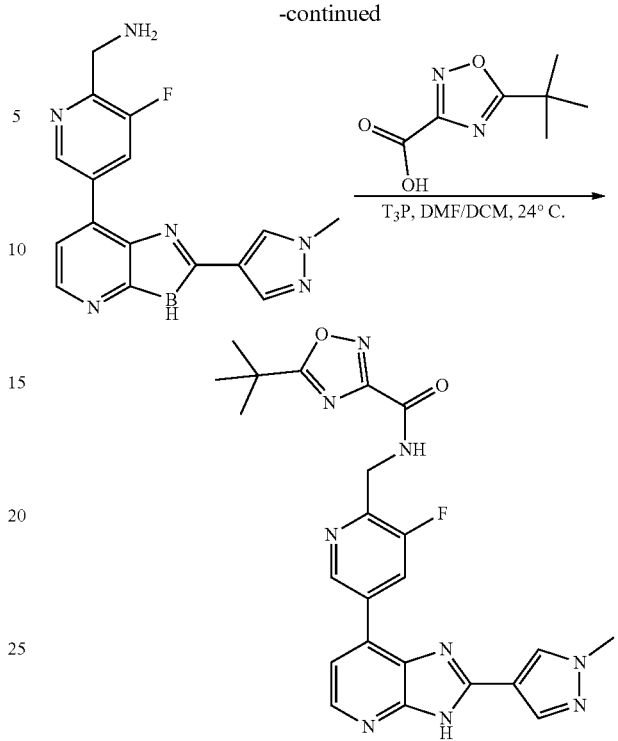

Example 12. 5-tert-Butyl-[1,2,4]oxadiazole-3-carboxylic acid {3-fluoro-5-[2-(1-methyl-1H-pyrazol-4-yl)-3H-imidazo[4,5-b]pyridin-7-yl]-pyridin-2-ylmethyl}-amide (12)

Method C: 7-Bromo-2-(1-methyl-1H-pyrazol-4-yl)-3H-imidazo[4,5-b]pyridine

A mixture of 2,3-diamino-4-bromopyridine (1000.00 mg; 5.32 mmol; 1.00 eq.), 1-methyl-1h-pyrazole-4-carboxylic acid (737.80 mg: 5.85 mmol: 1.10 eq.) and polyphosphoric acid (20.00 g) was heated at 130° C. overnight. LC-MS analysis indicated the reaction was complete. The reaction mixture was dissolved in water/ice (25 ml) and the pH was adjusted with ammonium chloride (1000.00 mg; 18.69 mmol; 3.52 eq.) followed by NaOH (11000.00 mg; 200.02 mmol; 37.61 eq.) (Pellets, portionwise addition, exothermic reaction) to pH=7 when the product precipitated. The suspension was chilled at 5° C. in ice for 30 min then filtered through a plastic filter unit. The precipitate was dried under high vacuum to afford the desired product 7-Bromo-2-(1-methyl-1H-pyrazol-4-yl)-3H-imidazo[4,5-b]pyridine (1293.00 mg; 4.65 mmol) as a beige amorphous solid. MS: m/z=278.1 [M+H]$^+$.

Method D: 3-Fluoro-5-[2-(1-methyl-1H-pyrazol-4-yl)-3H-imidazo[4,5-b]pyridin-7-yl]-pyridine-2-carbonitrile In a microwave vial containing 3-fluoro-5-(4,4,5,5-tetramethyl-1,3,2-dioxaborolan-2-yl)picolinonitrile (256.44 mg; 1.03 mmol; 1.15 eq.), 7-Bromo-2-(1-methyl-1H-pyrazol-4-yl)-3H-imidazo[4,5-b]pyridine (250.00 mg; 0.90 mmol; 1.00 eq.), [1,1'-bis(diphenylphosphino)ferrocene]dichloropalladium(ii), complex with dichloromethane (36.71 mg: 0.04 mmol; 0.05 eq.) and dipotassium carbonate (496.95 mg; 3.60 mmol; 4.00 eq.) was added dioxane (10.00 ml; 117.36 mmol; 130.56 eq.) and water (0.75 ml; 41.63 mmol; 46.31 eq.). The solution was evacuated and backfilled with nitrogen two times then stirred at 125° C. for 2 hours in the microwave reactor (Biotage). LC-MS-5 analysis indicated the reaction was complete. The reaction mixture was filtered and the residue was purified by medium pressure reverse phase chromatography on ARMEN-1 instrument (basic buffer) to afford the desired product 3-Fluoro-5-[2-(1-methyl-1H-pyrazol-4-yl)-3H-imidazo[4,5-b]pyridin-7-yl]-pyridine-2-carbonitrile as a beige amorphous solid. MS: m/z=320.2 [M+H]$^+$.

C-{3-Fluoro-5-[2-(1-methyl-1H-pyrazol-4-yl)-3H-imidazo[4,5-b]pyridin-7-yl]-pyridin-2-yl}-methyl-amineC-{3-Fluoro-5-[2-(1-methyl-1H-pyrazol-4-yl)-3H-imidazo[4,5-b]pyridin-7-yl]-pyridin-2-yl}-methylamine 3-Fluoro-5-[2-(1-methyl-1H-pyrazol-4-yl)-3H-imidazo [4,5-b]pyridin-7-yl]-pyridine-2-carbonitrile (287.02 mg; 0.90 mmol; 1.00 eq.) was dissolved in Methanol (100 ml) and passed through a RaNi catalyst cartridge on H-Cube from ThalesNano (full hydrogen, temperature: 35° C.; flow: 1 ml/min) to afford the desired product C-{3-Fluoro-5-[2-(1-methyl-1H-pyrazol-4-yl)-3H-imidazo[4,5-b]pyridin-7-yl]-pyridin-2-yl}-methylamine (90.00 mg; 0.28 mmol) to be used as such in the next synthetic step. MS: m/z=324.3 [M+H]$^+$.

Method E: 5-tert-Butyl-[1,2,4]oxadiazole-3-carboxylic acid {3-fluoro-5-[2-(1-methyl-1H-pyrazol-4-yl)-3H-imidazo[4,5-b]pyridin-7-yl]-pyridin-2-ylmethyl}-amide In a scintillation vial containing C-{3-Fluoro-5-[2-(1-methyl-1H-pyrazol-4-yl)-3H-imidazo[4,5-b]pyridin-7-yl]-pyridin-2-yl}-methylamine (20.00 mg; 0.06 mmol; 1.00 eq.), 5-tert-butyl-1,2,4-oxadiazole-3-carboxylic acid (13.16 mg; 0.08 mmol; 1.25 eq.), DIPEA (0.03 ml; 0.19 mmol; 3.00 eq.), DCM (10.00 ml) and DMF (1.00 ml) was added 2,4,6-Tripropyl-[1,3,5,2,4,6]trioxatriphosphinane 2,4,6-trioxide (0.05 ml; 0.08 mmol; 1.25 eq.). The reaction mixture was stirred at room temperature for 3 hours. LC-MS-5 analysis indicated the reaction was complete. The solvent was evaporated and the residue was dissolved in methanol/water. Purification by medium pressure reverse phase chromatography on ARMEN-1 instrument (basic buffer, Interchim 15 um particle size 55 g C18-Reverse Phase plastic column; flow: 30 ml/min; gradient: 20-80% water/acetonitrile in 20 min) afforded the desired product 5-tert-Butyl-[1,2,4]oxadiazole-3-carboxylic acid {3-fluoro-5-[2-(1-methyl-1H-pyrazol-4-yl)-3H-imidazo[4,5-b]pyridin-7-yl]-pyridin-2-ylmethyl}-amide (3.10 mg; 0.01 mmol) as a white amorphous solid. MS: m/z=476.2 [M+H]$^+$.

Example 13. 5-tert-Butyl-[1,3,4]oxadiazole-2-carboxylic acid {3-fluoro-5-[2-(1-methyl-1H-pyrazol-4-yl)-3H-imidazo[4,5-b]pyridin-7-yl]-pyridin-2-ylmethyl}-amide (13)

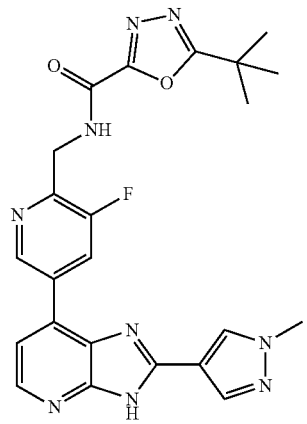 [SMILES: Cn1cc(-c2nc3c(-c4cnc(CNC(=O)c5nnc(C(C)(C)C)o5)c(F)c4)ccnc3[nH]2)cn1]

5-tert-Butyl-[1,3,4]oxadiazole-2-carboxylic acid {3-fluoro-5-[2-(1-methyl-1H-pyrazol-4-yl)-3H-imidazo[4,5-b]pyridin-7-yl]-pyridin-2-ylmethyl-amide (2.50 mg; 0.01 mmol)) was prepared from C-(3-Fluoro-5-[2-(1-methyl-1H-pyrazol-4-yl)-3H-imidazo[4,5-b]pyridin-7-yl]-pyridin-2-yl}-methylamine (20.00 mg; 0.06 mmol; 1.00 eq.) and 5-tert-butyl-1,3,4-oxadiazole-2-carboxylic acid (10.53 mg; 0.06 mmol; 1.00 eq.) using Method E from Example 12. HPLC: 91.5% purity. MS: m/z=476.2 [M+H]+

Scheme 6:

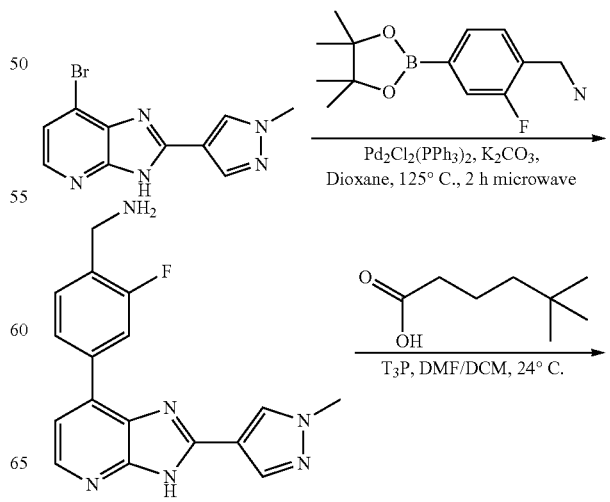

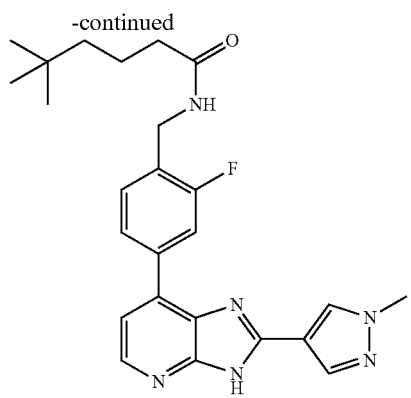

Example 14. 5,5-Dimethyl-hexanoic acid 2-fluoro-4-[2-(1H-pyrazol-4-yl)-3H-imidazo[4,5-b]pyridin-7-yl]-benzylamide (14)

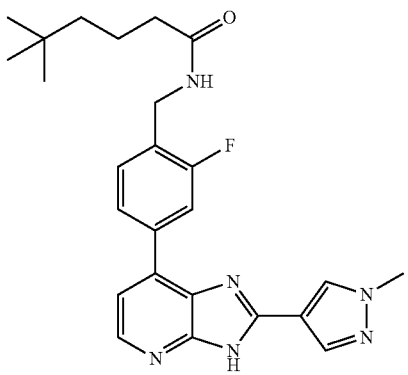 [SMILES: Cn1cc(-c2nc3c(-c4ccc(CNC(=O)CCCC(C)(C)C)c(F)c4)ccnc3[nH]2)cn1]

2-Fluoro-4-[2-(1-methyl-1H-pyrazol-4-yl)-3H-imidazo[4,5-b]pyridin-7-yl]-benzylamine In a microwave vial containing 4-(aminomethyl)-3-fluorophenylboronic acid, HCl salt (221.59 mg; 1.08 mmol; 1.20 eq.), 7-Bromo-2-(1-methyl-1H-pyrazol-4-yl)-3H-imidazo[4,5-b]pyridine (250.00 mg; 0.90 mmol; 1.00 eq.), [1,1'-bis(diphenylphosphino)ferrocene]dichloropalladium(ii), complex with dichloromethane (36.71 mg; 0.04 mmol; 0.05 eq.) and dipotassium carbonate (496.95 mg; 3.60 mmol; 4.00 eq.) was added dioxane (7.00 ml; 117.36 mmol; 130.55 eq.) and water (0.75 ml; 41.63 mmol; 46.31 eq.). The solution was evacuated and backfilled with nitrogen two times then stirred at 125° C. for 2 h in the microwave reactor (Biotage). The reaction mixture was purified by medium pressure reverse phase chromatography to afford the desired product 2-Fluoro-4-[2-(1-methyl-1H-pyrazol-4-yl)-3H-imidazo[4,5-b]pyridin-7-yl]-benzylamine (256.00 mg; 0.79 mmol) as a dark brown solid. HPLC: 95.0% purity. MS: m/z=323.2 [M+H]$^+$ 5,5-Dimethyl-hexanoic acid 2-fluoro-4-[2-(1-methyl-1H-pyrazol-4-yl)-3H-imidazo[4,5-b]pyridin-7-yl]-benzylamide 5,5-Dimethyl-hexanoic acid 2-fluoro-4-[2-(1-methyl-1H-pyrazol-4-yl)-3H-imidazo[4,5-b]pyridin-7-yl]-benzylamide (27.70 mg; 0.06 mmol) was prepared from 2-Fluoro-4-[2-(1-methyl-1H-pyrazol-4-yl)-3H-imidazo[4,5-b]pyridin-7-yl]-benzylamine (25.00 mg; 0.08 mmol; 1.00 eq.) and 5,5-Dimethyl-hexanoic acid (12.30 mg; 0.09 mmol; 1.10 eq.) using Method E from Example 12. HPLC: 99.0% purity. MS: m/z=449.4 [M+H]$^+$. $^1$H NMR (400 MHz, DMSO-d$_6$) δ 8.44 (s, 1H), 8.37 (t, J=5.8 Hz, 1H), 8.33-8.00 (m, 4H), 7.48 (m, 2H), 4.38 (d, J=5.8 Hz, 2H), 3.96 (s, 3H), 2.15 (t, J=7.4 Hz, 2H), 1.62-1.41 (m, 2H), 1.26-1.07 (m, 2H), 0.87 (s, 9H).

Example 15. 4-tert-Butyl-cyclohexanecarboxylic acid 2-fluoro-4-[2-(1-methyl-1H-pyrazol-4-yl)-3H-imidazo[4,5-b]pyridin-7-yl]-benzylamide (15)

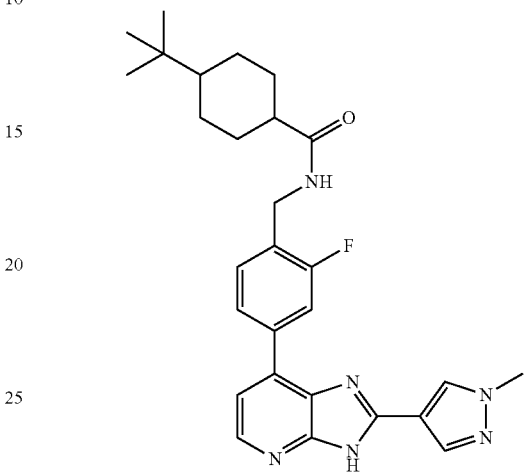

2-fluoro-4-[2-(1-methyl-1H-pyrazol-4-yl)-3H-imidazo[4,5-b]pyridin-7-yl]-benzylamide (15.60 mg; 0.03 mmol, 41.2% yield) was prepared from 2-Fluoro-4-[2-(1-methyl-1H-pyrazol-4-yl)-3H-imidazo[4,5-b]pyridin-7-yl]-benzylamine (25.00 mg: 0.08 mmol; 1.00 eq.) and 4-tert-butylcyclohexanecarboxylic acid (17.86 mg; 0.10 mmol; 1.25 eq.) using Method E from Example 12. HPLC: 99.0% purity. MS: m/z=489.5 [M+H]$^+$. $^1$H NMR (400 MHz, DMSO-d$_6$) δ 8.46 (s, 1H), 8.37-8.06 (m, 4H), 7.70-7.30 (m, 3H), 4.39 (dd, J=11.4, 5.7 Hz, 2H), 3.96 (s, 4H), 2.27-2.01 (m, 1H), 1.94-1.70 (m, 4H), 1.59-1.21 (m, 3H), 1.10-0.90 (m, 4H), 0.90-0.74 (m, 11H).

Example 16. 4-Cyclopentyl-N-{2-fluoro-4-[2-(1-methyl-1H-pyrazol-4-yl)-3H-imidazo[4,5-b]pyridin-7-yl]-benzyl}-butyramide (16)

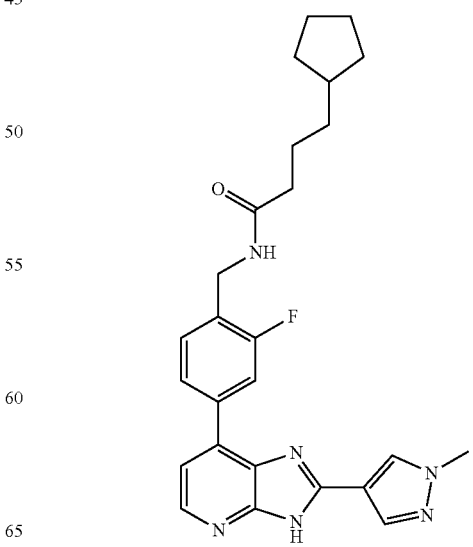

4-Cyclopentyl-N-{2-fluoro-4-[2-(1-methyl-1H-pyrazol-4-yl)-3H-imidazo[4,5-b]pyridin-7-yl]-benzyl}-butyramide (26.00 mg; 0.06 mmol, 72.8% yield) was prepared from 2-Fluoro-4-[2-(1-methyl-1H-pyrazol-4-yl)-3H-imidazo[4,5-b]pyridin-7-yl]-benzylamine (25.00 mg; 0.08 mmol; 1.00 eq.) and 4-Cyclopentyl-butyric acid (13.3 mg; 0.09 mmol; 1.1 eq.) using Method E from Example 12. HPLC: 99.0% purity. MS: m/z=461.4 [M+H]$^+$. $^1$H NMR (400 MHz, DMSO-d$_6$) δ δ 8.45 (s, 1H), 8.37 (t, J=5.8 Hz, 1H), 8.27 (dd, J=17.3, 8.1 Hz, 2H), 8.15 (s, 1H), 7.65-7.33 (m, 2H), 4.38 (d, J=5.8 Hz, 2H), 3.96 (s, 3H), 2.17 (t, J=7.4 Hz, 2H), 1.86-1.64 (m, 3H), 1.64-1.34 (m, 5H), 1.34-1.15 (m, 2H), 1.05 (m, 2H).

Example 17. N-{2-Fluoro-4-[2-(1-methyl-1H-pyrazol-4-yl)-3H-imidazo[4,5-b]pyridin-7-yl]-benzyl}-4-trifluoromethoxy-benzamide (17)

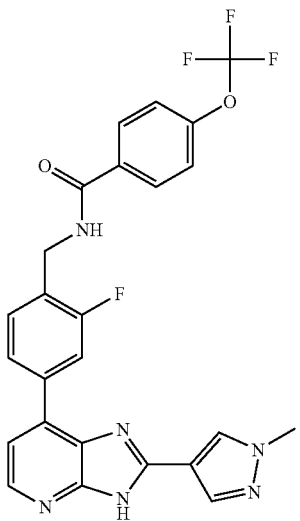 [SMILES: Cn1cc(-c2nc3c(-c4ccc(CNC(=O)c5ccc(OC(F)(F)F)cc5)c(F)c4)ccnc3[nH]2)cn1]

N-{2-Fluoro-4-[2-(1-methyl-1H-pyrazol-4-yl)-3H-imidazo[4,5-b]pyridin-7-yl]-benzyl}-4-trifluoromethoxy-benzamide (21.5 mg, 0.05 nmol, 81.1% yield) was prepared from 2-Fluoro-4-[2-(1-methyl-1H-pyrazol-4-yl)-3H-imidazo[4,5-b]pyridin-7-yl]-benzylamine (25.00 mg: 0.08 mmol: 1.00 eq.) and 4-(trifluoromethoxy)benzoyl chloride (20.9 mg; 0.09 mmol; 1.2 eq.) using Method E from Example 12. HPLC: 99.0% purity. MS: m/z=511.3 [M+H]$^+$. $^1$H NMR (400 MHz, DMSO-d$_6$) δ 10.20 (s, OH), 9.26 (t, J=5.7 Hz, 1H), 8.46 (s, 1H), 8.41-8.24 (m, 2H), 8.16 (d, J=7.4 Hz, 2H), 8.13-7.99 (m, 2H), 7.71-7.37 (m, 4H), 4.62 (d, J=5.7 Hz, 2H), 3.95 (s, 3H).

Example 18. N-{2-Fluoro-4-[2-(1-methyl-1H-pyrazol-4-yl)-3H-imidazo[4,5-b]pyridin-7-yl]-benzyl}-4-trifluoromethoxy-benzamide (18)

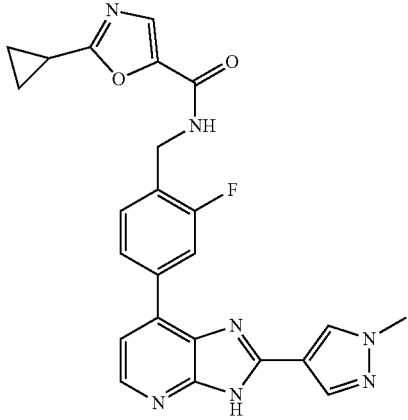 [SMILES: Cn1cc(-c2nc3c(-c4ccc(CNC(=O)c5cnc(C6CC6)o5)c(F)c4)ccnc3[nH]2)cn1]

N-{2-Fluoro-4-[2-(1-methyl-1H-pyrazol-4-yl)-3H-imidazo[4,5-b]pyridin-7-yl]-benzyl}-4-trifluoromethoxy-benzamide (21.0 mg, 0.05 mmol, 59.2% yield) was prepared from 2-Fluoro-4-[2-(1-methyl-1H-pyrazol-4-yl)-3H-imidazo[4,5-b]pyridin-7-yl]-benzylamine (25.00 mg; 0.08 mmol; 1.00 eq.) and 2-Cyclopropyl-oxazole-5-carboxylic acid (14.3 mg; 0.09 mmol; 1.2 eq.) using Method E from Example 12. HPLC: 98.0% purity. MS: m/z=458.3 [M+H]$^+$. $^1$H NMR (400 MHz, DMSO-d$_6$) δ 8.38 (s, 1H), 8.24 (d, J=5.1 Hz, 1H), 8.21-8.09 (m, 2H), 8.09-7.98 (m, 1H), 7.62 (s, 1H), 7.50 (t, J=8.1 Hz, 1H), 7.41 (d, J=5.2 Hz, 1H), 4.55 (s, 2H), 3.93 (s, 3H), 2.25-2.02 (m, 1H), 1.07 (ddt, J=13.6, 7.2, 2.4 Hz, 4H).

Example 19. 5-Methoxy-pyridine-2-carboxylic acid 2-fluoro-4-[2-(1-methyl-1H-pyrazol-4-yl)-3H-imidazo[4,5-b]pyridin-7-yl]-benzylamide (19)

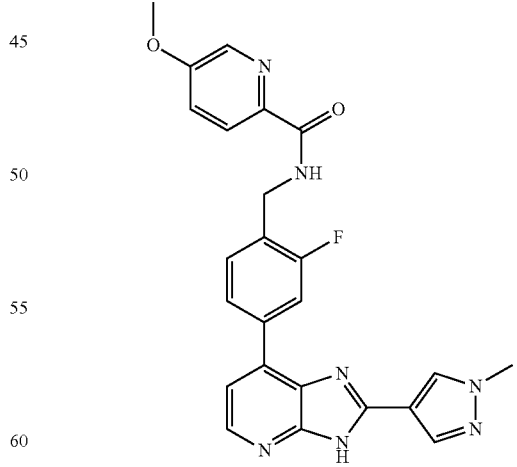

5-Methoxy-pyridine-2-carboxylic acid 2-fluoro-4-[2-(1-methyl-1H-pyrazol-4-yl)-3H-imidazo[4,5-b]pyridin-7-yl]-benzylamide (15.1 mg, 0.03 mmol, 56.0% yield) was prepared from 2-Fluoro-4-[2-(1-methyl-1H-pyrazol-4-yl)-3H-imidazo[4,5-b]pyridin-7-yl]-benzylamine (19.0 mg; 0.06 mmol; 1.00 eq.) and 5-methoxypyridine-2-carboxylic acid (10.8 mg; 0.07 mmol; 1.2 eq.) using Method E from Example 12. HPLC: 99.0% purity. MS: m/z=458.4 [M+H]⁺. ¹H NMR (400 MHz, DMSO-d₆) δ 9.20 (t, J=6.3 Hz, 1H), 8.45 (s, 1H), 8.36 (d, J=2.9 Hz, 1H), 8.29 (d, J=5.2 Hz, 1H), 8.18-7.94 (m, 2H), 7.58 (dd, J=8.8, 2.9 Hz, 1H), 7.50 (t, J=8.0 Hz, 2H), 4.63 (d, J=6.3 Hz, 2H), 3.95 (s, 3H), 3.93 (s, 3H).

Example 20. 1-Ethyl-1H-pyrazole-4-carboxylic acid 2-fluoro-4-[2-(1-methyl-1H-pyrazol-4-yl)-3H-imidazo[4,5-b]pyridin-7-yl]-benzylamide (20)

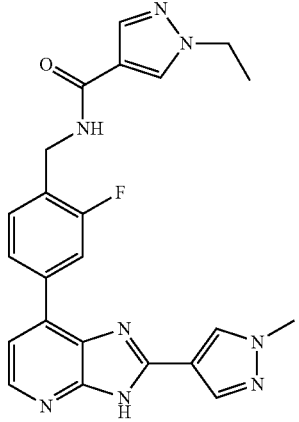 [SMILES: CCn1cc(C(=O)NCc2ccc(-c3ccnc4[nH]c(-c5cnn(C)c5)nc34)cc2F)cn1]

1-Ethyl-1H-pyrazole-4-carboxylic acid 2-fluoro-4-[2-(1-methyl-1H-pyrazol-4-yl)-3H-imidazo[4,5-b]pyridin-7-yl]-benzylamide (21.6 mg, 0.05 mmol, 62.7% yield) was prepared from 2-Fluoro-4-[2-(1-methyl-1H-pyrazol-4-yl)-3H-imidazo[4,5-b]pyridin-7-yl]-benzylamine (25.0 mg; 0.08 mmol; 1.00 eq.) and 1-ethyl-1h-pyrazole-4-carboxylic acid (11.9 mg; 0.09 mmol; 1.1 eq.) using Method E from Example 12. HPLC: 98.0% purity. MS: m/z=445.3 [M+H]⁺. ¹H NMR (400 MHz, DMSO-d₆) δ 8.65 (t, J=5.8 Hz, 1H), 8.44 (s, 1H), 8.37-8.19 (m, 2H), 8.14 (s, 2H), 7.92 (s, 1H), 7.64-7.37 (m, 2H), 4.54 (d, J=5.8 Hz, 2H), 4.17 (q. J=7.3 Hz, 2H), 3.95 (s, 3H), 1.39 (t, J=7.3 Hz, 3H).

Example 21. 4,4-Dimethyl-pentanoic acid 2-fluoro-4-[2-(1-methyl-1H-pyrazol-4-yl)-3H-imidazo[4,5-b]pyridin-7-yl]-benzylamide (21)

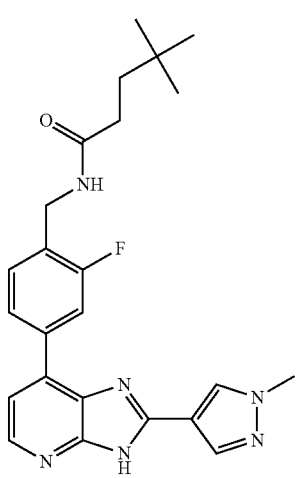 [SMILES: Cn1cc(-c2nc3c(-c4ccc(CNC(=O)CCC(C)(C)C)c(F)c4)ccnc3[nH]2)cn1]

4,4-Dimethyl-pentanoic acid 2-fluoro-4-[2-(1-methyl-1H-pyrazol-4-yl)-3H-imidazo[4,5-b]pyridin-7-yl]-benzylamide (25.8 mg, 0.06 mmol, 76.6% yield) was prepared from 2-Fluoro-4-[2-(1-methyl-1H-pyrazol-4-yl)-3H-imidazo[4,5-b]pyridin-7-yl]-benzylamine (25.0 mg; 0.08 mmol; 1.00 eq.) and 4,4-dimethylpentanoic acid (11.1 mg; 0.09 mmol; 1.1 eq.) using Method E from Example 12. HPLC: 99.0% purity. MS: m/z=435.4 [M+H]⁺. ¹H NMR (400 MHz, DMSO-d₆) δ 8.45 (s, 1H), 8.39 (t, J=5.6 Hz, 1H), 8.34-8.21 (m, 2H), 8.14 (d, J=7.9 Hz, 2H), 7.70-7.29 (m, 2H), 4.37 (d, J=5.7 Hz, 2H), 2.26-2.03 (m, 2H), 1.58-1.33 (m, 2H), 0.88 (s, 9H).

Example 22. 2-Trifluoromethyl-thiazole-4-carboxylic acid 2-fluoro-4-[2-(1-methyl-1H-pyrazol-4-yl)-3H-imidazo[4,5-b]pyridin-7-yl]-benzylamide (22)

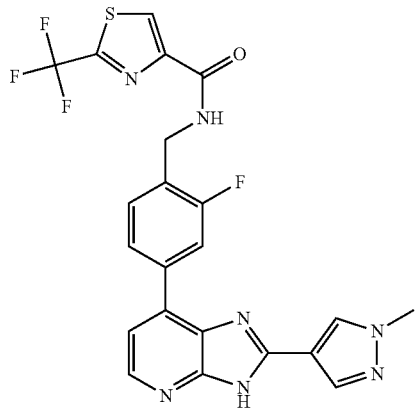 [SMILES: Cn1cc(-c2nc3c(-c4ccc(CNC(=O)c5csc(C(F)(F)F)n5)c(F)c4)ccnc3[nH]2)cn1]

2-Trifluoromethyl-thiazole-4-carboxylic acid 2-fluoro-4-[2-(1-methyl-1H-pyrazol-4-yl)-3H-imidazo[4,5-b]pyridin-7-yl]-benzylamide (11.5 mg, 0.02 mmol, 29.6% yield) was prepared from 2-Fluoro-4-[2-(1-methyl-1H-pyrazol-4-yl)-3H-imidazo[4,5-b]pyridin-7-yl]-benzylamine (25.0 mg; 0.08 mmol; 1.00 eq.) and 2-(trifluoromethyl)-1,3-thiazole-4-carboxylic acid (18.4 mg: 0.09 mmol; 1.2 eq.) using Method E from Example 12. HPLC: 99.0% purity. MS: m/z=435.4 [M+H]⁺. ¹H NMR (400 MHz, DMSO-d₆) δ 9.29 (t, J=6.1 Hz, 1H), 8.75 (s, 1H), 8.46 (s, 1H), 8.27 (dd, J=17.1, 5.9 Hz, 1H), 8.15 (s, 1H), 7.53 (t, J=7.9 Hz, 2H), 4.62 (d, J=6.1 Hz, 2H), 3.95 (s, 3H).

Example 23. 3-tert-Butoxy-N-{2-fluoro-4-[2-(1-methyl-1H-pyrazol-4-yl)-3H-imidazo[4,5-b]pyridin-7-yl]-benzyl}-propionamide (23)

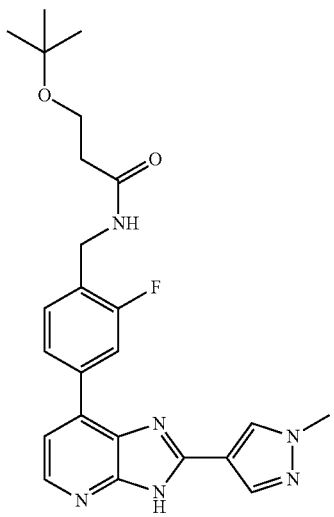 [SMILES: Cn1cc(-c2nc3c(-c4ccc(CNC(=O)CCOC(C)(C)C)c(F)c4)ccnc3[nH]2)cn1]

3-tert-Butoxy-N-{2-fluoro-4-[2-(1-methyl-1H-pyrazol-4-yl)-3H-imidazo[4,5-b]pyridin-7-yl]-benzyl}-propionamide (21.2 mg, 0.05 mmol, 60.7% yield)) was prepared from 2-Fluoro-4-[2-(1-methyl-1H-pyrazol-4-yl)-3H-imidazo[4,5-b]pyridin-7-yl]-benzylamine (25.0 mg; 0.08 mmol: 1.00 eq.) and 2-(trifluoromethyl)-1,3-thiazole-4-carboxylic acid (18.4 mg; 0.09 mmol; 1.2 eq.) using Method E from Example 12. HPLC: 99.0% purity. MS: m/z=451.4 [M+H]$^+$. $^1$H NMR (400 MHz, DMSO-d$_6$) δ 8.43 (s, 1H), 8.40 (t, J=5.9 Hz, 1H), 8.29 (d, J=5.2 Hz, 1H), 8.14 (d, J=0.7 Hz, 1H), 7.52 (t, J=8.1 Hz, 2H), 4.40 (d, J=5.8 Hz, 2H), 3.96 (s, 3H), 3.58 (t, J=6.3 Hz, 2H), 2.36 (t, J=6.3 Hz, 2H), 1.16 (s, 9H).

Example 24. 5-tert-Butyl-[1,3,4]oxadiazole-2-carboxylic acid 4-(2-cyclopropyl-3H-imidazo[4,5-b]pyridin-7-yl)-2-fluoro-benzylamide (24)

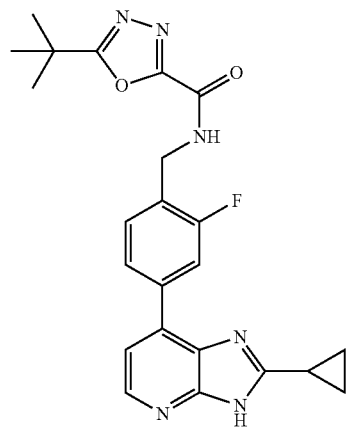 [SMILES: CC(C)(C)c1nnc(C(=O)NCc2ccc(-c3ccnc4[nH]c(C5CC5)nc34)cc2F)o1]

7-Chloro-2-cyclopropyl-3H-imidazo[4,5-b]pyridine

7-Chloro-2-cyclopropyl-3H-imidazo[4,5-b]pyridine (255.0 mg, 1.32 mmol, 63.0% yield) was obtained from 4-Chloro-pyridine-2,3-diamine (300.0 mg, 2.1 mmol, 1 eq) and cyclopropanecarboxylic acid (269.83 mg, 3.13 mmol, 1.5 eq) using Method C from Example 12. HPLC: 94.0% purity. MS: m/z=194.1 [M+H]$^+$. $^1$H NMR (400 MHz, DMSO-d$_6$) δ 13.12 (s, 1H, exch.), 8.14 (d, J=5.3 Hz, 1H), 7.27 (d, J=5.3 Hz, 1H), 2.16 (tt, J=7.7, 5.3 Hz, 1H), 1.13 (dtd, J=7.5, 4.2, 2.0 Hz, 4H).

4-(2-Cyclopropyl-3H-imidazo[4,5-b]pyridin-7-yl)-2-fluoro-benzylamine 4-(2-Cyclopropyl-3H-imidazo[4,5-b]pyridin-7-yl)-2-fluoro-benzylamine (168.4 mg, 0.6 mmol, 66.0% yield) was obtained from 7-Chloro-2-cyclopropyl-3H-imidazo[4,5-b]pyridine (175.0 mg, 0.9 mmol, 1 eq) and 4-(aminomethyl)-3-fluorophenylboronic acid, HCl salt (222.8 mg, 1.1 mmol, 1.2 eq) using Method D from Example 12. HPLC: 91.0% purity. MS: m/z=283.3 [M+H]$^+$. $^1$H NMR (400 MHz, DMSO-d$_6$) δ 8.40-7.87 (m, 2H), 7.64 (t, J=8.1 Hz, 1H), 7.48 (s, 1H), 3.85 (s, 2H), 2.28-2.09 (m, 1H), 1.13 (d, J=6.7 Hz, 4H).

5-tert-Butyl-[1,3,4]oxadiazole-2-carboxylic acid 4-(2-cyclopropyl-3H-imidazo[4,5-b]pyridin-7-yl)-2-fluoro-benzylamide 5-tert-Butyl-[1,3,4]oxadiazole-2-carboxylic acid 4-(2-cyclopropyl-3H-imidazo[4,5-b]pyridin-7-yl)-2-fluoro-benzylamide (17.5 mg, 0.04 mmol, 45.4% yield) was obtained from 4-(2-Cyclopropyl-3H-imidazo[4,5-b]pyridin-7-yl)-2-fluoro-benzylamine (25.0 mg, 0.09 mmol, 1.0 eq) and 5-tert-butyl-1,3,4-oxadiazole-2-carboxylic acid (18.1 mg, 0.1 mmol, 1.2 eq) using Method E from Example 12. HPLC: 92.0% purity. MS: m/z=435.4 [M+H]$^+$. $^1$H NMR (400 MHz, DMSO-d$_6$) δ 9.84 (s, 1H), 8.50-8.15 (m, 2H), 8.09 (d, J=8.1 Hz, 1H), 7.77-7.40 (m, 2H), 4.58 (d, J=5.7 Hz, 2H), 2.19 (td, J=9.0, 7.8, 4.5 Hz, 1H), 1.41 (s, 9H), 1.13 (m, 4H).

Example 25. 6-tert-Butyl-N-[4-(2-cyclopropyl-3H-imidazo[4,5-b]pyridin-7-yl)-2-fluoro-benzyl]-nicotinamide (25)

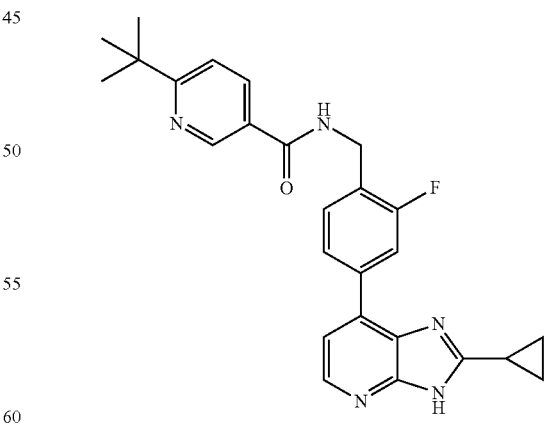

6-tert-Butyl-N-[4-(2-cyclopropyl-3H-imidazo[4,5-b]pyridin-7-yl)-2-fluoro-benzyl]-nicotinamide (23.4 mg, 0.05 mmol, 49.7% yield) was obtained using 4-(2-Cyclopropyl-3H-imidazo[4,5-b]pyridin-7-yl)-2-fluoro-benzylamine (30 mg, 0.1 mmol, 1 eq) and 6-tert-butylnicotinic acid (23.8 mg, 0.13 mmol, 1.25 eq) using Method E from Example 12.

HPLC: 95.5% purity. MS: m/z=444.2 [M+H]+. 1H NMR (400 MHz, DMSO-d6) δ 9.21 (t, J=5.8 Hz, 1H), 9.01 (dd, J=2.5, 0.9 Hz, 1H), 8.36-7.92 (m, 4H), 7.66-7.31 (m, 3H), 4.61 (d, J=5.7 Hz, 2H), 2.19 (tt, J=7.6, 6.1 Hz, 1H), 1.35 (s, 9H), 1.18-1.03 (m, 4H).

Example 26. 4-tert-Butyl-N-[4-(2-cyclopropyl-3H-imidazo[4,5-b]pyridin-7-yl)-2-fluoro-benzyl]-benzamide (26)

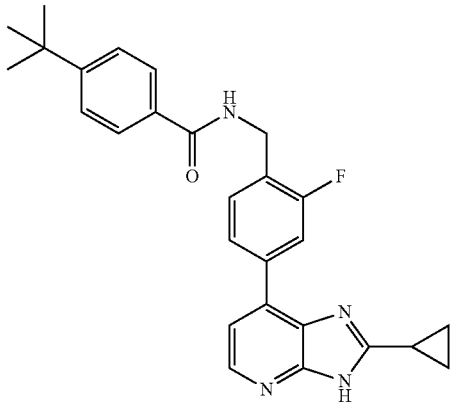 [SMILES: CC(C)(C)c1ccc(C(=O)NCc2ccc(-c3ccnc4[nH]c(C5CC5)nc34)cc2F)cc1]

4-tert-Butyl-N-[4-(2-cyclopropyl-3H-imidazo[4,5-b]pyridin-7-yl)-2-fluoro-benzyl]-benzamide was obtained using 4-(2-Cyclopropyl-3H-imidazo[4,5-b]pyridin-7-yl)-2-fluoro-benzylamine (20 mg, 0.07 mmol, 1 eq) and 4-tert-butylbenzoyl chloride (17.42 mg, 0.09 mmol, 1.25 eq) using Method E from Example 12. HPLC: 93.7% purity. MS: m/z=443.2 [M+H]+. 1H NMR (400 MHz, DMSO-d6) δ 9.02 (s, 1H), 8.36-8.16 (m, 1H), 8.07 (d, J=8.0 Hz, 1H), 7.97-7.82 (m, 2H), 7.68-7.35 (m, 3H), 4.59 (d, J=5.7 Hz, 2H), 2.19 (p, J=6.7 Hz, 1H), 1.32 (s, 9H), 1.17-1.02 (m, 4H).

Example 27. 5-tert-Butyl-[1,2,4]oxadiazole-3-carboxylic acid 4-(2-cyclopropyl-3H-imidazo[4,5-b]pyridin-7-yl)-2-fluoro-benzylamide (27)

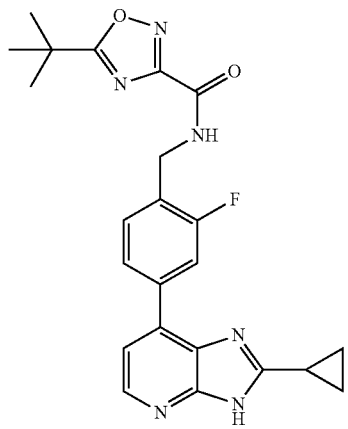 [SMILES: CC(C)(C)c1nc(C(=O)NCc2ccc(-c3ccnc4[nH]c(C5CC5)nc34)cc2F)no1]

5-tert-Butyl-[1,2,4]oxadiazole-3-carboxylic acid 4-(2-cyclopropyl-3H-imidazo[4,5-b]pyridin-7-yl)-2-fluoro-benzylamide was obtained using 4-(2-Cyclopropyl-3H-imidazo[4,5-b]pyridin-7-yl)-2-fluoro-benzylamine (25.0 mg, 0.09 mmol, 1 eq) and 5-tert-butyl-1,2,4-oxadiazole-3-carboxylic acid (18.84 mg, 0.11 mmol, 1.25 eq) using Method E from Example 12. HPLC: 95.4% purity. MS: m/z=435.4 [M+H]+.

Example 28. 3-tert-Butyl-[1,2,4]oxadiazole-5-carboxylic acid 4-(2-cyclopropyl-3H-imidazo[4,5-b]pyridin-7-yl)-2-fluoro-benzylamide (28)

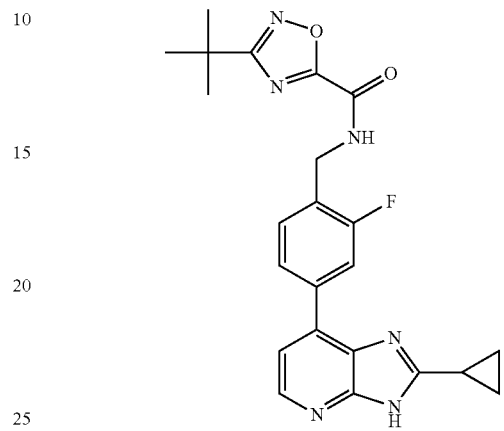

3-tert-Butyl-[1,2,4]oxadiazole-5-carboxylic acid 4-(2-cyclopropyl-3H-imidazo[4,5-b]pyridin-7-yl)-2-fluoro-benzylamide (13.0 mg, 0.03 mmol, 33.8% yield) was obtained using 4-(2-Cyclopropyl-3H-imidazo[4,5-b]pyridin-7-yl)-2-fluoro-benzylamine (25.0 mg, 0.09 mmol, 1 eq) and 3-tert-butyl-1,2,4-oxadiazole-5-carboxylic acid (18.1 mg, 0.11 mmol, 1.2 eq) using Method E from Example 12. HPLC: 96.0% purity. MS: m/z=435.3 [M+H]+. 1H NMR (400 MHz, DMSO-d6) δ 9.91 (s, 1H), 8.38-7.91 (m, 2H), 7.80-7.24 (m, 2H), 4.59 (s, 2H), 2.24-2.11 (m, 1H), 1.37 (s, 9H), 1.13 (m, 4H).

Example 29. 5-tert-Butyl-isoxazole-3-carboxylic acid 2-fluoro-4-[2-(2-oxo-piperidin-4-yl)-3H-imidazo[4,5-b]pyridin-7-yl]-benzylamide (29)

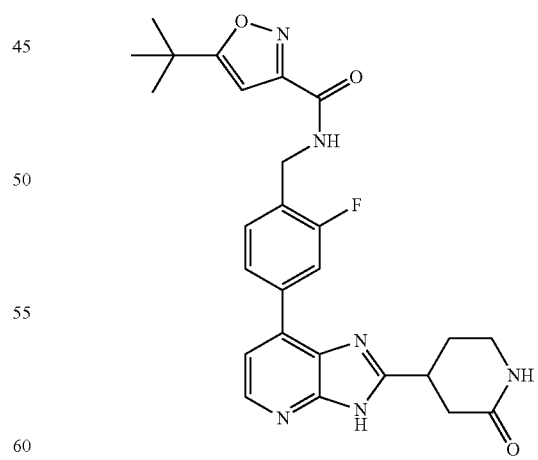

4-(7-Chloro-3H-imidazo[4,5-b]pyridin-2-yl)-piperidin-2-one 4-(7-Chloro-3H-imidazo[4,5-b]pyridin-2-yl)-piperidin-2-one (519 mg, 2.1 mmol, 99.1% yield) was obtained from 4-Chloro-pyridine-2,3-diamine (300.0 mg, 2.1 mmol, 1 eq) and 2-oxopiperidine-4-carboxylic acid (358.9 mg, 2.5 mmol, 1.2 eq) using Method C from Example 12. HPLC: 94.0% purity. MS: m/z=251.2 [M+H]⁺. ¹H NMR (400 MHz, DMSO-d₆) δ 8.23 (d, J=5.3 Hz, 1H), 7.60 (s, 1H), 7.34 (d, J=5.3 Hz, 1H), 3.63-3.04 (m, 3H), 2.62 (d, J=7.8 Hz, 2H), 2.21 (m, 1H), 2.09-1.82 (m, 1H).

4-[7-(4-Aminomethyl-3-fluoro-phenyl)-3H-imidazo[4,5-b]pyridin-2-yl]-piperidin-2-one 4-[7-(4-Aminomethyl-3-fluoro-phenyl)-3H-imidazo[4,5-b]pyridin-2-yl]-piperidin-2-one (128.2 mg, 0.38 mmol, 54.1% yield) was obtained from 4-(7-Chloro-3H-imidazo[4,5-b]pyridin-2-yl)-piperidin-2-one (175.0 mg, 0.7 mmol, 1 eq) and 4-(aminomethyl)-3-fluorophenylboronic acid, HCl salt (172.1 mg, 1.2 mmol, 1.2 eq) using Method D from Example 12. HPLC: 99.0% purity. MS: m/z=340.1 [M+H]⁺.

5-tert-Butyl-isoxazole-3-carboxylic acid 2-fluoro-4-[2-(2-oxo-piperidin-4-yl)-3H-imidazo[4,5-b]pyridin-7-yl]-benzylamide 5-tert-Butyl-isoxazole-3-carboxylic acid 2-fluoro-4-[2-(2-oxo-piperidin-4-yl)-3H-imidazo[4,5-b]pyridin-7-yl]-benzylamide (23.0 mg, 0.05 mmol, 53.0% yield) was obtained using 4-[7-(4-Aminomethyl-3-fluoro-phenyl)-3H-imidazo[4,5-b]pyridin-2-yl]-piperidin-2-one (30.0 mg, 0.09 mmol, 1.0 eq) and 5-tert-butylisoxazole-3-carboxylic acid (15.0 mg, 0.09 mmol, 1.0 eq) using Method E from Example 12. HPLC: 99.0% purity. MS: m/z=491.5 [M+H]⁺.

Example 30. 5-tert-Butyl-[1,2,4]oxadiazole-3-carboxylic acid 2-fluoro-4-[2-(2-oxo-piperidin-4-yl)-3H-imidazo[4,5-b]pyridin-7-yl]-benzylamide (30)

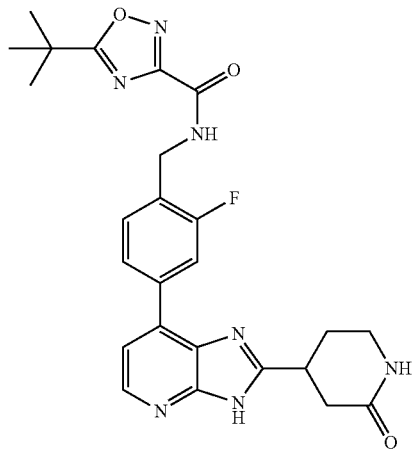 [SMILES: CC(C)(C)c1nc(C(=O)NCc2ccc(-c3ccnc4[nH]c(C5CCNC(=O)C5)nc34)cc2F)no1]

5-tert-Butyl-[1,2,4]oxadiazole-3-carboxylic acid 2-fluoro-4-[2-(2-oxo-piperidin-4-yl)-3H-imidazo[4,5-b]pyridin-7-yl]-benzylamide (7.0 mg, 0.01 mmol, 16.1% yield) was obtained using 4-[7-(4-Aminomethyl-3-fluoro-phenyl)-3H-imidazo[4,5-b]pyridin-2-yl]-piperidin-2-one (30.0 mg, 0.09 mmol, 1.0 eq) and 5-tert-butyl-1,2,4-oxadiazole-3-carboxylic acid (13.5 mg, 0.08 mmol, 0.9 eq) using Method E from Example 12. HPLC: 99.0% purity. MS: m/z=492.5 [M+H]⁺. ¹H NMR (400 MHz, DMSO-d₆) δ 9.52 (t, J=6.0 Hz, 1H), 8.46-7.91 (m, 3H), 7.79-7.40 (m, 3H), 4.59 (d, J=5.8 Hz, 2H), 3.33 (m, 3H), 2.72-2.55 (m, 1H), 2.32-1.87 (m, 2H), 1.44 (s, 9H).

Example 31. 3-tert-Butyl-[1,2,4]oxadiazole-5-carboxylic acid 2-fluoro-4-[2-(2-oxo-piperidin-4-yl)-3H-imidazo[4,5-b]pyridin-7-yl]-benzylamide (31)

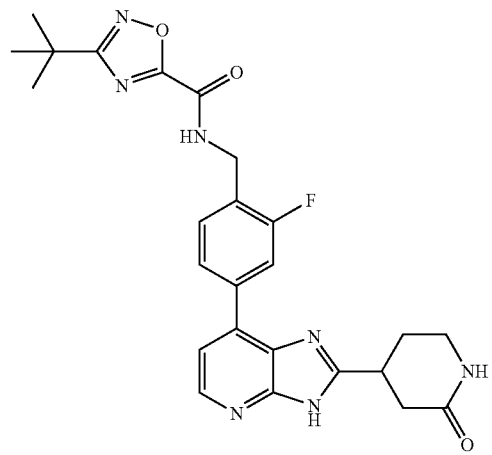 [SMILES: CC(C)(C)c1noc(C(=O)NCc2ccc(-c3ccnc4[nH]c(C5CCNC(=O)C5)nc34)cc2F)n1]

3-tert-Butyl-[1,2,4]oxadiazole-5-carboxylic acid 2-fluoro-4-[2-(2-oxo-piperidin-4-yl)-3H-imidazo[4,5-b]pyridin-7-yl]-benzylamide (15.0 mg, 0.03 mmol, 25.5% yield) was obtained using 4-[7-(4-Aminomethyl-3-fluoro-phenyl)-3H-imidazo[4,5-b]pyridin-2-yl]-piperidin-2-one (30.0 mg, 0.12 mmol, 1.0 eq) and [4-[[(3-tert-butyl-1,2,4-oxadiazole-5-carbonyl)amino]methyl]-3-fluoro-phenyl]boronic acid (38.4 mg, 0.12 mmol, 1.0 eq) using Method E from Example 12. HPLC: 95.0% purity. MS: m/z=492.4 [M+H]⁺.

Example 32. {2-Fluoro-4-[2-(1-methyl-1H-pyrazol-4-yl)-3H-imidazo[4,5-b]pyridin-7-yl]-phenyl}-methanol (32)

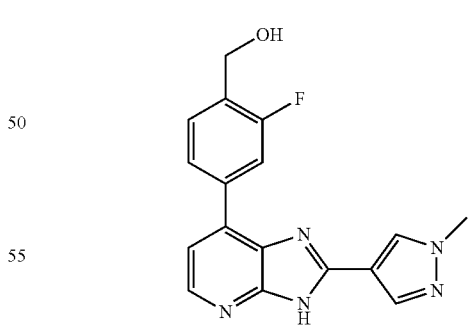

2-Fluoro-4-[2-(1-methyl-1H-pyrazol-4-yl)-3H-imidazo[4,5-b]pyridin-7-yl]-phenyl-methanol (60.0 mg, 0.19 mmol, 51.6% yield) was obtained from 7-Bromo-2-(1-methyl-1H-pyrazol-4-yl)-3H-imidazo[4,5-b]pyridine (100.0 mg, 0.36 mmol, 1 eq) and (3-fluoro-4-(hydroxymethyl)phenyl)boronic acid (170.0 mg, 1.2 mmol, 1.2 eq) using Method D from Example 12. HPLC: 98.0% purity. MS: m/z=324.3 [M+H]⁺.

Scheme 7

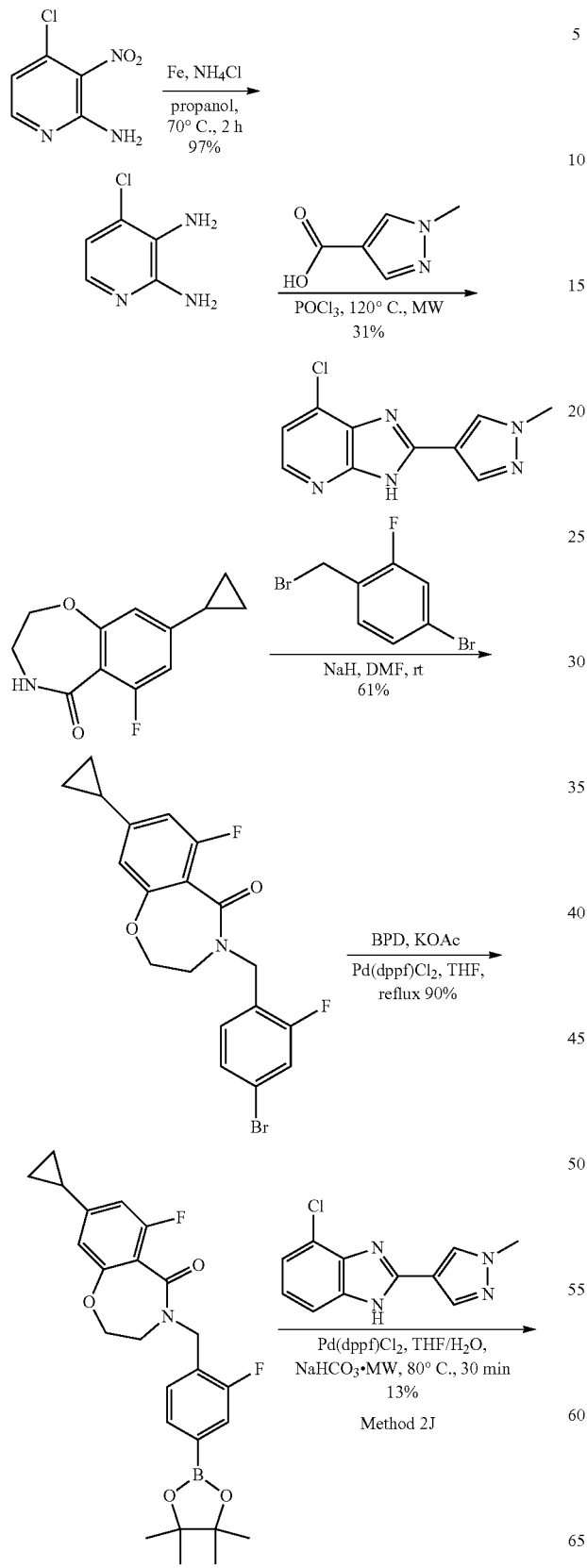

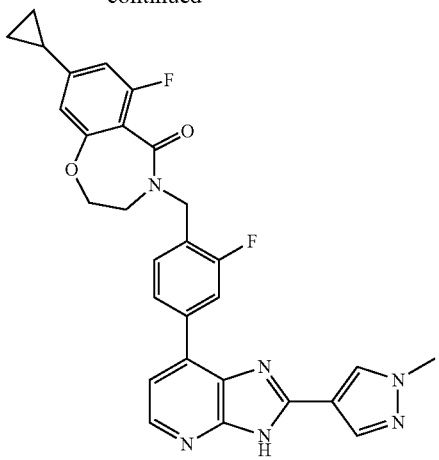

Example 34. 8-Cyclopropyl-6-fluoro-4-([2-fluoro-4-[2-(1-methyl-1H-pyrazol-4-yl)-3H-imidazo[4,5-b]pyridin-7-yl]phenyl]methyl)-2,3,4,5-tetrahydro-1,4-benzoxazepin-5-one (34)

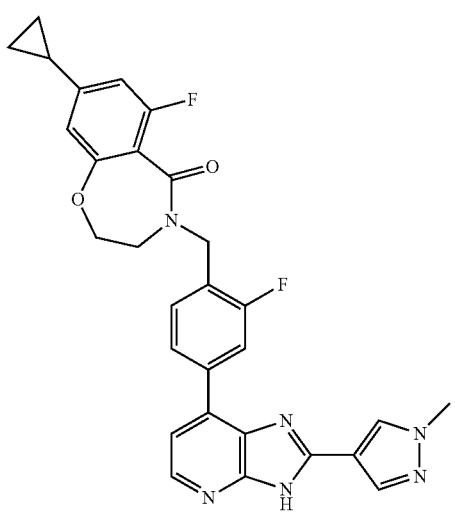 [SMILES: Cn1cc(-c2nc3c(-c4ccc(CN5CCOc6cc(C7CC7)cc(F)c6C5=O)c(F)c4)ccnc3[nH]2)cn1]

4-Chloropyridine-2,3-diamine

In a 100-mL round bottom flask, 4-chloro-3-nitropyridin-2-amine (2 g, 11.52 mmol, 1.00 equiv) was dissolved in propanol (20 mL) and water (10 mL), to which was added Fe powder (3.23 g, 57.84 mmol, 5.02 equiv) and NH₄Cl (3.06 g, 57.21 mmol, 4.96 equiv) in sequence at room temperature. The resulting mixture was stirred for 2 h at 70° C. After the reaction was done, the reaction mixture was cooled to room temperature and filtered through a Celite pad. The filtrate was concentrated under reduced pressure to afford 4-chloropyridine-2,3-diamine (1.6 g, 97%) as black solid.

4-[7-Chloro-3H-imidazo[4,5-b]pyridin-2-yl]-1-methyl-1H-pyrazole

In a 30-mL sealed tube, 4-chloropyridine-2,3-diamine (300 mg, 2.09 mm ol, 1.00 equiv) and 1-methyl-1H-pyrazole-4-carboxylic acid (264 mg, 2.09 mmol, 1.00 equiv) were mixed in POCl$_3$ (8 mL) at room temperature. The mixture was irradiated with microwave for 30 min at 120° C. After the reaction was done, the reaction mixture was cooled to room temperature and concentrated under reduced pressure. The residue was purified by reverse phase flash chromatography using the following conditions: column, C18 silica gel; mobile phase, methanol in water, 0% to 50% gradient in 20 min; detector, UV 254 nm. 4-[7-chloro-3H-imidazo[4,5-b]pyridin-2-yl]-1-methyl-1H-pyrazole 1 (50 mg, 31%) was obtained as brown solid.

4-[(4-Bromo-2-fluorophenyl)methyl]-8-cyclopropyl-6-fluoro-2,3,4,5-tetrahydro-1,4-benzoxazepin-5-one In a 50-mL round bottom flask, 8-cyclopropyl-6-fluoro-2,3,4,5-tetrahydro-1,4-benzoxazepin-5-one (400 mg, 1.81 mmol, 1.00 equiv) was dissolved in N,N-dimethylformamide (8 mL), to which was added sodium hydride (60% in oil, 144.8 mg, 3.62 mmol, 2.00 equiv) slowly at 0° C. The mixture was stirred for 1 h at room temperature, and then was cooled to 0° C. again and was added by 4-bromo-1-(bromomethyl)-2-fluorobenzene (577.7 mg, 2.16 mmol, 1.19 equiv). The reaction mixture was allowed to warm up to room temperature and stirred for 4 h at room temperature. When the reaction was done, it was quenched by 20 mL water and the mixture was extracted with ethyl acetate (3×30 mL). The combined organic layer was dried over sodium sulfate, dried over sodium sulfate and concentrated under reduced pressure. The residue was purified in a silica gel column eluting with ethyl acetate in petroleum ether (10% to 60% gradient) to afford 4-[(4-bromo-2-fluorophenyl)methyl]-8-cyclopropyl-6-fluoro-2,3,4,5-tetrahydro-1,4-benzoxazepin-5-one (450 mg, 61%) as white solid. MS: m/z=408.1 [M+H]$^+$ 8-Cyclopropyl-6-fluoro-4-[[2-fluoro-4-(tetramethyl-1,3,2-dioxaborolan-2-yl)phenyl]methyl]-2,3,4,5-tetrahydro-1,4-benzoxazepin-5-one In a 30-mL sealed tube, 4-[(4-bromo-2-fluorophenyl)methyl]-8-cyclopropyl-6-fluoro-2,3,4,5-tetrahydro-1,4-benzoxazepin-5-one (200 mg, 0.49 mmol, 1.00 equiv), 4,4,5,5-tetramethyl-2-(tetramethyl-1,3,2-dioxaborolan-2-yl)-1,3,2-dioxaborolane (149.8 mg, 0.59 mmol, 1.20 equiv), Pd(dppf)Cl$_2$.CH$_2$Cl$_2$ (40.9 mg, 0.05 mmol, 0.10 equiv) and KOAc (96.1 mg, 0.98 mmol, 2.00 equiv) were mixed in dioxane (8 mL) at room temperature. The resulting mixture was stirred for 5 h at 90° C. After the reaction was done, the reaction mixture was cooled to room temperature, diluted with 30 mL water and extracted with ethyl acetate (3×100 mL). The organic layers were combined, dried over sodium sulfate and concentrated under reduced pressure to afford 8-cyclopropyl-6-fluoro-4-[[2-fluoro-4-(tetramethyl-1,3,2-dioxaborolan-2-yl)phenyl]methyl]-2,3,4,5-tetrahydro-1,4-benzoxazepin-5-one (200 mg, 90%) as yellow oil.

Method 2J: 8-Cyclopropyl-6-fluoro-4-([2-fluoro-4-[2-(1-methyl-1H-pyrazol-4-yl)-3H-imidazo[4,5-b]pyridin-7-yl]phenyl]methyl)-2,3,45-tetrahydro-1,4-benzoxazepin-5-one In a 30-mL sealed tube purged and maintained with an inert atmosphere of argon, 8-cyclopropyl-6-fluoro-4-[[2-fluoro-4-(tetramethyl-1,3,2-dioxaborolan-2-yl)phenyl]methyl]-2,3,4,5-tetrahydro-1,4-benzoxazepin-5-one (200 mg, 0.44 mmol, 1.00 equiv), 4-[7-chloro-3H-imidazo[4,5-b]pyridin-2-yl]-1-methyl-1H-pyrazole (112.7 mg, 0.48 mmol, 1.10 equiv), sodium carbonate (98.3 mg, 0.93 mmol, 2.11 equiv) and Pd(dppf)Cl$_2$.CH$_2$Cl$_2$ (35.9 mg, 0.04 mmol, 0.10 equiv) were mixed in tetrahydrofuran (18 mL) and water (2 mL) at room temperature. The reaction mixture was irradiated with microwave for 1 h at 90° C. When the reaction was done, the reaction was quenched with 15 mL water and the resulting mixture was extracted with ethyl acetate (3×50 mL). The organic layers were combined, dried over sodium sulfate and concentrated under reduced pressure. The residue was purified by prep-HPLC with the following conditions: column, XBridge C18 OBD Prep Column, 5 um, 19 mm×150 mm; mobile phase, acetonitrile in water (with 10 mM NH$_4$HCO$_3$); 33% to 46% gradient in 8 min; detector, UV 254 nm. 8-cyclopropyl-6-fluoro-4-([2-fluoro-4-[2-(1-methyl-1H-pyrazol-4-yl)-3H-imidazo[4,5-b]pyridin-7-yl]phenyl]methyl)-2,3,4,5-tetrahydro-1,4-benzoxazepin-5-one (30 mg, 13%) was obtained as off-white solid. HPLC: 99.1% purity. MS: m/z=527.3 [M+H]$^+$. $^1$H NMR (400 MHz, DMSO-d$_6$): δ 8.44 (s, 1H), 8.37-8.16 (m, 3H), 8.14 (d, J=6.7 Hz, 1H), 7.53-7.51 (m, 2H), 6.92-6.73 (m, 1H), 6.68 (s, 1H), 4.86 (s, 2H), 4.43-4.13 (m, 2H), 3.93 (s, 3H), 3.71-3.51 (m, 2H), 2.01-1.95 (m, 1H), 1.10-0.94 (m, 2H), 0.85-0.57 (m, 2H).

Scheme 8

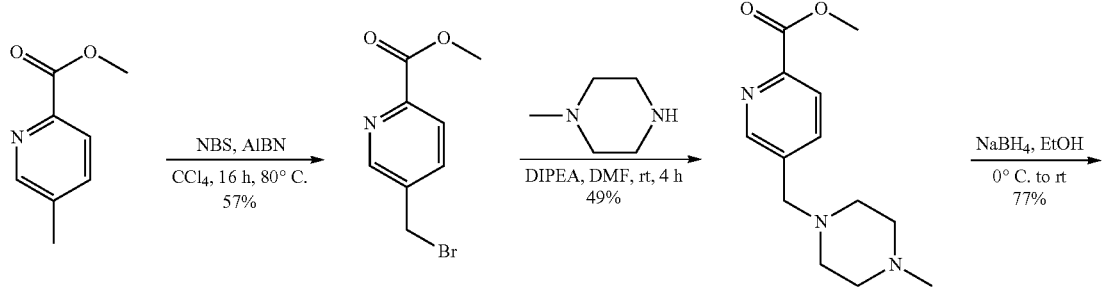

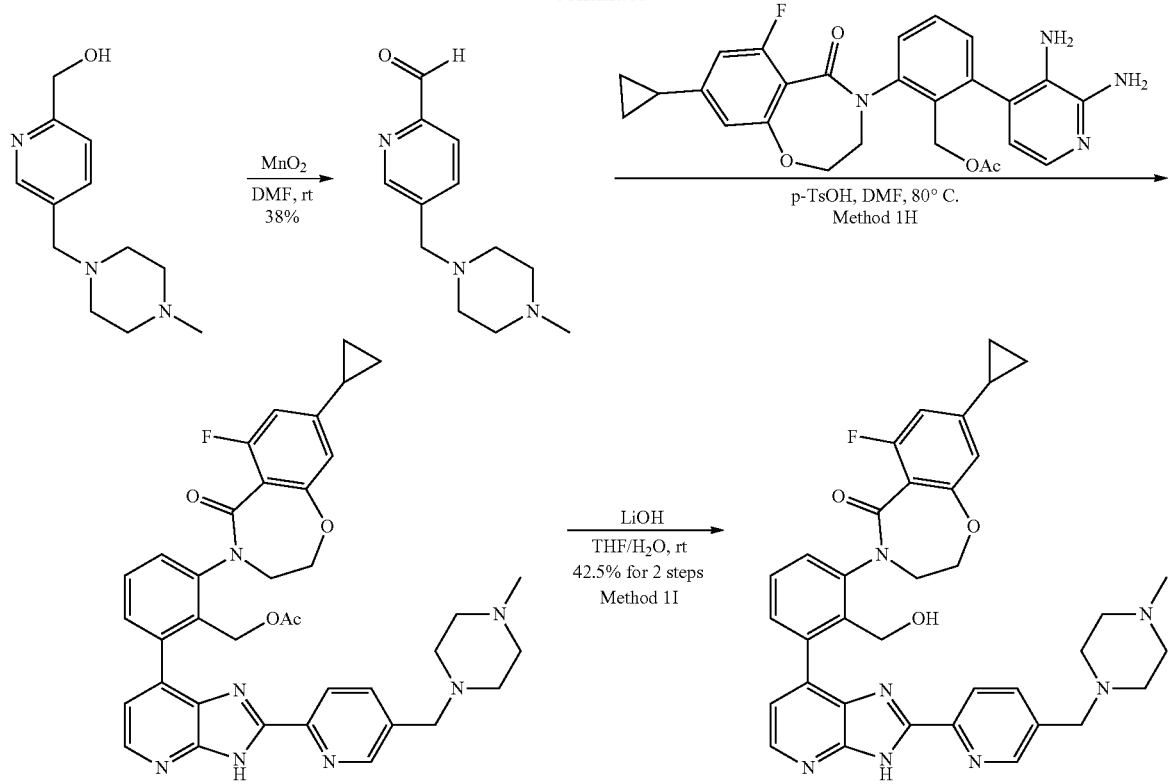

Example 35. 8-Cyclopropyl-6-fluoro-4-[2-(hydroxymethyl)-3-(2-[5-[(4-methylpiperazin-1-yl)methyl]pyridin-2-yl]-3H-imidazo[4,5-b]pyridin-7-yl)phenyl]-2,3,4,5-tetrahydro-1,4-benzoxazepin-5-one (35)

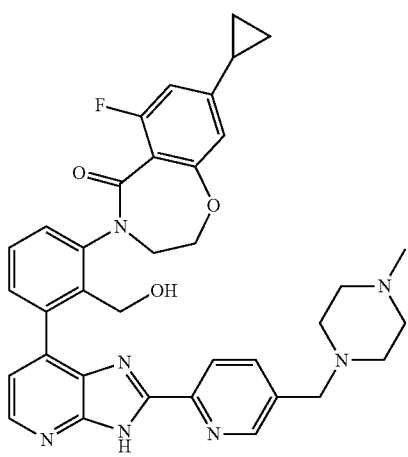 [SMILES: CN1CCN(Cc2ccc(-c3nc4c(-c5cccc(N6CCOc7cc(C8CC8)cc(F)c7C6=O)c5CO)ccnc4[nH]3)nc2)CC1]

5-(Bromomethyl)pyridine-2-carboxylate

In a 500-mL round bottom flask. NBS (14.13 g, 79.38 mmol, 1.20 equiv) and AIBN (217 mg, 1.32 mmol, 0.02 equiv) were added to a solution of methyl 5-methylpyridine-2-carboxylate (10 g, 66.15 mmol, 1.00 equiv) in CCl₄ (200 mL) at room temperature. The resulting solution was stirred for 16 h at 80° C. After the reaction was done, the reaction mixture was concentrated under reduced pressure. The residue was purified in a silica gel column eluting with ethyl acetate in petroleum ether (5% to 25% gradient) to afford methyl 5-(bromomethyl)pyridine-2-carboxylate (9.6 g, 57%) as yellow solid. MS: m/z=229.9 [M+H]⁺

Methyl 5-[(4-methylpiperazin-1-yl)methyl]pyridine-2-carboxylate

In a 50-mL round bottom flask with magnetic stir bar, methyl 5-(bromomethyl)pyridine-2-carboxylate (940 mg, 4.09 mmol, 1.00 equiv) and 1-methylpiperazine (449.6 mg, 4.49 mmol, 1.10 equiv) were dissolved in ACN (10 mL), to which DIEA (790.8 mg, 6.12 mmol, 1.50 equiv) was added at room temperature. The resulting solution was stirred for 4 h at room temperature. After the reaction was done, the reaction mixture was concentrated under reduced pressure. The residue was purified in a silica gel column eluting with methanol in dichloromethane (1% to 10% gradient) to afford methyl 5-[(4-methylpiperazin-1-yl)methyl]pyridine-2-carboxylate (500 mg, 49%) as brown solid.

[5-[(4-Methylpiperazin-1-yl)methyl]pyridin-2-yl]methanol

In a 25-mL round bottom flask, methyl 5-[(4-methylpiperazin-1-yl)methyl]pyridine-2-carboxylate (1.00 g, 4.01 mmol, 1.00 equiv) was dissolved in ethanol (5 mL) at 0° C. Then NaBH₄ (455.2 mg, 12.03 mmol, 3.00 equiv) was added slowly at 0° C. The resulting mixture was stirred for 12 h at room temperature. When the reaction was done, it was quenched by the addition of 15 mL sat. NH₄Cl solution and the mixture was extracted with ethyl acetate (3×50 mL). The organic layers were combined and concentrated under reduced pressure. The residue was purified by reverse phase flash chromatography using the following conditions: column, C18 silica gel; mobile phase, methanol in water, 0% to 99% gradient in 15 min; detector, UV 254 nm. [5-[(4-methylpiperazin-1-yl)methyl]pyridin-2-yl]methanol (720 mg, 77%) was obtained as a white solid.

5-[(4-Methylpiperazin-1-yl)methyl]pyridine-2-carbaldehyde

In a 50-mL round bottom flask, MnO$_2$ (5.89 g, 67.75 mmol, 50.0 equiv) was added to the solution of [5-[(4-methylpiperazin-1-yl)methyl]pyridin-2-yl]methanol (300 mg, 1.36 mmol, 1.00 equiv) in DMF (20 mL) at room temperature. The resulting solution was stirred for 12 h at room temperature. After the reaction was done, the insoluble solids in the reaction mixture were filtered out and the filtrate was concentrated under reduced pressure to afford 5-[(4-methylpiperazin-1-yl)methyl]pyridine-2-carbaldehyde (120 mg, 38%) as a white solid.

8-Cyclopropyl-6-fluoro-4-[2-(hydroxymethyl)-3-(2-[5-[(4-methylpiperazin-1-yl)methyl]pyridin-2-yl]-3H-imidazo[4,5-b]pyridin-7-yl)phenyl]-2,3,4,5-tetrahydro-1,4-benzoxazepin-5-one 8-cyclopropyl-6-fluoro-4-[2-(hydroxymethyl)-3-(2-[5-[(4-methylpiperazin-1-yl)methyl]pyridin-2-yl]-3H-imidazo[4,5-b]pyridin-7-yl)phenyl]-2,3,4,5-tetrahydro-1,4-benzoxazepin-5-one 60 mg (42.5% for two steps) was prepared from [2-(8-cyclopropyl-6-fluoro-5-oxo-2,3,4,5-tetrahydro-1,4-benzoxazepin-4-yl)-6-(2,3-diaminopyridin-4-yl)phenyl]methyl acetate and [(4-methylpiperazin-1-yl)methyl]pyridine-2-carbaldehyde using Method 1H and 1I. HPLC: 97.7% purity. MS: m/z=634.2 [M+H]$^+$. $^1$H NMR (400 MHz, CD$_3$OD): δ 8.78 (s, 1H), 8.65 (d, J=5.6 Hz, 1H), 8.42 (d, J=6.6 Hz, 1H), 8.06 (d, J=6.8 Hz, 1H), 7.75-7.55 (m, 4H), 6.82-6.76 (m, 2H), 4.62-4.40 (m, 4H), 4.05-3.98 (m, 2H), 3.80 (s, 2H), 3.28-3.02 (m, 5H), 2.87 (s, 3H), 2.76-2.42 (m, 3H), 2.02-1.96 (m, 1H), 1.15-1.10 (m, 2H), 0.81-0.75 (m, 2H).

Scheme 9

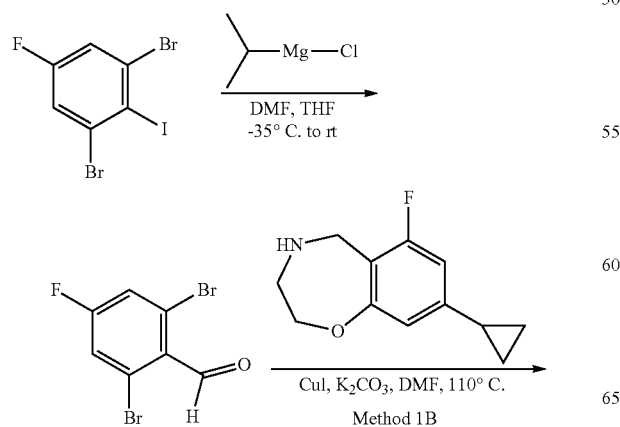

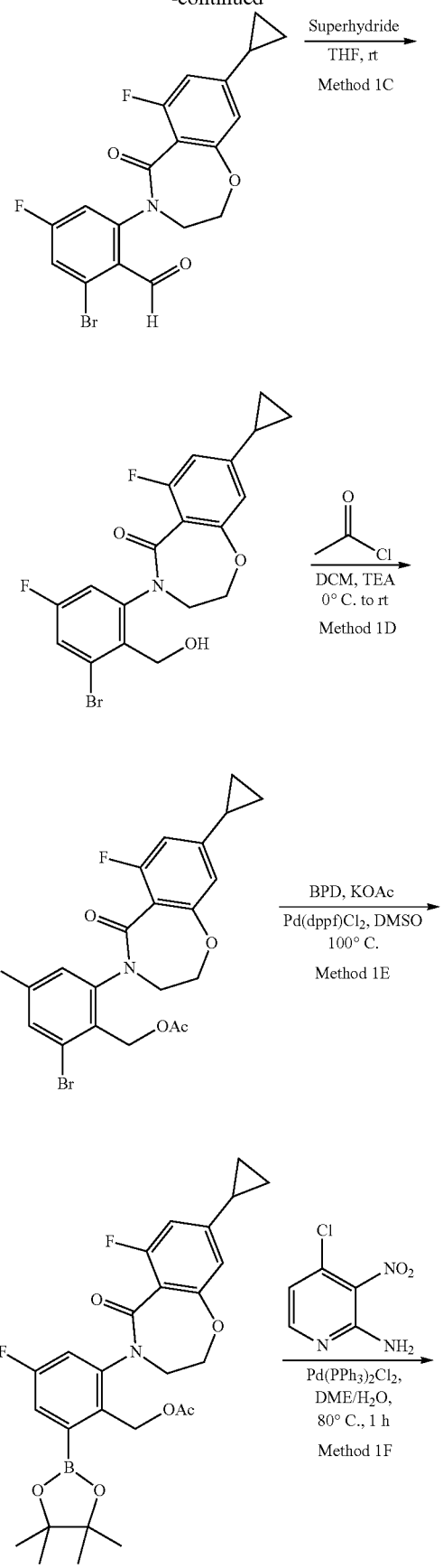

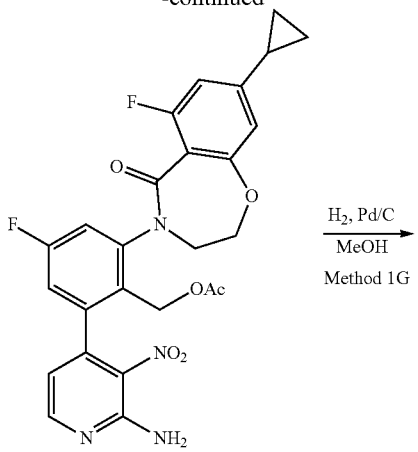

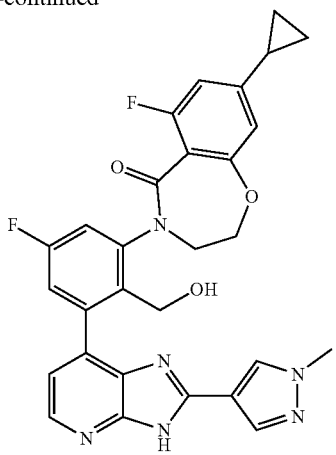

Example 37. 8-Cyclopropyl-6-fluoro-4-[5-fluoro-2-(hydroxymethyl)-3-[2-(1-methyl-1H-pyrazol-4-yl)-3H-imidazo [4,5-b]pyridin-7-yl]phenyl]-2,3,4,5-tetrahydro-1,4-benzoxazepin-5-one (37)

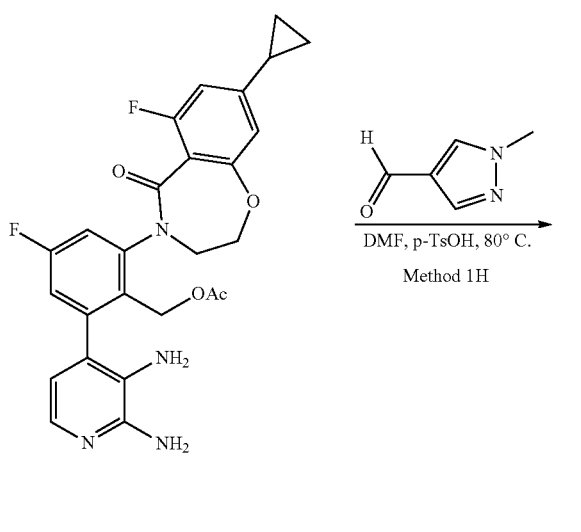

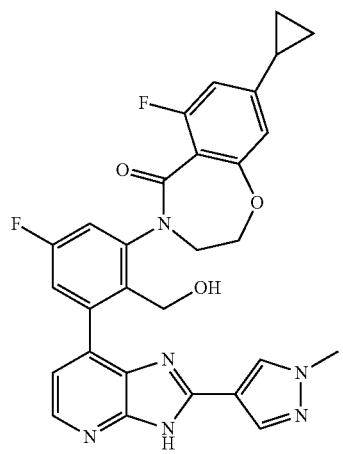 [SMILES: Cn1cc(-c2nc3c(-c4cc(F)cc(N5CCOc6cc(C7CC7)cc(F)c6C5=O)c4CO)ccnc3[nH]2)cn1]

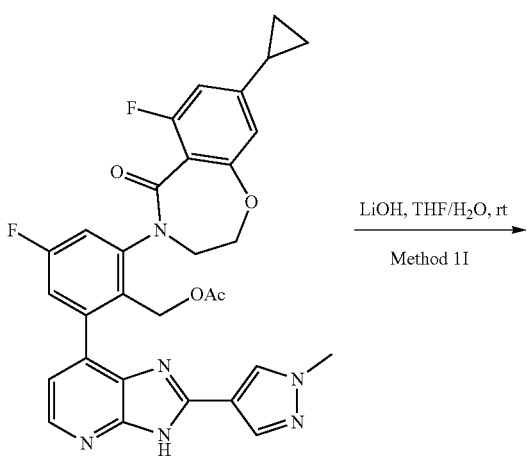

2,6-Dibromo-4-fluorobenzaldehyde

In a 100-mL round bottom flask, the solution of 1,3-dibromo-5-fluoro-2-iodobenzene (5.0 g, 13.2 mmol) in anhydrous toluene (30 mL) was cooled to −35° C. and was added by a solution of isopropylmagnesium chloride in THF (2.0 M, 8.4 mL, 17.1 mmol) dropwise over a period of 30 minutes while maintaining the internal temperature below −25° C. The resulting mixture was stirred for 1.5 h at −35° C. Then anhydrous DMF (4.7 mL, 60.73 mmol, 4.61 equiv) was added dropwise at −35° C. The reaction mixture was slowly warmed up to room temperature over 1 h period and stirred at room temperature for another 1.5 h. When the reaction was done, it was quenched by the addition of 30 mL hydrogen chloride solution (3 M). The mixture was extracted with ethyl acetate (3×50 mL) and the organic layers were combined, dried over sodium sulfate and concentrated under reduced pressure. The residue was purified in a silica gel column eluting with ethyl acetate in petroleum ether (5% to 10% gradient) to give 2,6-dibromo-4-fluorobenzaldehyde (1.8 g, 49%) as yellow solid.

8-Cyclopropyl-6-fluoro-4-[5-fluoro-2-(hydroxymethyl)-3-[2-(1-methyl-1H-pyrazol-4-yl)-3H-imidazo[4,5-b]pyridin-7-yl]phenyl]-2,3,4,5-tetrahydro-1,4-benzoxazepin-5-one 8-cyclopropyl-6-fluoro-4-[5-fluoro-2-(hydroxymethyl)-3-[2-(1-methyl-1H-pyrazol-4-yl)-3H-imidazo[4,5-b]pyridin-7-yl]phenyl]-2,3,4,5-tetrahydro-1,4-benzoxazepin-5-one 10 mg (1.8% for eight steps) was prepared from 2,6-dibromo-4-fluorobenzaldehyde, 8-cyclopropyl-6-fluoro-2,3,4,5-tetrahydro-1,4-benzoxazepin-5-one, 4,4,5,5-tetramethyl-2-(tetramethyl-1,3,2-dioxaborolan-2-yl)-1,3,2-dioxaborolane, 4-chloro-3-nitropyridin-2-amine, 1-methyl-1H-pyrazole-4-carbaldehyde using Method 1B, 1C, 1D, 1E, 1F, 1G, 1H and 1I. HPLC: 98.7% purity. MS: m/z=543.2 [M+H]$^+$. $^1$H NMR (300 MHz, DMSO-d$_6$): δ 13.51 (br s, 1H), 8.51-8.30 (m, 2H), 8.07 (s, 1H), 7.61-7.25 (m, 3H), 6.96-6.74 (m, 2H), 5.80 (br s, 1H), 4.52-4.49 (m, 2H), 4.30-4.18 (m, 2H), 3.92 (m, 5H), 1.98-1.97 (m, 1H), 1.10-0.97 (m, 2H), 0.85-0.74 (m, 2H).

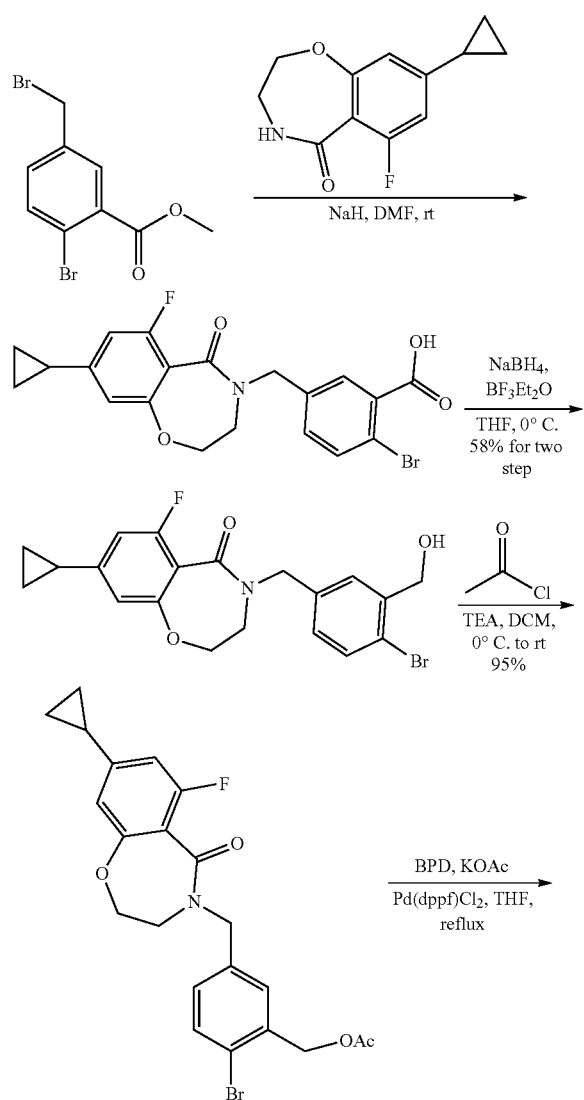

-continued

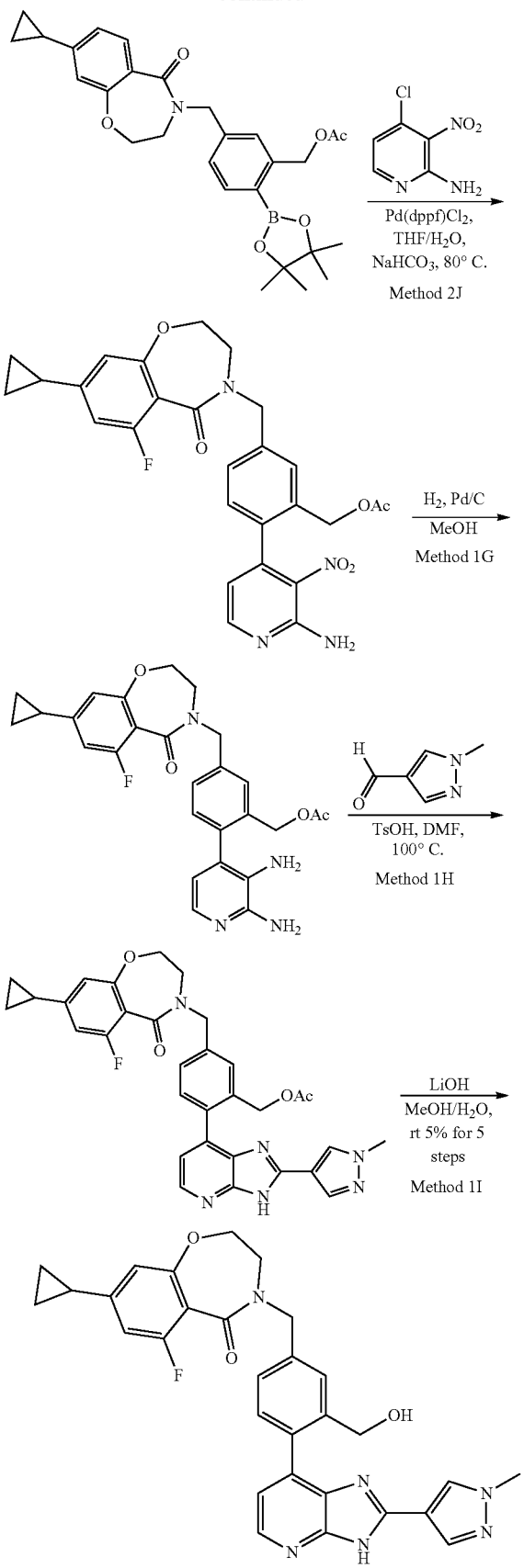

Example 38. 8-Cyclopropyl-6-fluoro-4-[[3-(hydroxymethyl)$_{0-4}$-[2-(1-methyl-1H-pyrazol-4-yl)-3H-imidazo[4,5-b]pyridin-7-yl]phenyl]methyl]-2,3,4,5-tetrahydro-1,4-benzoxazepin-5-one (38)

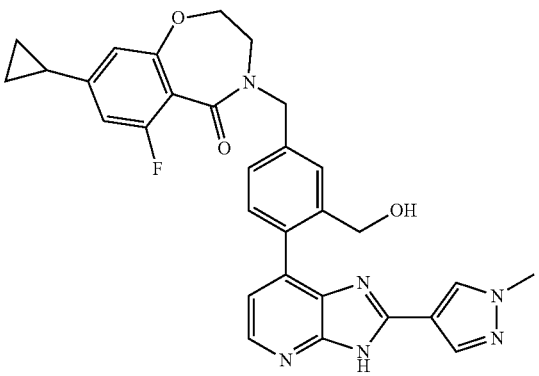 [SMILES: Cn1cc(-c2nc3c(-c4ccc(CN5CCOc6cc(C7CC7)cc(F)c6C5=O)cc4CO)ccnc3[nH]2)cn1]

2-Bromo-5-[(8-cyclopropyl-6-fluoro-5-oxo-2,3,4,5-tetrahydro-1,4-benzoxazepin-4-yl)methyl]benzoic acid In a 50-mL round bottom flask, sodium hydride (60% in oil, 72.2 mg, 1.80 mmol, 2.1 equiv) was added to a solution of 8-cyclopropyl-6-fluoro-2,3,4,5-tetrahydro-1,4-benzoxazepin-5-one (200 mg, 0.86 mmol, 1.00 equiv) in N,N-dimethylformamide (20 mL) at 0° C. The resulting mixture was stirred for 1 h at 0° C., and then was added by methyl 2-bromo-5-(bromomethyl)benzoate (306.3 mg, 0.94 mmol, 1.10 equiv). The reaction mixture was allowed to warm up to RT and stirred for 4 h. When the reaction was done, it was quenched by 20 mL water. The pH value of the mixture was adjusted to 4 using hydrogen chloride solution (3 M) and the resulting mixture was extracted with ethyl acetate (3×20 mL). The organic layers were combined, dried over sodium sulfate and concentrated under reduced pressure. The residue was purified in a silica gel column eluting with methanol in DCM (1% to 20% gradient) to afford 2-bromo-5-[(8-cyclopropyl-6-fluoro-5-oxo-2,3,4,5-tetrahydro-1,4-benzoxazepin-4-yl)methyl]benzoic acid (550 mg, crude) as yellow oil. MS: m/z=408.1 [M+H]$^+$ 4-[[4-Bromo-3-(hydroxymethyl)phenyl]methyl]-8-cyclopropyl-6-fluoro-2,3,4,5-tetrahydro-1,4-benzoxazepin-5-one In a 25-mL round bottom flask, NaBH$_4$ (264 mg, 6.63 mmol, 6.19 equiv) and BF$_3$.Et$_2$O (472 mg, 3.16 mmol, 2.95 equiv) were slowly added to a solution of 2-bromo-5-[(8-cyclopropyl-6-fluoro-5-oxo-2,3,4,5-tetrahydro-1,4-benzoxazepin-4-yl)methyl]benzoic acid (500 mg, 1.07 mmol, 1.00 equiv) in ethylene glycol dimethyl ether (5 mL) at 0° C. The resulting solution was then stirred for 2 h at room temperature. When the reaction was done, it was quenched by the addition of 20 ml H$_2$O. The mixture was extracted with ethyl acetate (3×20 ml) and the organic layers were combined, dried over sodium sulfate and concentrated under reduced pressure. The residue was purified in a silica gel column eluting with ethyl acetate in petroleum ether (5% to 50% gradient) to afford 4-[[4-bromo-3-(hydroxymethyl)phenyl]methyl]-8-cyclopropyl-6-fluoro-2,3,4,5-tetrahydro-1,4-benzoxazepin-5-one (200 mg, 58% for two steps) as colorless oil. MS: m/z=420.0 [M+H]$^+$.

[2-Bromo-5-[(8-cyclopropyl-6-fluoro-5-oxo-2,3,4,5-tetrahydro-1,4-benzoxazepin-4-yl)methyl]phenyl]methyl acetate At 0° C., in a 25-mL round bottom flask, 4-[[4-bromo-3-(hydroxymethyl)phenyl]methyl]-8-cyclopropyl-6-fluoro-2,3,4,5-tetrahydro-1,4-benzoxazepin-5-one (200 mg, 0.43 mmol, 1.00 equiv) and TEA (144.4 mg, 1.36 mmol, 3.12 equiv) were mixed in dichloromethane (3 mL), to which was added acetyl chloride (112.4 mg, 1.36 mmol, 3.13 equiv) dropwise. The resulting solution was then stirred for 2 h at room temperature. When the reaction was done, it was quenched by the addition of 5 mL of water/ice. The mixture was extracted with dichloromethane (3×20 mL) and the organic layers were combined, dried over sodium sulfate and concentrated under reduced pressure to afford [2-bromo-5-[(8-cyclopropyl-6-fluoro-5-oxo-2,3,4,5-tetrahydro-1,4-benzoxazepin-4-yl)methyl]phenyl]methyl acetate (191 mg, 95%) as yellow solid. MS: m/z=462.2 [M+H]$^+$.

[5-[(8-Cyclopropyl-6-fluoro-5-oxo-2,3,4,5-tetrahydro-1,4-benzoxazepin-4-yl)methyl]-2-(tetramethyl-1,3,2-dioxaborolan-2-yl)phenyl]methyl acetate In a 10-mL sealed tube purged and maintained with an inert atmosphere of nitrogen, [2-bromo-5-[(8-cyclopropyl-6-fluoro-5-oxo-2,3,4,5-tetrahydro-1,4-benzoxazepin-4-yl)methyl]phenyl]methyl acetate (230 mg, 0.47 mmol, 1.00 equiv), 4,4,4',4',5,5,5',5'-octamethyl-2,2'-bi(1,3,2-dioxaborolane) (198.4 mg, 0.74 mmol, 1.60 equiv), Pd(dppf)Cl$_2$.CH$_2$Cl$_2$ (57.2 mg, 0.07 mmol, 0.14 equiv), KOAc (63.8 mg, 0.62 mmol, 1.33 equiv) were mixed in tetrahydrofuran (5 mL). The resulting mixture was stirred for 12 h at 70° C. After the reaction was done, the reaction mixture was diluted with 30 mL water and extracted with ethyl acetate (3×100 mL). The organic layers were combined, dried over sodium sulfate and concentrated under reduced pressure to afford [5-[(8-cyclopropyl-6-fluoro-5-oxo-2,3,4,5-tetrahydro-1,4-benzoxazepin-4-yl)methyl]-2-(tetramethyl-1,3,2-dioxaborolan-2-yl)phenyl]methyl acetate (480 mg, crude) as yellow oil. MS: m/z=510.2 [M+H]$^+$.

8-Cyclopropyl-6-fluoro-4-[[3-(hydroxymethyl)$_{0-4}$-[2-(1-methyl-1H-pyrazol-4-yl)-3H-imidazo[4,5-b]pyridin-7-yl]phenyl]methyl]-2,3,4,5-tetrahydro-1,4-benzoxazepin-5-one 8-cyclopropyl-6-fluoro-4-[[3-(hydroxymethyl)$_{0-4}$-[2-(1-methyl-1H-pyrazol-4-yl)-3H-imidazo[4,5-b]pyridin-7-yl]phenyl]methyl]-2,3,4,5-tetrahydro-1,4-benzoxazepin-5-one 10 mg (5% for four steps) was prepared from [5-[(8-cyclopropyl-6-fluoro-5-oxo-2,3,4,5-tetrahydro-1,4-benzoxazepin-4-yl)methyl]-2-(tetramethyl-1,3,2-dioxaborolan-2-yl)phenyl]methyl acetate, 4-chloro-3-nitropyridin-2-amine and 1-methyl-1H-pyrazole-4-carbaldehyde using Method 2J, 1G, 1H and 1I. HPLC: 98.1% purity. MS: m/z=539.1 [M+H]$^+$. $^1$H NMR (300 MHz, DMSO-d$_6$): δ 13.34 (br s, 1H), 8.37-8.27 (m, 2H), 8.06 (s, 1H), 7.64 (s, 1H), 7.37-7.36 (m, 2H), 7.12-7.10 (m, 1H), 6.80-6.79 (m, 1H), 6.69 (s, 1H), 5.40 (s, 1H), 4.84 (s, 2H), 4.38 (s, 2H), 4.24 (s, 2H), 3.90 (s, 3H), 3.58-3.54 (m, 2H), 1.98-1.95 (m, 1H), 1.04-0.98 (m, 2H), 0.79-0.75 (m, 2H).

Scheme 11

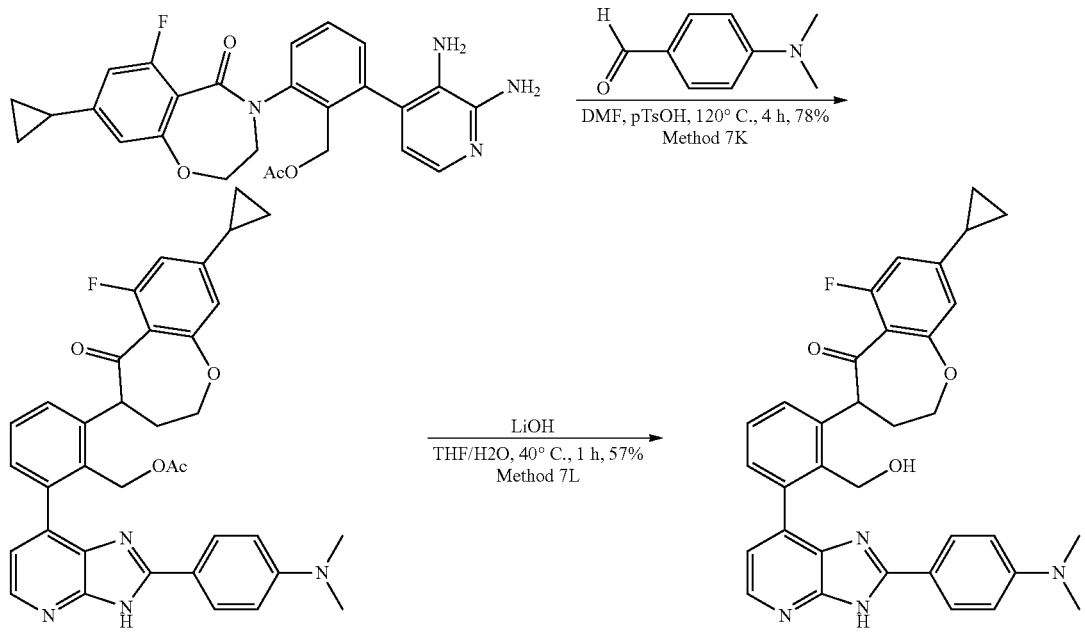

Example 39. 8-Cyclopropyl-4-(3-[2-[4-(dimethyl-amino)phenyl]-3H-imidazo[4,5-b]pyridin-7-yl]-2-(hydroxymethyl) phenyl)-6-fluoro-2,3,4,5-tetrahydro-1,4-benzoxazepin-5-one (39)

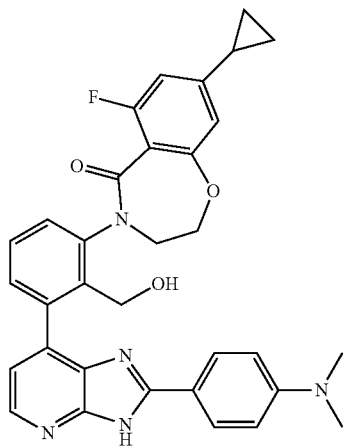 [SMILES: CN(C)c1ccc(-c2nc3c(-c4cccc(N5CCOc6cc(C7CC7)cc(F)c6C5=O)c4CO)ccnc3[nH]2)cc1]

Method 7K: [2-(8-Cyclopropyl-6-fluoro-5-oxo-2,3,4,5-tetrahydro-1,4-benzoxazepin-4-yl)-6-[2-[4-(dimethylamino) phenyl]-3H-imidazo[4,5-b]pyridin-7-yl] phenyl]methyl acetate In a 10-mL sealed tube, [2-(8-cyclopropyl-6-fluoro-5-oxo-2,3,4,5-tetrahydro-1,4-benzoxazepin-4-yl)-6-(2,3-di-aminopyridin-4-yl)phenyl]methyl acetate (90 mg, 0.19 mmol, 1.00 equiv) and 4-(dimethylamino) benzaldehyde (47.27 mg, 0.32 mmol, 1.51 equiv) were dissolved in N,N-dimethylformamide (5 mL), to which was added 4-methylbenzene-1-sulfonic acid (3.6 mg, 0.02 mmol, 0.10 equiv) slowly at room temperature. The resulting mixture was stirred for 4 h at 120° C. After the reaction was done, the reaction mixture was cooled to room temperature, diluted with 20 mL H2O and extracted with ethyl acetate (3×30 mL). The organic layers were combined, dried over sodium sulfate and concentrated under reduced pressure. The residue was purified in a silica gel column eluting with methanol in dichloromethane (1% to 10% gradient) to afford [2-(8-cyclopropyl-6-fluoro-5-oxo-2,3,4,5-tetrahydro-1,4-benzoxazepin-4-yl)-6-[2-[4-(dimethylamino)phenyl]-3H-imidazo[4,5-b]pyridin-7-yl]phenyl]methyl acetate (90 mg, 78%) as yellow oil.

Method 7L: 8-Cyclopropyl-4-(3-[2-[4-(dimethyl-amino)phenyl]-3H-imidazo[4,5-b]pyridin-7-yl]-2-(hydroxymethyl) phenyl)-6-fluoro-2,3,4,5-tetrahydro-1,4-benzoxazepin-5-one In a 50-mL round bottom flask, LiOH (10.7 mg, 0.45 mmol, 4.80 equiv) was added to the solution of [2-(8-cyclopropyl-6-fluoro-5-oxo-2,3,4,5-tetrahydro-1,4-benzoxazepin-4-yl)-6-[2-[4-(dimethylamino)phenyl]-3H-imidazo[4,5-b]pyridin-7-yl]phenyl]methyl acetate (90 mg, 0.09 mmol, 1.00 equiv, 62.6%) in tetrahydrofuran (7 mL) and water (4 mL) at room temperature. The resulting mixture was then stirred for 1 h at 40° C. After the reaction was done, the reaction mixture was cooled to room temperature, diluted with 10 mL H2O and extracted with ethyl acetate (3×10 mL). The organic layers were combined, dried over sodium sulfate and concentrated under reduced pressure. The residue was purified by prep-HPLC using the following conditions: column, XBridge BEH C18 OBD Prep Column, 5 um, 19 mm, 250 mm; mobile phase, acetonitrile in water (with 10 mM NH4HCO3), 53% to 63% gradient in 9 min; detector, UV 254 nm. 8-cyclopropyl-4-(3-[2-[4-(dimethyl-amino)phenyl]-3H-imidazo[4,5-b]pyridin-7-yl]-2-(hydroxymethyl)phenyl)-6-fluoro-2,3,4,5-tetrahydro-1,4-benzoxazepin-5-one (30 mg, 57%) was obtained as off-white solid. HPLC: 98.8% purity. MS: m/z=564.2 [M+H]+. 1H NMR (300 MHz, DMSO-d6): δ 13.44 (br s, 1H), 8.32 (d, J=5.1 Hz, 1H), 7.96 (d, J=9.0 Hz, 2H), 7.62-7.44 (m, 3H), 7.24-7.23 (m, 1H), 6.85-6.78 (m, 4H), 6.35 (br s, 1H), 4.50-4.33 (m, 3H), 4.22-4.18 (m, 1H), 3.96-3.95 (m, 2H), 2.99 (s, 6H), 2.01-1.98 (m, 1H), 1.04-1.02 (m, 2H), 0.79-0.77 (m, 2H).

Scheme 12

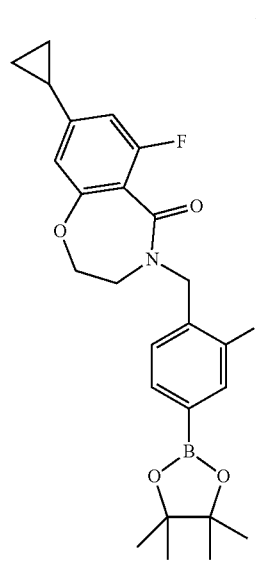

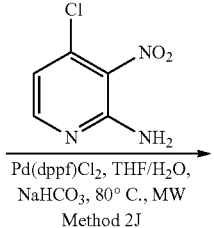

Pd(dppf)Cl₂, THF/H₂O,
NaHCO₃, 80° C., MW
Method 2J

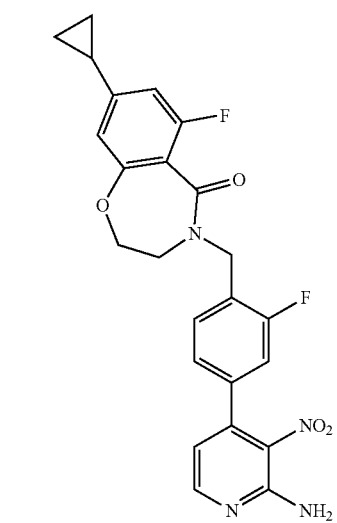

H₂, Pd/C
MeOH, rt
Method 1G

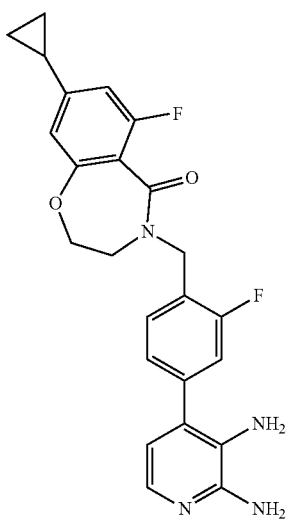

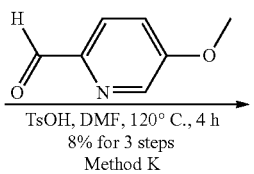

TsOH, DMF, 120° C., 4 h
8% for 3 steps
Method K

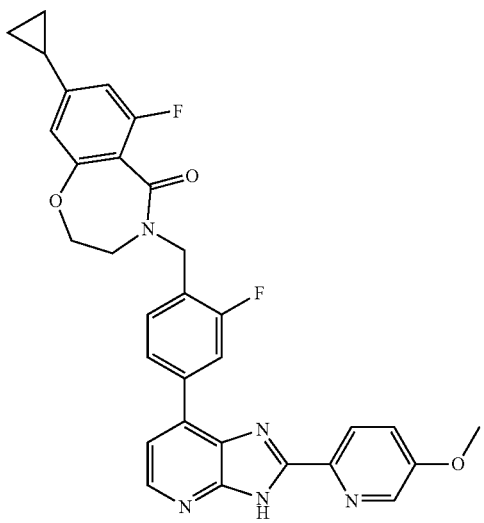 [SMILES: COc1ccc(-c2nc3c(-c4ccc(CN5CCOc6cc(C7CC7)cc(F)c6C5=O)c(F)c4)ccnc3[nH]2)nc1]

Example 40. 8-Cyclopropyl-6-fluoro-4-([2-fluoro-4-[2-(5-methoxypyridin-2-yl)-3H-imidazo[4,5-b]pyridin-7-yl] phenyl]methyl)-2,3,4,5-tetrahydro-1,4-benzoxazepin-5-one (40)

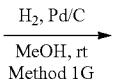

8-cyclopropyl-6-fluoro-4-([2-fluoro-4-[2-(5-methoxypyridin-2-yl)-3H-imidazo[4,5-b]pyridin-7-yl]phenyl]methyl)-2,3,4,5-tetrahydro-1,4-benzoxazepin-5-one 20 mg (8% for three steps) was prepared from 8-cyclopropyl-6-fluoro-4-[[2-fluoro-4-(tetramethyl-1,3,2-dioxaborolan-2-yl)phenyl]methyl]-2,3,4,5-tetrahydro-1,4-benzoxazepin-5-one, 4-chloro-3-nitropyridin-2-amine and 5-methoxypyridine-2-carbaldehyde using Method 2J, 1G and 7K. HPLC: 95.8% purity. MS: m/z=554.2 [M+H]⁺. ¹H NMR (300 MHz, DMSO-d₆): δ 13.74 (br s, 1H), 8.47 (s, 1H), 8.39-8.35 (m, 3H), 8.28-8.25 (m, 1H), 7.64-7.54 (m, 3H), 6.83-6.80 (m, 1H), 6.69 (s, 1H), 4.88 (s, 1H), 4.23-4.19 (m, 2H), 3.94 (s, 3H), 3.63-3.59 (m, 2H), 2.01-1.92 (m, 1H), 1.05-1.00 (m, 2H), 0.78-0.70 (m, 2H).

Scheme 13

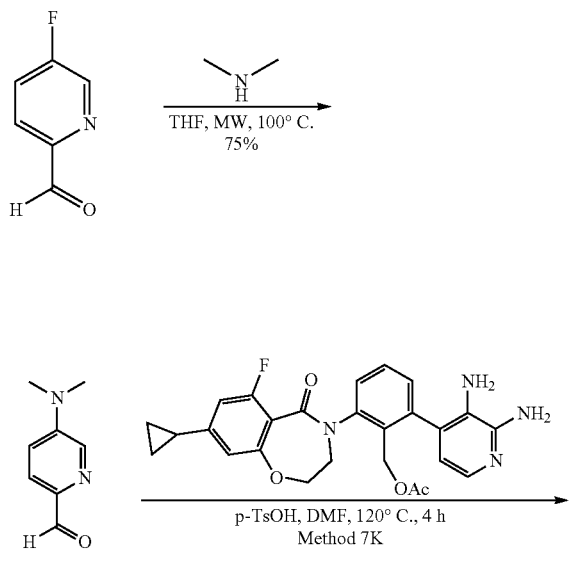

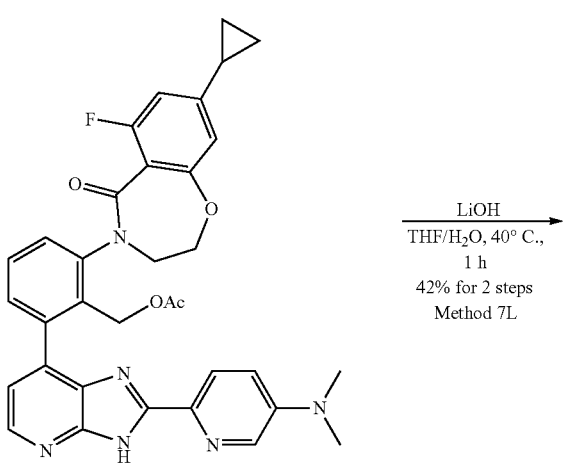

Example 41. 8-cyclopropyl-4-(3-[2-[5-(dimethylamino)pyridin-2-yl]-3H-imidazo[4,5-b]pyridin-7-yl]-2-(hydroxymethyl)phenyl)-6-fluoro-2,3,4,5-tetrahydro-1,4-benzoxazepin-5-one (41)

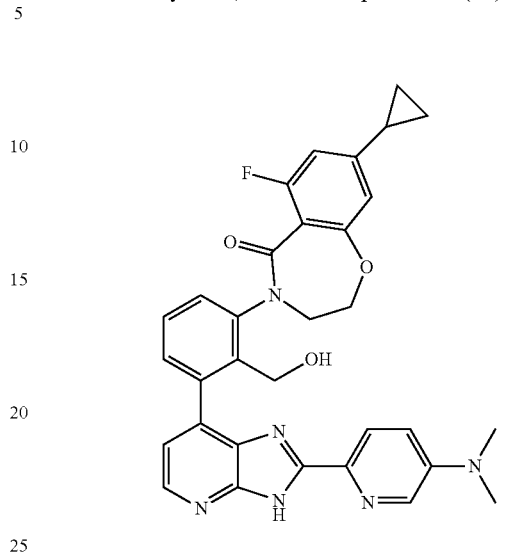

5-(Dimethylamino)pyridine-2-carbaldehyde

In a 10-mL sealed tube, 5-fluoropyridine-2-carbaldehyde (500 mg, 4.00 mmol, 1.00 equiv), dimethylamine hydrochloride (640 mg, 7.85 mmol, 1.96 equiv) and DIEA (3.1 g, 23.99 mmol, 6.00 equiv) were dissolved in tetrahydrofuran (5 mL) at room temperature. The resulting solution was then irradiated with microwave for 1 h at 100° C. After the reaction was done, the reaction mixture was cooled to room temperature, diluted with 50 mL DCM and washed with water (3×20 mL). The organic layer was dried over sodium sulfate and concentrated under reduced pressure. The residue was purified in a silica gel column eluting with methanol in dichloromethane (1% to 10% gradient) to afford 5-(dimethylamino)pyridine-2-carbaldehyde (450 mg, 75%) as yellow solid.

8-cyclopropyl-4-(3-[2-[5-(dimethylamino)pyridin-2-yl]-3H-imidazo[4,5-b]pyridin-7-yl]-2-(hydroxymethyl)phenyl)-6-fluoro-2,3,4,5-tetrahydro-1,4-benzoxazepin-5-one 8-cyclopropyl-4-(3-[2-[5-(dimethylamino)pyridin-2-yl]-3H-imidazo[4,5-b]pyridin-7-yl]-2-(hydroxymethyl) phenyl)-6-fluoro-2,3,4,5-tetrahydro-1,4-benzoxazepin-5-one 30 mg (42% for two steps) was prepared from [2-(8-cyclopropyl-6-fluoro-5-oxo-2,3,4,5-tetrahydro-1,4-benzoxazepin-4-yl)-6-(2,3-diaminopyridin-4-yl) phenyl]methyl acetate, 5-(dimethylamino)pyridine-2-carbaldehyde using Method 7K and 7L. HPLC: 95.1% purity. MS: m/z=565.2 [M+H]$^+$. $^1$H NMR (300 MHz, DMSO-d$_6$): δ 13.65 (br s, 1H), 8.37 (s, 1H), 8.36 (s, 1H), 8.07-7.96 (m, 1H), 7.69-7.45 (m, 3H), 7.29-7.21 (m, 2H), 6.86-6.78 (m, 2H), 6.08-6.07 (m, 1H), 4.49-4.47 (m, 2H), 4.40-4.33 (m, 1H), 4.24-4.20 (m, 1H), 3.97-3.96 (m, 2H), 3.10 (s, 6H), 2.07-2.00 (m, 1H), 1.05-1.03 (m, 2H), 0.78-0.70 (m, 2H).

Scheme 14

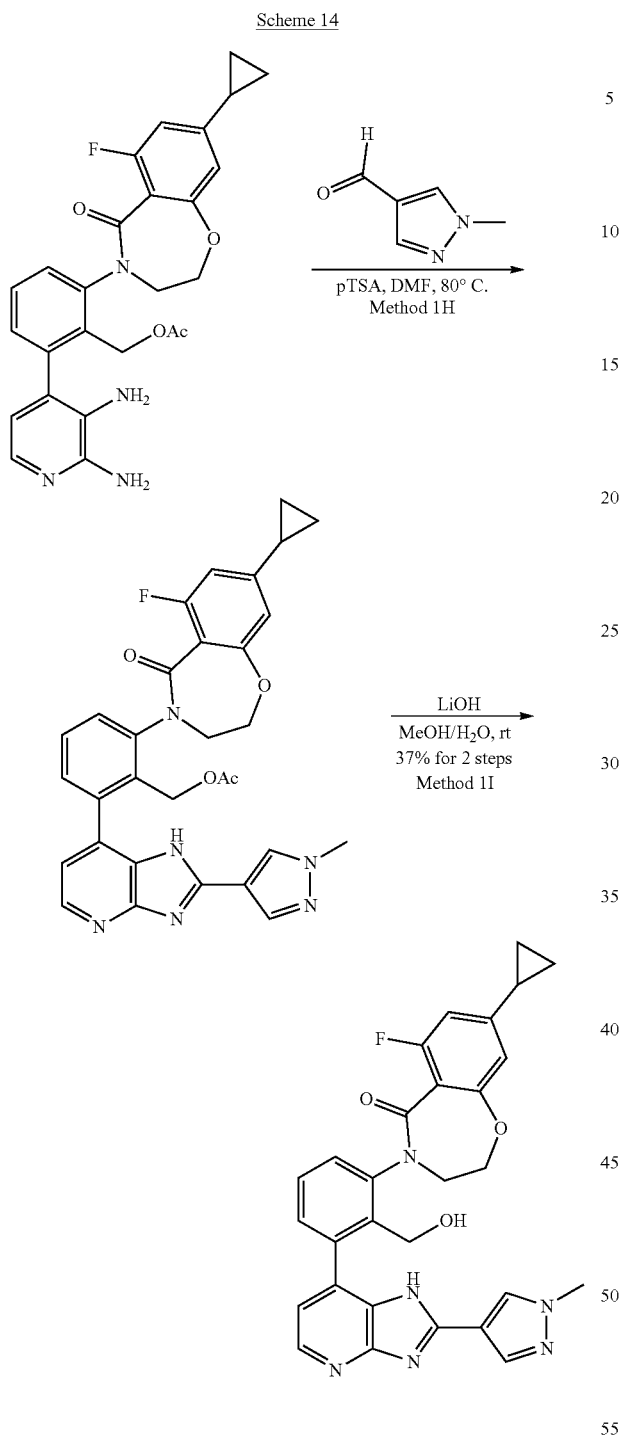

Example 42. 8-Cyclopropyl-6-fluoro-4-[2-(hydroxymethyl)-3-[2-(1-methyl-1H-pyrazol-4-yl)-1H-imidazo[4,5-b]pyridine-7-yl]phenyl]-2,3,4,5-tetrahydro-1,4-benzoxazepin-5-one (42)

8-cyclopropyl-6-fluoro-4-[2-(hydroxymethyl)-3-[2-(1-methyl-1H-pyrazol-4-yl)-1H-imidazo[4,5-b]pyridin-7-yl]phenyl]-2,3,4,5-tetrahydro-1,4-benzoxazepin-5-one 20 mg (37% for two steps) was prepared from [2-(8-cyclopropyl-6-fluoro-5-oxo-2,3,4,5-tetrahydro-1,4-benzoxazepin-4-yl)-6-(2,3-diaminopyridin-4-yl)phenyl] methyl acetate, 1-methyl-1H-pyrazole-4-carbaldehyde using Method 1H and 1I. HPLC: 97.0% purity. MS: m/z=525.2 [M+H]⁺. ¹H NMR (400 MHz, DMSO-d6): δ 13.53 (br s, 1H), 8.42-8.38 (m, 2H), 8.08 (s, 1H), 7.60-7.52 (m, 1H), 7.48-7.40 (m, 2H), 7.22 (d, J=6.3 Hz, 1H), 6.85-6.75 (m, 2H), 6.00 (br s, 1H), 4.52-4.40 (m, 2H), 4.40-4.15 (m, 2H), 3.97-3.82 (m, 5H), 2.01-1.95 (m, 1H), 1.09-0.99 (m, 2H), 0.80-0.72 (m, 2H).

Scheme 15

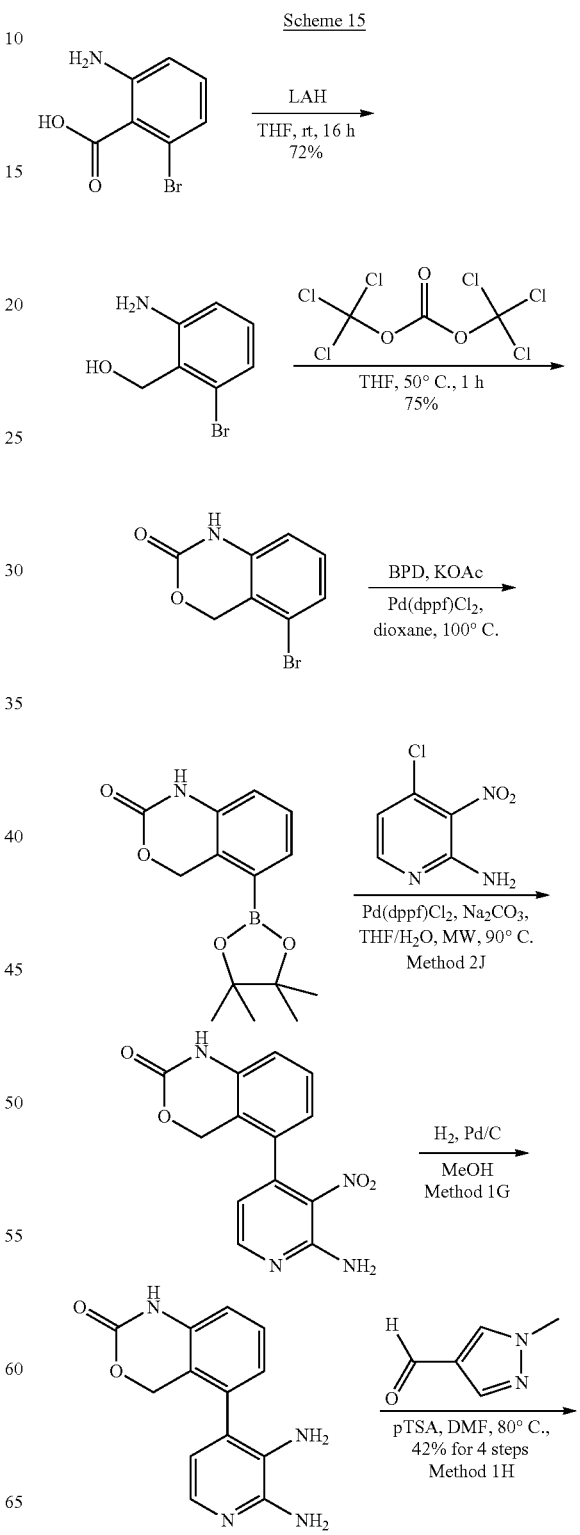

217

-continued

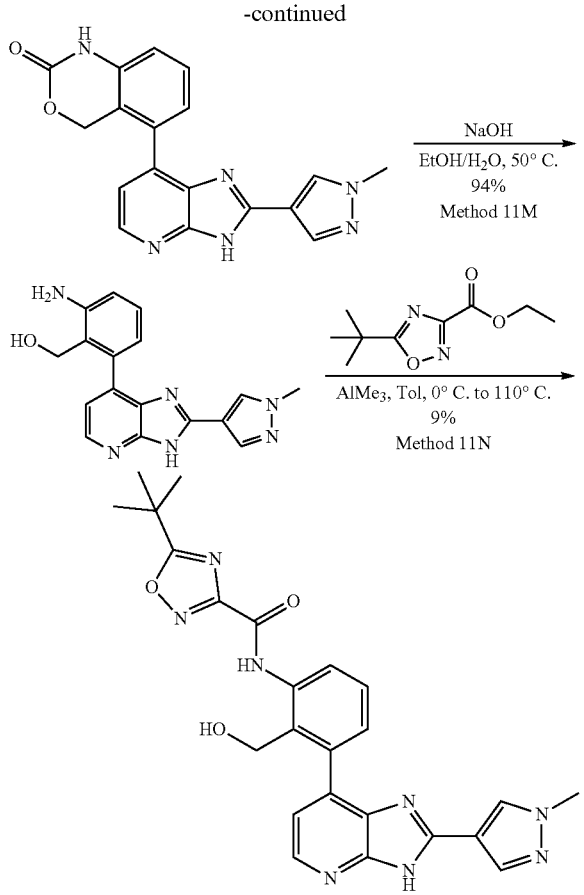

Example 43. 5-tert-Butyl-N-[2-(hydroxymethyl)-3-[2-(1-methyl-1H-pyrazol-4-yl)-3H-imidazo[4,5-b]pyridin-7-yl]phenyl]-1,2,4-oxadiazole-3-carboxamide (43)

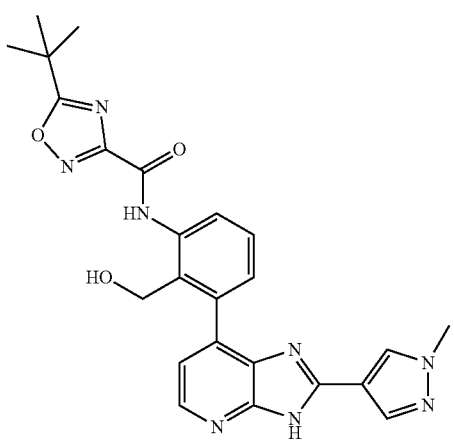 [SMILES: Cn1cc(-c2nc3c(-c4cccc(NC(=O)c5noc(C(C)(C)C)n5)c4CO)ccnc3[nH]2)cn1]

(2-Amino-6-bromophenyl)methanol

In a 1-L round bottom flask, 2-amino-6-bromobenzoic acid (15 g, 69.43 mmol, 1.00 equiv) was dissolved in tetrahydrofuran (300 mL), to which was added a solution of LiAlH$_4$ (7.906 g, 208.30 mmol, 3.00 equiv) in tetrahydrofuran (60 mL) dropwise at 0° C. The resulting solution was then stirred for 16 h at room temperature. When the reaction was done, it was quenched by the addition of NaSO$_4$.10H$_2$O (10 g). The resulting mixture was then filtered through a celite pad and the filtrate was concentrated under reduced pressure to afford (2-amino-6-bromophenyl)methanol (12.6 g, 72%) as a brown solid.

5-Bromo-2,4-dihydro-1H-3,1-benzoxazin-2-one

In a 1-L round-bottom flask purged and maintained with an inert atmosphere of nitrogen, (2-amino-6-bromophenyl)methanol (10.8 g, 49.89 mmol, 1.00 equiv) was dissolved in tetrahydrofuran (450 mL) at room temperature, to which was added ditrichloromethyl carbonate (6.48 g, 21.83 mmol, 0.35 equiv) slowly. The resulting solution was stirred for 1 h at 50° C. When the reaction was done, it was quenched by the addition of 500 mL water and the mixture was extracted with ethyl acetate (3×400 mL). The organic layers were combined, dried over sodium sulfate and concentrated under reduced pressure. The residue was purified in a silica gel column eluting with ethyl acetate/petroleum ether (30% to 60% gradient) to afford 5-bromo-2,4-dihydro-1H-3,1-benzoxazin-2-one (9 g, 75%) as a yellow solid.

5-(Tetramethyl-1,3,2-dioxaborolan-2-yl)-2,4-dihydro-1H-3,1-benzoxazin-2-one

In a 500-mL round bottom flask purged and maintained with an inert atmosphere of nitrogen, 5-bromo-2,4-dihydro-1H-3,1-benzoxazin-2-one (4.500 g, 18.75 mmol, 1.00 equiv) 4,4,5,5-tetramethyl-2-(tetramethyl-1,3,2-dioxaborolan-2-yl)-1,3,2-dioxaborolane (6.013 g, 23.68 mmol, 1.20 equiv), Pd(dppf)Cl$_2$.CH$_2$Cl$_2$ (1.611 g, 1.97 mmol, 0.10 equiv) and KOAc (2.905 g, 29.60 mmol, 1.50 equiv) were mixed in dioxane (150 mL). The resulting mixture was stirred for 16 h at 80° C. After the reaction was done, the reaction mixture was concentrated under reduced pressure to afford 5-(tetramethyl-1,3,2-dioxaborolan-2-yl)-2,4-dihydro-1H-3,1-benzoxazin-2-one (5.428 g, crude) as brown solid which was used for next step without further purification. MS: m/z=276.1 [M+H]$^+$.

5-[2-(1-Methyl-1H-pyrazol-4-yl)-3H-imidazo[4,5-b]pyridin-7-yl]-2,4-dihydro-1H-3,1-benzoxazin-2-one 5-[2-(1-methyl-1H-pyrazol-4-yl)-3H-imidazo[4,5-b]pyridin-7-yl]-2,4-dihydro-1H-3,1-benzoxazin-2-one 380 mg (42% for four steps) was prepared from 5-(tetramethyl-1,3,2-dioxaborolan-2-yl)-2,4-dihydro-1H-3,1-benzoxazin-2-one, 4-chloro-3-nitropyridin-2-amine and 1-methyl-1H-pyrazole-4-carbaldehyde using Method 2J, 1G and 1H. MS: m/z=347.0 [M+H]$^+$.

Method 11M: [2-Amino-6-[2-(1-methyl-1H-pyrazol-4-yl)-3H-imidazo[4,5-b]pyridin-7-yl]phenyl]methanol In a 250-mL round bottom flask, 5-[2-(1-methyl-1H-pyrazol-4-yl)-3H-imidazo[4,5-b]pyridin-7-yl]-2,4-dihydro-1H-3,1-benzoxazin-2-one (380 mg, 1.04 mmol, 1.00 equiv) was dissolved in ethanol (100 mL), to which was added a solution of sodium hydroxide (2 g, 50.0 mmol, 48.0 equiv) in water (100 mL) at room temperature. The resulting mixture was stirred for 2 h at 50° C. After the reaction was done, the reaction mixture was concentrated under reduced pressure and the remaining solution was extracted with ethyl acetate (3×100 mL). The organic layers were combined, dried over sodium sulfate and concentrated under reduced pressure to give [2-amino-6-[2-(1-methyl-1H-pyrazol-4-yl)-3H-imidazo[4,5-b]pyridin-7-yl]phenyl]methanol (330 mg, 94%) of as yellow solid. MS: m/z=321.1 [M+H]⁺.

Method 11N: 5-tert-Butyl-N-[2-(hydroxymethyl)-3-[2-(1-methyl-1H-pyrazol-4-yl)-3H-imidazo[4,5-b]pyridin-7-yl]phenyl]-1,2,4-oxadiazole-3-carboxamide In a 25-mL round bottom flask purged and maintained with an inert atmosphere of nitrogen, [2-amino-6-[2-(1-methyl-1H-pyrazol-4-yl)-3H-imidazo[4,5-b]pyridin-7-yl]phenyl]methanol (110 mg, 0.33 mmol, 1.00 equiv) was dissolved in toluene (5 mL), to which was added a solution of AlMe₃ (74.2 mg, 1.03 mmol, 3.00 equiv) in toluene (0.5 mL) dropwise at 0° C. The resulting mixture was stirred for 2 h at room temperature. Then ethyl 5-tert-butyl-1,2,4-oxadiazole-3-carboxylate (68.1 mg, 0.34 mmol, 1.00 equiv) was added. The reaction mixture was stirred for 16 h at 110° C. After the reaction was done, the reaction mixture was cooled to room temperature, quenched with 10 mL sat. NH₄Cl solution and extracted with ethyl acetate (3×10 mL). The organic layers were combined, dried over sodium sulfate and concentrated under reduced pressure. The residue was purified by reverse phase flash chromatography using the following conditions: column, C18 silica gel; mobile phase, methanol in water, 0% to 55% gradient in 10 min; detector. UV 254 nm. 5-tert-butyl-N-[2-(hydroxymethyl)-3-[2-(1-methyl-1H-pyrazol-4-yl)-3H-imidazo[4,5-b]pyridin-7-yl]phenyl]-1,2,4-oxadiazole-3-carboxamide (15 mg, 9%) was obtained as yellow solid. HPLC: 99.2% purity. MS: m/z=473.1 [M+H]⁺. ¹H NMR (400 MHz, DMSO-d₆): δ 13.52 (br s, 1H), 10.94 (br s, 1H), 8.41 (s, 1H), 8.33 (d, J=4.2 Hz, 1H), 8.18 (s, 1H), 8.10 (s, 1H), 7.52 (t, J=6.0 Hz, 1H), 7.26 (d, j=4.8 Hz, 1H), 7.27 (s, 1H), 5.95 (br s, 1H), 4.52 (s, 2H), 3.91 (s, 3H), 1.46 (s, 9H).

Scheme 16

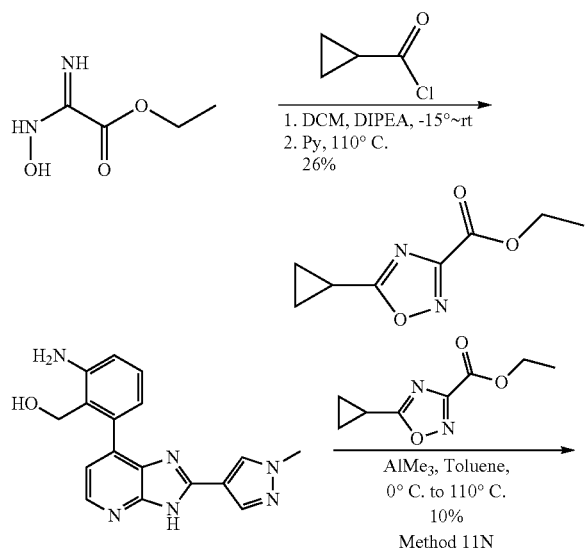

Method 11N

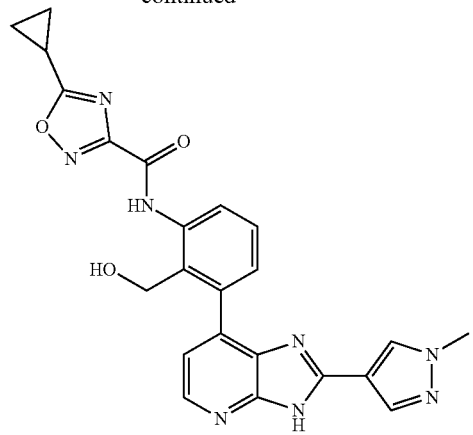

Example 44. 5-Cyclopropyl-N-[2-(hydroxymethyl)-3-[2-(1-methyl-1H-pyrazol-4-yl)-3H-imidazo[4,5-b]pyridin-7-yl]phenyl]-1,2,4-oxadiazole-3-carboxamide (44)

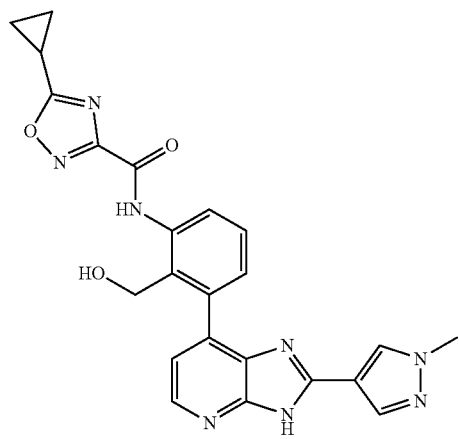 [SMILES: Cn1cc(-c2nc3c(-c4cccc(NC(=O)c5noc(C6CC6)n5)c4CO)ccnc3[nH]2)cn1]

Ethyl 5-cyclopropyl-1,2,4-oxadiazole-3-carboxylate

In a 25-mL round bottom flask, ethyl [(Z)—N-hydroxycarbamimidoyl]formate (500 mg, 3.78 mmol, 1.00 equiv) and DIEA (978 mg, 7.57 mmol, 2.00 equiv) were mixed in dichloromethane (5 mL), to which was added cyclopropanecarbonyl chloride (393 mg, 3.76 mmol, 0.99 equiv) dropwise at −15° C. The resulting solution was stirred for 16 h at room temperature. When the reaction was done, it was quenched by 10 mL water and the mixture was extracted with dichloromethane (3×5 mL). The organic layers were combined, dried over anhydrous sodium sulfate and concentrated under reduce pressure. The residue was then re-dissolved in pyridine (5 mL) at room temperature and the resulting solution was stirred for 16 h at 110° C. After the reaction was done, the reaction mixture was concentrated under reduced pressure and the residue was purified in a silica gel column eluting with ethyl acetate in petroleum ether (1% to 10% gradient) to afford ethyl 5-cyclopropyl-1,2,4-oxadiazole-3-carboxylate (180 mg, 26%) as yellow oil. MS: m/z=183.0 [M+H]⁺.

221

5-Cyclopropyl-N-[2-(hydroxymethyl)-3-[2-(1-methyl-1H-pyrazol-4-yl)-3H-imidazo[4,5-b]pyridin-7-yl]phenyl]-1,2,4-oxadiazole-3-carboxamide 5-cyclopropyl-N-[2-(hydroxyl methyl)-3-[2-(1-methyl-1H-pyrazol-4-yl)-3H-imidazo[4,5-b]pyridin-7-yl]phenyl]-1,2,4-oxadiazole-3-carboxamide 15 mg (10%) was prepared from 2-amino-6-[2-(1-methyl-1H-pyrazol-4-yl)-3H-imidazo[4,5-b]pyridin-7-yl]phenyl]methanol, ethyl 5-cyclopropyl-1,2,4-oxadiazole-3-carboxylate using Method 11N. HPLC: 96.3% purity. MS: m/z=457.1 [M+H]$^+$. $^1$H NMR (400 MHz, DMSO-d$_6$): δ 13.24 (br s, 1H), 10.86 (br s, 1H), 8.41 (s, 1H), 8.33 (d, J=4.2 Hz, 1H), 8.18 (s, 1H), 8.10 (s, 1H), 7.52 (t, J=6.0 Hz, 1H), 7.26 (d, J=4.8 Hz, 1H), 7.18 (s, 1H), 5.95 (br s, 1H), 4.52 (s, 2H), 3.91 (s, 3H), 2.40-2.45 (m, 1H), 1.35-1.28 (m, 2H), 1.25-1.18 (in, 2H).

Scheme 17

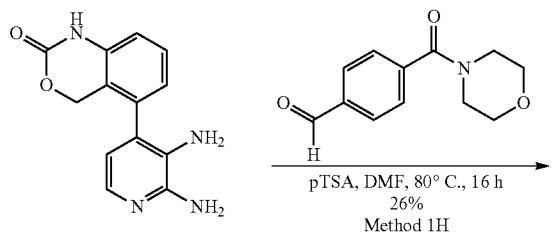

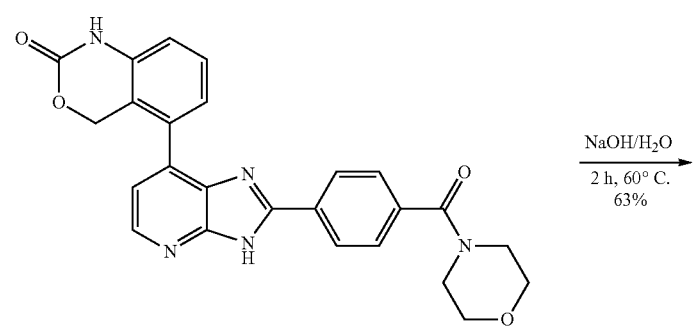

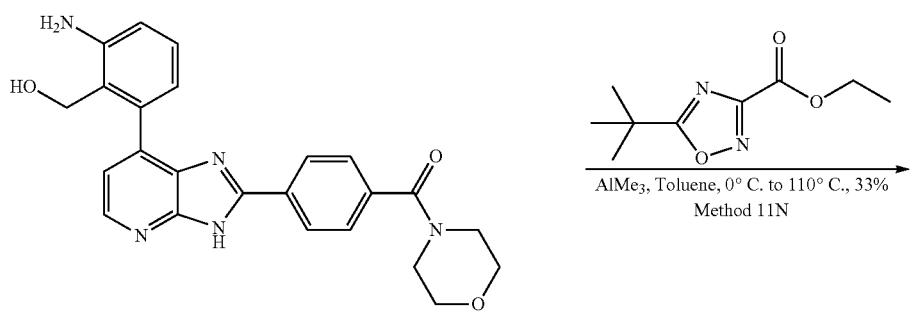

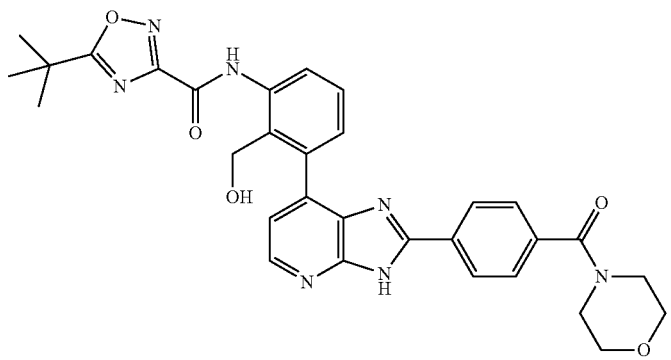

Example 45. 5-tert-Butyl-N-[2-(hydroxymethyl)-3-(2-[4-[(morpholin-4-yl)carbonyl]phenyl]-3H-imidazo[4,5-b]pyridin-7-yl)phenyl]-1,2,4-oxadiazole-3-carboxamide (45)

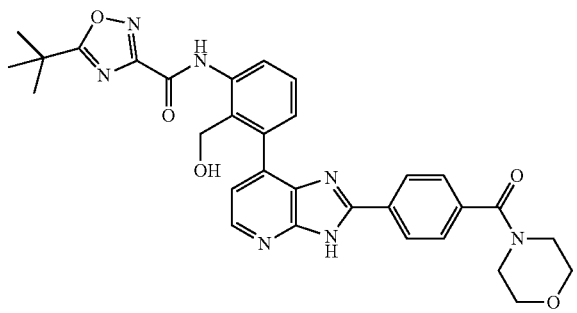 [SMILES: CC(C)(C)c1nc(C(=O)Nc2cccc(-c3ccnc4[nH]c(-c5ccc(C(=O)N6CCOCC6)cc5)nc34)c2CO)no1]

5-(2-[4-[(Morpholin-4-yl)carbonyl]phenyl]-3H-imidazo[4,5-b]pyridin-7-yl)-2,4-dihydro-1H-3,1-benzoxazin-2-one 5-(2-[4-[(morpholin-4-yl)carbonyl]phenyl]-3H-imidazo[4,5-b]pyridin-7-yl)-2,4-dihydro-1H-3,1-benzoxazin-2-one 120 mg (26%) was prepared from 5-(2,3-diaminopyridin-4-yl)-2,4-dihydro-1H-3,1-benzoxazin-2-one and 4-[(morpholin-4-yl)carbonyl]benzaldehyde using Method 1H. MS: m/z=456.0 [M+H]$^+$.

[2-Amino-6-(2-[4-[(morpholin-4-yl)carbonyl]phenyl]-3H-imidazo[4,5-b]pyridin-7-yl)phenyl]methanol In a 100-mL round bottom flask, 5-(2-[4-[(morpholin-4-yl)carbonyl]phenyl]-3H-imidazo[4,5-b]pyridin-7-yl)-2,4-dihydro-1H-3,1-benzoxazin-2-one (120 mg, 0.25 mmol, 1.00 equiv) was dissolved in ethanol (20 mL), to which was added a solution of sodium hydroxide (105.4 mg, 2.63 mmol, 10.00 equiv) in water (20 mL) at room temperature. The resulting solution was stirred for 2 h at 60° C. After the reaction was done, the reaction mixture was concentrated under reduced pressure and remaining mixture was extracted with ethyl acetate (5×15 mL). The organic layers were combined, dried over sodium sulfate and concentrated under reduced pressure to afford [2-amino-6-(2-[4-[(morpholin-4-yl)carbonyl]phenyl]-3H-imidazo[4,5-b]pyridin-7-yl)phenyl]methanol (70 mg, 63%) of as yellow solid. MS: m/z=430.0 [M+H]$^+$.

5-tert-Butyl-N-[2-(hydroxymethyl)-3-(2-[4-[(morpholin-4-yl)carbonyl]phenyl]-3H-imidazo[4,5-b]pyridin-7-yl)phenyl]-1,2,4-oxadiazole-3-carboxamide 5-tert-butyl-N-[2-(hydroxymethyl)-3-(2-[4-[(morpholin-4-yl)carbonyl]phenyl]-3H-imidazo[4,5-b]pyridin-7-yl)phenyl]-1,2,4-oxadiazole-3-carboxamide 45 mg (33%) was prepared from [2-amino-6-(2-[4-[(morpholin-4-yl)carbonyl]phenyl]-3H-imidazo[4,5-b]pyridin-7-yl)phenyl]methanol, ethyl 5-tert-butyl-1,2,4-oxadiazole-3-carboxylate using Method 11N. HPLC: 95.2% purity. MS: m/z=582.3 [M+H]$^+$. $^1$H NMR (300 MHz, CD$_3$OD): δ 8.49 (s, 1H), 8.34-8.25 (m, 3H); 7.64-7.56 (m, 3H); 7.38-7.32 (m, 2H); 4.64 (s, 2H); 3.78-3.33 (m, 8H); 1.53 (s, 9H).

Example 46. 4-tert-Butyl-N-[2-(hydroxymethyl)-3-(2-[4-[(morpholin-4-yl)carbonyl]phenyl]-3H-imidazo[4,5-b]pyridin-7-yl)phenyl]benzamide (46)

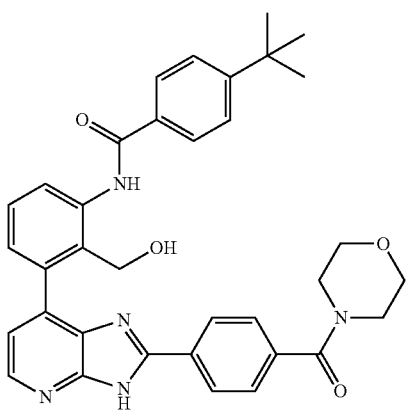 [SMILES: CC(C)(C)c1ccc(C(=O)Nc2cccc(-c3ccnc4[nH]c(-c5ccc(C(=O)N6CCOCC6)cc5)nc34)c2CO)cc1]

In a 8-mL vial, [2-amino-6-(2-[4-[(morpholin-4-yl)carbonyl]phenyl]-3H-imidazo[4,5-b]pyridin-7-yl)phenyl]methanol (43.0 mg, 0.10 mmol, 1.00 equiv) was dissolved in N,N-dimethylformamide (3 mL), to which were added 4-tert-butylbenzoic acid (19.6 mg, 0.11 mmol, 1.10 equiv), HOBT (14.9 mg, 0.11 mmol, 1.10 equiv), EDCl (25.0 mg, 0.13 mmol, 1.30 equiv) and DIEA (19.4 mg, 0.15 mmol, 1.50 equiv) at room temperature. The resulting solution was stirred overnight at room temperature. After the reaction was done, it was quenched by the addition of water (5 mL) and the resulting mixture was extracted with dichloromethane (3×20 mL). The organic layers were combined, dried over sodium sulfate and concentrated under reduced pressure. The residue was purified by reverse phase flash chromatography using the following conditions: column, C18 silica gel; mobile phase, ACN in water, 40% to 60% gradient in 20 min; detector, UV 254 nm. 4-tert-butyl-N-[2-(hydroxymethyl)-3-(2-[4-[(morpholin-4-yl)carbonyl]phenyl]-3H-imidazo[4,5-b]pyridin-7-yl)phenyl] benzamide (35 mg, 59%) was obtained as yellow solid. HPLC: 95.7% purity. MS: m/z=590.2 [M+H]$^+$. $^1$H-NMR (300 MHz, CD$_3$OD): δ 8.45-8.36 (m, 1H), 8.08-8.07 (m, 2H), 7.90-7.87 (m, 2H), 7.45-7.26 (m, 5H), 7.20 (d, J=4.0 Hz, 1H), 6.99 (d, J=5.2 Hz, 1H), 6.89-6.82 (m, 1H), 5.18-5.09 (m, 2H), 3.89-3.41 (m, 8H), 1.30-1.20 (m, 9H).

Scheme 18
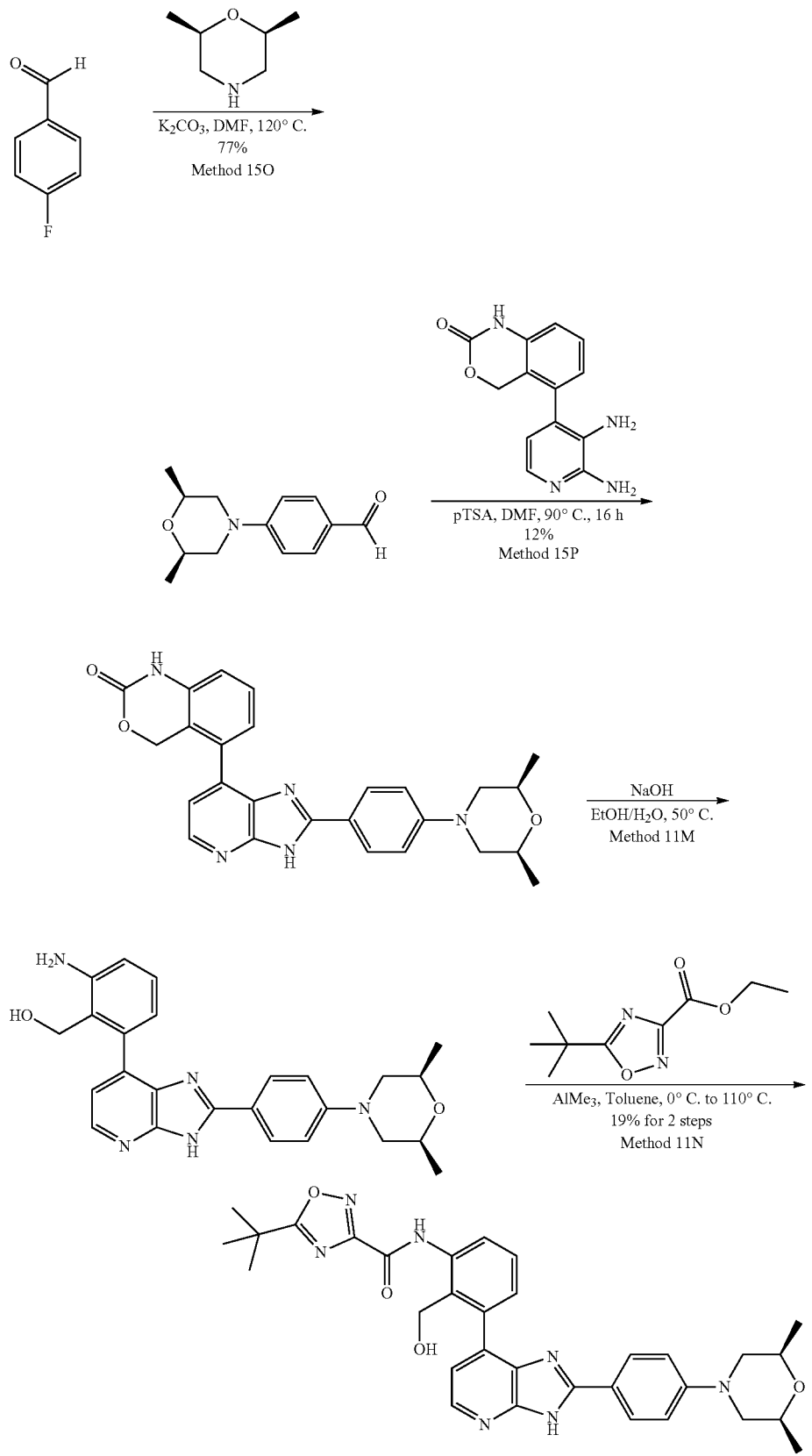

Example 47. 5-tert-Butyl-N-[3-(2-[4-[(2R,6S)-2,6-dimethylmorpholin-4-yl]phenyl]-3H-imidazo[4,5-b]pyridin-7-yl)-2-(hydroxymethyl)phenyl]-1,2,4-oxadiazole-3-carboxamide (47)

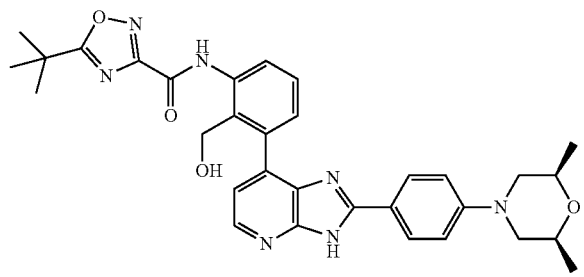 [SMILES: C[C@@H]1CN(c2ccc(-c3nc4c(-c5cccc(NC(=O)c6noc(C(C)(C)C)n6)c5CO)ccnc4[nH]3)cc2)C[C@H](C)O1]

Method 15O: 4-[(2R,6S)-2,6-dimethylmorpholin-4-yl]benzaldehyde

In a 100-mL round bottom flask, 4-fluorobenzaldehyde (2 g, 16.11 mmol, 1.00 equiv) and (2R,6S)-2,6-dimethylmorpholine (1.86 g, 16.15 mmol, 1.00 equiv) were mixed in N,N-dimethylformamide (20 mL), to which was added potassium carbonate (6.68 g, 48.3 mmol, 3.00 equiv) at room temperature. The resulting mixture was stirred overnight at 120° C. After the reaction was done, the reaction mixture was concentrated under reduced pressure, and then diluted with 50 mL H$_2$O. The resulting mixture was extracted with ethyl acetate (3×50 mL) and the organic layers were combined, dried over sodium sulfate and concentrated under reduced pressure. The residue was purified in a silica gel column eluting with ethyl acetate in petroleum ether (1% to 10% gradient) to afford 4-[(2R,6S)-2,6-dimethylmorpholin-4-yl]benzaldehyde (2.7 g, 77%) as yellow oil. MS: m/l=220.0 [M+H]$^+$.

Method 15P: 5-(2-[4-[(2R,6S)-2,6-dimethylmorpholin-4-yl]phenyl]-3H-imidazo[4,5-b]pyridin-7-yl)-2,4-dihydro-1H-3,1-benzoxazin-2-one In a 30-mL sealed tube, 5-(2,3-diaminopyridin-4-yl)-2,4-dihydro-1H-3,1-benzoxazin-2-one (160 mg, 0.62 mmol, 1.00 equiv.), 4-[(2R,6S)-2,6-dimethylmorpholin-4-yl]benzaldehyde (171 mg, 0.76 mmol, 1.22 equiv) and 4-methylbenzene-1-sulfonic acid (13.5 mg, 0.08 mmol, 0.13 equiv) were mixed in N,N-dimethylformamide (10 mL). The resulting mixture was stirred overnight at 90° C. After the reaction was done, the reaction mixture was cooled to room temperature, diluted with 10 mL H$_2$O and extracted with ethyl acetate (3×10 mL). The organic layers were combined, dried over sodium sulfate and concentrated under reduced pressure. The residue was purified by reverse phase flash chromatography using the following conditions: column, C18 silica gel; mobile phase, ACN in water, 0% to 35% gradient in 15 min; detector, UV 254 nm. 5-(2-[4-[(2R,6S)-2,6-dimethylmorpholin-4-yl]phenyl]-3H-imidazo[4,5-b]pyridin-7-yl)-2,4-dihydro-1H-3,1-benzoxazin-2-one (35 mg, 12%) was obtained as yellow solid. MS: m/z=456.2 [M+H]$^+$.

5-tert-Butyl-N-[3-(2-[4-[(2R,6S)-2,6-dimethylmorpholin-4-yl]phenyl]-3H-imidazo[4,5-b]pyridin-7-yl)-2-(hydroxymethyl)phenyl]-1,2,4-oxadiazole-3-carboxamide 5-tert-butyl-N-[3-(2-[4-[(2R,6S)-2,6-dimethylmorpholin-4-yl]phenyl]-3H-imidazo[4,5-b]pyridin-7-yl)-2-(hydroxymethyl) phenyl]-1,2,4-oxadiazole-3-carboxamide 10 mg (19% for 2 steps) was prepared from 5-(2-[4-[(2R,6S)-2,6-dimethylmorpholin-4-yl]phenyl]-3H-imidazo[4,5-b]pyridin-7-yl)-2,4-dihydro-1H-3,1-benzoxazin-2-one and ethyl 5-tert-butyl-1,2,4-oxadiazole-3-carboxylate using Method 11M and 11N. HPLC: 98.5% purity. MS: m/z=582.3 [M+H]$^+$. $^1$H-NMR (400 MHz, CD$_3$OD): δ 8.37-8.36 (in, 1H), 8.30-8.28 (in, 1H), 8.02-7.99 (m, 2H), 7.58-7.53 (m, 1H), 7.34-7.32 (m, 1H), 7.24-7.22 (m, 1H), 7.08-7.05 (m, 1H), 4.60 (s, 2H), 3.79 3.70 (m, 4H), 2.46-2.40 (m, 2H), 1.51 (s, 9H), 1.25 (in, 6H).

Scheme 19

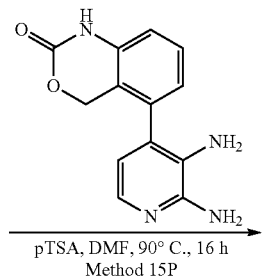

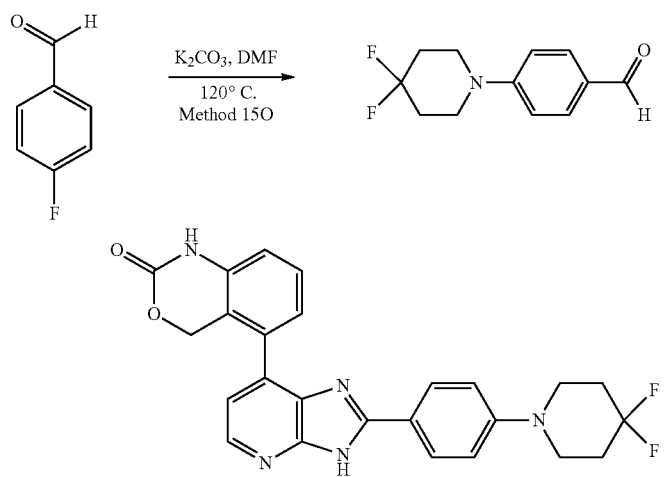

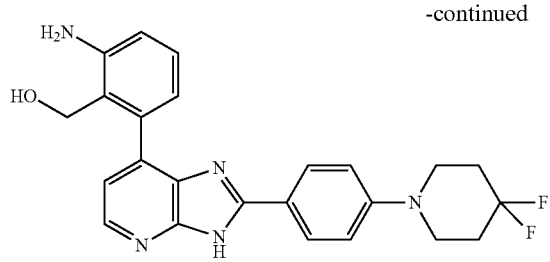
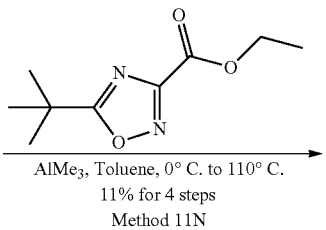

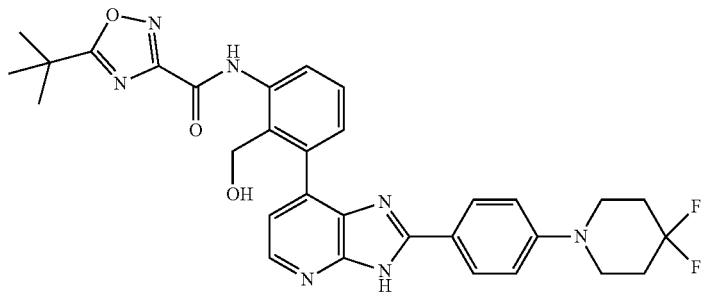

Example 48. 5-tert-Butyl-N-(3-[2-[4-(4,4-difluoropi-peridin-1-yl)phenyl]-3H-imidazo[4,5-b]pyridin-7-yl]-2-(hydroxymethyl)phenyl)-1,2,4-oxadiazole-3-carboxamide (48)

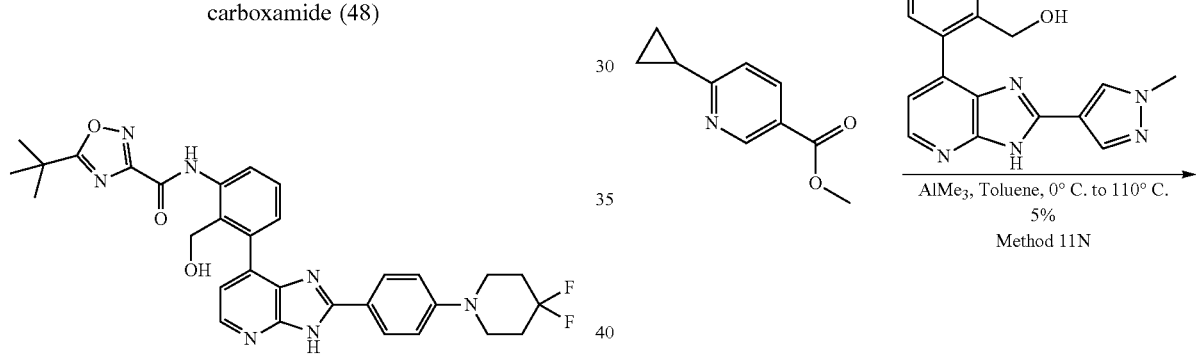

5-tert-butyl-N-(3-[2-[4-(4,4-difluoropiperidin-1-yl)phenyl]-3H-imidazo[4,5-b]pyridin-7-yl]-2-(hydroxymethyl)phenyl)-1,2,4-oxadiazole-3-carboxamide (6 mg, 11% for 4 steps) was prepared from 4-fluorobenzaldehyde, 4,4-difluoropiperidine hydrochloride, 5-(2,3-diaminopyridin-4-yl)-2,4-dihydro-1H-3,1-benzoxazin-2-one and 5-tert-butyl-1,2,4-oxadiazole-3-carboxylate using Method 15O, 15P, 11M and 11N. HPLC: 97.4% purity. MS: m/z=588.3 [M+H]$^+$. $^1$H-NMR (300 MHz, CD$_3$OD): δ 8.34-8.25 (m, 2H), 7.99-7.94 (m, 2H), 7.52 (t, J=6.0 Hz, 1H), 7.29 (d, J=4.2 Hz, 1H), 7.20 (s, 1H), 7.10-7.08 (m, 2H), 4.57 (s, 2H), 3.46-3.55 (m, 4H), 1.92-2.09 (m, 4H), 1.48 (s, 9H).

Scheme 20

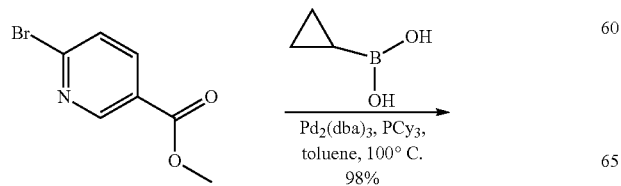

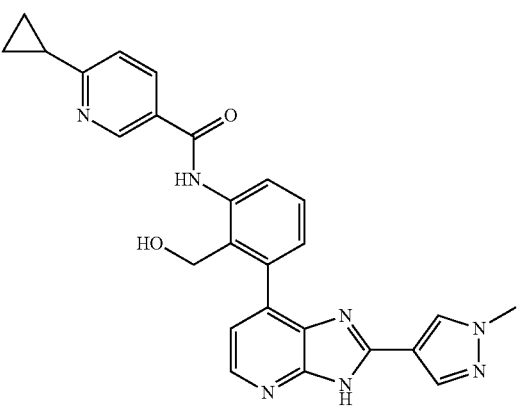

231

Example 49. 6-Cyclopropyl-N-[2-(hydroxymethyl)-3-[2-(1-methyl-1H-pyrazol-4-yl)-3H-imidazo[4,5-b]pyridin-7-yl]phenyl]pyridine-3-carboxamide (49)

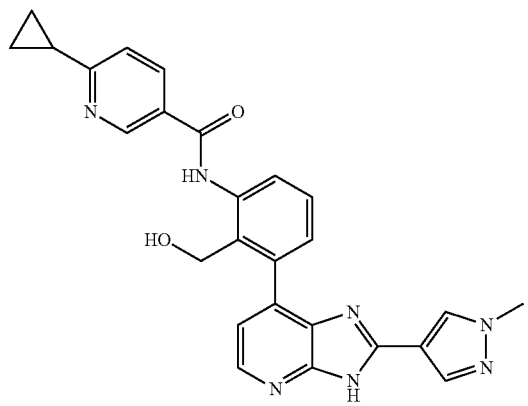 [SMILES: Cn1cc(-c2nc3c(-c4cccc(NC(=O)c5ccc(C6CC6)nc5)c4CO)ccnc3[nH]2)cn1]

Methyl 6-cyclopropylpyridine-3-carboxylate

In a 250-mL round bottom flask purged and maintained with an inert atmosphere of nitrogen, methyl 6-bromopyridine-3-carboxylate (2 g, 9.26 mmol, 1.00 equiv), cyclopropylboronic acid (1 g, 11.64 mmol, 1.26 equiv), tricyclohexylphosphane (778 mg, 2.77 mmol, 0.30 equiv), Pd$_2$(dba)$_3$·CHCl$_3$ (958 mg, 0.93 mmol, 0.10 equiv) and potassium carbonate (3.83 g, 27.71 mmol, 2.99 equiv) were mixed in a mixture of toluene and water (10:1, 44 mL) at room temperature. The resulting mixture was stirred overnight at 100° C. After the reaction was done, the reaction mixture was cooled to room temperature and filtered through a celite pad. The filtrate was concentrated under reduced pressure and the residue was purified in a silica gel column eluting with ethyl acetate in petroleum ether (5% to 15% gradient) to afford methyl 6-cyclopropylpyridine-3-carboxylate (1.6 g, 98%) as brown solid. MS: m/z=178.0 [M+H]$^+$.

6-Cyclopropyl-N-[2-(hydroxymethyl)-3-[2-(1-methyl-1H-pyrazol-4-yl)-3H-imidazo[4,5-b]pyridin-7-yl]phenyl]pyridine-3-carboxamide 6-cyclopropyl-N-[2-(hydroxymethyl)-3-[2-(1-methyl-1H-pyrazol-4-yl)-3H-imidazo[4,5-b]pyridin-7-yl]phenyl]pyridine-3-carboxamide (7.4 mg, 5%) was prepared from [2-amino-6-[2-(1-methyl-1H-pyrazol-4-yl)-3H-imidazo[4,5-b]pyridin-7-yl]phenyl] methanol and methyl 6-cyclopropylpyridine-3-carboxylate using Method 11N. HPLC: 99.4% purity. MS: m/z=466.3 [M+H]$^+$. $^1$H NMR (400 MHz, CD$_3$OD): δ 9.03 (s, 1H), 8.55 (d, J=5.6 Hz, 1H), 8.47 (s, 1H), 8.34-8.31 (m, 1H), 8.26 (s, 1H), 8.04 (d, J=8.0 Hz, 1H), 7.64 (t, J=8.0 Hz, 1H), 7.56 (d, J=5.6 Hz, 1H), 7.48 (d, J=8.0 Hz, 1H), 7.42 (d, J=7.6 Hz, 1H), 4.59 (s, 2H), 4.03 (s, 3H), 2.29-2.22 (m, 1H), 1.31-1.11 (m, 4H).

Scheme 21

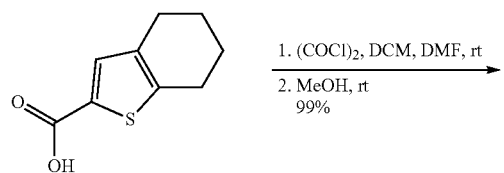

1. (COCl)$_2$, DCM, DMF, rt
2. MeOH, rt
99%

232

-continued

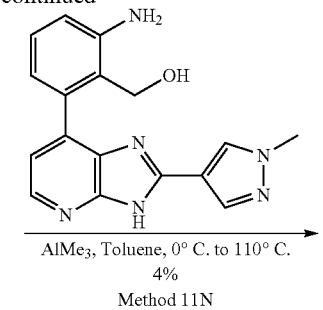

AlMe$_3$, Toluene, 0° C. to 110° C.
4%
Method 11N

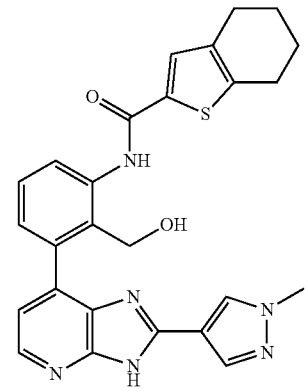

Example 50. N-[2-(hydroxymethyl)-3-[2-(1-methyl-1H-pyrazol-4-yl)-3H-imidazo[4,5-b]pyridin-7-yl]phenyl]-4,5,6,7-tetrahydro-1-benzothiophene-2-carboxamide (50)

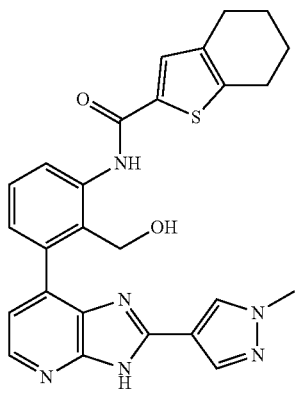 [SMILES: Cn1cc(-c2nc3c(-c4cccc(NC(=O)c5cc6c(s5)CCCC6)c4CO)ccnc3[nH]2)cn1]

Methyl 6-cyclopropylpyridine-3-carboxylate

In a 10-mL round bottom flask with magnetic stir bar, 4,5,6,7-tetrahydro-1-benzothiophene-2-carboxylic acid (50 mg, 0.27 mmol, 1.00 equiv) was dissolved in dichloromethane (1 mL), to which was added oxalic dichloride (52 mg, 0.41 mmol, 1.49 equiv) dropwise at room temperature. The resulting solution was stirred for 2 h at room temperature. After the reaction was done, the reaction mixture was concentrated under reduced pressure to afford the acid chloride intermediate, which was used directly in the next step. The acid chloride intermediate prepared above was re-dissolved in MeOH (5 mL) at 0° C. The resulting solution was stirred for 1 h at room temperature. After the reaction was done, the reaction mixture was concentrated under reduced pressure and the residue was purified in prep-TLC eluting with ethyl acetate in petroleum ether (1:1) to afford methyl 4,5,6,7-tetrahydro-1-benzothiophene-2-carboxylate (54 mg, 99%) as yellow oil. MS: m/z=197.1 [M+H]+.

N-[2-(hydroxymethyl)-3-[2-(1-methyl-1H-pyrazol-4-yl)-3H-imidazo[4,5-b]pyridin-7-yl]phenyl]-4,5,6,7-tetrahydro-1-benzothiophene-2-carboxamide N-[2-(hydroxymethyl)-3-[2-(1-methyl-1H-pyrazol-4-yl)-3H-imidazo[4,5-b]pyridin-7-yl]phenyl]-4,5,6,7-tetrahydro-1-benzothiophene-2-carboxamide 3.8 mg (4%) was prepared from [2-amino-6-[2-(1-methyl-1H-pyrazol-4-yl)-3H-imidazo[4,5-b]pyridin-7-yl]phenyl]methanol, methyl 4,5,6,7-tetrahydro-1-benzothiophene-2-carboxylate using Method 11N. HPLC: 97.1% purity. MS: m/z=485.1 [M+H]+. $^1$H NMR (400 MHz, DMSO-$d_6$): δ 13.45 (br s, 1H), 10.23 (s, 1H), 8.41-8.32 (m, 2H), 8.25-8.09 (m, 2H), 7.47-7.46 (m, 2H), 7.23-7.21 (m, 2H), 5.96 (s, 1H), 4.53 (s, 2H), 3.91 (s, 3H), 2.79-2.78 (m, 2H), 2.65-2.63 (m, 2H), 1.82-1.77 (m, 4H).

Scheme 22

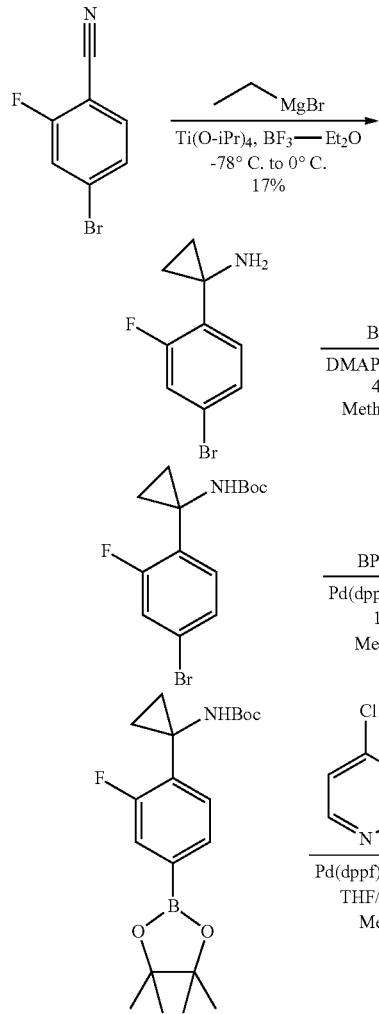

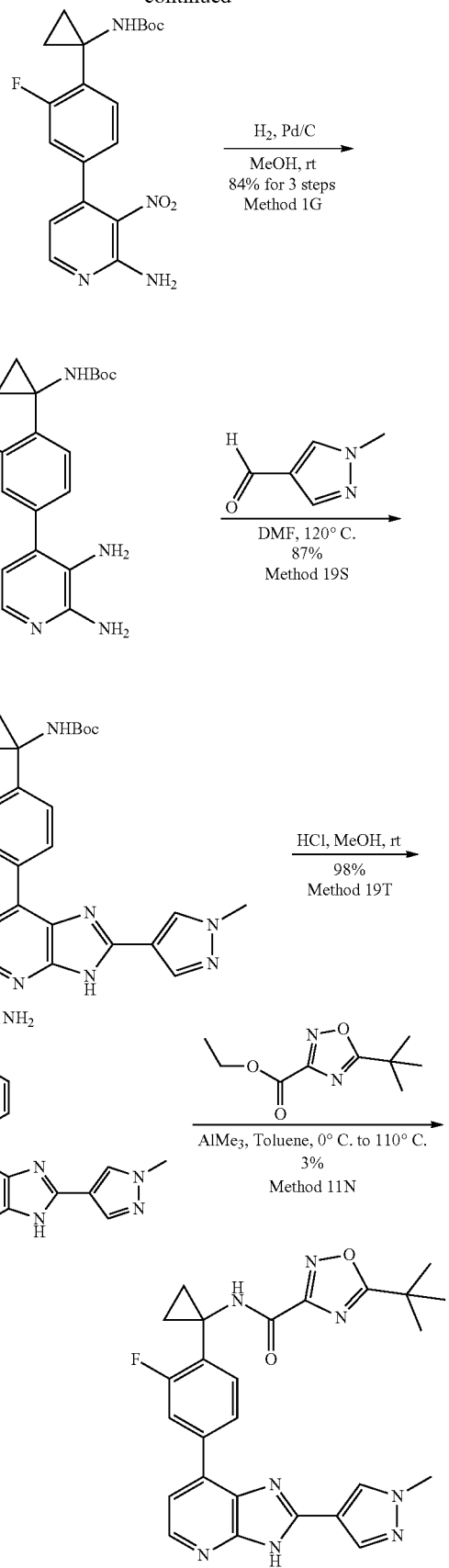

Example 51. 5-tert-Butyl-N-(1-[2-fluoro-4-[2-(1-methyl-1H-pyrazol-4-yl)-3H-imidazo[4,5-b]pyridin-7-yl]phenyl] cyclopropyl)-1,2,4-oxadiazole-3-carboxamide (51)

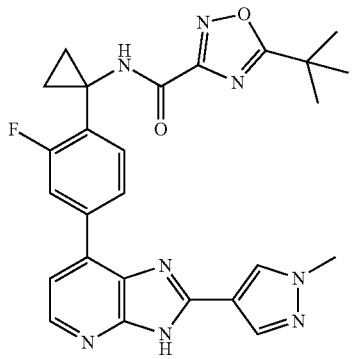 [SMILES: Cn1cc(-c2nc3c(-c4ccc(C5(NC(=O)c6noc(C(C)(C)C)n6)CC5)c(F)c4)ccnc3[nH]2)cn1]

1-(4-Bromo-2-fluorophenyl)cyclopropan-1-amine

At −78° C., in a 250-mL round bottom flask purged and maintained with an inert atmosphere of nitrogen, 4-bromo-2-fluorobenzonitrile (5.0 g, 25. mmol, 1.00 equiv) and Ti(Oi-Pr)$_4$ (7.85 g, 27.62 mmol, 1.10 equiv) were dissolved in ether (50 mL), to which was added ethyl magnesium bromide (7.260 g, 54.48 mmol, 2.18 equiv) dropwise. The resulting mixture was stirred at −78° C. for 10 min, warmed up to room temperature and stirred for 1 h at room temperature. Then BF$_3$.Et$_2$O (6.25 mL, 5.99 mmol, 0.24 equiv) was added dropwise and the resulting mixture was stirred for another 2 h at room temperature. When the reaction was done, it was quenched by the addition of 30 mL hydrogen chloride solution (1 M) and the mixture was washed with ethyl acetate (3×10 mL). The pH value of the aqueous layer was adjusted to 10 using NaOH solution (2 M) and the resulting mixture was exacted with EtOAc (3×100 mL). The organic layers were combined, dried over sodium sulfate and concentrated under reduced pressure to afford 1-(4-bromo-2-fluorophenyl)cyclopropan-1-amine (1 g, 17%) as yellow oil. MS: m/z=229.9[M+H]$^+$ Method 19Q: tert-Butyl N-[1-(4-bromo-2-fluorophenyl)cyclopropyl]carbamate In a 100-mL round bottom flask, 1-(4-bromo-2-fluorophenyl)cyclopropan-1-amine (950 mg, 4.13 mmol, 1.00 equiv) was dissolved in dichloromethane (15 mL), to which were added di-tert-butyl dicarbonate (1.13 g, 5.18 mmol, 1.25 equiv) and 4-dimethylaminopyridine (25.3 mg, 0.21 mmol, 0.05 equiv) at room temperature. The resulting mixture was stirred overnight at room temperature. After the reaction was done, the reaction mixture was diluted with 5 mL H$_2$O and extracted with ethyl acetate (3×6 mL). The organic layers were combined, dried over sodium sulfate and concentrated reduced pressure. The residue was purified in a silica gel column eluting with ethyl acetate in petroleum ether (10% to 50% gradient) to afford tert-butyl N-[1-(4-bromo-2-fluorophenyl)cyclopropyl]carbamate (0.55 g, 40%) as yellow solid. MS: m/z=273.8[M+H−56]$^+$ Method 19R: tert-Butyl N-[1-[2-fluoro-4-(tetramethyl-1,3,2-dioxaborolan-2-yl)phenyl]cyclopropyl] carbamate In a 50-mL round bottom flask purged and maintained with an inert atmosphere of nitrogen, tert-butyl N-[1-(4-bromo-2-fluorophenyl)cyclopropyl]carbamate (450 mg, 1.36 mmol, 1.00 equiv), 4,4,5,5-tetramethyl-2-(tetramethyl-1,3,2-dioxaborolan-2-yl)-1,3,2-dioxaborolane (520 mg, 2.05 mmol, 1.50 equiv), KOAc (270 mg, 2.75 mmol, 2.02 equiv) and Pd(dppf)Cl2.CH2Cl2 (111.7 mg, 0.14 mmol, 0.10 equiv) were mixed in N,N-dimethylformamide (6 mL). The resulting mixture was stirred overnight at 110° C. After the reaction was done, the reaction mixture was concentrated under vacuum to remove DMF, and then diluted with 50 mL DCM. The insoluble solids in the mixture were filtered out and the filtrate was washed with brine (4×5 mL). The organic layer was dried over sodium sulfate and concentrated under reduced pressure to afford tert-butyl N-[1-[2-fluoro-4-(tetramethyl-1,3,2-dioxaborolan-2-yl)phenyl]cyclopropyl] carbamate (0.516 g, crude) as black oil.

tert-Butyl N-[1-[4-(2,3-diaminopyridin-4-yl)-2-fluorophenyl]cyclopropyl]

Tert-butyl N-[1-[4-(2,3-diaminopyridin-4-yl)-2-fluorophenyl]cyclopropyl]carbamate 70 mg (84% for three steps) was prepared from tert-butyl N-[1-[2-fluoro-4-(tetramethyl-1,3,2-dioxaborolan-2-yl)phenyl]cyclopropyl]carbamate and 4-chloro-3-nitropyridin-2-amine using Method 2J and 1G. MS: m/z=359.0 [M+H]$^+$.

Method 19S: N-(1-[2-fluoro-4-[2-(1-methyl-1H-pyrazol-4-yl)-3H-imidazo[4,5-b]pyridin-7-yl]phenyl]cyclopropyl) carbamate In a 30-mL sealed tube, tert-butyl N-[1-[4-(2,3-diaminopyridin-4-yl)-2-fluorophenyl]cyclopropyl]carbamate (460 mg, 1.28 mmol, 1.00 equiv) was dissolved in N,N-dimethylformamide (10 mL), to which was added 1-methyl-1H-pyrazole-4-carbaldehyde (141 mg, 1.28 mmol, 1.00 equiv) at room temperature. The resulting solution was stirred for 18 h at 120° C. After the reaction was done, the reaction mixture was concentrated under reduced pressure. The residue was purified by reverse phase flash chromatography using the following conditions: column, C18 silica gel; mobile phase, acetonitrile in water, 0% to 50% gradient in 20 min; detector, UV 254 nm. tert-butyl N-(1-[2-fluoro-4-[2-(1-methyl-1H-pyrazol-4-yl)-3H-imidazo[4,5-b]pyridin-7-yl]phenyl]cyclopropyl)carbamate (500 mg, 87%) was obtained as brown oil. MS: m/z=449.0 [M+H]$^+$.

Method 19T: 1-[2-Fluoro-4-[2-(1-methyl-1H-pyrazol-4-yl)-3H-imidazo[4,5-b]pyridin-7-yl]phenyl] cyclopropan-1-amine In a 8-mL vial, tert-butyl N-(1-[2-fluoro-4-[2-(1-methyl-1H-pyrazol-4-yl)-3H-imidazo[4,5-b]pyridin-7-yl]phenyl] cyclopropyl)carbamate (500 mg, 1.11 mmol, 1.00 equiv) was dissolved in a solution of hydrogen chloride in methanol (4 M, 2 mL). The resulting solution was stirred for 1.5 h at room temperature. After the reaction was done, the reaction mixture was concentrated under reduced pressure to afford 1-[2-fluoro-4-[2-(1-methyl-1H-pyrazol-4-yl)-3H-imidazo [4,5-b]pyridine-7-yl]phenyl]cyclopropan-1-amine (380 mg, 98%) as brown oil.

5-tert-Butyl-N-(1-[2-fluoro-4-[2-(1-methyl-1H-pyrazol-4-yl)-3H-imidazo[4,5-b]pyridin-7-yl]phenyl] cyclopropyl)-1,2,4-oxadiazole-3-carboxamide 5-tert-butyl-N-(1-[2-fluoro-4-[2-(1-methyl-1H-pyrazol-4-yl)-3H-imidazo[4,5-b]pyridin-7-yl]phenyl]cyclopropyl)-

1,2,4-oxadiazole-3-carboxamide 10 mg (3%) was prepared from 1-[2-fluoro-4-[2-(1-methyl-1H-pyrazol-4-yl)-3H-imidazo[4,5-b]pyridin-7-yl]phenyl]cyclopropan-1-amine and 5-tert-butyl-1,2,4-oxadiazole-3-carboxylate using method 11N. HPLC: 95.9% purity. MS: m/z=501.2 [M+H]$^+$. $^1$H NMR (400 MHz, DMSO-d$_6$): δ 13.40 (br s, 1H), 9.72 (s, 1H), 8.46 (s, 1H), 8.29 (d, J=5.2 Hz, 1H), 8.25-8.02 (m, 3H), 7.78-7.65 (m, 1H), 7.50-7.49 (m, 1H), 3.95 (s, 3H), 1.41 (s, 9H), 1.33-1.32 (m, 4H).

Example 52. 3-(tert-Butoxy)-N-(1-[2-fluoro-4-[2-(1-methyl-1H-pyrazol-4-yl)-3H-imidazo[4,5-b]pyridin-7-yl]phenyl] cyclopropyl)azetidine-1-carboxamide (52)

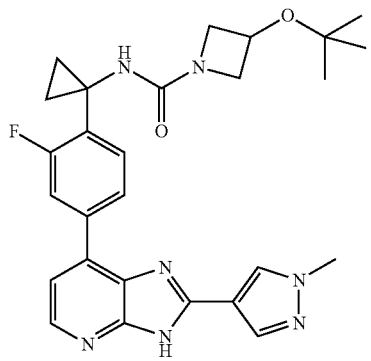 [SMILES: Cn1cc(-c2nc3c(-c4ccc(C5(NC(=O)N6CC(OC(C)(C)C)C6)CC5)c(F)c4)ccnc3[nH]2)cn1]

In a 25-mL round bottom flask, 1-[2-fluoro-4-[2-(1-methyl-1H-pyrazol-4-yl)-3H-imidazo[4,5-b]pyridin-7-yl]phenyl]cyclopropan-1-amine (90 mg, 0.26 mmol, 1.00 equiv) was dissolved in tetrahydrofuran (3 mL), to which were added triphosgene (169 mg, 0.57 mmol, 1.98 equiv) and DIEA (222 mg, 1.72 mmol, 5.98 equiv) in sequence at room temperature. The resulting solution was then stirred for 4 hours at room temperature. When the reaction was done, it was quenched by 3 mL H$_2$O and the resulting mixture was extracted with ethyl acetate (3×5 mL). The organic layers were combined, dried over sodium sulfate and concentrated reduced pressure to give the isocyanate intermediate, which was used directly in the next step. The residue obtained above was re-dissolved in tetrahydrofuran (3 mL), to which were added DIEA (222 mg, 1.72 mmol, 5.98 equiv) and 3-(tert-butoxy)azetidine (55.6 mg, 0.41 mmol, 1.50 equiv) at room temperature. The mixture was stirred overnight at room temperature. After the reaction was done, the reaction mixture was concentrated under reduced pressure and the residue was purified by prep-HPLC using the following conditions: column, Gemini-NX 5u C18 110A, AXIA Packed, 150×21.2 mm; mobile phase, acetonitrile in water (with 10 mM NH$_4$HCO$_3$), 32% to 40% gradient in 8 min; detector, UV 220 nm. 3-(tert-butoxy)-N-(1-[2-fluoro-4-[2-(1-methyl-1H-pyrazol-4-yl)-3H-imidazo[4,5-b]pyridin-7-yl]phenyl]cyclopropyl)azetidine-1-carboxamide (10 mg, 8%) product was obtained as white solid. HPLC: 97.3% purity. MS: m/z=504.3 [M+H]$^+$. $^1$H NMR (400 MHz, CD$_3$OD): δ 8.50-8.15 (m, 3H), 7.95-7.65 (m, 2H), 7.55-7.25 (m, 2H), 4.55-4.51 (m, 1H), 4.12-4.08 (m, 2H), 4.02 (s, 3H), 3.73-3.68 (m, 2H), 1.31-1.29 (m, 2H), 1.27-1.20 (m, 2H), 1.19 (s, 9H).

Scheme 23

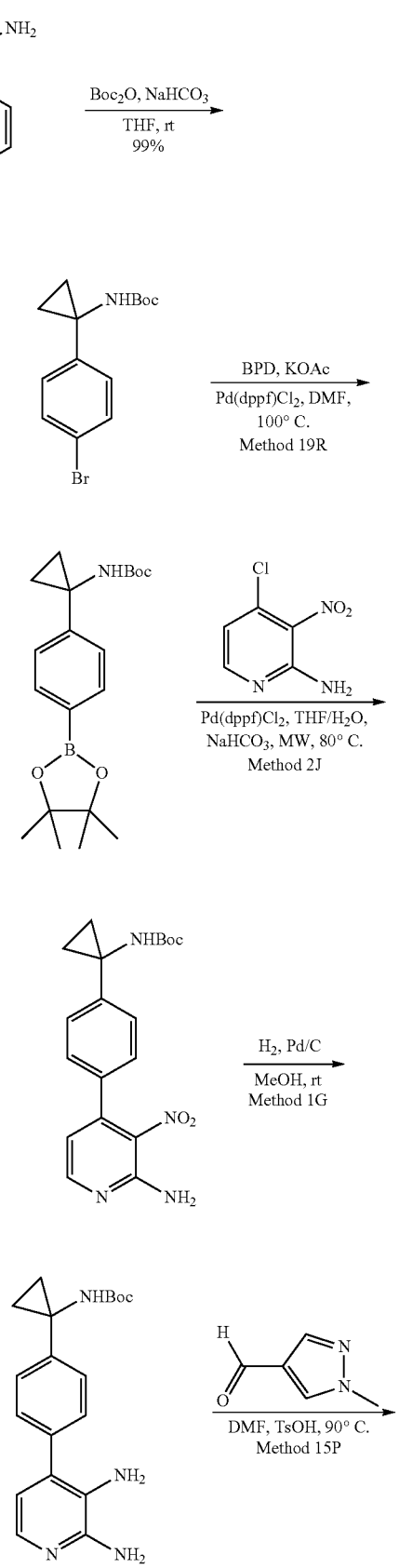

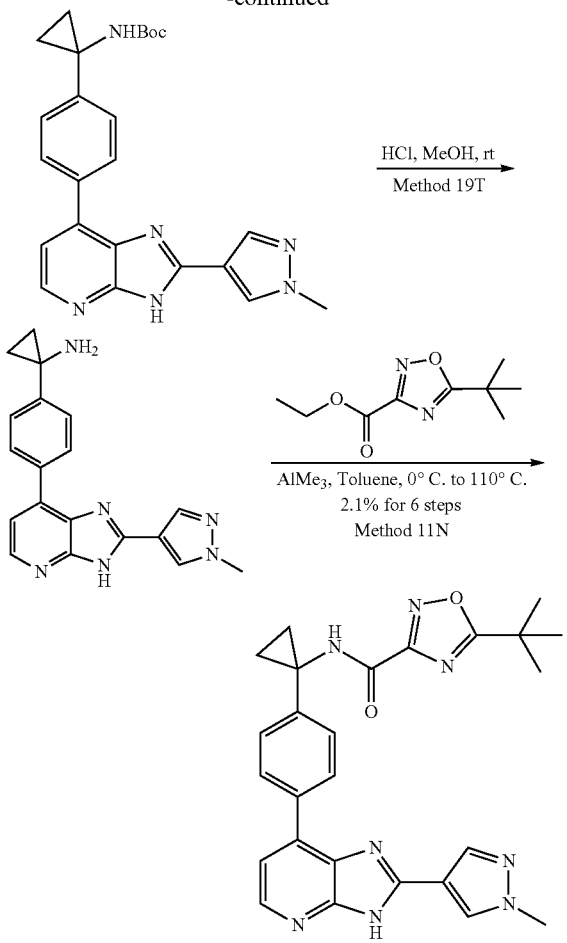

Example 53. 5-tert-Butyl-N-(1-[4-[2-(1-methyl-1H-pyrazol-4-yl)-3H-imidazo[4,5-b]pyridin-7-yl]phenyl]cyclopropyl)-1,2,4-oxadiazole-3-carboxamide (53)

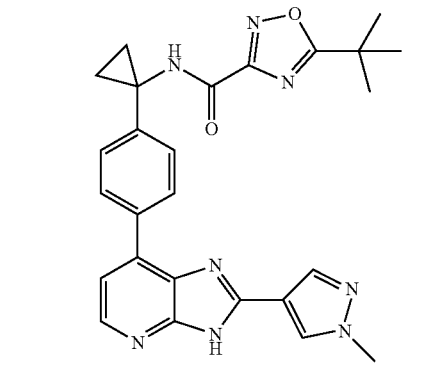 [SMILES: Cn1cc(-c2nc3c(-c4ccc(C5(NC(=O)c6noc(C(C)(C)C)n6)CC5)cc4)ccnc3[nH]2)cn1]

tert-Butyl N-[(1-(4-bromophenyl)cyclopropyl]carbamate

In a 100-mL round bottom flask, 1-(4-bromophenyl)cyclopropan-1-amine (1 g, 4.48 mmol, 1.00 equiv) and di-tert-butyl dicarbonate (3.1 g, 13.49 mmol, 3.01 equiv) were mixed in tetrahydrofuran (20 mL), to which was added a solution of sodium bicarbonate (5 g, 59.5 mmol, 13.29 equiv) in water (10 mL) at room temperature. The resulting solution was stirred overnight at room temperature. After the reaction was done, the reaction mixture was extracted with ethyl acetate (3×10 mL) and the organic layers were combined, dried over sodium sulfate and concentrated under reduced pressure. The residue was purified in a silica gel column eluting with ethyl acetate in petroleum ether (10% to 50% gradient) to afford tert-butyl N-[1-(4-bromophenyl)cyclopropyl]carbamate (1.47 g, 99%) as light yellow solid. MS: m/z=255.7 [M+H−56]$^+$.

5-tert-Butyl-N-(1-[4-[2-(1-methyl-1H-pyrazol-4-yl)-3H-imidazo[4,5-b]pyridin-7-yl]phenyl]cyclopropyl)-1,2,4-oxadiazole-3-carboxamide 5-tert-butyl-N-(1-[4-[2-(1-methyl-1H-pyrazol-4-yl)-3H-imidazo[4,5-b]pyridin-7-yl]phenyl]cyclopropyl)-1,2,4-oxadiazole-3-carboxamide 22.6 mg (2.1% for 6 steps) was prepared from tert-butyl N-[1-(4-bromophenyl)cyclopropyl]carbamate, 4,4,5,5-tetramethyl-2-(tetramethyl-1,3,2-dioxaborolan-2-yl)-1,3,2-dioxaborolane, 4-chloro-3-nitropyridin-2-amine and 5-tert-butyl-1,2,4-oxadiazole-3-carboxylate using Method 19R, 2J, 1G, 15P, 19T and 11N. HPLC: 99.9% purity. MS: m/z=483.1 [M+H]$^+$. $^1$H NMR (400 MHz, CD$_3$OD): δ 8.45-8.25 (m, 2H), 8.23-8.15 (m, 1H), 8.05-8.01 (m, 1H), 7.75 (s, 1H), 7.53-7.52 (m, 2H), 7.35-7.25 (m, 1H), 4.01 (s, 3H), 1.52 (s, 9H), 1.48 (s, 4H).

Scheme 24

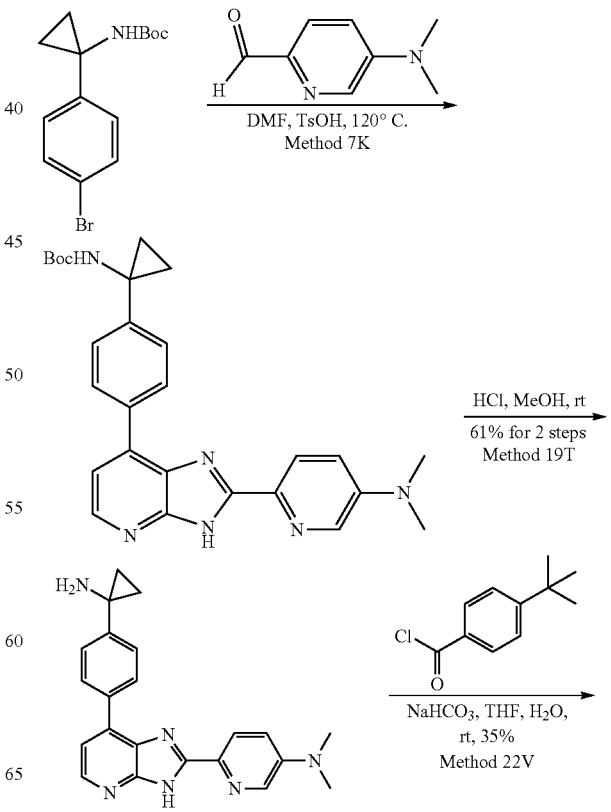

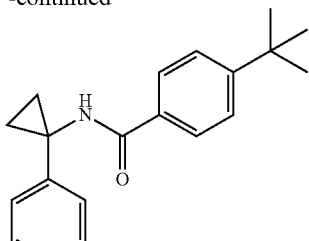

Example 54. 4-tert-Butyl-N-[1-(4-[2-[5-(dimethyl-amino)pyridin-2-yl]-3H-imidazo[4,5-b]pyridin-7-yl]phenyl) cyclopropyl]benzamide (54)

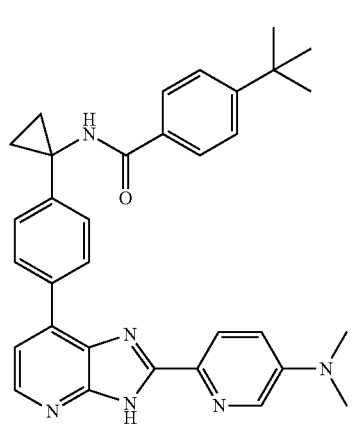 [SMILES: CN(C)c1ccc(-c2nc3c(-c4ccc(C5(NC(=O)c6ccc(C(C)(C)C)cc6)CC5)cc4)ccnc3[nH]2)nc1]

6-[7-[4-(1-Aminocyclopropyl)phenyl]-3H-imidazo[4,5-b]pyridin-2-yl]-N,N-dimethylpyridin-3-amine 6-[7-[4-(1-aminocyclopropyl)phenyl]-3H-imidazo[4,5-b]pyridine-2-yl]-N,N-dimethylpyridin-3-amine 78 mg (61% for 2 steps) was prepared from tert-butyl N-[1-[4-(2,3-diaminopyridin-4-yl)phenyl]cyclopropyl]carbamate and 5-(dimethylamino)pyridine-2-carbaldehyd using Method 7K and 19T. MS: m/z=371.1 [M+H]⁺.

Method 22V: 4-tert-Butyl-N-[1-(4-[2-[5-(dimethyl-amino)pyridin-2-yl]-3H-imidazo[4,5-b]pyridin-7-yl]phenyl) cycloorooyl]benzamide In a 25-mL round bottom flask, 6-[7-[4-(1-aminocyclopropyl)phenyl]-3H-imidazo[4,5-b]pyridin-2-yl]-N,N-dimethylpyridin-3-amine (78 mg, 0.19 mmol, 1.00 equiv) was dissolved in tetrahydrofuran (4 mL), to which was added a solution of sodium bicarbonate (106 mg, 1.26 mmol, 5.99 equiv) in water (0.4 mL) at room temperature. Then 4-tert-butylbenzoyl chloride (41 mg, 0.20 mmol, 0.99 equiv) was added slowly. The resulting solution was stirred overnight at room temperature. After the reaction was done, the insoluble solids in the reaction mixture were collected by filtration, rinsed with methanol (3×5 mL) and ether (2×5 mL). The obtained solids were dried in an oven under reduced pressure to afford 4-tert-butyl-N-[1-(4-[2-[5-(dimethylamino)pyridin-2-yl]-3H-imidazo[4,5-b]pyridin-7-yl]phenyl)cyclopropyl]benzamide (36 mg, 35%) as yellow solid. HPLC: 95.4% purity. MS: m/z=531.2 [M+H]⁺. ¹H NMR (400 MHz, CD₃OD): δ 9.38 (s, 1H), 8.57 (d, J=5.6 Hz, 1H), 8.48 (d, J=9.2 Hz, 1H), 8.21 (s, 1H), 7.95-7.85 (m, 4H), 7.75-7.68 (m, 1H), 7.60-7.52 (m, 1H), 7.45-7.35 (m, 4H), 3.12 (s, 6H), 1.36-1.26 (m, 4H), 1.25 (s, 9H).

Scheme 25

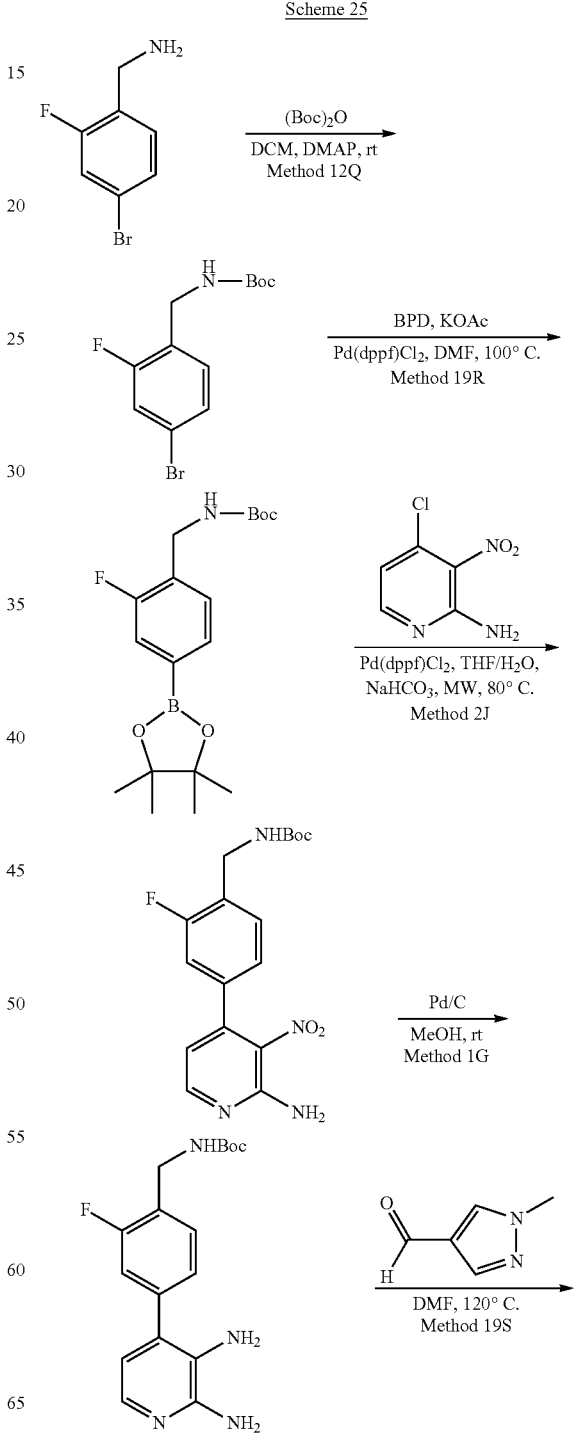

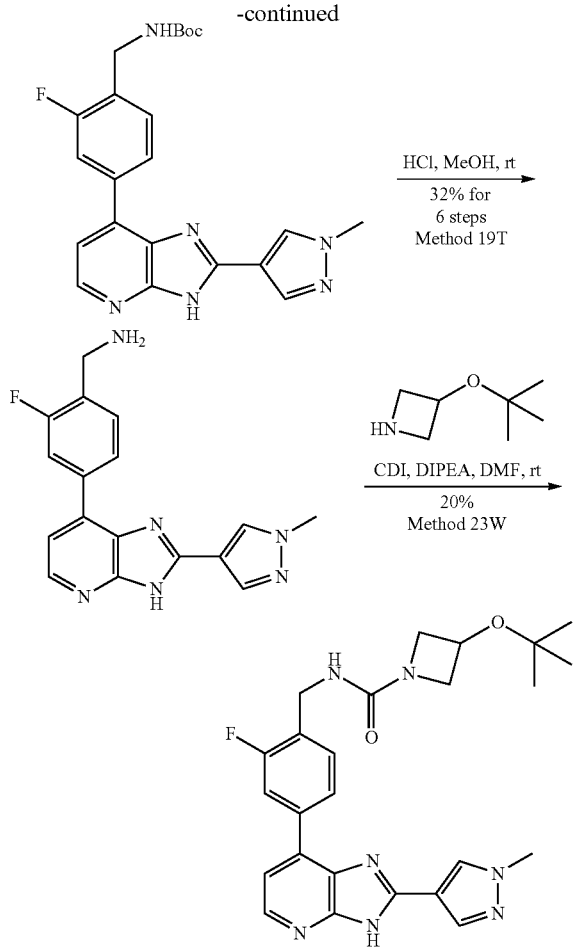

Example 55. 3-(tert-Butoxy)-N-([2-fluoro-4-[2-(1-methyl-1H-pyrazol-4-yl)-3H-imidazo[4,5-b]pyridin-7-yl]phenyl] methyl)azetidine-1-carboxamide (55)

[2-Fluoro-4-[2-(1-methyl-1H-pyrazol-4-yl)-3H-imidazo[4,5-b]pyridin-7-yl]phenyl]methanamine

[2-fluoro-4-[2-(1-methyl-1H-pyrazol-4-yl)-3H-imidazo[4,5-b]pyridin-7-yl]phenyl]methanamine 230 mg (32% for 6 steps) was prepared from (4-bromo-2-fluorophenyl)methanamine, di-tert-butyl dicarbonate, 4,4,5,5-tetramethyl-2-(tetramethyl-1,3,2-dioxaborolan-2-yl)-1,3,2-dioxaborolane, 4-chloro-3-nitropyridin-2-amine, 1-methyl-1H-pyrazole-4-carbaldehyde, 4-(dihydroxyboranyl)benzoic acid and 3,3-dimethylbutan-1-amine using Method 19Q, 19R, 2J, 1G, 19S, and 19T. MS: m/z=323.0 [M+H]$^+$.

Method 23W: 3-(tert-Butoxy)-N-([2-fluoro-4-[2-(1-methyl-1H-pyrazol-4-yl)-3H-imidazo[4,5-b]pyridin-7-yl]phenyl]methyl)azetidine-1-carboxamide In a 25-mL round bottom flask purged and maintained with an inert atmosphere of nitrogen, [2-fluoro-4-[2-(1-methyl-1H-pyrazol-4-yl)-3H-imidazo[4,5-b]pyridin-7-yl]phenyl]methanamine (100 mg, 0.31 mmol, 1.00 equiv) was dissolved in N,N-dimethylformamide (5 mL), to which were added CDI (100 mg, 0.62 mmol, 1.99 equiv) and DIPEA (200 mg, 1.55 mmol, 4.99 equiv) at room temperature. The mixture was stirred 1 h at room temperature, and then was added by 3-(tert-butoxy) azetidine (60 mg, 0.46 mmol, 1.50 equiv). The resulting mixture was stirred for 12 h at room temperature. After the reaction was done, the reaction mixture was diluted with 15 mL ethyl acetate and washed with brine (5×5 mL). The organic phase was dried over sodium sulfate and concentrated under reduced pressure. The residue was purified by prep-HPLC using the following conditions: column, Gemini-NX 5u C18 110A, AXIA Packed, 150×21.2 mm; mobile phase, acetonitrile in water (with 10 mM NH$_4$HCO$_3$), 25% to 50% gradient in 8 min; detector, UV 254 nm. 3-(tert-butoxy)-N-([2-fluoro-4-[2-(1-methyl-1H-pyrazol-4-yl)-3H-imidazo[4,5-b]pyridin-7-yl] phenyl]methyl)azetidine-1-carboxamide (30 mg, 20%) was obtained as white solid. HPLC: 98.3% purity. MS: m/z=478.1 [M+H]$^+$. $^1$H NMR (400 MHz, DMSO-d$_6$): δ 13.33 (br s, 1H), 8.46 (s, 1H), 8.29-8.21 (m, 2H), 8.14-8.13 (m, 2H), 7.57-7.45 (m, 2H), 7.00-6.95 (m, 1H), 4.55-4.45 (m, 1H), 4.47 (d, J=4.8 Hz, 2H), 4.04 (t, J=8 Hz, 2H), 3.95 (s, 3H), 3.63-3.60 (m, 2H), 1.13 (s, 9H)

Example 56. 6-Cyclopropyl-N-([2-fluoro-4-[2-(1-methyl-1H-pyrazol-4-yl)-3H-imidazo[4,5-b]pyridin-7-yl]phenyl]methyl)pyridine-3-carboxamide (56)

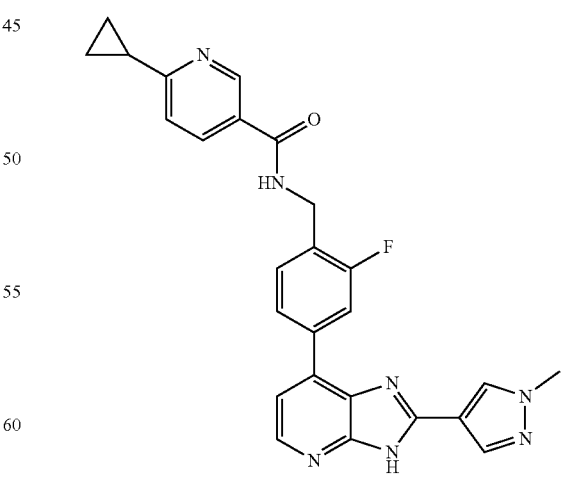

In a 10-mL round bottom flask purged and maintained with an inert atmosphere of nitrogen, [2-fluoro-4-[2-(1-methyl-1H-pyrazol-4-yl)-3H-imidazo[4,5-b]pyridin-7-yl]phenyl]methanamine (100 mg, 0.31 mmol, 1.00 equiv) and 6-cyclopropylpyridine-3-carboxylic acid (60.7 mg, 0.37 mmol, 1.20 equiv) were dissolved in N,N-dimethylformamide (2 mL), to which were added HATU (176.9 mg, 0.47 mmol, 1.50 equiv) and DIEA (120.3 mg, 0.93 mmol, 3.00 equiv) in sequence at room temperature. The resulting solution was stirred for 16 h at room temperature. When the reaction was done, it was quenched by the addition of 5 mL water and the mixture was extracted with dichloromethane (3×10 mL). The organic layers were combined, dried over sodium sulfate and concentrated under reduced pressure. The residue was purified by prep-HPLC using the following conditions: column, X Bridge C18, 19*150 mm, 5 um; mobile phase, acetonitrile in water (with 0.05% TFA), 30% to 70% gradient in 10 min; detector, UV, 254 nm. 6-cyclopropyl-N-([2-fluoro-4-[2-(1-methyl-1H-pyrazol-4-yl)-3H-imidazo[4,5-b]pyridin-7-yl] phenyl]methyl)pyridine-3-carboxamide (20 mg, 13%) was obtained as white solid. HPLC: 97.7% purity. MS: m/z=468.1 [M+H]$^+$. $^1$H NMR (400 MHz, DMSO-d$_6$): δ 13.39 (br s, 1H), 9.20-9.17 (m, 1H), 8.91 (d, J=2.0 Hz, 1H), 8.44 (s, 1H), 8.29-8.20 (m, 2H), 8.14-8.11 (m, 3H), 7.56-7.52 (m, 2H), 7.42 (d, J=8.0 Hz, 1H), 4.60 (s, 2H), 3.94 (s, 3H), 2.33-2.15 (m, 1H), 1.05-1.01 (m, 4H).

Scheme 26

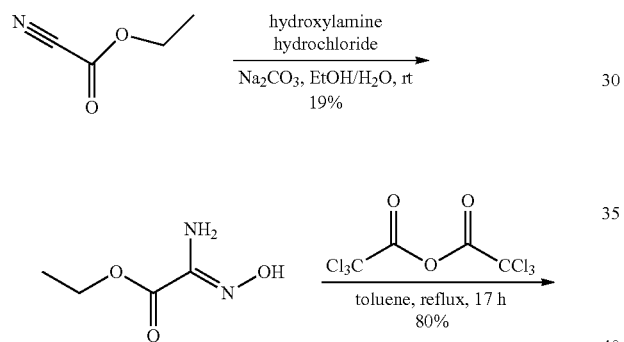

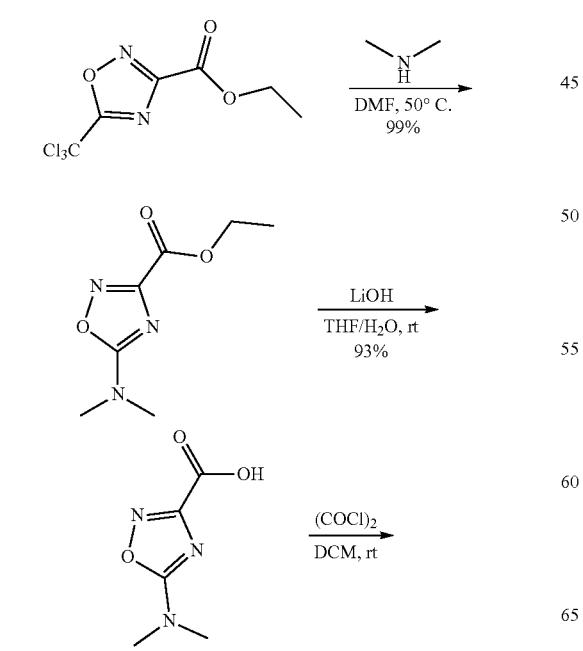

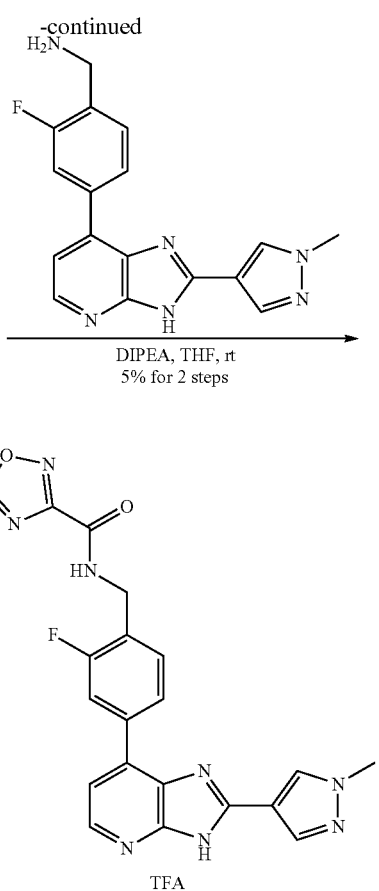

Example 57. 5-(Dimethylamino)-N-(2-fluoro-4-(2-(1-methyl-1H-pyrazol-4-yl)-3H-imidazo[4,5-b]pyridin-7-yl)benzyl)-1,2,4-oxadiazole-3-carboxamide 2,2,2-trifluoroacetate (57)

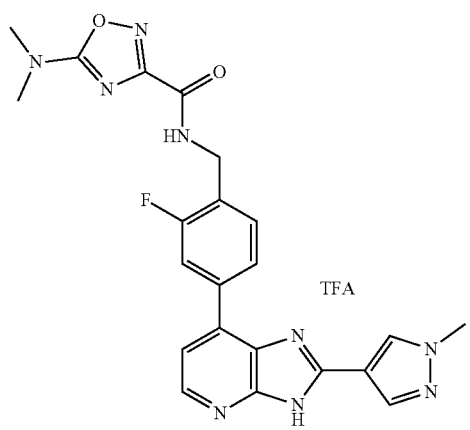

Ethyl [(Z)—N-hydroxycarbamimidoyl] formate

In a 250-mL round bottom flask purged and maintained with an inert atmosphere of nitrogen, 2-ethoxy-2-oxoacetonitrile (5 g, 50.46 mmol, 1.00 equiv) and sodium carbonate (8 g, 75.48 mmol, 1.50 equiv) was mixed in a mixture of ethanol (50 mL) and water (30 mL), to which was added hydroxylamine hydrochloride (5.2 g, 74.83 mmol, 1.48 equiv). The resulting mixture was stirred overnight at room temperature. After the reaction was done, the reaction mixture was concentrated under reduced pressure and the remaining solution was extracted with dichloromethane (3×30 mL). The organic layers were combined, dried over sodium sulfate and concentrated under reduced pressure to afford ethyl [(Z)—N-hydroxycarbamimidoyl] formate (1.3 g, 19%) as off-white solid. MS: m/z=133.0 [M+H]$^+$.

Ethyl 5-(trichloromethyl)-1,2,4-oxadiazole-3-carboxylate

In a 100-mL round bottom flask, trichloroacetyl 2,2,2-trichloroacetate (695 mg, 2.25 mmol, 1.00 equiv) and ethyl [(Z)—N-hydroxycarbamimidoyl]formate (300 mg, 2.27 mmol, 1.01 equiv) were dissolved in toluene (5 mL) at room temperature. The resulting solution was stirred overnight at 110° C. After the reaction was done, the reaction mixture was concentrated under reduced pressure, and then the residue was dissolved in 30 mL ethyl acetate and washed with brine (3×10 mL). The organic layer was dried over sodium sulfate and concentrated under reduced pressure to afford ethyl 5-(trichloromethyl)-1,2,4-oxadiazole-3-carboxylate (470 mg, 80%) as red oil.

Ethyl 5-(dimethylamino)-1,2,4-oxadiazole-3-carboxylate

In a 100-mL round bottom flask, ethyl 5-(trichloromethyl)-1,2,4-oxadiazole-3-carboxylate (330 mg, 1.27 mmol, 1.00 equiv) was dissolved in N,N-dimethylformamide (5 mL), to which were added dimethylamine hydrochloride (124 mg, 1.52 mmol, 1.20 equiv) and DIEA (495 mg, 3.83 mmol, 3.01 equiv) at room temperature. The resulting solution was stirred for 4 h at 50° C. After the reaction was done, the reaction mixture was cooled to room temperature, diluted with 20 mL H$_2$O and extracted with ethyl acetate (4×30 mL). The organic layers were combined, dried over sodium sulfate and concentrated under reduced pressure to afford ethyl 5-(dimethylamino)-1,2,4-oxadiazole-3-carboxylate (220 mg, 99%) as red oil. MS: m/z=186.1 [M+H]$^+$.

5-(Dimethylamino)-1,2,4-oxadiazole-3-carboxylic acid

In a 100-mL round bottom flask, ethyl 5-(dimethylamino)-1,2,4-oxadiazole-3-carboxylate (214 mg, 1.02 mmol, 1.00 equiv) was dissolved in a mixture of tetrahydrofuran (7 mL) and water (4 mL), to which was added LiOH (155 mg, 6.47 mmol, 6.32 equiv) at room temperature. The resulting mixture was stirred for 2 h at room temperature. After the reaction was done, the reaction mixture was concentrated under reduce pressure. The pH value of the remaining solution was adjusted to 2 using hydrogen chloride solution (1 M) and concentrated under reduced pressure. The residue was purified by reverse phase flash chromatography using the following conditions: column, C18 silica gel; mobile phase, water, 100% isocratic; detector, UV 254 nm. 5-(dimethylamino)-1,2,4-oxadiazole-3-carboxylic acid (150 mg, 93%) was obtained as yellow solid.

5-(Dimethylamino)-1,2,4-oxadiazole-3-carbonyl chloride

In a 8-mL vial, oxalic dichloride (60.2 mg, 0.47 mmol, 1.49 equiv) was added dropwise to the solution of 5-(dimethylamino)-1,2,4-oxadiazole-3-carboxylic acid (50 mg, 0.32 mmol, 1.00 equiv) in dichloromethane (3 mL, 47.19 mmol, 148.30 equiv) at room temperature. The resulting solution was stirred for 2 h at room temperature. After the reaction was done, the reaction mixture was concentrated under reduce pressure to afford 5-(dimethylamino)-1,2,4-oxadiazole-3-carbonyl chloride 56 mg (crude) as white solid, which was used in the next step directly without further purification.

5-(Dimethylamino)-N-(2-fluoro-4-(2-(1-methyl-1H-pyrazol-4-yl)-3H-imidazo[4,5-b]pyridin-7-yl)benzyl)-1,2,4-oxadiazole-3-carboxamide 2,2,2-trifluoroacetate Into a 8-mL vial, [2-fluoro-4-[2-(1-methyl-1H-pyrazol-4-yl)-3H-imidazo[4,5-b]pyridin-7-yl]phenyl]methanamine (103 mg, 0.32 mmol, 1.00 equiv) was dissolved in tetrahydrofuran (2 mL), to which were added 5-(dimethylamino)-1,2,4-oxadiazole-3-carbonyl chloride (56 mg, 0.32 mmol, 1.00 equiv) and DIEA (124 mg, 0.96 mmol, 3.00 equiv) in sequence at room temperature. The resulting solution was stirred overnight at room temperature. After the reaction was done, the reaction mixture was diluted with 10 mL DCM and washed with brine (3×3 mL). The organic phase was separated, dried over sodium sulfate and concentrated under reduced pressure. The residue was purified by prep-HPLC with the following conditions: column, XBridge BEH C18 OBD Prep Column, 5 um, 19 mm 250 mm; mobile phase, acetonitrile in water (with 0.05% TFA), 26% to 36% gradient in 8 min; detector, UV 254 nm. 5-(dimethylamino)-N-(2-fluoro-4-(2-(1-methyl-1H-pyrazol-4-yl)-3H-imidazo[4,5-b]pyridin-7-yl) benzyl)-1,2,4-oxadiazole-3-carboxamide 2,2,2-trifluoroacetate (9 mg, 5% for 2 steps) was obtained as yellow solid. HPLC: 95.4% purity. MS: m/z=462.0 [M+H]$^+$. $^1$H NMR (400 MHz, CD$_3$OD): δ 8.46-8.45 (m, 2H), 8.27 (s, 1H), 7.81-7.75 (m, 2H), 7.69-7.64 (m, 1H), 7.57 (d, J=6.4 Hz, 1H), 4.73 (s, 2H), 4.04 (s, 3H), 3.21 (s, 6H).

Scheme 27

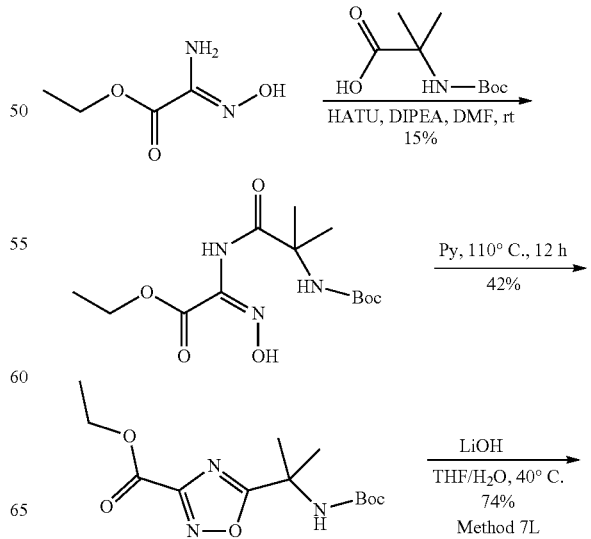

-continued

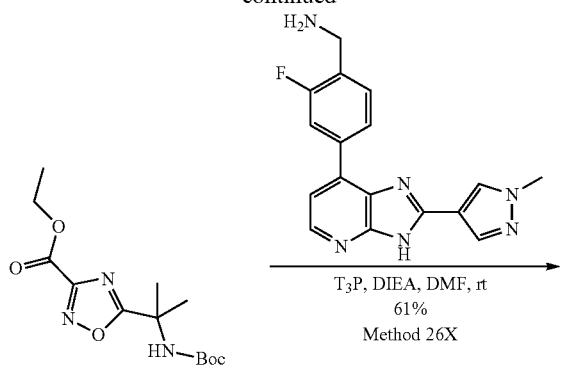

T₃P, DIEA, DMF, rt
61%
Method 26X

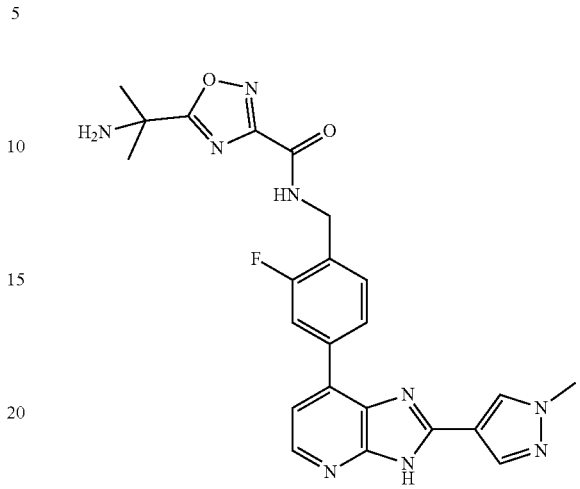

HCl, MeOH, rt
10%
Method 19T

Example 58. 5-(2-Aminopropan-2-yl)-N-([2-fluoro-4-[2-(1-methyl-1H-pyrazol-4-yl)-3H-imidazo[4,5-b]pyridin-7-yl]phenyl]methyl)-1,2,4-oxadiazole-3-carboxamide (58)

Ethyl (2E)-2-(2-[[(tert-butoxy)carbonyl]amino]-2-methylpropanamido)-2-(hydroxyimino)acetate In a 50-mL round bottom flask purged and maintained with an inert atmosphere of nitrogen, ethyl [(Z)—N-hydroxycarbamimidoyl]formate (820 mg, 6.21 mmol, 1.00 equiv) was dissolved in N,N-dimethylformamide (10 mL), to which were added HATU (3.54 g, 9.31 mmol, 1.50 equiv), DIEA (2.4 g, 18.57 mmol, 2.99 equiv) and 2-[[(tert-butoxy)carbonyl]amino]-2-methyl propanoic acid (1.26 g, 6.20 mmol, 1.00 equiv) at room temperature. The resulting solution was stirred overnight at room temperature. When the reaction was done, it was quenched by the addition of 10 mL water and the resulting mixture was extracted with dichloromethane (3×15 mL). The organic layers were combined, dried over sodium sulfate and concentrated under reduced pressure. The residue was purified in a silica gel column eluting with ethyl acetate in petroleum ether (10% to 50% gradient) to afford ethyl (2E)-2-(2-[[(tert-butoxy)carbonyl]amino]-2-methylpropanamido)-2-(hydroxyimino)acetate (300 mg, 15%) as light yellow solid.

Ethyl 5-(2-[[(tert-butoxy)carbonyl]amino]propan-2-yl)-1,2,4-oxadiazole-3-carboxylate In a 25-mL round bottom flask purged and maintained with an inert atmosphere of nitrogen, ethyl (2E)-2-(2-[[(tert-butoxy)carbonyl]amino]-2-methylpropanamido)-2-(hydroxyimino) acetate (300 mg, 0.95 mmol, 1.00 equiv) was dissolved in pyridine (10 mL) at room temperature. The resulting solution was then stirred overnight at 110° C. After the reaction was done, the reaction mixture was concentrated under reduced pressure and the residue was purified in a silica gel column eluting with ethyl acetate in petroleum ether (10% to 50% gradient) to afford ethyl 5-(2-[[(tert-butoxy)carbonyl]amino]propan-2-yl)-1,2,4-oxadiazole-3-carboxylate (120 mg, 42%) as off-white solid. MS: m/z=300.1 [M+H]⁺.

5-(2-[[tert-Butoxy)carbonyl]amino]propan-2-yl)-1,2,4-oxadiazole-3-carboxylic acid 5-(2-[[(tert-butoxy)carbonyl]amino]propan-2-yl)-1,2,4-oxadiazole-3-carboxylic acid 80 mg (74%) was prepared from ethyl 5-(2-[[(tert-butoxy)carbonyl]amino]propan-2-yl)-1,2,4-oxadiazole-3-carboxylate using Method 7L. MS: m/z=272.0 [M+H]$^+$.

Method 26X: tert-Butyl N-(2-[3-[([2-fluoro-4-[2-(1-methyl-1H-pyrazol-4-yl)-3H-imidazo[4,5-b]pyridin-7-yl]phenyl]methyl)carbamoyl]-1,2,4-oxadiazol-5-yl]propan-2-yl)carbamate In a 8-mL vial purged and maintained with an inert atmosphere of nitrogen, [2-fluoro-4-[2-(1-methyl-1H-pyrazol-4-yl)-3H-imidazo[4,5-b]pyridin-7-yl]phenyl]methanamine (55 mg, 0.17 mmol, 1.00 equiv) was dissolved in N,N-dimethylformamide (1.5 mL), to which were added T3P (326 mg, inf equiv), DIEA (133 mg, 1.03 mmol, 6.03 equiv) and 5-(2-[[(tert-butoxy)carbonyl] amino]propan-2-yl)-1,2,4-oxadiazole-3-carboxylic acid (70 mg, 0.26 mmol, 1.51 equiv) at room temperature. The resulting solution was then stirred for 1 h at room temperature. When the reaction was done, it was quenched by the addition of 5 mL water and the mixture was extracted with dichloromethane (3×5 mL). The organic layers were combined, dried over sodium sulfate and concentrated under reduced pressure to afford tert-butyl N-(2-[3-[([2-fluoro-4-[2-(1-methyl-1H-pyrazol-4-yl)-3H-imidazo[4,5-b]pyridin-7-yl]phenyl]methyl)carbamoyl]-1,2,4-oxadiazol-5-yl]propan-2-yl)carbamate (60 mg, 61%) as yellow oil.

5-(2-Aminopropan-2-yl)-N-([2-fluoro-4-[2-(1-methyl-1H-pyrazol-4-yl)-3H-imidazo[4,5-b]pyridin-7-yl]phenyl]methyl)-1,2,4-oxadiazole-3-carboxamide 5-(2-aminopropan-2-yl)-N-([2-fluoro-4-[2-(1-methyl-1H-pyrazol-4-yl)-3H-imidazo[4,5-b]pyridin-7-yl]phenyl]methyl)-1,2,4-oxadiazole-3-carboxamide 5 mg (10%) was prepared from tert-butyl N-(2-[3-[([2-fluoro-4-[2-(1-methyl-1H-pyrazol-4-yl)-3H-imidazo[4,5-b]pyridin-7-yl]phenyl]methyl)carbamoyl]-1,2,4-oxadiazol-5-yl]propan-2-yl)carbamate using Method 19T. HPLC: 98.2% purity. MS: m/z=476.3 [M+H]$^+$. $^1$H NMR (300 MHz, DMSO-d$_6$): δ 13.25 (br s, 1H), 9.58-9.54 (m, 1H), 8.45 (s, 1H), 8.29 (d, J=6.0 Hz, 2H), 8.14-8.12 (m, 2H), 7.54-7.49 (m, 2H), 4.59 (d, J=6.0 Hz, 2H), 3.94 (s, 3H), 2.51-2.43 (m, 2H), 1.49 (m, 6H).

Example 59. 5-Cyclopropyl-N-([2-fluoro-4-[2-(1-methyl-1H-pyrazol-4-yl)-3H-imidazo[4,5-b]pyridin-7-yl]phenyl] methyl)-1,2,4-oxadiazole-3-carboxamide (59)

5-cyclopropyl-N-([2-fluoro-4-[2-(1-methyl-1H-pyrazol-4-yl)-3H-imidazo[4,5-b]pyridin-7-yl]phenyl]methyl)-1,2,4-oxadiazole-3-carboxamide 15 mg (21%) was prepared from 5-cyclopropyl-1,2,4-oxadiazole-3-carboxylic acid, [2-fluoro-4-[2-(1-methyl-1H-pyrazol-4-yl)-3H-imidazo[4,5-b]pyridin-7-yl]phenyl]methanamine using Method 26X. HPLC: 98.5% purity. MS: m/z=459.2 [M+H]$^+$. $^1$H NMR (400 MHz, DMSO-d$_6$): δ 13.17 (br s, 1H), 9.53-9.52 (m, 1H), 8.45 (s, 1H), 8.30-8.24 (m, 2H), 8.14-8.13 (m, 2H), 7.56-7.46 (m, 2H), 4.57 (d, J=5.6 Hz, 2H), 3.95 (s, 3H), 2.50-2.39 (m, 1H), 1.35-1.28 (m, 2H), 1.25-1.15 (m, 2H).

Scheme 28

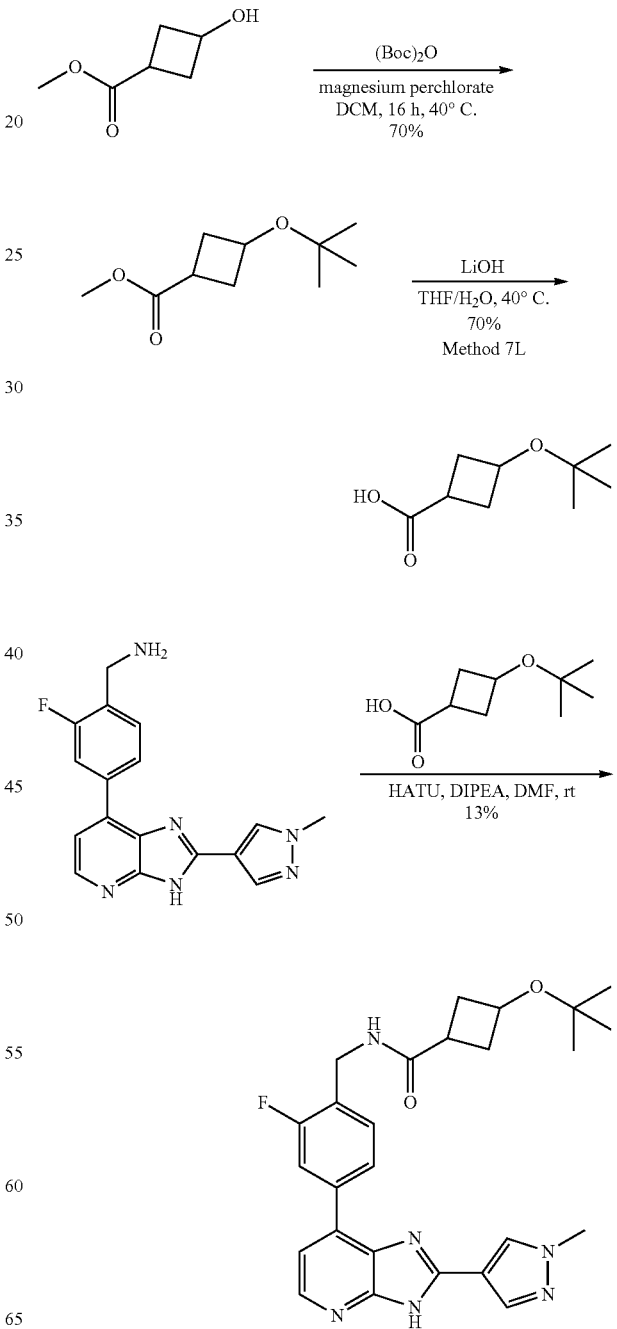

253

Example 60. 3-(tert-Butoxy)-N-([2-fluoro-4-[2-(1-methyl-1H-pyrazol-4-yl)-3H-imidazo[4,5-b]pyridin-7-yl]phenyl] methyl)cyclobutane-1-carboxamide (60)

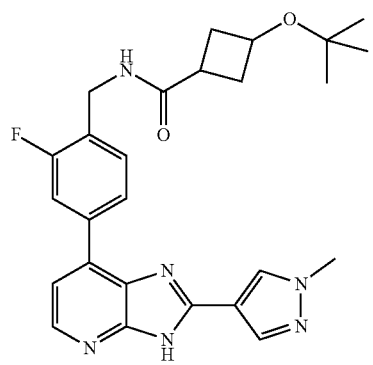 [SMILES: Cn1cc(-c2nc3c(-c4ccc(CNC(=O)C5CC(OC(C)(C)C)C5)c(F)c4)ccnc3[nH]2)cn1]

Methyl 3-(tert-butoxy)cyclobutane-1-carboxylate

In a 30-mL round bottom flask purged and maintained with an inert atmosphere of nitrogen, methyl 3-hydroxycyclobutane-1-carboxylate (200 mg, 1.54 mmol, 1.00 equiv) and di-tert-butyl dicarbonate (771.4 mg, 3.53 mmol, 2.30 equiv) were mixed in dichloromethane (10 mL), to which was added magnesium perchlorate (34.3 mg, 0.15 mmol, 0.10 equiv) at room temperature. The resulting solution was then stirred for 16 h at 40° C. When the reaction was done, it was quenched with 10 mL water and the mixture was extracted with dichloromethane (3×10 mL). The organic layers were combined, dried over sodium sulfate and concentrated under reduced pressure. The residue was purified by prep-TLC eluting with ethyl acetate in petroleum ether (50%) to afford methyl 3-(tert-butoxy)cyclobutane-1-carboxylate (200 mg, 70%) as yellow oil. MS: m/z=187.1 [M+H]⁺.

3-(tert-Butoxy)cyclobutane-1-carboxylic acid 3-(tert-butoxy)cyclobutane-1-carboxylic acid 85 mg (70%) was prepared from methyl 3-(tert-butoxy)cyclobutane-1-carboxylate using Method 7L. MS: m/z=173.0 [M+H]⁺.

3-(tert-Butoxy)-N-([2-fluoro-4-[2-(1-methyl-1H-pyrazol-4-yl)-3H-imidazo[4,5-b]pyridin-7-yl]phenyl]methyl)cyclobutane-1-carboxamide In a 20-mL round bottom flask purged and maintained with a atmosphere of nitrogen, [2-fluoro-4-[2-(1-methyl-1H-pyrazol-4-yl)-3H-imidazo[4,5-b]pyridine-7-yl]phenyl] methanamine (100 mg, 0.31 mmol, 1.00 equiv) was dissolved in N,N-dimethylformamide (5 ml), to which were added 3-(tert-butoxy)cyclobutane-1-carboxylic acid (80 mg, 0.46 mmol, 1.50 equiv), HATU (180 mg, 0.47 mmol, 1.50 equiv) and DIEA (240 mg, 1.86 mmol, 6.00 equiv) at room temperature. The resulting solution was stirred for 16 h at room temperature. When the reaction was done, it was quenched by 10 mL water and the mixture was extracted with dichloromethane (3×10 ml). The organic layers were combined, dried over sodium sulfate and concentrated under reduced pressure. The residue was purified by prep-HPLC

254 with the following conditions: column, XBridge C18 OBD Prep Column, 5 um, 19 mm, 250 mm; mobile phase, acetonitrile in water (with 10 mM NH₄HCO₃), 32% to 45% gradient in 9 min; detector, UV 254 nm. 3-(tert-butoxy)-N-([2-fluoro-4-[2-(1-methyl-1H-pyrazol-4-yl)-3H-imidazo[4,5-b]pyridin-7-yl]phenyl]methyl)cyclobutane-1-carboxamide (20 mg, 13%) was obtained as white solid. HPLC: 98.4% purity. MS: m/z=477.2 [M+H]⁺. ¹H NMR (300 MHz, CD₃OD): δ 8.33-8.32 (m, 2H), 8.18 (s, 1H), 7.80-7.60 (m, 2H), 7.50 (t, J=7.6 Hz, 1H), 7.39 (d, J=5.2 Hz, 1H), 4.50 (s, 2H), 4.12-4.10 (m, 1H), 4.00 (s, 3H), 2.75-2.59 (m, 1H), 2.52-2.36 (m, 2H), 2.18 (m, 2H), 1.19 (s, 9H).

Scheme 29

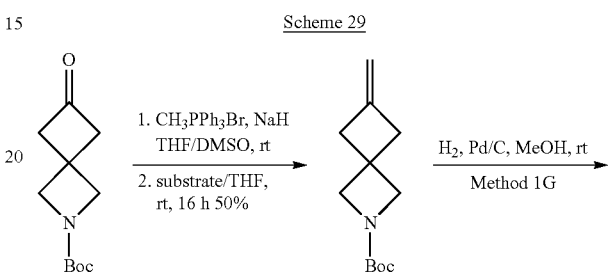

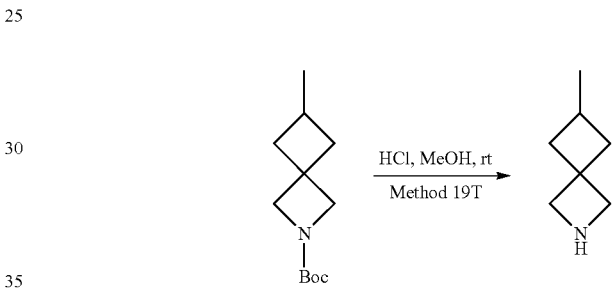

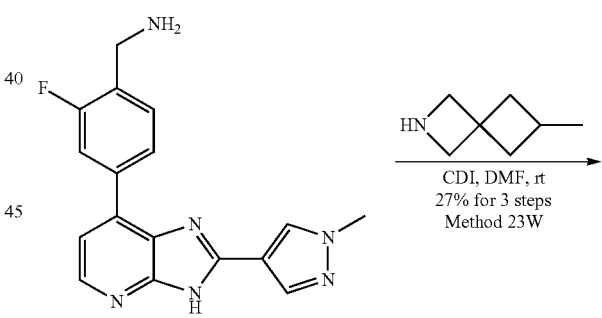

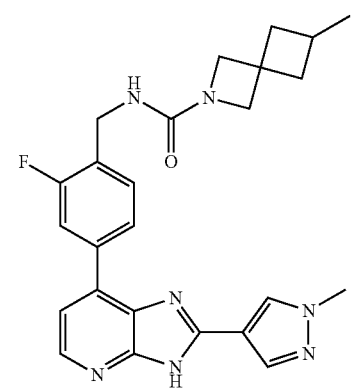

Example 61. N-([2-Fluoro-4-[2-(1-methyl-1H-pyrazol-4-yl)-3H-imidazo[4,5-b]pyridin-7-yl]phenyl]methyl)-6-methyl-2-azaspiro[3.3]heptane-2-carboxamide

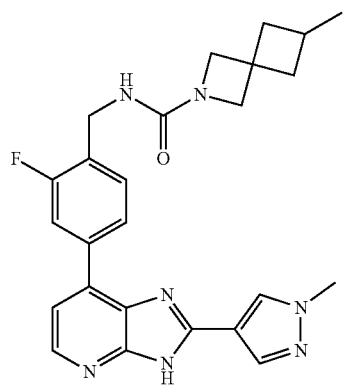 [SMILES: CC1CC2(C1)CN(C(=O)NCc1ccc(-c3ccnc4[nH]c(-c5cnn(C)c5)nc34)cc1F)C2]

tert-Butyl N-(2-[3-[([2-fluoro-4-[2-(1-methyl-1H-pyrazol-4-yl)-3H-imidazo[4,5-b]pyridin-7-yl]phenyl]methyl)carbamoyl]-1,2,4-oxadiazol-5-yl]propan-2-yl)carbamate In a 25-mL round bottom flask purged and maintained with an inert atmosphere of nitrogen, sodium hydride (60% in oil, 12.50 mg, 0.52 mmol, 1.10 equiv) was suspended in tetrahydrofuran (5 ml), to which was added a solution of methyltriphenylphosphanium bromide (507.3 mg, 1.42 mmol, 3.0 equiv) in DMSO (2 ml) dropwise at 0° C. The mixture was warmed up to room temperature and stirred for 2 h. Then a solution of tert-butyl 6-oxo-2-azaspiro[3.3]heptane-2-carboxylate (100 mg, 0.47 mmol, 1.00 equiv) in tetrahydrofuran (2 ml) was added at room temperature. The resulting mixture was stirred for another 16 h at room temperature. When the reaction was done, it was quenched by the addition of 10 mL water and the mixture was extracted with ethyl acetate (3×10 ml). The organic layers were combined, dried over sodium sulfate and concentrated under reduce pressure. The residue was purified in a silica gel column eluting with ethyl acetate in petroleum ether (5% to 20% gradient) to afford tert-butyl 6-methylidene-2-azaspiro[3.3]heptane-2-carboxylate (50 mg, 50%) as yellow solid.

N-([2-Fluoro-4-[2-(1-methyl-1H-pyrazol-4-yl)-3H-imidazo[4,5-b]pyridin-7-yl]phenyl]methyl)-6-methyl-2-azaspiro[3.3]-heptane-2-carboxamide N-([2-fluoro-4-[2-(1-methyl-1H-pyrazol-4-yl)-3H-imidazo[4,5-b]pyridin-7-yl]phenyl]methyl)-6-methyl-2-azaspiro[3.3]heptane-2-carboxamide 30 mg (27% for 3 steps) was prepared from tert-butyl 6-methylidene-2-azaspiro[3.3]heptane-2-carboxylate and [2-fluoro-4-[2-(1-methyl-1H-pyrazol-4-yl)-3H-imidazo[4,5-b]pyridin-7-yl]phenyl] methanamine using Method 1G, 19T and 23W. HPLC: 99.8% purity. MS: m/z=460.1 [M+H]$^+$. $^1$H NMR (300 MHz, CD$_3$OD): δ 8.31-8.21 (m, 2H), 8.10 (s, 1H), 7.82-7.75 (m, 2H), 7.49 (t, J=7.8 Hz, 1H), 7.35 (br s, 1H), 4.42 (s, 2H), 3.95-3.94 (m, 5H), 3.83 (s, 2H), 2.37-2.13 (m, 3H), 1.78-1.73 (m, 2H), 1.04-1.02 (m, 3H).

Scheme 30

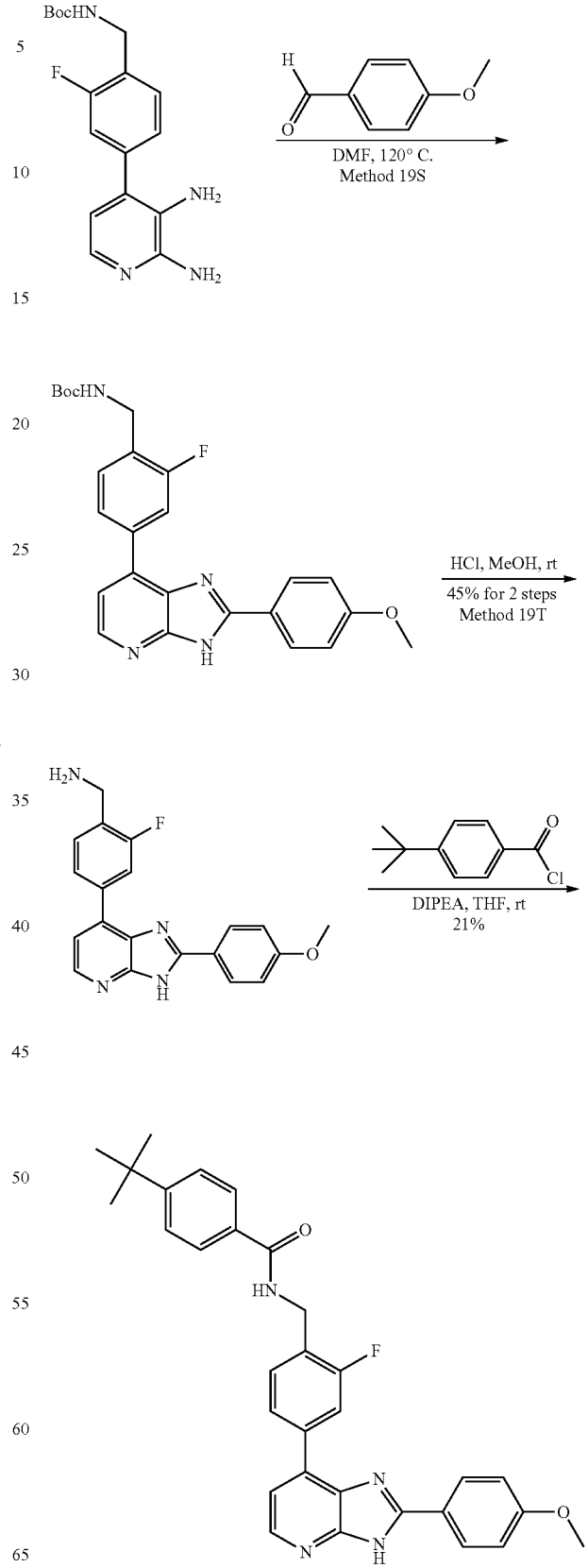

Example 62. 4-tert-Butyl-N-([2-fluoro-4-[2-(4-methoxyphenyl)-3H-imidazo[4,5-b]pyridin-7-yl]phenyl]methyl) benzamide (62)

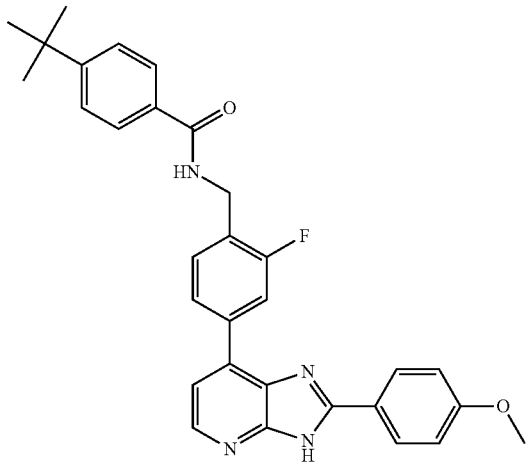 [SMILES: COc1ccc(-c2nc3c(-c4ccc(CNC(=O)c5ccc(C(C)(C)C)cc5)c(F)c4)ccnc3[nH]2)cc1]

[2-Fluoro-4-[2-(4-methoxyphenyl)-3H-imidazo[4,5-b]pyridin-7-yl]phenyl]methanamine

[2-fluoro-4-[2-(4-methoxyphenyl)-3H-imidazo[4,5-b]pyridin-7-yl]phenyl]methanamine 200 mg (45% for 2 steps) was prepared from tert-butyl N-[[4-(2,3-diaminopyridin-4-yl)-2-fluorophenyl]methyl]carbamate and 4-methoxybenzaldehyde using Method 19S and 19T. MS: m/z=349.0 [M+H]$^+$.

4-tert-Butyl-N-([2-fluoro-4-[2-(4-methoxyphenyl)-3H-imidazo[4,5-b]pyridin-7-yl]phenyl]methyl) benzamide At 0° C., in a 10-mL 3-necked round-bottom flask purged and maintained with an inert atmosphere of nitrogen, [2-fluoro-4-[2-(4-methoxyphenyl)-3H-imidazo[4,5-b]pyridin-7-yl]phenyl]methanamine (100 mg, 0.29 mmol, 1.00 equiv) and DIEA (185.5 mg, 1.44 mmol, 5.00 equiv) were dissolved in tetrahydrofuran (2 mL), to which was added 4-tert-butylbenzoyl chloride (67.7 mg, 0.34 mmol, 1.20 equiv) slowly. The resulting solution was stirred for 30 min at 0° C. When the reaction was done, it was quenched by 10 mL water and the mixture was extracted with dichloromethane (3×10 ml). The organic layers were combined, dried over sodium sulfate and concentrated under reduced pressure. The residue was purified by prep-HPLC with the following conditions: column, XBridge C18 OBD Prep Column, 5 um, 19 mm, 250 mm; mobile phase, acetonitrile in water (with 10 mM NH$_4$HCO$_3$), 58% to 61% gradient in 11 min; detector, UV 254 nm. 4-tert-butyl-N-([2-fluoro-4-[2-(4-methoxyphenyl)-3H-imidazo[4,5-b]pyridin-7-yl]phenyl]methyl)benzamide 30 mg (21%) was obtained as white solid. HPLC: 98.9% purity. MS: m/z=509.0 [M+H]$^+$. $^1$H NMR (400 MHz, DMSO-d$_6$): δ 13.54 (br s, 1H), 9.06-9.04 (m, 1H), 8.33-8.22 (m, 5H), 7.89-7.87 (m, 2H), 7.55-7.50 (m, 4H), 7.15-7.13 (m, 2H), 4.60 (s, 2H), 3.85 (s, 3H), 3.32-3.30 (m, 1H), 1.30 (s, 9H).

Example 63. 4-Cyclopropyl-N-([2-fluoro-4-[2-(4-methoxyphenyl)-3H-imidazo[4,5-b]pyridin-7-yl]phenyl]methyl) benzamide (63)

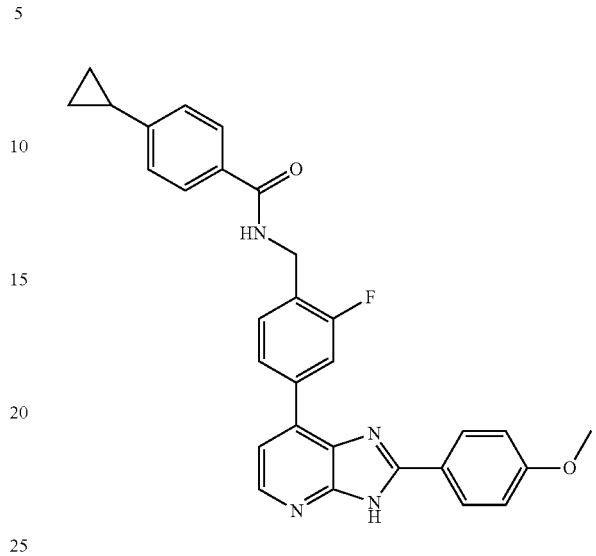

At −10° C., in a 10-mL round-bottom flask purged and maintained with an inert atmosphere of nitrogen, [2-fluoro-4-[2-(4-methoxyphenyl)-3H-imidazo[4,5-b]pyridin-7-yl]phenyl]methanamine (100 mg, 0.29 mmol, 1.00 equiv) and DIEA (185.5 mg, 1.44 mmol, 5.00 equiv) were dissolved in tetrahydrofuran (2 mL), to which was added 4-cyclopropylbenzoyl chloride (62.2 mg, 0.34 mmol, 1.20 equiv) slowly. The mixture was stirred for 30 min at −10° C. When the reaction was done, it was quenched by 10 mL water and the mixture was extracted with dichloromethane (3×10 ml). The organic layers were combined, dried over sodium sulfate and concentrated under reduced pressure. The residue was purified by prep-HPLC with the following conditions: column, XBridge C18 OBD Prep Column, 5 um, 19 mm, 250 mm; mobile phase, acetonitrile in water (with 10 mM NH$_4$HCO$_3$), 20% to 50% gradient in 10 min; detector, UV 254 nm. 4-cyclopropyl-N-([2-fluoro-4-[2-(4-methoxyphenyl)-3H-imidazo[4,5-b]pyridin-7-yl]phenyl]methyl)benzamide 30 mg (21%) was obtained as a white solid. HPLC: 97.4% purity. MS: m/z=493.1 [M+H]$^+$. $^1$H NMR (400 MHz, DMSO-d$_6$): δ 13.20 (br s, 1H), 9.03-9.00 (m, 1H), 8.34-8.22 (m, 5H), 7.84-7.82 (m, 2H), 7.55-7.51 (m, 2H), 7.19-7.13 (m, 4H), 4.60 (s, 2H), 3.85 (s, 3H), 2.02-1.95 (m, 1H), 1.04-0.99 (m, 2H), 0.77-0.74 (m, 2H).

Scheme 31

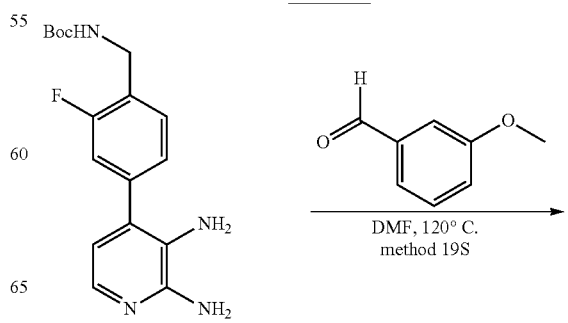

259

-continued

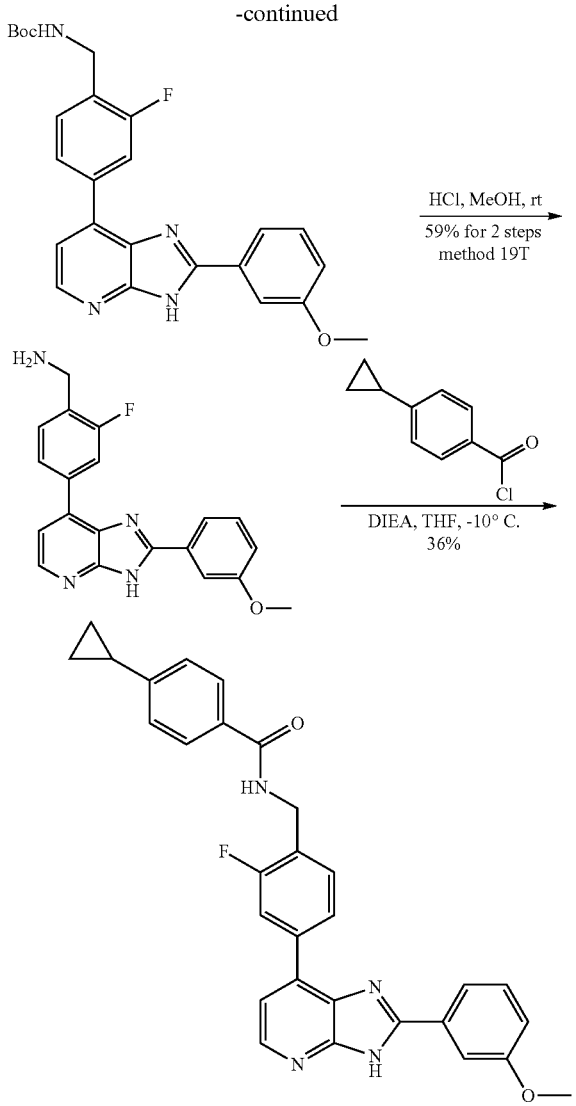

Example 64. 4-Cyclopropyl-N-([2-fluoro-4-[2-(3-methoxyphenyl)-3H-imidazo[4,5-b]pyridin-7-yl]phenyl]methyl) benzamide (64)

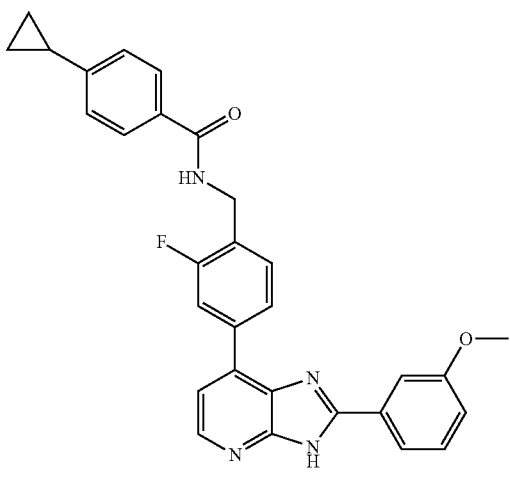 [SMILES: COc1cccc(-c2nc3c(-c4ccc(CNC(=O)c5ccc(C6CC6)cc5)c(F)c4)ccnc3[nH]2)c1]

260

[2-Fluoro-4-[2-(3-methoxyphenyl)-3H-imidazo[4,5-b]pyridin-7-yl]phenyl]methanamine

[2-fluoro-4-[2-(3-methoxyphenyl)-3H-imidazo[4,5-b]pyridin-7-yl]phenyl]methanamine 120 mg (59% for 2 steps) was prepared from N-[[4-(2,3-diaminopyridin-4-yl)-2-fluorophenyl]methyl]carbamate, 3-methoxybenzaldehyde using Method 19S and 19T. MS: m/z=349.0 [M+H]+.

4-Cyclopropyl-N-([2-fluoro-4-[2-(3-methoxyphenyl)-3H-imidazo[4,5-b]pyridin-7-yl]phenyl]methyl) benzamide At −10° C., in a 10-mL round-bottom flask purged and maintained with an inert atmosphere of nitrogen, [2-fluoro-4-[2-(3-methoxyphenyl)-3H-imidazo[4,5-b]pyridin-7-yl]phenyl] methanamine (60 mg, 0.17 mmol, 1.00 equiv) and DIEA (111 mg, 1.72 mmol, 5.00 equiv) were dissolved in tetrahydrofuran (2 mL), to which was added 4-cyclopropylbenzoyl chloride (37 mg, 0.41 mmol, 1.20 equiv) slowly. The resulting solution was stirred for 30 min at −10° C. When the reaction was done, it was quenched by 10 mL water and the mixture was extracted with dichloromethane (3×10 ml). The organic layers were combined, dried over sodium sulfate and concentrated under reduced pressure. The residue was purified by prep-HPLC with the following conditions: Column: X Bridge C18, 19*150 mm, 5 um; Mobile Phase acetonitrile in water (with 0.05% TFA) 30% to 70% gradient in 10 min. detector, UV 254 nm. 4-cyclopropyl-N-([2-fluoro-4-[2-(3-methoxyphenyl)-3H-imidazo[4,5-b]pyridin-7-yl]phenyl]methyl)benzamide 30 mg (36%) was obtained as a white solid. HPLC: 98.4% purity. MS: m/z=493.1[M+H]+. $^1$H NMR (400 MHz, DMSO-$d_6$): δ 12.31 (br s, 1H), 9.04-9.01 (m, 1H), 8.46-8.41 (m, 3H), 7.88-7.82 (m, 4H), 7.59-7.47 (m, 3H), 7.19-7.11 (m, 3H), 4.60 (s, 2H), 3.87 (s, 3H), 2.02-1.95 (m, 1H), 1.02-1.01 (m, 2H), 0.75-0.74 (m, 2H).

Scheme 32

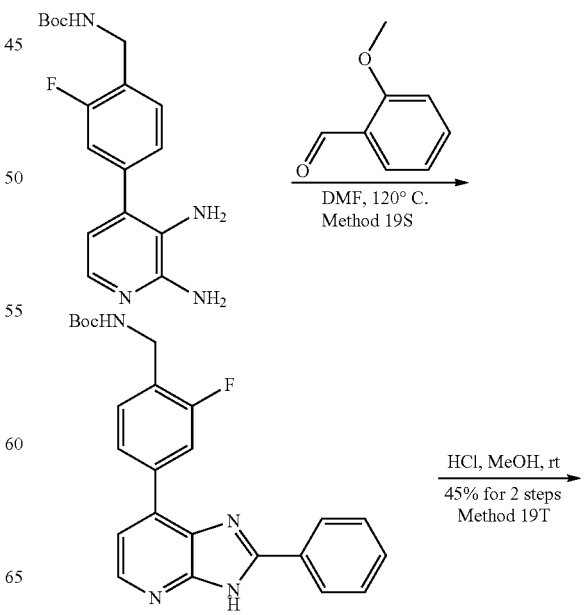

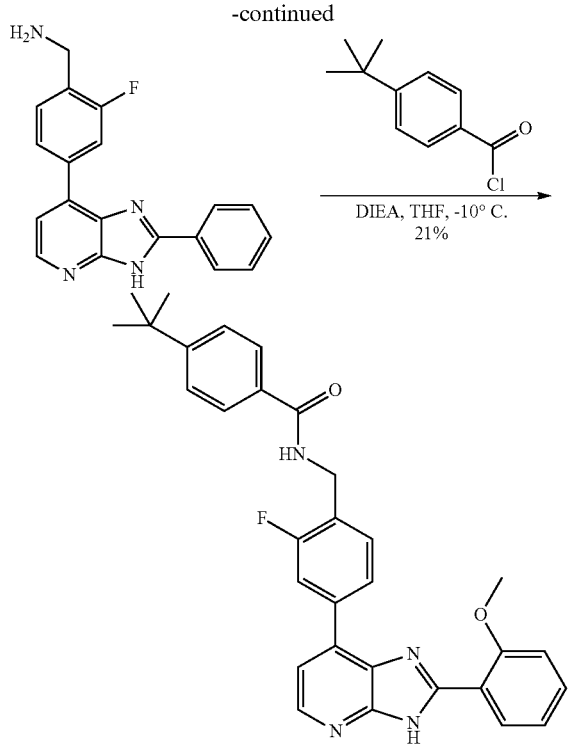

Example 65. 4-Cyclopropyl-N-([2-fluoro-4-[2-(2-methoxyphenyl)-3H-imidazo[4,5-b]pyridin-7-yl]phenyl]methyl) benzamide (65)

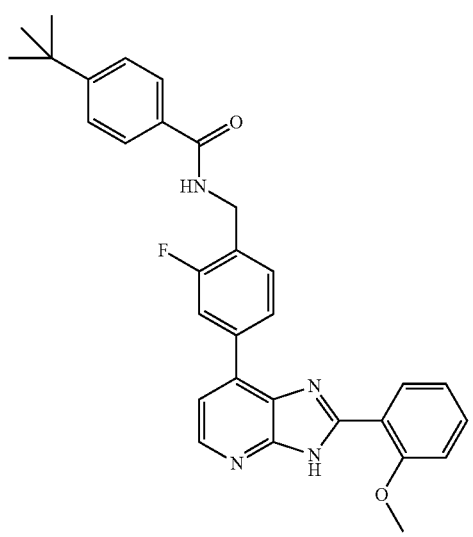 [SMILES: COc1ccccc1-c1nc2c(-c3ccc(CNC(=O)c4ccc(C(C)(C)C)cc4)c(F)c3)ccnc2[nH]1]

tert-Butyl N-([2-fluoro-4-[2-(2-methoxyphenyl)-3H-imidazo[4,5-b]pyridin-7-yl]phenyl]methyl) carbamate tert-butyl N-([2-fluoro-4-[2-(2-methoxyphenyl)-3H-imidazo[4,5-b]pyridin-7-yl]phenyl]methyl)carbamate 120 mg (45% for 2 steps) was prepared from N-[[4-(2,3-diamino-pyridin-4-yl)-2-fluorophenyl]methyl]carbamate, 2-methoxybenzaldehyde using Method 19S and 19T. MS: m/z=349.0 [M+H]$^+$.

4-Cyclopropyl-N-([2-fluoro-4-[2-(2-methoxyphenyl)-3H-imidazo[4,5-b]pyridin-7-yl]phenyl]methyl) benzamide At −10° C., in a 10-mL round-bottom flask purged and maintained with an inert atmosphere of nitrogen, [2-fluoro-4-[2-(2-methoxyphenyl)-3H-imidazo[4,5-b]pyridin-7-yl]phenyl] methanamine (100 mg, 0.29 mmol, 1.00 equiv) and DIEA (185 mg, 1.44 mmol, 5.00 equiv) were dissolved in tetrahydrofuran (2 ml), to which was added 4-cyclopropylbenzoyl chloride (62.22 mg, 0.34 mmol, 1.20 equiv) slowly. The mixture was then stirred for 30 min at −10° C. When the reaction was done, it was quenched by 10 mL water and the mixture was extracted with dichloromethane (3×10 ml). The organic layers were combined, dried over sodium sulfate and concentrated under reduced pressure. The residue was purified by prep-HPLC with the following conditions: column, XBridge C18 OBD Prep Column, 5 um, 19 mm, 250 mm; mobile phase, acetonitrile in water (with 10 mM NH$_4$HCO$_3$), 57% to 61% gradient in 10 min; detector, UV 254 nm. 4-cyclopropyl-N-([2-fluoro-4-[2-(2-methoxyphenyl)-3H-imidazo[4,5-b]pyridin-7-yl]phenyl]methyl)benzamide 30 mg (21%) was obtained as a white solid. HPLC: 98.7% purity. MS: m/z=509.3 [M+H]$^+$. $^1$H NMR (400 MHz, DMSO-d$_6$): δ 12.88 (br s, 1H), 9.02-9.00 (m, 1H), 8.39-8.23 (m, 4H), 7.84-7.82 (m, 2H), 7.61-7.51 (m, 3H), 7.26-7.13 (m, 4H), 4.59 (s, 2H), 4.01 (s, 3H), 2.50-1.95 (m, 1H), 1.04-0.99 (m, 2H), 0.77-0.73 (m, 2H).

Scheme 33

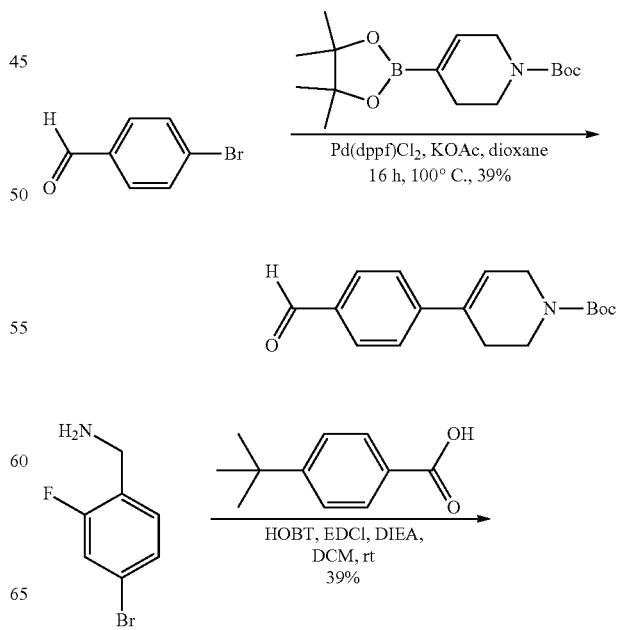

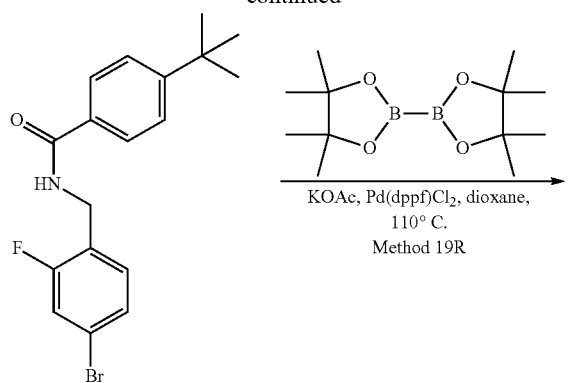
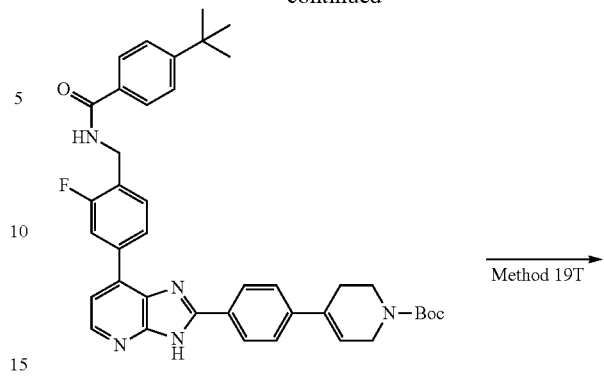
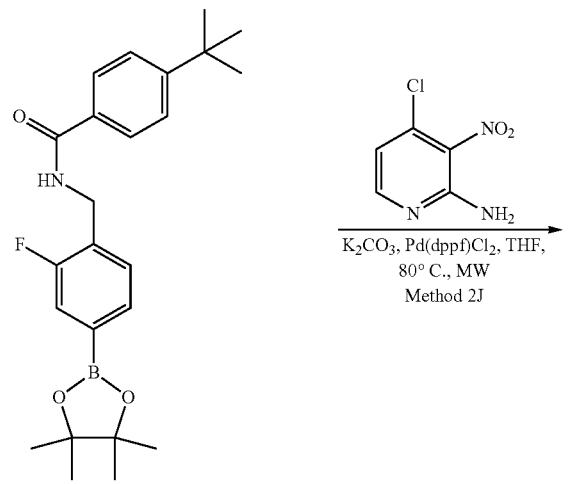
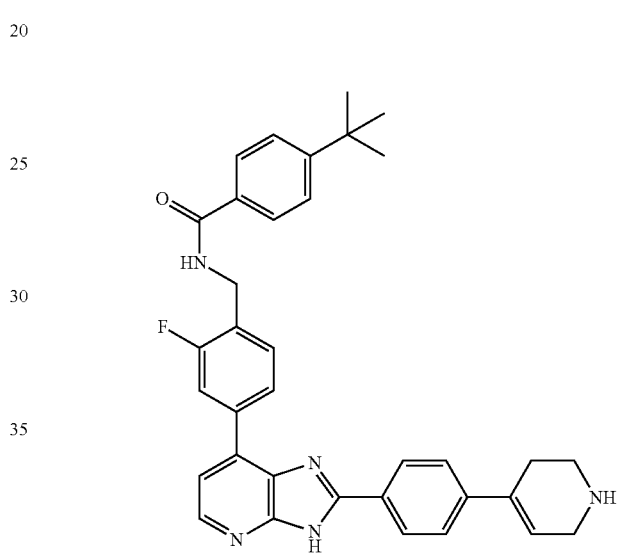
Example 66. 4-tert-Butyl-N-[(2-fluoro-4-[2-[4-(1,2,3,6-tetrahydropyridin-4-yl)phenyl]-3H-imidazo[4,5-b]pyridin-7-yl]phenyl)methyl]benzamide (66)
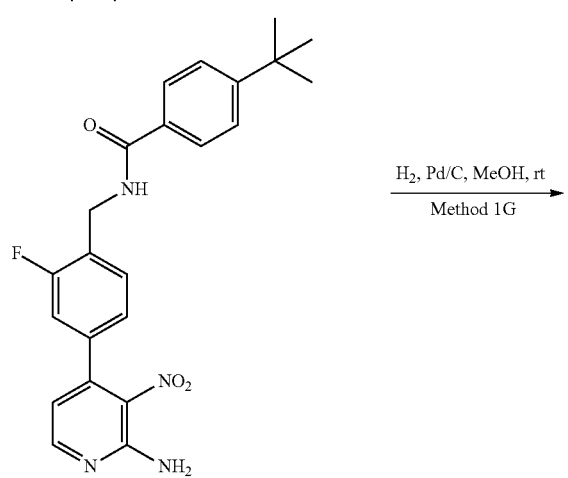
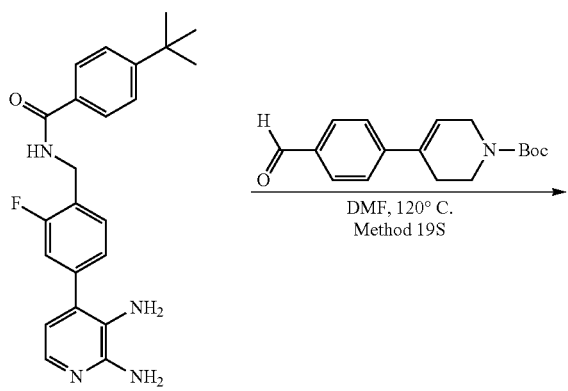
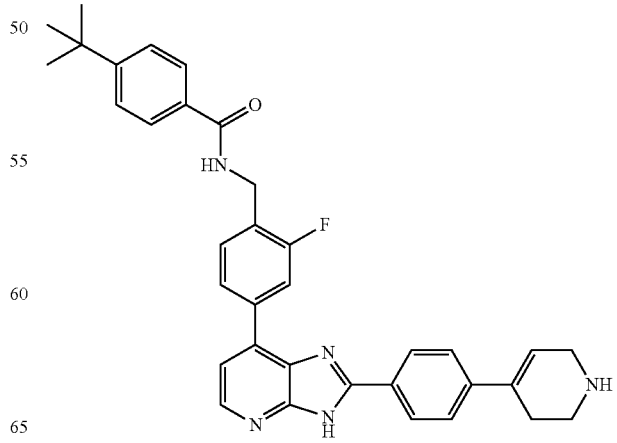

tert-Butyl 4-(4-formylphenyl)-1,2,3,6-tetrahydro-pyridine-1-carboxylate

In a 25-ml, round bottom flask purged and maintained with an inert atmosphere of nitrogen, 4-bromobenzaldehyde (200 mg, 1.08 mmol, 1.00 equiv), tert-butyl 4-(tetramethyl-1,3,2-dioxaborolan-2-yl)-1,2,3,6-tetrahydropyridine-1-carboxylate (501 mg, 1.62 mmol, 1.50 equiv), Pd(dppf)Cl$_2$ (79 mg, 0.11 mmol, 0.10 equiv) and KOAc (212 mg, 2.16 mmol, 2.00 equiv) were mixed in dioxane (5 mL) at room temperature. The resulting mixture was stirred for 16 h at 100° C. After the reaction was done, the reaction was cooled to room temperature, diluted with 5 mL water and extracted with ethyl acetate (3×20 mL). The organic layers were combined, dried over sodium sulfate and concentrated under reduced pressure. The residue was purified in a silica gel column eluting with ethyl acetate in petroleum ether (5% to 30% gradient) to afford tert-butyl 4-(4-formylphenyl)-1,2,3,6-tetrahydropyridine-1-carboxylate (120 mg, 39%) as white solid.

N-[(4-Bromo-2-fluorphenyl)methyl]-4-tert-butylbenzamide

In a 25-mL round bottom flask purged and maintained with an inert atmosphere of nitrogen, (4-bromo-2-fluorophenyl)methanamine (1.000 g, 4.90 mmol, 1.00 equiv) was dissolved in dichloromethane (20 mL), to which were added 4-tert-butylbenzoic acid (1.310 g, 7.35 mmol, 1.50 equiv), HOBT (993 mg, 7.35 mmol, 1.50 equiv), EDCl (1.409 g, 7.35 mmol, 1.50 equiv) and DIEA (1.267 g, 9.80 mmol, 2.00 equiv) in sequence at room temperature. The resulting solution was stirred for 16 h at room temperature. When the reaction was done, it was quenched by the addition of 10 mL water and the mixture was extracted with ethyl acetate (3×20 mL). The organic layers were combined, dried over sodium sulfate and concentrated under reduced pressure. The residue was purified in a silica gel column eluting with ethyl acetate in petroleum ether (5% to 30% gradient) to afford N-[(4-bromo-2-fluorophenyl)methyl]-4-tert-butylbenzamide (700 mg, 39%) as yellow solid.

4-tert-Butyl-N-[(2-fluoro-4-[2-[4-(1,2,3,6-tetrahydropyridin-4-yl)phenyl]-3H-imidazo[4,5-b]pyridin-7-yl]phenyl)methyl]benzamide 4-tert-butyl-N-[(2-fluoro-4-[2-[4-(1,2,3,6-tetrahydropyridin-4-yl)phenyl]-3H-imidazo[4,5-b]pyridin-7-yl]phenyl)methyl]benzamide 10 mg (2% for 5 steps) was prepared from N-[(4-bromo-2-fluorophenyl)methyl]-4-tert-butylbenzamide, 4,4,4',4',5,5,5',5'-octamethyl-2,2'-bi(1,3,2-dioxaborolane) and tert-butyl 4-(4-formylphenyl)-1,2,3,6-tetrahydropyridine-1-carboxylate using Method 19R, 2J, 1G, 19S and 19T. HPLC: 96.9% purity. MS: m/z=560.3 [M+H]$^+$. $^1$H NMR (400 MHz, CD$_3$OD): δ 8.52 (s, 1H), 8.31 (d, J=8.4 Hz, 2H), 7.92-7.83 (m, 4H), 7.74-7.65 (m, 4H), 7.55 (d, J=8.4 Hz, 2H), 6.38 (s, 1H), 4.75 (s, 2H), 3.92-3.91 (m, 2H), 3.54-3.51 (m, 2H), 2.90-2.89 (m, 2H), 1.37 (m, 9H).

Example 67. 5-tert-Butyl-N-([2-fluoro-4-[2-(1-methyl-1H-pyrazol-4-yl)-3H-imidazo[4,5-b]pyridin-7-yl]phenyl]methyl)-1,2-oxazole-3-carboxamide (67)

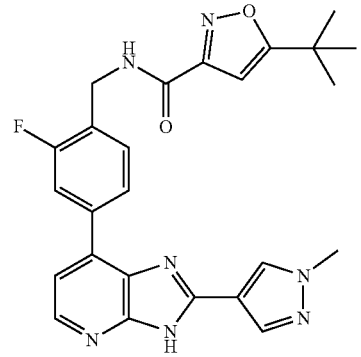

5-tert-butyl-N-([2-fluoro-4-[2-(1-methyl-1H-pyrazol-4-yl)-3H-imidazo[4,5-b]pyridin-7-yl]phenyl]methyl)-1,2-oxazole-3-carboxamide 20 mg (14%) was prepared from [2-fluoro-4-[2-(1-methyl-1H-pyrazol-4-yl)-3H-imidazo[4,5-b]pyridin-7-yl]phenyl] methanamine and 5-tert-butyl-1,2-oxazole-3-carboxylic acid using Method 26X. HPLC: 98.8% purity. MS: m/z=474.3 [M+H]$^+$. $^1$H NMR (400 MHz, DMSO-d$_6$): δ 13.40 (br s, 1H), 9.35-9.34 (m, 1H), 8.45 (s, 1H), 8.30-8.25 (m, 2H), 8.16-8.14 (m, 2H), 7.54-7.49 (m, 2H), 6.61 (s, 1H), 4.58-4.56 (m, 2H), 3.95 (s, 3H), 1.34 (s, 9H).

Example 68. 5-Cyclopropyl-N-([2-fluoro-4-[2-(1-methyl-1H-pyrazol-4-yl)-3H-imidazo[4,5-b]pyridin-7-yl]phenyl] methyl)-1,2,4-oxadiazole-3-carboxamide (68) (MSC2574688)

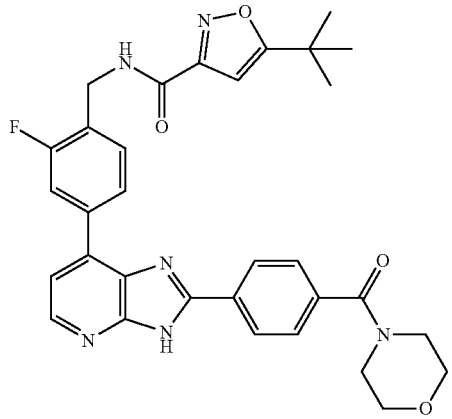 [SMILES: CC(C)(C)c1cc(C(=O)NCc2ccc(-c3ccnc4[nH]c(-c5ccc(C(=O)N6CCOCC6)cc5)nc34)cc2F)no1]

5-cyclopropyl-N-([2-fluoro-4-[2-(1-methyl-1H-pyrazol-4-yl)-3H-imidazo[4,5-b]pyridin-7-yl]phenyl]methyl)-1,2,4-oxadiazole-3-carboxamide 15 mg (9.7% for 3 steps) was prepared from 5 N-[(tert-butoxy)carbonyl]-N-[[4-(2,3-diaminopyridin-4-yl)-2-fluorophenyl]methyl]carbamate, 4-[(morpholin-4-yl)carbonyl]benzaldehyde and 5-cyclopropyl-1,2,4-oxadiazole-3-carboxylic acid using Method 7K, 19T and 26X. HPLC: 98.2% purity. MS: m/z=584.3 [M+H]$^+$. $^1$H-NMR (400 MHz, DMSO-d$_6$): δ 9.58-9.55 (m, 1H), 8.40-8.31 (m, 4H), 8.21 (d, J=4.0 Hz, 1H), 7.62-7.53 (m, 4H), 4.61-4.59 (m, 2H), 3.65-3.33 (m, 8H), 1.44 (s, 9H).

Scheme 34

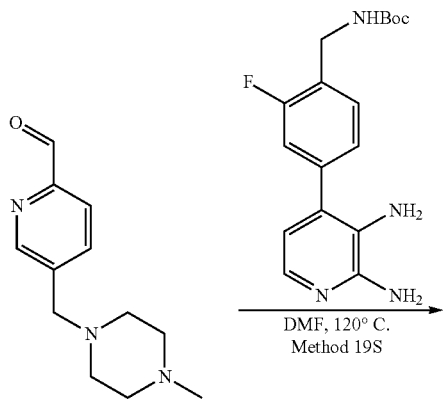

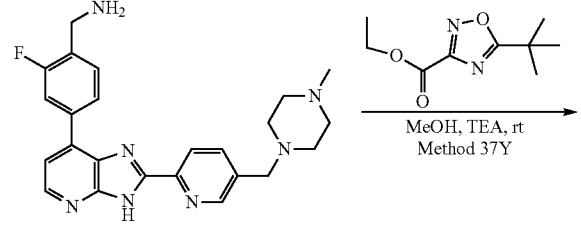

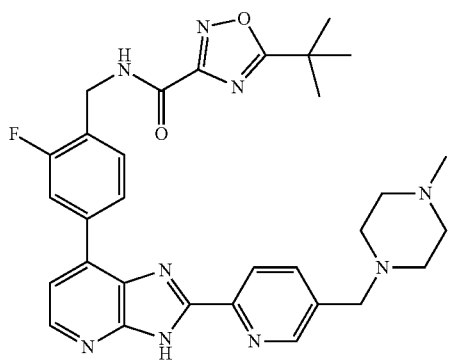 [SMILES: CN1CCN(Cc2ccc(-c3nc4c(-c5ccc(CNC(=O)c6noc(C(C)(C)C)n6)c(F)c5)ccnc4[nH]3)nc2)CC1]

Example 69. 5-tert-Butyl-N-[[2-fluoro-4-(2-[5-[(4-methylpiperazin-1-yl)methyl]pyridin-2-yl]-3H-imidazo[4,5-b]pyridin-7-yl)phenyl]methyl]-1,2,4-oxadiazole-3-carboxamide (69)

[2-Fluoro-4-(2-[5-[(4-methylpiperazin-1-yl)methyl] pyridin-2-yl]-3H-imidazo[4,5-b]pyridin-7-yl)phenyl] methanamine

[2-fluoro-4-(2-[5-[(4-methylpiperazin-1-yl)methyl]pyridin-2-yl]-3H-imidazo[4,5-b]pyridin-7-yl)phenyl]methanamine 100 mg (38% for 2 steps) was prepared from tert-butyl N-[[4-(2,3-diaminopyridin-4-yl)-2-fluorophenyl] methyl]carbamate and 5-[(4-methylpiperazin-1-yl)methyl] pyridine-2-carbaldehyde using Method 19S and 19T. MS: m/z=432.1 [M+H]+

Method 37Y: 5-tert-Butyl-N-[[2-fluoro-4-(2-[5-[(4-methylpiperazin-1-yl)methyl]pyridin-2-yl]-3H-imidazo[4,5-b]pyridin-7-yl)phenyl]methyl]-1,2,4-oxadiazole-3-carboxamide In a 25-mL round bottom flask purged and maintained with an inert atmosphere of nitrogen, [2-fluoro-4-(2-[5-[(4-methylpiperazin-1-yl)methyl]pyridin-2-yl]-3H-imidazo[4, 5-b]pyridin-7-yl)phenyl]methanamine (80 mg, 0.19 mmol, 1.00 equiv) was dissolved in methanol (3 ml), to which were added ethyl 5-tert-butyl-1,2,4-oxadiazole-3-carboxylate (44 mg, 0.22 mmol, 1.20 equiv) and TEA (93.80 mg, 0.93 mmol, 5.00 equiv) at room temperature. The resulting solution was stirred for 16 h at room temperature. When the reaction was done, it was quenched by the addition of 5 mL water and the mixture was extracted with ethyl acetate (3×20 mL). The organic layers were combined, dried over sodium sulfate and concentrated under reduced pressure. The residue was purified by prep-HPLC using the following conditions: column: Gemini-NX 5u C18 110A, AXIA Packed 150×21.2 mm; mobile phase, acetonitrile in water (with 10 mM NH$_4$HCO$_3$), 30% to 60% gradient in 10 min; detector, UV 254 nm. 5-tert-butyl-N-[[2-fluoro-4-(2-[5-[(4-methylpiperazin-1-yl)methyl]pyridin-2-yl]-3H-imidazo[4,5-b]pyridin-7-yl)phenyl]methyl]-1,2,4-oxadiazole-3-carboxamide (10 mg, 9%) was obtained as white solid. HPLC: 98.1% purity. MS: m/z=584.5 [M+H]+. $^1$H-NMR (300 MHz, DMSO-d$_6$): δ 13.84 (br s, 1H), 9.56 (t, J=6.3 Hz, 1H), 8.66 (s, 1H), 8.42-8.19 (m, 4H), 7.95-7.92 (m, 1H), 7.62-7.52 (m, 2H), 4.61-4.59 (m, 2H), 3.60 (s, 2H), 2.42-2.27 (m, 8H), 2.15 (s, 3H), 1.43 (s, 9H).

Scheme 35

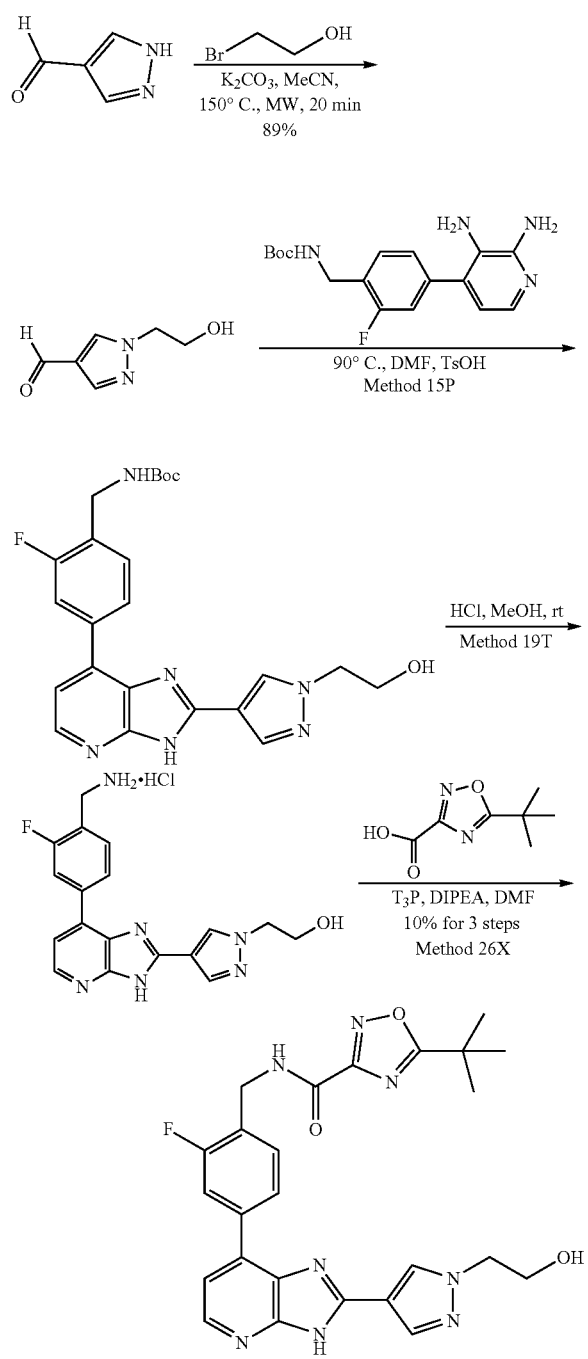

Example 70. 5-tert-Butyl-N-[(2-fluoro-4-[2-[1-(2-hydroxyethyl)-1H-pyrazol-4-yl]-3H-imidazo[4,5-b]pyridin-7-yl] phenyl)methyl]-1,2,4-oxadiazole-3-carboxamide (70)

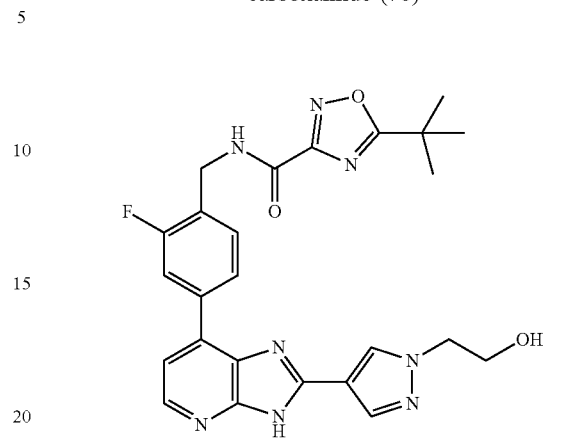

1-(2-Hydroxyethyl)-1H-pyrazole-4-carbaldehyde

In a 30-mL sealed tube, 1H-pyrazole-4-carbaldehyde (500 mg, 5.20 mmol, 1.00 equiv), potassium carbonate (1.08 mg, 7.80 mmol, 1.50 equiv) and 2-bromoethan-1-ol (775.3 mg, 6.20 mmol, 1.19 equiv) were mixed in $CH_3CN$ (10 mL) at room temperature. The reaction mixture was then irradiated with microwave for 40 min at 150° C. After the reaction was done, the reaction mixture was cooled to room temperature, filtered through a celite pad and the filtrate was concentrated under reduced pressure. The residue was purified in a silica gel column eluting with dichloromethane/methanol (1% to 5% gradient) to afford 1-(2-hydroxyethyl)-1H-pyrazole-4-carbaldehyde (650 mg, 89%) as yellow solid. MS: m/z=140.8 [M+H]+

5-tert-Butyl-N-[(2-fluoro-4-[2-[1-(2-hydroxyethyl)-1H-pyrazol-4-yl]-3H-imidazo[4,5-b]pyridin-7-yl] phenyl)methyl]-1,2,4-oxadiazole-3-carboxamide 5-tert-butyl-N-[(2-fluoro-4-[2-[1-(2-hydroxyethyl)-1H-pyrazol-4-yl]-3H-imidazo[4,5-b]pyridin-7-yl]phenyl) methyl]-1,2,4-oxadiazole-3-carboxamide 10 mg (10% for 3 steps) was prepared from tert-butyl N-[[4-(2,3-diaminopyridin-4-yl)-2-fluorophenyl]methyl]carbamate, 1-(2-hydroxyethyl)-1H-pyrazole-4-carbaldehyde and 5-tert-butyl-1,2,4-oxadiazole-3-carboxylic acid using Method 15P, 19T and 26X. HPLC: 97.2% purity. MS: m/z=505.1 [M+H]+. $^1$H-NMR (300 MHz, $CD_3OD$): δ 8.56 (s, 1H), 8.48 (br s, 1H), 8.31 (s, 1H), 7.77-7.58 (m, 4H), 4.75-4.74 (m, 2H), 4.38-4.34 (m, 2H), 3.96-3.95 (m, 2H), 1.49 (s, 9H).

Scheme 36

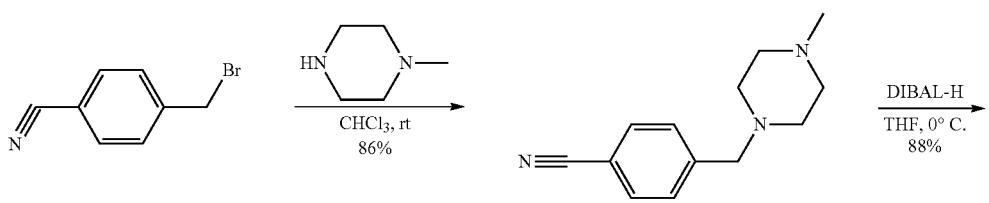

-continued
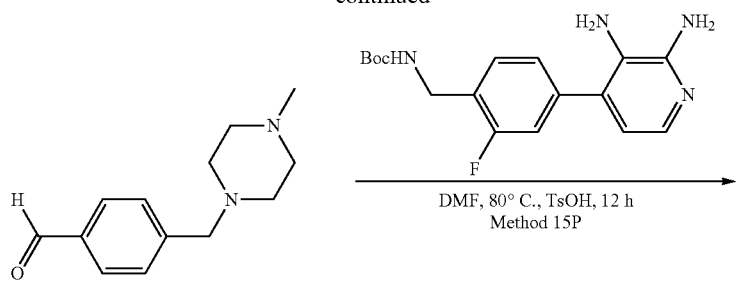
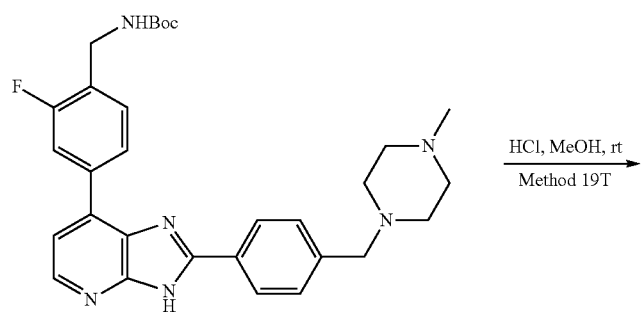
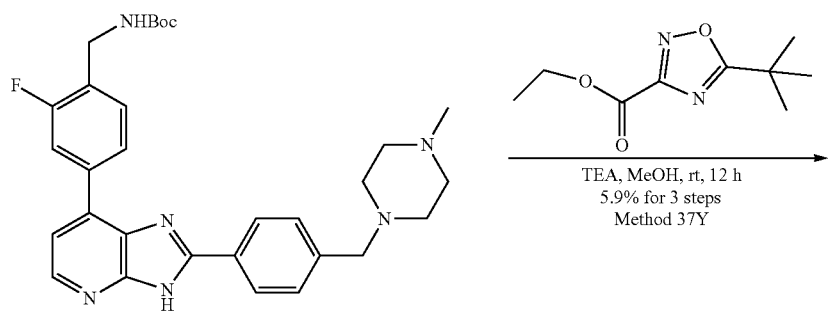
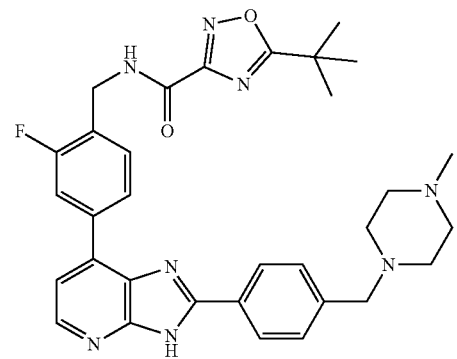

Example 71. 5-tert-Butyl-N-[[2-fluoro-4-(2-[4-[(4-methylpiperazin-1-yl)methyl]phenyl]-1H-imidazo[4,5-b]pyridin-7-yl)phenyl]methyl]-1,2,4-oxadiazole-3-carboxamide (71)

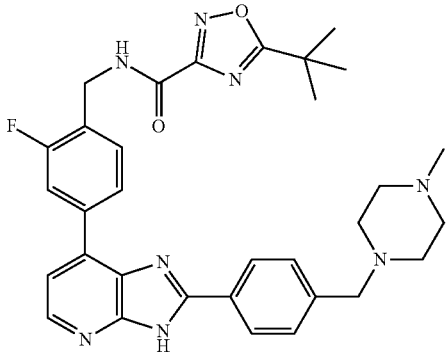 [SMILES: CN1CCN(Cc2ccc(-c3nc4c(-c5ccc(CNC(=O)c6noc(C(C)(C)C)n6)c(F)c5)ccnc4[nH]3)cc2)CC1]

4-[(4-Methylpiperazin-1-yl)methyl]benzonitrile

In a 100-mL round bottom flask purged and maintained with an inert atmosphere of nitrogen, 1-methylpiperazine (5 g, 47.42 mmol, 1.72 equiv) was dissolved in chloroform (50 mL), to which was added 4-(bromomethyl) benzonitrile (5.68 g, 27.52 mmol, 1.00 equiv) dropwise at 0° C. The resulting mixture was then stirred for 4 h at room temperature. When the reaction was done, it was quenched by the addition of 10 mL water and the mixture was extracted with dichloromethane (3×15 mL). The organic layers were combined, dried over sodium sulfate and concentrated under reduced pressure to afford 4-[(4-methylpiperazin-1-yl)methyl]benzonitrile (5.1 g, 86%) as yellow solid. MS: m/z=215.1 [M+H]$^+$.

4-[(4-Methylpiperazin-1-yl)methyl]benzaldehyde

In a 50-mL round bottom flask purged and maintained with an inert atmosphere of nitrogen, 4-[(4-methylpiperazin-1-yl)methyl] benzonitrile (2 g, 8.83 mmol, 1.00 equiv) was dissolved in tetrahydrofuran (20 mL), to which was added DIBAL solution (1 M in THF, 14 mL, 141.2 mmol, 16.0 equiv) dropwise over 5 min period at 0° C. The resulting solution was stirred for 2 h at room temperature. When the reaction was done, it was quenched by 5 mL water and the mixture was extracted with dichloromethane (3×50 mL). The organic layers were combined, dried over sodium sulfate and concentrated under reduced pressure to afford 4-[(4-methylpiperazin-1-yl)methyl]benzaldehyde (1.7 g, 88%) as yellow solid. MS: m/z=219.0 [M+H]$^+$.

5-tert-Butyl-N-[[2-fluoro-4-(2-[4-[(4-methylpiperazin-1-yl)methyl]phenyl]-1H-imidazo[4,5-b]pyridin-7-yl)phenyl]methyl]-1,2,4-oxadiazole-3-carboxamide 5-tert-butyl-N-[[2-fluoro-4-(2-[4-[(4-methylpiperazin-1-yl)methyl]phenyl]-1H-imidazo[4,5-b]pyridin-7-yl)phenyl]methyl]-1,2,4-oxadiazole-3-carboxamide 10 mg (5.9% for 3 steps) was prepared from tert-butyl N-[[4-(2,3-diaminopyridin-4-yl)-2-fluorophenyl]methyl]carbamate, 4-[(4-methylpiperazin-1-yl)methyl]benzaldehyde and methyl 5-tert-butyl-1,2,4-oxadiazole-3-carboxylate using Method 15P, 19T and 37Y. HPLC: 98.8% purity. MS: m/z=483.4 [M+H]$^+$. $^1$H-NMR (400 MHz, DMSO-d$_6$): δ 13.70 (br s, 1H), 9.57-9.54 (m, 1H), 8.38-8.30 (m, 2H), 8.24-8.22 (m, 3H), 7.61-7.49 (m, 4H), 4.61-4.59 (m, 2H), 3.54 (s, 2H), 2.51-2.50 (m, 8H), 2.16 (s, 3H), 1.44 (s, 9H).

Scheme 37

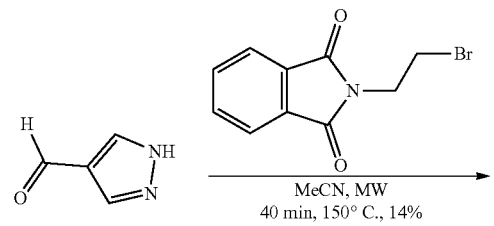

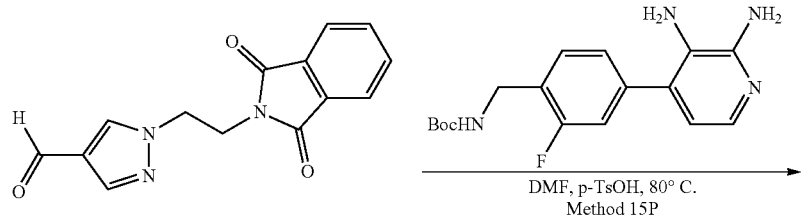

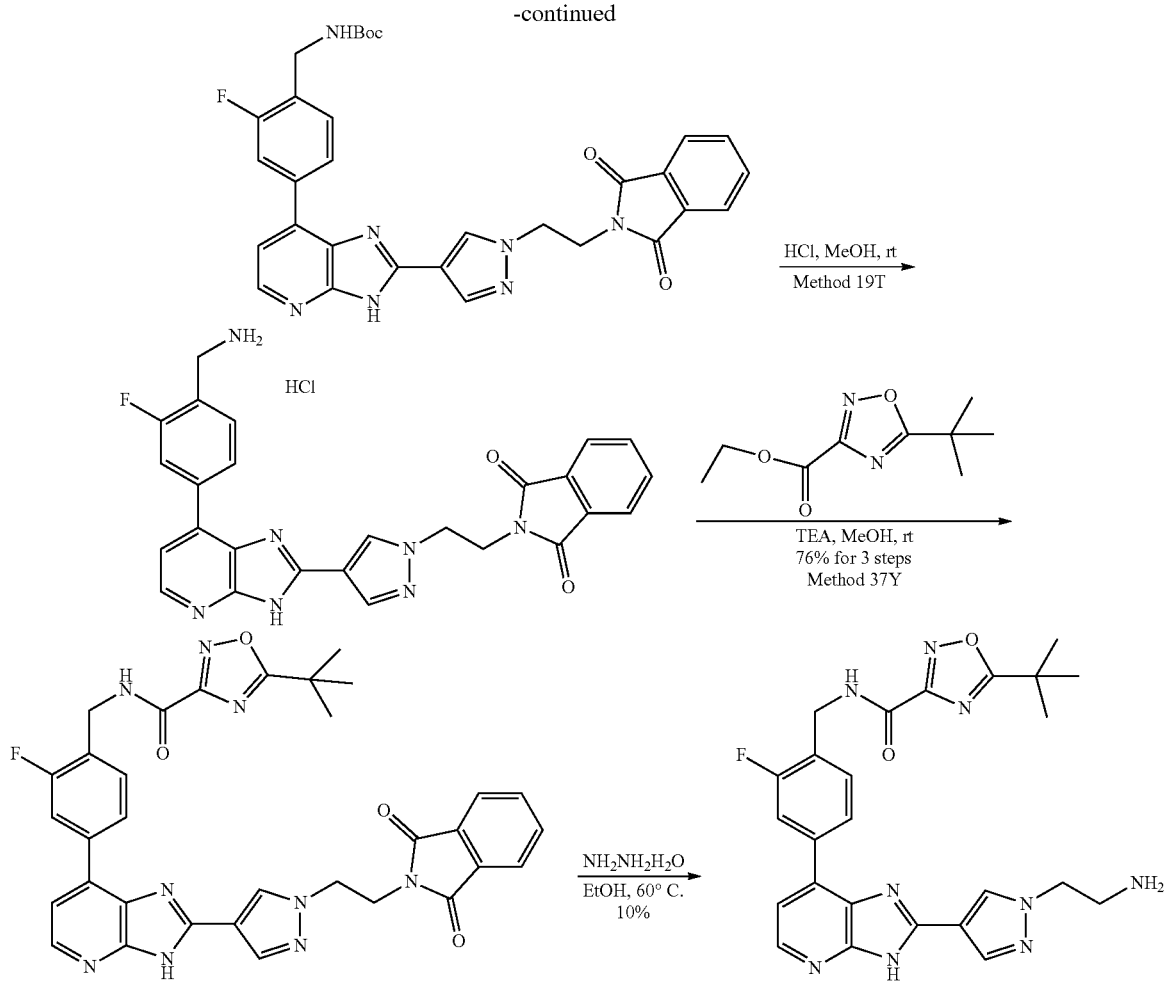

Example 72. N-[(4-[2-[1-(2-aminoethyl)-1H-pyrazol-4-yl]-3H-imidazo[4,5-b]pyridin-7-yl]-2-fluorophenyl)methyl]-5-tert-butyl-1,2,4-oxadiazole-3-carboxamide (72)

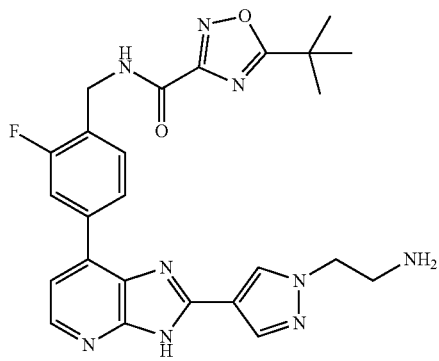 [SMILES: CC(C)(C)c1nc(C(=O)NCc2ccc(-c3ccnc4[nH]c(-c5cnn(CCN)c5)nc34)cc2F)no1]

1-[2-(1,3-Dioxo-2,3-dihydro-1H-isoindol-2-yl)ethyl]-1H-pyrazole-4-carbaldehyde

In a 30-mL vial, 1H-pyrazole-4-carbaldehyde (2.0 g, 20.81 mmol, 1.00 equiv), 2-(2-bromoethyl)-2,3-dihydro-1H-isoindole-1,3-dione (6.3 g, 24.98 mmol, 1.20 equiv) and $Cs_2CO_3$ (13.5 g, 41.63 mmol, 2.00 equiv) were mixed in $CH_3CN$ (10 mL) at room temperature. The resulting mixture was irradiated with microwave for 40 min at 150° C. After the reaction was done, the reaction mixture was cooled to room temperature, diluted with 10 mL water and extracted with ethyl acetate (3×10 ml). The organic layers were combined, dried over sodium sulfate and concentrated under reduced pressure. The residue was purified in a silica gel column eluting with ethyl acetate in petroleum ether (1% to 50% gradient) to afford 1-[2-(1,3-dioxo-2,3-dihydro-1H-isoindol-2-yl)ethyl]-1H-pyrazole-4-carbaldehyde (800 mg, 14%) as white solid. MS: m/z=270.0 [M+H]$^+$.

5-tert-Butyl-N-[[4-(2-[1-[2-(1,3-dioxo-2,3-dihydro-1H-isoindol-2-yl)ethyl]-1H-pyrazol-4-yl]-3H-imidazo [4,5-b]pyridin-7-yl)-2-fluorophenyl]methyl]-1,2,4-oxadiazole-3-carboxamide 5-tert-butyl-N-[[4-(2-[1-[2-(1,3-dioxo-2,3-dihydro-1H-isoindol-2-yl)ethyl]-1H-pyrazol-4-yl]-3H-imidazo[4,5-b] pyridin-7-yl)-2-fluorophenyl]methyl]-1,2,4-oxadiazole-3-carboxamide 150 mg (76% for 3 steps) was prepared from tert-butyl N-[[4-(2,3-diaminopyridin-4-yl)-2-fluorophenyl] methyl]carbamate, 1-[2-(1,3-dioxo-2,3-dihydro-1H-isoindol-2-yl)ethyl]-1H-pyrazole-4-carbaldehyde and ethyl 5-tert-butyl-1,2,4-oxadiazole-3-carboxylate using Method 19S, 19T and 37Y. MS: m/z=634.1 [M+H]+.

N-[(4-[2-[1-(2-aminoethyl)-1H-pyrazol-4-yl]-3H-imidazo[4,5-b]pyridin-7-yl]-2-fluorophenyl)methyl]-5-tert-butyl-1,2,4-oxadiazole-3-carboxamide In a 10-mL round bottom flask purged and maintained with an inert atmosphere of nitrogen, 5-tert-butyl-N-[[4-(2-[1-[2-(1,3-dioxo-2,3-dihydro-1H-isoindol-2-yl)ethyl]-1H-pyrazol-4-yl]-3H-imidazo[4,5-b]pyridin-7-yl)-2-fluorophenyl]methyl]-1,2,4-oxadiazole-3-carboxamide (120 mg, 0.19 mmol, 1.00 equiv) was dissolved in ethanol (3 mL), to which was added hydrazine hydrate (18.9 mg, 0.38 mmol, 2.00 equiv) at room temperature. The resulting solution was then stirred for 2 h at 60° C. After the reaction was done, the reaction mixture was cooled to room temperature, diluted with 5 mL water and extracted with dichloromethane (3×10 mL). The organic layers were combined, dried over sodium sulfate and concentrated under reduced pressure. The residue was purified in a silica gel column eluting with methanol in dichloromethane (5% to 20% gradient) to afford N-[(4-[2-[1-(2-aminoethyl)-1H-pyrazol-4-yl]-3H-imidazo[4,5-b]pyridin-7-yl]-2-fluorophenyl)methyl]-5-tert-butyl-1,2,4-oxadiazole-3-carboxamide (10 mg, 10%) as white solid. HPLC: 99.3% purity. MS: m/z=504.2 [M+H]+. 1H-NMR (400 MHz, CD3OD): δ 8.42 (s, 1H), 8.34 (d, J=5.2 Hz, 1H), 8.25 (s, 1H), 7.88-7.86 (m, 2H), 7.64-7.60 (m, 1H), 7.43-7.41 (m, 1H), 4.89 (s, 2H), 4.34 (t, J=6.0 Hz, 2H), 3.18-3.15 (m, 2H), 1.50 (s, 9H).

Example 73. 5-tert-Butyl-N-([2-fluoro-4-[2-(3-methoxyphenyl)-3H-imidazo[4,5-b]pyridin-7-yl]phenyl]methyl)-1,2,4-oxadiazole-3-carboxamide (73)

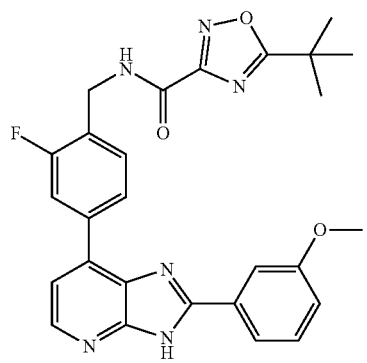 [SMILES: COc1cccc(-c2nc3c(-c4ccc(CNC(=O)c5noc(C(C)(C)C)n5)c(F)c4)ccnc3[nH]2)c1]

5-tert-butyl-N-([2-fluoro-4-[2-(3-methoxyphenyl)-3H-imidazo[4,5-b]pyridin-7-yl]phenyl]methyl)-1,2,4-oxadiazole-3-carboxamide 10 mg (3% for 3 steps) was prepared from tert-butyl N-[[4-(2,3-diaminopyridin-4-yl)-2-fluorophenyl]methyl]carbamate, 3-methoxybenzaldehyde and 5-tert-butyl-1,2,4-oxadiazole-3-carboxylate using Method 19S, 19T and 37Y. HPLC: 99.4% purity. MS: m/z=501.3 [M+H]+. 1H-NMR (400 MHz, DMSO-d6): δ 9.55 (t, J=6.0 Hz, 1H), 8.36-8.35 (m, 2H), 8.21 (s, 1H), 7.93-7.88 (m, 2H), 7.86 (m, 3H), 7.55 (t, J=8.0 Hz, 1H), 7.48 (t, J=7.9 Hz, 1H), 4.61-4.59 (m, 2H), 3.87 (s, 3H), 1.43 (s, 9H).

Example 74. 5-tert-Butyl-N-[(2-fluoro-4-[2-[3-(trifluoromethoxy)phenyl]-3H-imidazo[4,5-b]pyridin-7-yl]phenyl) methyl]-1,2,4-oxadiazole-3-carboxamide; trifluoroacetic acid (74)

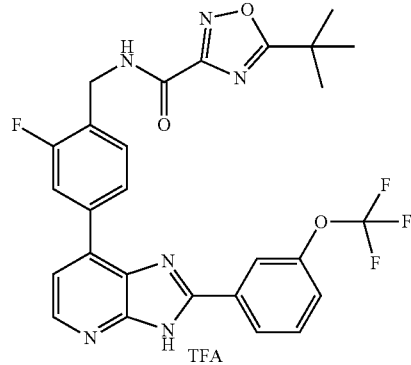 [SMILES: CC(C)(C)c1nc(C(=O)NCc2ccc(-c3ccnc4[nH]c(-c5cccc(OC(F)(F)F)c5)nc34)cc2F)no1]

5-tert-butyl-N-[(2-fluoro-4-[2-[3-(trifluoromethoxy)phenyl]-3H-imidazo[4,5-b]pyridin-7-yl]phenyl)methyl]-1,2,4-oxadiazole-3-carboxamide; trifluoroacetic acid 10 mg (4.8% for 3 steps) was prepared from tert-butyl N-[[4-(2,3-diaminopyridin-4-yl)-2-fluorophenyl]methyl]carbamate, 3-(trifluoromethoxy)benzaldehyde, 5-tert-butyl-1,2,4-oxadiazole-3-carboxylate using Method 19P, 19T and 37Y. HPLC: 99.6% purity. MS: m/z=555.6 [M+H]+. 1H-NMR (300 MHz, DMSO-d6): δ 13.81 (br s, 1H), 9.54 (t, J=6.1 Hz, 1H), 8.43 (d, J=5.1 Hz, 1H), 8.35-8.34 (in, 2H), 8.22 (d, J=13.1 Hz, 2H), 7.70 (t. J=8.0 Hz, 1H), 7.67-7.50 (m, 3H), 4.64-4.55 (m, 2H), 1.43 (s, 9H).

Scheme 38

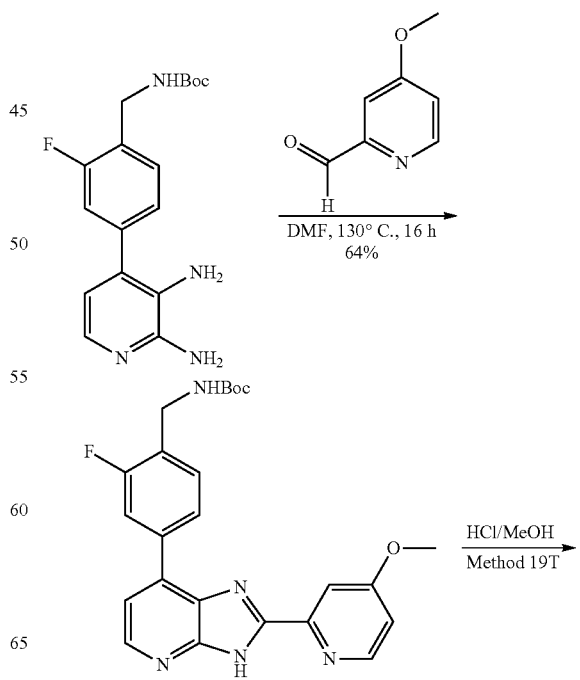

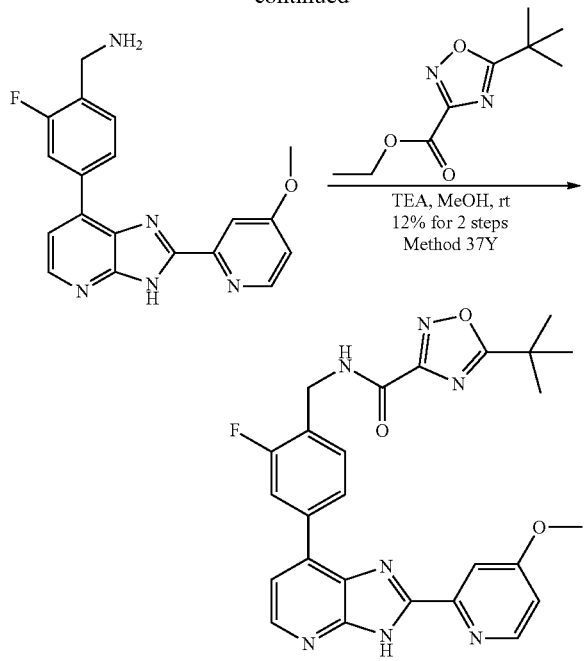

Example 75. 5-tert-Butyl-N-([2-fluoro-4-[2-(4-methoxypyridin-2-yl)-3H-imidazo[4,5-b]pyridin-7-yl]phenyl]methyl)-1,2,4-oxadiazole-3-carboxamide (75)

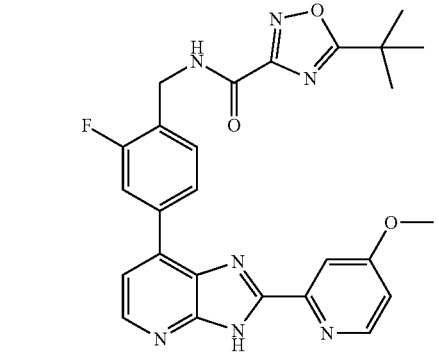 [SMILES: COc1ccnc(-c2nc3c(-c4ccc(CNC(=O)c5noc(C(C)(C)C)n5)c(F)c4)ccnc3[nH]2)c1]

N-([2-Fluoro-4-[2-(4-methoxypyridin-2-yl)-3H-imidazo[4,5-b]pyridin-7-yl]phenyl]methyl)carbamate In a 30-mL round bottom flask purged and maintained with an inert atmosphere of nitrogen, tert-butyl N-[[4-(2,3-diaminopyridin-4-yl)-2-fluorophenyl]methyl]carbamate (150 mg, 0.45 mmol, 1.00 equiv) and 4-methoxypyridine-2-carbaldehyde (74 mg, 0.54 mmol, 1.20 equiv) were dissolved in N,N-dimethylformamide (5 ml) at room temperature. The resulting solution was then stirred for 16 h at 130° C. After the reaction was done, the reaction mixture was concentrated under reduced pressure. The residue was purified in a silica gel column eluting with methanol in dichloromethane (1% to 10% gradient) to afford tert-butyl N-([2-fluoro-4-[2-(4-methoxypyridin-2-yl)-3H-imidazo[4,5-b] pyridin-7-yl]phenyl]methyl) carbamate (130 mg, 64%) as yellow solid. MS: m/z=450.2[M+H]+.

5-tert-Butyl-N-([2-fluoro-[2-(4-methoxypyridin-2-yl)-3H-imidazo[4,5-b]pyridin-7-yl]phenyl]methyl)-1,2,4-oxadiazole-3-carboxamide 5-tert-butyl-N-([2-fluoro-4-[2-(4-methoxypyridin-2-yl)-3H-imidazo[4,5-b]pyridin-7-yl]phenyl]methyl)-1,2,4-oxadiazole-3-carboxamide 15 mg (12% for 2 steps) was prepared from tert-butyl N-([2-fluoro-4-[2-(4-methoxypyridin-2-yl)-3H-imidazo[4,5-b]pyridin-7-yl]phenyl]methyl) carbamate and 5-tert-butyl-1,2,4-oxadiazole-3-carboxylate using Method 19T and 37Y. HPLC: 99.3% purity. MS: m/z=502.1 [M+H]+. 1H-NMR (300 MHz, CD3OD): δ 8.73 (d, J=6.6 Hz, 1H), 8.66 (d, J=5.7 Hz 1H), 8.32 (d, J=2.6 Hz, 1H), 8.11-7.94 (m, 2H), 7.84 (d, J=5.7 Hz, 1H), 7.70 (t, J=7.8 Hz, 1H), 7.57-7.55 (m, 1H), 4.77 (s, 2H), 4.23 (s, 3H), 1.50 (s, 9H).

Scheme 39

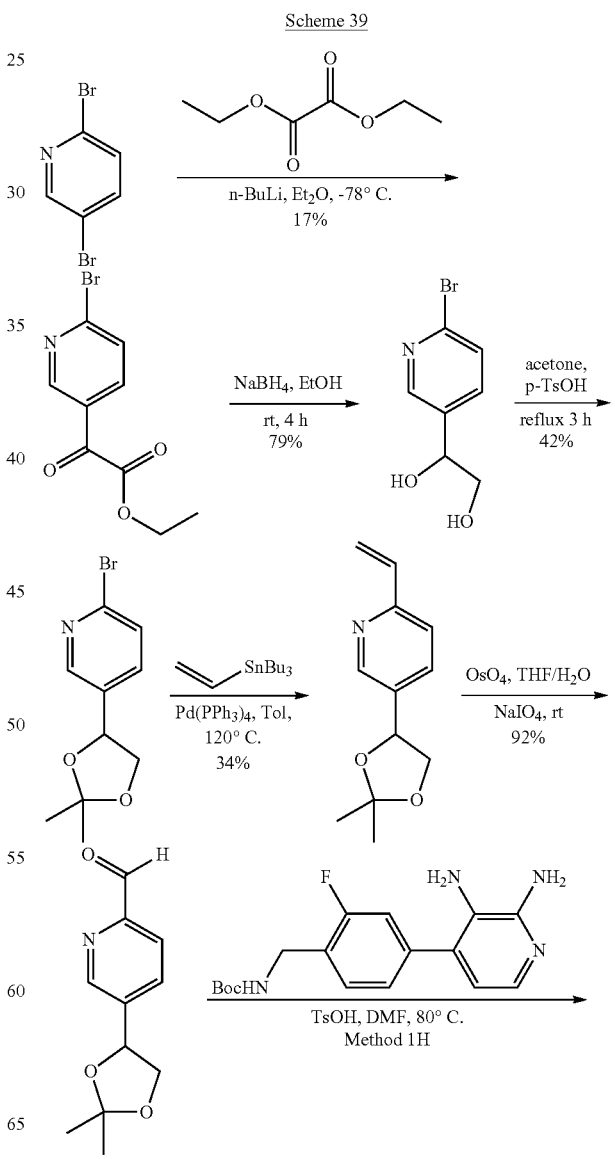

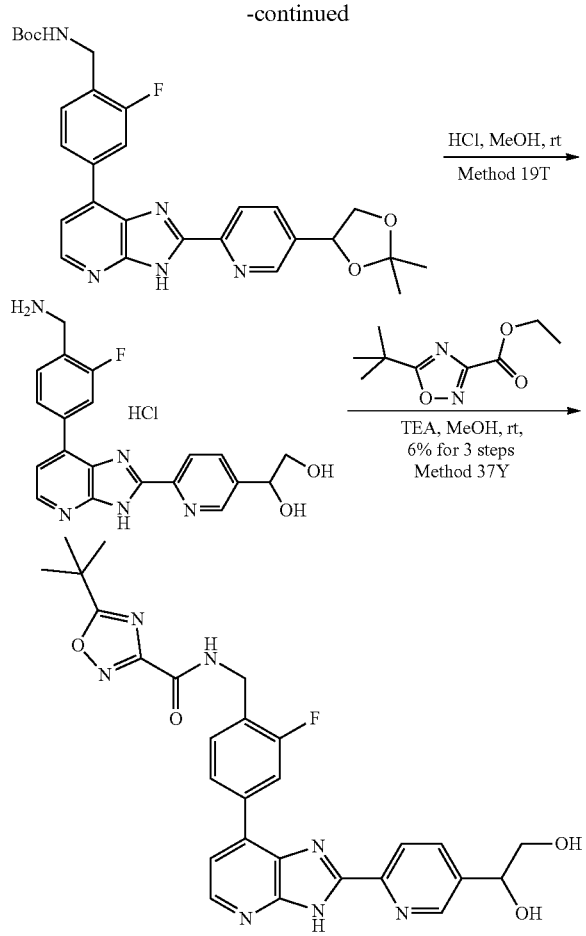

Example 76. 5-tert-Butyl-N-[(4-[2-[5-(1,2-dihydroxyethyl)pyridin-2-yl]-3H-imidazo[4,5-b]pyridin-7-yl]-2-fluorophenyl)methyl]-1,2,4-oxadiazole-3-carboxamide (76)

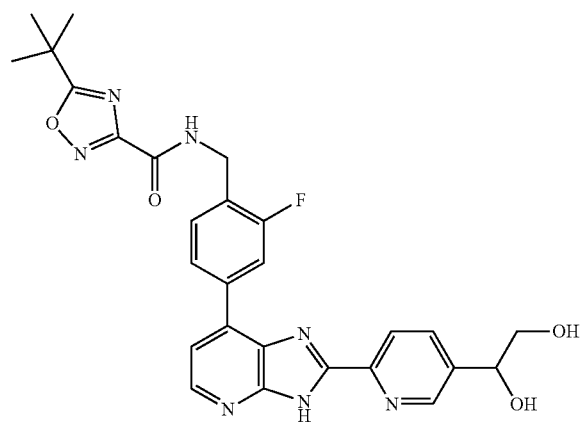 [SMILES: CC(C)(C)c1nc(C(=O)NCc2ccc(-c3ccnc4[nH]c(-c5ccc(C(O)CO)cn5)nc34)cc2F)no1]

Ethyl 2-(6-bromopyridin-3-yl)-2-oxoacetate

At −78° C., in a 500-mL round bottom flask purged and maintained with an inert atmosphere of nitrogen, 2,5-dibromopyridine (10 g, 42.2 mmol, 1.00 equiv) was dissolved in Et$_2$O (200 mL), to which was added the solution of n-BuLi (1 M in THF, 21.23 mL, 212.3 mmol, 5.03 equiv) dropwise. The resulting solution was stirred at −78° C. for 1 h under nitrogen, and then was added by diethyl oxalate (8 mL, 38.32 mmol, 0.91 equiv) dropwise. The reaction was allowed to stir at −78° C. for 10 min, warmed up to 0° C. and stirred for another 2 h at 0° C. When the reaction was done, it was quenched by 50 mL sat. NH$_4$Cl solution and the mixture was extracted with DCM (2×100 mL). The organic layers were combined, dried over sodium sulfate and concentrated under reduced pressure. The residue was purified in a silica gel column eluting with ethyl acetate in petroleum ether (5% to 20% gradient) to afford ethyl 2-(6-bromopyridin-3-yl)-2-oxoacetate (1.8 g, 17%) as yellow oil. MS: m/z=258.2 [M+H]$^+$.

1-(6-Bromopyridin-3-yl)ethane-1,2-diol

In a 100-mL round bottom flask, ethyl 2-(6-bromopyridin-3-yl)-2-oxoacetate (1.8 g, 6.97 mmol, 1.00 equiv) was dissolved in ethanol (20 mL), to which was slowly added NaBH$_4$ (480 mg, 12.69 mmol, 1.82 equiv) at 0° C. The resulting solution was then stirred for 4 h at room temperature. When the reaction was done, it was quenched by 15 mL water and the mixture was extracted with dichloromethane (3×20 mL). The organic layers were combined, dried over sodium sulfate and concentrated under reduced pressure to afford 1-(6-bromopyridin-3-yl)ethane-1,2-diol (1.2 g, 79%) as yellow solid. MS: m/z=218.0 [M+H]$^+$.

2-Bromo-5-(2,2-dimethyl-1,3-dioxolan-4-yl)pyridine

In a 100-mL round bottom flask purged and maintained with an inert atmosphere of nitrogen, 1-(6-bromopyridin-3-yl)ethane-1,2-diol (900 mg, 4.13 mmol, 1.00 equiv) was dissolved in acetone (15 mL), to which was added pyridinium ptoluenesulfonate (320 mg, 5.51 mmol, 1.33 equiv) at room temperature. The resulting solution was then stirred for 3 h at 60° C. After the reaction was done, the reaction mixture was diluted with 45 mL dichloromethane and washed with 10 mL water. The organic layer was separated, dried over sodium sulfate and concentrated under reduced pressure. The residue was purified in a silica gel column eluting with ethyl acetate in petroleum ether (5% to 50% gradient) to afford 2-bromo-5-(2,2-dimethyl-1,3-dioxolan-4-yl)pyridine (450 mg, 42%) as yellow oil. MS: m/z=258.1 [M+H]$^+$.

5-(2,2-Dimethyl-1,3-dioxolan-4-yl)-2-ethenylpyridine

In a 25-mL round bottom flask purged and maintained with an inert atmosphere of nitrogen, 2-bromo-5-(2,2-dimethyl-1,3-dioxolan-4-yl)pyridine (150 mg, 0.58 mmol, 1.00 equiv), tributyl(ethenyl)stannane (277 mg, 0.87 mmol, 1.48 equiv) and Pd(PPh$_3$)$_4$ (67 mg, 0.06 mmol, 0.10 equiv) were mixed in toluene (5 mL) at room temperature. The resulting mixture was then stirred overnight at 120° C. After the reaction was done, the reaction mixture was concentrated under reduced pressure. The residue was diluted with 30 mL dichloromethane and washed with 10 mL water. The organic layer was separated, dried over sodium sulfate and concentrated under reduced pressure. The residue was purified in a silica gel column eluting with ethyl acetate in petroleum ether (5% to 50% gradient) to afford 5-(2,2-dimethyl-1,3-dioxolan-4-yl)-2-ethenylpyridine (40 mg, 34%) as yellow oil. MS: m/z=206.0 [M+H]+.

5-(2,2-Dimethyl-1,3-dioxolan-4-yl)-2-ethenylpyridine

In a 50-mL round bottom flask, 5-(2,2-dimethyl-1,3-dioxolan-4-yl)-2-ethenylpyridine (300 mg, 1.46 mmol, 1.00 equiv) was dissolved in a mixture of tetrahydrofuran (2 mL) and water (0.4 mL), to which was added NaIO$_4$ (1.25 g, 5.84 mmol, 4.00 equiv) and OsO4 solution (17 M in water, 0.4 mL, 7.73 mmol, 5.29 equiv) at room temperature. The resulting mixture was then stirred for 2 h at room temperature. After the reaction was done, the reaction mixture was diluted with 5 ml water and extracted with ethyl acetate (3×5 ml). The organic layers were combined, dried over sodium sulfate and concentrated under reduced pressure to afford 5-(2,2-dimethyl-1,3-dioxolan-4-yl)pyridine-2-carbaldehyde (280 mg, 92%) as black oil. MS: m/z=208.0[M+H]+.

5-tert-Butyl-N-[(4-[2-[5-(1,2-dihydroxyethyl)pyridin-2-yl]-3H-imidazo[4,5-b]pyridin-7-yl]-2-fluorophenyl)methyl]-1,2,4-oxadiazole-3-carboxamide 5-tert-butyl-N-[(4-[2-[5-(1,2-dihydroxyethyl)pyridin-2-yl]-3H-imidazo[4,5-b]pyridin-7-yl]-2-fluorophenyl)methyl]-1,2,4-oxadiazole-3-carboxamide 5.5 mg (6% for 3 steps) was prepared from tert-butyl N-[[4-(2,3-diaminopyridin-4-yl)-2-fluorophenyl]methyl]carbamate, 5-(2,2-dimethyl-1,3-dioxolan-4-yl)pyridine-2-carbaldehyde, 5-tert-butyl-1,2,4-oxadiazole-3-carboxylate using Method 1H, 19T and 37Y. HPLC: 98.3% purity. MS: m/z=532.2 [M+H]+. 1H-NMR (400 MHz, DMSO-d$_6$): δ 13.90 (br s, 1H), 9.54 (t, J=6.0 Hz, 1H), 8.72 (d, J=1.9 Hz, 1H), 8.45-8.33 (m, 2H), 8.22-8.19 (m, 2H), 8.01-7.97 (m, 1H), 7.69-7.50 (m, 2H), 4.71 (t, J=5.9 Hz, 1H), 4.60-4.59 (m, 2H), 3.66-3.45 (m, 4H), 1.43 (s, 9H).

Scheme 40

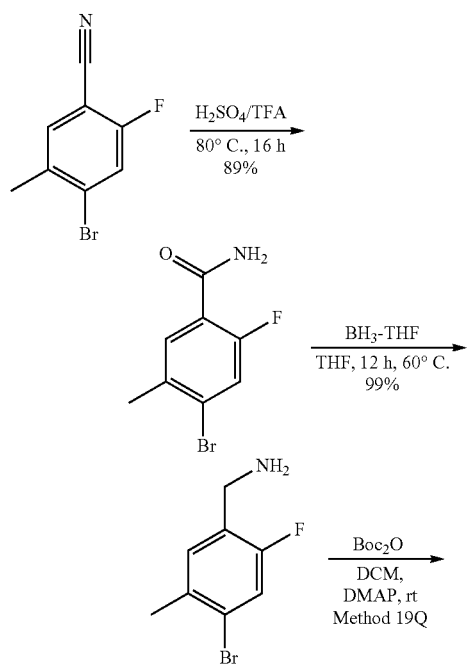

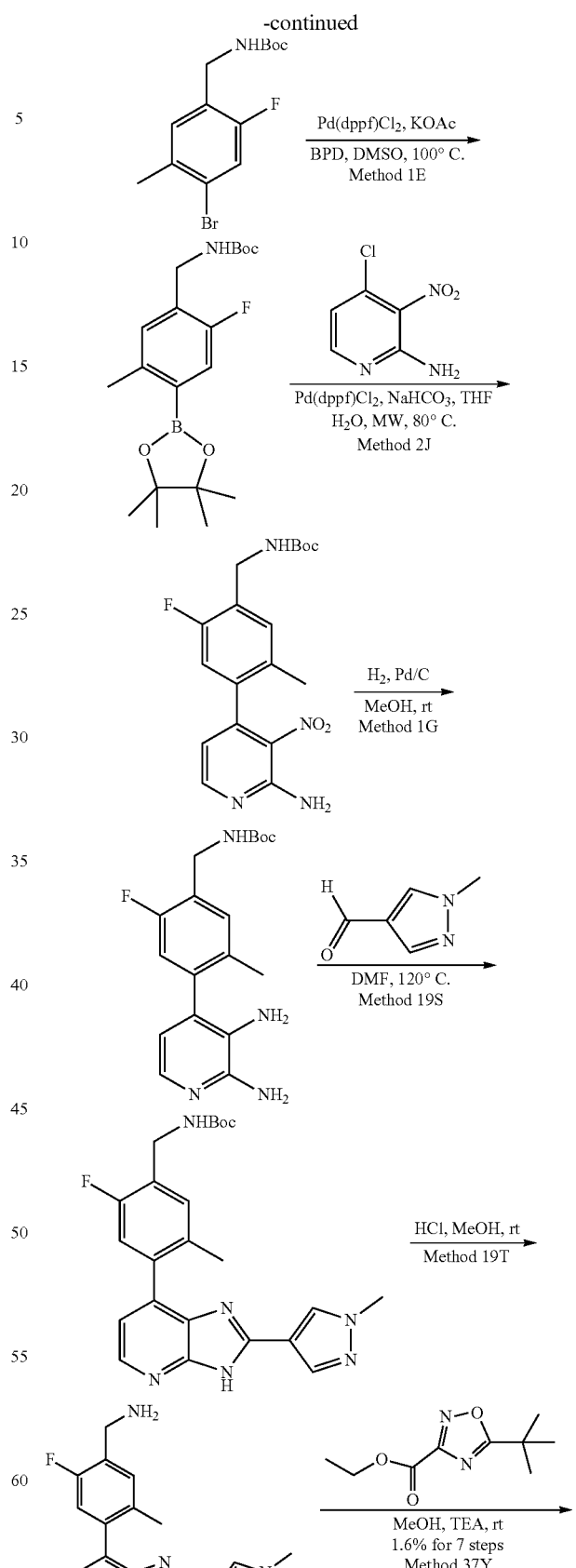

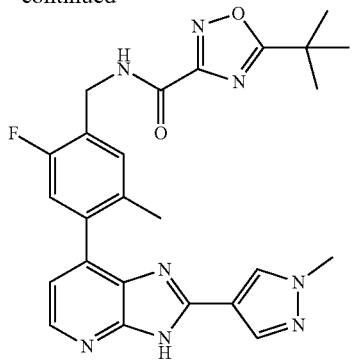

Example 77. 5-tert-butyl-N-([2-fluoro-5-methyl-4-[2-(1-methyl-1H-pyrazol-4-yl)-3H-imidazo[4,5-b]pyridin-7-yl] phenyl]methyl)-1,2,4-oxadiazole-3-carboxamide

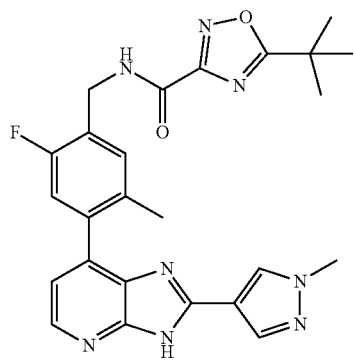 [SMILES: Cc1cc(CNC(=O)c2noc(C(C)(C)C)n2)c(F)cc1-c1ccnc2[nH]c(-c3cnn(C)c3)nc12]

4-Bromo-2-fluoro-5-methylbenzamide

In a 100-mL round bottom flask, 4-bromo-2-fluoro-5-methylbenzonitrile (5 g, 23.36 mmol, 1.00 equiv) was dissolved in a mixture of sulfuric acid (40 mL) and trifluoroacetic acid (10 mL) at room temperature. The resulting solution was then stirred overnight at 80° C. When the reaction was done, it was diluted with 200 mL water/ice and precipitation happened. The resulting precipitate was collected by filtration, rinsed with water and dried under reduced pressure to afford 4-bromo-2-fluoro-5 methylbenzamide (4.8 g, 89%) as white solid. MS: m/z=232.1 [M+H]$^+$.

5-(2,2-Dimethyl-1,3-dioxolan-4-yl)-2-ethenylpyridine

In a 100-mL round bottom flask, 4-bromo-2-fluoro-5-methylbenzamide (2.14 g, 9.22 mmol, 1.00 equiv) was dissolved in THF (920 mL), to which was added the BH$_3$ solution (1M in THF, 20.9 mL, 209 mmol, 22.66 equiv) at room temperature. The resulting solution was stirred overnight at 60° C. When the reaction was done, it was quenched by the slow addition of 5 mL hydrogen chloride solution (6 N) and the pH value of resulting mixture was adjusted to 9 using NaHCO$_3$. The mixture was extracted with ethyl acetate (3×20 mL) and the organic layers were combined, dried over sodium sulfate and concentrated under reduced pressure to afford (4-bromo-2-fluoro-5-methylphenyl)methanamine (2.0 g, 99%) as light yellow oil. MS: m/z=218.1 [M+H]$^+$.

5-tert-butyl-N-([2-fluoro-5-methyl-4-[2-(1-methyl-1H-pyrazol-4-yl)-3H-imidazo[4,5-b]pyridin-7-yl] phenyl]methyl)-1,2,4-oxadiazole-3-carboxamide 5-tert-butyl-N-([2-fluoro-5-methyl-4-[2-(1-methyl-1H-pyrazol-4-yl)-3H-imidazo[4,5-b]pyridin-7-yl]phenyl] methyl)-1,2,4-oxadiazole-3-carboxamide 15 mg (1.6% for 7 steps) was prepared from (4-bromo-2-fluoro-5-methylphenyl)methanamine, di-tert-butyl dicarbonate, 4,4,4',4',5,5,5',5'-octamethyl-2,2'-bi(1,3,2-dioxaborolane), 4-chloro-3-nitropyridin-2-amine, 1-methyl-1H-pyrazole-4-carbaldehyde and 5-tert-butyl-1,2,4-oxadiazole-3-carboxylate using Method 19Q, 1E, 2J, 1G, 19S, 19T and 37Y. HPLC: 99.8% purity. MS: m/z=489.1 [M+H]$^+$. $^1$H-NMR (400 MHz, CD$_3$OD): δ 8.36-8.30 (m, 2H), 8.15 (s, 1H), 7.45-7.42 (m, 1H), 7.17-7.13 (m, 2H), 4.70 (s, 2H), 3.98 (s, 3H), 2.17 (s, 3H), 1.50 (s, 9H).

Example 78. 5-tert-Butyl-N-([2-fluoro-4-[2-(3-methoxyphenyl)-3H-imidazo[4,5-b]pyridin-7-yl]-5-methylphenyl] methyl)-1,2,4-oxadiazole-3-carboxamide (78)

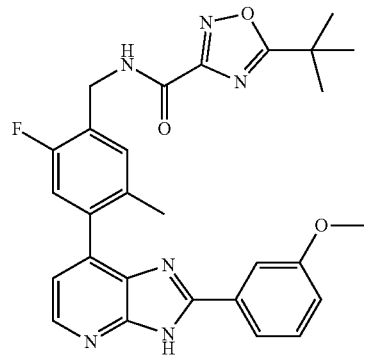 [SMILES: COc1cccc(-c2nc3c(-c4cc(F)c(CNC(=O)c5noc(C(C)(C)C)n5)cc4C)ccnc3[nH]2)c1]

5-tert-butyl-N-([2-fluoro-4-[2-(3-methoxyphenyl)-3H-imidazo[4,5-b]pyridin-7-yl]-5-methylphenyl]methyl)-1,2,4-oxadiazole-3-carboxamide 15 mg (6% for 3 steps) was prepared from tert-butyl N-([2-fluoro-4-[2-(3-methoxyphenyl)-3H-imidazo[4,5-b]pyridin-7-yl]-5-methylphenyl]methyl)carbamate, 3-methoxybenzaldehyde, 5-tert-butyl-1,2,4-oxadiazole-3-carboxylate using Method 15P, 19T and 37Y. HPLC: 98.2% purity. MS: m/z=515.2 [M+H]$^+$. $^1$H-NMR (300 MHz, CD$_3$OD): δ 8.46-8.39 (m, 2H), 7.78-7.70 (m, 2H), 7.47-7.41 (m, 2H), 7.20-7.18 (m, 2H), 7.12-7.08 (m, 1H), 4.71 (s, 2H), 3.88 (s, 3H), 2.2-2.17 (m, 3H), 1.52 (s, 9H).

Example 79. 5-tert-Butyl-N-[(2-fluoro-4-[2-[5-(4-methylpiperazin-1-yl)pyridin-2-yl]-3H-imidazo[4,5-b]pyridin-7-yl]phenyl)methyl]-1,2,4-oxadiazole-3-carboxamide (79)

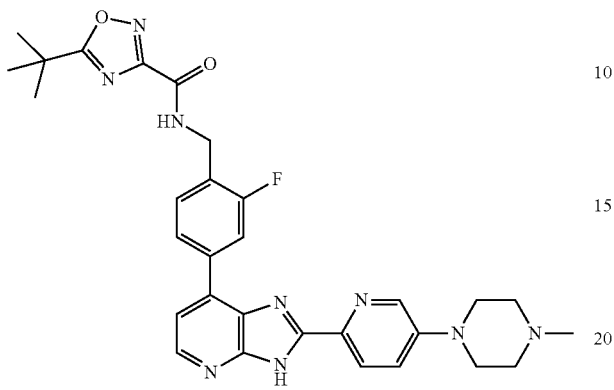

5-tert-butyl-N-[(2-fluoro-4-[2-[5-(4-methylpiperazin-1-yl)pyridin-2-yl]-3H-imidazo[4,5-b]pyridin-7-yl]phenyl)methyl]-1,2,4-oxadiazole-3-carboxamide 13 mg (7.2% for 4 steps) was prepared from 5-fluoropyridine-2-carbaldehyde, 1-methylpiperazine, tert-butyl N-[[4-(2,3-diaminopyridin-4-yl)-2-fluorophenyl] methyl]carbamate, 5-tert-butyl-1,2,4-oxadiazole-3-carboxylate using Method 15O, 15P, 19T and 37Y. HPLC: 99.1% purity. MS: m/z=570.4 [M+H]$^+$. $^1$H-NMR (400 MHz, CD$_3$OD): δ 8.46 (s, 1H), 8.40 (s, 1H), 8.29 (d, J=8.8 Hz, 1H), 8.25-7.90 (m, 2H), 7.70-7.58 (m, 1H), 7.55-7.45 (m, 2H), 4.76 (s, 2H), 3.47-3.44 (m, 4H), 2.68-2.65 (m, 4H), 2.66 (s, 3H), 1.51 (s, 9H).

Example 80. 5-tert-Butyl-N-[(2-fluoro-4-[2-[5-(pyrrolidin-1-yl)pyridin-2-yl]-3H-imidazo[4,5-b]pyridin-7-yl]phenyl)methyl]-1,2,4-oxadiazole-3-carboxamide (80)

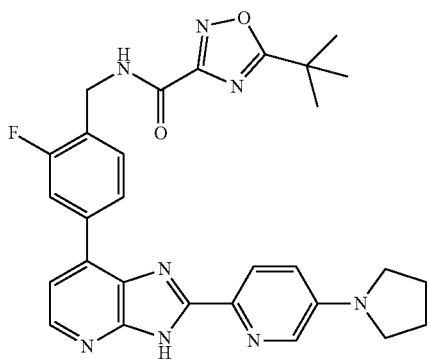 [SMILES: CC(C)(C)c1nc(C(=O)NCc2ccc(-c3ccnc4[nH]c(-c5ccc(N6CCCC6)cn5)nc34)cc2F)no1]

5-tert-butyl-N-[(2-fluoro-4-[2-[5-(pyrrolidin-1-yl)pyridin-2-yl]-3H-imidazo[4,5-b]pyridin-7-yl]phenyl)methyl]-1,2,4-oxadiazole-3-carboxamide 10 mg (4% for 4 steps) was prepared from 5-fluoropyridine-2-carbaldehyde, pyrrolidine, tert-butyl N-[[4-(2,3-diaminopyridin-4-yl)-2-fluorophenyl]methyl]carbamate and 5-tert-butyl-1,2,4-oxadiazole-3-carboxylate using Method 15O, 15P, 19T and 37Y. HPLC: 92.0% purity. MS: m/z=541.4 [M+H]$^+$. $^1$H-NMR (300 MHz, DMSO-d$_6$): δ 13.42 (br s, 1H), 9.54 (s, 1H), 8.35-8.33 (m, 2H), 8.29-8.26 (m, 2H), 8.07 (s, 1H), 7.63-7.55 (m, 2H), 7.10-7.09 (m, 1H), 4.60-4.58 (m, 2H), 3.39-3.36 (m, 4H), 2.01-2.00 (m, 4H), 1.44 (s, 9H).

Example 81. 5-tert-Butyl-N-[(4-[2-[5-(2,6-dimethylmorpholin-4-yl)pyridin-2-yl]-3H-imidazo[4,5-b]pyridin-7-yl]-2-fluorophenyl)methyl]-1,2,4-oxadiazole-3-carboxamide (81)

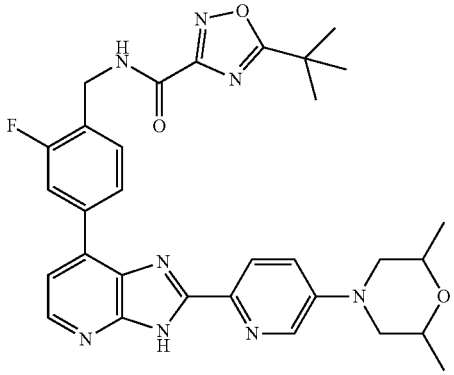 [SMILES: CC1CN(c2ccc(-c3nc4c(-c5ccc(CNC(=O)c6noc(C(C)(C)C)n6)c(F)c5)ccnc4[nH]3)nc2)CC(C)O1]

5-tert-butyl-N-[(4-[2-[5-(2,6-dimethylmorpholin-4-yl)pyridin-2-yl]-3H-imidazo[4,5-b]pyridin-7-yl]-2-fluorophenyl)methyl]-1,2,4-oxadiazole-3-carboxamide 30 mg (13.8% for 4 steps) was prepared from 5-fluoropyridine-2-carbaldehyde, 2,6-dimethylmorpholine, tert-butyl N-[[4-(2,3-diaminopyridin-4-yl)-2-fluorophenyl]methyl]carbamate, 5-tert-butyl-1,2,4-oxadiazole-3-carboxylate using Method 15O, 15P, 19T and 37Y. HPLC: 97.8% purity. MS: m/z=585.3 [M+H]$^+$. $^1$H-NMR (400 MHz, DMSO-d$_6$): δ 9.57 (s, 1H), 8.46-8.44 (m, 1H), 8.37-8.27 (m, 2H), 8.27-8.16 (m, 2H), 7.60-7.48 (m, 3H), 4.61-4.59 (m, 2H), 3.87-3.85 (m, 2H), 3.74-3.65 (m, 2H), 2.46-2.40 (m, 2H), 1.45 (s, 9H), 1.23-1.18 (m, 6H).

Example 82. 5-tert-Butyl-N-[(4-[2-[5-(4,4-difluoropiperidin-1-yl)pyridin-2-yl]-3H-imidazo[4,5-b]pyridin-7-yl]-2-fluorophenyl)methyl]-1,2,4-oxadiazole-3-carboxamide (82)

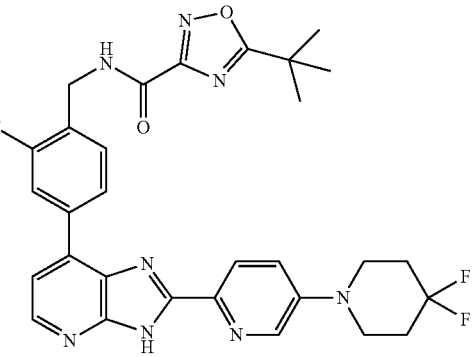

5-tert-butyl-N-[(4-[2-[5-(4,4-difluoropiperidin-1-yl)pyridin-2-yl]-3H-imidazo[4,5-b]pyridin-7-yl]-2-fluorophenyl)methyl]-1,2,4-oxadiazole-3-carboxamide 20 mg (12.3% for 4 steps) was prepared from 5-fluoropyridine-2-carbaldehyde, 4,4-difluoropiperidine hydrochloride, tert-butyl N-[[4-

(2,3-diaminopyridin-4-yl)-2-fluorophenyl]methyl] carbamate, 5-tert-butyl-1,2,4-oxadiazole-3-carboxylate using Method 15O, 15P, 19T and 37Y. HPLC: 96.5% purity. MS: m/z=591.1 [M+H]⁺. ¹H-NMR (300 MHz, DMSO-d$_6$): δ 13.65 (br s, 1H), 9.59-9.48 (m, 1H), 8.50 (d, J=2.8 Hz, 1H), 8.39-8.11 (m, 4H), 7.64-7.48 (m, 3H), 4.61-4.59 (m, 2H), 3.59-3.57 (t, J=5.9 Hz, 4H), 2.10-2.06 (m, 4H), 1.43 (s, 9H).

Example 83. 5-tert-Butyl-N-[(2-fluoro-4-[2-[5-(piperidin-1-yl)pyridin-2-yl]-3H-imidazo[4,5-b]pyridin-7-yl]phenyl) methyl]-1,2,4-oxadiazole-3-carboxamide (83)

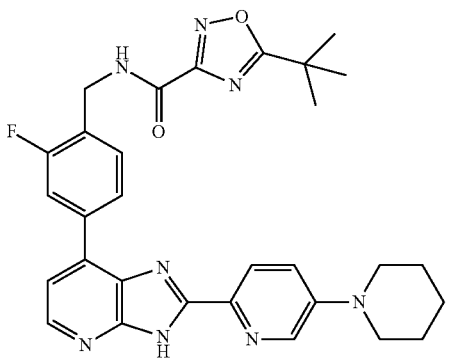 [SMILES: CC(C)(C)c1nc(C(=O)NCc2ccc(-c3ccnc4[nH]c(-c5ccc(N6CCCCC6)cn5)nc34)cc2F)no1]

5-tert-butyl-N-[(2-fluoro-4-[2-[5-(piperidin-1-yl)pyridin-2-yl]-3H-imidazo[4,5-b]pyridin-7-yl]phenyl)methyl]-1,2,4-oxadiazole-3-carboxamide 20 mg (7% for 4 steps) was prepared from 5-fluoropyridine-2-carbaldehyde, piperidine, tert-butyl N-[[4-(2,3-diaminopyridin-4-yl)-2-fluorophenyl]methyl]carbamate and 5-tert-butyl-1,2,4-oxadiazole-3-carboxylate using Method 15O, 15P, 19T and 37Y. HPLC: 98.9% purity. MS: m/z=555.2 [M+H]⁺. ¹H-NMR (300 MHz, DMSO-d$_6$): δ 9.57-9.54 (m, 1H), 8.43-8.36 (m, 2H), 8.26-8.11 (m, 3H), 7.60-7.45 (m, 3H), 4.61-4.59 (m, 2H), 3.40-3.39 (m, 4H), 1.63-1.59 (m, 6H), 1.43 (s, 9H).

Example 84. 5-tert-butyl-N-[(2-fluoro-4-[2-[5-(4-hydroxypiperidin-1-yl)pyridin-2-yl]-3H-imidazo[4,5-b]pyridin-7-yl]phenyl)methyl]-1,2,4-oxadiazole-3-carboxamide (84)

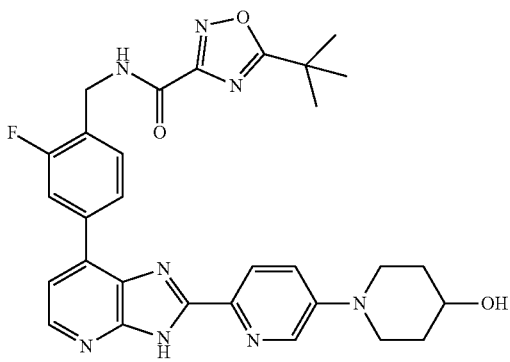 [SMILES: CC(C)(C)c1nc(C(=O)NCc2ccc(-c3ccnc4[nH]c(-c5ccc(N6CCC(O)CC6)cn5)nc34)cc2F)no1]

5-tert-butyl-N-[(2-fluoro-4-[2-[5-(4-hydroxypiperidin-1-yl)pyridin-2-yl]-3H-imidazo[4,5-b]pyridin-7-yl]phenyl)methyl]-1,2,4-oxadiazole-3-carboxamide 18 mg (13% for 4 steps) was prepared from 5-fluoropyridine-2-carbaldehyde, piperidin-4-ol, tert-butyl N-[[4-(2,3-diaminopyridin-4-yl)-2-fluorophenyl]methyl]carbamate, 5-tert-butyl-1,2,4-oxadiazole-3-carboxylate using Method 15O, 15P, 19T and 37Y. HPLC: 96.7% purity. MS: m/z=571.3 [M+H]⁺. ¹H-NMR (400 MHz, DMSO-d$_6$): δ 9.56 (t, J=6.0 Hz, 1H), 8.44-8.40 (m, 1H), 8.35-8.30 (m, 2H), 8.28-8.16 (m, 2H), 7.88 (m, 1H), 7.58-7.50 (m, 3H), 4.61-4.60 (m, 2H), 3.79-3.71 (m, 3H), 3.13-3.08 (m, 2H), 2.12-1.61 (m, 2H), 1.53-1.43 (m, 12H).

Example 85. 5-tert-Butyl-N-[(2-fluoro-4-[2-[5-(1-methyl-1,2,3,6-tetrahydropyridin-4-yl)pyridin-2-yl]-3H-imidazo[4,5-b]pyridin-7-yl]phenyl)methyl]-1,2,4-oxadiazole-3-carboxamide; trifluoroacetic acid (85)

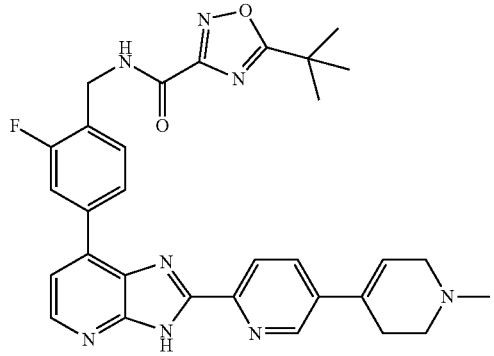 [SMILES: CN1CC=C(c2ccc(-c3nc4c(-c5ccc(CNC(=O)c6noc(C(C)(C)C)n6)c(F)c5)ccnc4[nH]3)nc2)CC1]

5-tert-butyl-N-[(2-fluoro-4-[2-[5-(1-methyl-1,2,3,6-tetrahydropyridin-4-yl)pyridin-2-yl]-3H-imidazo[4,5-b]pyridin-7-yl]phenyl)methyl]-1,2,4-oxadiazole-3-carboxamide; trifluoroacetic acid 3 mg (0.8% for 4 steps) was prepared from 5-bromopyridine-2-carbaldehyde, 1-methyl-4-(tetramethyl-1,3,2-dioxaborolan-2-yl)-1,2,3,6-tetrahydropyridine, tert-butyl N-[[4-(2,3-diaminopyridin-4-yl)-2-fluorophenyl]methyl]carbamate, 5-tert-butyl-1,2,4-oxadiazole-3-carboxylate using Method 1F, 15O, 19T and 37Y. HPLC: 96.0% purity. MS: m/z=567.4 [M+H]⁺. ¹H-NMR (400 MHz, DMSO-d6): δ 13.92 (s, 1H), 9.84 (br s, 1H), 9.55 (t, J=6.0 Hz, 1H), 8.95-8.88 (m, 1H), 8.48-8.28 (m, 3H), 8.26-8.09 (m, 2H), 7.68-7.51 (m, 2H), 6.51 (s, 1H), 4.61-4.59 (m, 2H), 3.92-3.91 (s, 2H), 3.44-3.31 (m, 3H), 2.90-2.89 (m, 4H), 1.44 (s, 9H).

Example 86. 5-tert-Butyl-N-[(2-fluoro-4-[2-[4-(1-methyl-1,2,3,6-tetrahydropyridin-4-yl)phenyl]-3H-imidazo[4,5-b]pyridin-7-yl]phenyl)methyl]-1,2,4-oxadiazole-3-carboxamide; Trifluoroacetic Acid (86)

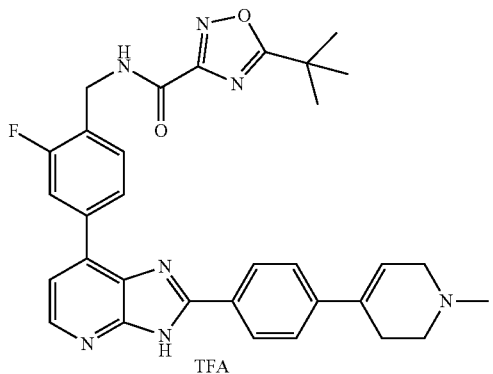 [SMILES: CN1CC=C(c2ccc(-c3nc4c(-c5ccc(CNC(=O)c6noc(C(C)(C)C)n6)c(F)c5)ccnc4[nH]3)cc2)CC1]

TFA 5-tert-butyl-N-[(2-fluoro-4-[2-[4-(1-methyl-1,2,3,6-tetrahydropyridin-4-yl)phenyl]-3H-imidazo[4,5-b]pyridin-7-yl]phenyl)methyl]-1,2,4-oxadiazole-3-carboxamide, trifluoroacetic acid salt 5 mg (0.6% for 3 steps) was prepared from tert-butyl N-[[4-(2,3-diaminopyridin-4-yl)-2-fluorophenyl]methyl]carbamate, 4-(1-methyl-1,2,3,6-tetrahydropyridin-4-yl)benzaldehyde and 5-tert-butyl-1,2,4-oxadiazole-3-carboxylate using Method 15O, 19T and 37Y. HPLC: 96.2% purity. MS: m/z=566.4 [M+H]$^+$. $^1$H-NMR (300 MHz, DMSO-d$_6$): δ 9.56 (t, J=5.6 Hz, 1H), 8.41-8.29 (m, 5H), 8.22-8.19 (m, 4H), 7.72 (d, J=8.4 Hz, 1H), 7.65-7.49 (m, 2H), 4.60 (d, J=4.1 Hz, 2H), 3.91 (s, 1H), 3.37 (s, 1H), 2.87-2.85 (m, 5H), 1.42 (s, 9H).

Example 87. 5-tert-Butyl-N-([3-[2-(1-methyl-1H-pyrazol-4-yl)-3H-imidazo[4,5-b]pyridin-7-yl]phenyl]methyl)-1,2,4-oxadiazole-3-carboxamide (87)

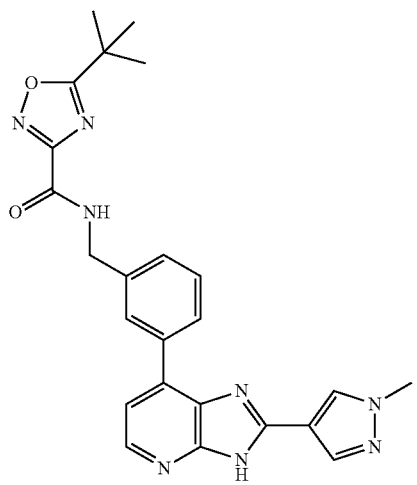 [SMILES: Cn1cc(-c2nc3c(-c4cccc(CNC(=O)c5noc(C(C)(C)C)n5)c4)ccnc3[nH]2)cn1]

5-tert-butyl-N-([3-[2-(1-methyl-1H-pyrazol-4-yl)-3H-imidazo[4,5-b]pyridin-7-yl]phenyl]methyl)-1,2,4-oxadiazole-3-carboxamide 31.4 mg (1.2% for 7 steps) was prepared from (3-bromophenyl)methanamine, di-tert-butyl dicarbonate, 4,4,4',4',5,5,5',5'-octamethyl-2,2'-bi(1,3,2-dioxaborolane), 4-chloro-3-nitropyridin-2-amine, 1-methyl-1H-pyrazole-4-carbaldehyde, 5-tert-butyl-1,2,4-oxadiazole-3-carboxylate using Method 19Q, 19R, 2J, 1G, 19S, 19T and 37Y. HPLC: 99.8% purity. MS: m/z=557.1 [M+H]$^+$. $^1$H-NMR (400 MHz, DMSO): δ 13.33 (br s, 1H), 9.58-9.54 (m, 1H), 8.40-8.37 (m, 2H), 8.29-8.27 (m, 1H), 8.21-8.18 (m, 1H), 8.07 (s, 1H), 7.54-7.40 (m, 3H), 4.60-4.58 (m, 2H), 3.95 (s, 3H), 1.40 (s, 9H).

Scheme 41

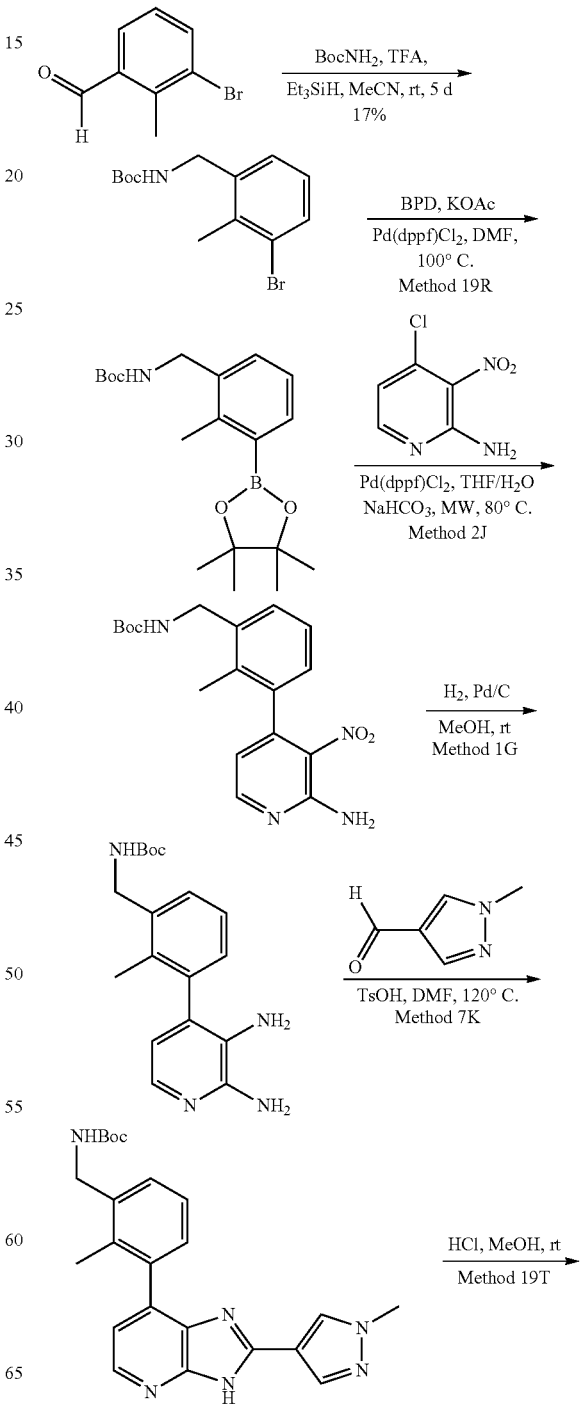

293

-continued

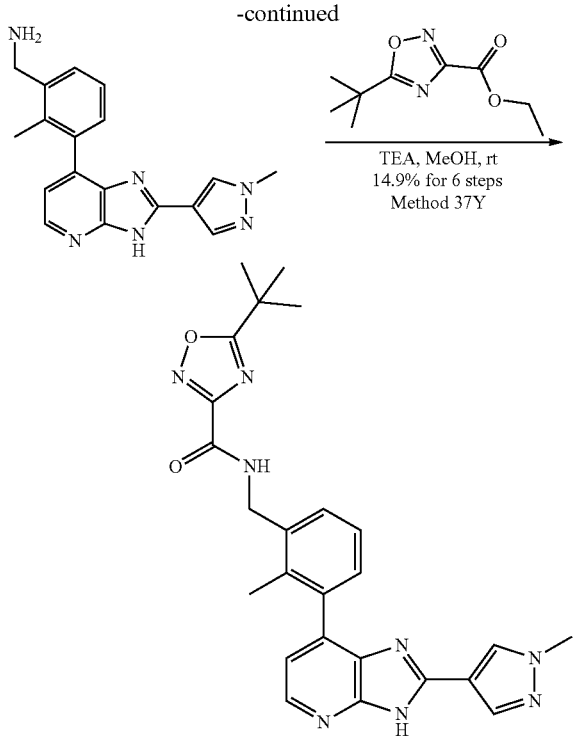

Example 88. 5-tert-Butyl-N-([2-methyl-3-[2-(1-methyl-1H-pyrazol-4-yl)-3H-imidazo[4,5-b]pyridin-7-yl]phenyl] methyl)-1,2,4-oxadiazole-3-carboxamide (88)

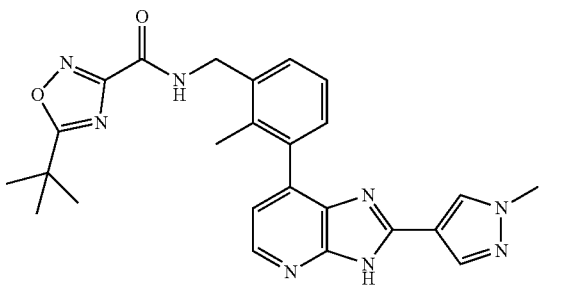 [SMILES: Cc1c(CNC(=O)c2noc(C(C)(C)C)n2)cccc1-c1ccnc2[nH]c(-c3cnn(C)c3)nc12]

tert-Butyl N-[(3-bromo-2-methylphenyl)methyl] carbamate

In a 50-mL round bottom flask, 3-bromo-2-methylbenzaldehyde (2 g, 10.0 mmol, 0.34 equiv) was dissolved in acetonitrile (24 mL), to which were added tert-butyl carbamate (3.5 g, 29.88 mmol, 1.00 equiv), Et$_3$SiH (3.5 g, 30.10 mmol, 1.01 equiv) and trifluoroacetic acid (940 mg, 8.24 mmol, 0.28 equiv) at room temperature. The resulting solution was then stirred for 5 days at room temperature. After the reaction was done and the reaction mixture was concentrated under reduced pressure to afford tert-butyl N-[(3-bromo-2-methylphenyl) methyl]carbamate (1.5 g, 17%) as yellow solid.

294

5-tert-Butyl-N-([2-methyl-3-[2-(1-methyl-1H-pyrazol-4-yl)-3H-imidazo[4,5-b]pyridin-7-yl]phenyl] methyl)-1,2,4-oxadiazole-3-carboxamide 5-tert-butyl-N-([2-methyl-3-[2-(1-methyl-1H-pyrazol-4-yl)-3H-imidazo[4,5-b]pyridin-7-yl]phenyl]methyl)-1,2,4-oxadiazole-3-carboxamide 40.5 mg (14.9% for 6 steps) was prepared from (tert-butyl N-[(3-bromo-2-methylphenyl) methyl]carbamate, 4,4,4',4',5,5,5',5'-octamethyl-2,2'-bi(1,3,2-dioxaborolane), 4-chloro-3-nitropyridin-2-amine, 1-methyl-1H-pyrazole-4-carbaldehyde and 5-tert-butyl-1,2,4-oxadiazole-3-carboxylate using Method 19Q, 19R, 2J, 1G, 7K, 19T and 37Y. HPLC: 98.2% purity. MS: m/z=471.2 [M+H]$^+$. $^1$H-NMR (300 MHz, DMSO-d$_6$): δ 13.30 (br s, 1H), 12.55 (br s, 1H), 9.48 (t, J=6.0 Hz, 1H), 8.48-8.33 (m, 2H), 8.08-8.05 (m, 1H), 7.48-7.21 (m, 3H), 7.05-7.03 (m, 1H), 4.56 (d, J=6.0 Hz, 2H), 3.92-3.89 (m, 3H), 2.14-2.13 (m, 3H), 1.45 (s, 9H).

Example 89. 4-tert-Butyl-N-[(4-[2-[5-(dimethylamino)pyridin-2-yl]-3H-imidazo[4,5-b]pyridin-7-yl]-2-fluorophenyl) methyl]benzamide (89)

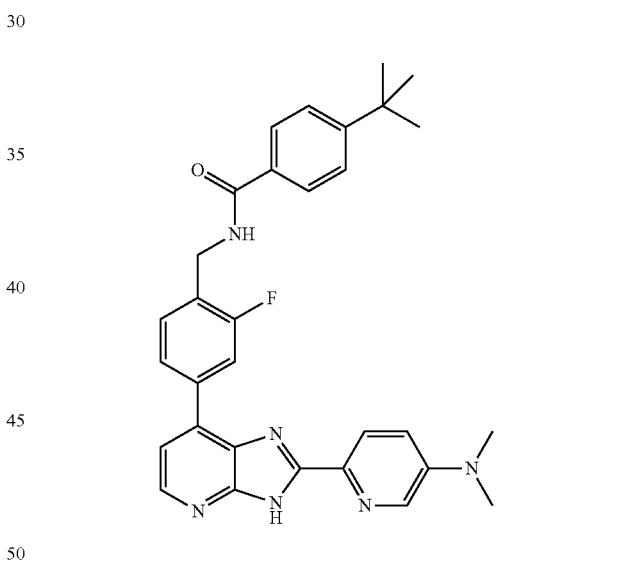

4-tert-butyl-N-[(4-[2-[5-(dimethylamino)pyridin-2-yl]-3H-imidazo[4,5-b]pyridin-7-yl]-2-fluorophenyl)methyl] benzamide 20 mg (7.3% for 3 steps) was prepared from tert-butyl N-[[4-(2,3-diaminopyridin-4-yl)-2-fluorophenyl] methyl]carbamate, 5-(dimethylamino)pyridine-2-carbaldehyde, 4-tert-butylbenzoyl chloride using Method 7K, 19T and 22V. HPLC: 98.9% purity. MS: m/z=523.2 [M+H]$^+$. $^1$H-NMR (400 MHz, DMSO-d$_6$): δ 13.48 (br s, 1H), 9.04 (t, J=5.8 Hz, 1H), 8.29-8.27 (m, 2H), 8.23-8.11 (m, 3H), 7.90-7.83 (m, 2H), 7.55-7.46 (m, 4H), 7.24-7.21 (m, 1H), 4.61-4.59 (m, 2H), 3.05 (s, 6H), 1.29 (s, 9H).

Example 90. 3-(tert-Butoxy)-N-[(4-[2-[5-(dimethylamino)pyridin-2-yl]-3H-imidazo[4,5-b]pyridin-7-yl]-2-fluorophenyl)methyl]azetidine-1-carboxamide (90)

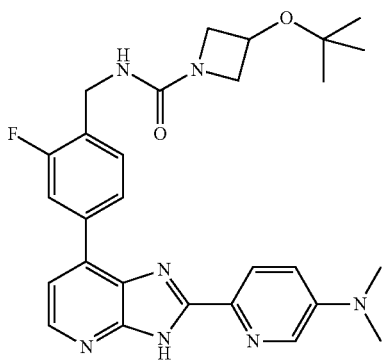 [SMILES: CN(C)c1ccc(-c2nc3c(-c4ccc(CNC(=O)N5CC(OC(C)(C)C)C5)c(F)c4)ccnc3[nH]2)nc1]

3-(tert-butoxy)-N-[(4-[2-[5-(dimethylamino)pyridin-2-yl]-3H-imidazo[4,5-b]pyridin-7-yl]-2-fluorophenyl)methyl]azetidine-1-carboxamide 20 mg (14.0%) was prepared from (6-[7-[4-(aminomethyl)-3-fluorophenyl]-3H-imidazo[4,5-b]pyridin-2-yl]-N,N-dimethylpyridin-3-amine and 3-(tert-butoxy)azetidine using Method 23W. HPLC: 97.5% purity. MS: m/z=518.2 [M+H]$^+$. $^1$H-NMR (300 MHz, DMSO-d$_6$): δ 13.48 (s, 1H), 8.33 (t, J=5.4 Hz, 1H), 8.23-8.20 (m, 3H), 8.12 (d, J=7.8 Hz, 1H), 7.55-7.47 (m, 2H), 7.29-7.25 (m, 1H), 6.94 (t, J=5.9 Hz, 1H), 4.47 (t, J=6.3 Hz, 1H), 4.32-4.31 (m, 2H), 4.07-4.02 (m, 2H), 3.64-3.59 (m, 2H), 3.07 (s, 6H), 1.12 (s, 9H).

Scheme 42

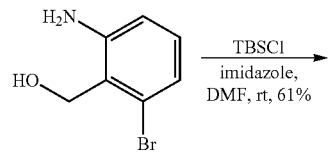

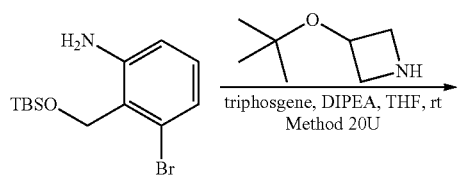

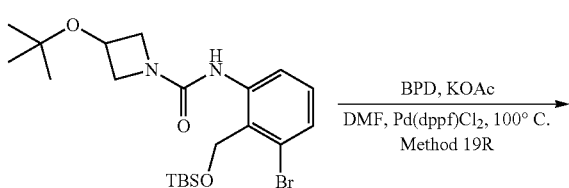

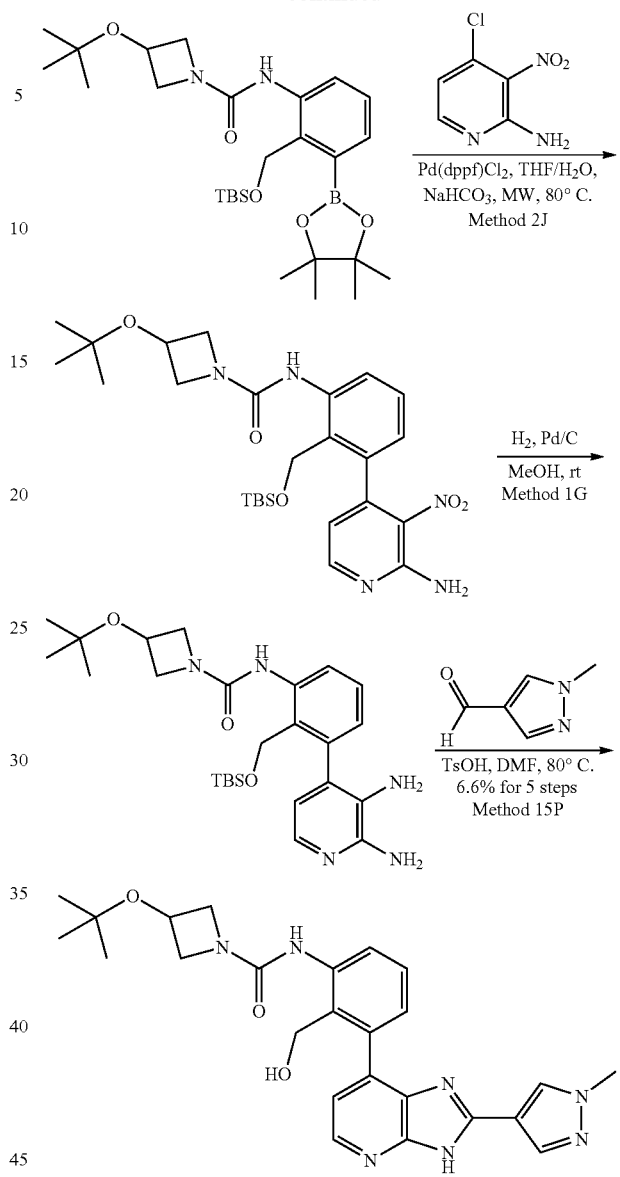

Example 91. 3-(tert-Butoxy)-N-[2-(hydroxymethyl)-3-[2-(1-methyl-1H-pyrazol-4-yl)-3H-imidazo[4,5-b]pyridin-7-yl]phenyl]azetidine-1-carboxamide (91)

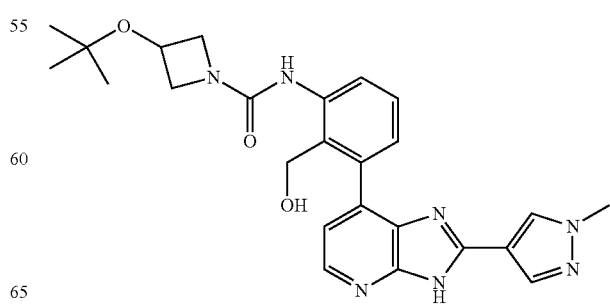

4-tert-Butyl-N-[(4-[2-[5-(dimethylamino)pyridin-2-yl]-3H-imidazo[4,5-b]pyridin-7-yl]-2-fluorophenyl)methyl]benzamide At 0° C., in a 100-mL round bottom flask, (2-amino-6-bromophenyl) methanol (950 mg, 4.70 mmol, 1.00 equiv) and imidazole (1.01 g, 14.09 mmol, 3.00 equiv) were dissolved in N,N-dimethylformamide (15 mL), to which was added TBSCl (1.49 g, 9.39 mmol, 2.00 equiv). The resulting solution was then stirred overnight at room temperature. After the reaction was done, the reaction mixture was concentrated under reduced pressure and the residue was diluted with 30 mL ethyl acetate. The mixture was washed with brine (4×10 mL), and then the organic phase was dried over sodium sulfate and concentrated under reduced pressure. The residue was purified in a silica gel column eluting with ethyl acetate in petroleum ether (5% to 25% gradient) to afford 3-bromo-2-[[(tert-butyldimethylsilyl) oxy]methyl] aniline (0.95 g, 61%) as brown oil. MS: m/z=316.2 [M+H]$^+$.

3-(tert-Butoxy)-N-[2-(hydroxymethyl)-3-[2-(1-methyl-1H-pyrazol-4-yl)-3H-imidazo[4,5-b]pyridin-7-yl]phenyl]azetidine-1-carboxamide 3-(tert-butoxy)-N-[2-(hydroxymethyl)-3-[2-(1-methyl-1H-pyrazol-4-yl)-3H-imidazo[4,5-b]pyridin-7-yl]phenyl] azetidine-1-carboxamide 20 mg (6.6% for 5 steps) was prepared from 3-bromo-2-[[(tert-butyldimethylsilyl)oxy] methyl]aniline, 3-(tert-butoxy)azetidine, 4,4,4',4',5,5,5',5'-octamethyl-2,2'-bi(1,3,2-dioxaborolane), 4-chloro-3-nitropyridin-2-amine, 1-methyl-1H-pyrazole-4-carbaldehyde using Method 20U, 19R, 2J, 1G and 15P. HPLC: 96.1% purity. MS: m/z=476.1 [M+H]$^+$. $^1$H-NMR (400 MHz, DMSO-d$_6$): δ 13.45 (br s, 1H), 8.59-8.25 (m, 3H), 8.22-8.01 (m, 1H), 7.98-7.85 (m, 1H), 7.49-7.31 (m, 1H), 7.15-7.14 (m, 1H), 7.05-7.03 (m, 1H), 5.85 (s, 1H), 4.65-4.55 (m, 1H), 4.42-4.41 (m, 2H), 4.25-4.15 (m, 2H), 3.91 (s, 3H), 3.85-3.65 (m, 2H), 1.15 (s, 9H).

Scheme 43

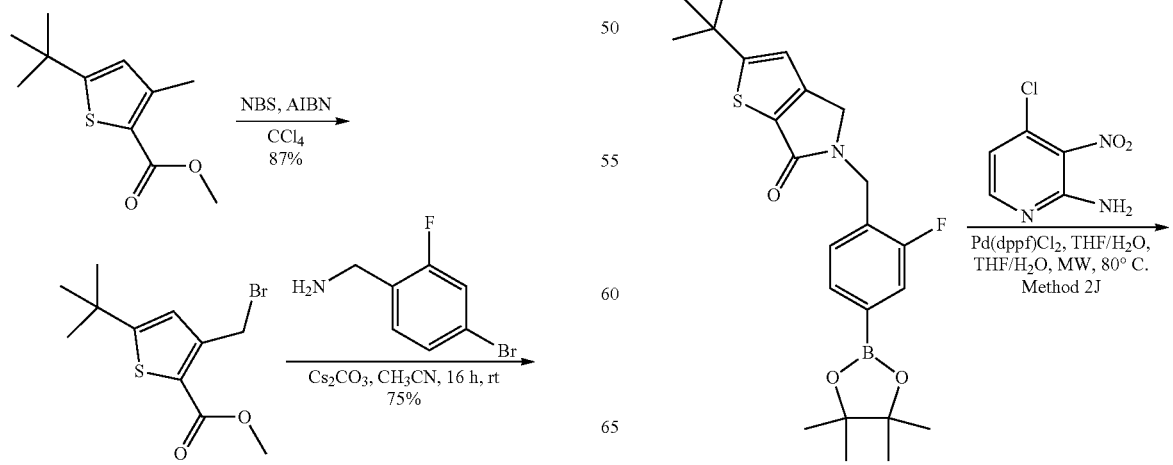

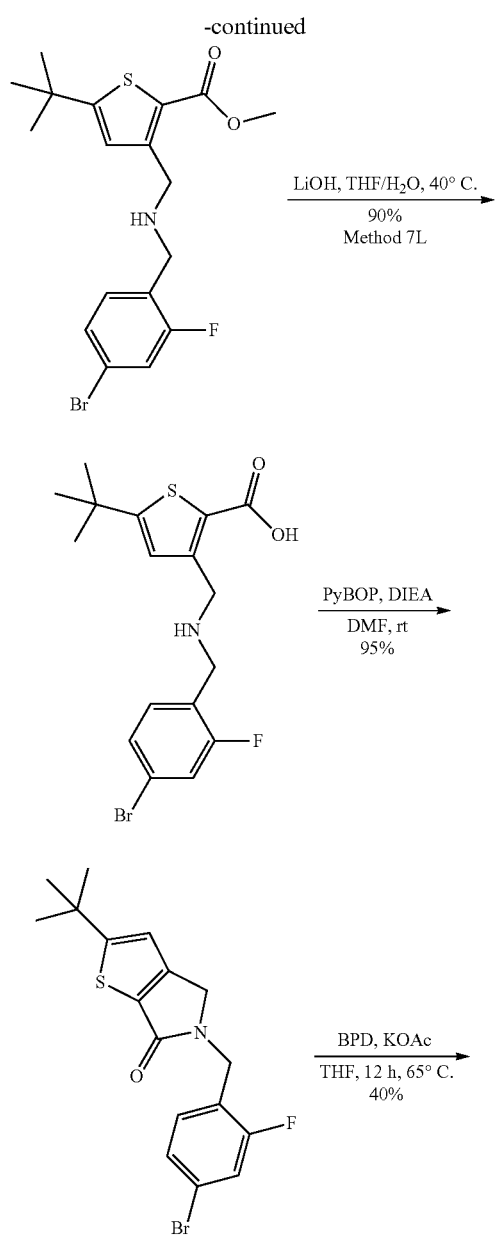

-continued

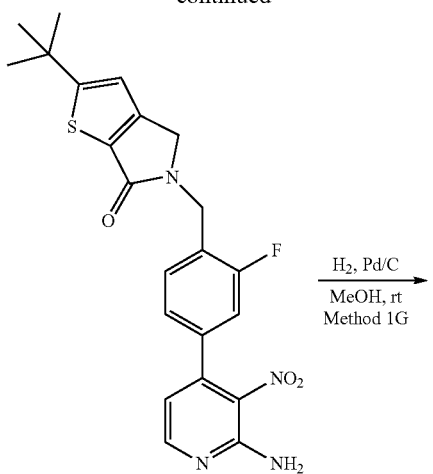

H₂, Pd/C
MeOH, rt
Method 1G

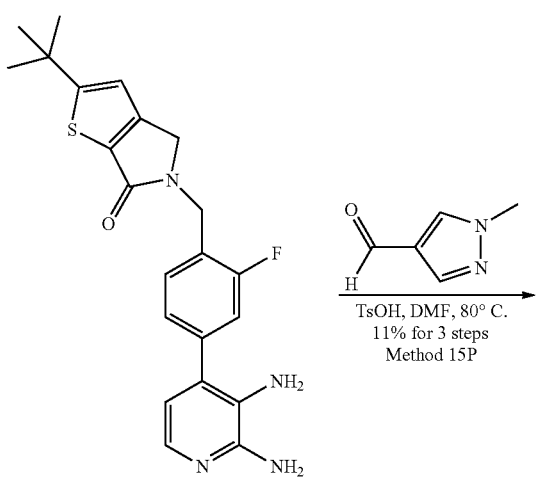

TsOH, DMF, 80° C.
11% for 3 steps
Method 15P

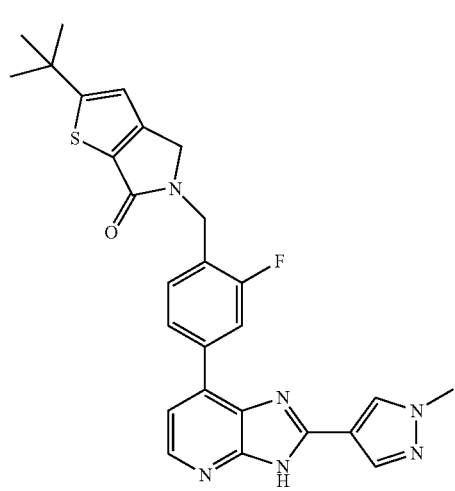 [SMILES: Cn1cc(-c2nc3c(-c4ccc(CN5Cc6cc(C(C)(C)C)sc6C5=O)c(F)c4)ccnc3[nH]2)cn1]

Example 92. 2-tert-Butyl-5-([2-fluoro-4-[2-(1-methyl-1H-pyrazol-4-yl)-3H-imidazo[4,5-b]pyridin-7-yl]phenyl] methyl)-4H,5H,6H-thieno[2,3-c]pyrrol-6-one (92)

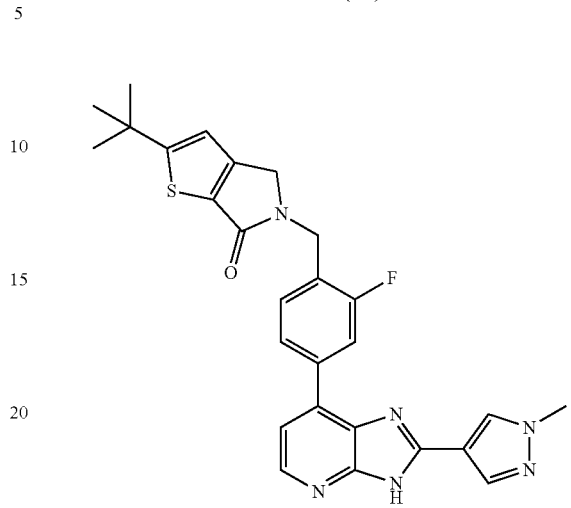

Methyl 3-(bromomethyl)-5-tert-butylthiophene-2-carboxylate

In a 100-mL round bottom flask, methyl 5-tert-butyl-3-methylthiophene-2-carboxylate (1.00 g, 4.71 mmol, 1.00 equiv) was dissolved in CCl₄ (40 mL), to which were added NBS (1.01 g, 5.67 mmol, 1.20 equiv) and AIBN (77.34 mg, 0.47 mmol, 0.10 equiv) at room temperature. The resulting solution was then stirred for 16 h at 90° C. After the reaction was done, the reaction mixture was concentrated under reduced pressure and the residue was diluted with 30 mL ethyl acetate. The mixture was washed with brine (4×10 mL) and dried over sodium sulfate. The solvent was removed under reduced pressure to afford methyl 3-(bromomethyl)-5-tert-butylthiophene-2-carboxylate (1.2 g, 87%) as yellow oil.

Methyl 3-[[(4-bromo-2-fluorophenyl)methyl]amino]methyl)-5-tert-butylthiophene-2-carboxylate In a 50-mL round bottom flask, methyl 3-(bromomethyl)-5-tert-butylthiophene-2-carboxylate (700 mg, 2.40 mmol, 1.00 equiv) was dissolved in acetonitrile (10 mL), to which were added (4-bromo-2-fluorophenyl)methanamine (1.47 g, 7.21 mmol, 3.00 equiv) and Cs₂CO₃ (861.53 mg, 2.64 mmol, 1.10 equiv) at room temperature. The resulting mixture was then stirred for 16 h at room temperature. After the reaction was done, the reaction mixture was concentrated under reduced pressure and the residue was purified in a silica gel column eluting with ethyl acetate in petroleum ether (5% to 50% gradient) to afford methyl 3-([[(4-bromo-2-fluorophenyl)methyl]amino]methyl)-5-tert-butylthiophene-2-carboxylate (750 mg, 75%) as yellow solid. MS: m/z=414.0 [M+H]⁺.

3-([[(4-Bromo-2-fluorophenyl)methyl]amino]methyl)-5-tert-butylthiophene-2-carboxylic acid 3-([[(4-bromo-2-fluorophenyl)methyl]amino]methyl)-5-tert-butylthiophene-2-carboxylic acid 700 mg (90%) was prepared from methyl 3-([[(4-bromo-2-fluorophenyl)methyl]amino]methyl)-5-tert-butylthiophene-2-carboxylate using Method 7L.

3-([[(4-Bromo-2-fluorophenyl)methyl]amino]methyl)-5-tert-butylthiophene-2-carboxylic acid In a 100-mL round-bottom flask, 3-([[(4-bromo-2-fluorophenyl)methyl]amino]methyl)-5-tert-butylthiophene-2-carboxylic acid (700 mg, 1.46 mmol, 1.00 equiv) was dissolved in N,N-dimethylformamide (10 mL), to which were added PyBOP (591.4 mg, 1.14 mmol, 1.30 equiv) and DIEA (339 mg, 2.62 mmol, 3.00 equiv) at room temperature. The resulting solution was then stirred for 16 h at room temperature. After the reaction was done, the reaction mixture was concentrated under reduced pressure and the residue was diluted with 30 mL ethyl acetate. The mixture was washed with brine (4×10 mL) and dried over sodium sulfate. The solvent was removed under reduced pressure and the residue was purified in a silica gel column eluting with ethyl acetate in petroleum ether (5% to 25% gradient) to afford 5-[(4-bromo-2-fluorophenyl)methyl]-2-tert-butyl-4H,5H,6H-thieno[2,3-c]pyrrol-6-one (700 mg, 95%) as yellow solid. MS: m/z=381.2 [M+H]⁺.

3-([[(4-Bromo-2-fluorophenyl)methyl]amino]methyl)-5-tert-butylthiophene-2-carboxylic acid In a 50-mL round bottom flask purged and maintained with an inert atmosphere of nitrogen, 5-[(4-bromo-2-fluorophenyl)methyl]-2-tert-butyl-4H,5H,6H-thieno[2,3-c]pyrrol-6-one (700 mg, 1.74 mmol, 1.00 equiv) 4,4,5,5-tetramethyl-2-(tetramethyl-1,3,2-dioxaborolan-2-yl)-1,3,2-dioxaborolane (557.98 mg, 2.09 mmol, 1.20 equiv), KOAc (359.40 mg, 3.48 mmol, 2.00 equiv) and Pd(dppf)Cl₂·CH₂Cl₂ (149.53 mg, 0.18 mmol, 0.10 equiv) were mixed in tetrahydrofuran (10 mL) at room temperature. The resulting solution was then stirred for 16 h at 70° C. After the reaction was done, the reaction mixture was concentrated under reduced pressure and the residue was purified in a silica gel column eluting with ethyl acetate in petroleum ether (5% to 50% gradient) to afford 2-tert-butyl-5-[[2-fluoro-4-(tetramethyl-1,3,2-dioxaborolan-2-yl)phenyl]methyl]-4H,5H,6H-thieno[2,3-c]pyrrol-6-one (300 mg, 40%) as yellow solid.

2-tert-Butyl-5-([2-fluoro-4-[2-(1-methyl-1H-pyrazol-4-yl)-3H-imidazo[4,5-b]pyridin-7-yl]phenyl]methyl)-4H,5H,6H-thieno[2,3-c]pyrrol-6-one 2-tert-butyl-5-([2-fluoro-4-[2-(1-methyl-1H-pyrazol-4-yl)-3H-imidazo[4,5-b]pyridin-7-yl]phenyl]methyl)-4H,5H,6H-thieno[2,3-c]pyrrol-6-one 23 mg (11% for 3 steps) was prepared from 2-tert-butyl-5-[[2-fluoro-4-(tetramethyl-1,3,2-dioxaborolan-2-yl)phenyl]methyl]-4H,5H,6H-thieno[2,3-c]pyrrol-6-one, 4-chloro-3-nitropyridin-2-amine, 1-methyl-1H-pyrazole-4-carbaldehyde using Method 2J, 1G and 15P. HPLC: 98.9% purity. MS: m/z=501.1 [M+H]⁺. ¹H-NMR (400 MHz, DMSO-d₆): δ 8.45 (s, 1H), 8.30-8.29 (m, 2H), 8.17-8.14 (m, 2H), 7.47-7.44 (m, 2H), 7.05 (s, 1H), 4.81 (s, 2H), 4.38 (s, 2H), 3.95 (s, 3H), 1.39 (s, 9H).

Scheme 44

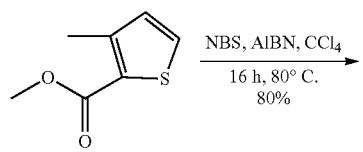

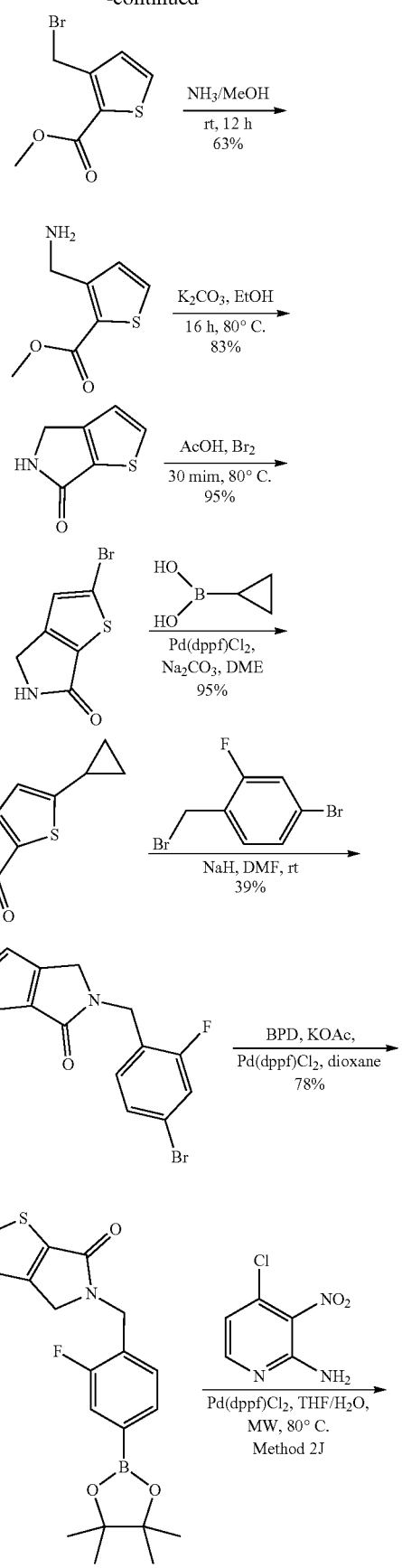

303
-continued

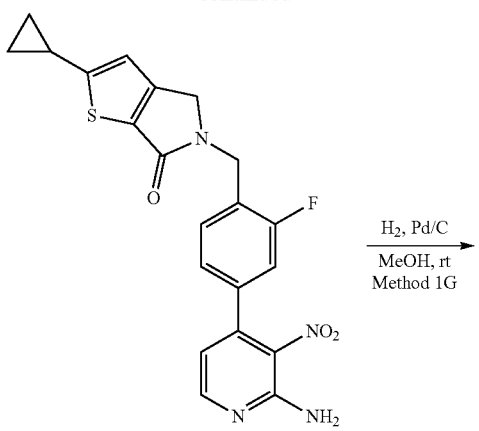

H₂, Pd/C
MeOH, rt
Method 1G

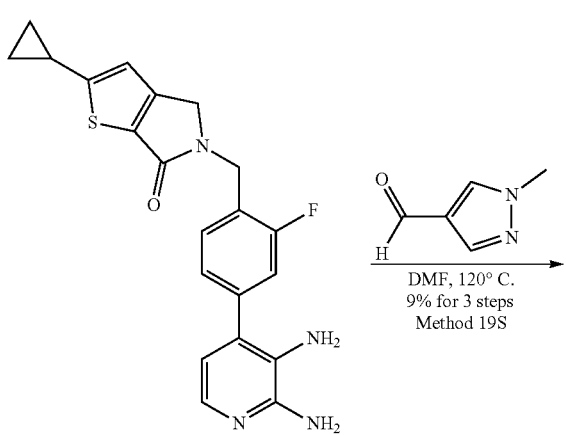

DMF, 120° C.
9% for 3 steps
Method 19S

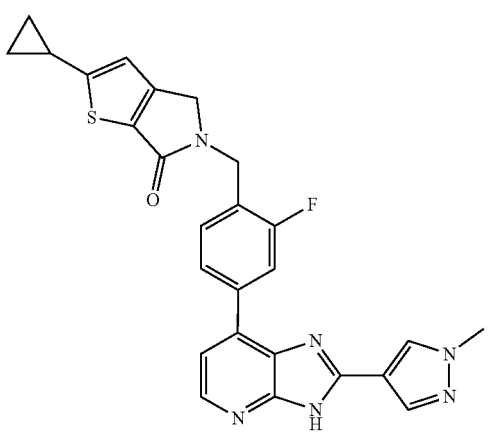 [SMILES: Cn1cc(-c2nc3c(-c4ccc(CN5Cc6cc(C7CC7)sc6C5=O)c(F)c4)ccnc3[nH]2)cn1]

304

Example 93. 2-Cyclopropyl-5-([2-fluoro-4-[2-(1-methyl-1H-pyrazol-4-yl)-3H-imidazo[4,5-b]pyridin-7-yl]phenyl] methyl)-4H,5H,6H-thieno[2,3-c]pyrrol-6-one (93)

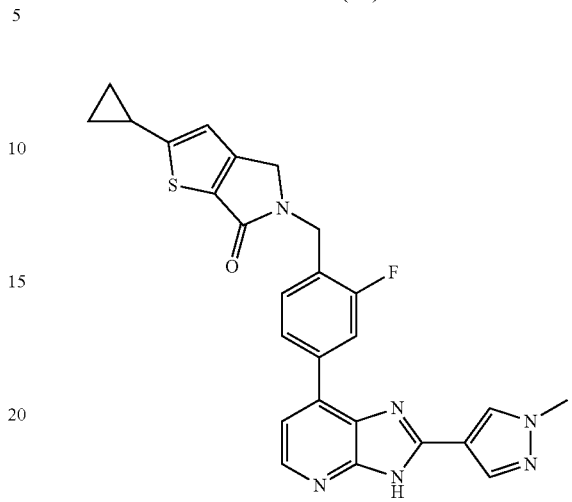

Methyl 3-(bromomethyl)thiophene-2-carboxylate

In a 250-mL round bottom flask purged and maintained with an inert atmosphere of nitrogen, methyl 3-methylthiophene-2-carboxylate (10 g, 64.02 mmol, 1.00 equiv) was dissolved in CCl₄ (120 mL), to which were added NBS (17.09 g, 96.03 mmol, 1.50 equiv) and AIBN (2.103 g, 12.81 mmol, 0.20 equiv) at room temperature. The resulting solution was then stirred for 16 h at 80° C. When the reaction was done, it was quenched by 50 mL water and the mixture was extracted with ethyl acetate (3×100 mL). The organic layers were combined, dried over sodium sulfate and concentrated under reduced pressure. The residue was purified in a silica gel column eluting with ethyl acetate in petroleum ether (5% to 30% gradient) to afford methyl 3-(bromomethyl)thiophene-2-carboxylate (12 g, 80%) as yellow solid. MS: m/z=235.1 [M+H]⁺.

Methyl 3-(aminomethyl)thiophene-2-carboxylate

In a 250-mL round bottom flask purged and maintained with an inert atmosphere of nitrogen, methyl 3-(bromomethyl)thiophene-2-carboxylate (7 g, 29.77 mmol, 1.00 equiv) was dissolved in the solution of NH₃ in methanol (7N, 100 mL) at room temperature. The resulting solution was then stirred for 2 h at room temperature. After the reaction was done, the reaction mixture was concentrated under reduced pressure to afford methyl 3-(aminomethyl)thiophene-2-carboxylate (3.2 g, 63%) as a yellow solid. MS: m/z=172.0 [M+H]⁺.

4H,5H,6H-thieno[2,3-c]pyrrol-6-one

In a 500-mL round bottom flask purged and maintained with an inert atmosphere of nitrogen, methyl 3-(aminomethyl)thiophene-2-carboxylate (2.2 g, 12.85 mmol, 1.0 equiv) was dissolved in methanol (300 mL), to which was added potassium carbonate (3.552 g, 25.70 mmol, 2.0 equiv) at room temperature. The resulting mixture was then stirred for 16 h at 80° C. After the reaction was done, the reaction mixture was concentrated under reduced pressure. The residue was diluted with 50 mL water and extracted with ethyl acetate (3×100 mL). The organic layers were combined, dried over sodium sulfate and concentrated under reduced pressure. The residue was purified in a silica gel column eluting with methanol in dichloromethane (5% to 10% gradient) to afford 4H,5H,6H-thieno[2,3-c]pyrrol-6-one (1.1 g, 62%) as white solid.

2-Bromo-4H,5H,6H-thieno[2,3-c]pyrrol-6-one

In a 100-mL round bottom flask purged and maintained with an inert atmosphere of nitrogen, 4H,5H,6H-thieno[2,3-c]pyrrol-6-one (1 g, 7.19 mmol, 1.00 equiv) was dissolved in a mixture of water (2 mL) and AcOH (10 mL), to which was added $Br_2$ (1.72 g, 10.78 mmol, 1.50 equiv) dropwise at room temperature. The resulting solution was stirred for 2 h at room temperature. After the reaction was done, the reaction mixture was extracted with ethyl acetate (3×10 mL). The organic layers were combined, dried over sodium sulfate and concentrated reduced pressure. The residue was purified in a silica gel column eluting with methanol in dichloromethane (5% to 10% gradient) to afford 2-bromo-4H,5H,6H-thieno[2,3-c]pyrrol-6-one 1.3 g (83%) as yellow solid. MS: m/z=218.0 [M+H]$^+$.

2-Cyclopropyl-4H,5H,6H-thieno[2,3-c]pyrrol-6-one

In a 30-mL sealed tube purged and maintained with an inert atmosphere of nitrogen, 2-bromo-4H,5H,6H-thieno[2,3-c]pyrrol-6-one (1.200 g, 5.50 mmol, 1.00 equiv), cyclopropylboronic acid (567 mg, 6.60 mmol, 1.20 equiv), Pd(dppf)Cl$_2$ (403 mg, 0.55 mmol, 0.10 equiv) and potassium carbonate (1.521 g, 11.01 mmol, 2.00 equiv) were mixed in ethylene glycol dimethyl ether (15 mL) at room temperature. The resulting mixture was stirred for 30 min at 80° C. After the reaction was done and the reaction mixture was cooled to room temperature, diluted with 60 mL ethyl acetate and washed with water (3×10 mL). The organic layer was dried over sodium sulfate and concentrated under reduced pressure. The residue was purified in a silica gel column eluting with methanol in dichloromethane (5% to 10% gradient) to afford 2-cyclopropyl-4H,5H,6H-thieno[2,3-c]pyrrol-6-one (950 mg, 95%) as yellow solid. MS: m/z=180.2 [M+H]$^+$.

5-[(4-Bromo-2-fluorophenyl)methyl]-2-cyclopropyl-4H,5H,6H-thieno[2,3-c]pyrrol-6-one At 0° C., in a 100-mL round-bottom flask purged and maintained with an inert atmosphere of nitrogen, 2-cyclopropyl-4H,5H,6H-thieno[2,3-c]pyrrol-6-one (1.000 g, 5.58 mmol, 1.00 equiv) was dissolved in tetrahydrofuran (20 mL), to which was added sodium hydride (60% in oil, 245 mg, 6.13 mmol, 1.10 equiv) slowly. The mixture was stirred at 0° C. for 15 min and then was added by 4-bromo-1-(bromomethyl)-2-fluorobenzene (1.644 g, 6.14 mmol, 1.10 equiv). The reaction mixture was allowed to warm up to room temperature and stirred for 16 h at room temperature. When the reaction was done, it was quenched by 20 mL water and the mixture was extracted with ethyl acetate (3×20 mL). The organic layers were combined, dried over sodium sulfate and concentrated under reduced pressure. The residue was purified in a silica gel column eluting with ethyl acetate in petroleum ether (5% to 50% gradient) to afford 5-[(4-bromo-2-fluorophenyl)methyl]-2-cyclopropyl-4H,5H,6H-thieno[2,3-c]pyrrol-6-one (800 mg, 39%) as yellow solid. MS: m/z=366.1 [M+H]$^+$.

2-Cyclopropyl-5-[[2-fluoro-4-(tetramethyl-1,3,2-dioxaborolan-2-yl)phenyl]methyl]-4H,5H,6H-thieno[2,3-c]pyrrol-6-one In a 100-mL round bottom flask purged and maintained with an inert atmosphere of nitrogen, 5-[(4-bromo-2-fluorophenyl)methyl]-2-cyclopropyl-4H,5H,6H-thieno[2,3-c]pyrrol-6-one (800 mg, 2.18 mmol, 1.00 equiv), 4,4,5,5-tetramethyl-2-(tetramethyl-1,3,2-dioxaborolan-2-yl)-1,3,2-dioxaborolane (832 mg, 3.28 mmol, 1.50 equiv), Pd(dppf)Cl$_2$ (159.8 mg, 0.22 mmol, 0.10 equiv) and potassium carbonate (603 mg, 4.37 mmol, 2.00 equiv) were mixed in dioxane (20 mL). The resulting mixture was then stirred for 16 h at 100° C. After the reaction was done and the reaction mixture was concentrated under reduced pressure and the residue was purified in a silica gel column eluting with ethyl acetate in petroleum ether (5% to 10% gradient) to afford 2-cyclopropyl-5-[[2-fluoro-4-(tetramethyl-1,3,2-dioxaborolan-2-yl)phenyl]methyl]-4H,5H,6H-thieno[2,3-c]pyrrol-6-one (700 mg, 78%) as a yellow solid.

2-cyclopropyl-5-([2-fluoro-4-[2-(1-methyl-1H-pyrazol-4-yl)-3H-imidazo[4,5-b]pyridin-7-yl]phenyl]methyl)-4H,5H,6H-thieno[2,3-c]pyrrol-6-one 2-cyclopropyl-5-([2-fluoro-4-[2-(1-methyl-1H-pyrazol-4-yl)-3H-imidazo[4,5-b]pyridin-7-yl]phenyl]methyl)-4H,5H,6H-thieno[2,3-c]pyrrol-6-one 20 mg (9% for 3 steps) was prepared from 2-cyclopropyl-5-[[2-fluoro-4-(tetramethyl-1,3,2-dioxaborolan-2-yl)phenyl]methyl]-4H,5H,6H-thieno[2,3-c]pyrrol-6-one, 4-chloro-3-nitropyridin-2-amine, 1-methyl-1H-pyrazole-4-carbaldehyde using Method 2J, 1G and 19S. HPLC: 97.7% purity. MS: m/z=485.1 [M+H]$^+$. $^1$H-NMR (400 MHz, DMSO-d$_6$): δ 13.41 (br s, 1H), 8.44 (s, 1H), 8.31-8.28 (m, 2H), 8.18-8.14 (m, 2H), 7.53-7.41 (m, 2H), 6.93 (s, 1H), 4.78 (s, 2H), 4.35 (s, 2H), 3.94 (s, 3H), 2.28-2.21 (m, 1H), 1.11-1.06 (m, 2H), 0.78-0.74 (m, 2H).

Scheme 45

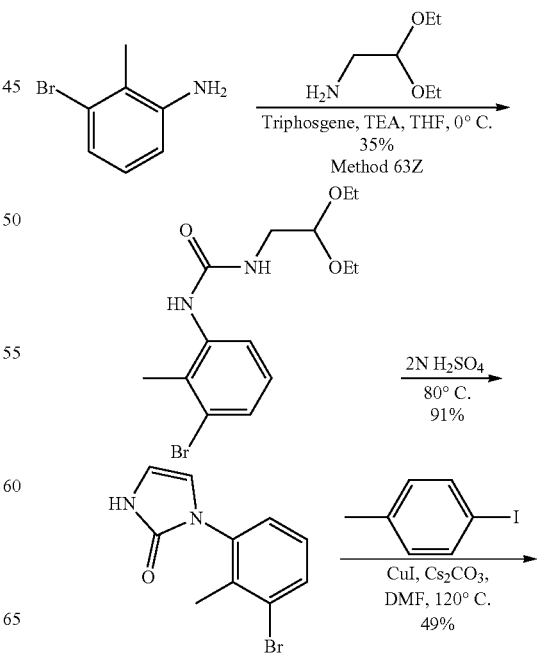

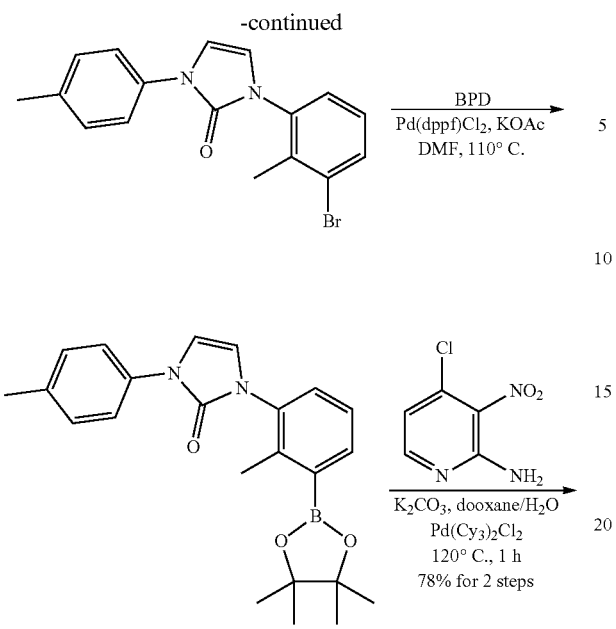

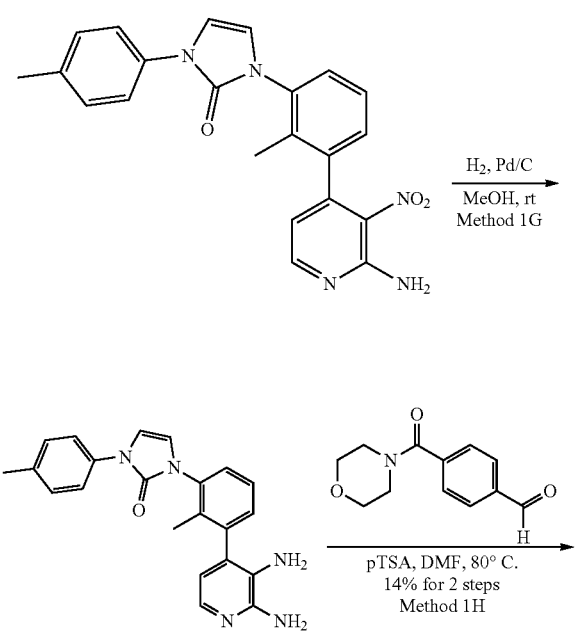

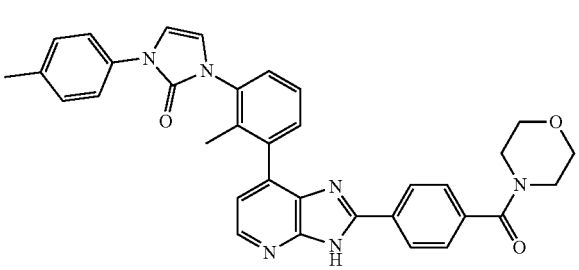

Example 95. 1-[2-Methyl-3-(2-[4-[(morpholin-4-yl)carbonyl]phenyl]-3H-imidazo[4,5-b]pyridin-7-yl)phenyl]-3-(4-methylphenyl)-2,3-dihydro-1H-imidazol-2-one (95)

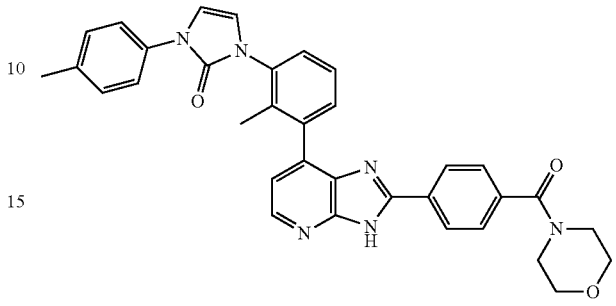

Method 63Z: 1-(3-Bromo-2-methylphenyl)-3-(2,2-diethoxyethyl)urea

In a 100-mL round bottom flask purged and maintained with an inert atmosphere of nitrogen, 3-bromo-2-methylaniline (2.00 g, 10.75 mmol, 1.00 equiv) and TEA (2.24 ml 3.00 equiv) were dissolved in tetrahydrofuran (25 ml), to which were added triphosgene (1.59 g, 5.36 mmol, 0.50 equiv) slowly at 0° C. The resulting solution was stirred for 3 h at 0° C., and then was added by 2,2-diethoxyethan-1-amine (1.72 g, 12.91 mmol, 1.20 equiv) and TEA (2.24 ml 3.00 equiv) in sequence. The reaction mixture was then stirred for another 18 h at room temperature. When the reaction was done, it was quenched by 10 mL water and the mixture was extracted with ethyl acetate (3×10 mL). The organic layers were combined, dried over sodium sulfate and concentrated under reduced pressure. The residue was purified in a silica gel column eluting with acetone in petroleum ether (10% to 50% gradient) to afford 1-(3-bromo-2-methylphenyl)-3-(2,2-diethoxyethyl)urea (1.3 g, 35%) as white solid. MS: m/z=345.2 [M+H]$^+$.

1-(3-Bromo-2-methylphenyl)-2,3-dihydro-1H-imidazol-2-one

In a 100-mL round bottom flask purged and maintained with an inert atmosphere of nitrogen, 1-(3-bromo-2-methylphenyl)-3-(2,2-diethoxyethyl)urea (1.20 g, 3.48 mmol, 1.00 equiv) was dissolved in sulfuric acid solution (2 N, 10 mL). The resulting solution was then stirred for 6 h at 80° C. After the reaction was done, the reaction mixture as cooled to room temperature and the pH value of the mixture was adjusted to 9 using sodium bicarbonate. The resulting mixture was extracted with ethyl acetate (3×10 mL) and the organic layers were combined, dried over sodium sulfate and concentrated under reduced pressure to afford 1-(3-bromo-2-methylphenyl)-2,3-dihydro-1H-imidazol-2-one (800 mg, 91%) as yellow solid. MS: m/z=253.0 [M+H]$^+$.

1-(3-Bromo-2-methylphenyl)-3-(4-methylphenyl)-2,3-dihydro-1H-imidazol-2-one

In a 25-mL round bottom flask purged and maintained with an inert atmosphere of nitrogen, 1-(3-bromo-2-methylphenyl)-2,3-dihydro-1H-imidazol-2-one (300 mg, 1.19 mmol, 1.00 equiv), 1-iodo-4-methylbenzene (439.4 mg, 2.02 mmol, 1.70 equiv), (2-aminoethyl) dimethylamine (62.7 mg, 0.71 mmol, 0.60 equiv), Cs$_2$CO$_3$ (656.5 mg, 2.02 mmol, 1.70 equiv) and CuI (56.4 mg, 0.30 mmol, 0.25 equiv) were mixed in dioxane (5 ml) at room temperature. The resulting mixture was then stirred for 18 h at 120° C. After the reaction was done, the reaction mixture was diluted with 10 mL water and extracted with ethyl acetate (3×20 ml). The organic layers were combined and dried over sodium sulfate and concentrated under reduced pressure. The residue was purified in a silica gel column eluting with ethyl acetate in petroleum ether (1% to 20% gradient) to afford 1-(3-bromo-2-methylphenyl)-3-(4-methylphenyl)-2,3-dihydro-1H-imidazol-2-one (200 mg, 49%) as yellow oil. MS: m/z=343.2[M+H]$^+$.

1-[2-Methyl-3-(tetramethyl-1,3,2-dioxaborolan-2-yl)phenyl]-3-(4-methylphenyl)-2,3-dihydro-1H-imidazol-2-one In a 10-mL round bottom flask purged and maintained with an inert atmosphere of nitrogen, 1-(3-bromo-2-methylphenyl)-3-(4-methylphenyl)-2,3-dihydro-1H-imidazol-2-one (200.0 mg, 0.58 mmol, 1.00 equiv) 4,4,5,5-tetramethyl-2-(tetramethyl-1,3,2-dioxaborolan-2-yl)-1,3,2-dioxaborolane (222.0 mg, 0.87 mmol, 1.50 equiv), Pd(dppf)Cl$_2$ (42.6 mg, 0.06 mmol, 0.10 equiv) and KOAc (379.7 mg, 1.17 mmol, 2.00 equiv) were mixed in dioxane (5 ml) at room temperature. The resulting mixture was then stirred for 18 h at 110° C. After the reaction was done, the reaction mixture was diluted with 5 mL water and extracted with ethyl acetate (3×20 ml). The organic layers were combined, dried over sodium sulfate and concentrated under reduced pressure to afford 1-[2-methyl-3-(tetramethyl-1,3,2-dioxaborolan-2-yl)phenyl]-3-(4-methylphenyl)-2,3-dihydro-1H-imidazol-2-one (250 mg, crude) as brown oil.

1-[3-(2-Amino-3-nitropyridin-4-yl)-2-methylphenyl]-3-(4-methylphenyl)-2,3-dihydro-1H-imidazol-2-one In a 25-mL round bottom flask purged and maintained with an inert atmosphere of nitrogen, 1-[2-methyl-3-(tetramethyl-1,3,2-dioxaborolan-2-yl)phenyl]-3-(4-methylphenyl)-2,3-dihydro-1H-imidazol-2-one (100.0 mg, 0.26 mmol, 1.00 equiv), 4-chloro-3-nitropyridin-2-amine (66.7 mg, 0.38 mmol, 1.50 equiv), Pd(PCy$_3$)$_2$Cl$_2$ (35 mg, 0.05 mmol, 0.18 equiv) and Cs$_2$CO$_3$ (167.0 mg, 0.51 mmol, 2.00 equiv) were mixed in dioxane (5 ml) at room temperature. The resulting mixture was then stirred for 18 h at 120° C. After the reaction was done, the reaction mixture was diluted with 5 mL water and extracted with ethyl acetate (3×10 ml). The organic layers were combined, dried over sodium sulfate and concentrated under reduced pressure. The residue was purified in a silica gel column eluting with ethyl acetate in petroleum ether (1% to 20% gradient) to afford 1-[3-(2-amino-3-nitropyridin-4-yl)-2-methylphenyl]-3-(4-methylphenyl)-2,3-dihydro-1H-imidazol-2-one (80 mg, 78% for 2 steps) as yellow solid. MS: m/z=402.2[M+H]$^+$.

1-[2-Methyl-3-(2-[4-[(morpholin-4-yl)carbonyl]phenyl]-3H-imidazo[4,5-b]pyridin-7-yl)phenyl]-3-(4-methylphenyl)-2,3-dihydro-1H-imidazol-2-one 1-[2-methyl-3-(2-[4-[(morpholin-4-yl)carbonyl]phenyl]-3H-imidazo[4,5-b]pyridin-7-yl)phenyl]-3-(4-methylphenyl)-2,3-dihydro-1H-imidazol-2-one 30 mg (14% for 2 steps) was prepared from 1-[3-(2-amino-3-nitropyridin-4-yl)-2-methylphenyl]-3-(4-methylphenyl)-2,3-dihydro-1H-imidazol-2-one, 4-[(morpholin-4-yl)carbonyl] benzaldehyde using Method 1G and 1H. HPLC: 98.2% purity. MS: m/z=571.1 [M+H]$^+$. $^1$H-NMR (400 MHz, CD$_3$OD): δ 8.53 (s, 1H), 8.39-8.33 (m, 2H), 7.63-7.56 (m, 7H), 7.34-7.28 (m, 3H), 7.08 (s, 1H), 6.88 (s, 1H), 3.79-3.68 (m, 6H), 3.50-3.45 (m, 2H), 2.41 (s, 3H), 2.10 (s, 3H).

Scheme 46

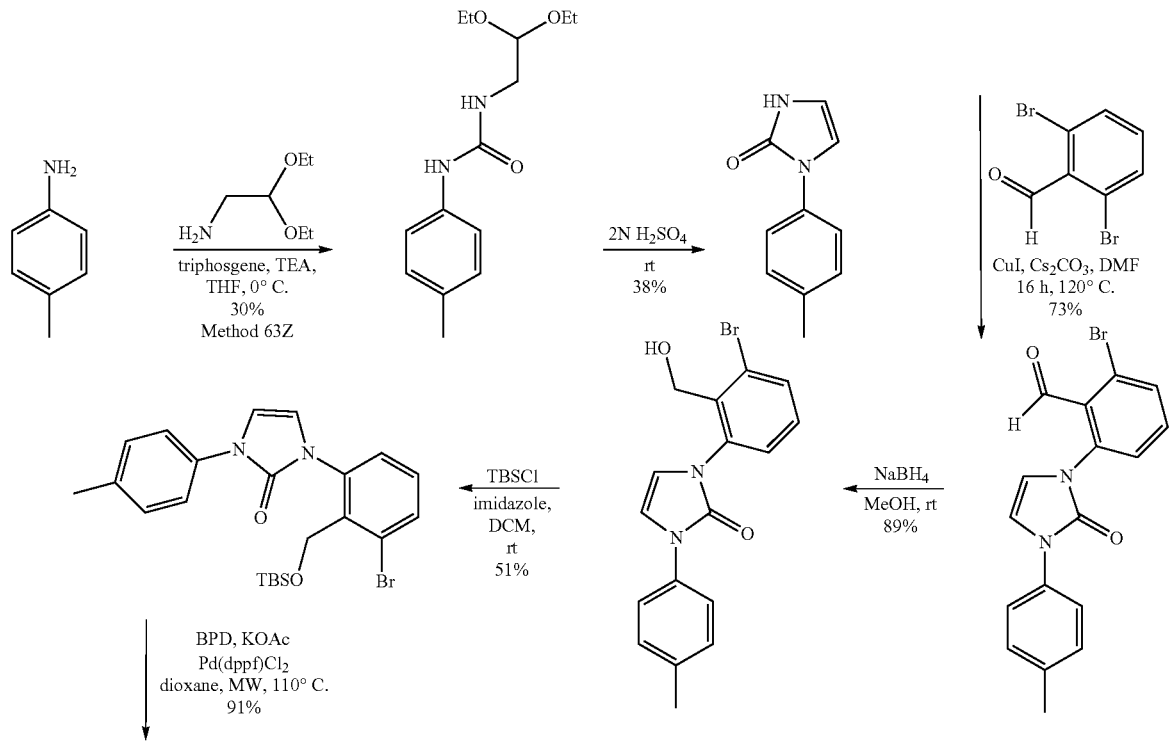

311
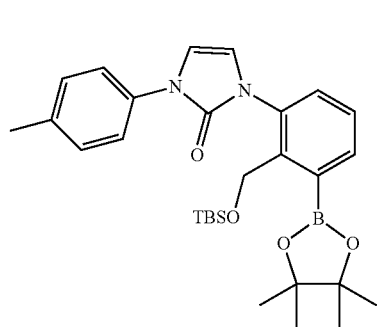
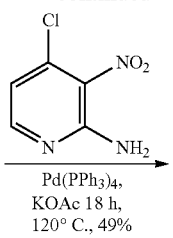
Pd(PPh$_3$)$_4$,
KOAc 18 h,
120° C., 49%
312
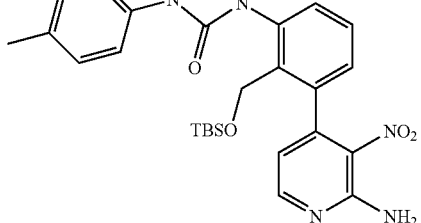
H$_2$, Pd/C
MeOH, rt
95%
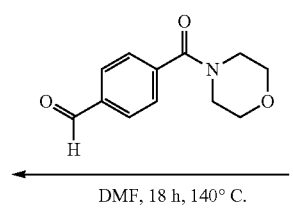
DMF, 18 h, 140° C.
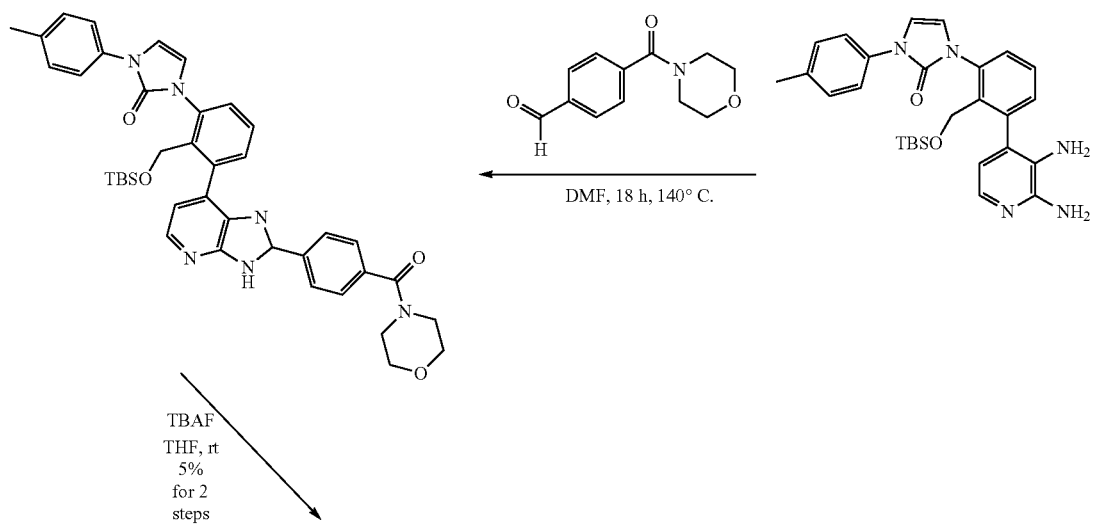
TBAF
THF, rt
5%
for 2
steps
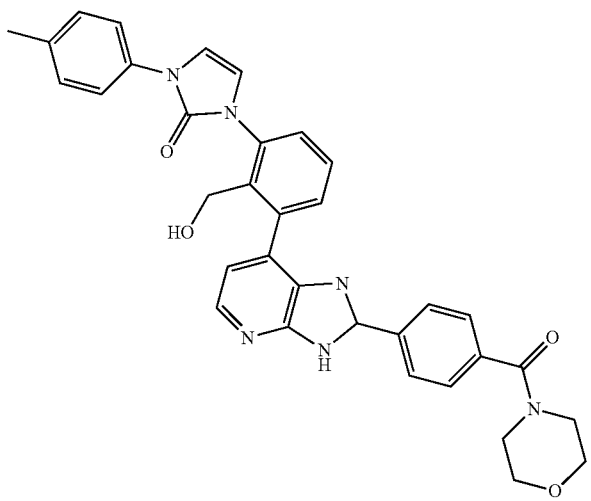

Example 96. 1-[2-(Hydroxymethyl)-3-(2-[4-[(morpholin-4-yl)carbonyl]phenyl]-3H-imidazo[4,5-b]pyridin-7-yl) phenyl]-3-(4-methylphenyl)-2,3-dihydro-1H-imidazol-2-one (96)

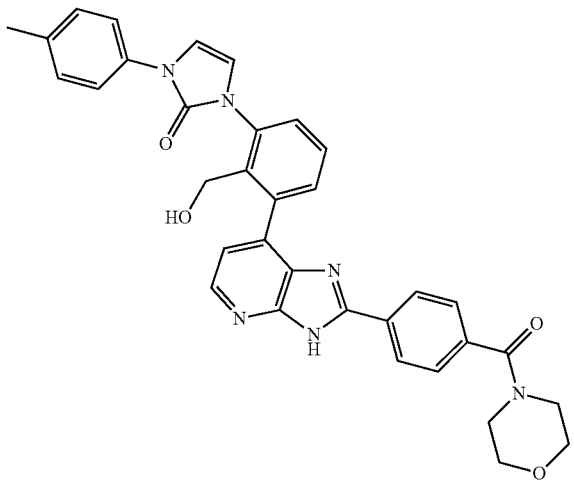 [SMILES: Cc1ccc(-n2ccn(-c3cccc(-c4ccnc5[nH]c(-c6ccc(C(=O)N7CCOCC7)cc6)nc45)c3CO)c2=O)cc1]

3-(2,2-Diethoxyethyl)-1-(4-methylphenyl)urea 3-(2,2-diethoxyethyl)-1-(4-methylphenyl)urea 1.5 g (30%) was prepared from 4-methylaniline, 2,2-diethoxyethan-1l-amine using Method 63Z. MS: m/z=267.2 [M+H]$^+$.

1-(4-Methylphenyl)-2,3-dihydro-1H-imidazol-2-one

In a 100-mL round bottom flask purged and maintained with an inert atmosphere of nitrogen, 3-(2,2-diethoxyethyl)-1-(4-methylphenyl)urea (800 mg, 3.00 mmol, 1.00 equiv) was dissolved in sulfuric acid solution (0.5 N, 10 mL) at room temperature. The resulting solution was then stirred for 6 h at room temperature. After the reaction was done, the reaction mixture as cooled to room temperature and the pH value of the mixture was adjusted to 9 with sodium bicarbonate. The resulting mixture was extracted with ethyl acetate (3×10 mL) and the organic layers were combined, dried over sodium sulfate and concentrated under reduced pressure to afford 1-(4-methylphenyl)-2,3-dihydro-1H-imidazol-2-one 200 mg (38%) as brown oil. MS: m/z=174.2 [M+H]$^+$.

2-Bromo-6-[3-(4-methylphenyl)-2-oxo-2,3-dihydro-1H-imidazol-1-yl]benzaldehyde

In a 25-mL round bottom flask purged and maintained with an inert atmosphere of nitrogen, 1-(4-methylphenyl)-2,3-dihydro-1H-imidazol-2-one (200 mg, 1.15 mmol, 1.00 equiv), (2-aminoethyl) dimethylamine (60.7 mg, 0.69 mmol, 0.60 equiv), 2,6-dibromobenzaldehyde (515.1 mg, 1.95 mmol, 1.70 equiv), Cs$_2$CO$_3$ (635.9 mg, 1.95 mmol, 1.70 equiv) and CuI (54.6 mg, 0.29 mmol, 0.25 equiv) were mixed in dioxane (5 mL). The resulting mixture was then stirred for 16 h at 120° C. After the reaction was done, the reaction mixture was cooled to room temperature, diluted with 10 mL water and extracted with dichloromethane (3×10 mL). The organic layers were combined, dried over sodium sulfate and concentrated under reduced pressure. The residue was purified in a silica gel column eluting with methanol in dichloromethane (1% to 20% gradient) to afford 2-bromo-6-[3-(4-methylphenyl)-2-oxo-2,3-dihydro-1H-imidazol-1-yl]benzaldehyde (300 mg, 73%) as yellow solid. MS: m/z=357.0 [M+H]$^+$.

1-[3-Bromo-2-(hydroxy methyl)phenyl]-3-(4-methylphenyl)-2,3-dihydro-1H-imidazol-2-one In a 50-mL round bottom flask, 2-bromo-6-[3-(4-methylphenyl)-2-oxo-2,3-dihydro-1H-imidazol-1-yl]benzaldehyde (200 mg, 0.56 mmol, 1.00 equiv) was dissolved in methanol (20 mL), to which was added NaBH$_4$ (40 mg, 1.00 mmol, 1.79 equiv) slowly at 0° C. The resulting mixture was then stirred for 16 h at room temperature. When the reaction was done, it was quenched by 10 mL water and the mixture was extracted with dichloromethane (3×10 mL). The organic layers were combined, dried over sodium sulfate and concentrated under reduced pressure to afford 1-[3-bromo-2-(hydroxymethyl)phenyl]-3-(4-methylphenyl)-2,3-dihydro-1H-imidazol-2-one (180 mg, 89%) as white solid. MS: m/z=359.0 [M+H]$^+$.

1-(3-Bromo-2-[[(tert-butyldimethylsilyl)oxy]methyl]phenyl)-3-(4-methylphenyl)-2,3-dihydro-1H-imidazol-2-one In a 50-mL round bottom flask, 1H-imidazole (113.7 mg, 1.67 mmol, 2.00 equiv) and 1-[3-bromo-2-(hydroxymethyl)phenyl]-3-(4-methylphenyl)-2,3-dihydro-1H-imidazol-2-one (300 mg, 0.84 mmol, 1.00 equiv) were dissolved in dichloromethane (10 ml), to which was added TBSCl (188.8 mg, 1.25 mmol, 1.50 equiv) slowly at room temperature. The resulting solution was then stirred for 18 h at room temperature. After the reaction was done, the reaction mixture was diluted with 10 mL water and extracted with ethyl acetate (3×10 ml). The organic layers were combined, dried over sodium sulfate and concentrated under reduced pressure. The residue was purified in a silica gel column eluting with ethyl acetate in petroleum ether (1% to 20% gradient) to afford 1-(3-bromo-2-[[(tert-butyldimethylsilyl)oxy]methyl]phenyl)-3-(4-methylphenyl)-2,3-dihydro-1H-imidazol-2-one (200 mg, 51%) as white solid. MS: m/z=472.2 [M+H]$^+$.

1-(2-[[(tert-Butyldimethylsilyl)oxy]methyl]3-tetramethyl-1,3,2-dioxaborolan-2-yl)phenyl)-3-(4-methylphenyl)-2,3-dihydro-1H-imidazol-2-one In a 25-mL round bottom flask purged and maintained with an inert atmosphere of nitrogen, 1-(3-bromo-2-[[(tert-butyldimethylsilyl)oxy]methyl]phenyl)-3-(4-methylphenyl)-2,3-dihydro-1H-imidazol-2-one (200 mg, 0.42 mmol, 1.00 equiv), 4,4,5,5-tetramethyl-2-(tetramethyl-1,3,2-dioxaborolan-2-yl)-1,3,2-dioxaborolane (160.9 mg, 0.63 mmol, 1.50 equiv), Pd(dppf)Cl$_2$ (30.9 mg, 0.04 mmol, 0.10 equiv) and KOAc (82.91 mg, 0.84 mmol, 2.00 equiv) were mixed in dioxane (10 ml) at room temperature. The resulting mixture was then irradiated with microwave for 1 h at 100° C. After the reaction was done, the reaction mixture was cooled to room temperature, diluted with 10 mL water and extracted with ethyl acetate (3×10 ml). The organic layers were combined, dried over sodium sulfate and concentrated under reduced pressure. The residue was purified in a silica gel column eluting with ethyl acetate in petroleum ether (1% to 20% gradient) to afford 1-(2-[[(tert-butyldimethylsilyl)oxy]methyl]-3-(tetramethyl-1,3,2-dioxaborolan-2-yl)phenyl)-3-(4-methylphenyl)-2,3-dihydro-1H-imidazol-2-one (200 mg, 91%) as brown solid.

1-[3-(2-Amino-3-nitropyridin-4-yl)-2-[[(tert-butyldimethylsilyl)oxy]methyl]phenyl]-3-(4-methylphenyl)-2,3-dihydro-1H-imidazol-2-one A 10-mL round bottom flask purged and maintained with an inert atmosphere of nitrogen, 1-(2-[[(tert-butyldimethylsilyl)oxy]methyl]-3-(tetramethyl-1,3,2-dioxaborolan-2-yl)phenyl)-3-(4-methylphenyl)-2,3-dihydro-1H-imidazol-2-one (100 mg, 0.19 mmol, 1.00 equiv), 4-chloro-3-nitropyridin-2-amine (50 mg, 0.29 mmol, 1.50 equiv), Pd(PPh$_3$)$_4$ (22 mg, 0.02 mmol, 0.10 equiv) and KOAc (37.7 mg, 0.38 mmol, 2.00 equiv) were mixed in dioxane (5 ml) at room temperature. The resulting mixture was then stirred for 18 h at 120° C. After the reaction was done, the reaction mixture was cooled to room temperature, diluted with 10 mL water and extracted with ethyl acetate (3×10 ml). The organic layers were combined, dried over sodium sulfate and concentrated under reduced pressure. The residue was purified in a silica gel column eluting with methanol in dichloromethane (1% to 20% gradient) to afford 1-[3-(2-amino-3-nitropyridin-4-yl)-2-[[(tert-butyldimethylsilyl)oxy]methyl]phenyl]-3-(4-methyl phenyl)-2,3-dihydro-1H-imidazol-2-one (50 mg, 49%) as yellow solid. MS: m/z=532.4 [M+H]$^+$.

1-(2-[[(tert-Butyldimethylsilyl)oxy]methyl]-3-(2,3-diaminopyridin-4-yl)phenyl)-3-(4-methylphenyl)-2,3-dihydro-1H-imidazol-2-one 1-(2-[[(tert-butyldimethylsilyl)oxy]methyl]-3-(2,3-diaminopyridin-4-yl)phenyl)-3-(4-methylphenyl)-2,3-dihydro-1H-imidazol-2-one 90 mg (95%) was prepared from 1-[3-(2-amino-3-nitropyridin-4-yl)-2-[[(tert-butyldimethylsilyl)oxy]methyl]phenyl]-3-(4-methylphenyl)-2,3-dihydro-1H-imidazol-2-one using method 1G.

1-[2-Methyl-3-(2-[4-[(morpholin-4-yl)carbonyl]phenyl]-3H-imidazo[4,5-b]pyridin-7-yl)phenyl]-3-(4-methylphenyl)-2,3-dihydro-1H-imidazol-2-one In a 25-mL round bottom flask purged and maintained with an inert atmosphere of nitrogen, 1-(2-[[(tert-butyldimethylsilyl)oxy]methyl]-3-(2,3-diaminopyridin-4-yl)phenyl)-3-(4-methylphenyl)-2,3-dihydro-1H-imidazol-2-one (90 mg, 0.18 mmol, 1.00 equiv) was dissolved in N,N-dimethylformamide (20 mL), to which was added 4-[(morpholin-4-yl)carbonyl]benzaldehyde (87 mg, 0.40 mmol, 2.21 equiv) at room temperature. The resulting solution was then stirred for 18 h at 140° C. After the reaction was done, the reaction mixture was cooled to room temperature, diluted with 10 mL water and extracted with ethyl acetate (3×10 ml). The organic layers were combined, dried over sodium sulfate and concentrated under reduced pressure. The residue was purified in a silica gel column eluting with methanol in dichloromethane (1% to 20% gradient) to afford 1-(2-[[(tert-butyldimethylsilyl)oxy]methyl]-3-(2-[4-[(morpholin-4-yl)carbonyl]phenyl]-3H-imidazo[4,5-b]pyridin-7-yl) phenyl)-3-(4-methylphenyl)-2,3-dihydro-1H-imidazol-2-one (150 mg, crude) as yellow solid. MS: m/z=701.4 [M+H]$^+$.

1-[2-(Hydroxymethyl)-3-(2-[4-[(morpholin-4-yl)carbonyl]phenyl]-3H-imidazo[4,5-b]pyridin-7-yl)phenyl]-3-(4-methylphenyl)-2,3-dihydro-1H-imidazol-2-one In a 25-mL round bottom flask purged and maintained with an inert atmosphere of nitrogen, 1-(2-[[(tert-butyldimethylsilyl)oxy]methyl]-3-(2-[4-[(morpholin-4-yl)carbonyl]phenyl]-3H-imidazo[4,5-b]pyridin-7-yl)phenyl)-3-(4-methylphenyl)-2,3-dihydro-1H-imidazol-2-one (80 mg, 0.11 mmol, 1.00 equiv) was dissolved in tetrahydrofuran (5 ml), to which was added TBAF (59.69 mg, 0.23 mmol, 2.00 equiv) at room temperature. The resulting solution was then stirred for 18 h at room temperature. After the reaction was done, the reaction mixture was concentrated. The residue was diluted with 10 mL water and extracted with ethyl acetate (3×10 ml). The organic layers were combined, dried over sodium sulfate and concentrated under reduced pressure. The residue was purified in a silica gel column eluting with methanol in dichloromethane (1% to 15% gradient) to afford 1-[2-(hydroxymethyl)-3-(2-[4-[(morpholin-4-yl)carbonyl]phenyl]-3H-imidazo[4,5-b]pyridin-7-yl)phenyl]-3-(4-methylphenyl)-2,3-dihydro-1H-imidazol-2-one (10 mg, 5% for 2 steps) as white solid. HPLC: 95.1% purity. MS: m/z=587.2 [M+H]$^+$. $^1$H-NMR (300 MHz, CD$_3$OD): δ 8.45 (d, J=5.1 Hz, 1H), 8.24-8.22 (m, 2H), 7.67-7.51 (m, 7H), 7.33-7.26 (m, 3H), 7.02-6.96 (m, 2H), 4.42 (s, 2H), 3.83-3.57 (m, 6H), 3.56-3.35 (m, 2H), 2.35 (s, 3H).

Example 97: 5-tert-Butyl-[1,3,4]oxadiazole-2-carboxylic acid (1-{4-[2-(1-methyl-1H-pyrazol-4-yl)-3H-imidazo[4,5-b]pyridin-7-yl]-phenyl}-cyclopropyl)-amide (97)

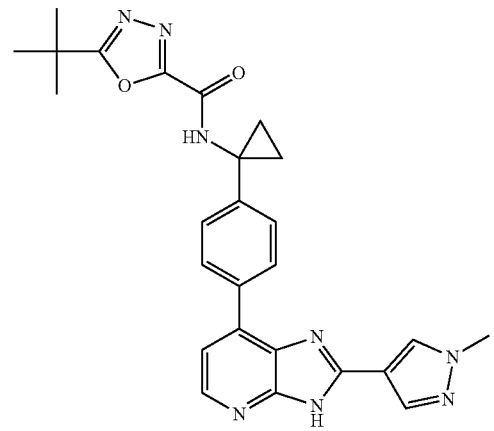 [SMILES: Cn1cc(-c2nc3c(-c4ccc(C5(NC(=O)c6nnc(C(C)(C)C)o6)CC5)cc4)ccnc3[nH]2)cn1]

5-tert-Butyl-[1,3,4]oxadiazole-2-carboxylic acid {1-[4-(4,4,5,5-tetramethyl-[1,3,2]dioxaborolan-2-yl)-phenyl]-cyclopropyl}-amide To a 20 mL vial with stirbar was added 1-(4-(4,4,5,5-tetramethyl-1,3,2-dioxaborolan-2-yl)phenyl)cyclopropanamine (150.00 mg: 0.58 mmol; 1.00 eq.), 5-tert-butyl-1,3,4-oxadiazole-2-carboxylic acid (98.49 mg; 0.58 mmol; 1.00 eq.), propylphosphonic anhydride (50% in DMF) (0.43 ml; 0.72 mmol; 1.25 eq.), and DIPEA (0.29 ml; 1.74 mmol; 3.00 eq.) in DCM (5.00 ml; 78.00 mmol; 134.76 eq.). Reaction stirred at RT overnight. To the reaction mixture was added 10 mL DCM and the reaction mixture was washed with 20 mL 2N aq HCl, 20 mL 2N aq NaOH, and 20 mL brine. The organic phase were dried (Na$_2$SO$_4$), concentrated, and purified by flash chromatography (KP-sil column, 25 g; 5-50% EtOAc/hexanes 15 CV). Concentrated product fractions and dried to afford 30 mg (13%) of the title compound as a white solid. HPLC: 82% purity. MS: 412 [M+H]$^+$

5-tert-Butyl-[1,3,4]oxadiazole-2-carboxylic acid (1-[4-[2-(1-methyl-1H-pyrazol-4-yl)-3H-imidazo[4,5-b]pyridin-7-yl]-phenyl]-cyclopropyl)-amide To a 10 mL reaction tube with a stir bar was added 7-bromo-2-(1-methyl-1H-pyrazol-4-yl)-3H-imidazo[4,5-b]pyridine (20.00 mg; 0.07 mmol; 1.00 eq.), 5-tert-Butyl-[1,3,4]oxadiazole-2-carboxylic acid (1-[4-(4,4,5,5-tetramethyl-[1,3,2]dioxaborolan-2-yl)-phenyl]-cyclopropyl-amide (30.91 mg; 0.08 mmol; 1.10 eq.), and 1,1'-bis(diphenylphosphino)ferrocene-palladium(ii)dichloride dichloromethane complex (5.58 mg; 0.01 mmol; 0.10 eq.). The tube was sealed and flushed with argon. To the reaction mixture was added 1M potassium phosphate, dibasic (0.14 ml; 0.14 mmol; 2.00 eq.), 1M sodium acetate (0.14 ml; 0.14 mmol; 2.00 eq.), and ACN (1.00 ml; 19.15 mmol; 280.24 eq.) via syringe. The reaction tube was degassed with argon and heated to 110° C. for 2 h. The reaction mixture was allowed to cool to RT, filtered through celite, and concentrated under reduced pressure. The residue was purified by flash chromatography (10 g KP-sil column; 2-10% MeOH/CH$_2$Cl$_2$ 15 CV). Concentrated product containing fractions under reduced pressure and dried to afford 16 mg (49%) of the title compound as a beige solid. HPLC: 94% purity. MS: 483 [M+H]$^+$. $^1$H NMR (500 MHz, DMSO-d$_6$) δ 13.31 (s, 1H), 10.08 (s, 1H), 8.41 (s, 1H), 8.28-8.20 (m, 3H), 8.11 (s, 1H), 7.43 (d, J=5.1 Hz, 1H), 7.41-7.35 (m, 2H), 3.93 (s, 3H), 1.41 (s, 9H), 1.38 (s, 4H).

Example 98: 3-tert-Butyl-[1,2,4]oxadiazole-5-carboxylic acid (1-{4-[2-(1-methyl-1H-pyrazol-4-yl)-3H-imidazo[4,5-b]pyridin-7-yl]-phenyl}-cyclopropyl)-amide (98)

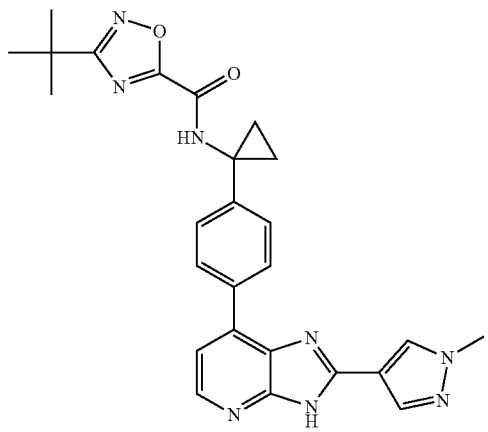 [SMILES: Cn1cc(-c2nc3c(-c4ccc(C5(NC(=O)c6nc(C(C)(C)C)no6)CC5)cc4)ccnc3[nH]2)cn1]

3-tert-Butyl-[1,2,4]oxadiazole-5-carboxylic acid {1-[4-(4,4,5,5-tetramethyl-[1,3,2]dioxaborolan-2-yl)-phenyl]-cyclopropyl}-amide Prepared via method analogous to compound 97 using 1-(4-(4,4,5,5-tetramethyl-1,3,2-dioxaborolan-2-yl)phenyl)cyclopropanamine (150.00 mg; 0.58 mmol; 1.00 eq.), 3-tert-butyl-1,2,4-oxadiazole-5-carboxylic acid (98.49 mg; 0.58 mmol; 1.00 eq.), propylphosphonic anhydride (0.43 ml; 0.72 mmol; 1.25 eq.), and DIPEA (0.29 ml; 1.74 mmol; 3.00 eq.) in DCM (5.00 ml; 78.00 mmol; 134.76 eq.) to afford 108 mg (45%) of the title compound as a white solid. HPLC: 84% purity. MS: 412 [M+H]$^+$.

3-tert-Butyl-[1,2,4]oxadiazole-5-carboxylic acid (1-{4-[2-(1-methyl-1H-pyrazol-4-yl)-3H-imidazo[4,5-b]pyridin-7-yl]-phenyl}-cyclopropyl)-amide Prepared via method analogous to compound 97 using 7-Bromo-2-(1-methyl-1H-pyrazol-4-yl)-3H-imidazo[4,5-b]pyridine (40.00 mg; 0.14 mmol; 1.00 eq.), 3-tert-Butyl-[1,2,4]oxadiazole-5-carboxylic acid {1-[4-(4,4,5,5-tetramethyl-[1,3,2]dioxaborolan-2-yl)-phenyl]-cyclopropyl}-amide (67.44 mg; 0.16 mmol; 1.20 eq.), 1,1'-bis(diphenylphosphino)ferrocene-palladium(ii)dichloride dichloromethane complex (11.16 mg; 0.01 mmol; 0.10 eq.), 1M potassium phosphate, dibasic (0.27 ml; 0.27 mmol; 2.00 eq.), 1M sodium acetate (0.27 ml; 0.27 mmol; 2.00 eq.), and ACN (2.00 ml; 38.29 mmol; 280.24 eq.) to afford 35 mg (53%) of the title compound as a beige solid. HPLC: 94% purity. MS: 483 [M+H]$^+$. $^1$H NMR (500 MHz, DMSO-d$_6$) δ 13.31 (s, 1H), 10.14 (s, 1H), 8.41 (s, 1H), 8.28-8.20 (m, 3H), 8.12 (s, 1H), 7.44 (d, J=5.1 Hz, 1H), 7.41-7.36 (m, 2H), 3.94 (s, 3H), 1.41-1.37 (m, 13H).

Example 99: 6-tert-Butyl-8-fluoro-2-{2-fluoro-4-[2-(1-methyl-1H-pyrazol-4-yl)-3H-imidazo[4,5-b]pyridin-7-yl]-benzyl}-2H-phthalazin-1-one (99)

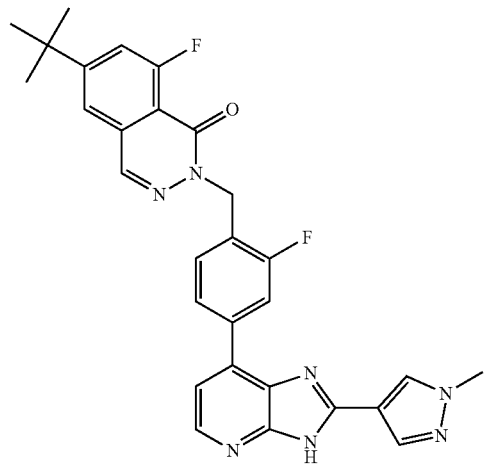 [SMILES: Cn1cc(-c2nc3c(-c4ccc(Cn5ncc6cc(C(C)(C)C)cc(F)c6c5=O)c(F)c4)ccnc3[nH]2)cn1]

2-(4-Bromo-2-fluoro-benzyl)-6-tert-butyl-8-fluoro-2H-phthalazin-1-one

To a 20 mL reaction vial with stirbar was added 6-(tert-butyl)-8-fluorophthalazin-1(2h)-one (200.00 mg; 0.91 mmol; 1.00 eq.), 4-bromo-2-fluorobenzyl bromide (267.63 mg; 1.00 mmol; 1.10 eq.), and cesium carbonate (591.75 mg; 1.82 mmol; 2.00 eq.) in ACN (6.00 ml; 114.88 mmol; 126.50 eq.). The reaction vial was sealed and heated to 80° C. overnight. Concentrated and purified by flash chromatography (KP-sil column, 10 g; 5-50% EtOAc/hexanes 15 CV). Concentrated product fractions and dried to afford 218 mg (59%) of the title compound as a orange solid. HPLC: 97% purity. MS: 408 [M+H]$^+$

6-tert-Butyl-8-fluoro-2-[2-fluoro-4-(4,4,5,5-tetramethyl-[1,3,2]dioxaborolan-2-yl)-benzyl]-2H-phthalazin-1-one To a 10 mL reaction vial with stirbar was added 2-(4-Bromo-2-fluoro-benzyl)-6-tert-butyl-8-fluoro-2H-phthalazin-1-one (100.00 mg; 0.25 mmol; 1.00 eq.), bis(pinacolato)diboron (124.71 mg; 0.49 mmol; 2.00 eq.), tris(dibenzylideneacetone)dipalladium(0)-chloroform adduct (25.42 mg; 0.02 mmol; 0.10 eq.), Dicyclohexyl-(2',4',6'-triisopropyl-biphenyl-2-yl)-phosphane (23.41 mg; 0.05 mmol; 0.20 eq.), and potassium acetate (72.30 mg; 0.74 mmol; 3.00 eq.). The vial was sealed and flushed with Ar. To this was added dioxane (2.00 ml; 23.47 mmol; 95.59 eq.) via syringe. The reaction mixture was degassed with Ar and then heated to 65° C. overnight with stirring. Loaded directly onto 25 g KP-sil samplet and purified by flash chromatography (KP-sil, 25 g: 0%-50% EtOAc/hex 15 CV). Concentrated product fractions and dried on pump to afford 106 mg (95%) of the title compound as a brown solid. HPLC: 64% purity. MS: 455 [M+H]$^+$.

6-tert-Butyl-8-fluoro-{2-[2-fluoro-4-[2-(1-methyl-1H-pyrazol-4-yl)-3H-imidazo[4,5-b]pyridin-7-yl]-benzyl}-2H-phthalazin-1-one Prepared via method analogous to compound 97 using 7-Bromo-2-(1-methyl-1H-pyrazol-4-yl)-3H-imidazo[4,5-b]pyridine (50.00 mg: 0.17 mmol; 1.00 eq.), 6-tert-Butyl-8-fluoro-2-[2-fluoro-4-(4,4,5,5-tetramethyl-[1,3,2]dioxaborolan-2-yl)-benzyl]-2H-phthalazin-1-one (96.99 mg; 0.21 mmol; 1.25 eq.), 1,1'-bis(diphenylphosphino)ferrocene-palladium(ii)dichloride dichloromethane complex (13.95 mg: 0.02 mmol; 0.10 eq.), 1M potassium phosphate, dibasic (0.34 ml; 0.34 mmol; 2.00 eq.), 1M sodium acetate (0.34 ml; 0.34 mmol; 2.00 eq.), and ACN (2.50 ml; 47.86 mmol; 280.24 eq.) to give 53 mg (59%) of the title compound as a beige solid. HPLC: 97% purity. MS: 526 [M+H]$^+$. $^1$H NMR (500 MHz, DMSO-d$_6$) δ 13.40 (s, 1H), 8.51-8.40 (m, 2H), 8.31-8.21 (m, 2H), 8.16-8.07 (m, 2H), 7.81 (s, 1H), 7.73 (dt, J=13.3, 2.1 Hz, 1H), 7.51 (dd, J=5.3, 2.5 Hz, 1H), 7.41 (td, J=8.0, 2.1 Hz, 1H), 5.42 (d, J=2.5 Hz, 2H), 3.32 (d, J=3.0 Hz, 2H), 1.36 (d, J=2.4 Hz, 9H).

Example 100: 6-tert-Butyl-2-{2-fluoro-4-[2-(1-methyl-1H-pyrazol-4-yl)-3H-imidazo[4,5-b]pyridin-7-yl]-benzyl}-3,4-dihydro-2H-isoquinolin-1-one (100)

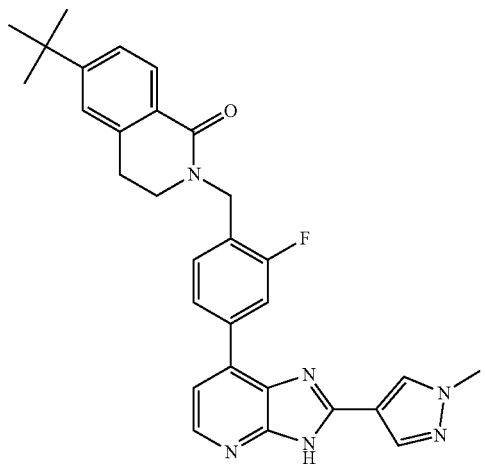 [SMILES: Cn1cc(-c2nc3c(-c4ccc(CN5CCc6cc(C(C)(C)C)ccc6C5=O)c(F)c4)ccnc3[nH]2)cn1]

2-(4-Bromo-2-fluoro-benzyl)-6-tert-butyl-3,4-dihydro-2H-isoquinolin-1-one

Prepared via method analogous to compound 99 using 6-tert-butyl-3,4-dihydroisoquinolin-1(2h)-one (125.00 mg; 0.61 mmol; 1.00 eq.), 4-bromo-2-fluorobenzyl bromide (181.22 mg; 0.68 mmol; 1.10 eq.), and cesium carbonate (0.05 ml; 0.68 mmol; 1.10 eq.) in ACN (5.00 ml; 95.73 mmol: 155.68 eq.) to afford 58 mg (24%) of the title compound as a white solid. HPLC: 92% purity. MS: 391 [M+H]$^+$.

6-tert-Butyl-2-[2-fluoro-4-(4,4,5,5-tetramethyl-[1,3,2]dioxaborolan-2-yl)-benzyl]-3,4-dihydro-2H-isoquinolin-1-one Prepared via method analogous to compound 99 using 2-(4-Bromo-2-fluoro-benzyl)-6-tert-butyl-3,4-dihydro-2H-isoquinolin-1-one (45.00 mg; 0.12 mmol; 1.00 eq.), bis(pinacolato)diboron (58.56 mg; 0.23 mmol; 2.00 eq.), tris(dibenzylideneacetone)dipalladium(0)-chloroform adduct (11.93 mg; 0.01 mmol; 0.10 eq.), dicyclohexyl-(2',4',6'-triisopropyl-biphenyl-2-yl)-phosphane (10.99 mg; 0.02 mmol; 0.20 eq.), and potassium acetate (33.95 mg: 0.35 mmol; 3.00 eq.) in dioxane (2.00 ml; 23.47 mmol: 203.57 eq.) to afford 40 mg (79%) of the title compound as a brown solid. HPLC: 88% purity. MS: 438 [M+H]$^+$.

6-tert-Butyl-2-{2-fluoro-4-[2-(1-methyl-1H-pyrazol-4-yl)-3H-imidazo[4,5-b]pyridin-7-yl]-benzyl}-3,4-dihydro-2H-isoquinolin-1-one Prepared via method analogous to compound 97 using 7-Bromo-2-(1-methyl-1H-pyrazol-4-yl)-3H-imidazo[4,5-b]pyridine (25.00 mg; 0.09 mmol; 1.00 eq.), 6-tert-Butyl-2-[2-fluoro-4-(4,4,5,5-tetramethyl-[1,3,2]dioxaborolan-2-yl)-benzyl]-3,4-dihydro-2H-isoquinolin-1-one (42.95 mg; 0.10 mmol; 1.15 eq.), 1,1'-bis(diphenylphosphino)ferrocene-palladium(ii)dichloride dichloromethane complex (6.97 mg; 0.01 mmol; 0.10 eq.) 1M potassium phosphate, dibasic (0.17 ml; 0.17 mmol; 2.00 eq.), 1M sodium acetate (0.17 ml; 0.17 mmol; 2.00 eq.), and ACN to afford 18 mg (41%) of the title compound as a brown solid. HPLC: 99% purity. MS: 509 [M+H]$^+$. $^1$H NMR (500 MHz, DMSO-d$_6$) δ 13.40 (s, 1H), 8.44 (s, 1H), 8.33-8.24 (m, 2H), 8.17 (d, J=8.0 Hz, 1H), 8.13 (s, 1H), 7.86 (d, J=8.2 Hz, 1H), 7.56-7.52 (m, 1H), 7.49 (t, J=7.9 Hz, 1H), 7.41 (dd, J=8.3, 1.9 Hz, 1H), 7.33 (s, 1H), 4.83 (s, 2H), 3.94 (s, 3H), 3.62 (t, J=6.6 Hz, 2H), 3.03 (t, J=6.5 Hz, 2H), 1.30 (s, 9H).

Example 101: N-{2-Methyl-4-[2-(1-methyl-1H-pyrazol-4-yl)-3H-imidazo[4,5-b]pyridin-7-yl]-benzyl}-oxalamide (101)

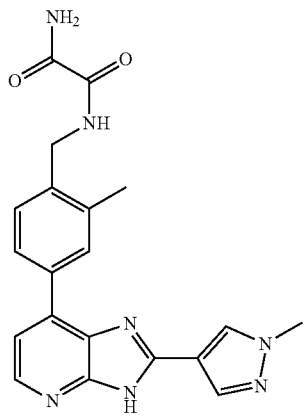 [SMILES: Cc1cc(-c2ccnc3[nH]c(-c4cnn(C)c4)nc23)ccc1CNC(=O)C(N)=O]

3-tert-Butyl-[1,2,4]oxadiazole-5-carboxylic acid 4-bromo-2-methyl-benzylamide Prepared via method analogous to compound 97 using (4-bromo-2-methylphenyl)methanamine (200.00 mg; 1.00 mmol; 1.00 eq.), 3-tert-butyl-1,2,4-oxadiazole-5-carboxylic acid (170.10 mg; 1.00 mmol; 1.00 eq.), 50% propylphosphonic anhydride in DMF (0.74 ml; 1.25 mmol; 1.25 eq.), DIPEA (0.50 ml; 3.00 mmol; 3.00 eq.), and DCM (8.00 ml; 124.80 mmol; 124.85 eq.) to afford 161 mg (46%) of the title compound as a pale yellow oil. HPLC: 100% purity. MS: 353 $[M+H]^+$.

3-tert-Butyl-[1,2,4]oxadiazole-5-carboxylic acid 2-methyl-4-(4,4,5,5-tetramethyl-[1,3,2]dioxaborolan-2-yl)-benzylamide Prepared via method analogous to compound 99 using 3-tert-Butyl-[1,2,4]oxadiazole-5-carboxylic acid 4-bromo-2-methyl-benzylamide (160.00 mg; 0.45 mmol; 1.00 eq.), bis(pinacolato)diboron (230.71 mg; 0.91 mmol; 2.00 eq.), tris(dibenzylideneacetone)dipalladium(0)-chloroform adduct (47.02 mg; 0.05 mmol; 0.10 eq.), dicyclohexyl-(2',4',6'-triisopropyl-biphenyl-2-yl)-phosphane (43.31 mg; 0.09 mmol; 0.20 eq.), and potassium acetate (133.74 mg; 1.36 mmol; 3.00 eq.) in dioxane (4.00 ml; 46.94 mmol; 103.34 eq.) to afford 122 mg (67%) of the title compound as a brown solid. HPLC: 66% purity. MS: 400 $[M+H]^+$.

N-{2-Methyl-4-[2-(1-methyl-1H-pyrazol-4-yl)-3H-imidazo[4,5-b]pyridin-7-yl]-benzyl}-oxalamide To a 10 mL reaction tube with stirbar was added 7-bromo-2-(1-methyl-1H-pyrazol-4-yl)-3H-imidazo[4,5-b]pyridine (60.00 mg; 0.20 mmol; 1.00 eq.), 3-tert-Butyl-[1,2,4]oxadiazole-5-carboxylic acid 2-methyl-4-(4,4,5,5-tetramethyl-[1,3,2]dioxaborolan-2-yl)-benzylamide (122.76 mg; 0.31 mmol; 1.50 eq.), and 1,1'-bis(diphenylphosphino)ferrocene-palladium(ii)dichloride dichloromethane complex (16.74 mg; 0.02 mmol; 0.10 eq.). The tube was sealed and flushed with Ar. To the reaction mixture was added 1M potassium phosphate, dibasic (0.41 ml; 0.41 mmol; 2.00 eq.), 1M sodium acetate (0.41 ml; 0.41 mmol; 2.00 eq.), and ACN (2.50 ml; 47.86 mmol; 233.54 eq.) via syringe. The reaction tube was degassed with Ar and heated to 130° C. for 1 h in microwave reactor. The reaction mixture was filtered through celite and concentrated. Purified by flash chromatography (10 g KP-sil column; 2-10% MeOH/CH$_2$Cl$_2$ 20 CV). Concentrated product fractions and dried on pump to afford 28 mg (35%) of the title compound as a beige solid. HPLC: 100% purity. MS: 390 $[M+H]^+$. $^1$H NMR (500 MHz, DMSO-d$_6$) δ 13.30 (s, 1H), 9.22 (t, J=6.3 Hz, 1H), 8.43 (s, 1H), 8.25 (d, J=5.2 Hz, 1H), 8.18-8.09 (m, 3H), 8.08 (s, 1H), 7.84 (s, 1H), 7.45 (d, J=5.2 Hz, 1H), 7.32 (d, J=8.1 Hz, 1H), 4.39 (s, 2H), 3.94 (s, 3H), 2.42 (s, 3H).

Example 102: N-(1-{2-Fluoro-4-[2-(1-methyl-1H-pyrazol-4-yl)-3H-imidazo[4,5-b]pyridin-7-yl]-phenyl}-1-methyl-ethyl)-oxalamide (102)

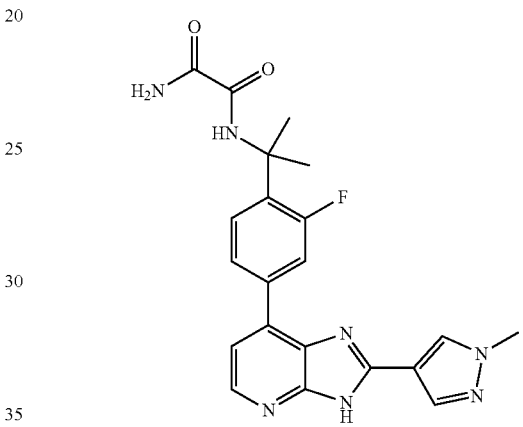

3-tert-Butyl-[1,2,4]oxadiazole-5-carboxylic acid [1-(4-bromo-2-fluoro-phenyl)-1-methyl-ethyl]-amide Prepared via method analogous to compound 97 using 2-(4-bromo-2-fluorophenyl)propan-2-amine (200.00 mg: 0.86 mmol; 1.00 eq.), 3-tert-butyl-1,2,4-oxadiazole-5-carboxylic acid (146.64 mg; 0.86 mmol; 1.00 eq.), 50% propylphosphonic anhydride in DMF (0.64 ml; 1.08 mmol: 1.25 eq.), and DIPEA (0.43 ml; 2.59 mmol; 3.00 eq.) in DCM (8.00 ml; 124.80 mmol; 144.83 eq.) to afford 132 mg (40%) of the title compound as an off-white solid. HPLC: 100% purity. MS: 385 $[M+H]^+$.

3-tert-Butyl-[1,2,4]oxadiazole-5-carboxylic acid {1-[2-fluoro-4-(4,4,5,5-tetramethyl-[1,3,2]dioxaborolan-2-yl)-phenyl]-1-methyl-ethyl}-amide Prepared via method analogous to compound 99 using 3-tert-Butyl-[1,2,4]oxadiazole-5-carboxylic acid [1-(4-bromo-2-fluoro-phenyl)-1-methyl-ethyl]-amide (130.00 mg; 0.34 mmol; 1.00 eq.), bis(pinacolato)diboron (171.83 mg; 0.68 mmol; 2.00 eq.), tris(dibenzylideneacetone)dipalladium(0)-chloroform adduct (35.02 mg; 0.03 mmol: 0.10 eq.), dicyclohexyl-(2',4',6'-triisopropyl-biphenyl-2-yl)-phosphane (32.26 mg; 0.07 mmol; 0.20 eq.), and potassium acetate (99.61 mg; 1.01 mmol; 3.00 eq.) in dioxane (3.00 ml; 35.21 mmol; 104.06 eq.) to afford 125 mg (86%) of the title compound as a beige solid. HPLC: 65% purity. MS: 431 $[M+H]^+$.

N-(1-{2-Fluoro-4-[2-(1-methyl-1H-pyrazol-4-yl)-3H-imidazo[4,5-b]pyridin-7-yl]-phenyl}-1-methyl-ethyl)-oxalamide Prepared via method analogous to compound 101 using 7-bromo-2-(1-methyl-1H-pyrazol-4-yl)-3H-imidazo[4,5-b]pyridine (55.00 mg; 0.19 mmol; 1.00 eq.), 3-tert-Butyl-[1,2,4]oxadiazole-5-carboxylic acid {(1-[2-fluoro-4-(4,4,5,5-tetramethyl-[1,3,2]dioxaborolan-2-yl)-phenyl]-1-methyl-ethyl}-amide (121.55 mg; 0.28 mmol; 1.50 eq.), 1,1'-bis(diphenylphosphino)ferrocene-palladium(ii)dichloride dichloromethane complex (15.34 mg; 0.02 mmol; 0.10 eq.), 1M potassium phosphate, dibasic (0.38 ml; 0.38 mmol; 2.00 eq.), sodium acetate (0.38 ml; 0.38 mmol; 2.00 eq.), and ACN (2.50 ml; 47.86 mmol; 254.77 eq.) to afford 43 mg (54%) of the title compound as a beige solid. HPLC: 100% purity. MS: 422 [M+H]$^+$. $^1$H NMR (500 MHz, DMSO-d$_6$) δ 13.32 (s, 1H), 8.53 (s, 1H), 8.46 (s, 1H), 8.28 (d, J=5.2 Hz, 1H), 8.23-7.95 (m, 4H), 7.81 (d, J=2.1 Hz, 1H), 7.54-7.42 (m, 2H), 3.94 (s, 3H), 1.75 (s, 6H).

Example 103: 5-tert-Butyl-[1,3,4]oxadiazole-2-carboxylic acid 2-methyl-4-[2-(1-methyl-1H-pyrazol-4-yl)-3H-imidazo[4,5-b]pyridin-7-yl]-benzylamide (103)

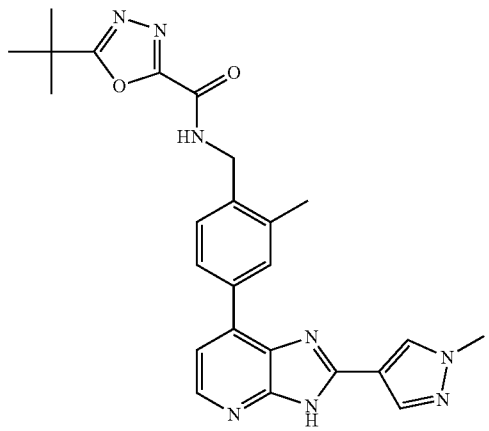 [SMILES: Cc1cc(-c2ccnc3[nH]c(-c4cnn(C)c4)nc23)ccc1CNC(=O)c1nnc(C(C)(C)C)o1]

5-tert-Butyl-[1,3,4]oxadiazole-2-carboxylic acid 4-bromo-2-methyl-benzylamide

Prepared via method analogous to compound 97 using (4-bromo-2-methylphenyl)methanamine (200.00 mg; 1.00 mmol; 1.00 eq.), 5-tert-butyl-1,3,4-oxadiazole-2-carboxylic acid (170.10 mg; 1.00 mmol: 1.00 eq.), 50% propylphosphonic anhydride in DMF (0.74 ml; 1.25 mmol; 1.25 eq.), and DIPEA (0.50 ml; 3.00 mmol; 3.00 eq.) in DCM (8.00 ml; 124.80 mmol; 124.85 eq.) to afford 175 mg (50%) of the title compound as a pale yellow oil. HPLC: 100% purity. MS: 353 [M+H]$^+$.

5-tert-Butyl-[1,3,4]oxadiazole-2-carboxylic acid 2-methyl-4-(4,4,5,5-tetramethyl-[1,3,2]dioxaborolan-2-yl)-benzylamide Prepared via method analogous to compound 99 using 5-tert-Butyl-[1,3,4]oxadiazole-2-carboxylic acid 4-bromo-2-methyl-benzylamide (170.00 mg; 0.48 mmol; 1.00 eq.), bis(pinacolato)diboron (245.12 mg; 0.97 mmol; 2.00 eq.), tris(dibenzylideneacetone)dipalladium(0)-chloroform adduct (49.96 mg: 0.05 mmol; 0.10 eq.), dicyclohexyl-(2',4',6'-triisopropyl-biphenyl-2-yl)-phosphane (46.02 mg; 0.10 mmol; 0.20 eq.), and potassium acetate (142.10 mg; 1.45 mmol; 3.00 eq.) in dioxane (4.50 ml; 52.81 mmol; 109.42 eq.) to afford 213 mg (111%) of the title compound as a yellow oil. HPLC: 78% purity. MS: 400 [M+H]$^+$.

5-tert-Butyl-[1,3,4]oxadiazole-2-carboxylic acid 2-methyl-4-[2-(1-methyl-1H-pyrazol-4-yl)-3H-imidazo[4,5-b]pyridin-7-yl]-benzylamide Prepared via method analogous to compound 97 using 7-bromo-2-(1-methyl-1H-pyrazol-4-yl)-3H-imidazo[4,5-b]pyridine (60.00 mg; 0.20 mmol; 1.00 eq.), 5-tert-Butyl-[1,3,4]oxadiazole-2-carboxylic acid 2-methyl-4-(4,4,5,5-tetramethyl-[1,3,2]dioxaborolan-2-yl)-benzylamide (122.76 mg; 0.31 mmol; 1.50 eq.), 1,1'-bis(diphenylphosphino)ferrocene-palladium(ii)dichloride dichloromethane complex (16.74 mg; 0.02 mmol; 0.10 eq.), 1M potassium phosphate, dibasic (0.41 ml; 0.41 mmol; 2.00 eq.), 1M sodium acetate (0.41 ml; 0.41 mmol; 2.00 eq.), and ACN (2.50 ml; 47.86 mmol; 233.54 eq.) to afford 61 mg (63%) of the title compound as a brown solid. HPLC: 96% purity. MS: 471 [M+H]$^+$. $^1$H NMR (500 MHz, DMSO-d$_6$) δ 13.30 (s, 1H), 9.79 (t, J=5.7 Hz, 1H), 8.41 (d, J=3.5 Hz, 1H), 8.30-8.23 (m, 1H), 8.20-8.11 (m, 2H), 8.09 (d, J=2.4 Hz, 1H), 7.48-7.39 (m, 2H), 4.55-4.50 (m, 2H), 3.94 (s, 3H), 2.45 (s, 3H), 1.40 (s, 9H).

Example 104: 5-tert-Butyl-[1,3,4]oxadiazole-2-carboxylic acid (1-{2-fluoro-4-[2-(1-methyl-1H-pyrazol-4-yl)-3H-imidazo[4,5-b]pyridin-7-yl]-phenyl}-1-methyl-ethyl)-amide (104)

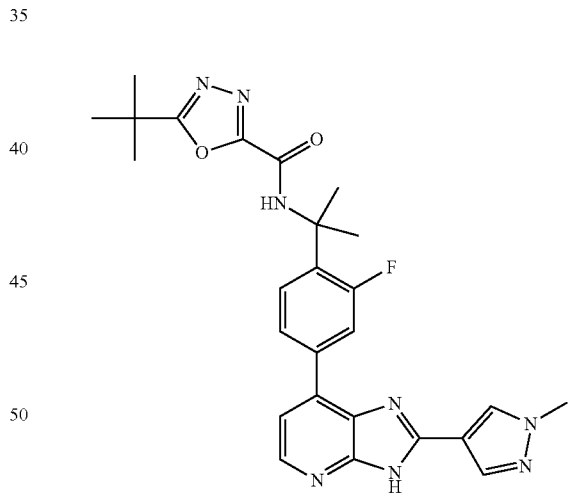

5-tert-Butyl-[1,3,4]oxadiazole-2-carboxylic acid [1-(4-bromo-2-fluoro-phenyl)-1-methyl-ethyl]-amide Prepared via method analogous to compound 97.1 using 2-(4-bromo-2-fluorophenyl)propan-2-amine (200.00 mg: 0.86 mmol; 1.00 eq.), 5-tert-butyl-1,3,4-oxadiazole-2-carboxylic acid (146.64 mg; 0.86 mmol: 1.00 eq.), 50% propylphosphonic anhydride in DMF (0.64 ml; 1.08 mmol; 1.25 eq.), and DIPEA (0.43 ml; 2.59 mmol; 3.00 eq.) in DCM (8.00 ml; 124.80 mmol; 144.83 eq.) to afford 113 mg (34%) of the title compound as a yellow solid. HPLC: 94% purity. MS: 385 [M+H]$^+$.

Prepared via method analogous to compound 99.2 using 5-tert-butyl-[1,3,4]oxadiazole-2-carboxylic acid [1-(4-bromo-2-fluoro-phenyl)-1-methyl-ethyl]-amide (110.00 mg; 0.29 mmol; 1.00 eq.), bis(pinacolato)diboron (145.39 mg; 0.57 mmol; 2.00 eq.), tris(dibenzylideneacetone)dipalladium(0)-chloroform adduct (29.63 mg; 0.03 mmol; 0.10 eq.), dicyclohexyl-(2',4',6'-triisopropyl-biphenyl-2-yl)-phosphane (27.29 mg; 0.06 mmol; 0.20 eq.), and potassium acetate (84.29 mg: 0.86 mmol; 3.00 eq.) in dioxane (3.00 ml; 35.21 mmol: 122.99 eq.) to afford 123 mg (100%) of the title compound as a beige solid. HPLC: 90% purity. MS: 432 [M+H]$^+$.

5-tert-Butyl-[1,3,4]oxadiazole-2-carboxylic acid (1-{2-fluoro-4-[2-(1-methyl-1H-pyrazol-4-yl)-3H-imidazo[4,5-b]pyridin-7-yl]-phenyl}-1-methyl-ethyl)-amide Prepared via method analogous to compound 97 using 7-bromo-2-(1-methyl-1H-pyrazol-4-yl)-3H-imidazo[4,5-b]pyridine (55.00 mg; 0.19 mmol; 1.00 eq.), 5-tert-butyl-[1,3,4]oxadiazole-2-carboxylic acid {1-[2-fluoro-4-(4,4,5,5-tetramethyl-[1,3,2]dioxaborolan-2-yl)-phenyl]-1-methyl-ethyl}-amide (121.55 mg; 0.28 mmol; 1.50 eq.), 1,1'-bis(diphenylphosphino)ferrocene-palladium(ii)dichloride dichloromethane complex (15.34 mg; 0.02 mmol; 0.10 eq.) 1M potassium phosphate, dibasic (0.38 ml; 0.38 mmol; 2.00 eq.), 1M sodium acetate (0.38 ml; 0.38 mmol; 2.00 eq.), and ACN (2.50 ml; 47.86 mmol; 254.77 eq.) to afford 49 mg (52%) of the title compound as a beige solid. HPLC: 100% purity. MS: 503 [M+H]$^+$. $^1$H NMR (500 MHz, DMSO-d$_6$) δ 13.39 (s, 1H), 9.41 (s, 1H), 8.45 (s, 1H), 8.29 (d, J=5.4 Hz, 1H), 8.24-8.12 (m, 2H), 8.09 (dd, J=8.3, 1.9 Hz, 1H), 7.57 (t, J=8.7 Hz, 1H), 7.51 (d, J=5.3 Hz, 1H), 3.94 (s, 3H), 1.80 (s, 6H), 1.39 (s, 9H).

Example 105: 3-tert-Butyl-[1,2,4]oxadiazole-5-carboxylic acid 3-hydroxymethyl-4-[2-(1-methyl-1H-pyrazol-4-yl)-3H-imidazo[4,5-b]pyridin-7-yl]-benzylamide (105)

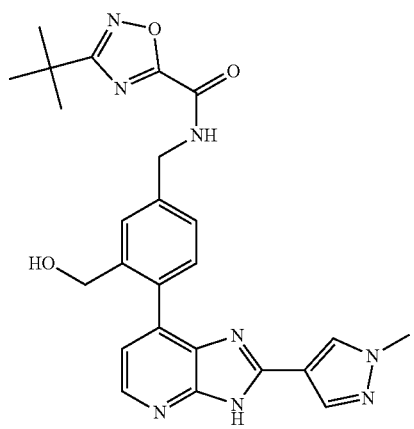 [SMILES: Cn1cc(-c2nc3c(-c4ccc(CNC(=O)c5nc(C(C)(C)C)no5)cc4CO)ccnc3[nH]2)cn1]

3-tert-Butyl-[1,2,4]oxadiazole-5-carboxylic acid (1-hydroxy-1,3-dihydro-benzo[c][1,2]oxaborol-5-ylmethyl)-amide To a 20 mL reaction vial with stirbar was added 2,1-benzoxaborole-5-methanamine, 1,3-dihydro-1-hydroxy- (200.00 mg; 1.23 mmol; 1.00 eq.), 3-tert-butyl-1,2,4-oxadiazole-5-carboxylic acid (261.02 mg; 1.53 mmol; 1.25 eq.) and PyBrop (715.08 mg; 1.53 mmol; 1.25 eq.). The vial was sealed and flushed with Ar. To this mixture was added DMF (8.00 ml; 103.76 mmol; 84.55 eq.) and n,n-diisopropylethylamine (610.00 µl; 3.68 mmol; 3.00 eq.). The reaction mixture was stirred at RT for 12 h and was then poured into 30 mL water. The mixture was extracted with 20 mL EtOAc (3×), dried over anhydrous Na$_2$SO$_4$, and concentrated. Purified by flash chromatography (25 g 15 uM PF-Sil column, 2-10% MeOH/CH$_2$Cl$_2$ 15 CV. 40 mL/min). Concentrated product fractions and dried to afford 180 mg (47%) of the title compound as a pale yellow oil. HPLC: 95% purity. MS: 316 [M+H]$^+$.

3-tert-Butyl-[1,2,4]oxadiazole-5-carboxylic acid 3-hydroxymethyl-4-[2-(1-methyl-1H-pyrazol-4-yl)-3H-imidazo[4,5-b]pyridin-7-yl]-benzylamide To a 10 mL reaction tube with stirbar was added 7-bromo-2-(1-methyl-1H-pyrazol-4-yl)-3H-imidazo[4,5-b]pyridine (60.00 mg; 0.20 mmol; 1.00 eq.), 3-tert-butyl-[1,2,4]oxadiazole-5-carboxylic acid (1-hydroxy-1,3-dihydro-benzo[c][1,2]oxaborol-5-ylmethyl)-amide (96.88 mg; 0.31 mmol; 1.50 eq.), and 1,1'-bis(diphenylphosphino)ferrocene-palladium(ii)dichloride dichloromethane complex (16.74 mg; 0.02 mmol; 0.10 eq.). The tube was sealed and flushed with Ar. To the reaction mixture was added 1M potassium phosphate, dibasic (0.41 ml; 0.41 mmol; 2.00 eq.), 1M sodium acetate (0.41 ml; 0.41 mmol; 2.00 eq.), and ACN (2.50 ml; 47.86 mmol; 233.54 eq.) via syringe. The reaction tube was degassed with Ar and heated to 130 C for 1 h in microwave reactor. The reaction mixture was filtered through celite and concentrated. Purified by HPLC. (Interchim prep HPLC: C-18 (10 um), 30×150 mm, 0.1% NH$_4$OH modified mobile phases (A=water, B=ACN), Method 35% ACN isocratic for 1 min then ramp to 80% ACN over 12 min at 60 mL/min to afford 33 mg (33%) of the title compound as an off-white solid. HPLC: 100% purity. MS: 487 [M+H]$^+$. $^1$H NMR (500 MHz, DMSO-d$_6$) δ 13.37 (s, 1H), 9.98 (t, J=6.1 Hz, 1H), 8.38 (s, 1H), 8.28 (d, J=4.9 Hz, 1H), 8.06 (s, 1H), 7.63 (s, 1H), 7.43-7.27 (m, 2H), 7.09 (s, 1H), 5.37 (s, 1H), 4.55 (d, J=6.2 Hz, 2H), 4.38 (s, 2H), 3.90 (s, 3H), 1.37 (s, 9H).

Example 106: 4-tert-Butyl-N-(1-{2-fluoro-4-[2-(1-methyl-1H-pyrazol-4-yl)-3H-imidazo[4,5-b]pyridin-7-yl]-phenyl}-1-methyl-ethyl)-benzamide (106)

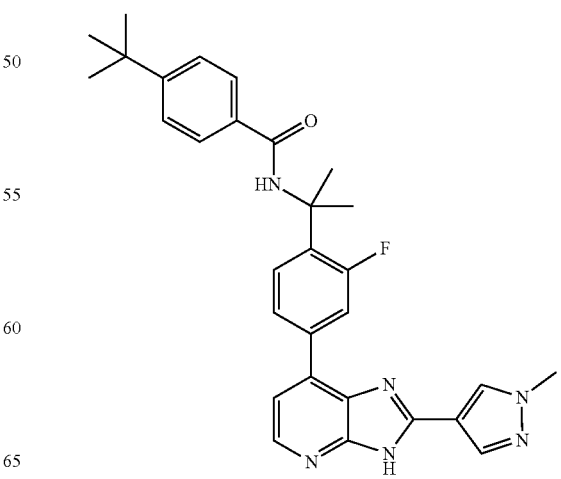

N-[1-(4-Bromo-2-fluoro-phenyl)-1-methyl-ethyl]-4-tert-butyl-benzamide

To a 20 mL reaction vial with stirbar was added 2-(4-bromo-2-fluorophenyl)propan-2-amine (150.00 mg; 0.65 mmol; 1.00 eq.) and sodium bicarbonate (135.73 mg; 1.62 mmol; 2.50 eq.) suspended in water (0.15 ml; 8.33 mmol; 12.88 eq.) and THF (1.50 ml; 18.51 mmol: 28.65 eq.). Cooled to 0° C. Added 4-tert-butyl-benzoyl chloride (129.22 µl; 0.71 mmol; 1.10 eq.) and allowed to slowly warm to RT with stirring overnight. Concentrated under reduced pressure and purified using flash chromatography (10 g KP-Sil column, 20-70% EtOAc/Hexanes). Collected fractions containing the desired product, concentrated, and dried to afford 183 mg (72%) of the title compound as an off-white solid. HPLC: 100% purity. MS: 393 [M+H]$^+$.

4-(tert-butyl)-N-(2-(2-fluoro-4-(4,4,5,5-tetramethyl-1,32-dioxaborolan-2-yl)phenyl)propan-2-yl)benzamide Prepared via method analogous to compound 99 using N-[1-(4-Bromo-2-fluoro-phenyl)-1-methyl-ethyl]-4-tert-butyl-benzamide (100.00 mg; 0.25 mmol; 1.00 eq.), bis(pinacolato)diboron (129.46 mg; 0.51 mmol; 2.00 eq.), tris(dibenzylideneacetone)dipalladium(0)-chloroform adduct (26.38 mg; 0.03 mmol; 0.10 eq.), dicyclohexyl-(2',4',6'-triisopropyl-biphenyl-2-yl)-phosphane (24.30 mg; 0.05 mmol; 0.20 eq.), and potassium acetate (75.05 mg; 0.76 mmol; 3.00 eq.) in dioxane (2.50 ml; 29.34 mmol; 115.10 eq.) to afford 219 mg of the title compound as a brown wax. HPLC: 75% purity. MS: 440 [M+H]$^+$.

4-tert-Butyl-N-(1-{2-fluoro-4-[2-(1-methyl-1H-pyrazol-4-yl)-3H-imidazo[4,5-b]pyridin-7-yl]-phenyl}-1-methyl-ethyl)-benzamide Prepared via method analogous to compound 97 using 7-bromo-2-(1-methyl-1H-pyrazol-4-yl)-3H-imidazo[4,5-b]pyridine (50.00 mg; 0.17 mmol; 1.00 eq.), 4-tert-Butyl-N-{1-[2-fluoro-4-(4,4,5,5-tetramethyl-[1,3,2]dioxaborolan-2-yl)-phenyl]-1-methyl-ethyl}-benzamide (112.56 mg; 0.26 mmol; 1.50 eq.), 1,1'-bis(diphenylphosphino)ferrocene-palladium(ii)dichloride dichloromethane complex (13.95 mg; 0.02 mmol; 0.10 eq.), 1M potassium phosphate, dibasic (0.34 ml; 0.34 mmol: 2.00 eq.), sodium acetate (0.34 ml; 0.34 mmol; 2.00 eq.), and ACN (2.50 ml; 47.86 mmol; 280.24 eq.) to afford 44 mg (50%) of the title compound as a beige solid. HPLC: 97% purity. MS: 511 [M+H]$^+$. $^1$H NMR (500 MHz, DMSO-d$_6$) δ 13.37 (s, 1H), 8.46 (d, J=16.9 Hz, 2H), 8.27 (d, J=5.3 Hz, 1H), 8.17-8.09 (m, 2H), 8.05 (d, J=8.3 Hz, 1H), 7.79 (d, J=8.1 Hz, 2H), 7.56-7.43 (m, 4H), 3.93 (s, 3H), 1.79 (s, 6H), 1.30 (s, 9H).

Example 107: 4-tert-Butyl-N-{2-methyl-4-[2-(1-methyl-1H-pyrazol-4-yl)-3H-imidazo[4,5-b]pyridin-7-yl]-benzyl}-benzamide (107)

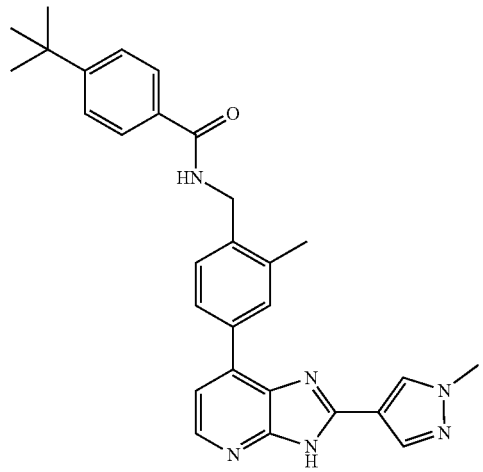 [SMILES: Cc1cc(-c2ccnc3[nH]c(-c4cnn(C)c4)nc23)ccc1CNC(=O)c1ccc(C(C)(C)C)cc1]

N-(4-Bromo-2-methyl-benzyl)-4-tert-butyl-benzamide

Prepared via method analogous to compound 106 using (4-bromo-2-methylphenyl)methanamine (150.00 mg; 0.75 mmol; 1.00 eq.) and sodium bicarbonate (157.45 mg; 1.87 mmol; 2.50 eq.) suspended in water (0.15 ml; 8.33 mmol; 11.11 eq.) and THF (1.50 ml; 18.51 mmol; 24.70 eq.) to afford 179 mg (66%) of the title compound as a white solid. HPLC: 100% purity. MS: 361 [M+H]$^+$.

4-tert-Butyl-N-[2-methyl-4-(4,4,5,5-tetramethyl-[1,3,2]dioxaborolan-2-yl)-benzyl]-benzamide Prepared via method analogous to compound 99 using N-(4-Bromo-2-methyl-benzyl)-4-tert-butyl-benzamide (100.00 mg; 0.28 mmol; 1.00 eq.), bis(pinacolato)diboron (140.96 mg; 0.56 mmol; 2.00 eq.), tris(dibenzylideneacetone)dipalladium(0)-chloroform adduct (28.73 mg; 0.03 mmol; 0.10 eq.), dicyclohexyl-(2',4',6'-triisopropyl-biphenyl-2-yl)-phosphane (26.46 mg; 0.06 mmol; 0.20 eq.), and potassium acetate (81.72 mg; 0.83 mmol; 3.00 eq.) in dioxane (2.50 ml; 29.34 mmol: 105.71 eq.) to afford 195 mg (172%) of the title compound as a beige solid. HPLC: 80% purity. MS: 408 [M+H]$^+$.

4-tert-Butyl-N-{2-methyl-4-[2-(1-methyl-1H-pyrazol-4-yl)-3H-imidazo[4,5-b]pyridin-7-yl]-benzyl}-benzamide Prepared via method analogous to compound 97 using 7-bromo-2-(1-methyl-1H-pyrazol-4-yl)-3H-imidazo[4,5-b]pyridine (50.00 mg; 0.17 mmol; 1.00 eq.), 4-tert-Butyl-N-[2-methyl-4-(4,4,5,5-tetramethyl-[1,3,2]dioxaborolan-2-yl)-benzyl]-benzamide (104.36 mg; 0.26 mmol; 1.50 eq.), 1,1'-bis(diphenylphosphino)ferrocene-palladium(ii)dichloride dichloromethane complex (13.95 mg; 0.02 mmol; 0.10 eq.), 1M potassium phosphate, dibasic (0.34 ml; 0.34 mmol; 2.00 eq.), 1M sodium acetate (0.34 ml; 0.34 mmol; 2.00 eq.), and ACN (2.50 ml; 47.86 mmol; 280.24 eq.) to afford 42 mg (51%) of the title compound as a beige solid. HPLC: 100% purity. MS: 479 [M+H]$^+$. $^1$H NMR (500 MHz, DMSO-d$_6$) δ 13.30 (s, 1H), 8.94 (t, J=5.8 Hz, 1H), 8.42 (s, 1H), 8.25 (d, J=5.5 Hz, 1H), 8.16 (d, J=8.0 Hz, 1H), 8.11 (d, J=12.0 Hz, 2H), 7.91-7.85 (m, 2H), 7.53-7.49 (m, 2H), 7.45 (d, J=5.3 Hz, 1H), 7.38 (d, J=8.1 Hz, 1H), 4.54 (d, J=5.8 Hz, 2H), 3.93 (s, 3H), 2.46 (s, 3H), 1.31 (s, 9H).

Example 108: 4-tert-Butyl-N-{4-[2-(1-methyl-1H-pyrazol-4-yl)-3H-imidazo[4,5-b]pyridin-7-yl]-2-trifluoromethyl-benzyl}-benzamide (108)

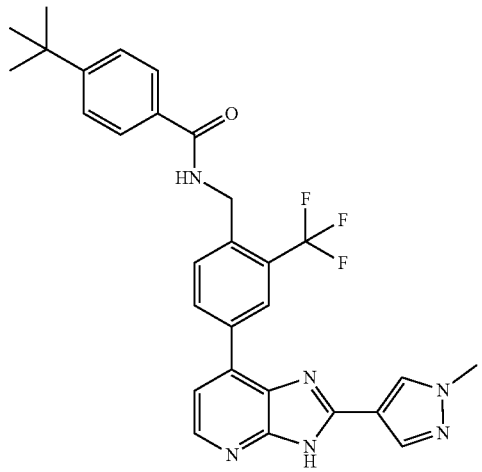 [SMILES: Cn1cc(-c2nc3c(-c4ccc(CNC(=O)c5ccc(C(C)(C)C)cc5)c(C(F)(F)F)c4)ccnc3[nH]2)cn1]

N-(4-Bromo-2-trifluoromethyl-benzyl)-4-tert-butyl-benzamide

Prepared via method analogous to compound 106 using [4-bromo-2-(trifluoromethyl)phenyl]methanamine (62.50 µl; 0.39 mmol; 1.00 eq.), sodium bicarbonate (82.67 mg; 0.98 mmol; 2.50 eq.) suspended in water (0.10 ml; 5.55 mmol; 14.10 eq.) and THF (1.00 ml; 12.34 mmol; 31.36 eq.) to afford 114 mg (70%) of the title compound as a white solid. HPLC: 98% purity. MS: 415 [M+H]$^+$.

4-tert-Butyl-N-[4-(4,4,5,5-tetramethyl-[1,3,2]dioxaborolan-2-yl)-2-trifluoromethyl-benzyl]-benzamide Prepared via method analogous to compound 99 using N-(4-Bromo-2-trifluoromethyl-benzyl)-4-tert-butyl-benzamide (110.00 mg: 0.27 mmol: 1.00 eq.), bis(pinacolato) diboron (134.86 mg; 0.53 mmol; 2.00 eq.), tris(dibenzylideneacetone)dipalladium-chloroform adduct (27.49 mg; 0.03 mmol: 0.10 eq.), 2-(dicyclohexylphosphino)-2',4',6'-triisopropylbiphenyl (25.32 mg; 0.05 mmol; 0.20 eq.), and potassium acetate (78.18 mg; 0.80 mmol; 3.00 eq.) in dioxane (2.00 ml; 23.47 mmol; 88.40 eq.) to afford 150 mg (122%) of the title compound as a brown solid. MS: 462 [M+H]$^+$.

4-tert-Butyl-N-{4-[2-(1-methyl-1H-pyrazol-4-yl)-3H-imidazo[4,5-b]pyridin-7-yl]-2-trifluoromethyl-benzyl}-benzamide Prepared via method analogous to compound 97 using 7-bromo-2-(1-methyl-1H-pyrazol-4-yl)-3H-imidazo[4,5-b]pyridine (50.00 mg; 0.17 mmol; 1.00 eq.), 4-tert-Butyl-N-[4-(4,4,5,5-tetramethyl-[1,3,2]dioxaborolan-2-yl)-2-trifluoromethyl-benzyl]-benzamide (102.43 mg; 0.22 mmol; 1.30 eq.), 1,1'-bis(diphenylphosphino)ferrocene-palladium(ii)dichloride dichloromethane complex (13.95 mg: 0.02 mmol; 0.10 eq.), 1M potassium phosphate, dibasic (0.34 ml; 0.34 mmol; 2.00 eq.), 1M sodium acetate (0.34 ml; 0.34 mmol: 2.00 eq.), and ACN (2.50 ml; 47.86 mmol: 280.24 eq.) to afford 39 mg (43%) of the title compound as a beige solid. HPLC: 97% purity. MS: 533 [M+H]$^+$. $^1$H NMR (500 MHz, DMSO-d$_6$) δ 13.43 (s, 1H), 9.15 (t, J=5.8 Hz, 1H), 8.82 (s, 1H), 8.57 (d, J=8.3 Hz, 1H), 8.39 (s, 1H), 8.31 (d, J=5.0 Hz, 1H), 8.12 (s, 1H), 7.91 (d, J=8.3 Hz, 2H), 7.67 (d, J=8.2 Hz, 1H), 7.58 (d, J=5.3 Hz, 1H), 7.54 (d, J=8.3 Hz, 2H), 4.74 (d, J=5.9 Hz, 2H), 3.95 (s, 3H), 1.32 (s, 9H).

Example 109: 5-tert-Butyl-[1,3,4]oxadiazole-2-carboxylic acid 4-[2-(1-methyl-1H-pyrazol-4-yl)-3H-imidazo[4,5-b]pyridin-7-yl]-benzylamide (109)

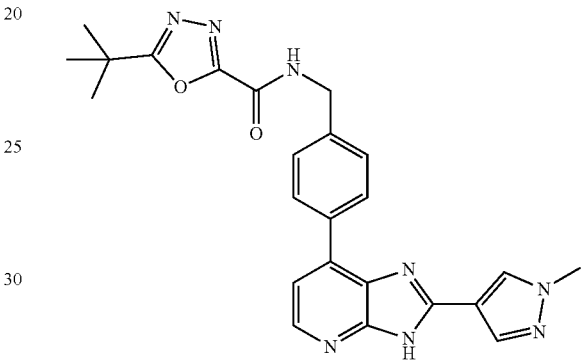

7-Chloro-2-(1-methyl-1H-pyrazol-4-yl)-3H-imidazo[4,5-b]pyridine

To a 100 mL pressure flask with stirbar was added 2-bromo-7-chloro-3H-imidazo[4,5-b]pyridine (1500.00 mg; 6.45 mmol; 1.00 eq.), 1-methylpyrazole-4-boronic acid pinacol ester (1611.07 mg; 7.74 mmol; 1.20 eq.), and 1,1'-bis(diphenylphosphino)ferrocene-palladium(ii)dichloride dichloromethane complex (790.41 mg; 0.97 mmol; 0.15 eq.), The flask was sealed and flushed with Ar. To the reaction mixture was added potassium phosphate, dibasic (12.91 ml; 12.91 mmol; 2.00 eq.), Sodium acetate (12.91 ml; 12.91 mmol; 2.00 eq.), and ACN (40.00 ml; 765.84 mmol; 118.69 eq.) via syringe. The reaction flask was degassed with Ar, sealed with a threaded teflon pressure cap and heated to 120 C for 2 h. The reaction mixture was cooled to RT and filtered through celite, washing with dichloromethane. Concentrated under reduced pressure and the residue was purified by flash chromatography (15 uM 200 g silica column; 5-20% MeOH/CH$_2$Cl$_2$ 10 CV.). Concentrated product containing fractions and dried to afford 795 mg (53%) of the title compound as a brown solid. HPLC: 98% purity. MS: 234 [M+H]$^+$. $^1$H NMR (500 MHz, DMSO-d$_6$) δ 13.55 (s, 1H), 8.46 (s, 1H), 8.17 (d, J=5.4 Hz, 1H), 8.13 (s, 1H), 7.32 (d, J=5.5 Hz, 1H), 3.94 (s, 3H).

4-[2-(1-Methyl-1H-pyrazol-4-yl)-3H-imidazo[4,5-b]pyridin-7-yl]-benzylamine

Prepared via method analogous to compound 97 using 7-chloro-2-(1-methyl-1H-pyrazol-4-yl)-3H-imidazo[4,5-b]pyridine (250.00 mg; 1.07 mmol; 1.00 eq.), 4-aminomethylphenylboronic acid, pinacol ester, hcl (374.96 mg; 1.39 mmol: 1.30 eq.), 1,1'-bis(diphenylphosphino)ferrocene-palladium(ii)dichloride dichloromethane complex (87.38 mg; 0.11 mmol: 0.10 eq.) 1M potassium phosphate, dibasic (3.21 ml; 3.21 mmol: 3.00 eq.), 1M sodium acetate (3.21 ml; 3.21 mmol; 3.00 eq.), and ACN (10.00 ml; 191.46 mmol; 178.94 eq.) to afford 187 mg (57%) of the title compound as a brown solid. HPLC: 74% purity. MS: 305 [M+H]$^+$.

5-tert-Butyl-[1,3,4]oxadiazole-2-carboxylic acid 4-[2-(1-methyl-1H-pyrazol-4-yl)-3H-imidazo[4,5-b]pyridin-7-yl]-benzylamide To a 10 mL reaction tube with stirbar was added 5-tert-butyl-1,3,4-oxadiazole-2-carboxylic acid (41.93 mg; 0.25 mmol; 1.25 eq.), 4-[2-(1-Methyl-1H-pyrazol-4-yl)-3H-imidazo[4,5-b]pyridin-7-yl]-benzylamine (60.00 mg; 0.20 mmol; 1.00 eq.) and pybop (153.89 mg; 0.30 mmol: 1.50 eq.), Tube was sealed and flushed with Ar. To this mixture was added DMF (2.50 ml; 32.42 mmol; 164.47 eq.) and n,n-diisopropylethylamine (98.00 µl; 0.59 mmol; 3.00 eq.), The reaction was stirred at RT for 12 h. Added 20 mL of water and transferred into sep funnel. Extracted with 20 mL EtOAc (3×), dichloromethane (1×) and washed combined organics with brine, dried over anhydrous $Na_2SO_4$ and concentrated under reduced pressure. Purified by flash chromatography (4 g PF-Si-HP 15 uM column; 5-10%% MeOH/$CH_2Cl_2$ 15 column vol.). Concentrated product fractions and dried to afford 38 mg (42%) of the title compound as a white solid. HPLC: 98% purity. MS: 457 [M+H]$^+$. $^1$H NMR (500 MHz, DMSO-$d_6$) δ 13.35 (s, 1H), 9.89 (t, J=6.2 Hz, 1H), 8.45 (s, 1H), 8.38-8.05 (m, 4H), 7.52 (d, J=8.1 Hz, 2H), 7.45 (d, J=5.2 Hz, 1H), 4.55 (d, J=6.3 Hz, 2H), 3.94 (s, 3H), 1.41 (s, 9H).

Example 110: 4-tert-Butyl-N-{4-[2-(1-methyl-1H-pyrazol-4-yl)-3H-imidazo[4,5-b]pyridin-7-yl]-benzyl}-benzamide (110)

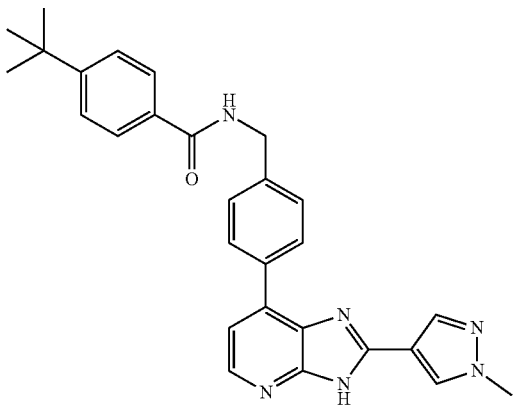 [SMILES: Cn1cc(-c2nc3c(-c4ccc(CNC(=O)c5ccc(C(C)(C)C)cc5)cc4)ccnc3[nH]2)cn1]

4-tert-Butyl-N-[4-(4,4,5,5-tetramethyl-[1,3,2]dioxaborolan-2-yl)-benzyl]-benzamide Prepared via method analogous to compound 106 using 4-aminomethylphenylboronic acid, pinacol ester, hcl (250.00 mg; 0.93 mmol; 1.00 eq.), sodium bicarbonate (194.76 mg: 2.32 mmol; 2.50 eq.) suspended in water (0.40 ml; 22.20 mmol; 23.94 eq.) and THF (4.00 ml; 49.37 mmol; 53.24 eq.) to afford 310 mg (85%) of the title compound as a white solid. MS: 394 [M+H]$^+$.

4-tert-Butyl-N-{4-[2-(1-methyl-1H-pyrazol-4-yl)-3H-imidazo[4,5-b]pyridin-7-yl]-benzyl}-benzamide Prepared via method analogous to compound 97 using 7-chloro-2-(1-methyl-1H-pyrazol-4-yl)-3H-imidazo[4,5-b]pyridine (30.00 mg: 0.13 mmol: 1.00 eq.), 4-tert-Butyl-N-[4-(4,4,5,5-tetramethyl-[1,3,2]dioxaborolan-2-yl)-benzyl]-benzamide (60.60 mg; 0.15 mmol; 1.20 eq.), 1,1'-bis(diphenylphosphino)ferrocene-palladium(ii)dichloride dichloromethane complex (10.49 mg; 0.01 mmol; 0.10 eq.), 1M potassium phosphate, dibasic (0.26 ml; 0.26 mmol; 2.00 eq.), 1M sodium acetate (0.26 ml; 0.26 mmol; 2.00 eq.), and ACN (1.50 ml; 38.29 mmol; 298.24 eq.) to afford 22 mg (37%) of the title compound as a beige solid. HPLC: 100% purity. MS: 465 [M+H]$^+$. $^1$H NMR (500 MHz, DMSO-$d_6$) δ 13.31 (s, 1H), 9.06 (t, J=6.0 Hz, 1H), 8.42 (s, 1H), 8.32-8.23 (m, 3H), 8.12 (s, 1H), 7.88 (d, J=8.3 Hz, 2H), 7.53-7.43 (m, 5H), 4.57 (d, J=6.0 Hz, 2H), 3.93 (s, 3H), 1.31 (s, 9H).

Example 111: 5-tert-Butyl-[1,3,4]oxadiazole-2-carboxylic acid 2-fluoro-4-[2-(1-methyl-1H-pyrazol-4-yl)-3H-imidazo[4,5-b]pyridin-7-yl]-benzylamide (111)

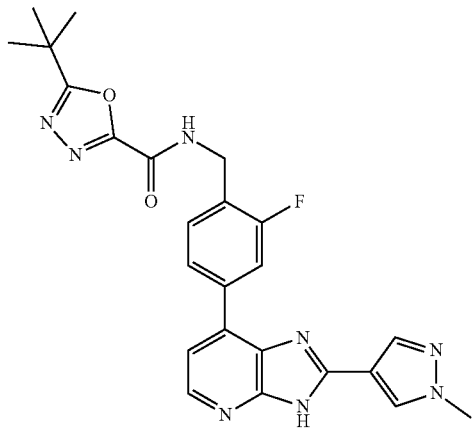 [SMILES: Cn1cc(-c2nc3c(-c4ccc(CNC(=O)c5nnc(C(C)(C)C)o5)c(F)c4)ccnc3[nH]2)cn1]

2-Fluoro-4-[2-(1-methyl-1H-pyrazol-4-yl)-3H-imidazo[4,5-b]pyridin-7-yl]-benzylamine Prepared via method analogous to compound 97 using 7-chloro-2-(1-methyl-1H-pyrazol-4-yl)-3H-imidazo[4,5-b]pyridine (250.00 mg; 1.07 mmol; 1.00 eq.), 4-(aminomethyl)-3-fluorophenylboronic acid, hcl (285.73 mg; 1.39 mmol; 1.30 eq.), 1,1'-bis(diphenylphosphino)ferrocene-palladium(ii)dichloride dichloromethane complex (87.38 mg; 0.11 mmol; 0.10 eq.), 1M potassium phosphate, dibasic (3.21 ml; 3.21 mmol; 3.00 eq.), 1M sodium acetate (3.21 ml; 3.21 mmol; 3.00 eq.), and ACN (10.00 ml; 191.46 mmol; 178.94 eq.) to afford 118 mg (34%) of the title compound as a beige solid. HPLC: 95% purity. MS: 323 [M+H]$^+$.

5-tert-Butyl-[1,3,4]oxadiazole-2-carboxylic acid 2-fluoro-4-[2-(1-methyl-1H-pyrazol-4-yl)-3H-imidazo[4,5-b]pyridin-7-yl]-benzylamide Prepared via method analogous to compound 105 using 2-fluoro-4-[2-(1-methyl-1H-pyrazol-4-yl)-3H-imidazo[4,5- b]pyridin-7-yl]-benzylamine (60.00 mg; 0.19 mmol; 1.00 eq.), 5-tert-butyl-1,3,4-oxadiazole-2-carboxylic acid (38.01 mg; 0.22 mmol; 1.20 eq.), PyBrop (112.81 mg; 0.24 mmol; 1.30 eq.), DMF (3.00 ml; 38.91 mmol; 209.03 eq.) and n,n-diisopropylethylamine (92.53 µl; 0.56 mmol; 3.00 eq.) to afford 43 mg (49%) of the title compound as a white solid. HPLC: 100% purity. MS: 475 [M+H]⁺. ¹H NMR (500 MHz, DMSO-d₆) δ 13.40 (s, 1H), 9.86 (t, J=6.1 Hz, 1H), 8.44 (s, 1H), 8.32-8.23 (m, 2H), 8.19-8.11 (m, 2H), 7.59-7.51 (m, 2H), 4.59 (d, J=6.0 Hz, 2H), 3.94 (s, 3H), 1.40 (s, 9H).

Example 112: 3-tert-Butyl-[1,2,4]oxadiazole-5-carboxylic acid 2-fluoro-4-[2-(1-methyl-1H-pyrazol-4-yl)-3H-imidazo[4,5-b]pyridin-7-yl]-benzylamide (112)

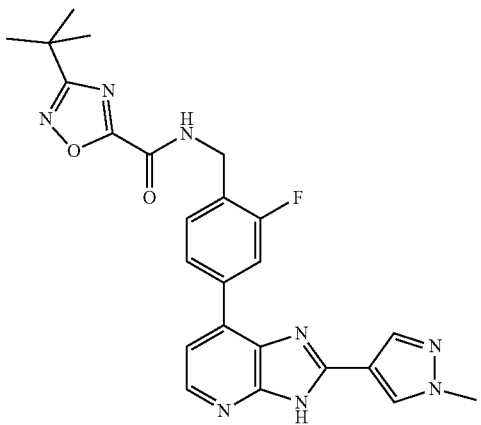 [SMILES: Cn1cc(-c2nc3c(-c4ccc(CNC(=O)c5nc(C(C)(C)C)no5)c(F)c4)ccnc3[nH]2)cn1]

Prepared via method analogous to compound 105 using 2-fluoro-4-[2-(1-methyl-1H-pyrazol-4-yl)-3H-imidazo[4,5-b]pyridin-7-yl]-benzylamine (60.00 mg; 0.19 mmol; 1.00 eq.), 3-tert-butyl-1,2,4-oxadiazole-5-carboxylic acid (41.18 mg; 0.24 mmol; 1.30 eq.), PyBrop (112.81 mg; 0.24 mmol; 1.30 eq.), DMF (3.00 ml; 38.91 mmol; 209.03 eq.) and n,n-diisopropylethylamine (92.53 µl; 0.56 mmol; 3.00 eq.) to afford 20 mg (23%) of the title compound as a white solid. HPLC: 100% purity. MS: 475 [M+H]⁺. ¹H NMR (500 MHz, DMSO-d₆) δ 1H NMR (500 MHz, DMSO-d₆) δ 9.93 (s, 1H), 8.41 (s, 1H), 8.31-8.18 (m, 2H), 8.17-8.05 (m, 2H), 7.56 (t, J=8.1 Hz, 1H), 7.46 (d, J=5.4 Hz, 1H), 4.59 (s, 2H), 3.94 (s, 3H), 1.37 (s, 9H).

Example 113: 4-tert-Butyl-N-(1-{4-[2-(1-methyl-1H-pyrazol-4-yl)-3H-imidazo[4,5-b]pyridin-7-yl]-phenyl}-cyclopropyl)-benzamide (113)

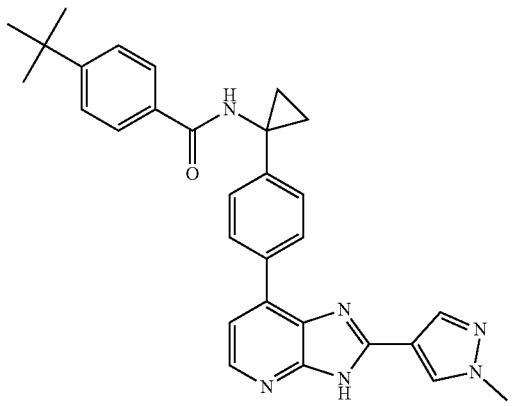 [SMILES: Cn1cc(-c2nc3c(-c4ccc(C5(NC(=O)c6ccc(C(C)(C)C)cc6)CC5)cc4)ccnc3[nH]2)cn1]

4-tert-Butyl-N-{1-[4-(4,4,5,5-tetramethyl-[1,3,2]dioxaborolan-2-yl)-phenyl]-cyclopropyl}-benzamide Prepared via method analogous to compound 106 using 1-(4-(4,4,5,5-tetramethyl-1,3,2-dioxaborolan-2-yl)phenyl)cyclopropanamine (200.00 mg; 0.77 mmol; 1.00 eq.), sodium bicarbonate (162.08 mg; 1.93 mmol; 2.50 eq.) suspended in water (0.40 ml; 22.20 mmol; 28.77 eq.) and THF (4.00 ml; 49.37 mmol; 63.97 eq.) to afford 71 mg (22%) of the title compound as a white solid. MS: 420 [M+H]⁺.

4-tert-Butyl-N-(1-{4-[2-(1-methyl-1H-pyrazol-4-yl)-3H-imidazo[4,5-b]pyridin-7-yl]-phenyl}-cyclopropyl)-benzamide Prepared via method analogous to compound 97 using 7-chloro-2-(1-methyl-1H-pyrazol-4-yl)-3H-imidazo[4,5-b]pyridine (25.00 mg; 0.11 mmol; 1.00 eq.), 4-tert-Butyl-N-{1-[4-(4,4,5,5-tetramethyl-[1,3,2]dioxaborolan-2-yl)-phenyl]-cyclopropyl}-benzamide (53.84 mg; 0.13 mmol; 1.20 eq.), 1,1'-bis(diphenylphosphino)ferrocene-palladium(ii)dichloride dichloromethane complex (8.74 mg; 0.01 mmol; 0.10 eq.), 1M potassium phosphate, dibasic (0.21 ml; 0.21 mmol; 2.00 eq.), 1M sodium acetate (0.21 ml; 0.21 mmol; 2.00 eq.), and ACN (1.00 ml; 19.15 mmol; 178.94 eq.) to afford 28 mg (53%) of the title compound as a white solid. HPLC: 82% purity. MS: 491 [M+H]⁺. ¹H NMR (500 MHz, DMSO-d₆) δ 13.22 (s, 1H), 9.19 (s, 1H), 8.42 (s, 1H), 8.24 (t, J=7.4 Hz, 2H), 8.12 (s, 1H), 7.88 (d, J=8.3 Hz, 2H), 7.50 (d, J=8.3 Hz, 2H), 7.33 (d, J=8.2 Hz, 2H), 7.06-7.00 (m, 1H), 6.64 (d, J=8.7 Hz, 1H), 3.93 (s, 3H), 1.36 (dd, J=12.0, 2.4 Hz, 4H), 1.31 (s, 9H).

Example 114: 2-(3-Hydroxy-3-methyl-butyl)-5-{2-[4-(morpholine-4-carbonyl)-phenyl]-3H-imidazo[4,5-b]pyridin-7-yl}-2,3-dihydro-isoindol-1-one (114)

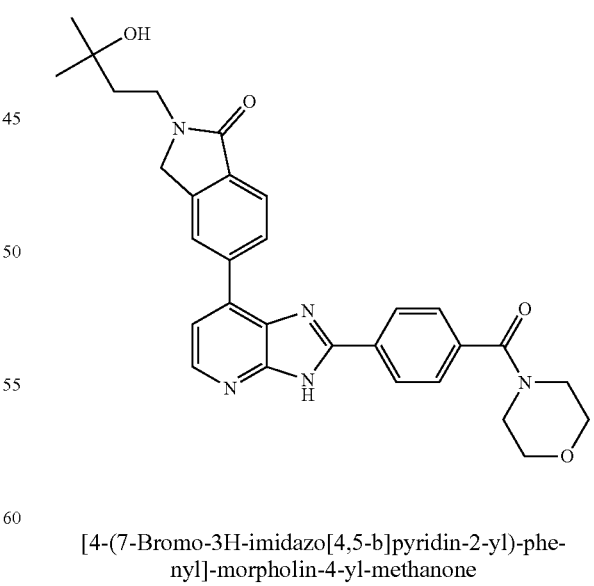

[4-(7-Bromo-3H-imidazo[4,5-b]pyridin-2-yl)-phenyl]-morpholin-4-yl-methanone

To a 20 mL reaction tube with stirbar was added a solution of 2,3-diamino-4-bromopyridine (500.00 mg; 2.66 mmol; 1.00 eq.) and 4-(morpholine-4-carbonyl)-benzaldehyde (612.15 mg; 2.79 mmol; 1.05 eq.) in DMF (10.00 ml; 129.70 mmol; 48.77 eq.), To this was added p-toluenesulfonic acid monohydrate (50.58 mg; 0.27 mmol; 0.10 eq.) and the reaction mixture was heated at 85° C. for 12 h. The reaction was allowed to cool to RT and was then poured into 20 mL sat. aq. NaHCO$_3$ and transferred to a sep funnel. Extracted with ethyl acetate (3×10 mL). The combined organics were washed with sat. aq. NaHCO3(20 mL) and brine (20 mL), dried over anhydrous Na$_2$SO$_4$, and concentrated under reduced pressure. Purified by flash chromatography (50 g KP-NH column: 2-10% MeOH/CH2Cl2 15 CV). Concentrated product containing fractions and dried to afford 240 mg (23%) of the title compound as a beige solid. HPLC: 99% purity. MS: 388 [M+H]$^+$. $^1$H NMR (500 MHz, DMSO-d$_6$) δ 14.01 (s, 1H), 8.32 (d, J=7.9 Hz, 2H), 8.21 (d, J=5.3 Hz, 1H), 7.62 (d, J=8.0 Hz, 2H), 7.56 (d, J=5.3 Hz, 1H), 3.73-3.53 (m, 6H), 3.49-3.34 (m, 2H).

2-(3-Hydroxy-3-methyl-butyl)-5-{2-[4-(morpholine-4-carbonyl)-phenyl]-3H-imidazo[4,5-b]pyridin-7-yl}-2,3-dihydro-isoindol-1-one Prepared via method analogous to compound 97 using [4-(7-Bromo-3H-imidazo[4,5-b]pyridin-2-yl)-phenyl]-morpholin-4-yl-methanone (30.00 mg; 0.08 mmol; 1.00 eq.), 2-(3-hydroxy-3-methylbutyl)-5-(tetramethyl-1,3,2-dioxaborolan-2-yl)-2,3-dihydro-1H-isoindol-1-one (32.10 mg; 0.09 mmol; 1.20 eq.), 1,1'-bis(diphenylphosphino)ferrocene-palladium(ii)dichloride dichloromethane complex (6.33 mg; 0.01 mmol; 0.10 eq.), 1M potassium phosphate, dibasic (0.15 ml; 0.15 mmol; 2.00 eq.), 1M sodium acetate (0.15 ml; 0.15 mmol; 2.00 eq.), and ACN (1.50 ml; 28.72 mmol; 370.70 eq.) to afford 14 mg (34%) of the title compound as an off white solid. HPLC: 100% purity. MS: 526 [M+H]$^+$. $^1$H NMR (500 MHz, DMSO-d$_6$) δ 8.65 (s, 1H), 8.49 (d, J=8.1 Hz, 1H), 8.37 (d, J=8.1 Hz, 2H), 8.34 (d, J=5.1 Hz, 1H), 7.82 (d, J=7.9 Hz, 1H), 7.57 (d, J=8.0 Hz, 2H), 7.50 (d, J=5.1 Hz, 1H), 4.62 (s, 2H), 4.37 (s, 1H), 3.72-3.41 (m, 10H), 1.77-1.70 (m, 2H), 1.17 (s, 6H).

Example 115: 6-tert-Butyl-2-(4-{2-[4-(morpholine-4-carbonyl)-phenyl]-3H-imidazo[4,5-b]pyridin-7-yl}-benzyl)-3,4-dihydro-2H-isoquinolin-1-one (115)

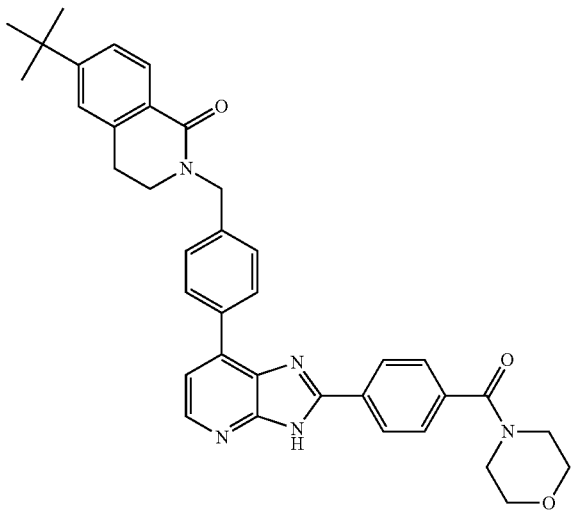 [SMILES: CC(C)(C)c1ccc2c(c1)CCN(Cc1ccc(-c3ccnc4[nH]c(-c5ccc(C(=O)N6CCOCC6)cc5)nc34)cc1)C2=O]

2-(4-Bromo-benzyl)-6-tert-butyl-3,4-dihydro-2H-isoquinolin-1-one

Prepared via method analogous to compound 99 using 6-tert-butyl-3,4-dihydroisoquinolin-1(2h)-one (125.00 mg; 0.61 mmol; 1.00 eq.), 4-bromobenzyl bromide (169.05 mg; 0.68 mmol; 1.10 eq.), and cesium carbonate (0.05 ml; 0.68 mmol: 1.10 eq.) in ACN (5.00 ml; 95.73 mmol; 155.68 eq.) to afford 103 mg (45%) of the title compound as a white solid. MS: 373 [M+H]$^+$.

6-tert-Butyl-2-[4-(4,4,5,5-tetramethyl-[1,3,2]dioxaborolan-2-yl)-benzyl]-3,4-dihydro-2H-isoquinolin-1-one Prepared via method analogous to compound 99 using 2-(4-bromo-benzyl)-6-tert-butyl-3,4-dihydro-2H-isoquinolin-1-one (100.00 mg; 0.27 mmol; 1.00 eq.), bis(pinacolato)diboron (136.42 mg; 0.54 mmol; 2.00 eq.), tris(dibenzylideneacetone)dipalladium-chloroform adduct (27.80 mg; 0.03 mmol: 0.10 eq.), 2-(dicyclohexylphosphino)-2',4',6'-triisopropylbiphenyl (25.61 mg; 0.05 mmol; 0.20 eq.), and potassium acetate (79.08 mg; 0.81 mmol; 3.00 eq.) in dioxane (2.00 ml; 23.47 mmol: 87.39 eq.) to afford 55 mg (49%) of the title compound as a purple solid. HPLC: 82% purity. MS: 420 [M+H]$^+$.

6-tert-Butyl-2-(4-{2-[4-(morpholine-4-carbonyl)-phenyl]-3H-imidazo[4,5-b]pyridin-7-yl}-benzyl)-3,4-dihydro-2H-isoquinolin-1-one Prepared via method analogous to compound 97 using [4-(7-bromo-3H-imidazo[4,5-b]pyridin-2-yl)-phenyl]-morpholin-4-yl-methanone (40.00 mg; 0.10 mmol; 1.00 eq.), 6-tert-Butyl-2-[4-(4,4,5,5-tetramethyl-[1,3,2]dioxaborolan-2-yl)-benzyl]-3,4-dihydro-2H-isoquinolin-1-one (56.32 mg; 0.13 mmol; 1.30 eq.), 1,1'-bis(diphenylphosphino)ferrocene-palladium(ii)dichloride dichloromethane complex (8.44 mg; 0.01 mmol; 0.10 eq.) 1M potassium phosphate, dibasic (0.21 ml; 0.21 mmol; 2.00 eq.), 1M sodium acetate (0.21 ml; 0.21 mmol; 2.00 eq.), and ACN (2.00 ml; 38.29 mmol; 370.70 eq.) to afford 21 mg (34%) of the title compound as a beige solid. HPLC: 94% purity. MS: 600 [M+H]$^+$. $^1$H NMR (500 MHz, DMSO-d$_6$) δ 8.43-8.35 (m, 3H), 8.34 (d, J=8.0 Hz, 2H), 7.89 (d, J=8.1 Hz, 1H), 7.59 (d, J=7.9 Hz, 2H), 7.56-7.46 (m, 3H), 7.42 (d, J=8.2 Hz, 1H), 7.32 (s, 1H), 4.81 (s, 2H), 3.77-3.58 (m, 6H), 3.57 (t, J=6.7 Hz, 2H), 3.47-3.35 (m, 2H), 3.01 (t, J=6.5 Hz, 2H), 1.30 (s, 9H).

Example 116: 5-tert-Butyl-[1,2,4]oxadiazole-3-carboxylic acid 2-fluoro-4-[2-(1-methyl-1H-pyrazol-4-yl)-3H-imidazo[4,5-b]pyridin-7-yl]-benzylamide (116)

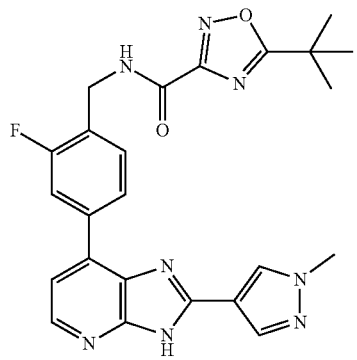 [SMILES: Cn1cc(-c2nc3c(-c4ccc(CNC(=O)c5noc(C(C)(C)C)n5)c(F)c4)ccnc3[nH]2)cn1]

Prepared via method analogous to compound 105 using 2-fluoro-4-[2-(1-methyl-1H-pyrazol-4-yl)-3H-imidazo[4,5-b]pyridin-7-yl]-benzylamine (75.00 mg; 0.23 mmol; 1.00 eq.), 5-tert-butyl-[1,2,4]oxadiazole-3-carboxylic acid sodium (55.88 mg; 0.29 mmol; 1.25 eq.), PyBrop (135.58 mg; 0.29 mmol; 1.25 eq.), DMF (3.00 ml; 38.91 mmol; 167.22 eq.) and n,n-diisopropylethylamine (115.66 µl; 0.70 mmol; 3.00 eq.) to afford 65 mg (59%) of the title compound as a white solid. HPLC: 100% purity. MS: 475 [M+H]$^+$. $^1$H NMR (500 MHz, DMSO-d$_6$) δ 13.40 (s, 1H), 9.54 (t, J=6.0 Hz, 1H), 8.45 (s, 1H), 8.31-8.23 (m, 2H), 8.20-8.10 (m, 2H), 7.56-7.49 (m, 2H), 4.59 (d, J=6.0 Hz, 2H), 3.95 (s, 3H), 1.44 (s, 9H).

Example 118: 4-tert-Butyl-N-(2-fluoro-4-{2-[4-(morpholine-4-carbonyl)-phenyl]-3H-imidazo[4,5-b]pyridin-7-yl}-benzyl)-benzamide (118)

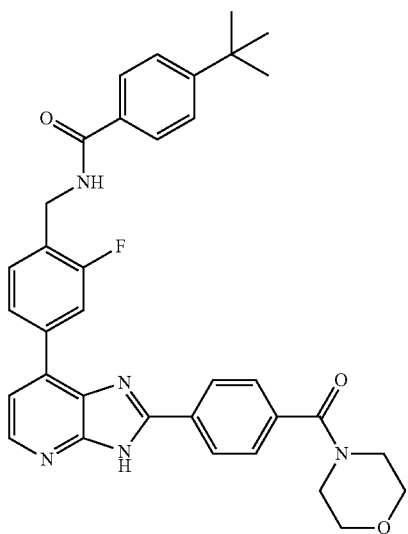 [SMILES: CC(C)(C)c1ccc(C(=O)NCc2ccc(-c3ccnc4[nH]c(-c5ccc(C(=O)N6CCOCC6)cc5)nc34)cc2F)cc1]

Prepared via method analogous to compound 114 using 4-tert-butyl-N-[4-(2,3-diamino-pyridin-4-yl)-2-fluoro-benzyl]-benzamide (50.00 mg; 0.13 mmol; 1.00 eq.), 4-(morpholine-4-carbonyl)-benzaldehyde (30.72 mg; 0.14 mmol; 1.10 eq.), DMF (1.50 ml; 19.45 mmol; 152.70 eq.) and p-toluenesulfonic acid monohydrate (2.42 mg; 0.01 mmol; 0.10 eq.) to afford 26 mg (34%) of the title compound as a pale yellow solid. HPLC: 91% purity. MS: 592 [M+H]$^+$. $^1$H NMR (500 MHz, DMSO-d$_6$) δ 13.85 (s, 1H), 9.05 (t. J=5.9 Hz, 1H), 8.40 (d, J=5.2 Hz, 1H), 8.38-8.28 (m, 3H), 8.22 (d, J=8.2 Hz, 1H), 7.88 (d, J=8.3 Hz, 2H), 7.66-7.58 (m, 3H), 7.58-7.48 (m, 3H), 4.61 (d, J=5.7 Hz, 2H), 3.76-3.51 (m, 6H), 3.48-3.32 (m, 2H), 1.31 (s, 9H).

Example 119: 5-tert-Butyl-[1,2,4]oxadiazole-3-carboxylic acid 2-fluoro-4-{2-[1-(2-morpholin-4-yl-ethyl)-1H-pyrazol-4-yl]-3H-imidazo[4,5-b]pyridin-7-yl}-benzylamide (119)

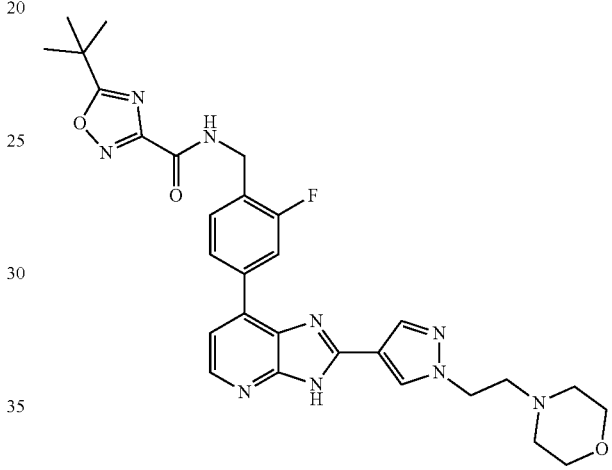

7-Chloro-2-[1-(2-morpholin-4-yl-ethyl)-1H-pyrazol-4-yl]-3H-imidazo[4,5-b]pyridine 2-Bromo-7-chloro-3H-imidazo[4,5-b]pyridine (450.00 mg; 1.94 mmol; 1.00 eq.), 4-{2-[4-(4,4,5,5-Tetramethyl-[1,3,2]dioxaborolan-2-yl)-pyrazol-1-yl]-ethyl)}-morpholine (713.59 mg; 2.32 mmol; 1.20 eq.), disodium carbonate (3.87 ml; 3.87 mmol; 2.00 eq.), Sodium acetate (3.87 ml; 3.87 mmol; 2.00 eq.), and ACN (10.00 ml; 191.46 mmol; 98.91 eq.) were combined under N$_2$ (g) and cyclopentyl(diphenyl)phosphane; dichloromethane; dichloropalladium; iron (237.12 mg; 0.29 mmol; 0.15 eq.) was added. The vial was capped and purged with N$_2$ (g) for 15 min, then heated to 120° C. for 2 h then cooled to RT. The reaction mixture was filtered through Celite and washed with MeOH/DCM. The solvent was evaporated to a brown residue, which was purified by flash column chromatography (Biotage, 0-20% MeOH/DCM, 55 g KPNH silica). The title compound 5-tert-Butyl-[1,2,4]oxadiazole-3-carboxylic acid 2-fluoro-4-{2-[1-(2-morpholin-4-yl-ethyl)-1H-pyrazol-4-yl]-3H-imidazo[4,5-b]pyridin-7-yl}-benzylamide was obtained as a brown solid (544 mg, 100% yield). LC-MS: 334.2 [M+2H]$^{2+}$.

2-Fluoro-4-{2-[1-(2-morpholin-4-yl-ethyl)-1H-pyrazol-4-yl]-3H-imidazo[4,5-b]pyridin-7-yl}-benzylamine 7-Chloro-2-[1-(2-morpholin-4-yl-ethyl)-1H-pyrazol-4-yl]-3H-imidazo[4,5-b]pyridine (100.00 mg; 0.30 mmol; 1.00 eq.), [4-(aminomethyl)-3-fluoro-phenyl]boronic acid (101.54 mg; 0.60 mmol; 2.00 eq.), potassium carbonate (166.12 mg; 1.20 mmol; 4.00 eq.), water (0.20 ml), THF (2.00 ml) were combined under $N_2$ (g) as cyclopentyl (diphenyl)phosphane; dichloromethane; dichloropalladium; iron (24.54 mg; 0.03 mmol; 0.10 eq.) was added. The vial was capped and purged with $N_2$ (g) 15 min, then heated to 140° C. for 45 min in the Biotage microwave (high absorption) and cooled to RT. LC-MS after this time shows target mass (423.1). The reaction mixture was filtered through Celite, washed with DCM/MeOH, and evaporated to a brown solid, which was subjected to flash chromatography (Biotage, 0-20% MeOH/DCM, KPNH silica) to afford desired target 2-Fluoro-4-{2-[1-(2-morpholin-4-yl-ethyl)-1H-pyrazol-4-yl]-3H-imidazo[4,5-b]pyridin-7-yl}-benzylamine as a brown solid (42.1 mg, 33.2% purity). HPLC: 84.9% purity. MS: 423.3 [M+2H]2+. $^1$H NMR (500 MHz, Methanol-d4): δ 8.44 (br s, 1H), 8.32 (br s, 1H), 8.20 (br s, 1H), 7.82 (m, 2H), 7.61 (t, 1H), 7.39 (br m, 1H), 4.38 (br t, 2H), 3.95 (br s, 2H), 3.67 (br s, 4H), 2.87 (br t, 2H), 2.52 (br s, 4H).

5-tert-Butyl-[1,2,4]oxadiazole-3-carboxylic acid 2-fluoro-4-{2-[1-(2-morpholin-4-yl-ethyl)-1H-pyrazol-4-yl]-3H-imidazo[4,5-b]pyridin-7-yl}-benzylamide 2-Fluoro-4-{2-[1-(2-morpholin-4-yl-ethyl)-1H-pyrazol-4-yl]-3H-imidazo[4,5-b]pyridin-7-yl}-benzylamine (66.00 mg; 0.16 mmol; 1.00 eq.), 5-tert-Butyl-[1,2,4]oxadiazole-3-carboxylic acid (34.64 mg; 0.20 mmol; 1.30 eq.), 2,4,6-Tripropyl-[1,3,4,2,4,6]trioxatriphosphinane 2,4,6-trioxide (0.50 ml; 1.12 mmol; 7.12 eq.), DIPEA (0.08 ml; 0.47 mmol; 3.00 eq.), and ACN (0.50 ml; 9.57 mmol; 61.13 eq.) were combined and stirred under $N_2$ (g) at RT overnight. LC-MS after this time shows total conversion to product (1.404 min, 575.3). The reaction mixture was concentrated and the residue was subjected to preparative HPLC (Interchim system: 120 g C-18 silica, mobile phase A: 0.1% formic acid in water; mobile phase B: acetonitrile) to afford 5-tert-Butyl-[1,2,4]oxadiazole-3-carboxylic acid 2-fluoro-4-{2-[1-(2-morpholin-4-yl-ethyl)-1H-pyrazol-4-yl]-3H-imidazo[4,5-b]pyridin-7-yl}-benzylamide as a beige solid (1,3,2 mg, 15% yield). HPLC: 100% purity. LC-MS: 574.3 [M+H]+. 1H NMR (500 MHz, DMSO-d$_6$): δ 9.54 (br s, 1H), 8.62 (br s, 1H), 8.32 (br s, 1H), 8.23 (br s, 1H), 8.10 (br m, 1H), 7.53 (br s, 2H), 4.59 (br s, 4H), 3.77 (br s, 4H), 3.50 (br s, 2H), 3.12 (br s, 4H), 1.43 (s, 9H).

Example 120: 5-tert-Butyl-[1,3,4]oxadiazole-2-carboxylic acid 2-fluoro-4-{2-[1-(2-morpholin-4-yl-ethyl)-1H-pyrazol-4-yl]-3H-imidazo[4,5-b]pyridin-7-yl}-benzylamide (120)

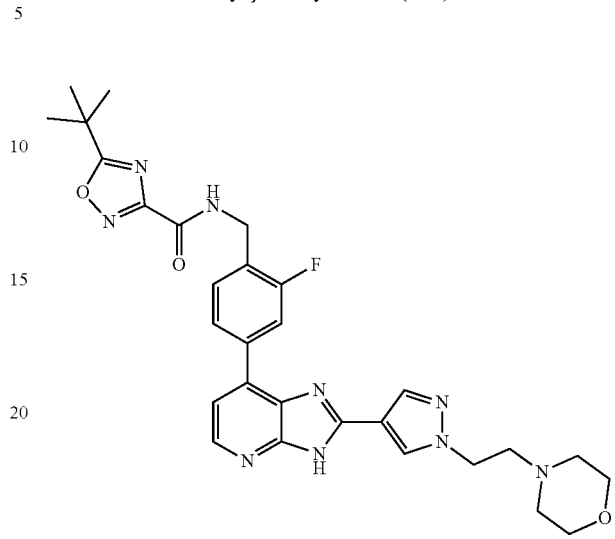

7-Chloro-2-[1-(2-morpholin-4-yl-ethyl)-1H-pyrazol-4-yl]-3H-imidazo[4,5-b]pyridine 2-Bromo-7-chloro-3H-imidazo[4,5-b]pyridine (200.00 mg; 0.86 mmol; 1.00 eq.), 4-{2-[4-(4,4,5,5-Tetramethyl-[1,3,2]dioxaborolan-2-yl)-pyrazol-1-yl]-ethyl}-morpholine (317.15 mg; 1.03 mmol; 1.20 eq.), disodium carbonate (1.72 ml; 1.72 mmol; 2.00 eq.), Sodium acetate (1.72 ml; 1.72 mmol; 2.00 eq.), and ACN (4.30 ml; 82.33 mmol; 95.69 eq.) were combined under $N_2$ (g) and cyclopentyl(diphenyl)phosphane; dichloromethane; dichloropalladium; iron (105.39 mg; 0.13 mmol; 0.15 eq.) was added. The flask was capped and purged with $N_2$ (g) for 15 min, then heated to 120° C. for 2 h. and then cooled to RT. The reaction mixture was filtered through Celite, which was washed with MeOH/DCM. The filtrate was concentrated under reduced pressure to afford a brown residue which was then dissolved in DCm and subjected to flash chromatography (Biotage, 0 to 20% MeOH/DCM, KPNH silica column) to obtain 7-Chloro-2-[1-(2-morpholin-4-yl-ethyl)-1H-pyrazol-4-yl]-3H-imidazo[4,5-b]pyridine as a brown solid (220 mg, 77% purity). LC-MS: 334.1 [M+2H]2+. HPLC: 92.4% purity. 1H NMR (500 MHz, DMSO-d$_6$): δ 8.52 (br s, 2H), 8.16 (br m, 2H), 7.32 (br m, 1H), 3.91 (br t, 2H), 3.30 (br s, 4H), 2.75 br t, 2H), 2.44 (br s, 4H).

2-Fluoro-4-{2-[1-(2-morpholin-4-yl-ethyl)-1H-pyrazol-4-yl]-3H-imidazo[4,5-b]pyridin-7-yl}-benzylamine 7-Chloro-2-[1-(2-morpholin-4-yl-ethyl)-1H-pyrazol-4-yl]-3H-imidazo[4,5-b]pyridine (100.00 mg; 0.30 mmol; 1.00 eq.), [4-(aminomethyl)-3-fluoro-phenyl]boronic acid (101.54 mg; 0.60 mmol; 2.00 eq.), potassium carbonate (166.12 mg; 1.20 mmol; 4.00 eq.), water (0.20 ml), THF (2.00 ml) were combined under $N_2$ (g) as cyclopentyl (diphenyl)phosphane; dichloromethane; dichloropalladium; iron (24.54 mg; 0.03 mmol; 0.10 eq.) was added. The reaction was purged with $N_2$ (g) for 15 min, then heated to 140° C. for 45 min in the Biotage microwave (high absorption) and cooled to RT. The reception mixture was filtered through Celite, washed with DCM/MeOH, and evaporated to a brown solid. The solid was subjected to flash chromatography (Biotage, 0-20% MeOH/DCM, 28 g KPNH silica) to afford 2-Fluoro-4-{2-[1-(2-morpholin-4-yl-ethyl)-1H-pyrazol-4-yl]-3H-imidazo[4,5-b]pyridin-7-yl}-benzylamine as a brown solid (26.5 mg, 21% yield). LC-MS: 422.2 [M+H]+. HPLC: 85% purity.

5-tert-Butyl-[1,3,4]oxadiazole-2-carboxylic acid 2-fluoro-4-{2-[1-(2-morpholin-4-yl-ethyl)-1H-pyrazol-4-yl]-3H-imidazo[4,5-b]pyridin-7-yl}-benzylamide 2-Fluoro-4-{2-[1-(2-morpholin-4-yl-ethyl)-1H-pyrazol-4-yl]-3H-imidazo[4,5-b]pyridin-7-yl}-benzylamine (36.00 mg; 0.09 mmol; 1.00 eq.), 5-tert-Butyl-[,3,4]oxadiazole-2-carboxylic acid (18.90 mg; 0.11 mmol: 1.30 eq.), 2,4,6-Tripropyl-[1,3,5,2,4,6]trioxatriphosphinane 2,4,6-trioxide (0.30 ml; 0.67 mmol; 7.83 eq.), DIPEA (0.04 ml; 0.26 mmol; 3.00 eq.), and ACN (0.45 ml; 8.62 mmol; 100.87 eq.) were combined under N$_z$(g) and stirred at RT for an hour. The reaction mixture was subjected to preparative HPLC (Interchim system; 120 g C-18 silica, mobile phase A: 0.1% formic acid in water; mobile phase B: acetonitrile). The fractions were combined, concentrated, and lyophilized to afford 5-tert-Butyl-[1,3,4]oxadiazole-2-carboxylic acid 2-fluoro-4-{2-[1-(2-morpholin-4-yl-ethyl)-1H-pyrazol-4-yl]-3H-imidazo[4,5-b]pyridin-7-yl}-benzylamide as a beige solid (42 mg, 86% yield). LC-MS: 575.2 [M+2H]2+. HPLC: 95.5% purity. 1H NMR (500 MHz, DMSO-d$_6$): δ7.70 (br s, 1H), 7.56 (br s, 1H), 7.49 (br s, 1H), 7.09 (d, 1H), 7.06 (m, 1H), 6.83 (br t, 1H), 6.65 (br m, 1H), 3.98 (br s, 2H), 3.89 (br s, 1H), 3.10 (br s, 2H), 2.85 (br s, 2H), 2.67 (br s, 2H), 2.32 (br s, 2H), 0.66 (s, 9H).

Example 121: (4-tert-Butyl-phenyl)-(2-{4-[2-(1-methyl-1H-pyrazol-4-yl)-3H-imidazo[4,5-b]pyridin-7-yl]-phenyl}-pyrrolidin-1-yl)-methanone (121)

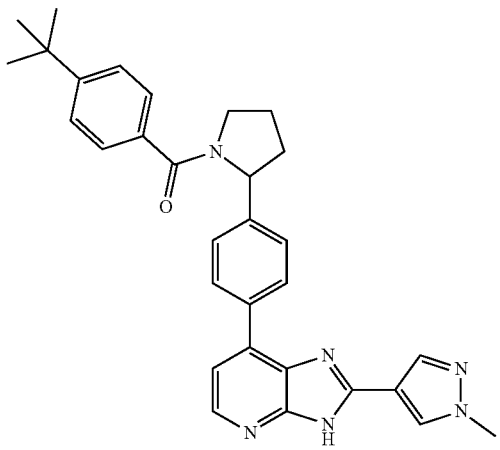 [SMILES: Cn1cc(-c2nc3c(-c4ccc(C5CCCN5C(=O)c5ccc(C(C)(C)C)cc5)cc4)ccnc3[nH]2)cn1]

7-Chloro-2-(1-methyl-1H-pyrazol-4-yl)-3H-imidazo[4,5-b]pyridine

To a microwave vial with stirbar was added 2-bromo-7-chloro-3H-imidazo[4,5-b]pyridine (0.40 g; 1.72 mmol; 1.00 eq.), 1-methylpyrazole-4-boronic acid pinacol ester (0.43 g; 2.06 mmol; 1.20 eq.) under N$_2$ (g), then 1,1'-bis(diphenylphosphino)ferrocene-palladium(ii)dichloride dichloromethane complex (0.21 g; 0.26 mmol; 0.15 eq.), disodium carbonate (3.44 ml; 3.44 mmol: 2.00 eq.), Sodium acetate (3.44 ml; 3.44 mmol; 2.00 eq.), and ACN (8.00 ml; 153.17 mmol; 89.02 eq.), The flask was capped and purged with N$_2$ (g) for 15 min, then heated to 120° C. for 2 hours, then cooled to RT. The reaction mixture was filtered through Celite, and the Celite was washed with DCM/MeOH. The filtrate was concentrated and subjected to flash chromatography (Biotage, 55 g KPNH silica, 0-20% MeOH/DCM). 7-Chloro-2-(1-methyl-1H-pyrazol-4-yl)-3H-imidazo[4,5-b]pyridine was isolated as a purple-white solid (402 mg, 100%). LC-MS: 233.3 [MH]. HPLC: 100% purity.

2-{4-[2-(1-Methyl-1H-pyrazol-4-yl)-3H-imidazo[4,5-b]pyridin-7-yl]-phenyl}-pyrrolidine-1-carboxylic acid tert-butyl ester 7-Chloro-2-(1-methyl-1H-pyrazol-4-yl)-3H-imidazo[4,5-b]pyridine (50.00 mg; 0.21 mmol; 1.00 eq.), 2-[4-(4,4,5,5-Tetramethyl-[1,3,2]dioxaborolan-2-yl)-phenyl]-pyrrolidine-1-carboxylic acid tert-butyl ester (95.86 mg; 0.26 mmol; 1.20 eq.), potassium phosphate, dibasic (0.43 ml; 0.43 mmol; 2.00 eq.), Sodium acetate (0.43 ml; 0.43 mmol: 2.00 eq.), and ACN (2.00 ml) were combined under N$_2$ (g) as cyclopentyl(diphenyl)phosphane; dichloromethane; dichloropalladium; iron (17.48 mg; 0.02 mmol; 0.10 eq.) was added. The flask was capped and purged with N$_2$ (g) for 15 min. The reaction mixture was then heated to 110° C. for 4 h, and then allowed to cool to RT. The reaction mixture was filtered through Celite, and the Celite was washed with MeOH/DCM. The filtrate was concentrated to a brown oil that was subjected to preparative HPLC (Interchim system; 120 g C-18 silica, mobile phase A: 0.1% formic acid in water; mobile phase B: acetonitrile). The purer fractions were concentrated and lyophilized to afford 2-{4-[2-(1-Methyl-1H-pyrazol-4-yl)-3H-imidazo[4,5-b]pyridin-7-yl]-phenyl}-pyrrolidine-1-carboxylic acid tert-butyl ester as a tan solid (62 mg, 65% yield). LC-MS: 444.2 [MH]. HPLC: 87% purity. 1H NMR (500 MHz, methanol-d$_4$): δ 8.35 (s, 1H), 8.19 (s, 1H), 7.90 (br m, 1H), 7.68 (br m, 1H), 7.65 (m, 1H), 7.55 (m, 1H), 7.42 (m, 2H), 4.96 (br m, 2H), 4.00 (s, 3H), 3.64 (br m, 3H), 2.66 (br m, 2H), 1.48 (s, 4H), 1.26 (s, 5H).

2-(1-Methyl-1H-pyrazol-4-yl)-7-(4-pyrrolidin-2-yl-phenyl)-3H-imidazo[4T5-b]pyridine 2-{4-[2-(1-Methyl-1H-pyrazol-4-yl)-3H-imidazo[4,5-b]pyridin-7-yl]-phenyl}-pyrrolidine-1-carboxylic acid tert-butyl ester (62.00 mg; 0.14 mmol; 1.00 eq.), hydrogen chloride (6.00 ml; 12.00 mmol; 86.04 eq.), and methanol (1.20 ml; 29.62 mmol; 212.40 eq.) were combined under N$_2$ (g), the vial was capped, and reaction mixture was stirred at RT 3 h. After this time, LC-MS showed full conversion to product. The solvent was evaporated under reduced pressure and the residue wasp unified by flash column chromatography (Biotage, 28 g KPNH silica, 0-50% MeOH/ethyl acetate). 2-(1-Methyl-1H-pyrazol-4-yl)-7-(4-pyrrolidin-2-yl-phenyl)-3H-imidazo[4,5-b]pyridine was obtained as a brown residue (12.4 mg, 26% yield). LC-MS: 345.1 [M+H]+. HPLC: 100% purity. $^1$H NMR (500 MHz, Methanol-d4): δ 8.36 (br s, 2H), 8.19 (d, 2H), 8.07 (br s, 1H), 7.45 (br s, 2H), 7.35 (br s, 1H), 4.20 (br t, 2H), 3.23 (m, 2H), 3.07 (m, 2H), 2.23 (m, 1H).

(4-tert-Butyl-phenyl)-(2-{4-[2-(1-methyl-1H-pyrazol-4-yl-3H-imidazo[4,5-b]pyridin-7-yl]-phenyl}-pyrrolidin-1-yl)-methanone 2-(1-Methyl-1H-pyrazol-4-yl)-7-(4-pyrrolidin-2-yl-phenyl)-3H-imidazo[4,5-b]pyridine (12.00 mg; 0.03 mmol; 1.00 eq.), 4-tert-butyl-benzoyl chloride (0.02 ml; 0.11 mmol; 3.16 eq.), sodium hydrogen carbonate (4.39 mg; 0.05 mmol; 1.50 eq.), water (0.01 ml; 0.56 mmol; 15.93 eq.), and THF (0.13 ml; 1.60 mmol; 46.05 eq.) were combined at 0° C. (ice bath) and capped under $N_2$ (g). The reaction mixture was allowed to warm to RT overnight. The reaction mixture was concentrated and subjected to preparative HPLC (Interchim system; 120 g C-18 silica, mobile phase A: 0.1% formic acid in water; mobile phase B: acetonitrile). The pure fractions were concentrated and lyophilized to afford (4-tert-butyl-phenyl)-(2-{4-[2-(1-methyl-1H-pyrazol-4-yl)-3H-imidazo[4,5-b]pyridin-7-yl]-phenyl}-pyrrolidin-1-yl)-methanone as a yellow solid (17 mg, 100% yield). LC-MS: 505.2 $[M+H]^+$. HPLC: 95.4% purity. $^1$H NMR (500 MHz, DMSO-$d_6$): δ7.65 (m, 2H), 7.15 (d, 2H), 7.09 (m, 2H), 5.76 (m, 6H), 4.56 (br t, 1H), 3.16 (br m, 2H), 2.93 (br m, 2H), 1.79 (m, 2H), 0.57 (s, 9H).

Example 122: 5-(Tetrahydro-pyran-4-yl)-[1,3,4]oxadiazole-2-carboxylic acid 2-fluoro-4-{2-[1-(2-morpholin-4-yl-ethyl)-1H-pyrazol-4-yl]-3H-imidazo[4,5-b]pyridin-7-yl}-benzylamide (122)

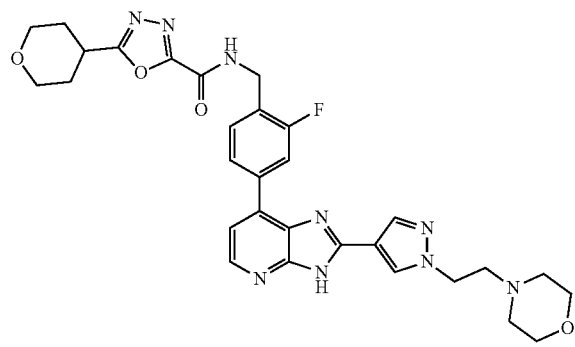 [SMILES: O=C(NCc1ccc(-c2ccnc3[nH]c(-c4cnn(CCN5CCOCC5)c4)nc23)cc1F)c1nnc(C2CCOCC2)o1]

7-Chloro-2-[1-(2-morpholin-4-yl-ethyl)-1H-pyrazol-4-yl]-3H-imidazo[4,5-b]pyridine 2-Bromo-7-chloro-3H-imidazo[4,5-b]pyridine (200.00 mg; 0.86 mmol; 1.00 eq.), 4-{2-[4-(4,4,5,5-Tetramethyl-[1,3,2]dioxaborolan-2-yl)-pyrazol-1-yl]-ethyl}-morpholine (317.15 mg; 1.03 mmol; 1.20 eq.), disodium carbonate (1.72 ml; 1.72 mmol; 2.00 eq.), sodium acetate (1.72 ml; 1.72 mmol; 2.00 eq.), and ACN (4.30 ml; 82.33 mmol; 95.69 eq.) were combined under $N_2$ (g) and cyclopentyl(diphenyl)phosphane; dichloromethane; dichloropalladium; iron (105.39 mg; 0.13 mmol; 0.15 eq.) was added. The flask was capped and purged with $N_2$ (g) for 15 min, then heated to 120° C. for 2 h, after which it was then cooled to RT. The reaction mixture was filtered through Celite and the Celite pad was washed with MeOH/DCM. The filtrate was concentrated to afford a brown residue which was dissolved in DCM and subjected to flash chromatography (Biotage, 0 to 20% MeOH/DCM, 55 g KPNH-silica). The product eluted with 10% MeOH/DCM. 7-Chloro-2-[1-(2-morpholin-4-yl-ethyl)-1H-pyrazol-4-yl]-3H-imidazo[4,5-b]pyridine was obtained as a brown solid (255 mg, 77% yield). LC-MS: 334.1 $[M+H]^+$. HPLC: 92.4% purity.

2-Fluoro-4-{2-[1-(2-morpholin-4-yl-ethyl)-1H-pyrazol-4-yl]-3H-imidazo[4,5-b]pyridin-7-yl}-benzylamine 2-Fluoro-4-{2-[1-(2-morpholin-4-yl-ethyl)-1H-pyrazol-4-yl]-3H-imidazo[4,5-b]pyridin-7-yl}-benzylamine (36.00 mg; 0.09 mmol; 1.00 eq.), 5-tert-butyl-[1,3,4]oxadiazole-2-carboxylic acid (18.90 mg; 0.11 mmol; 1.30 eq.), 2,4,6-tripropyl-[1,3,5,2,4,6]trioxatriphosphinane 2,4,6-trioxide (0.30 ml; 0.67 mmol; 7.83 eq.), DIPEA (0.04 ml; 0.26 mmol; 3.00 eq.), and ACN (0.45 ml; 8.62 mmol; 100.87 eq.) were combined under $N_2$ (g) and stirred at RT. The cloudy brown mixture turned into a clear brown solution within an hour. The reaction mixture was concentrated and subjected to preparative HPLC (Interchim system; 120 g C-18 silica, mobile phase A: 0.1% formic acid in water; mobile phase B: acetonitrile). The pure fractions were concentrated and lyophilized to afford 2-fluoro-4-{2-[1-(2-morpholin-4-yl-ethyl)-1H-pyrazol-4-yl]-3H-imidazo[4,5-b]pyridin-7-yl}-benzylamine as a beige solid (41 mg, 83% yield). LC-MS: 575.2 $[M+H]^+$. HPLC: 98.0% purity.

5-(Tetrahydro-pyran-4-yl)-[1,3,4]oxadiazole-2-carboxylic acid 2-fluoro-4-{2-[1-(2-morpholin-4-yl-ethyl)-1H-pyrazol-4-yl]-3H-imidazo[4,5-b]pyridin-7-yl}-benzylamide 2-Fluoro-4-{2-[1-(2-morpholin-4-yl-ethyl)-1H-pyrazol-4-yl]-3H-imidazo[4,5-b]pyridin-7-yl}-benzylamine (66.00 mg: 0.16 mmol; 1.00 eq.), 5-(tetrahydro-pyran-4-yl)-[1,3,4]oxadiazole-2-carboxylic acid ethyl ester (46.05 mg; 0.20 mmol; 1.30 eq.), ethyl-diisopropyl-amine (0.10 ml; 0.63 mmol; 4.00 eq.), and acetonitrile (0.50 ml) were combined and capped under $N_2$ (g) and stirred at RT overnight. The reaction mixture was concentrated and subjected to preparative HPLC (Interchim system; 120 g C-18 silica, mobile phase A: 0.1% formic acid in water; mobile phase B: acetonitrile). The purer fractions were concentrated and lyophilized to afford 5-(tetrahydro-pyran-4-yl)-[,3,4]oxadiazole-2-carboxylic acid 2-fluoro-4-{2-[1-(2-morpholin-4-yl-ethyl)-1H-pyrazol-4-yl]-3H-imidazo[4,5-b]pyridin-7-yl}-benzylamide as a light yellow solid (18.4 mg, 20% yield). LC-MS: 602.3 $[M+H]^+$. HPLC: 98.3% purity. $^1$H NMR (500 MHz, Methanol-d4): δ 8.51 (br s, 1H), 8.37 (br m, 1H), 8.30 (br s, 1H), 7.87 (d, 1H), 7.80 (d, 1H), 7.47 (br m, 1H), 4.74 (br m, 3H), 4.01 (m, 2H), 3.92 (br m, 2H), 3.71 (br m, 2H), 2.06 (br m, 2H), 1.96 (q, 2H), 1.38 (s, 9H).

Example 124: 3-tert-Butyl-[1,2,4]oxadiazole-5-carboxylic acid 2-fluoro-4-{2-[1-(tetrahydro-pyran-4-yl)-1H-pyrazol-4-yl]-3H-imidazo[4,5-b]pyridin-7-yl}-benzylamide (124)

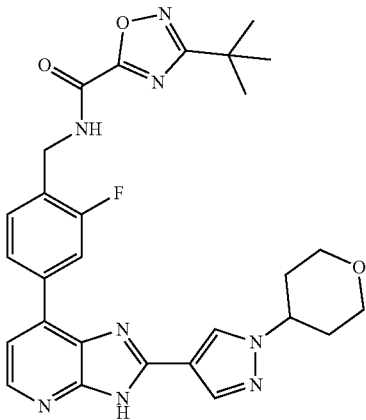 [SMILES: CC(C)(C)c1noc(C(=O)NCc2ccc(-c3ccnc4[nH]c(-c5cnn(C6CCOCC6)c5)nc34)cc2F)n1]

7-Chloro-2-[1-(tetrahydro-pyran-4-yl)-1H-pyrazol-4-yl]-3H-imidazo[4,5-b]pyridine 2-Bromo-7-chloro-3H-imidazo[4,5-b]pyridine (450.00 mg; 1.94 mmol; 1.00 eq.), 1-(tetrahydro-pyran-4-yl)-4-(4,4,5,5-tetramethyl-[1,3,2]dioxaborolan-2-yl)-1H-pyrazole (646.13 mg; 2.32 mmol; 1.20 eq.), disodium carbonate (3.87 ml; 3.87 mmol; 2.00 eq.), sodium acetate (3.87 ml; 3.87 mmol; 2.00 eq.), and ACN (10.00 ml; 191.46 mmol; 98.91 eq.) were combined under $N_2$ (g) and then cyclopentyl (diphenyl)phosphane; dichloromethane; dichloropalladium; iron (237.12 mg; 0.29 mmol; 0.15 eq.) were added. The flask was capped and purged with $N_2$ (g) for 15 min. The reaction mixture was heated to 120° C. for 2 h, and then allowed to cool to RT. The reaction mixture was filtered through Celite, which was then washed with MeOH/DCM. The filtrate was concentrated to a brown oil, which was subjected to flash chromatography twice (Biotage, 0 to 20% MeOH/DCM, 55 g KPNH silica) to afford 7-chloro-2-[1-(tetrahydro-pyran-4-yl)-1H-pyrazol-4-yl]-3H-imidazo[4,5-b]pyridine as a brown solid (513 mg, 87% yield). LC-MS: 304.1 [M+2H]2+. HPLC: 90.2% purity.

2-Fluoro-4-{2-[1-(tetrahydro-pyran-4-yl)-1H-pyrazol-4-yl]-3H-imidazo[4,5-b]pyridin-7-yl}-benzylamine 7-Chloro-2-[1-(tetrahydro-pyran-4-yl)-1H-pyrazol-4-yl]-3H-imidazo[4,5-b]pyridine (120.00 mg; 0.40 mmol; 1.00 eq.), [4-(aminomethyl)-3-fluoro-phenyl]boronic acid hydrochloride (162.31 mg; 0.79 mmol; 2.00 eq.), dipotassium carbonate (218.40 mg; 1.58 mmol; 4.00 eq.), ACN (2.00 ml; 38.29 mmol; 96.93 eq.), and water (0.20 ml; 11.10 mmol; 28.10 eq.) were combined under $N_2$ (g) as cyclopentyl (diphenyl)phosphane; dichloromethane; dichloropalladium; iron (32.26 mg; 0.04 mmol; 0.10 eq.) were added. The flask was capped and purged with $N_2$ (g) for 15 min, then heated to 120° C. in the Biotage microwave for 2 h (high absorption), and then cooled to RT. The reaction mixture was loaded directly onto KPNH silica and subjected to flash chromatography (Biotage system; 0-20% MeOH/DCM) to afford 2-fluoro-4-{2-[1-(tetrahydro-pyran-4-yl)-1H-pyrazol-4-yl]-3H-imidazo[4,5-b]pyridin-7-yl}-benzylamine as a brown solid (134 mg, 87% yield). LC-MS: 397 [M+2H]2+.

3-tert-Butyl-[124]oxadiazole-5-carboxylic acid 2-fluoro-4-{2-[1-(tetrahydro-pyran-4-yl)-1H-pyrazol-4-yl]-3H-imidazo[4,5-b]pyridin-7-yl}-benzylamide 2-Fluoro-4-{2-[1-(tetrahydro-pyran-4-yl)-1H-pyrazol-4-yl]-3H-imidazo[4,5-b]pyridin-7-yl}-benzylamine (30.00 mg; 0.08 mmol; 1.00 eq.), 3-tert-Butyl-[1,2,4]oxadiazole-5-carboxylic acid (18.60 mg; 0.11 mmol; 1.30 eq.), 2,4,6-tripropyl-[1,3,5,2,4,6]trioxatriphosphinane 2,4,6-trioxide (0.30 ml; 0.66 mmol; 7.83 eq.), ethyl-diisopropyl-amine (0.04 ml; 0.25 mmol; 3.00 eq.), and acetonitrile (0.50 ml) were combined under $N_2$ (g) and stirred at RT overnight. The reaction mixture was loaded onto Interchim column and subjected to preparative HPLC (Interchim, 120 g C-18 silica, 0-100% 0.1% formic acid (aq)/ACN) to afford 3-tert-butyl-[1,2,4]oxadiazole-5-carboxylic acid 2-fluoro-4-{2-[1-(tetrahydro-pyran-4-yl)-1H-pyrazol-4-yl]-3H-imidazo[4,5-b]pyridin-7-yl}-benzylamide as a beige solid (5 mg, 10% yield). LC-MS: 545.3 [M+H]$^+$. HPLC: 100% purity. $^1$H NMR (DMSO-d$_6$): 59.96 (br s, 2H), 8.56 (br s, @H), 8.33 (s, 1H), 8.22 (s, 1H), 7.60 (m, 1H), 7.53 (br s, 1H), 4.61 (br m, 2H), 4.56 (br m, 1H), 4.02 (d, 2H), 2.05 (br m, 6H), 1.36 (s, 9H).

Example 125: 5-tert-Butyl-[1,3,4]thiadiazole-2-carboxylic acid 2-fluoro-4-[2-(1-oxetan-3-yl-1H-pyrazol-4-yl)-3H-imidazo[4,5-b]pyridin-7-yl]-benzylamide (125)

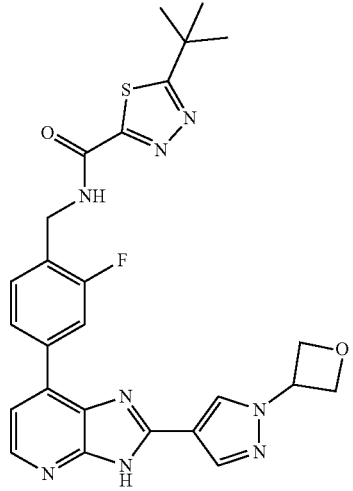 [SMILES: CC(C)(C)c1nnc(C(=O)NCc2ccc(-c3ccnc4[nH]c(-c5cnn(C6COC6)c5)nc34)cc2F)s1]

7-Chloro-2-(1-oxetan-3-yl-1H-pyrazol-4-yl)-3H-imidazo[4,5-b]pyridine

2-Bromo-7-chloro-3H-imidazo[4,5-b]pyridine (200.00 mg; 0.86 mmol; 1.00 eq.), 1-xxetan-3-yl-4-(4,4,5,5-tetramethyl-[1,3,2]dioxaborolan-2-yl)-1H-pyrazole (258.21 mg; 1.03 mmol; 1.20 eq.), disodium carbonate (1.72 ml; 1.72 mmol; 2.00 eq.), sodium acetate (1.72 ml; 1.72 mmol; 2.00 eq.), and ACN (4.30 ml; 82.33 mmol; 95.69 eq.) were combined under $N_2$ (g), then cyclopentyl(diphenyl)phosphane; dichloromethane; dichloropalladium; iron (105.39 mg; 0.13 mmol; 0.15 eq.) were added. The flask was capped and purged with N₂ (g) for 15 min. The reaction mixture was heated to 120° C. for 2 hours, and then allowed to cool to RT. The reaction mixture was filtered through Celite and the filtrate was concentrated to afford a brown residue that was dissolved in DCM and subjected to flash chromatography (Biotage, 0 to 20% MeOH/DCM, 55 g KPNH-silica) to afford 7-chloro-2-(1-oxetan-3-yl-1H-pyrazol-4-yl)-3H-imidazo[4,5-b]pyridine as a brown solid (263 mg, 94% yield). LC-MS: 276.0 [M+H]+. HPLC: 94.2% purity.

2-Fluoro-4-[2-(1-oxetan-3-yl-1H-pyrazol-4-yl)-3H-imidazo[4,5-b]pyridin-7-yl]-benzylamine 7-Chloro-2-(1-oxetan-3-yl-1H-pyrazol-4-yl)-3H-imidazo[4,5-b]pyridine (276.80 mg; 1.00 mmol; 1.00 eq.), [4-(aminomethyl)-3-fluoro-phenyl]boronic acid hydrochloride (412.49 mg; 2.01 mmol; 2.00 eq.), dipotassium carbonate (555.04 mg; 4.02 mmol: 4.00 eq.), THF (10.00 ml; 123.43 mmol; 122.94 eq.), and water (1.00 ml; 55.51 mmol; 55.29 eq.) were combined under N₂ (g) as cyclopentyl(diphenyl) phosphane; dichloromethane; dichloropalladium; iron (81.99 mg; 0.10 mmol; 0.10 eq.) were added. The flask was capped and purged with N₂ (g) for 15 min, then heated for 2 h in the Biotage microwave at 130° C. (high absorption), and then allowed to cool to RT. The mixture was filtered through Celite and the Celite pad was washed with MeOH/DCM. The filtrate was concentrated to give a brown residue that was subjected to flash chromatography (Biotage, 55 g KPNH silica, 0-20% MeOH/DCM) to afford 2-fluoro-4-[2-(1-oxetan-3-yl-1H-pyrazol-4-yl)-3H-imidazo[4,5-b]pyridin-7-yl]-benzylamine as a brown solid (298.3 mg, 82% yield). LC-MS: 366.2 [M+2H]2+.

5-tert-Butyl-[1,3,4]thiadiazole-2-carboxylic acid 2-fluoro-4-[2-(1-oxetan-3-yl-1H-pyrazol-4-yl)-3H-imidazo[4,5-b]pyridin-7-yl]-benzylamide 2-Fluoro-4-[2-(1-oxetan-3-yl-1H-pyrazol-4-yl)-3H-imidazo[4,5-b]pyridin-7-yl]-benzylamine (40.00 mg; 0.11 mmol; 1.00 eq.), 5-tert-butyl-[1,3,4]thiadiazole-2-carboxylic acid sodium (28.57 mg; 0.14 mmol; 1.25 eq.), bromo(tripyrrolidin-1-yl)phosphonium hexafluorophosphate (63.97 mg: 0.14 mmol: 1.25 eq.), ethyl-diisopropyl-amine (0.05 ml; 0.33 mmol; 3.00 eq.), and DMF (2.00 ml; 25.94 mmol; 236.29 eq.) were combined, capped under N₂ (g), and stirred at RT overnight. The reaction mixture was loaded onto an Interchim column and subjected to preparative HPLC (120 g C-18 silica, 0-100% 0.1% formic acid (aq)/ACN) to afford 5-tert-butyl-[1,3,4]thiadiazole-2-carboxylic acid 2-fluoro-4-[2-(1-oxetan-3-yl-1H-pyrazol-4-yl)-3H-imidazo[4,5-b]pyridin-7-yl]-benzylamide as a beige solid (9 mg, 15% yield). LC-MS: 533.2 [M+H]+. HPLC: 99.0% purity. ¹H NMR (DMSO-d₆) δ 9.80 (br m, 1H), 8.64 (s, 1H), 8.33 (s, 1H), 8.20 (m, 1H), 8.08 (m, 1H), 7.52 (m, 2H), 5.73 (m, 1H), 4.98 (m, 3H), 4.63 (d, 2H), 3.03 (br m, 2H), 1.48 (s, 9H).

Example 126: 5-tert-Butyl-[1,3,4]oxadiazole-2-carboxylic acid 2-fluoro-4-{2-[1-(tetrahydro-pyran-4-yl)-1H-pyrazol-4-yl]-3H-imidazo[4,5-b]pyridin-7-yl}-benzylamide (126)

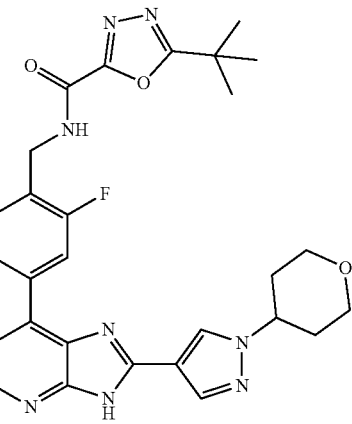

7-Chloro-2-[1-(2-morpholin-4-yl-ethyl)-1H-pyrazol-4-yl]-3H-imidazo[4,5-b]pyridine 2-Bromo-7-chloro-3H-imidazo[4,5-b]pyridine (450.00 mg; 1.94 mmol; 1.00 eq.), 1-(tetrahydro-pyran-4-yl)-4-(4,4,5,5-tetramethyl-[1,3,2]dioxaborolan-2-yl)-1H-pyrazole (646.13 mg; 2.32 mmol; 1.20 eq.), disodium carbonate (3.87 ml; 3.87 mmol; 2.00 eq.), sodium acetate (3.87 ml; 3.87 mmol; 2.00 eq.), and ACN (10.00 ml; 191.46 mmol; 98.91 eq.) were combined under N₂ (g) and then cyclopentyl (diphenyl)phosphane; dichloromethane; dichloropalladium; iron (237.12 mg; 0.29 mmol; 0.15 eq.) were added. The flask was capped and then purged with N₂ (g) for 15 min. The reaction mixture was heated to 120° C. for 2 h and allowed to cool to to RT. The reaction mixture was filtered through Celite and the pad was washed with MeOH/DCM. The filtrated was concentrated to a brown oil, which was subjected to flash chromatography twice (Biotage, 0 to 20% MeOH/DCM, 55 g KPNH silica) to afford 7-chloro-2-[1-(2-morpholin-4-yl-ethyl)-1H-pyrazol-4-yl]-3H-imidazo[4,5-b]pyridine as a brown solid (513 mg, 87% yield). LC-MS: 304.1 [M+H]⁺. HPLC: 90.2% purity.

2-Fluoro-4-{2-[1-(tetrahydro-pyran-4-yl)-1H-pyrazol-4-yl]-3H-imidazo[4,5-b]pyridin-7-yl}-benzylamine 7-Chloro-2-[1-(tetrahydro-pyran-4-yl)-1H-pyrazol-4-yl]-3H-imidazo[4,5-b]pyridine (120.00 mg; 0.40 mmol; 1.00 eq.), [4-(aminomethyl)-3-fluoro-phenyl]boronic acid hydrochloride (162.31 mg; 0.79 mmol; 2.00 eq.), dipotassium carbonate (218.40 mg; 1.58 mmol; 4.00 eq.), ACN (2.00 ml; 38.29 mmol; 96.93 eq.), and water (0.20 ml; 11.10 mmol; 28.10 eq.) were combined under N₂ (g) and then cyclopentyl (diphenyl)phosphane; dichloromethane; dichloropalladium; iron (32.26 mg; 0.04 mmol; 0.10 eq.) were added. The flask was capped and purged with N₂ (g) for 15 min, then heated to 120° C. in the Biotage microwave for 2 h (high absorption) and then cooled to RT. The reaction mixture was loaded onto 55 g KPNH silica and subjected to flash chromatography (Biotage system; 0-20% MeOH/DCM) to afford 2-fluoro-4-{2-[1-(tetrahydro-pyran-4-yl)-1H-pyrazol-4-yl]-

3H-imidazo[4,5-b]pyridin-7-yl}-benzylamine as a brown solid (134 mg, 87% yield). LC-MS: 394.0 [M+2H]2+.

5-tert-Butyl-[1,3,4]oxadiazole-2-carboxylic acid 2-fluoro-4-{2-[1-(tetrahydro-pyran-4-yl)-1H-pyrazol-4-yl]-3H-imidazo[4,5-b]pyridin-7-yl}-benzylamide 2-Fluoro-4-{(2-[1-(tetrahydro-pyran-4-yl)-1H-pyrazol-4-yl]-3H-imidazo[4,5-b]pyridin-7-yl}-benzylamine (30.00 mg; 0.08 mmol; 1.00 eq.), 5-tert-butyl-[,3,4]oxadiazole-2-carboxylic acid (18.60 mg; 0.11 mmol; 1.30 eq.), ethyl-diisopropyl-amine (0.04 ml; 0.25 mmol; 3.00 eq.), and acetonitrile (0.50 ml) were capped under $N_2$ (g), and stirred at RT overnight. The reaction mixture was subjected to preparative HPLC (Interchim, 120 g C-18 silica, 0-100% 0.1% formic acid (aq)/ACN) to afford 5-tert-butyl-[1,3,4]oxadiazole-2-carboxylic acid 2-fluoro-4-{2-[1-(tetrahydro-pyran-4-yl)-1H-pyrazol-4-yl]-3H-imidazo[4,5-b]pyridin-7-yl}-benzylamide as a beige solid (7.1 mg, 16% yield). LC-MS: 545.3 [M+H]$^+$. HPLC: 100% purity. $^1$H NMR (DMSO-$d_6$): δ 9.88 (br s, 1H), 8.56 (s, 1H), 8.34 (s, 1H), 8.22 (s, 1H), 7.60 (br m, 2H), 0.54 (br s, 1H), 5.96 (s, 1H), 4.61 (m, 4H), 3.99 (m, 2H), 2.05 (br m, 4H), 1.37 (s, 9H).

Example 127: 5-tert-Butyl-[1,2,4]oxadiazole-3-carboxylic acid 2-fluoro-4-{2-[1-(tetrahydro-pyran-4-yl)-1H-pyrazol-4-yl]-3H-imidazo[4,5-b]pyridin-7-yl}-benzylamide (127)

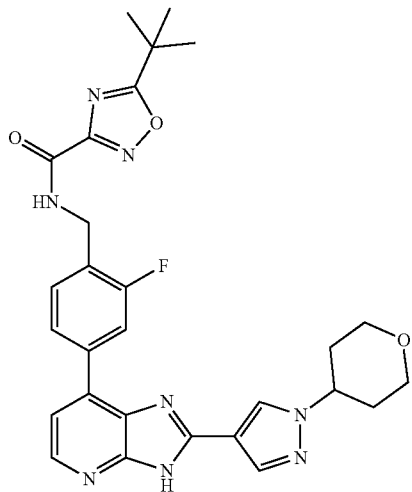 [SMILES: CC(C)(C)c1nc(C(=O)NCc2ccc(-c3ccnc4[nH]c(-c5cnn(C6CCOCC6)c5)nc34)cc2F)no1]

2-Fluoro-4-{2-[1-(tetrahydro-pyran-4-yl)-1H-pyrazol-4-yl]-3H-imidazo[4,5-b]pyridin-7-yl}-benzylamine (30.00 mg; 0.08 mmol; 1.00 eq.), 5-tert-butyl-[1,2,4]oxadiazole-3-carboxylic acid (18.60 mg; 0.11 mmol; 1.30 eq.), 2,4,6-tripropyl-[1,3,5,2,4,6]trioxatriphosphinane 2,4,6-trioxide (0.30 ml; 0.66 mmol: 7.83 eq.), ethyl-diisopropyl-amine (0.04 ml; 0.25 mmol; 3.00 eq.), and acetonitrile (0.50 ml) were combined under $N_2$ (g), capped, and stirred at RT overnight. The reaction mixture was subjected to preparative HPLC (Interchim, 120 g C-18 silica, 0-100% 0.1% formic acid (aq)/ACN) to afford 5-tert-butyl-[1,2,4]oxadiazole-3-carboxylic acid 2-fluoro-4-{2-[1-(tetrahydro-pyran-4-yl)-1H-pyrazol-4-yl]-3H-imidazo[4,5-b]pyridin-7-yl}-benzylamide as a beige solid (19 mg, 42% yield). HPLC: 100% purity. $^1$H NMR (DMSO-$d_6$): δ 9.53 (br t, 1H), 8.56 (s, 1H), 8.32 (m, 1H), 8.21 (s, 1H), 8.18 (br m, 1H), 8.10 (br m, 1H), 7.52 (m, 2H), 4.60 (br m, 2H), 9.55 (m, 1H), 4.01 (br d, 2H), 2.03 (br m, 6H), 1.43 (s, 9H).

3-tert-Butyl-[1,2,4]oxadiazole-5-carboxylic acid 2-fluoro-4-[2-(1-oxetan-3-yl-1H-pyrazol-4-yl)-3H-imidazo[4,5-b]pyridin-7-yl]-benzylamide 2-Fluoro-4-[2-(1-oxetan-3-yl-1H-pyrazol-4-yl)-3H-imidazo[4,5-b]pyridin-7-yl]-benzylamine (40.00 mg; 0.11 mmol; 1.00 eq.), 3-tert-butyl-[1,2,4]oxadiazole-5-carboxylic acid (23.35 mg: 0.14 mmol; 1.25 eq.), bromo(tripyrrolidin-1-yl)phosphonium hexafluorophosphate (63.97 mg; 0.14 mmol; 1.25 eq.), ethyl-diisopropyl-amine (0.05 ml; 0.33 mmol; 3.00 eq.), and DMF (2.00 ml) were combined at RT, capped under $N_2$ (g) and stirred overnight. The reaction mixture was subjected to preparative HPLC (Interchim, 120 g C-18 silica, 0-100% 0.1% formic acid (aq)/ACN) to afford 3-tert-butyl-[1,2,4]oxadiazole-5-carboxylic acid 2-fluoro-4-[2-(1-oxetan-3-yl-1H-pyrazol-4-yl)-3H-imidazo[4,5-b]pyridin-7-yl]-benzylamide as a white solid (18.6 mg, 33% yield). LC-MS: 517.3 [M+H]$^+$. HPLC: 100% purity. $^1$H NMR (500 MHz, DMSO-d6): δ 9.94 (br m, 1H), 8.63 (s, 1H), 8.32 (br m, 2H), 8.19 (br s, 1H), 8.10 (br s, 1H), 7.59 (br t, 1H), 7.53 (br m, 1H), 5.72 (br m, 1H), 4.95 (br m, 3H), 4.61 (br m, 2H), 1.37 (s, 9H).

Example 129: 5-(tert-butyl)-N-(2-fluoro-4-(2-(1-(oxetan-3-yl)-1H-pyrazol-4-yl)-3H-imidazo[4,5-b]pyridin-7-yl)benzyl)-1,2,4-oxadiazole-3-carboxamide (129)

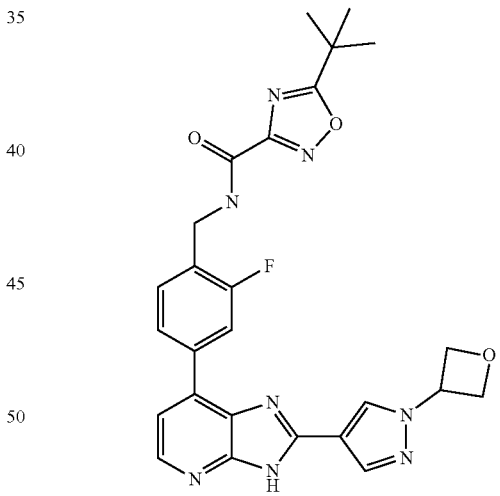

2-Fluoro-4-[2-(1-oxetan-3-yl-1H-pyrazol-4-yl)-3H-imidazo[4,5-b]pyridin-7-yl]-benzylamine (40.00 mg; 0.11 mmol; 1.00 eq.), 5-tert-butyl-[1,2,4]oxadiazole-3-carboxylic acid (23.35 mg; 0.14 mmol; 1.25 eq.), bromo(tripyrrolidin-1-yl)phosphonium hexafluorophosphate (63.97 mg: 0.14 mmol; 1.25 eq.), ethyl-diisopropyl-amine (0.05 ml; 0.33 mmol; 3.00 eq.), and DMF (2.00 ml; 25.94 mmol; 236.29 eq.) were combined at RT and capped under $N_2$ (g). The reaction mixture was stirred overnight and then subjected to preparative HPLC (Interchim, 120 g C-18 silica, 0-100% 0.1% FA (aq)/ACN) to afford 5-tert-butyl-[1,2,4]oxadiazole-3-carboxylic acid 2-fluoro-4-[2-(1-oxetan-3-yl-1H-pyrazol-4-yl)-3H-imidazo[4,5-b]pyridin-7-yl]-benzylamide as a white fluffy solid (26.5 mg, 27% yield). LC-MS: 516.4 [MH]. HPLC: 98.9% purity. $^1$H NMR (500 MHz, DMSO-$d_6$): δ 9.53 (br m, 1H), 8.63 (s, 1H), 8.32 (s, 2H), 8.18 (br m, 1H), 8.10 (br m, 1H), 7.53 (br m, 2H), 5.72 (br m, 1H), 4.95 (br m, 4H), 4.60 (br m, 2H), 1.43 (s, 9H).

Example 130: 4,5,6,7-Tetrahydro-benzo[b]thiophene-2-carboxylic acid 4-[2-(1-ethyl-1H-pyrazol-4-yl)-3H-imidazo[4,5-b]pyridin-7-yl]-2-fluoro-benzylamide (130)

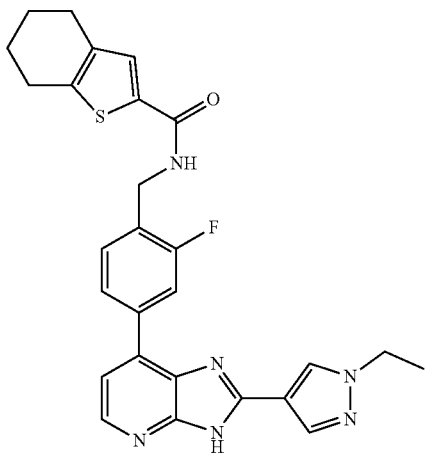 [SMILES: CCn1cc(-c2nc3c(-c4ccc(CNC(=O)c5cc6c(s5)CCCC6)c(F)c4)ccnc3[nH]2)cn1]

7-chloro-2-(1-ethyl-1H-pyrazol-4-yl)-3H-imidazo[4,5-b]pyridine

2-Bromo-7-chloro-3H-imidazo[4,5-b]pyridine (2.15 mmol; 1.00 eq.; 500.00 mg), 1-Ethyl-4-(4,4,5,5-tetramethyl-[1,3,2]dioxaborolan-2-yl)-1H-pyrazole (2.58 mmol: 1.20 eq.; 573.23 mg), and 1,1'-bis(diphenylphosphino)ferrocene-palladium(ii)dichloride dichloromethane complex (0.43 mmol; 0.20 eq.; 351.29 mg). The tube was sealed and flushed with Ar. To the reaction mixture was added potassium carbonate (5.38 mmol; 2.50 eq.; 743.15 mg), dioxane, and water via syringe. The reaction tube was degassed (vacuum followed by nitrogen) and heated to 120 C for 2 h in microwave. The reaction was cooled to room temperature and the catalyst was removed via filtration. The filtrant was diluted with 50 mL ETOAc at which point a gray solid formed. The solid was removed via filtration and dried on the filter. LC-MS is consistent with desired product. Gives 7-Chloro-2-(1-ethyl-1H-pyrazol-4-yl)-3H-imidazo[4,5-b]pyridine (126.00 mg; 0.46 mmol). MS: m/z=248.7 [M+H]$^+$.

(4-(2-(1-ethyl-1H-pyrazol-4-yl)-3H-imidazo[4,5-b]pyridin-7-yl)-2-fluorophenyl)methanamine To a 20 mL reaction tube with stir bar was added 7-Chloro-2-(1-ethyl-1H-pyrazol-4-yl)-3H-imidazo[4,5-b]pyridine (0.97 mmol; 1.00 eq.; 240.00 mg), 4-(aminomethyl)-3-fluorophenylboronic acid, HCl (1.26 mmol; 1.30 eq.; 258.76 mg), 1,1'-bis(diphenylphosphino)ferrocene-palladium(ii)dichloride dichloromethane complex (0.10 mmol; 0.10 eq.: 79.13 mg) along with potassium carbonate (2.91 mmol; 3.00 eq.; 401.75 mg), dioxane (46.94 mmol; 48.45 eq.; 4136.00 mg; 4.00 ml) was added to the solids followed by water (55.51 mmol; 57.29 eq.; 1000.00 mg; 1.00 ml). The reaction tube was vacuum evacuated and then degassed with nitrogen. The mixture was then heated to 140 C overnight in a metal heating block. Filtered using one of the 45 micron filters to remove the catalyst. The reaction was then purified on 75 g of silica using a gradient of 0-10% MeOH/EtOAc for 10 CV's then increased to 20% MeOH for 4 CV then increased to 50% MeOH/EtOAc at which point the desired product eluted as a wide peak (254 nm). Combined relevant fractions and concentrated to dryness to give 4-[2-(1-Ethyl-1H-pyrazol-4-yl)-3H-imidazo[4,5-b]pyridin-7-yl]-2-fluoro-benzylamine (221.00 mg; 0.64 mmol). MS: m/z=337 [M+H]$^+$. 1H NMR (400 MHz, DMSO-$d_6$) δ 8.51 (d, J=6.7 Hz, 1H), 8.39-8.00 (m, 4H), 7.67 (t, J=8.0 Hz, 1H), 7.51 (br. s, 1H), 4.26 (q, J=7.5 Hz, 2H), 3.35 (s, 2H), 1.61-1.34 (m, 3H).

4,5,6,7-Tetrahydro-benzo[b]thiophene-2-carboxylic acid 4-[2-(1-ethyl-1H-pyrazol-4-yl)-3H-imidazo[4,5-b]pyridin-7-yl]-2-fluoro-benzylamide 4-[2-(1-Ethyl-1H-pyrazol-4-yl)-3H-imidazo[4,5-b]pyridin-7-yl]-2-fluoro-benzylamine (0.25 mmol: 1.00 eq.: 120.00 mg) was combined with 2,4,6-Tripropyl-[1,3,5,2,4,6]trioxatriphosphinane 2,4,6-trioxide (0.30 mmol; 1.20 eq.; 190.70 mg; 0.19 ml) DIPEA (0.75 mmol; 3.00 eq.: 96.83 mg: 0.12 ml)n into DCM, was then added and the reaction was stirred at RT for 2 hrs. Note: Solubility of the starting material was very poor in DCM. Added a few drops of anhydrous DMF to dissolve solids. Added 20 mg of and 100 uL of 2,4,6-Tripropyl-[1,3,5,2,4,6]trioxatriphosphinane 2,4,6-trioxide (0.30 mmol; 1.20 eq.; 190.70 mg; 0.19 ml) and continued stirring for 5 hrs. The reaction was diluted with 1 mL DMSO then purified on the ISCO Puriflash system on 125 g C18 using a gradient of 5-100% CH3CN/H2O (0.1% NH$_4$OH). Fractions containing the desired product were frozen then concentrated to dryness on the Lyophilizer to give 4,5,6,7-Tetrahydro-benzo[b]thiophene-2-carboxylic acid 4-[2-(1-ethyl-1H-pyrazol-4-yl)-3H-imidazo[4,5-b]pyridin-7-yl]-2-fluoro-benzylamide (8.60 mg; 0.02 mmol). MS: m/z=337.4 [M+H]$^+$. $^1$H NMR (400 MHz, DMSO-$d_6$) δ 13.43 (s, 1H), 8.93 (s, 1H), 8.64-8.02 (m, 5H), 7.73-7.28 (m, 2H), 4.47-4.37 (m, 2H), 3.96 (s, 3H), 2.79-2.51 (m, 4H), 2.10-1.39 (m, 4H) 1.89-1.47 (m, 3H).

Example 131: 5-tert-Butyl-[1,2,4]oxadiazole-3-carboxylic acid 4-[2-(1-ethyl-1H-pyrazol-4-yl)-3H-imidazo[4,5-b]pyridin-7-yl]-2-fluoro-benzylamide (131)

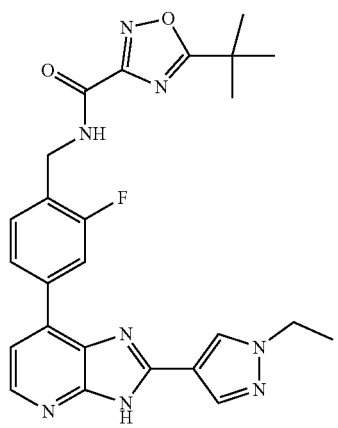

The title compound was made in manner to that described for example 130 using 4-[2-(1-Ethyl-1H-pyrazol-4-yl)-3H-imidazo[4,5-b]pyridin-7-yl]-2-fluoro-benzylamine (0.28 mmol; 1.00 eq.; 95.00 mg), 2,4,6-Tripropyl-[1,3,5,2,4,6]trioxatriphosphinane 2,4,6-trioxide (0.34 mmol; 1.20 eq.; 215.67 mg; 0.22 ml), DIPEA (0.85 mmol; 3.00 eq.; 109.51 mg; 0.14 ml), and 5-tert-Butyl-[1,2,4]oxadiazole-3-carboxylic acid (0.34 mmol: 1.20 eq.; 57.67 mg) 7 mg) to give 5-tert-Butyl-[1,2,4]oxadiazole-3-carboxylic acid 4-[2-(1-ethyl-1H-pyrazol-4-yl)-3H-imidazo[4,5-b]pyridin-7-yl]-2-fluoro-benzylamide (7.10 mg; 0.01 mmol). MS: m/z=489.2 [M+H]⁺. 1H NMR (400 MHz, DMSO-d₆) δ 9.52 (s, 1H), 8.37 (s, 2H), 8.12 (d, J=37.0 Hz, 3H), 7.50 (t, J=8.0 Hz, 1H), 7.34 (s, 1H), 4.59 (s, 2H), 4.23 (q, J=7.3 Hz, 2H), 1.73-1.16 (m, 12H).

Example 132: N-(2-fluoro-4-(2-(1-methyl-1H-pyrazol-4-yl)-3H-imidazo[4,5-b]pyridin-7-yl)benzyl)-4,5,6,7-tetrahydrobenzo[b]thiophene-2-carboxamide (132)

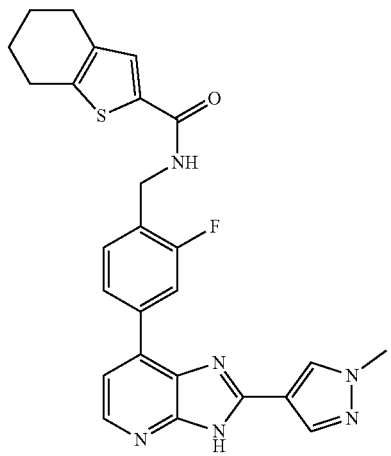 [SMILES: Cn1cc(-c2nc3c(-c4ccc(CNC(=O)c5cc6c(s5)CCCC6)c(F)c4)ccnc3[nH]2)cn1]

(4-(2-(1-ethyl-1H-pyrazol-4-yl)-3H-imidazo[4,5-b]pyridin-7-yl)-2-fluorophenyl)methanamine To a 20 mL reaction tube with stirbar was added 7-Chloro-2-(1-ethyl-1H-pyrazol-4-yl)-3H-imidazo[4,5-b]pyridine (0.50 mmol; 1.00 eq.; 123.00 mg), 4-(aminomethyl)-3-fluorophenylboronic acid, hcl (0.65 mmol; 1.30 eq.; 132.62 mg), and 1,1'-bis(diphenylphosphino)ferrocene-palladium (ii)dichloride dichloromethane complex (0.05 mmol; 0.10 eq.; 40.55 mg). The tube was sealed and flushed with argon. To the reaction mixture was added potassium phosphate, dibasic (1.49 mmol; 3.00 eq.; 1683.48 mg; 1.49 ml), Sodium acetate (1.49 mmol; 3.00 eq.; 1.49 ml), and ACN (191.46 mmol; 385.54 eq.; 7860.00 mg; 10.00 ml) via syringe. The reaction tube was degassed with argon and heated to 110 C overnight. The reaction was purified directly by flash chromatography (Silica; 2-10% MeOH/CH₂Cl₂) to give 4-[2-(1-Ethyl-1H-pyrazol-4-yl)-3H-imidazo[4,5-b]pyridin-7-yl]-2-fluoro-benzylamine (100.00 mg; 0.24 mmol). MS: m/z=337.3 [M+H]⁺. ¹H NMR (400 MHz, DMSO-d₆) δ 8.46 (s, 1H), 8.40-8.03 (m, 4H), 7.69 (t, J=8.0 Hz, 1H), 7.54 (s, 1H), 3.97 (s, 3H), 3.91 (2, 2H), 3.32 (br. s, 2H).

4,5,6,7-Tetrahydro-benzo[b]thiophene-2-carboxylic acid 2-fluoro-4-[2-(1-methyl-1H-pyrazol-4-yl)-3H-imidazo[4,5-b]pyridin-7-yl]-benzylamide The title compound was made in a manner similar to analogs described above using 2-Fluoro-4-[2-(1-methyl-1H-pyrazol-4-yl)-3H-imidazo[4,5-b]pyridin-7-yl]-benzylamine (0.22 mmol; 1.00 eq.; 100.00 mg), 2,4,6-Tripropyl-[1,3,5,2,4,6]trioxatriphosphinane 2,4,6-trioxide (0.26 mmol; 1.20 eq.; 165.83 mg; 0.17 ml), DIPEA (0.65 mmol; 3.00 eq.; 84.20 mg; 0.11 ml), 2 mL DCM. Give 4,5,6,7-Tetrahydro-benzo[b]thiophene-2-carboxylic acid 2-fluoro-4-[2-(1-methyl-1H-pyrazol-4-yl)-3H-imidazo[4,5-b]pyridin-7-yl]-benzylamide (12.10 mg; 0.02 mmol). MS: m/z=486.5 [M+H]⁺. ¹H NMR (400 MHz, DMSO-d₆) δ 13.40 (s, 1H), 8.93 (s, 1H), 8.65-8.07 (m, 5H), 7.73-7.28 (m, 2H), 4.47-4.37 (m, 2H), 3.96 (s, 3H), 2.79-2.51 (m, 4H), 2.10-1.39 (m, 4H).

Example 133: 5-tert-Butyl-isoxazole-3-carboxylic acid 4-[2-(1-ethyl-1H-pyrazol-4-yl)-3H-imidazo[4,5-b]pyridin-7-yl]-2-fluoro-benzylamide (133)

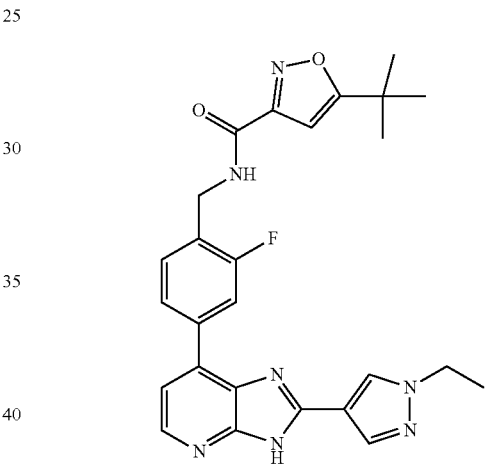

The title compound was made in a manner similar as to that described for example 130 using 4-[2-(1-Ethyl-1H-pyrazol-4-yl)-3H-imidazo[4,5-b]pyridin-7-yl]-2-fluoro-benzylamine (0.51 mmol; 1.00 eq.; 171.00 mg) was combined with DIPEA (1.53 mmol; 3.00 eq.: 197.11 mg; 0.25 ml) and 5-tert-Butyl-isoxazole-3-carboxylic acid (0.61 mmol; 1.20 eq.; 103.21 mg) into DCM. DIPEA (1.53 mmol; 3.00 eq.; 197.11 mg: 0.25 ml) was then added followed by 2,4,6-Tripropyl-[1,3,5,2,4,6]trioxatriphosphinane 2,4,6-trioxide (0.61 mmol; 1.20 eq.; 388.21 mg; 0.39 ml) (T3P). After 5 hours LC-MS shows about 15% desired product with starting material remaining. The reaction was quenched with MeOH (2 mL) then purified directly on waters reverse phase system using a gradient of 5-95% CH3CN/H2O (0.1% ammonium hydroxide) (4 injections of 1 mL each) to give 5-tert-Butyl-isoxazole-3-carboxylic acid 4-[2-(1-ethyl-1H-pyrazol-4-yl)-3H-imidazo[4,5-b]pyridin-7-yl]-2-fluoro-benzylamide (2.80 mg; 0.01 mmol). NMR has some solvent peaks in aliphatic region otherwise clean. Give 3 mg (1%) of the title compound as a. HPLC(Column): (percent area) %. MS: m/z=487.2 [M+H]⁺. 1H NMR (400 MHz, DMSO-d₆) δ 9.53 (s, 1H), 8.35 (s, 2H), 8.23-8.09 (m, 3H), 7.49 (t, J=8.0 Hz, 1H), 7.31 (s, 1H), 4.60 (s, 2H), 4.40-4.28 (m, 2H), 1.73-1.16 (m, 9H), 1.02-0.75 (m, 3H).

Example 134: 5-tert-Butyl-[1,2,4]oxadiazole-3-carboxylic acid 2-fluoro-4-[2-(1,2,3,6-tetrahydro-pyridin-4-yl)-3H-imidazo[4,5-b]pyridin-7-yl]-benzylamide (134)

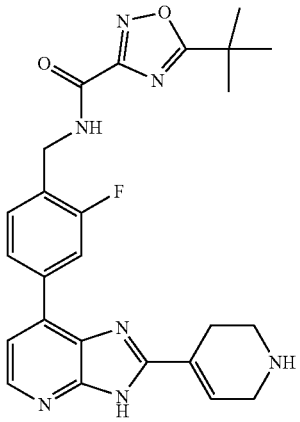 [SMILES: CC(C)(C)c1nc(C(=O)NCc2ccc(-c3ccnc4[nH]c(C5=CCNCC5)nc34)cc2F)no1]

4-[7-(4-{[(5-tert-Butyl-[1,2,4]oxadiazole-3-carbonyl)-amino]-methyl}-3-fluoro-phenyl)-3H-imidazo[4,5-b]pyridin-2-yl]-3,6-dihydro-2H-pyridine-1-carboxylic acid tert-butyl ester (0.19 mmol; 1.00 eq.; 120.00 mg) was combined with DCM (156.01 mmol; 831.50 eq.; 13250.00 mg; 5.00 ml) and then treated with TFA (134.62 mmol; 717.53 eq.; 15350.00 mg; 5.00 ml). The mixture was stirred under nitrogen for 1.5 hours. TLC (5% MeOH/EtOAC) shows reaction has gone to completion. The reaction was then concentrated to dryness and placed on the pump for 24 hours to give 5-tert-Butyl-[1,2,4]oxadiazole-3-carboxylic acid 2-fluoro-4-[2-(1,2,3,6-tetrahydro-pyridin-4-yl)-3H-imidazo[4,5-b]pyridin-7-yl]-benzylamide (11.18 mg; 0.02 mmol). MS: m/z=476.5 [M+H]$^+$. 1H NMR (400 MHz, Methanol-d$_4$) δ 8.38 (d, J=5.2 Hz, 1H), 7.93 (s, 1H), 7.59 (t, J=7.9 Hz, 1H), 7.49 (d, J=5.2 Hz, 1H), 6.89 (dd, J=3.8, 2.1 Hz, 1H), 4.74 (s, 2H), 3.90-3.81 (m, 2H), 3.47-3.33 (m, 2H), 3.03-2.85 (m, 2H), 1.51 (s, 9H).

Example 135: 5-(tert-butyl)-N-(4-(2-(1-ethyl-1H-pyrazol-4-yl)-3H-imidazo[4,5-b]pyridin-7-yl)-2-fluorobenzyl)-1,3,4-oxadiazole-2-carboxamide (135)

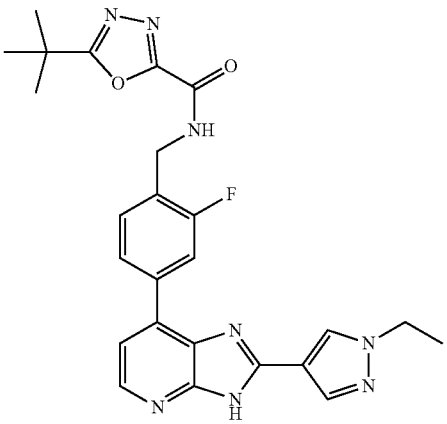 [SMILES: CCn1cc(-c2nc3c(-c4ccc(CNC(=O)c5nnc(C(C)(C)C)o5)c(F)c4)ccnc3[nH]2)cn1]

The title compound was made in manner to that described for example 130 using 4-[2-(1-Ethyl-1H-pyrazol-4-yl)-3H-imidazo[4,5-b]pyridin-7-yl]-2-fluoro-benzylamine (0.33 mmol; 1.00 eq.; 110.00 mg), 5-tert-Butyl-[1,3,4]oxadiazole-2-carboxylic acid (0.39 mmol; 1.20 eq.; 66.78 mg). DIPEA (0.98 mmol; 3.00 eq.; 126.80 mg; 0.16 ml), and 2,4,6-Tripropyl-[1,3,5,2,4,6]trioxatriphosphinane 2,4,6-trioxide (0.47 mmol; 1.44 eq.; 300.00 mg; 0.30 ml) (T3P) to give 5-tert-Butyl-[1,3,4]oxadiazole-2-carboxylic acid 4-[2-(1-ethyl-1H-pyrazol-4-yl)-3H-imidazo[4,5-b]pyridin-7-yl]-2-fluoro-benzylamide (24.10 mg; 0.05 mmol) as a white solid. MS: m/z=489.5 [M+H]$^+$. 1H NMR (400 MHz, DMSO-d6) d 13.21 (s, 1H), 9.53 (s, 1H), 8.37 (s, 2H), 8.12 (d, J=37.0 Hz, 3H), 7.51 (t, J=8.0 Hz, 1H), 7.33 (s, 1H), 4.55 (s, 2H), 4.21 (q, J=7.3 Hz, 2H), 1.75-1.17 (m, 12H).

Example 136: 3-(tert-butyl)-N-(2-fluoro-4-(2-(1,2,3,6-tetrahydropyridin-4-yl)-3H-imidazo[4,5-b]pyridin-7-yl)benzyl)-1,2,4-oxadiazole-5-carboxamide (136)

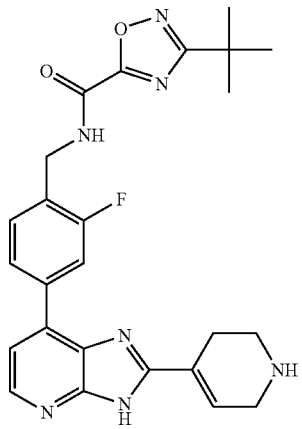 [SMILES: CC(C)(C)c1noc(C(=O)NCc2ccc(-c3ccnc4[nH]c(C5=CCNCC5)nc34)cc2F)n1]

1 tert-butyl 4-(7-(4-((3-(tert-butyl)-1,2,4-oxadiazole-5-carboxamido)methyl)-3-fluorphenyl)-3H-imidazo[4,5-b]pyridin-2-yl)-3,6-dihydropyridine-1(2H)-carboxylate 4-[7-(4-Aminomethyl-3-fluoro-phenyl)-3H-imidazo[4,5-b]pyridin-2-yl]-3,6-dihydro-2H-pyridine-1-carboxylic acid tert-butyl ester (0.12 mmol; 1.00 eq.; 51.00 mg) was combined with 3-tert-Butyl-[1,2,4]oxadiazole-5-carboxylic acid (0.14 mmol; 1.20 eq.; 24.59 mg) into a solution of DIPEA (0.36 mmol; 3.00 eq.; 46.69 mg; 0.06 ml) in DCM. 2,4,6-Tripropyl-[1,3,5,2,4,6]trioxatriphosphinane 2,4,6-trioxide (0.47 mmol; 3.91 eq.; 300.00 mg; 0.30 ml) (T3P) was then added and the reaction was stirred at RT for 1 hr. All solvent was then removed and the residue was dissolved in 5 mL DMSO. The reaction was then purified on 175 g of C18 (15 micron) column and a gradient of 20-100% CH$_3$CN/H2O (0.1% ammonium hydroxide) to give 4-[7-(4-{[(3-tert-Butyl-[1,2,4]oxadiazole-5-carbonyl)-amino]-methyl}-3-fluoro-phenyl)-3H-imidazo[4,5-b]pyridin-2-yl]-3,6-dihydro-2H-pyridine-1-carboxylic acid tert-butyl ester (13.00 mg; 0.02 mmol) as a white solid. MS: m/z=576.6 [M+H]$^+$.

3-(tert-butyl)-N-(2-fluoro-4-(2-(1,2,3,6-tetrahydro-pyridin-4-yl)-3H-imidazo[4,5-b]pyridin-7-yl)benzyl)-1,2,4-oxadiazole-5-carboxamide 4-[7-(4-{[(3-tert-Butyl-[1,2,4]oxadiazole-5-carbonyl)-amino]-methyl}-3-fluoro-phenyl)-3H-imidazo[4,5-b]pyridin-2-yl]-3,6-dihydro-2H-pyridine-1-carboxylic acid tert-butyl ester (0.04 mmol; 1.00 eq.; 24.00 mg) was combined with TFA (2.00 ml) into DCM (31.20 mmol; 831.50 eq.; 2650.00 mg; 2.00 ml). The mixture was stirred at RT for 2 hours. All solvent was then removed and the residue was purified on the Waters-2 Prep System using a gradient of 20-80% CHeCN/Water (0.1% Ammonium Hydroxde) over 27 minutes. The desired product elutes around 18 minutes. Fractions containing the desired product (as judged by LC-MS analysis) were combined then concentrated to dryness on the Genevac EZ-2 Plus to give 3-tert-Butyl-[1,2,4]oxadiazole-5-carboxylic acid 2-fluoro-4-[2-(1,2,3,6-tetrahydro-pyridin-4-yl)-3H-imidazo[4,5-b]pyridin-7-yl]-benzylamide (12.00 mg; 0.02 mmol). MS: m/z=576.6 [M+H]$^+$. $^1$H NMR (400 MHz, Methanol-d$_4$) δ 8.36 (s, 1H), 7.93 (s, 1H), 7.59 (t, J=7.9 Hz, 1H), 7.49 (d, J=5.2 Hz, 1H), 6.89 (dd, J=3.8, 2.1 Hz, 1H), 4.74 (s, 2H), 3.90-3.81 (m, 2H), 3.47-3.33 (m, 2H), 3.01-2.88 (m, 2H), 1.49 (s, 9H).

Example 137: tert-butyl 4-(7-(4-((5-(tert-butyl)-1,2,4-oxadiazole-3-carboxamido)methyl)-3-fluorophenyl)-3H-imidazo[4,5-b]pyridin-2-yl)-5,6-dihydropyridine-1(2H)-carboxylate (137)

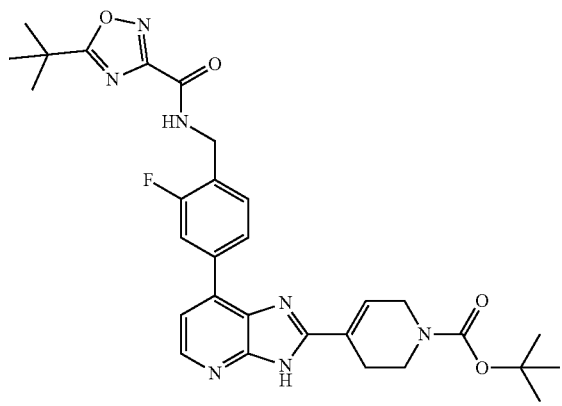 [SMILES: CC(C)(C)OC(=O)N1CC=C(c2nc3c(-c4ccc(CNC(=O)c5noc(C(C)(C)C)n5)c(F)c4)ccnc3[nH]2)CC1]

4-(7-Chloro-3H-imidazo[4,5-b]pyridin-2-yl)-3,6-dihydro-2H-pyridine-1-carboxylic Acid Tert-Butyl Ester 2-Bromo-7-chloro-3H-imidazo[4,5-b]pyridine (4.30 mmol; 1.00 eq.; 1000.00 mg), potassium carbonate (12.91 mmol; 3.00 eq.; 1783.57 mg), and 1,1'-bis(diphenylphosphino)ferrocene-palladium(ii)dichloride dichloromethane complex (0.43 mmol; 0.10 eq.; 351.29 mg). The tube was sealed and flushed with argon. To the reaction mixture was added dioxane (117.36 mmol; 27.28 eq.; 10340.00 mg; 10.00 ml) and water (55.51 mmol; 12.90 eq.: 1000.00 mg; 1.00 ml) via syringe. The reaction tube was degassed with argon and heated to 120 C for 2 h in microwave. Cooled to room temperature and filtered through celite, washing with dichloromethane/MeOH 1:1 (75 mL total). Purified by flash chromatography (SiO$_2$ 50 g; 2-10% MeOH/CH2Cl2 10 CV.) Concentrated product fractions and dried on pump. The material will be carried forward without additional purification. Obtained 4-(7-Chloro-3H-imidazo[4,5-b]pyridin-2-yl)-3,6-dihydro-2H-pyridine-1-carboxylic acid tert-butyl ester (1001.60 mg; 2.57 mmol) brown solid as product. MS: m/z=335.8 [M+H]$^+$.

4-[7-(4-Aminomethyl-3-fluoro-phenyl)-3H-imidazo[4,5-b]pyridin-2-yl]-3,6-dihydro-2H-pyridine-1-carboxylic acid tert-butyl ester 4-(7-Chloro-3H-imidazo[4,5-b]pyridin-2-yl)-3,6-dihydro-2H-pyridine-1-carboxylic acid tert-butyl ester (1.33 mmol; 1.00 eq.; 444.00 mg), 4-(aminomethyl)-3-fluorophenylboronic acid, hcl (1.72 mmol: 1.30 eq.: 354.15 mg), and 1,1'-bis(diphenylphosphino)ferrocene-palladium(ii)dichloride dichloromethane complex (0.13 mmol; 0.10 eq.; 108.30 mg). The tube was sealed and flushed with Ar. The reaction tube was degassed with Ar and heated to 140° C. overnight. Purified on 100 g SiO2 using a gradient of 0-100% of 50% MeOH/EtOAC to give 4-[7-(4-Aminomethyl-3-fluoro-phenyl)-3H-imidazo[4,5-b]pyridin-2-yl]-3,6-dihydro-2H-pyridine-1-carboxylic acid tert-butyl ester (171.00 mg; 0.40 mmol). MS: m/z=423.2 [M+H]$^+$.

4-[7-(4-{[(5-tert-Butyl-[12.4]oxadiazole-3-carbonyl)-amino]-methyl}-3-fluoro-phenyl)-3H-imidazo[4,5-b]pyridin-2-yl]-3,6-dihydro-2H-pyridine-1-carboxylic acid tert-butyl ester To a 5 mL reaction tube with stirbar was added 4-[7-(4-Aminomethyl-3-fluoro-phenyl)-3H-imidazo[4,5-b]pyridin-2-yl]-3,6-dihydro-2H-pyridine-1-carboxylic acid tert-butyl ester (0.09 mmol; 1.00 eq.; 40.00 mg), 5-tert-Butyl-[1,2,4]oxadiazole-3-carboxylic acid (0.11 mmol; 1.20 eq.; 19.29 mg) and DIPEA (0.28 mmol: 3.00 eq.; 36.62 mg; 0.05 ml). Tube was sealed and flushed with Ar. To this mixture was added 2,4,6-Tripropyl-[1,3,5,2,4,6]trioxatriphosphinane 2,4,6-trioxide (0.11 mmol; 1.20 eq.: 72.13 mg; 0.07 ml) via syringe. Reaction was stirred at rt 1.5 hrs. The reaction was then purified on 175 g of C18 (15 micron) column and a gradient of 20-100% CH3CN/H2O (0.1% ammonium hydroxide) over 38 minutes (COMPOUND ELUTES VERY LATE AT 100%) to give 4-[7-(4-{[(5-tert-Butyl-[1,2,4]oxadiazole-3-carbonyl)-amino]-methyl}-3-fluoro-phenyl)-3H-imidazo[4,5-b]pyridin-2-yl]-3,6-dihydro-2H-pyridine-1-carboxylic acid tert-butyl ester (110.00 mg; 0.18 mmol). MS: m/z=576.3 [M+H]$^+$. $^1$H NMR (400 MHz, Chloroform-d) ? 8.39 (s, 1H), 8.28-7.86 (m, 2H), 7.62 (t, J=8.1 Hz, 1H), 7.42 (d, J=25.8 Hz, 2H), 6.87 (s, 1H), 4.82 (s, 2H), 4.29 (s, 1H), 3.75 (s, 2H), 2.91 (s, 1H), 2.35 (s, 1H), 1.66-1.49 (m, 18H).

Example 138: 5-(tert-butyl)-N-(4-(2-(3,6-dihydro-2H-pyran-4-yl)-3H-imidazo[4,5-b]pyridin-7-yl)-2-fluorobenzyl)-1,3,4-oxadiazole-2-carboxamide (138)

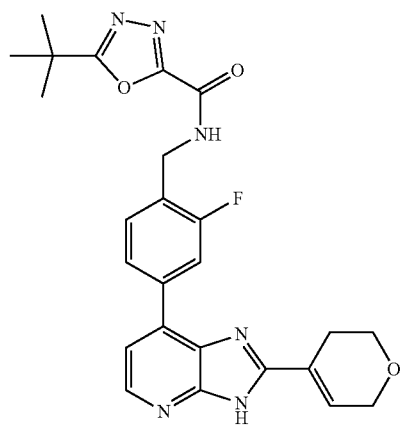 [SMILES: CC(C)(C)c1nnc(C(=O)NCc2ccc(-c3ccnc4[nH]c(C5=CCOCC5)nc34)cc2F)o1]

The title compound was made in a manner similar to that described for example 139 using 7-Chloro-2-(3,6-dihydro-2H-pyran-4-yl)-3H-imidazo[4,5-b]pyridine (0.31 mmol; 1.00 eq.; 72.00 mg), (4-((5-(tert-butyl)-1,3,4-oxadiazole-2-carboxamido)methyl)-3-fluorophenyl)boronic acid (0.37 mmol; 1.20 eq.; 117.72 mg), potassium carbonate (1.22 mmol; 4.00 eq.; 168.89 mg) and 1,1'-bis(diphenylphosphino)ferrocene-palladium(ii)dichloride dichloromethane complex (0.03 mmol; 0.10 eq.; 24.95 mg). Dioxane (23.47 mmol; 76.83 eq.; 2068.00 mg; 2.00 ml) and water (27.75 mmol; 90.85 eq.; 500.00 mg; 0.50 ml) to give 5-tert-Butyl-[1,3,4]oxadiazole-2-carboxylic acid 4-[2-(3,6-dihydro-2H-pyran-4-yl)-3H-imidazo[4,5-b]pyridin-7-yl]-2-fluoro-benzylamide (11.00 mg; 0.02 mmol.) MS: m/z=477.5 [M+H]$^+$.

Example 139: 5-tert-Butyl-[1,3,4]oxadiazole-2-carboxylic acid 2-fluoro-4-[2-(1-methyl-1,2,3,6-tetrahydro-pyridin-4-yl)-3H-imidazo[4,5-b]pyridin-7-yl]-benzylamide (139)

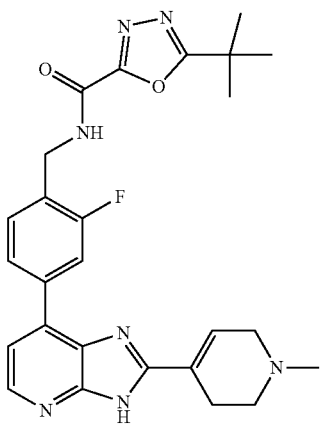 [SMILES: CN1CC=C(c2nc3c(-c4ccc(CNC(=O)c5nnc(C(C)(C)C)o5)c(F)c4)ccnc3[nH]2)CC1]

2-Fluoro-4-[2-(1-methyl-1,2,3,6-tetrahydro-pyridin-4-yl)-3H-imidazo[4,5-b]pyridin-7-yl]-benzylamine 7-Chloro-2-(1-methyl-1,2,3,6-tetrahydro-pyridin-4-yl)-3H-imidazo[4,5-b]pyridine (0.85 mmol; 1.00 eq.; 212.00 mg), 4-(aminomethyl)-3-fluorophenylboronic acid, hcl (1.11 mmol; 1.30 eq.; 227.63 mg), and 1,1'-bis(diphenylphosphino)ferrocene-palladium(ii)dichloride dichloromethane complex (0.09 mmol; 0.10 eq.; 69.61 mg). The tube was sealed and flushed with Ar. To the reaction mixture was added potassium carbonate (1.70 mmol; 2.00 eq.; 235.61 mg), dioxane (46.94 mmol; 55.07 eq.; 4136.00 mg; 4.00 ml), and water (55.51 mmol; 65.12 eq.; 1000.00 mg; 1.00 ml) via syringe. The reaction tube was degassed with argon and heated to 140° C. overnight. The reaction was then filtered through Celite and purified directly on C18 using a gradient 20-60% CH3CN/H2O (0.1% Ammonium Hydroxide.) Gives 2-Fluoro-4-[2-(1-methyl-1,2,3,6-tetrahydro-pyridin-4-yl)-3H-imidazo[4,5-b]pyridin-7-yl]-benzylamine (51.00 mg; 0.14 mmol.) MS: m/z=338.2 [M+H]$^+$.

5-tert-Butyl-[1,3,4]oxadiazole-2-carboxylic acid 2-fluoro-4-[2-(1-methyl-1,2,3,6-tetrahydro-pyridin-4-yl)-3H-imidazo[4,5-b]pyridin-7-yl]-benzylamide 2-Fluoro-4-[2-(1-methyl-1,2,3,6-tetrahydro-pyridin-4-yl)-3H-imidazo[4,5-b]pyridin-7-yl]-benzylamine (0.15 mmol; 1.00 eq.; 51.00 mg) was combined with 5-tert-Butyl-[1,3,4]oxadiazole-2-carboxylic acid (0.18 mmol; 1.20 eq.; 30.87 mg) into a solution of DIPEA (0.45 mmol; 3.00 eq.; 58.61 mg; 0.08 ml) in DCM. 2,4,6-Tripropyl-[1,3,5,2,4,6]trioxatriphosphinane 2,4,6-trioxide (0.47 mmol; 3.12 eq.; 300.00 mg; 0.30 ml) (T3P) was then added and the reaction was stirred at RT for 1 hr. All solvent was then removed and the residue was dissolved in 5 mL DMSO. Reaction was then purified on the waters reverse phase purification system using a gradient of 10-60% CH3CN/H2O (0.1% ammonium hydroxide.) Gives 5-tert-Butyl-[1,3,4]oxadiazole-2-carboxylic acid 2-fluoro-4-[2-(1-methyl-1,2,3,6-tetrahydro-pyridin-4-yl)-3H-imidazo[4,5-b]pyridin-7-yl]-benzylamide (10.70 mg; 0.02 mmol) as a white solid. MS: m/z=248.7 [M+H]$^+$.

Example 140: 5-tert-Butyl-[1,3,4]oxadiazole-2-carboxylic acid 2-fluoro-4-[2-(1,2,3,6-tetrahydro-pyridin-4-yl)-3H-imidazo[4,5-b]pyridin-7-yl]-benzylamide (140)

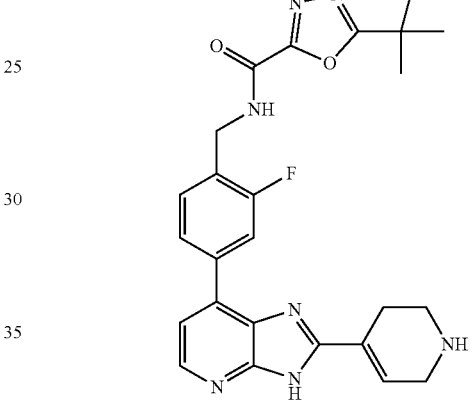

tert-butyl 4-(7-chloro-3H-imidazo[4,5-b]pyridin-2-yl)-3,6-dihydropyridine-1 (2H)-carboxylate 2-Bromo-7-chloro-3H-imidazo[4,5-b]pyridine (4.30 mmol: 1.00 eq.; 1000.00 mg), potassium carbonate (12.91 mmol; 3.00 eq.; 1783.57 mg), and 1,1'-bis(diphenylphosphino)ferrocene-palladium(ii)dichloride dichloromethane complex (0.43 mmol; 0.10 eq.; 351.29 mg). The tube was sealed and flushed with argon. To the reaction mixture was added dioxane (117.36 mmol; 27.28 eq.; 10340.00 mg; 10.00 ml) and water (55.51 mmol; 12.90 eq.; 1000.00 mg; 1.00 ml) via syringe. The reaction tube was degassed with argon and heated to 120° C. for 2 h in microwave. Reaction then left standing overnight at RT. The reaction mix was then filtered through celite and the filter was washed with DCM/MeOH 1:1 (150 mL total). The filtrate was concentrated and loaded onto 25 g KP-NH samplet (dryload method with 25 g SiO2) Purified by column chromatography (HP-Si 50 g; 2-10% MeOH/DCM 10 CV.) Gives 4-(7-Chloro-3H-imidazo[4,5-b]pyridin-2-yl)-3,6-dihydro-2H-pyridine-1-carboxylic acid tert-butyl ester (1001.60 mg; 2.57 mmol) as a brown solid as product. MS: m/z=335.1 [M+H]$^+$.

tert-butyl 4-(7-(4-(aminomethyl)-3-fluorophenyl)-3H-imidazo[4,5-b]pyridin-2-yl)-3,6-dihydropyridine-1(2H)-carboxylate 4-(7-Chloro-3H-imidazo[4,5-b]pyridin-2-yl)-3,6-dihydro-2H-pyridine-1-carboxylic acid tert-butyl ester (1.49 mmol; 1.00 eq.; 500.00 mg), 4-(aminomethyl)-3-fluorophenylboronic acid, HCl (1.94 mmol; 1.30 eq.; 398.82 mg), potassium carbonate (2.99 mmol; 2.00 eq.; 412.80 mg) and 1,1'-bis(diphenylphosphino)ferrocene-palladium(ii)dichloride dichloromethane complex (0.15 mmol; 0.10 eq.; 121.96 mg). The tube was sealed and flushed with argon. To the reaction mixture was added dioxane (46.94 mmol; 31.43 eq.: 4136.00 mg: 4.00 ml) and water (55.51 mmol; 37.17 eq.; 1000.00 mg; 1.00 ml) via syringe. The reaction tube was degassed with argon and heated to 140° C. overnight. Purified on 100 g SiO$_2$ using a gradient of 0-100% of 50% MeOH/EtOAc to give 4-[7-(4-Aminomethyl-3-fluoro-phenyl)-3H-imidazo[4,5-b]pyridin-2-yl]-3,6-dihydro-2H-pyridine-1-carboxylic acid tert-butyl ester (186.00 mg; 0.43 mmol) which was used without additional purification. MS: m/z=424.2 [M+H]$^+$.

5-tert-butyl 4-(7-(4-((5-(tert-butyl)-1,3,4-oxadiazole-2-carboxamido)methyl)-3-fluorophenyl)-3H-imidazo[4,5-b]pyridin-2-yl)-3,6-dihydropyridine-1 (2H)-carboxylate 4-[7-(4-Aminomethyl-3-fluoro-phenyl)-3H-imidazo[4,5-b]pyridin-2-yl]-3,6-dihydro-2H-pyridine-1-carboxylic acid tert-butyl ester (0.12 mmol; 1.00 eq.; 51.00 mg) was combined with 5-tert-Butyl-[1,3,4]oxadiazole-2-carboxylic acid (0.14 mmol; 1.20 eq.; 24.59 mg) into a solution of DIPEA (0.36 mmol; 3.00 eq.; 46.69 mg; 0.06 ml) in DCM. 2,4,6-Tripropyl-[1,3,5,2,4,6]trioxatriphosphinane 2,4,6-trioxide (0.47 mmol; 3.91 eq.: 300.00 mg: 0.30 ml) (T3P) was then added and the reaction was stirred at RT for 1 hr. All solvent was then removed and the residue was dissolved in 5 mL DMSO. The material was purified on via reverse phase chromatography using 80 g of C18 (30 micron) and a gradient of 20-90% CH$_3$CN/H$_2$O (0.1% ammonium hydroxide) to give 4-[7-(4-({[(5-tert-Butyl-[1,3,4]oxadiazole-2-carbonyl)-amino]-methyl}-3-fluoro-phenyl)-3H-imidazo[4,5-b]pyridin-2-yl]-3,6-dihydro-2H-pyridine-1-carboxylic acid tert-butyl ester (51.00 mg; 0.09 mmol) as a white solid. MS: m/z=576.2 [M+H]$^+$.

5-tert-Butyl-[1,3,4]oxadiazole-2-carboxylic acid 2-fluoro-4-[2-(1,2,3,6-tetrahydro-pyridin-4-yl)-3H-imidazo[4,5-b]pyridin-7-yl]-benzylamide 4-[7-(4-([(5-tert-Butyl-[1,3,4]oxadiazole-2-carbonyl)-amino]-methyl)-3-fluoro-phenyl)-3H-imidazo[4,5-b]pyridin-2-yl]-3,6-dihydro-2H-pyridine-1-carboxylic acid tert-butyl ester (0.02 mmol; 1.00 eq.; 14.00 mg) was combined with 4N HCl in Dioxane (1.00 ml) into DCM (31.20 mmol; 1425.43 eq.; 2650.00 mg; 2.00 ml). The mixture was stirred at RT for 1 hr. The material was then concentrated to dryness and purified via reverse phase chromatography using 80 g of C18 (30 micron) and a gradient of 20-90% CH$_3$CN/H$_2$O (0.1% ammonium hydroxide) to give 5-tert-Butyl-[1,3,4] oxadiazole-2-carboxylic acid 2-fluoro-4-[2-(1,2,3,6-tetrahydro-pyridin-4-yl)-3H-imidazo[4,5-b]pyridin-7-yl]-benzylamide (3.2 mg, 0.01 mmol) as a white solid. MS: m/z=576.6 [M+H]$^+$. $^1$H NMR (400 MHz, Methanol-d$_4$) δ 8.36 (s, 1H), 7.93 (s, 1H), 7.59 (t, J=7.9 Hz, 1H), 7.49 (d, J=5.2 Hz, 1H), 6.89 (dd, J=3.8, 2.1 Hz, 1H), 4.73 (s, 2H), 3.89-3.80 (m, 2H), 3.46-3.31 (m, 2H), 3.01-2.87 (m, 2H), 1.51 (s, 9H)

5-tert-Butyl-[1,3,4]oxadiazole-2-carboxylic acid 2-fluoro-4-[2-(1-methyl-2-oxo-1,2-dihydro-pyridin-4-yl)-3H-imidazo[4,5-b]pyridin-7-yl]-benzylamide 4-(7-Chloro-3H-imidazo[4,5-b]pyridin-2-yl)-1-methyl-1H-pyridin-2-one (0.25 mmol; 1.00 eq.: 64.00 mg), (4-((5-(tert-butyl)-1,3,4-oxadiazole-2-carboxamido)methyl)-3-fluorophenyl)boronic acid (0.29 mmol; 1.20 eq.; 94.60 mg), potassium carbonate (0.98 mmol; 4.00 eq.; 135.73 mg) and 1,1'-bis(diphenylphosphino)ferrocene-palladium(ii)dichloride dichloromethane complex (0.02 mmol; 0.10 eq.: 20.05 mg), dioxane (117.36 mmol: 478.02 eq.; 10340.00 mg; 2.00 ml) and water (55.51 mmol; 226.10 eq.; 1000.00 mg; 0.50 ml) were then added and the reaction tube was evacuated then back filled with nitrogen three times. The mixture was then heated to 140° C. overnight. The crude reaction was then purified directly on 175 g 15 micron C18 using a gradient of 5-95% CH3CN/H2O (0.1% ammonium hydroxide). Fractions containing desired product were combined and concentrated to dryness on rotovap then dried on high vac for 1 hr. 5-tert-Butyl-[1,3,4]oxadiazole-2-carboxylic acid 2-fluoro-4-[2-(1-methyl-2-oxo-1,2-dihydro-pyridin-4-yl)-3H-imidazo[4,5-b]pyridin-7-yl]-benzylamide (3.60 mg; 0.01 mmol) as a dark brown solid. MS: m/z=502.2 [M+H]$^+$. 1H NMR (400 MHz, Chloroform-d) d 8.40 (s, 1H), 8.22 (d, J=20.0 Hz, 2H), 8.10-7.79 (m, 3H), 7.58-7.31 (m, 3H), 6.50 (s, 1H), 5.77-5.68 (m, 2H), 4.62-4.50 (m, 2H), 3.38 (s, 3H), 1.48 (s, 9H).

Example 142: 5-Isopropyl-[1,3,4]oxadiazole-2-carboxylic acid 2-fluoro-4-[2-(1,2,3,6-tetrahydro-pyridin-4-yl)-3H-imidazo[4,5-b]pyridin-7-yl]-benzylamide (142)

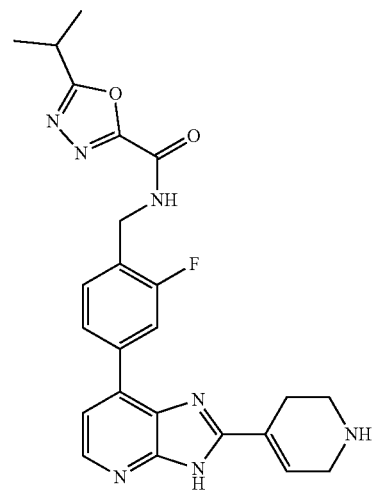 [SMILES: CC(C)c1nnc(C(=O)NCc2ccc(-c3ccnc4[nH]c(C5=CCNCC5)nc34)cc2F)o1]

4-[7-(3-Fluoro-4-{[(5-isopropyl-[1,3,4]oxadiazole-2-carbonyl)-amino]-methyl}-phenyl)-3H-imidazo[4,5-b]pyridin-2-yl]-3,6-dihydro-2H-pyridine-1-carboxylic acid tert-butyl ester To a 5 mL reaction tube with stirbar was added 4-[7-(4-Aminomethyl-3-fluoro-phenyl)-3H-imidazo[4,5-b]pyridin-2-yl]-3,6-dihydro-2H-pyridine-1-carboxylic acid tert-butyl ester (0.14 mmol; 1.00 eq.; 60.00 mg) described above, 5-Isopropyl-[1,3,4]oxadiazole-2-carboxylic acid (0.18 mmol; 1.25 eq.; 27.65 mg) and pybrop (0.18 mmol; 1.25 eq.; 82.56 mg). Tube was sealed and flushed with Ar. To this mixture was added DMF (25.94 mmol; 183.08 eq.; 1896.00 mg; 2.00 ml) and n,n-diisopropylethylamine (0.43 mmol; 3.00 eq.; 54.94 mg; 70.43 μl). Reaction was stirred at RT overnight. 1.5 mL of DMSO as added to the reaction and this material was purified on using a 175 g C18 (15 micron) column and a gradient of 20-100% $CH_3CN/H_2O$ (0.1% ammonium hydroxide) to give 4-[7-(3-Fluoro-4-{[(5-isopropyl-[1,3,4]oxadiazole-2-carbonyl)-amino]-methyl}-phenyl)-3H-imidazo[4,5-b]pyridin-2-yl]-3,6-dihydro-2H-pyridine-1-carboxylic acid tert-butyl ester (10.00 mg; 0.02 mmol). MS: m/z=562.6 $[M+H]^+$.

5-Isopropyl-[1,3,4]oxadiazole-2-carboxylic acid 2-fluoro-4-[2-(1,2,36-tetrahydro-pyridin-4-yl)-3H-imidazo[4,5-b]pyridin-7-yl]-benzylamide 4-[7-(3-Fluoro-4-{[(5-isopropyl-[1,3,4]oxadiazole-2-carbonyl)-amino]-methyl}-phenyl)-3H-imidazo[4,5-b]pyridin-2-yl]-3,6-dihydro-2H-pyridine-1-carboxylic acid tert-butyl ester (0.02 mmol; 1.00 eq.; 13.00 mg) was combined with DCM (156.01 mmol; 7488.36 eq.; 13250.00 mg: 1.50 ml) and then treated with TFA (134.62 mmol; 6462.00 eq.; 15350.00 mg; 1.50 ml). The mixture was stirred under nitrogen for 1.5 hours. The reaction was then purified directly on 55 g of C18 using a gradient of 20-80% $CH_3CN/H_2O$ (0.1% Ammonium Hydroxide) to give 5-Isopropyl-[1,3,4]oxadiazole-2-carboxylic acid 2-fluoro-4-[2-(1,2,3,6-tetrahydro-pyridin-4-yl)-3H-imidazo[4,5-b]pyridin-7-yl]-benzylamide (2.00 mg; 0.00 mmol). MS: m/z=462.4 $[M+H]^+$. $^1$H NMR (400 MHz, Methanol-$d_4$) δ 8.36 (s, 1H), 7.93 (s, 1H), 7.59 (t. J=7.9 Hz, 1H), 7.49 (d, J=5.2 Hz, 1H), 6.89 (dd, J=3.8, 2.1 Hz, 1H), 4.73 (s, 2H), 3.89-3.80 (m, 2H), 3.46-3.31 (m, 3H), 3.01-2.87 (m, 2H), 1.49-1.39 (m, 6H).

Example 143: 4-[7-(4-{[(5-tert-Butyl-[1,2,4]oxadiazole-3-carbonyl)-amino]-methyl}-3-fluoro-phenyl)-3H-imidazo[4,5-b]pyridin-2-yl]-3,6-dihydro-2H-pyridine-1-carboxylic Acid Dimethylamide (143)

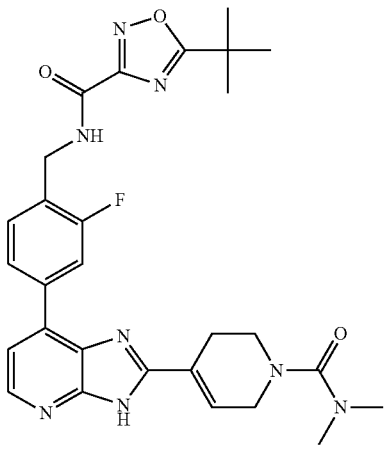 [SMILES: CN(C)C(=O)N1CC=C(c2nc3c(-c4ccc(CNC(=O)c5noc(C(C)(C)C)n5)c(F)c4)ccnc3[nH]2)CC1]

5-tert-Butyl-[1,2,4]oxadiazole-3-carboxylic acid 2-fluoro-4-[2-(1,2,3,6-tetrahydro-pyridin-4-yl)-3H-imidazo[4,5-b]pyridin-7-yl]-benzylamide (0.02 mmol; 1.00 eq.; 11.20 mg) was dissolved in DCM along with DIPEA (0.24 mmol; 10.00 eq.; 30.44 mg; 0.04 ml). dimethylcarbamoyl chloride (0.04 mmol; 1.50 eq.; 3.80 mg) was then added in one portion. The reaction was then stirred at RT for 1 hr. The reaction was quenched with a saturated solution of sodium bicarbonate. 10 mL of DCM was added. The reaction was shaken then the phases were allowed to separate. The organic (bottom) phase was removed with a pipette and then combined and concentrated to dryness. Residue was dissolved in 5 mL DMSO then purified using reverse phase C18 (10 micron) with a gradient of 5-95% MeOH in Water (0.1% ammonium hydroxide) to give 4-[7-(4-{[(5-tert-Butyl-[1,2,4]oxadiazole-3-carbonyl)-amino]-methyl}-3-fluoro-phenyl)-3H-imidazo[4,5-b]pyridin-2-yl]-3,6-dihydro-2H-pyridine-1-carboxylic acid dimethylamide (6.20 mg; 0.01 mmol) as a white solid. MS: m/z=547.6 $[M+H]^+$. $^1$H NMR (400 MHz, DMSO-$d_6$) δ 13.30 (s, 1H), 9.53 (s, 1H), 8.52-7.99 (m, 2H), 7.83-7.35 (m, 2H), 6.93 (s, 1H), 4.68-4.42 (m, 2H), 3.95 (s, 2H), 2.91-2.67 (m, 10H), 1.48 (s, 9H).

Example 144: 3-(tert-butyl)-N-(2-fluoro-4-(2-(1-methyl-1H-pyrazol-4-yl)-3H-imidazo[4,5-b]pyridin-7-yl)benzyl)isoxazole-5-carboxamide (144)

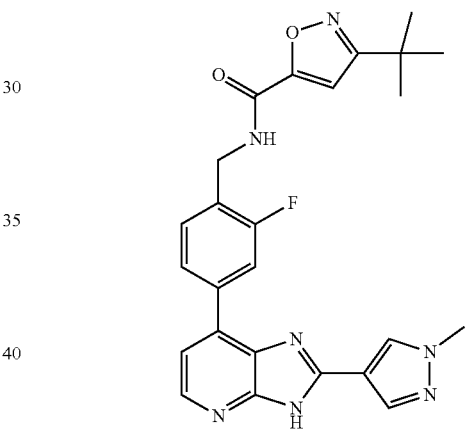

Into a dry 40 mL reaction vial was combined 2-Fluoro-4-[2-(1-methyl-1H-pyrazol-4-yl)-3H-imidazo[4,5-b]pyridin-7-yl]-benzylamine (0.43 mmol; 1.00 eq.; 200.00 mg), DIPEA (1.30 mmol; 3.00 eq.; 168.40 mg; 0.22 ml), and DCM (78.00 mmol; 179.60 eq.; 6625.00 mg; 5.00 ml). 3-tert-Butyl-isoxazole-5-carbonyl chloride (0.48 mmol; 1.10 eq.; 89.64 mg) was then added drop wise to the reaction via syringe addition and the reaction was stirred at RT for 1 hour. The reaction was quenched with a saturated solution of sodium hydrogen carbonate (10 mL) then diluted with DCM (20 mL). The reaction was capped and shaken and the phases were allowed to separate for 15 minutes. The organic (bottom) phase was collected. The organic phase was then purified on Biotage-2 using 100 g of KPH SiO2 using a gradient of 0-15% MeOH in EtOAC over 38 minutes (compound elutes at 10% MeOH/EtOAC) to give 3-tert-Butyl-isoxazole-5-carboxylic acid 2-fluoro-4-[2-(1-methyl-1H-pyrazol-4-yl)-3H-imidazo[4,5-b]pyridin-7-yl]-benzylamide (194.00 mg; 0.40 mmol) as a white solid upon drying. MS: m/z=474.5 $[M+H]^+$. 1H NMR (400 MHz, Chloroform-d) d 8.40 (s, 1H), 8.22 (d, J=20.0 Hz, 2H), 8.10-7.79 (m, 2H), 7.58-7.31 (m, 3H), 6.50 (s, 1H), 4.82-4.70 (m, 2H), 4.05 (s, 3H), 1.49 (s, 9H).

Example 145: 5-(tert-butyl)-N-(4-(2-(4-(dimethyl-amino)phenyl)-3H-imidazo[4,5-b]pyridin-7-yl)-2-fluorobenzyl)-1,2,4-oxadiazole-3-carboxamide (145)

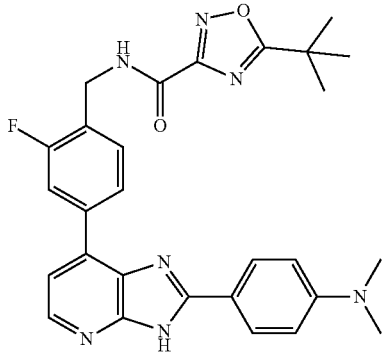 [SMILES: CN(C)c1ccc(-c2nc3c(-c4ccc(CNC(=O)c5noc(C(C)(C)C)n5)c(F)c4)ccnc3[nH]2)nc1]

4-(7-chloro-3H-imidazo[4,5-b]pyridin-2-yl)-N,N-dimethylaniline

4-Chloro-pyridine-2,3-diamine (2.09 mmol; 1.00 eq.; 300.00 mg), polyphosphoric acid (12750.00 mg) and 4-dimethylaminobenzoic acid (2.51 mmol; 1.20 eq.; 414.20 mg) were heated at 130° C. overnight. The reaction mixture was poured into water/ice (50 ml) and the pH was adjusted with ammonium chloride (18.69 mmol; 8.95 eq.; 1000.00 mg) and NaOH (200.02 mmol; 95.72 eq.; 8000.00 mg) to neutral. Additional Sodium hydroxide was added as single pellets so that the temperature of the aqueous solution not to exceed 50 C (cooling by adding ice pellets from time to time). The product precipitated at pH=8 (litmus paper) and the suspension was chilled at 5° C. in ice for 30 min then filtered on a plastic filter unit. The precipitate was dried under high vacuum to afford the desired compound [4-(7-Chloro-3H-imidazo[4,5-b]pyridin-2-yl)-phenyl]-dimethyl-amine (582.00 mg; 2.13 mmol) as a tan amorphous solid. MS: m/z=273.1 [M+H]$^+$.

4-(7-(4-(aminomethyl)-3-fluorophenyl)-3H-imidazo[4,5-b]pyridin-2-yl)-N,N-dimethylaniline To a 20 mL reaction tube with stirbar was added [4-(7-Bromo-3H-imidazo[4,5-b]pyridin-2-yl)-phenyl]-dimethyl-amine (1.86 mmol; 1.00 eq.; 589.00 mg), 4-(aminomethyl)-3-fluorophenylboronic acid, hcl (2.23 mmol: 1.20 eq.; 457.75 mg), potassium carbonate (7.43 mmol; 4.00 eq.; 1026.58 mg) and 1,1'-bis(diphenylphosphino)ferrocene-palladium(ii)dichloride dichloromethane complex (0.19 mmol; 0.10 eq.; 151.65 mg). Dioxane (117.36 mmol; 63.20 eq.; 10340.00 mg; 10.00 ml) and water (55.51 mmol; 29.89 eq.; 1000.00 mg; 1.00 ml) were then added and the reaction tube was evacuated then back filled with nitrogen three times. The mixture was then heated to 140° C. overnight. The reaction was loaded directly onto 50 g SiO2 and purified by flash chromatography (2-10% MeOH/CH$_2$Cl$_2$ 15 CV) to give {4-[7-(4-Aminomethyl-3-fluoro-phenyl)-3H-imidazo[4,5-b]pyridin-2-yl]-phenyl}-dimethyl-amine (77.00 mg; 0.21 mmol). MS: m/z=362.4 [M+H]$^+$.

5-(tert-butyl)-N-(4-(2-(4-(dimethylamino)phenyl)-3H-imidazo[4,5-b]pyridin-7-yl)-2-fluorobenzyl)-1,2,4-oxadiazole-3-carboxamide To a 5 mL reaction tube with stirbar was added {4-[7-(4-Aminomethyl-3-fluoro-phenyl)-3H-imidazo[4,5-b]pyridin-2-yl]-phenyl}-dimethyl-amine (0.21 mmol; 1.00 eq.; 77.00 mg), 5-tert-Butyl-[1,2,4]oxadiazole-3-carboxylic acid sodium (0.27 mmol; 1.25 eq.: 51.17 mg) and pybrop (0.27 mmol; 1.25 eq.; 124.15 mg). Tube was sealed and flushed with Ar. To this mixture was added DMF (12.97 mmol; 60.88 eq.; 948.00 mg; 2.00 ml) and n,n-diisopropylethyl-amine (0.64 mmol; 3.00 eq.; 82.61 mg; 105.91 µl). Reaction was stirred at rt overnight. 1 mL of the DMF was removed on rotovap and the reaction was diluted with DCM (20 mL). Washed with a solution of bicarbonate (sat.) followed by water (2×s). Organic layer was concentrated to about 2 mL on rotory evaporator, then loaded on 25 g SiO2 and purified by flash chromatography (0-10% MeOH/CH$_2$Cl$_2$). Added MeOH (5 mL) to the resulting residue and a light yellow solid formed which was collected via filtration. Solids were washed three times with MeOH (5 mL each) and then dried on the pump to give 5-tert-Butyl-[1,2,4]oxadiazole-3-carboxylic acid 4-[2-(4-dimethylamino-phenyl)-3H-imidazo[4,5-b]pyridin-7-yl]-2-fluoro-benzylamide (41.30 mg; 0.08 mmol) MS: m/z=514.5 [M+H]$^+$. 1H NMR (400 MHz, DMSO-d$_6$) δ 9.51 (s, 1H), 8.48 (d, J=11.8 Hz, 1H), 8.17 (dd, J=25.2, 7.7 Hz, 4H), 7.58-7.21 (m, 2H), 6.83 (d, J=8.1 Hz, 2H), 4.59 (s, 2H), 3.00 (s, 6H), 1.47 (s, 9H).

Example 146: 5-tert-Butyl-[1,2,4]oxadiazole-3-carboxylic acid 4-[2-(5-dimethylamino-pyridin-2-yl)-3H-imidazo[4,5-b]pyridin-7-yl]-2-fluoro-benzylamide (146)

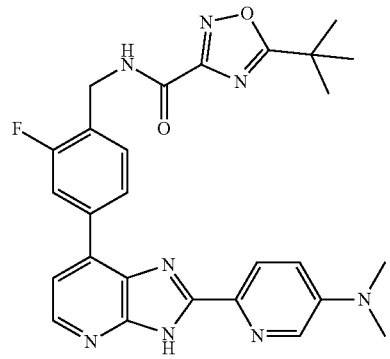

[6-(7-Chloro-3H-imidazo[4,5-b]pyridin-2-yl)-pyridin-3-yl]-dimethyl-amine

4-Chloro-pyridine-2,3-diamine (1.39 mmol; 1.00 eq.; 200.00 mg), polyphosphoric acid (12750.00 mg) and 5-Dimethylamino-pyridine-2-carboxylic acid (1.67 mmol; 1.20 eq.; 277.78 mg) were heated at 130° C. over 2 days. The reaction mixture was then treated with water (50 ml). A spatula was then used to break apart the thick viscous material and dissolve into the water. Some ice was then added and the pH was adjusted with ammonium chloride (18.69 mmol; 13.42 eq.; 1000.00 mg) and NaOH (200.02 mmol; 143.58 eq.: 8000.00 mg) to neutral. The product precipitated at pH=8 (litmus paper) and the suspension was chilled at 5° C. in ice for 30 min then filtered on a plastic filter unit. The precipitate was dried under high vacuum to afford the desired compound [6-(7-Chloro-3H-imidazo[4,5-b]pyridin-2-yl)-pyridin-3-yl]-dimethyl-amine (445.00 mg; 1.63 mmol) as a tan amorphous solid. The material was carried forward without purification. MS: m/z=248.7 [M+H]$^+$.

{6-[7-(4-Aminomethyl-3-fluoro-phenyl)-3H-imidazo[4,5-b]pyridin-2-yl]-pyridin-3-yl}-dimethyl-amine

[6-(7-Bromo-3H-imidazo[4,5-b]pyridin-2-yl)-pyridin-3-yl]-dimethyl-amine (1.40 mmol; 1.00 eq.; 446.00 mg), 4-(aminomethyl)-3-fluorophenylboronic acid, hcl (1.68 mmol; 1.20 eq.; 345.54 mg), potassium carbonate (5.61 mmol; 4.00 eq.; 774.93 mg) and 1,1'-bis(diphenylphosphino)ferrocene-palladium(ii)dichloride dichloromethane complex (0.14 mmol; 0.10 eq.; 114.47 mg). dioxane (117.36 mmol; 83.72 eq.: 10340.00 mg; 10.00 ml) and water (55.51 mmol; 39.60 eq.; 1000.00 mg; 1.00 ml) were then added and the reaction tube was evacuated then back filled with nitrogen three times. The mixture was then heated to 140 C overnight. Loaded directly onto 50 g SiO2 and purified by Biotage chromatography (2-10% MeOH/CH2Cl2 15 CV). Concentrated product fractions and dried on pump. Gives {6-[7-(4-Aminomethyl-3-fluoro-phenyl)-3H-imidazo[4,5-b]pyridin-2-yl]-pyridin-3-yl}-dimethyl-amine (59.00 mg; 0.10 mmol.) MS: m/z=363.2 [M+H]$^+$.

5-tert-Butyl-[1,2,4]oxadiazole-3-carboxylic acid 4-[2-(5-dimethylamino-pyridin-2-yl)-3H-imidazo[4,5-b]pyridin-7-yl]-2-fluoro-benzylamide {6-[7-(4-Aminomethyl-3-fluoro-phenyl)-3H-imidazo[4,5-b]pyridin-2-yl]-pyridin-3-yl}-dimethyl-amine (0.16 mmol; 1.00 eq.; 59.00 mg), 5-tert-Butyl-[1,2,4]oxadiazole-3-carboxylic acid sodium (0.20 mmol; 1.25 eq.; 39.10 mg) and pybrop (0.20 mmol; 1.25 eq.; 94.87 mg). Tube was sealed and flushed with Ar. To this mixture was added DMF (25.94 mmol; 159.33 eq.; 1896.00 mg; 2.00 ml) and n,n-diisopropylethylamine (0.49 mmol; 3.00 eq.; 63.12 mg; 80.93 μl). Reaction was stirred at rt overnight. About 1 mL of the DMF was removed on rotovap and the reaction was diluted with DCM (20 mL). Washed with sodium hydrogen carbonate (sat.) followed by water (2×s). Organic layer was concentrated to about 10 mL on rotovap then attempted purification of half (5 mL) on 25 g SiO$_2$ (15 micron) by flash chromatography using a gradient of 0-10% MeOH/CH$_2$Cl$_2$ over 38 minutes, then 10-20% for 10 minutes, then flushed with 40% MeOH/DCM for 5 min). This material was purified using a 30 mm×250 mm Sunfire OBD C18 column and a gradient of 5-95% CH$_3$CN/H$_2$O (0.1% ammonium hydroxide) over 25 minutes to give 5-tert-Butyl-[1,2,4]oxadiazole-3-carboxylic acid 4-[2-(5-dimethylamino-pyridin-2-yl)-3H-imidazo[4,5-b]pyridin-7-yl]-2-fluoro-benzylamide (26.30 mg; 0.05 mmol.) MS: m/z=514.2 [M+H]$^+$. $^1$H NMR (400 MHz, DMSO-d$_4$) δ 9.53 (s, 1H), 8.42-8.12 (m, 4H), 7.56 (s, 2H), 7.27 (d, J=9.0 Hz, 1H), 4.61 (s, 2H), 3.08 (s, 6H), 1.44 (s, 9H).

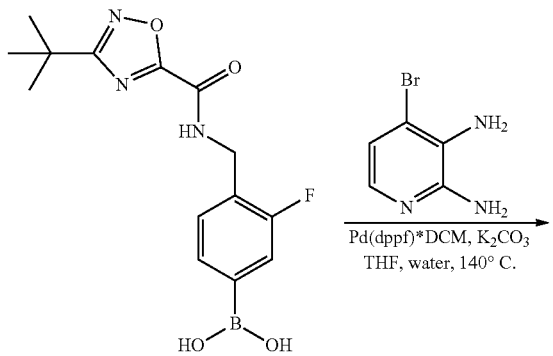

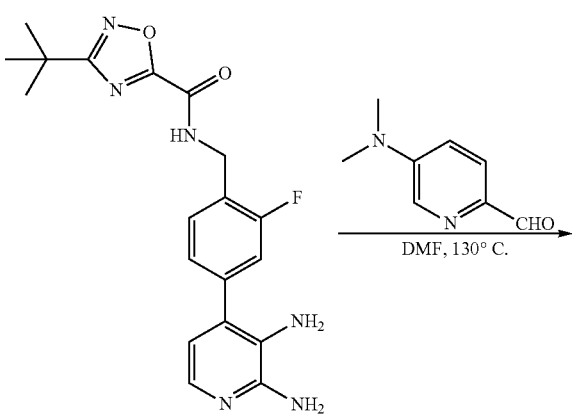

Scheme 47

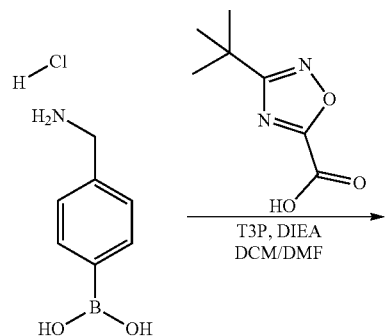

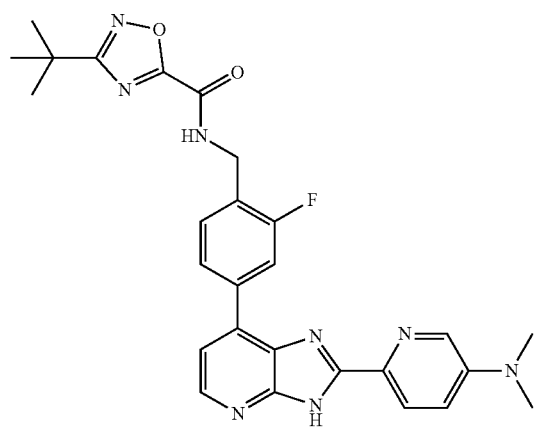

369

Example 148. 3-(tert-butyl)-N-(4-(2-(5-(dimethylamino)pyridin-2-yl)-3H-imidazo[4,5-b]pyridin-7-yl)-2-fluorobenzyl)-1,2,4-oxadiazole-5-carboxamide (148)

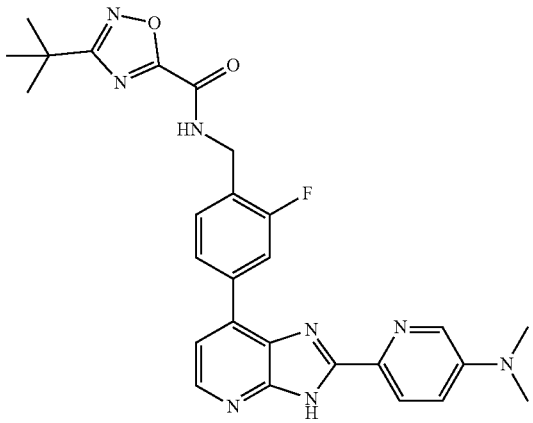 [SMILES: CN(C)c1ccc(-c2nc3c(-c4ccc(CNC(=O)c5nc(C(C)(C)C)no5)c(F)c4)ccnc3[nH]2)nc1]

(4-((3-(tert-butyl)-1,2,4-oxadiazole-5-carboxamido)methyl)-3-fluorophenyl)boronic acid To a reaction flask with a magnetic stirbar was added 3-tert-butyl-1,2,4-oxadiazole-5-carboxylic acid (4.56 g; 26.77 mmol; 1.10 eq.), DCM (100.00 ml), and N,N-diisopropylethylamine (16.96 ml; 97.36 mmol; 4.00 eq.), The stirring suspension was then treated with a 50% ethyl acetate solution of 2,4,6-tripropyl-[1,3,5,2,4,6]trioxatriphosphinane 2,4,6-trioxide (23.20 ml; 36.51 mmol; 1.50 eq.), The solids were not completely dissolved after 5 min so DMF (15 mL) was added. The reaction mixture was stirred at room temperature and after 15 min the murky solution was treated with 4-(aminomethyl)-3-fluorophenylboronic acid HCl salt (5.00 g; 24.34 mmol; 1.00 eq.) as a solid. Stirring was continued at RT (pH=9). After 3 hr an additional 5.0 mL $T_3P$ (50% in ethyl acetate) was added and the reaction was stirred over the weekend. LC-MS analysis 3 days later showed no change. The reaction was partially concentrated, taken up in ethyl acetate (150 mL), washed with water (3×50 mL) and brine (1×25 mL), dried (Na2SO4), filtered, and concentrated to a yield 4.27 g of a golden oil which was purified via flash chromatography (Biotage): 100 g column using 0-10% MeOH/DCM over 20 min at a flow rate of 50 mL/min. Product eluted ~16 min. The product fractions were combined, concentrated and dried to yield 3.32 g (43%) of (4-((3-(tert-butyl)-1,2,4-oxadiazole-5-carboxamido)methyl)-3-fluorophenyl)boronic acid as a golden oil. HPLC: 93% purity. MS: 322 [M+H]$^+$ 3-(tert-butyl)-N-(4-(2,3-diaminopyridin-4-yl)-2-fluorobenzyl)-1,2,4-oxadiazole-5-carboxamide 4-Bromo-pyridine-2,3-diamine (1.60 g; 8.51 mmol: 1.00 eq.), [4-[[(3-tert-butyl-1,2,4-oxadiazole-5-carbonyl)amino]methyl]-3-fluoro-phenyl]boronic acid (3.28 g; 10.21 mmol; 1.20 eq.), 1,1'-bis(diphenylphosphino)ferrocene-palladium (ii)dichloride dichloromethane complex (694.92 mg; 0.85 mmol; 0.10 eq.), and potassium carbonate (4.70 g; 34.04 mmol; 4.00 eq.) were combined in a microwave tube. The tube was sealed and then evacuated/N$_2$-backfilled (3×). Then THF/water (5:1. 24 mL) was then added. The tube was evacuated/N$_2$-backfilled (3×) again and irradiated in a microwave at 120 degrees C. for 1 hr. LC-MS indicated product as the major UV peak (MSES+: 385) and no starting material. The reaction was diluted with water (100 mL) and ethyl acetate (100 mL), filtered through Celite, and partially concentrated. The black solution was diluted with ethyl acetate (50 mL) and then filtered through Celite again. The resulting layers were separated and the aqueous layer was extracted with ethyl acetate (2×30 mL). The combined ethyl acetate layer was concentrated on SiO$_2$ and purified on a 100 g Biotage column using 80-100% ethyl acetate/hexane over 10 min at a flow rate of 50 mL/min. The product fractions were combined, concentrated, and dried to yield 2.08 g (64%) of 3-(tert-butyl)-N-(4-(2,3-diaminopyridin-4-yl)-2-fluorobenzyl)-1,2,4-oxadiazole-5-carboxamide as a tan brittle foam. HPLC: 98% purity. MS: 385 [M+H]$^+$.

3-(tert-butyl)-N-(4-(2-(5-(dimethylamino)pyridin-2-yl)-3H-imidazo[4,5-b]pyridin-7-yl)-2-fluorobenzyl)-1,2,4-oxadiazole-5-carboxamide Into a 20-mL reaction vial was added 3-tert-butyl-[1,2,4] oxadiazole-5-carboxylic acid 4-(2,3-diamino-pyridin-4-yl)-2-fluoro-benzylamide (150.00 mg; 0.39 mmol; 1.00 eq.), 5-dimethylamino-pyridine-2-carbaldehyde (73.25 mg; 0.49 mmol; 1.25 eq.), and DMF (3.00 mL). The vial was sealed and the resulting solution was stirred for 15 h at 120 degrees Celsius. LC-MS at 15 h r indicated both starting materials were present in addition to product. The reaction was then quenched by the addition of water (20 mL). The resulting solution was extracted with dichloromethane (3×25 mL) and the organic layers were combined. The DCM layer had solids present which were filtered and rinsed with DCM. LC-MS of the DCM filtrate showed no product present. The solid was dried under high vacuum to yield 62 mg (31%) of 3-(tert-butyl)-N-(4-(2-(5-(dimethylamino)pyridin-2-yl)-3H-imidazo[4,5-b]pyridin-7-yl)-2-fluorobenzyl)-1,2,4-oxadiazole-5-carboxamide (MSC2578488A-1) as a yellow solid. HPLC: 100% purity. MS: 515 [M+H]$^+$ ion. $^1$H NMR (400 MHz, DMSO-d$_6$) δ 13.46 (s, 1H), 9.92 (s, 1H), 8.36-8.20 (m, 4H), 7.63-7.55 (m, 2H), 7.29-7.26 (d, 1H), 4.63-4.61 (bs, 2H), 3.08 (s, 6H), 1.39 (s, 9H).

Example 149. 3-(tert-butyl)-N-(2-fluoro-4-(2-(pyridin-3-yl)-3H-imidazo[4,5-b]pyridin-7-yl)benzyl)-1,2,4-oxadiazole-5-carboxamide (149)

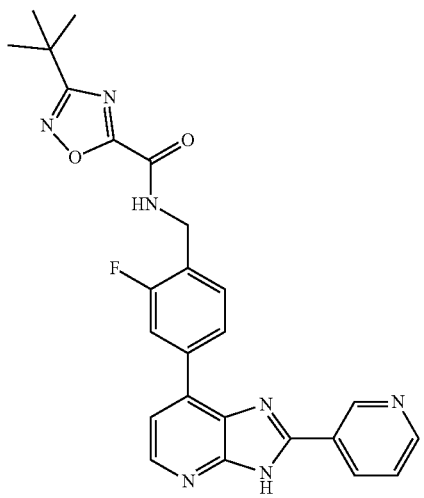 [SMILES: CC(C)(C)c1noc(C(=O)NCc2ccc(-c3ccnc4[nH]c(-c5cccnc5)nc34)cc2F)n1]

Into a 20-mL reaction vial was added 3-tert-Butyl-[1,2,4]oxadiazole-5-carboxylic acid 4-(2,3-diamino-pyridin-4-yl)-2-fluoro-benzylamide (150.00 mg; 0.39 mmol; 1.00 eq.), pyridine-3-carbaldehyde (52.24 mg; 0.49 mmol; 1.25 eq.), and DMF (3.00 ml; 38.77 mmol; 99.34 eq.), The resulting solution was placed under nitrogen atmosphere and stirred overnight at 130 degrees Celsius. After 20 hr the reaction was then quenched by the addition of water (20 mL). The resulting solution was extracted with dichloromethane (3×25 mL) and the organic layers were combined. The DCM was concentrated and the residue was dissolved in DMSO (2.0 mL) and purified directly via prep HPLC (Interchim P4250; 30×150 mm C-18 column; 0.1% formic acid modified mobile phases (A=water, B=ACN); gradient 20-55% B over 15 min at 60 mL/min). The product eluted at 47% ACN. The product fractions were combined and lyophilized to yield 28 mg of 3-(tert-butyl)-N-(2-fluoro-4-(2-(pyridin-3-yl)-3H-imidazo[4,5-b]pyridin-7-yl)benzyl)-1,2,4-oxadiazole-5-carboxamide as a white solid. HPLC: 100% purity. MS: 472 [M+H]$^+$ ion. $^1$H NMR (400 MHz, DMSO-d$_6$) δ 13.95 (s, 1H), 9.93 (s, 1H), 9.45 (s, 1H), 8.75 (bs, 1H), 8.61 (d, 1H), 8.45 (d, 1H), 8.32 (d, 1H), 8.26 (d, 1H), 7.65 (m, 3H), 4.62 (s, 2H), 1.39 (s, 9H).

Example 150. 3-(tert-butyl)-N-(2-fluoro-4-(2-(pyridin-4-yl)-3H-imidazo[4,5-b]pyridin-7-yl)benzyl)-1,2,4-oxadiazole-5-carboxamide (150)

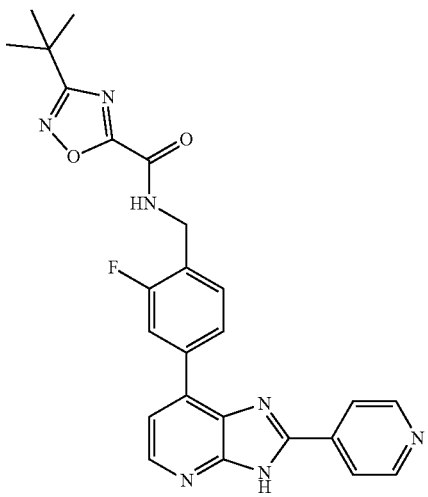 [SMILES: CC(C)(C)c1noc(C(=O)NCc2ccc(-c3ccnc4[nH]c(-c5ccncc5)nc34)cc2F)n1]

Into a 20-mL reaction vial was added 3-tert-butyl-[1,2,4]oxadiazole-5-carboxylic acid 4-(2,3-diamino-pyridin-4-yl)-2-fluoro-benzylamide (150.00 mg; 0.39 mmol; 1.00 eq.), pyridine-4-carbaldehyde (52.24 mg; 0.49 mmol; 1.25 eq.), and DMF (3.00 ml; 38.77 mmol; 99.34 eq.). The resulting solution was placed under nitrogen atmosphere and stirred overnight at 130 degrees Celsius. After 20 hr the reaction was then quenched by the addition of water (20 mL). The resulting solution was extracted with dichloromethane (3×25 mL) and the organic layers were combined. The DCM was concentrated and the residue was dissolved in DMSO (2.0 mL) and purified directly via prep HPLC (Interchim P4250; 30×150 mm C-18 column: 0.1% formic acid modified mobile phases (A=water, B=ACN); gradient 20-55% B over 15 min at 60 mL/min). The product eluted at 45% ACN. The product fractions were combined and lyophilized to yield 5 mg (3%) of 3-(tert-butyl)-N-(2-fluoro-4-(2-(pyridin-3-yl)-3H-imidazo[4,5-b]pyridin-7-yl)benzyl)-1,2,4-oxadiazole-5-carboxamide as a white solid. HPLC: 100% purity. MS: 472 [M+H]$^+$ ion. $^1$H NMR (400 MHz, DMSO-d6) δ 9.95 (t, 1H), 8.80 (d, 2H), 8.47 (d, 1H), 8.29 (d, 1H), 8.22 (d, 3H), 7.63 (m, 2H), 4.63 (s, 2H), 1.39 (s, 9H).

Example 151. 3-(tert-butyl)-N-(2-fluoro-4-(2-(2-methoxypyridin-3-yl)-3H-imidazo[4,5-b]pyridin-7-yl)benzyl)-1,2,4-oxadiazole-5-carboxamide (151)

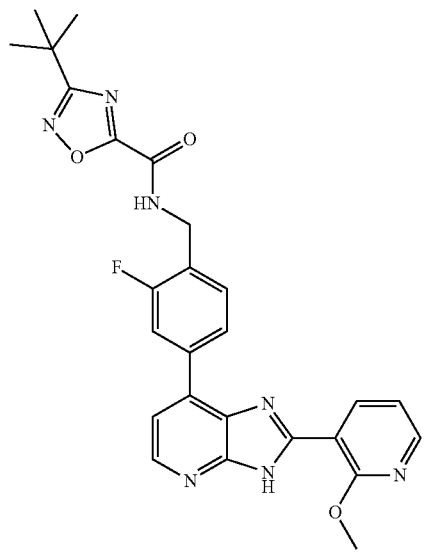 [SMILES: COc1ncccc1-c1nc2c(-c3ccc(CNC(=O)c4nc(C(C)(C)C)no4)c(F)c3)ccnc2[nH]1]

Into a 20-mL reaction vial was added 3-tert-butyl-[1,2,4]oxadiazole-5-carboxylic acid 4-(2,3-diamino-pyridin-4-yl)-2-fluoro-benzylamide (150.00 mg; 0.39 mmol: 1.00 eq.), 2-methoxy-pyridine-3-carbaldehyde (66.89 mg; 0.49 mmol; 1.25 eq.), and DMF (3.00 ml; 38.77 mmol; 99.34 eq.), The resulting solution was placed under nitrogen atmosphere and stirred overnight at 130 degrees Celsius. After 20 hr the reaction was then quenched by the addition of water (20 mL). The resulting solution was extracted with dichloromethane (3×25 mL) and the organic layers were combined. The DCM was concentrated and the residue was dissolved in DMSO (2.0 mL) and purified directly via prep HPLC (Interchim P4250; 30×150 mm C-18 column: 0.1% formic acid modified mobile phases (A=water, B=ACN); gradient 20-70% B over 15 min at 60 mL/min). The product eluted with 68% ACN. The product fractions were combined and lyophilized to yield 16 mg (8%) of 3-(tert-butyl)-N-(2-fluoro-4-(2-(2-methoxypyridin-3-yl)-3H-imidazo[4,5-b]pyridin-7-yl)benzyl)-1,2,4-oxadiazole-5-carboxamide as a white solid. HPLC: 98% purity. MS: 502 [M+H]$^+$ ion. $^1$H NMR (400 MHz, DMSO-d$_6$) δ 13.07 (s, 1H), 9.93 (s, 1H), 8.63 (d, 1H), 8.45 (bs, 1H), 8.38 (bs, 1H), 8.32 (d, 1H), 8.24 (d, 1H), 7.59 (m, 2H), 7.25 (t, 1H), 4.62 (d, 2H), 4.10 (s, 3H), 1.39 (s, 9H).

Example 152. 3-(tert-butyl)-N-(2-fluoro-4-(2-(3-methoxypyridin-2-yl)-3H-imidazo[4,5-b]pyridin-7-yl)benzyl)-1,2,4-oxadiazole-5-carboxamide (152)

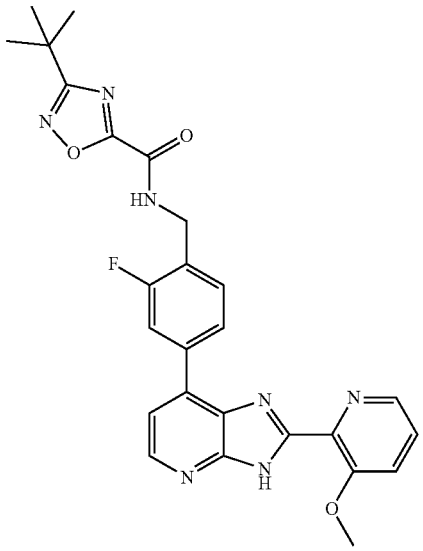 [SMILES: COc1cccnc1-c1nc2c(-c3ccc(CNC(=O)c4nc(C(C)(C)C)no4)c(F)c3)ccnc2[nH]1]

Into a 20-mL reaction vial was added 3-tert-butyl-[1,2,4]oxadiazole-5-carboxylic acid 4-(2,3-diamino-pyridin-4-yl)-2-fluoro-benzylamide (150.00 mg; 0.39 mmol; 1.00 eq.), 3-methoxy-pyridine-2-carbaldehyde (66.89 mg; 0.49 mmol; 1.25 eq.), and DMF (3.00 ml; 38.77 mmol; 99.34 eq.), The resulting solution was placed under nitrogen atmosphere and stirred overnight at 130 degrees Celsius. After 20 hr the reaction was then quenched by the addition of water (20 mL). The resulting solution was extracted with dichloromethane (3×25 mL) and the organic layers were combined. The DCM was concentrated and the residue was dissolved in DMSO (2.0 mL) and purified directly via prep HPLC (Interchim P4250; 30×150 mm C-18 column; 0.1% formic acid modified mobile phases (A=water, B=ACN); gradient 20-55% B over 15 min at 60 mL/min). The product eluted with 47% ACN. The product fractions were combined and lyophilized to yield 36 mg (18%) of 3-(tert-butyl)-N-(2-fluoro-4-(2-(3-methoxypyridin-2-yl)-3H-imidazo[4,5-b]pyridin-7-yl)benzyl)-1,2,4-oxadiazole-5-carboxamide as a white solid. HPLC: 94% purity. MS: 502 [M+H]$^+$ ion. $^1$H NMR (400 MHz, DMSO-d$_6$) δ 13.40 (s, 1H), 9.93 (t, 1H), 8.46 (m, 2H), 8.38 (bs, 1H), 8.22 (d, 1H), 7.75 (d, 1H), 7.66 (bs, 1H), 7.56 (m, 2H), 4.61 (d, 2H), 3.98 (s, 3H), 1.38 (s, 9H).

Scheme 48

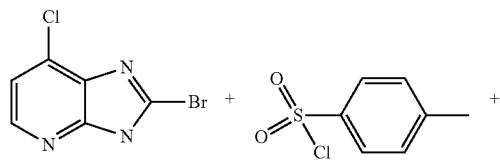

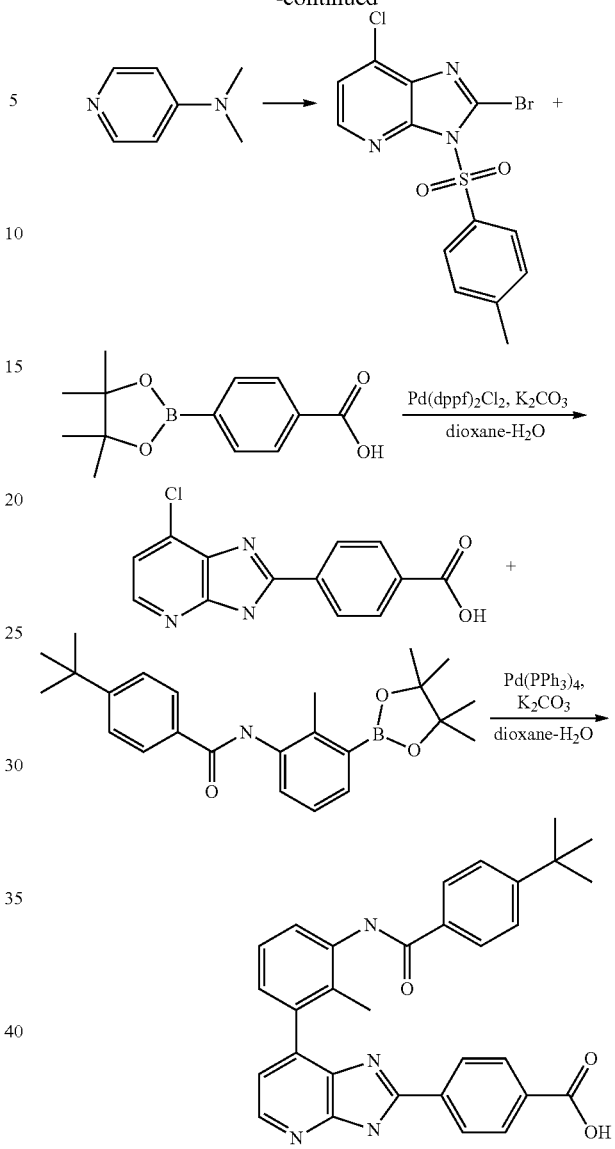

Example 153. 4-{7-[3-(4-tert-Butyl-benzoylamino)-2-methyl-phenyl]-3H-imidazo[4,5-b]pyridin-2-yl}-benzoic acid (153)

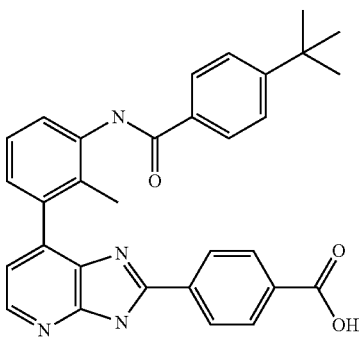 [SMILES: Cc1c(NC(=O)c2ccc(C(C)(C)C)cc2)cccc1-c1ccnc2[nH]c(-c3ccc(C(=O)O)cc3)nc12]

2-Bromo-7-chloro-3-(toluene-4-sulfonyl)-3H-imidazo[4,5-b]pyridine

In a microwave vial containing 2-bromo-7-chloro-3H-imidazo[4,5-b]pyridine (150.00 mg; 0.65 mmol; 1.00 eq.) and p-toluenesulfonyl chloride (141.47 mg: 0.74 mmol; 1.15 eq.) in 1,2-dichloroethane (2.00 ml) was added DIPEA (320.76 μl; 1.94 mmol; 3.00 eq.) and catalytic amount of DMAP (3.94 mg; 0.03 mmol; 0.05 eq.), The turbid mixture was stirred at rt for 16 and concentrated. 10 mL EtOH was added into the residue, filtered and dried to afford the title compound with an off-white solid. No further purification was performed and the crude intermediate was directly used in the next step.

4-(7-Chloro-3H-imidazo[4,5-b]pyridin-2-yl)-benzoic acid

In a microwave vial containing 2-bromo-7-chloro-3-(toluene-4-sulfonyl)-3H-imidazo[4,5-b]pyridine (100.00 mg; 0.26 mmol; 1.00 eq.), 4-(4,4,5,5-tetramethyl-[1,3,2]dioxaborolan-2-yl)-benzoic acid (76.99 mg; 0.31 mmol; 1.20 eq.) and dipotassium carbonate (78.64 mg; 0.57 mmol; 2.20 eq.) was added dioxane (6.00 ml; 93.89 mmol; 363.02 eq.) and water (1.50 ml; 111.02 mmol; 429.26 eq.), The solution was purged with $N_2$ for 1 min before [1,1'-bis(diphenylphosphino)ferrocene]dichloropalladium(ii), complex with dichloromethane (21.12 mg: 0.03 mmol; 0.10 eq.) was added. The reaction mixture was stirred at 115° C. for 1 h before it was filtered through Celite pad, concentrated and used in the next step without further purification.

4-{7-[3-(4-tert-Butyl-benzoylamino)-2-methyl-phenyl]-3H-imidazo[4,5-b]pyridin-2-yl}-benzoic acid In a microwave vial containing 4-tert-butyl-N-[2-methyl-3-(4,4,5,5-tetramethyl-[1,3,2]dioxaborolan-2-yl)-phenyl]-benzamide (122.72 mg: 0.31 mmol; 1.20 eq.), 4-(7-Chloro-3H-imidazo[4,5-b]pyridin-2-yl)-benzoic acid (71.16 mg; 0.26 mmol; 1.00 eq.) in Propan-2-ol (6.00 ml; 78.48 mmol; 301.83 eq.) and water (1.80 ml; 99.92 mmol; 384.30 eq.) was added dipotassium carbonate (79.05 mg; 0.57 mmol; 2.20 eq.), The reaction was degassed for 1 min before tetrakis(triphenylphosphine)palladium(0) (45.07 mg; 0.04 mmol; 0.15 eq.) (solid supported 0.02 mmol/g) was added. The reaction mixture was stirred at 85° C. for 24 h before it was filtered through a Celite pad and subjected to preparative HPLC (0.1% $NH_4OH$ in ACN). The collected fractions of the desired product were lyophilized to afford the title product (7.5 mg, 5.7%) as a white solid. HPLC: 98%, RT=2.90 min. MS: m/z=505 [M+H]$^+$. $^1$H-NMR (DMSO-D6) δ 9.91 (s, 1H), 8.46 (m, 1H), 8.31 (m, 2H), 8.13 (m, 2H), 8.02 (m, 2H), 7.54 (m, 3H), 7.36 (m, 1H), 7.27 (m, 1H), 7.19 (m, 1H), 2.07 (s, 3H), 1.25 (s, 9H).

Scheme 49

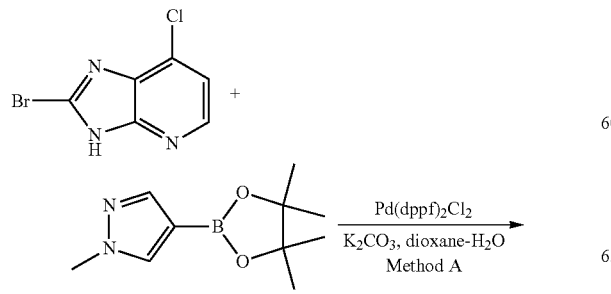

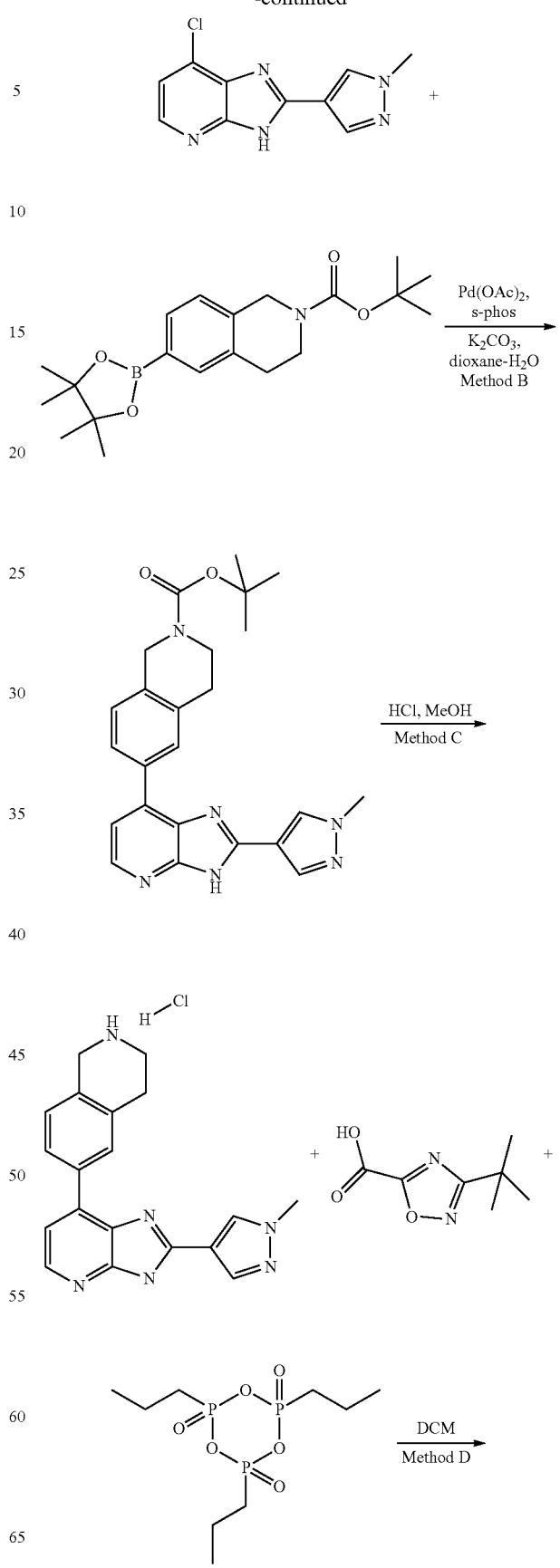

-continued

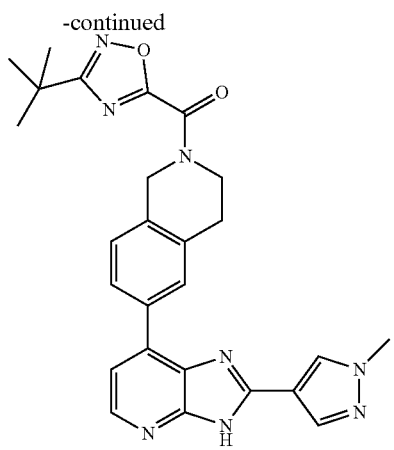

Example 154. (3-tert-Butyl-[1,2,4]oxadiazol-5-yl)-{6-[2-(1-methyl-1H-pyrazol-4-yl)-3H-imidazo[4,5-b]pyridin-7-yl]-3,4-dihydro-1H-isoquinolin-2-yl}-methanone (154)

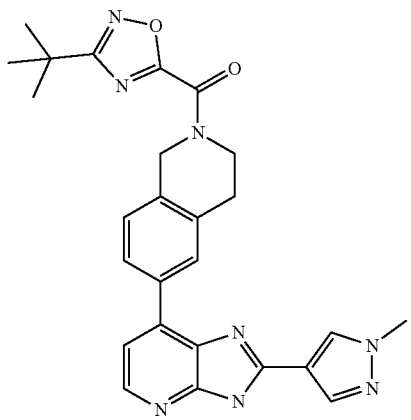 [SMILES: Cn1cc(-c2nc3c(-c4ccc5c(c4)CCN(C(=O)c4nc(C(C)(C)C)no4)C5)ccnc3[nH]2)cn1]

7-Chloro-2-(1-methyl-1H-pyrazol-4-yl)-3H-imidazo[4,5-b]pyridine (Method F)

In a microwave vial containing 2-bromo-7-chloro-3h-imidazo[4,5-b]pyridine (300.00 mg; 1.29 mmol; 1.00 eq.), 1-methylpyrazole-4-boronic acid pinacol ester (268.51 mg; 1.29 mmol: 1.00 eq.), [1,1'-bis(diphenylphosphino)ferrocene]dichloropalladium(ii), complex with dichloromethane (105.39 mg; 0.13 mmol; 0.10 eq.) and dipotassium carbonate (535.07 mg; 3.87 mmol: 3.00 eq.) was added dioxane (5.00 ml; 58.68 mmol; 45.47 eq.) and water (0.50 ml; 27.75 mmol; 21.51 eq.), The vial was evacuated and filled with nitrogen. The reaction mixture was stirred at 130° C. for 16 h before it was filtered with a Celite pad, concentrated and used in the next step directly.

6-[2-(1-Methyl-1H-pyrazol-4-yl)-3H-imidazo[4,5-b]pyridin-7-yl]-3,4-dihydro-1H-isoquinoline-2-carboxylic acid tert-butyl ester (Method G)

In a microwave vial containing the concentrated crude 7-chloro-2-(1-methyl-1H-pyrazol-4-yl)-3H-imidazo[4,5-b]pyridine (100.00 mg; 0.43 mmol; 1.00 eq.) was added 6-(4,4,5,5-Tetramethyl-[1,3,2]dioxaborolan-2-yl)-3,4-dihydro-1H-isoquinoline-2-carboxylic acid tert-butyl ester (230.64 mg; 0.64 mmol; 1.50 eq.), palladium(ii) acetate (14.41 mg: 0.06 mmol; 0.15 eq.), 2-dicyclohexylphosphino-2',6'-dimethoxybiphenyl (52.71 mg; 0.13 mmol; 0.30 eq.), dipotassium carbonate (130.13 mg; 0.94 mmol: 2.20 eq.) in dioxane (4.00 ml; 35.21 mmol; 82.27 eq.) and water (1.00 ml; 41.63 mmol; 97.28 eq.), The mixture was stirred at 130° C. for 24 h before it was filtered through a Celite pad, dried and carried to the next step.

6-[2-(1-Methyl-1H-pyrazol-4-yl)-3H-imidazo[4,5-b]pyridin-7-yl]-1,2,3,4-tetrahydro-isoquinoline hydrochloride (Method H)

In a round bottom flask containing 6-[2-(1-Methyl-1H-pyrazol-4-yl)-3H-imidazo[4,5-b]pyridin-7-yl]-3,4-dihydro-1H-isoquinoline-2-carboxylic acid tert-butyl ester (184.25 mg; 0.43 mmol; 1.00 eq.) was added methanol (6.00 ml) and hydrogen chloride (1.10 ml; 4.28 mmol; 10.00 eq.), The reaction mixture was stirred at rt for 16 before it was concentrated and used in the next step.

(3-tert-Butyl-[1,2,4]oxadiazol-5-yl)-{6-[2-(1-methyl-H-pyrazol-4-yl)-3H-imidazo[4,5-b]pyridin-7-yl]-3,4-dihydro-1H-isoquinolin-2-yl}-methanone (Method 1)

In a round bottom flask containing 6-[2-(1-Methyl-1H-pyrazol-4-yl)-3H-imidazo[4,5-b]pyridin-7-yl]-1,2,3,4-tetrahydro-isoquinoline hydrochloride (146.74 mg; 0.40 mmol; 1.00 eq.) and 3-tert-Butyl-[1,2,4]oxadiazole-5-carboxylic acid (68.07 mg; 0.40 mmol; 1.00 eq.) in DCM (3.00 ml; 46.80 mmol; 117.00 eq.) was added DIPEA (0.53 ml; 3.20 mmol; 8.00 eq.), After stirring for 10 min, 2,4,6-Tripropyl-[1,3,5,2,4,6]trioxatriphosphinane 2,4,6-trioxide (127.27 mg; 0.40 mmol; 1.00 eq.) was slowly added. The mixture was stirred for 30 min before it was purified with basic Waters prep-HPLC system (44% ACN/H2O). The collected fractions of the desired product were lyophilized to afford the title product (52 mg, 26.7%) as a white solid. HPLC: 99%, RT=2.83 min. MS: m/z=483 [M+H]+. 1H-NMR (DMSO-D6) δ 8.43 (m, 1H), 8.08-8.25 (m, 3H), 7.51 (m, 1H), 4.91 (m, 2H), 4.0 (m, 5H), 3.07 (m, 2H), 1.38 (s, 9H).

Example 155. (3-tert-Butyl-[1,2,4]oxadiazol-5-yl)-{7-[2-(1-methyl-1H-pyrazol-4-yl)-3H-imidazo[4,5-b]pyridin-7-yl]-3,4-dihydro-1H-isoquinolin-2-yl}-methanone (155)

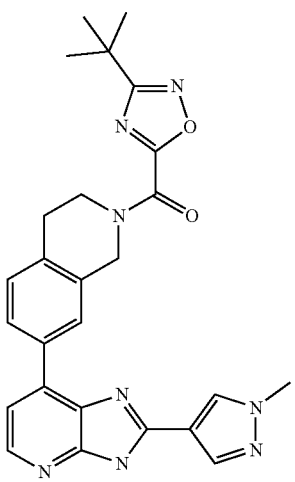 [SMILES: Cn1cc(-c2nc3c(-c4ccc5c(c4)CN(C(=O)c4nc(C(C)(C)C)no4)CC5)ccnc3[nH]2)cn1]

(3-tert-Butyl-[1,2,4]oxadiazol-5-yl)-(7-[2-(1-methyl-1H-pyrazol-4-yl)-3H-imidazo[4,5-b]pyridin-7-yl]-3,4-dihydro-1H-isoquinolin-2-yl)-methanone was prepared from 7-Bromo-2-(1-methyl-1H-pyrazol-4-yl)-3H-imidazo[4,5-b]pyridine, 7-(4,4,5,5-Tetramethyl-[1,3,2]dioxaborolan-2-yl)-3,4-dihydro-1H-isoquinoline-2-carboxylic acid tert-butyl ester and 3-tert-Butyl-[1,2,4]oxadiazole-5-carboxylic acid using Methods G, H and I as a white solid (50 mg, 35.7%). HPLC: 99%, RT=2.86 min. MS: m/z=483 [M+H]⁺. ¹H-NMR (DMSO-D6) δ 8.0-8.44 (m, 4H), 7.37 (m, 2H), 5.0 (m, 2H), 3.92 (m, 5H), 3.01 (m, 2H), 1.38 (s, 9H).

Example 156. (3-tert-Butyl-[1,2,4]oxadiazol-5-yl)-{5-[2-(1-methyl-1H-pyrazol-4-yl)-3H-imidazo[4,5-b]pyridin-7-yl]-1,3-dihydro-isoindol-2-yl}-methanone (156)

(3-tert-Butyl-[1,2,4]oxadiazol-5-yl)-{5-[2-(1-methyl-1H-pyrazol-4-yl)-3H-imidazo[4,5-b]pyridin-7-yl]-1,3-dihydro-isoindol-2-yl}-methanone was prepared from 7-Bromo-2-(1-methyl-1H-pyrazol-4-yl)-3H-imidazo[4,5-b]pyridine, tert-butyl 5-(4,4,5,5-tetramethyl-1,3,2-dioxaborolan-2-yl)isoindoline-2-carboxylate and 3-tert-Butyl-[1,2,4]oxadiazole-5-carboxylic acid using Methods G, H, and I as a white solid (14 mg, 24.7%). HPLC: 99%. RT=2.77 min. MS: m/z=469 [M+H]⁺. ¹H-NMR (DMSO-D6) δ 8.25-8.47 (m, 4H), 8.19 (m, 1H), 7.53 (m, 1H), 7.49 (m, 1H), 5.29 (m, 2H), 5.0 (m, 2H), 4.0 (m, 3H), 1.48 (s, 9H). This is a mixture of two isomers.

Scheme 50

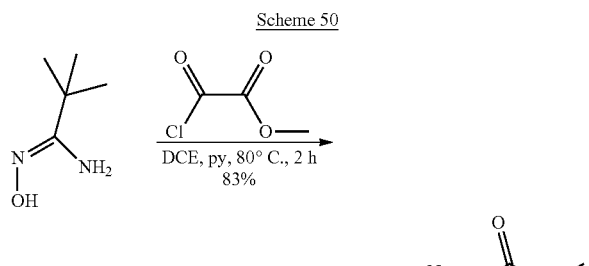

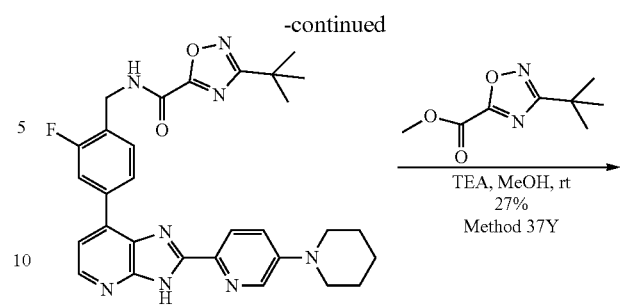

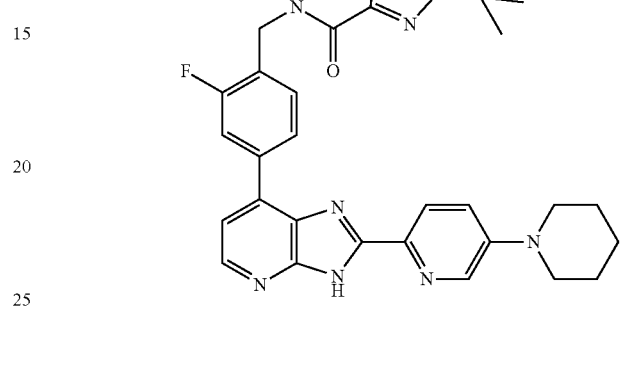

Example 157. 3-tert-Butyl-N-[(2-fluoro-4-[2-[5-(piperidin-1-yl)pyridin-2-yl]-3H-imidazo[4,5-b]pyridin-7-yl]phenyl)methyl]-1,2,4-oxadiazole-5-carboxamide

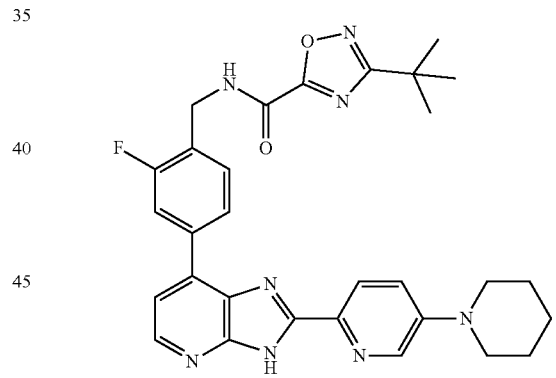

Methyl 3-tert-butyl-1,2,4-oxadiazole-5-carboxylate

In a 100-mL round bottom flask with magnetic stir bar, (Z)—N-hydroxy-2,2-dimethylpropimidamide (2 g, 16.36 mmol, 1.00 equiv) and pyridine (4.1 g, 51.83 mmol, 3.17 equiv) were dissolved in DCE (20 mL), to which was added methyl 2-chloro-2-oxoacetate (2.3 g, 17.84 mmol, 1.09 equiv) dropwise at 0° C. The resulting solution was then stirred for 2 h at 80° C. After the reaction was done, the reaction mixture was diluted with 40 mL hydrogen chloride solution (2 N) and extracted with dichloromethane (3×40 mL). The organic layers were combined, dried over sodium sulfate and concentrated under reduced pressure to afford methyl 3-tert-butyl-1,2,4-oxadiazole-5-carboxylate as yellow oil (2.5 g, 83% yield). MS: m/z=185.0 [M+H]⁺.

3-tert-Butyl-N-[(2-fluoro-4-[2-[5-(piperidin-1-yl) pyridin-2-yl]-3H-imidazo[4,5-b]pyridin-7-yl]phenyl) methyl]-1,2,4-oxadiazole-5-carboxamide 3-tert-butyl-N-[(2-fluoro-4-[2-[5-(piperidin-1-yl)pyridin-2-yl]-3H-imidazo[4,5-b]pyridin-7-yl]phenyl)methyl]-1,2,4-oxadiazole-5-carboxamide 13 mg (27%) was prepared from (2-fluoro-4-[2-[5-(piperidin-1-yl)pyridin-2-yl]-3H-imidazo[4,5-b]pyridin-7-yl]phenyl)methanamine and methyl 3-tert-butyl-1,2,4-oxadiazole-5-carboxylate using Method 37Y. HPLC: 98.9% purity. MS: m/z=555.4 [M+H]$^+$. $^1$H-NMR (300 MHz, DMSO-$d_6$): δ 13.53 (br s, 1H), 9.92 (t, J=5.9 Hz, 1H), 8.45-8.27 (m, 3H), 8.25-8.15 (m, 2H), 7.65-7.43 (m, 3H), 4.60 (d, J=5.9 Hz, 2H), 3.32 (m, 4H), 1.69-1.59 (m, 6H), 1.37 (s, 9H).

Scheme 51

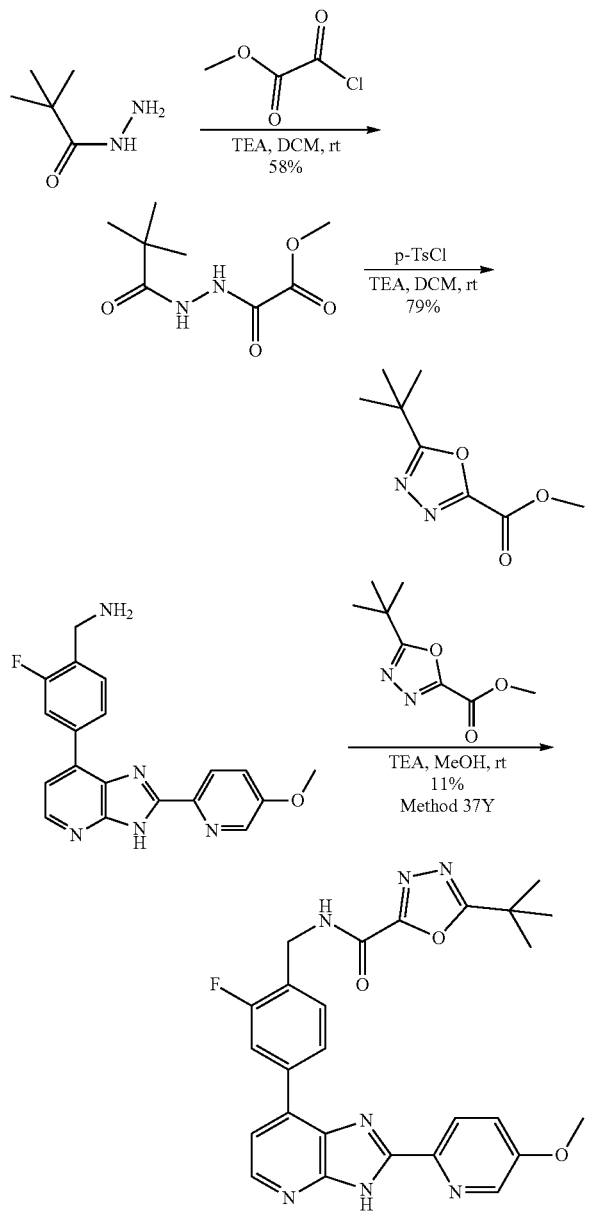

Example 158. 5-tert-butyl-N-([2-fluoro-4-[2-(5-methoxypyridin-2-yl)-3H-imidazo[4,5-b]pyridin-7-yl]phenyl]methyl)-1,3,4-oxadiazole-2-carboxamide

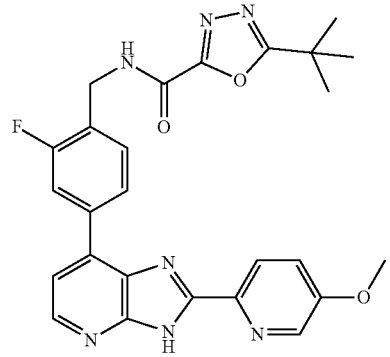 [SMILES: COc1ccc(-c2nc3c(-c4ccc(CNC(=O)c5nnc(C(C)(C)C)o5)c(F)c4)ccnc3[nH]2)nc1]

Methyl 2-(2,2-dimethylpropanehydrazido)-2-oxoacetate

In a 100-mL round bottom flask with magnetic stir bar, 2,2-dimethylpropanehydrazide (1.0 g, 8.61 mmol, 1.00 equiv) and TEA (1.132 g, 11.19 mmol, 1.30 equiv) were dissolved in dichloromethane (20 mL), to which was added methyl 2-chloro-2-oxoacetate (1.160 g, 9.47 mmol, 1.10 equiv) dropwise at 0° C. The resulting mixture was warmed up to room temperature and stirred for 16 h at room temperature. After the reaction was done, the reaction mixture was diluted with 20 mL water and extracted with dichloromethane (3×40 mL). The organic layers were combined, dried over sodium sulfate and concentrated under reduced pressure to afford methyl 2-(2,2-dimethylpropanehydrazido)-2-oxoacetate as light yellow solid (1.01 g, 58%).

Methyl 5-tert-butyl-1,3,4-oxadiazole-2-carboxylate

In a 100-mL round bottom flask with magnetic stir bar, methyl 2-(2,2-dimethylpropanehydrazido)-2-oxoacetate (900 mg, 4.45 mmol, 1.0 equiv) and TEA (585.5 mg, 5.79 mmol, 1.30 equiv) were dissolved in dichloromethane (30 mL), to which was added 4-methylbenzene-1-sulfonyl chloride (933.4 mg, 4.90 mmol, 1.10 equiv) slowly at 0° C. The resulting solution was warmed up to room temperature and stirred for 12 h at room temperature. After the reaction was done, the reaction mixture was diluted with 10 mL water and extracted with dichloromethane (3×10 mL). The organic layers were combined, dried over sodium sulfate and concentrated under reduced pressure. The residue was purified in a silica gel column eluting with methanol in dichloromethane (1% to 10% gradient) to afford methyl 5-tert-butyl-1,3,4-oxadiazole-2-carboxylate (650 mg, 79% yield) as yellow solid. MS: m/z=184.9 [M+H]$^+$.

5-tert-butyl-N-([2-fluoro-4-[2-(5-methoxypyridin-2-yl)-3H-imidazo[4,5-b]pyridin-7-yl]phenyl]methyl)-1,3,4-oxadiazole-2-carboxamide 5-tert-butyl-N-([2-fluoro-4-[2-(5-methoxypyridin-2-yl)-3H-imidazo[4,5-b]pyridin-7-yl]phenyl]methyl)-1,3,4-oxadiazole-2-carboxamide 10 mg (11%) was prepared from [2-fluoro-4-[2-(5-methoxypyridin-2-yl)-3H-imidazo[4,5-b]pyridin-7-yl]phenyl]methanamine and methyl 5-tert-butyl- 1,3,4-oxadiazole-2-carboxylate using Method 37Y. HPLC: 97.7% purity. MS: m/z=502.3 [M+H]$^+$. $^1$H-NMR (400 MHz, DMSO-d$_6$): δ 13.17 (br s, 1H), 9.90-9.87 (m, 1H), 8.48 (s, 1H), 8.38-8.36 (m, 2H), 8.32-8.29 (m, 1H), 8.22-8.20 (m, 1H), 7.51-7.64 (m, 3H), 4.64-4.60 (m, 2H), 3.98 (s, 3H), 1.48 (s, 9H).

Example 159. 3-tert-butyl-N-([2-fluoro-4-[2-(4-methoxypyridin-2-yl)-3H-imidazo[4,5-b]pyridin-7-yl]phenyl]methyl)-1,2,4-oxadiazole-5-carboxamide

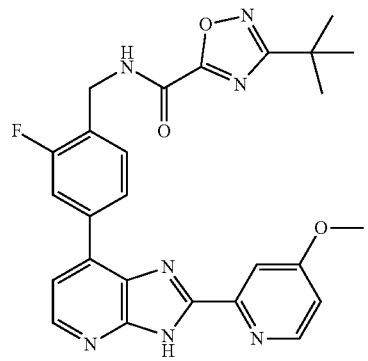 [SMILES: COc1ccnc(-c2nc3c(-c4ccc(CNC(=O)c5nc(C(C)(C)C)no5)c(F)c4)ccnc3[nH]2)c1]

3-tert-butyl-N-([2-fluoro-4-[2-(4-methoxypyridin-2-yl)-3H-imidazo[4,5-b]pyridin-7-yl]phenyl]methyl)-1,2,4-oxadiazole-5-carboxamide 10 mg (15% for three steps) was prepared from tert-butyl N-[[4-(2,3-diaminopyridin-4-yl)-2-fluorophenyl]methyl]carbamate, 4-methoxypyridine-2-carbaldehyde and methyl 3-tert-butyl-1,2,4-oxadiazole-5-carboxylate using Method 15P, 19T and 37Y. HPLC: 95.1% purity. MS: m/z=502.2 [M+H]$^+$. $^1$H-NMR (400 MHz, DMSO-d$_6$): δ 13.89 (br s, 1H), 9.94 (m, 1H), 8.60-8.58 (m, 1H), 8.43-8.42 (m, 1H), 8.30-8.20 (m, 2H), 7.90-7.89 (m, 1H), 7.63-7.59 (m, 2H), 7.18-7.16 (m, 1H), 4.62-4.60 (m, 2H), 3.96 (s, 3H), 1.36 (s, 9H).

Scheme 52

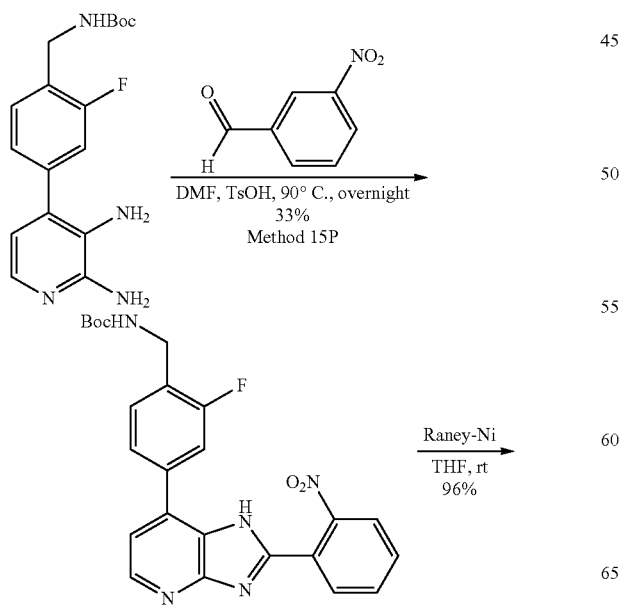

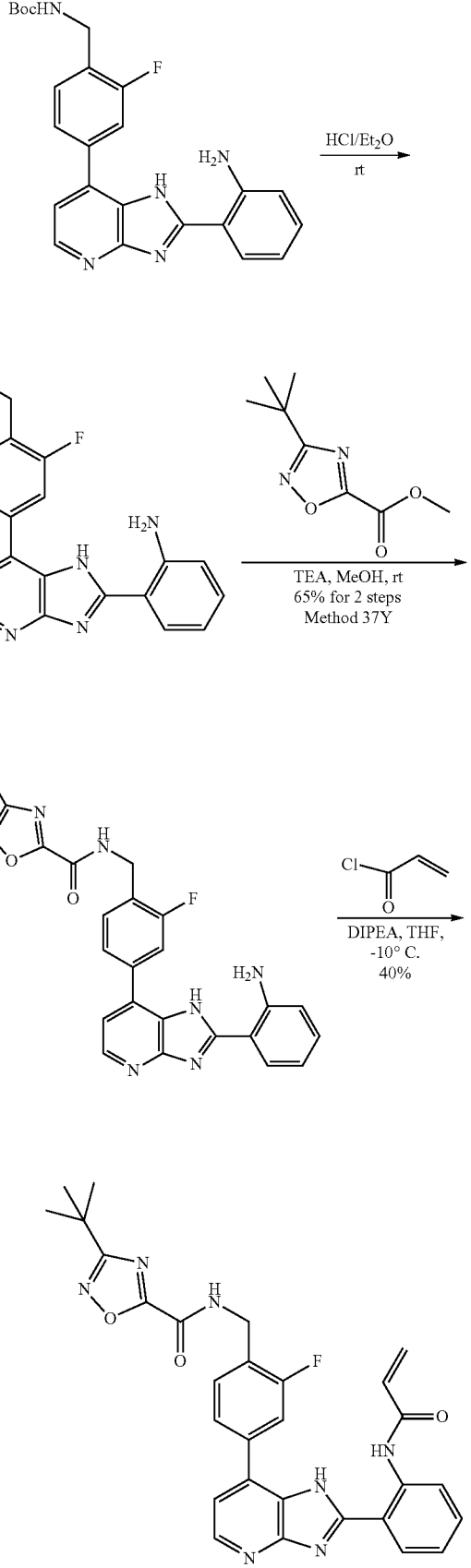

Example 160. 3-tert-butyl-N-[(2-fluoro-4-[2-[2-(prop-2-enamido)phenyl]-3H-imidazo[4,5-b]pyridin-7-yl]phenyl)methyl]-1,2,4-oxadiazole-5-carboxamide

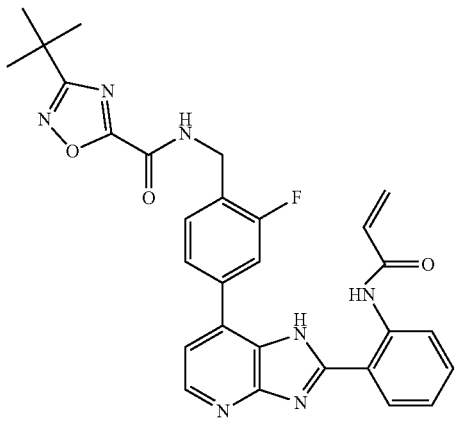 [SMILES: C=CC(=O)Nc1ccccc1-c1nc2nccc(-c3ccc(CNC(=O)c4nc(C(C)(C)C)no4)c(F)c3)c2[nH]1]

tert-Butyl N-([2-fluoro-4-[2-(2-nitrophenyl)-3H-imidazo[4,5-b]pyridin-7-yl]phenyl]methyl) carbamate tert-butyl N-([2-fluoro-4-[2-(2-nitrophenyl)-3H-imidazo[4,5-b]pyridin-7-yl]phenyl]methyl)carbamate 100 mg (33%) was prepared from tert-butyl N-[[4-(2,3-diaminopyridin-4-yl)-2-fluorophenyl]methyl]carbamat, 2-nitrobenzaldehyde using Method 15P. MS: m/z=464.2 [M+H]+.

tert-Butyl N-([4-[2-(2-aminophenyl)-3H-imidazo[4,5-b]pyridin-7-yl]-2-fluorophenyl]methyl) carbamate In a 25-ml round bottom flask with magnetic stir bar, Raney-Ni (20 mg, 0.23 mmol, 1.00 equiv) was added to a solution of tert-butyl N-([2-fluoro-4-[2-(2-nitrophenyl)-3H-imidazo[4,5-b]pyridin-7-yl]phenyl]methyl)carbamate (100 mg, 0.22 mmol, 1.00 equiv) in tetrahydrofuran (5 mL) under nitrogen atmosphere at room temperature. The reaction flask was then vacuumed and flushed with hydrogen. The reaction mixture was hydrogenated at room temperature for 2 hours under hydrogen atmosphere using a hydrogen balloon. After the reaction was done, the reaction mixture was filtered through a Celite pad and concentrated under reduced pressure to afford tert-butyl N-([4-[2-(2-aminophenyl)-3H-imidazo[4,5-b]pyridin-7-yl]-2-fluorophenyl]methyl)carbamate (90 mg, 96%) as yellow oil. MS: m/z=434.2 [M+H]+.

2-[7-[4-(aminomethyl)-3-fluorophenyl]-3H-imidazo[4,5-b]pyridin-2-yl]aniline)

In a 25-mL round bottom flask with magnetic stir bar, tert-butyl N-([4-[2-(2-aminophenyl)-3H-imidazo[4,5-b]pyridin-7-yl]-2-fluorophenyl]methyl)carbamate (85 mg, 0.20 mmol, 1.00 equiv) was dissolved in tetrahydrofuran (5 mL), to which was added a solution of HCl in Et$_2$O (4 N, 30 mL) at room temperature. The resulting mixture was then stirred for 1 h at room temperature. After the reaction was done, the reaction mixture was concentrated under reduced pressure to afford 2-[7-[4-(aminomethyl)-3-fluorophenyl]-3H-imidazo[4,5-b]pyridin-2-yl]aniline (80 mg, crude) as a yellow solid. MS: m/z=334.2 [M+H]+.

N-([4-[2-(2-aminophenyl)-3H-imidazo[4,5-b]pyridin-7-yl]-2-fluorophenyl]methyl)-3-tert-butyl-1,2,4-oxadiazole-5-carboxamide N-([4-[2-(2-aminophenyl)-3H-imidazo [4,5-b]pyridin-7-yl]-2-fluorophenyl]methyl)-3-tert-butyl-1,2,4-oxadiazole-5-carboxamide 60 mg (65% for two steps) was prepared from 2-[7-[4-(aminomethyl)-3-fluorophenyl]-3H-imidazo[4,5-b]pyridin-2-yl]aniline and methyl 3-tert-butyl-1,2,4-oxadiazole-5-carboxylate using Method 37Y. MS: m/z=486.3 [M+H]+.

3-tert-butyl-N-[(2-fluoro-4-[2-[2-(prop-2-enamido)phenyl]-3H-imidazo[4,5-b]pyridin-7-yl]phenyl) methyl]-1,2,4-oxadiazole-5-carboxamide In a 25-mL round-bottom flask, N-([4-[2-(2-aminophenyl)-3H-imidazo[4,5-b]pyridin-7-yl]-2-fluorophenyl] methyl)-3-tert-butyl-1,2,4-oxadiazole-5-carboxamide (45 mg, 0.09 mmol, 1.00 equiv) and DIEA (12.6 mg, 0.10 mmol, 1.05 equiv) were dissolved in tetrahydrofuran (5 mL), to which was added prop-2-enoyl chloride (8.8 mg, 0.10 mmol, 1.05 equiv) dropwise at −10° C. The resulting solution was then stirred for 0.5 h at −10° C. After the reaction was done, the reaction mixture was diluted with 30 mL water and extracted with dichloromethane (3×20 mL). The organic layers were combined, dried over sodium sulfate and concentrated under reduced pressure. The residue was purified by prep-HPLC using the following conditions: column, S XBridge C18 OBD Prep Column, 5 um, 19 mm×250 mm; mobile phase, acetonitrile in water (with 10 mM NH$_4$HCO$_3$), 52% to 62% gradient in 8 min; detector, UV 254 nm. 3-tert-butyl-N-[(2-fluoro-4-[2-[2-(prop-2-enamido) phenyl]-3H-imidazo[4,5-b]pyridin-7-yl]phenyl) methyl]-1, 2,4-oxadiazole-5-carboxamide (20 mg, 40%) was obtained as yellow solid. HPLC: 95.9% purity. MS: m/z=540.3 [M+H]+. $^1$H-NMR (400 MHz, DMSO-d$_6$): δ 13.20 (br s, 1H), 10.00-9.99 (m, 1H), 8.80-8.78 (m, 1H), 8.45-8.43 (m, 1H), 8.34-8.32 (m, 1H), 8.05-8.03 (m, 2H), 7.64-7.50 (m, 3H), 7.3

Example 161. 3-tert-butyl-N-([2-fluoro-4-[2-(5-methoxypyridin-2-yl)-3H-imidazo[4,5-b]pyridin-7-yl]phenyl]methyl)-1,2,4-oxadiazole-5-carboxamide

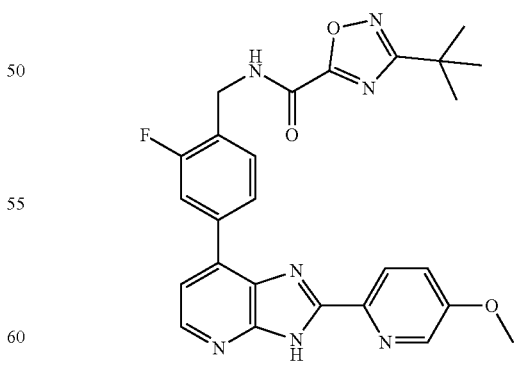

3-tert-butyl-N-([2-fluoro-4-[2-(5-methoxypyridin-2-yl)-3H-imidazo[4,5-b]pyridin-7-yl]phenyl]methyl)-1,2,4-oxadiazole-5-carboxamide 23.4 mg (25% for 3 steps) was prepared from tert-butyl N-[[4-(2,3-diaminopyridin-4-yl)-2-fluorophenyl]methyl]carbamate, 5-methoxypyridine-2-carbaldehyde, HCl in MeOH and methyl 3-tert-butyl-1,2,4-oxadiazole-5-carboxylate using Method 15P, 19T and 37Y. HPLC: 97.6% purity. MS: m/z=502.2 [M+H]+. 1H-NMR (400 MHz, DMSO-d6): δ 13.75 (br s, 1H), 9.96-9.92 (m, 1H), 8.47 (s, 1H), 8.46-8.36 (m, 2H), 8.36-8.30 (m, 1H), 8.21 (d, J=8.0 Hz, 1H), 7.64-7.58 (m, 3H), 4.61 (d, J=6.0 Hz, 2H), 3.95 (s, 3H), 1.37 (s, 9H).

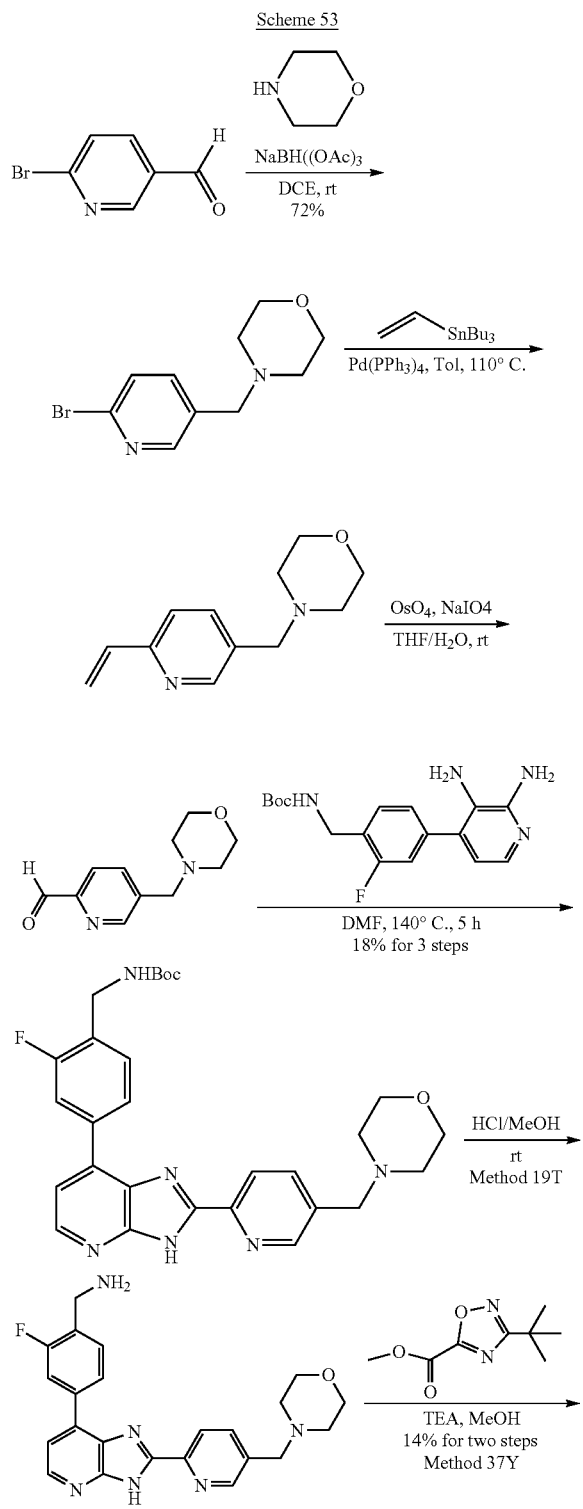

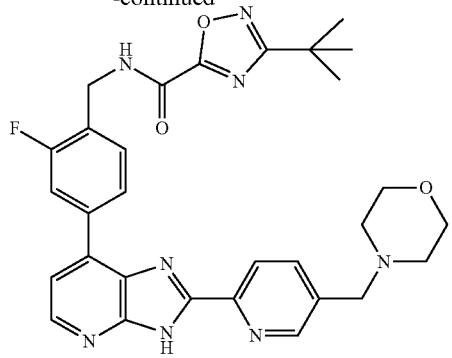

Example 162. 3-tert-butyl-N-[(2-fluoro-4-[2-[5-(morpholin-4-ylmethyl)pyridin-2-yl]-3H-imidazo[4,5-b]pyridin-7-yl] phenyl)methyl]-1,2,4-oxadiazole-5-carboxamide

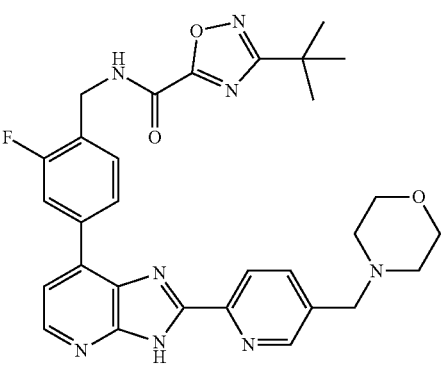 [SMILES: CC(C)(C)c1noc(C(=O)NCc2ccc(-c3ccnc4[nH]c(-c5ccc(CN6CCOCC6)cn5)nc34)cc2F)n1]

4-[(6-bromopyridin-3-yl)methyl]morpholine

In a 50-mL round bottom flask, 6-bromopyridine-3-carbaldehyde (1.200 g, 6.45 mmol, 1.00 equiv) and morpholine (843 mg, 9.68 mmol, 1.50 equiv) were dissolved in 1,2-dichloroethane (15 mL), to which were added NaBH(OAc)3 (4.102 g, 19.35 mmol, 3.00 equiv) and acetic acid (416 mg, 10.35 mmol 1.07 equiv) at 0° C. The resulting solution was warmed up to room temperature and stirred for 5 h at room temperature. When the reaction was done, it was quenched by the addition of 20 mL sat. sodium bicarbonate solution and the pH value of the resulting mixture was adjusted to 9 using sodium hydroxide solution (1 M). The mixture was then extracted with ethyl acetate (3×30 mL) and the organic layers were combined, dried over anhydrous sodium sulfate and concentrated under reduced pressure. The residue was purified in a silica gel column eluting with ethyl acetate in petroleum ether (5% to 50% gradient) to afford 4-[(6-bromopyridin-3-yl)methyl]morpholine (1.2 g, 72%) as light yellow solid.

4-[(6-ethenylpyridin-3-yl)methyl]morpholine

In a 50-mL round bottom flask purged and maintained with an inert atmosphere of nitrogen, 4-[(6-bromopyridin-3-yl)methyl]morpholine (256 mg, 1.00 mmol, 1.00 equiv), tributyl(ethenyl)stannane (748 mg, 2.24 mmol, 1.52 equiv)

and Pd(PPh$_3$)$_4$ (181 mg, 0.14 mmol, 0.10 equiv, 90%) were mixed in toluene (6 mL) at room temperature. The resulting mixture was then stirred overnight at 110° C. After the reaction was done, the reaction mixture was diluted with water (50 mL) and extracted with dichloromethane (3×150 mL). The organic layers were combined, dried over sodium sulfate and concentrated under reduced pressure. The residue was purified in a silica gel column eluting with methanol in dichloromethane (1% to 10% gradient) to afford 4-[(6-ethenylpyridin-3-yl)methyl]morpholine (310 mg, crude) as yellow oil. MS: m/z=205.0 [M+H]$^+$.

5-(morpholin-4-ylmethyl)pyridine-2-carbaldehyde

In a 25-mL round bottom flask, 4-[(6-ethenylpyridin-3-yl)methyl]morpholine (179.8 mg, 0.88 mmol, 1.00 equiv) was dissolved in tetrahydrofuran (5 mL), to which were added NaIO$_4$ (1300 mg, 5.77 mmol, 4.00 equiv) and a suspension of OsO$_4$ (284 mg, 1.18 mmol, 1.27 equiv) in water (1 ml). The resulting mixture was then stirred for 2 days at room temperature. When the reaction was done, it was quenched by the addition of 10 mL Na$_2$S$_2$O$_3$ and the mixture was extracted with dichloromethane (3×15 mL). The organic layers were combined, dried over sodium sulfate and concentrated under reduced pressure to afford 5-(morpholin-4-ylmethyl)pyridine-2-carbaldehyde (300 mg, crude) as brown oil.

Tert-butyl N-[(2-fluoro-4-[2-[5-(morpholin-4-ylmethyl)pyridin-2-yl]-1H-imidazo[4,5-b]pyridin-7-yl]phenyl)methyl]carbamate In a 10-mL vial with magnetic stir bar, tert-butyl N-[[4-(2,3-diaminopyridin-4-yl)-2-fluorophenyl]methyl]carbamate (135 mg, 0.41 mmol, 1.08 equiv) and 5-(morpholin-4-ylmethyl)pyridine-2-carbaldehyde (77 mg, 0.37 mmol, 1.00 equiv) were dissolved in N,N-dimethylformamide (2 mL) at room temperature. The resulting solution was then stirred for 5 h at 140° C. After the reaction was done, the reaction mixture was concentrated under reduced pressure and the residue was purified in a silica gel column eluting with methanol in dicloromethane (1% to 10% gradient) to afford tert-butyl N-[(2-fluoro-4-[2-[5-(morpholin-4-ylmethyl)pyridin-2-yl]-1H-imidazo[4,5-b]pyridin-7-yl]phenyl)methyl]carbamate (55 mg, 18% for 3 steps) as yellow solid. MS: m/z=519.5 [M+H]$^+$.

3-tert-butyl-N-[(2-fluoro-4-[2-[5-(morpholin-4-ylmethyl)pyridin-2-yl]-3H-imidazo[4,5-b]pyridin-7-yl]phenyl)methyl]-1,2,4-oxadiazole-5-carboxamide 3-tert-butyl-N-[(2-fluoro-4-[2-[5-(morpholin-4-ylmethyl)pyridin-2-yl]-3H-imidazo[4,5-b]pyridin-7-yl]phenyl)methyl]-1,2,4-oxadiazole-5-carboxamide 5 mg (14% for two steps) was prepared from tert-butyl N-[(2-fluoro-4-[2-[5-(morpholin-4-ylmethyl)pyridin-2-yl]-3H-imidazo[4,5-b]pyridin-7-yl]phenyl)methyl]carbamate, methyl 3-tert-butyl-1,2,4-oxadiazole-5-carboxylate using Method 19T and 37Y. HPLC: 98.9% purity. MS: m/z=571.3 [M+H]$^+$. $^1$H NMR (300 MHz, DMSO-d$_6$): 13.89 (br s, 1H), 9.94 (t, J=5.9 Hz, 1H), 8.72-8.64 (m, 1H), 8.45-8.16 (m, 4H), 7.96 (dd, J=8.1, 2.1 Hz, 1H), 7.63-7.59 (m, 2H), 4.61 (d, J=5.9 Hz, 2H), 3.64-3.55 (m, 6H), 2.41 (t, J=4.5 Hz, 4H), 1.37 (s, 9H).

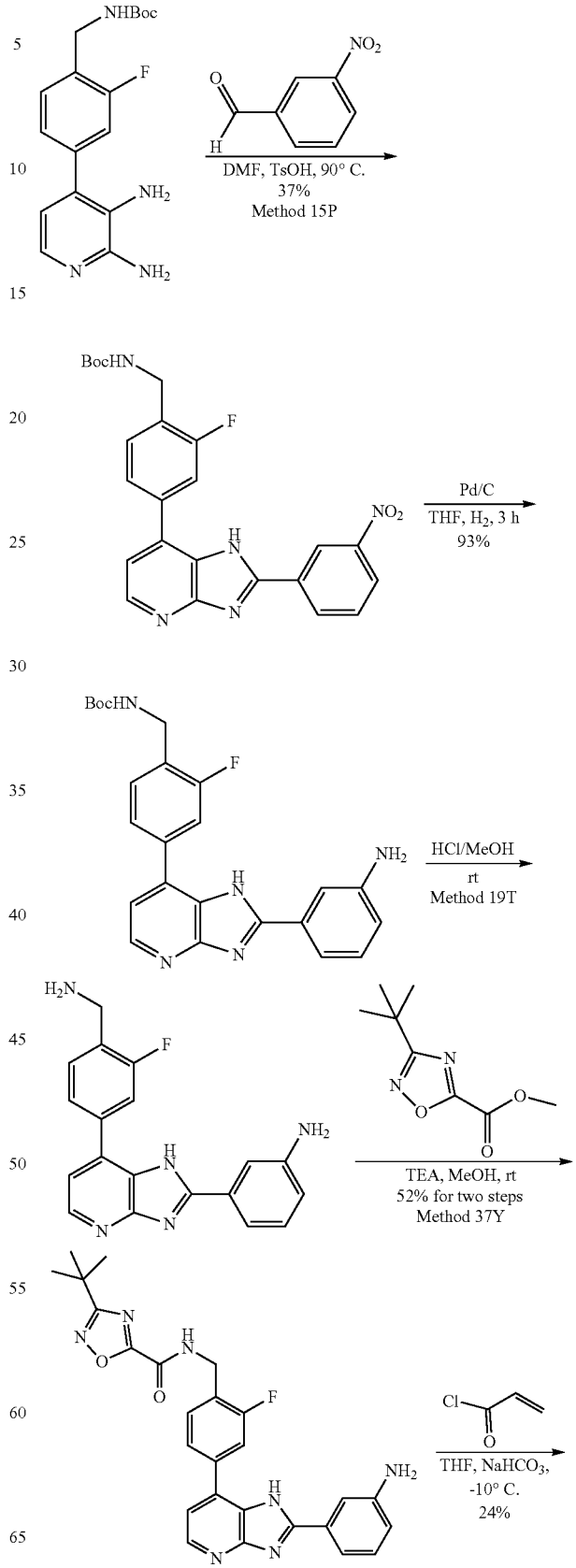

Scheme 54

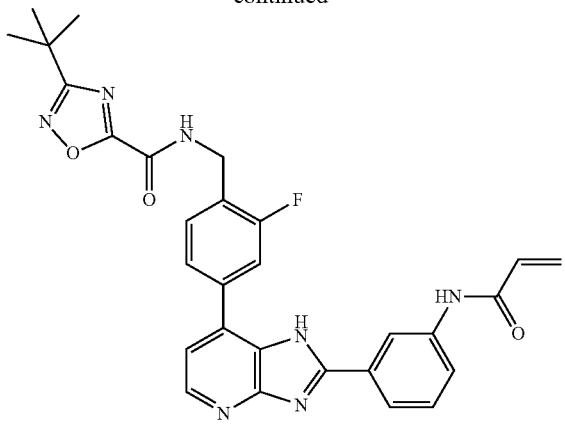

Example 163. 3-tert-butyl-N-[(2-fluoro-4-[2-[3-(prop-2-enamido)phenyl]-3H-imidazo[4,5-b]pyridin-7-yl]phenyl)methyl]-1,2,4-oxadiazole-5-carboxamide

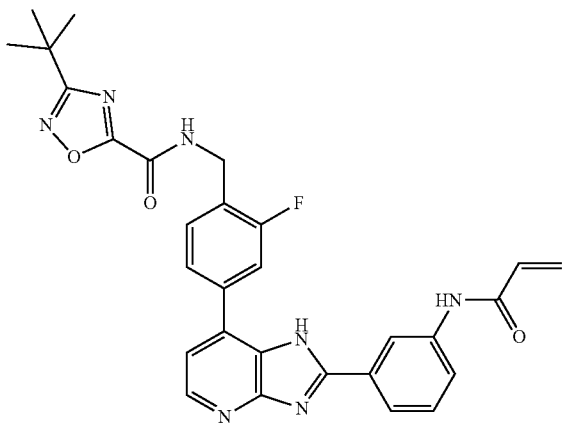 [SMILES: C=CC(=O)Nc1cccc(-c2nc3nccc(-c4ccc(CNC(=O)c5nc(C(C)(C)C)no5)c(F)c4)c3[nH]2)c1]

tert-butyl N-([2-fluoro-4-[2-(3-nitrophenyl)-3H-imidazo[4,5-b]pyridin-7-yl]phenyl]methyl) carbamate tert-butyl N-([2-fluoro-4-[2-(3-nitrophenyl)-3H-imidazo[4,5-b]pyridin-7-yl]phenyl]methyl)carbamate 156 mg (37%) was prepared from tert-butyl N-[[4-(2,3-diaminopyridin-4-yl)-2-fluorophenyl]methyl]carbamate and 3-nitrobenzaldehyde using Method 15P. MS: m/z=464.2 [M+H]⁺.

tert-butyl N-([4-[2-(3-aminophenyl)-3H-imidazo[4,5-b]pyridin-7-yl]-2-fluorophenyl]methyl) carbamate At room temperature, in a 25-mL round bottom flask, tert-butyl N-([2-fluoro-4-[2-(3-nitrophenyl)-3H-imidazo[4,5-b]pyridin-7-yl]phenyl]methyl)carbamate (120.0 mg, 0.26 mmol, 1.00 equiv) was dissolved in tetrahydrofuran (6 mL), to which was added palladium carbon (10%, 27.5 mg, 0.03 mmol, 0.10 equiv) under nitrogen atmosphere. The reaction flask was then vacuumed and flushed with hydrogen. The reaction mixture was hydrogenated at room temperature for 3 hours under hydrogen atmosphere using a hydrogen balloon. After the reaction was done, the reaction mixture was filtered through a Celite pad and concentrated under reduced pressure to afford tert-butyl N-([4-[2-(3-aminophenyl)-3H-imidazo[4,5-b]pyridin-7-yl]-2-fluorophenyl]methyl) carbamate 105 mg (93%) as yellow solid. MS: m/z=434.0 [M+H]⁺.

N-([4-[2-(3-aminophenyl)-3H-imidazo[4,5-b]pyridin-7-yl]-2-fluorophenyl]methyl)-3-tert-butyl-1,2,4-oxadiazole-5-carboxamide N-([4-[2-(3-aminophenyl)-3H-imidazo[4,5-b]pyridin-7-yl]-2-fluorophenyl]methyl)-3-tert-butyl-1,2,4-oxadiazole-5-carboxamide 70 mg (52% for two steps) was prepared from tert-butyl N-([4-[2-(3-aminophenyl)-3H-imidazo[4,5-b]pyridin-7-yl]-2-fluorophenyl]methyl)carbamate, HCl in MeOH and methyl 3-tert-butyl-1,2,4-oxadiazole-5-carboxylate using Method 19T and 37Y. MS: m/z=486.1 [M+H]⁺.

3-tert-butyl-N-[(2-fluoro-4-[2-[3-(prop-2-enamido)phenyl]-3H-imidazo[4,5-b]pyridin-7-yl]phenyl)methyl]-1,2,4-oxadiazole-5-carboxamide In a 25-mL round bottom flask, N-([4-[2-(3-aminophenyl)-3H-imidazo[4,5-b]pyridin-7-yl]-2-fluorophenyl]methyl)-3-tert-butyl-1,2,4-oxadiazole-5-carboxamide (60.0 mg, 0.12 mmol, 1.00 equiv) and DIEA (16.0 mg, 0.12 mmol, 1.00 equiv) were dissolved in tetrahydrofuran (6 mL), to which was added prop-2-enoyl chloride (11.19 mg, 0.12 mmol, 1.00 equiv) dropwise at −10° C. The resulting mixture was then stirred for 1 h at −10° C. When the reaction was done, it was quenched by the addition of 10 mL water and the mixture was extracted with dichloromethane (3×10 ml). The organic layers were combined, dried over sodium sulfate and concentrated under reduced pressure. The residue was purified by prep-HPLC using the following: column, XBridge BEH130 Prep C18 OBD Column, 19*100 mm 5 μm 13 nm; mobile phase, acetonitrile in water (with 10 mM NH₄HCO₃), 43% to 53% gradient in 9 min; detector, UV 254 nm. 3-tert-butyl-N-[(2-fluoro-4-[2-[3-(prop-2-enamido)phenyl]-3H-imidazo[4,5-b]pyridin-7-yl]phenyl)methyl]-1,2,4-oxadiazole-5-carboxamide (16 mg, 24%) was obtained as white solid. HPLC: 99.2% purity. MS: m/z=540.3 [M+H]⁺. ¹H NMR (400 MHz, DMSO-d₆): δ 13.74 (br s, 1H), 10.41 (s, 1H), 9.98-9.95 (m, 1H), 8.40-8.38 (m, 1H), 8.28-8.25 (m, 1H), 8.18-8.17 (m, 2H), 7.96-7.94 (m, 2H), 7.63-7.51 (m, 3H), 6.53-6.46 (m, 1H), 6.33-6.28 (m, 1H), 5.82-5.79 (m, 1H), 4.62-4.61 (m, 2H), 1.53 (s, 9H).

Example 164. 3-tert-butyl-N-[(4-[2-[5-(4,4-difluoropiperidin-1-yl)pyridin-2-yl]-3H-imidazo[4,5-b]pyridin-7-yl]-2-fluorophenyl)methyl]-1,2,4-oxadiazole-5-carboxamide

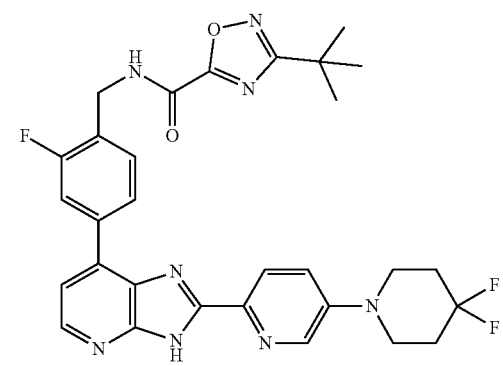 [SMILES: CC(C)(C)c1noc(C(=O)NCc2ccc(-c3ccnc4[nH]c(-c5ccc(N6CCC(F)(F)CC6)cn5)nc34)cc2F)n1]

3-tert-butyl-N-[(4-[2-[5-(4,4-difluoropiperidin-1-yl)pyridin-2-yl]-3H-imidazo[4,5-b]pyridin-7-yl]-2-fluorophenyl)methyl]-1,2,4-oxadiazole-5-carboxamide 7.4 mg (8%) was prepared from (4-[2-[5-(4,4-difluoropiperidin-1-yl)pyridin-2-yl]-3H-imidazo[4,5-b]pyridin-7-yl]-2-fluorophenyl)methanamine, methyl 3-tert-butyl-1,2,4-oxadiazole-5-carboxylate using Method 37Y. HPLC: 93.0% purity. MS: m/z=591.2 [M+H]$^+$. $^1$H-NMR (400 MHz, DMSO-d$_6$): δ 13.61 (br s, 1H), 10.05-9.95 (m, 1H), 8.34 (s, 1H), 8.38-8.28 (m, 2H), 8.25-8.15 (m, 2H), 7.65-7.55 (m, 3H), 4.60 (d, J=6.0 Hz, 2H), 3.59-3.56 (m, 4H), 2.2.0-2.02 (m, 4H), 1.37 (s, 9H).

Scheme 55

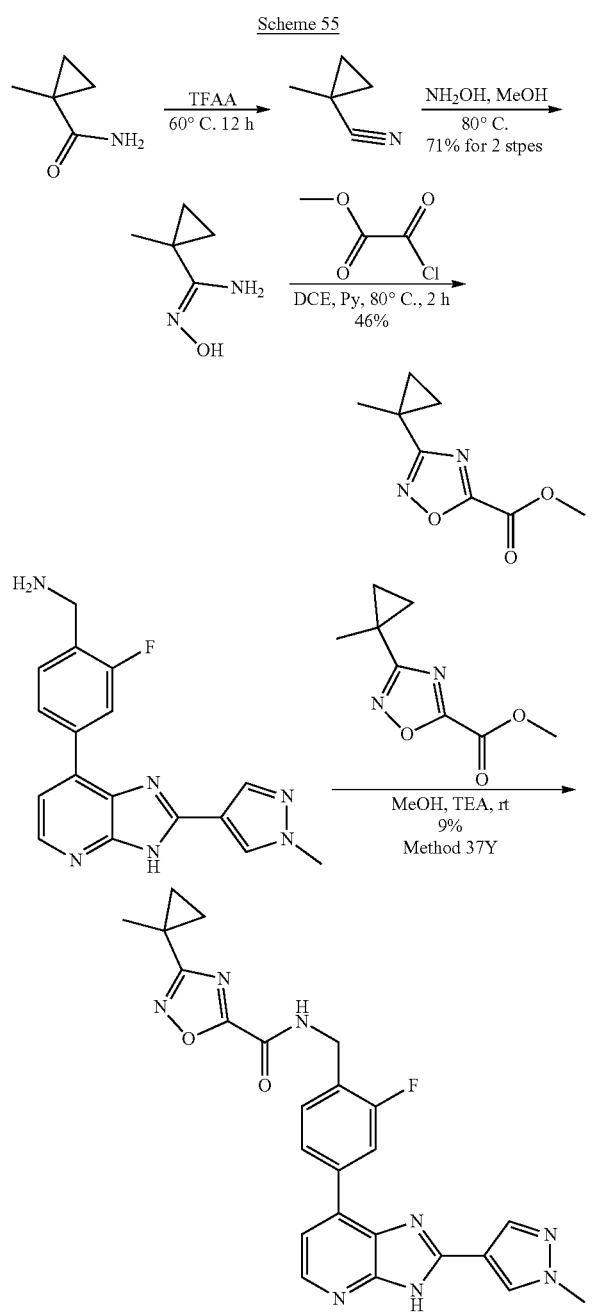

Example 165. N-([2-fluoro-4-[2-(1-methyl-1H-pyrazol-4-yl)-3H-imidazo[4,5-b]pyridin-7-yl] phenyl]methyl)-3-(1-methylcyclopropyl)-1,2,4-oxadiazole-5-carboxamide

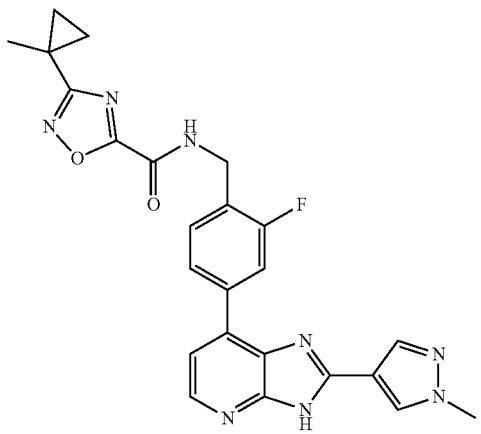

1-Methylcyclopropane-1-carbonitrile

In a 30-mL sealed tube, 1-methylcyclopropane-1-carboxamide (800 mg, 8.07 mmol, 1.00 equiv) was dissolved in tetrahydrofuran (20 mL), to which was added TFAA (8.4 g, 39.99 mmol, 4.96 equiv) at room temperature. The resulting solution was then stirred for 12 h at 60° C. After the reaction was done, the reaction mixture was concentrated under reduced pressure and the residue was dissolved in 5 mL water. The pH value of the resulting mixture was adjusted to 8 using sat. sodium bicarbonate solution and the mixture was extracted with dichloromethane (3×30 mL). The organic layers were combined, dried over sodium sulfate and concentrated under reduced pressure to afford 1-methylcyclopropane-1-carbonitrile (2 g, crude) as yellow oil.

(Z)—N-hydroxy-1-methylcycloprop-1l-carboximidamide

In a 50-mL round bottom flask, 1-methylcyclopropane-1-carbonitrile (1.6 g, 0.2 mmol, 1.00 equiv) was dissolved in ethanol (20 mL), to which was added a solution of hydroxylamine (1 g, 0.3 mmol, 1.54 equiv) in MeOH at room temperature. The resulting solution was then stirred overnight at 80° C. After the reaction was done, the reaction mixture was concentrated under reduced pressure to afford (Z)—N-hydroxy-1-methylcycloprop-1-carboximidamide (700 mg, 71% for 2 steps) as yellow oil.

Methyl 3-(1-methylcyclopropyl)-1,2,4-oxadiazole-5-carboxylate

In a 25-mL round bottom flask, (Z)—N-hydroxy-1-methylcycloprop-1-carboximidamide (544 mg, 4.77 mmol, 1.00 equiv) and pyridine (1.4 g, 17.70 mmol, 3.71 equiv) were dissolved in DCE (10 mL), to which was added methyl 2-chloro-2-oxoacetate (853.4 mg, 6.97 mmol, 1.46 equiv) dropwise at 0° C. The resulting mixture was stirred for 0.5 h at room temperature, and then heated to 80° C. and stirred for another 2 h at 80° C. When the reaction was done, it was quenched by 10 mL water and the mixture was extracted with dichloromethane (3×10 ml). The organic layers were combined, dried over sodium sulfate and concentrated under reduced pressure to afford methyl 3-(1-methylcyclopropyl)-1,2,4-oxadiazole-5-carboxylate (400 mg, 46%) as yellow oil N-([2-fluoro-4-[2-(1-methyl-1H-pyrazol-4-yl)-3H-imidazo[4,5-b]pyridin-7-yl]phenyl]methyl)-3-(1-methylcyclopropyl)-1,2,4-oxadiazole-5-carboxamide N-([2-fluoro-4-[2-(1-methyl-1H-pyrazol-4-yl)-3H-imidazo[4,5-b]pyridin-7-yl]phenyl]methyl)-3-(1-methylcyclopropyl)-1,2,4-oxadiazole-5-carboxamide 10 mg (9%) was prepared from [2-fluoro-4-[2-(1-methyl-1H-pyrazol-4-yl)-3H-imidazo[4,5-b]pyridin-7-yl]phenyl]methanamine, methyl 3-(1-methylcyclopropyl)-1,2,4-oxadiazole-5-carboxylate using Method 37Y. HPLC: 96.9% purity. MS: m/z=473.2 [M+H]$^+$. $^1$H-NMR (400 MHz, DMSO-d$_6$): δ 13.39 (br s, 1H), 9.88-9.86 (m, 1H), 8.44 (s, 1H), 8.29-8.25 (m, 2H), 8.15-8.13 (m, 2H), 7.55-7.53 (m, 2H), 4.58-4.56 (m, 2H), 3.95 (s, 3H), 1.49 (s, 3H), 1.19-1.18 (m, 2H), 1.00-0.99 (m, 2H).

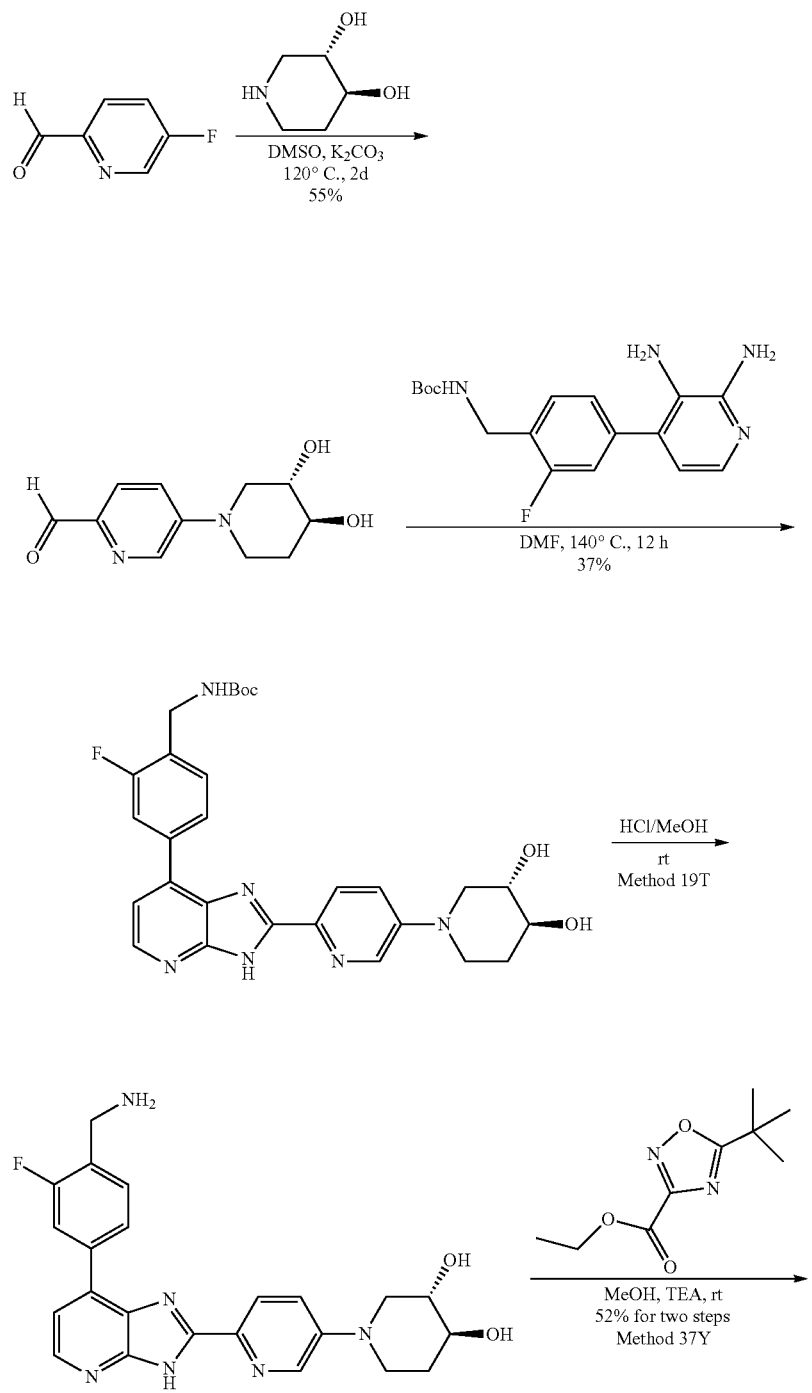

Scheme 56

Example 166. 3-tert-butyl-N-[[4-(2-[5-[(3S,4S)-3,4-dihydroxypiperidin-1-yl]pyridin-2-yl]-3H-imidazo[4,5-b]pyridin-7-yl)-2-fluorophenyl]methyl]-1,2,4-oxadiazole-5-carboxamide

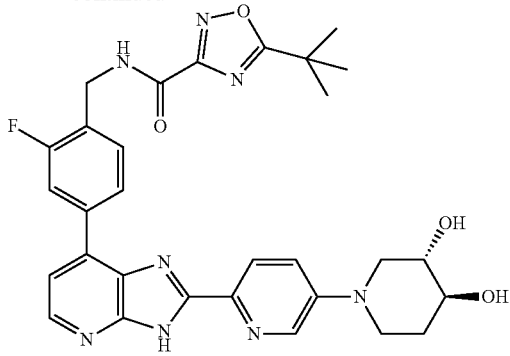 [SMILES: CC(C)(C)c1nc(C(=O)NCc2ccc(-c3ccnc4[nH]c(-c5ccc(N6CC[C@H](O)[C@@H](O)C6)cn5)nc34)cc2F)no1]

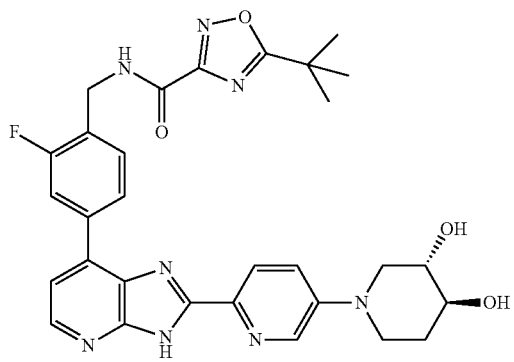

5-[(3S,4S)-3,4-dihydroxypiperidin-1-yl]pyridine-2-carbaldehyde

In a 30-mL sealed tube, 5-fluoropyridine-2-carbaldehyde (300 mg, 2.28 mmol, 1.00 equiv) and (3S,4S)-piperidine-3,4-diol (281 mg, 2.28 mmol, 1.00 equiv) were dissolved in DMSO (5 mL), to which was added potassium carbonate (993 mg, 6.83 mmol, 3.00 equiv) at room temperature. The resulting mixture was then stirred for 2 days at 120° C. After the reaction was done, the reaction mixture was concentrated under reduced pressure and the residue was diluted with 50 mL H$_2$O. The resulting mixture was extracted with ethyl acetate (3×50 mL) and the organic layers were combined, dried over sodium sulfate and concentrated under reduced pressure. The residue was purified in a silica gel column eluting with methanol in dichloromethane (1% to 10% gradient) to afford 5-[(3S,4S)-3,4-dihydroxypiperidin-1-yl]pyridine-2-carbaldehyde (280 mg, 55%) as yellow oil. MS: m/z=223.0 [M+H]$^+$.

N-[[4-(2-[5-[(3S,4S)-3,4-dihydroxypiperidin-1-yl]pyridin-2-yl]-3H-imidazo[4,5-b]pyridin-7-yl)-2-fluorophenyl]methyl]carbamate In a 20-mL vial, tert-butyl N-[[4-(2,3-diaminopyridin-4-yl)-2-fluorophenyl]methyl]carbamate (135 mg, 0.41 mmol, 1.00 equiv) and 5-[(3S,4S)-3,4-dihydroxypiperidin-1-yl]pyridine-2-carbaldehyde (95 mg, 0.43 mmol, 1.00 equiv) were dissolved in N,N-dimethylformamide (3 mL) at room temperature. The resulting solution was then stirred for 12 h at 140° C. After the reaction was done, the reaction mixture was concentrated under reduced pressure and the residue was purified in a silica gel column eluting with methanol in dichloromethane (1% to 10% gradient) to afford tert-butyl N-[[4-(2-[5-[(3S,4S)-3,4-dihydroxypiperidin-1-yl]pyridin-2-yl]-3H-imidazo[4,5-b]pyridin-7-yl)-2-fluorophenyl]methyl]carbamate (80 mg, 37%) as yellow solid. MS: m/z=535.1 [M+H]$^+$.

3-tert-butyl-N-[[4-(2-[5-[(3S,4S)-3,4-dihydroxypiperidin-1-yl]pyridin-2-yl]-3H-imidazo[4,5-b]pyridin-7-yl)-2-fluorophenyl]methyl]-1,2,4-oxadiazole-5-carboxamide 3-tert-butyl-N-[[4-(2-[5-[(3S,4S)-3,4-dihydroxypiperidin-1-yl]pyridin-2-yl]-3H-imidazo [4,5-b]pyridin-7-yl)-2-fluorophenyl]methyl]-1,2,4-oxadiazole-5-carboxamide 29.1 mg (52% for two steps) was prepared from tert-butyl N-[[4-(2-[5-[(3S,4S)-3,4-dihydroxypiperidin-1-yl] pyridin-2-yl]-3H-imidazo[4,5-b]pyridin-7-yl)-2-fluorophenyl]methyl]carbamate, methyl 3-tert-butyl-1,2,4-oxadiazole-5-carboxylate using Method 19T and 37Y. HPLC: 95.3% purity. MS: m/z=587.3 [M+H]$^+$. $^1$H-NMR (300 MHz, DMSO-d$_6$): δ 13.54 (br s, 1H), 9.92 (t, J=6.0 Hz, 1H), 8.44-8.26 (m, 3H), 8.25-8.14 (m, 2H), 7.65-7.42 (m, 3H), 5.03 (d, J=4.1 Hz, 1H), 4.87 (d, J=4.0 Hz, 1H), 4.60 (d, J=5.9 Hz, 2H), 3.84-3.68 (m, 2H), 3.41-3.40 (m, 2H), 3.12-2.98 (m, 1H), 2.88-2.86 (m, 1H), 1.93 (d, J=13.1 Hz, 1H), 1.46-1.45 (m, 1H), 1.37 (s, 9H).

Scheme 57
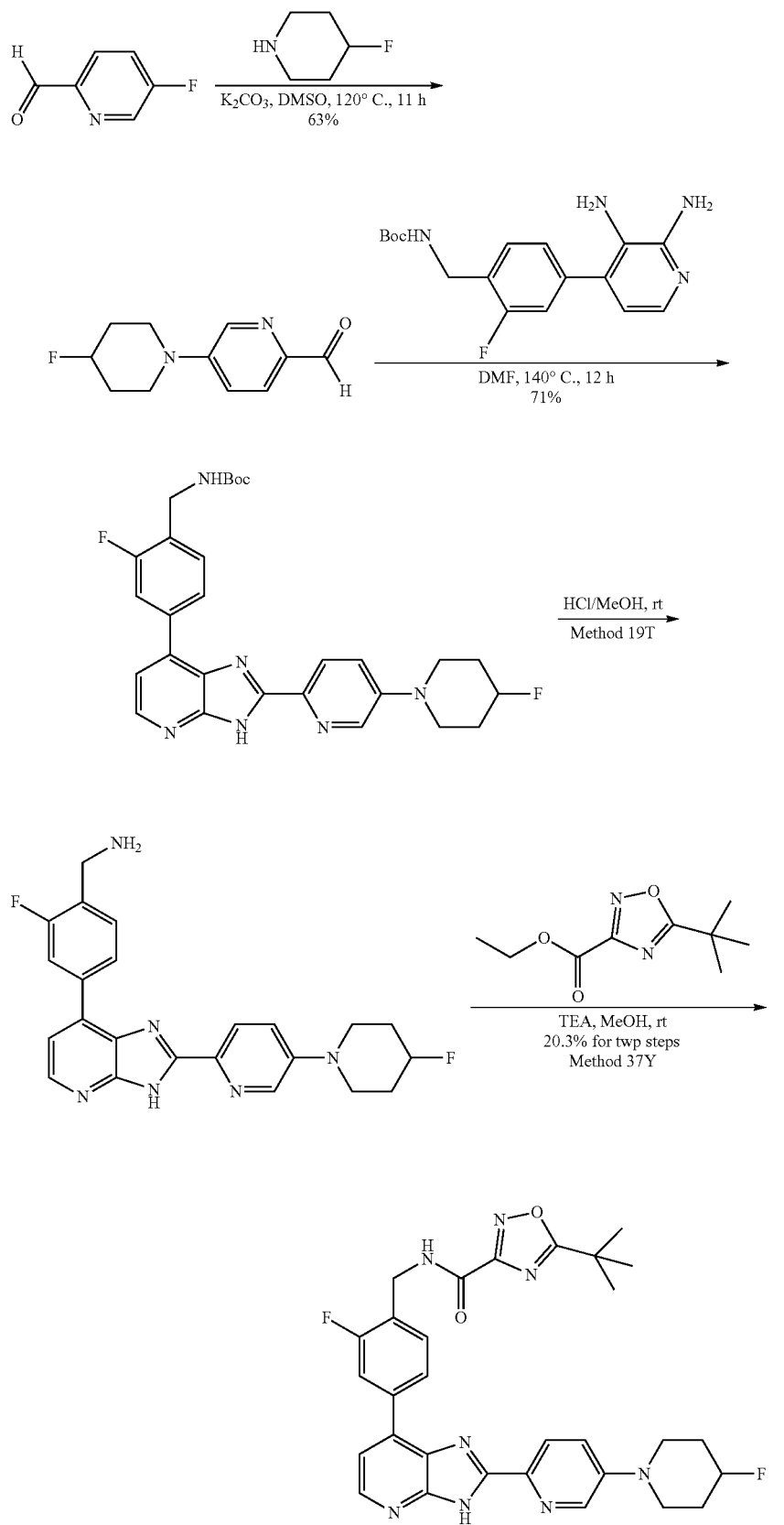

Example 167. 5-tert-butyl-N-[(2-fluoro-4-[2-[5-(4-fluoropiperidin-1-yl)pyridin-2-yl]-3H-imidazo[4,5-b]pyridin-7-yl]phenyl)methyl]-1,2,4-oxadiazole-3-carboxamide

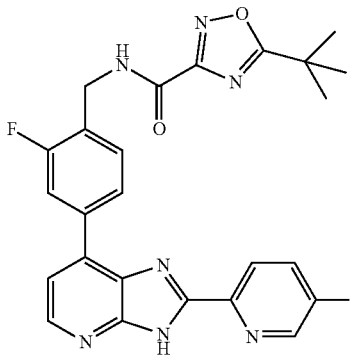

5-(4-fluoropiperidin-1-yl)pyridine-2-carbaldehyde

In a 8-mL vial, 5-fluoropyridine-2-carbaldehyde (300 mg, 2.28 mmol, 1.00 equiv) and 4-fluoropiperidine (243 mg, 2.24 mmol, 0.98 equiv) were dissolved in N,N-dimethylformamide (3 mL), to which was added potassium carbonate (993.6 mg, 6.83 mmol, 3.00 equiv) at room temperature. The resulting mixture was then stirred overnight at 120° C. After the reaction was done, the reaction mixture was concentrated under reduced pressure and the residue was diluted with 50 mL $H_2O$. The resulting mixture was extracted with ethyl acetate (3×50 mL) and the organic layers were combined, dried over sodium sulfate and concentrated under reduced pressure. The residue was purified in a silica gel column eluting with methanol in dicloromethane (1% to 10% gradient) to afford 5-(4-fluoropiperidin-1-yl)pyridine-2-carbaldehyde 300 mg (63%) as brown solid. MS: m/z=209.0 [M+H]$^+$.

tert-butyl N-[(2-fluoro-4-[2-[5-(4-fluoropiperidin-1-yl)pyridin-2-yl]-3H-imidazo[4,5-b]pyridin-7-yl]phenyl)methyl]carbamate In a 8-mL vial, tert-butyl N-[[4-(2,3-diaminopyridin-4-yl)-2-fluorophenyl]methyl]carbamate (108 mg, 0.32 mmol, 1.00 equiv) was dissolved in N,N-dimethylformamide (2 mL), to which was added 5-(4-fluoropiperidin-1-yl)pyridine-2-carbaldehyde (67.5 mg, 0.32 mmol, 1.00 equiv) at room temperature. The resulting solution was then stirred for 11 h at 140° C. After the reaction was done, the reaction mixture was concentrated under reduced pressure and the residue was purified in a silica gel column eluting with methanol in dicloromethane (1% to 10% gradient) to afford tert-butyl N-[(2-fluoro-4-[2-[5-(4-fluoropiperidin-1-yl)pyridin-2-yl]-3H-imidazo[4,5-b]pyridin-7-yl]phenyl)methyl]carbamate (150 mg, 71%) as brown solid. MS: m/z=521.2 [M+H]$^+$.

5-tert-butyl-N-[(2-fluoro-4-[2-[5-(4-fluoropiperidin-1-yl)pyridin-2-yl]-3H-imidazo[4,5-b]pyridin-7-yl]phenyl)methyl]-1,2,4-oxadiazole-3-carboxamide 5-tert-butyl-N-[(2-fluoro-4-[2-[5-(4-fluoropiperidin-1-yl)pyridin-2-yl]-3H-imidazo[4,5-b]pyridin-7-yl]phenyl) methyl]-1,2,4-oxadiazole-3-carboxamide 21.9 mg (20.3% for two steps) was prepared from tert-butyl N-[(2-fluoro-4-[2-[5-(4-fluoropiperidin-1-yl)pyridin-2-yl]-3H-imidazo[4,5-b]pyridin-7-yl] phenyl)methyl]carbamate, ethyl 5-tert-butyl-1,2,4-oxadiazole-3-carboxylate using Method 19T and 37Y. HPLC: 93.0% purity. MS: m/z=573.2 [M+H]$^+$. $^1$H-NMR (300 MHz, DMSO-d$_6$): δ 13.58 (br s, 1H), 9.55 (m, 1H), 8.47 (s, 1H), 8.34-8.30 (m, 2H), 8.23-8.18 (m, 2H), 7.58-7.52 (m, 3H), 4.99-4.75 (m, 1H), 4.59 (d, J=6.0 Hz, 2H), 3.65-3.51 (m, 2H), 3.43-3.37 (m, 2H), 2.09-1.95 (m, 2H), 1.88-1.75 (m, 2H), 1.44 (s, 9H).

Scheme 58

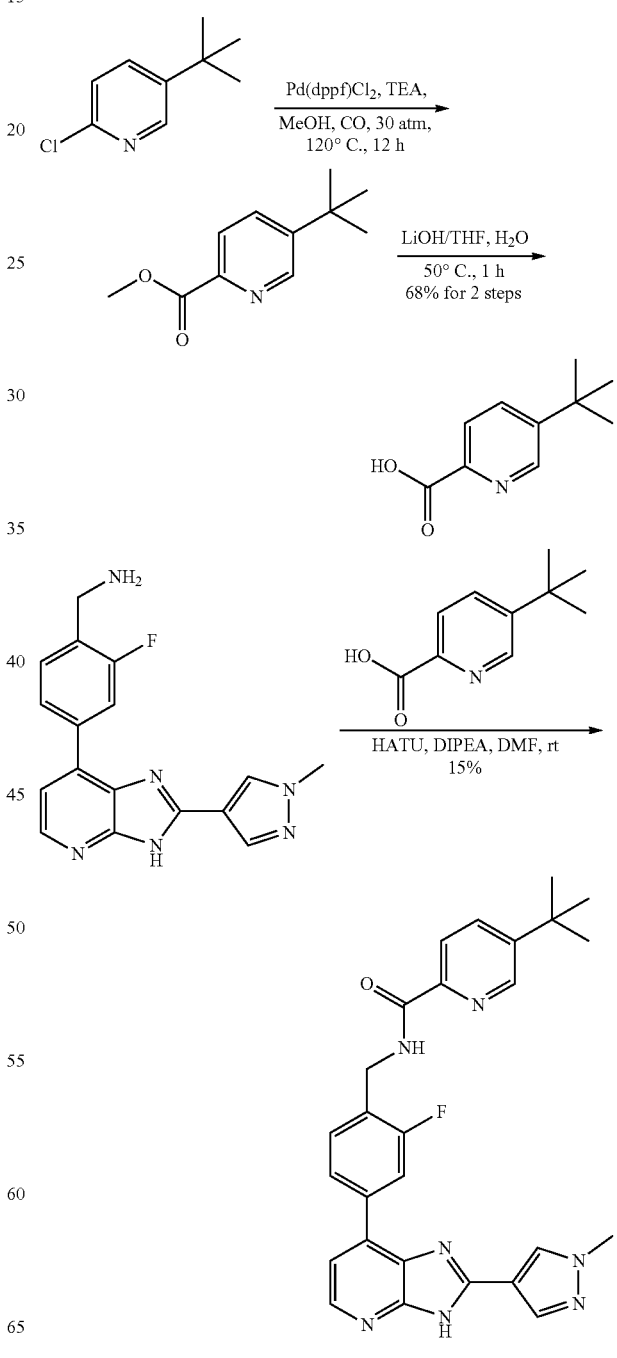

Example 168. 5-tert-butyl-N-([2-fluoro-4-[2-(1-methyl-1H-pyrazol-4-yl)-3H-imidazo[4,5-b]pyridin-7-yl]phenyl]methyl)pyridine-2-carboxamide

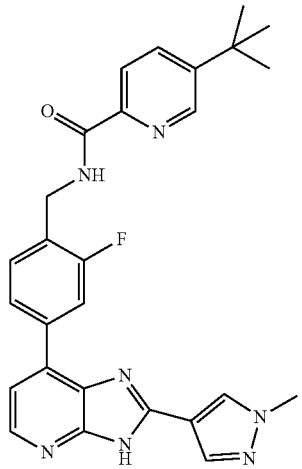 [SMILES: Cn1cc(-c2nc3c(-c4ccc(CNC(=O)c5ccc(C(C)(C)C)cn5)c(F)c4)ccnc3[nH]2)cn1]

methyl 5-tert-butylpyridine-2-carboxylate

In a 25-mL pressure tank, 5-tert-butyl-2-chloropyridine (100 mg, 0.59 mmol, 1.00 equiv) was dissolved in 10 mL MeOH, to which were added Pd(dppf)Cl$_2$·CH$_2$Cl$_2$ (10 mg, 0.01 mmol, 0.02 equiv) and TEA (121 mg, 1.20 mmol, 1.00 equiv) at room temperature. The resulting mixture was purged with nitrogen for 5 minutes, and then was pressurized to 30 atm with carbon monoxide at 120° C. and stirred for 12 hours at 120° C. After the reaction was done, the reaction mixture was cooled to room temperature and filtered to remove insoluble solids. The filtrate was concentrated under reduced pressure to afford methyl 5-tert-butylpyridine-2-carboxylate (110 mg, crude) yellow solid. MS: m/z=194.0[M+H]$^+$

5-tert-butylpyridine-2-carboxylic acid

In a 50-mL round bottom flask, methyl 5-tert-butylpyridine-2-carboxylate (90 mg, 0.47 mmol, 1.00 equiv) was dissolved in a mixture of tetrahydrofuran and water (2:1, 3 mL), to which was added LiOH (40 mg, 1.67 mmol, 3.59 equiv) at room temperature. The resulting solution was then stirred for 1 h at 50° C. After the reaction was done, the reaction mixture was concentrated under reduced pressure. The pH value of the remaining solution was adjusted to 6 using HCl solution (1 M) and the resulting solution was extracted with ethyl acetate (3×30 mL). The organic layers were combined, dried over sodium sulfate and concentrated under reduced pressure to afford 5-tert-butylpyridine-2-carboxylic acid (60 mg, 68% for 2 steps) as yellow oil. MS: m/z=180.0[M+H]$^+$

5-tert-butyl-N-([2-fluoro-4-[2-(1-methyl-1H-pyrazol-4-yl)-3H-imidazo[4,5-b]pyridin-7-yl]phenyl]methyl)pyridine-2-carboxamide In a 50-mL round bottom flask, [2-fluoro-4-[2-(1-methyl-1H-pyrazol-4-yl)-3H-imidazo[4,5-b]pyridin-7-yl]phenyl]methanamine (90 mg, 0.28 mmol, 1.00 equiv) was dissolvent in N,N-dimethylformamide (15 mL), to which were added 5-tert-butylpyridine-2-carboxylic acid (60.3 mg, 0.34 mmol, 1.21 equiv), HATU (176 mg, 0.46 mmol, 1.66 equiv) and DIEA (120 mg, 0.93 mmol, 3.33 equiv) in sequence at room temperature. The resulting solution was then stirred overnight at room temperature. After the reaction was done, it was quenched by the addition of water (5 mL) and the resulting mixture was extracted with dichloromethane (3×20 mL). The organic layers were combined, dried over sodium sulfate and concentrated under reduced pressure. The residue was purified by prep-HPLC with the following conditions: column, XBridge Shield RP18 OBD Column, δ μm, 19*150 mm; mobile phase, MeCN in water (with 10 mM NH$_4$HCO$_3$), 40% to 57% gradient in 6 min; detector, UV 254 nm 5-tert-butyl-N-([2-fluoro-4-[2-(1-methyl-1H-pyrazol-4-yl)-3H-imidazo[4,5-b]pyridin-7-yl]phenyl] methyl) pyridine-2-carboxamide (20 mg, 15%) was obtained as white solid. HPLC: 95.5% purity. MS: m/z=484.3 [M+H]$^+$. $^1$H-NMR (400 MHz, DMSO-d$_6$): δ 13.42 (br s, 1H), 9.35 (m, 1H), 8.73-8.72 (m, 1H), 8.44 (s, 1H), 8.27 (m, 2H), 8.13 (s, 2H), 8.02-8.00 (m, 2H), 7.48 (m, 2H), 4.64-4.62 (m, 2H), 3.94 (s, 3H), 1.36 (s, 9H).

Example 169. 5-tert-butyl-N-[(2-fluoro-4-[2-[5-(1-methylpiperidin-4-yl)pyridin-2-yl]-3H-imidazo[4,5-b]pyridin-7-yl]phenyl)methyl]-1,2,4-oxadiazole-3-carboxamide

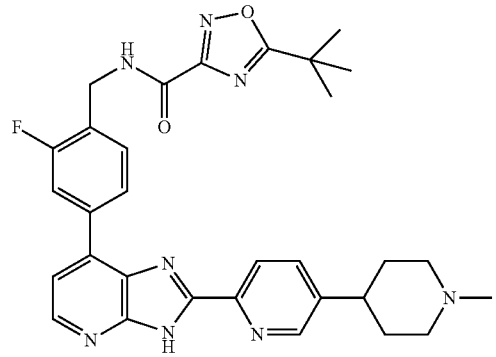 [SMILES: CN1CCC(c2ccc(-c3nc4c(-c5ccc(CNC(=O)c6noc(C(C)(C)C)n6)c(F)c5)ccnc4[nH]3)nc2)CC1]

5-tert-butyl-N-[(2-fluoro-4-[2-[5-(1-methylpiperidin-4-yl)pyridin-2-yl]-3H-imidazo[4,5-b]pyridin-7-yl]phenyl) methyl]-1,2,4-oxadiazole-3-carboxamide 4.6 mg (6% for three steps) was prepared from tert-butyl N-[(2-fluoro-4-[2-[5-(1-methyl-1,2,3,6-tetrahydropyridin-4-yl)pyridin-2-yl]-3H-imidazo[4,5-b]pyridin-7-yl] phenyl)methyl]carbamate, ethyl 5-tert-butyl-1,2,4-oxadiazole-3-carboxylate using Method 1G, 19T and 37Y. HPLC: 98.0% purity. MS: m/z=569.7 [M+H]$^+$. $^1$H-NMR (300 MHz, DMSO-d$_6$): δ 13.59 (br s, 1H), 9.55 (t, J=5.9 Hz, 1H), 8.67 (d, J=2.1 Hz, 1H), 8.67 (s, 1H), 8.41-8.33 (m, 4H), 8.00-7.81 (m, 1H), 8.00-7.81 (m, 1H), 7.70-7.41 (m, 2H), 4.68-4.50 (m, 2H), 3.04-2.78 (m, 2H), 2.77-2.56 (m, 1H), 2.21 (s, 3H), 2.10-1.86 (m, 2H), 1.90-1.63 (m, 4H), 1.43 (s, 9H).

Scheme 59

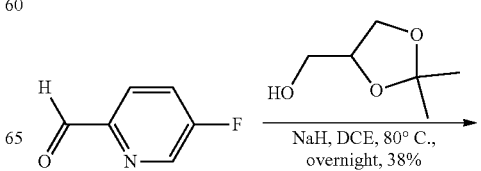

-continued
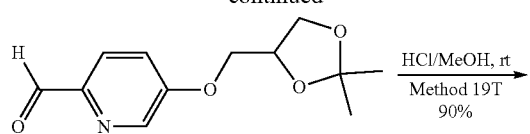
HCl/MeOH, rt
Method 19T
90%
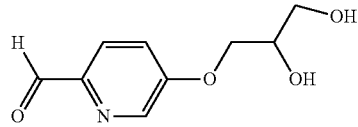
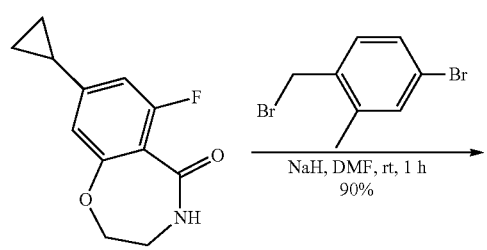
NaH, DMF, rt, 1 h
90%
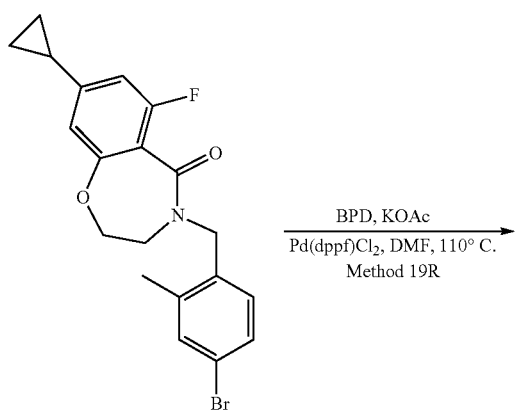
BPD, KOAc
Pd(dppf)Cl$_2$, DMF, 110° C.
Method 19R
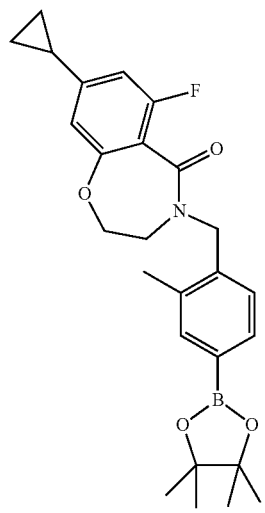
Pd(dppf)Cl$_2$, Na$_2$CO$_3$,
THF/H$_2$O, MW, 80° C.
Method 2J
-continued
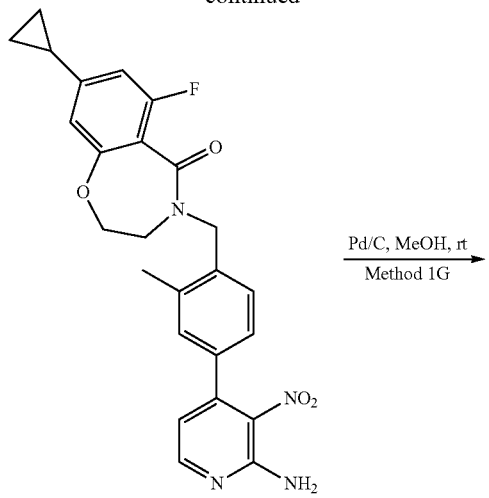
Pd/C, MeOH, rt
Method 1G
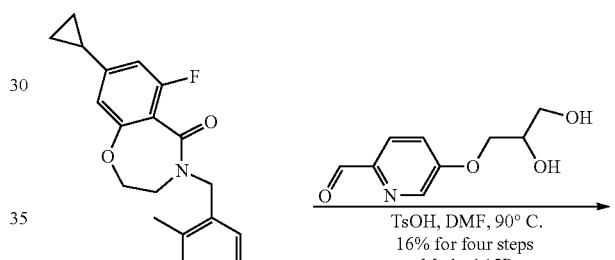
TsOH, DMF, 90° C.
16% for four steps
Method 15P
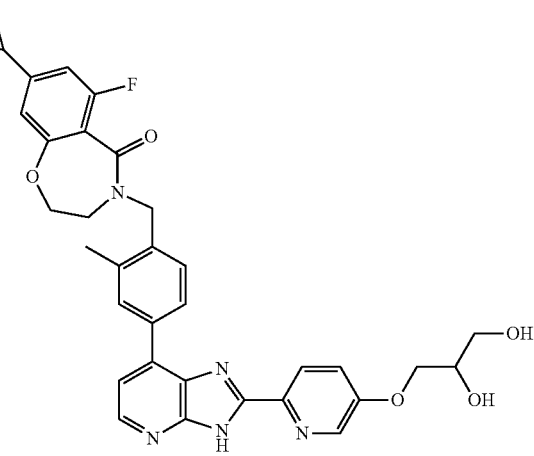

Example 170. 8-cyclopropyl-4-[(4-[2-[5-(2,3-dihydroxypropoxy)pyridin-2-yl]-3H-imidazo[4,5-b]pyridin-7-yl]-2-methylphenyl)methyl]-6-fluoro-2,3,4,5-tetrahydro-1,4-benzoxazepin-5-one

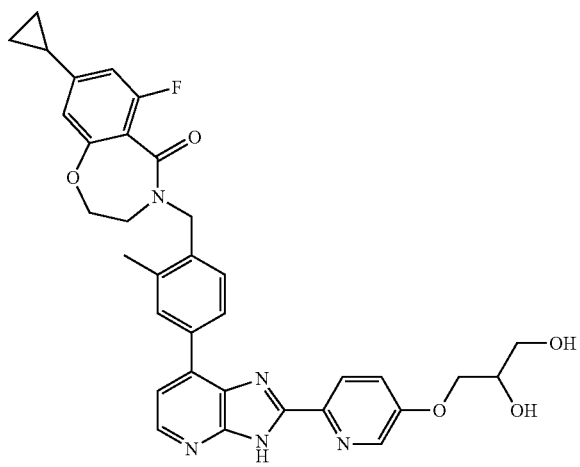 [SMILES: Cc1cc(-c2ccnc3[nH]c(-c4ccc(OCC(O)CO)cn4)nc23)ccc1CN1CCOc2cc(C3CC3)cc(F)c2C1=O]

5-[(2,2-dimethyl-1,3-dioxolan-4-yl)methoxy]pyridine-2-carbaldehyde

In a 50-mL round bottom flask, 5-fluoropyridine-2-carbaldehyde (560 mg, 4.48 mmol, 1.00 equiv) and (2,2-dimethyl-1,3-dioxolan-4-yl)methanol (2.96 g, 22.40 mmol, 5.00 equiv) were mixed in DCE (8.00 mL, 101.05 mmol, 22.57 equiv) at room temperature. The resulting solution was then stirred overnight at 80° C. When the reaction is done, it was quenched by the addition of sat.NH$_4$Cl solution (200 mL) and the resulting mixture was extracted with ethyl acetate (3×150 mL). The organic layers were combined, dried over sodium sulfate and concentrated under reduced pressure. The residue was purified in a silica gel column eluting with ethyl acetate in petroleum ether (1% to 20% gradient) to afford 400 mg (38%) 5-[(2,2-dimethyl-1,3-dioxolan-4-yl)methoxy]pyridine-2-carbaldehyde as light yellow oil. MS: m/z=238.2 [M+H]$^+$.

5-(2,3-dihydroxypropoxy)pyridine-2-carbaldehyde 5-(2,3-dihydroxypropoxy) pyridine-2-carbaldehyde 160 mg (90%) was prepared from 5-[(2,2-dimethyl-1,3-dioxolan-4-yl)methoxy]pyridine-2-carbaldehyde using Method 19T. MS: m/z=198.0 [M+H]$^+$.

4-[(4-bromo-2-methylphenyl)methyl]-8-cyclopropyl-6-fluoro-2,3,4,5-tetrahydro-1,4-benzoxazepin-5-one In a 100-mL round bottom flask with magnetic stir bar, 8-cyclopropyl-6-fluoro-2,3,4,5-tetrahydro-1,4-benzoxazepin-5-one (540 mg, 2.44 mmol, 1.00 equiv) was dissolved in N,N-dimethylformamide (10 mL), to which was added sodium hydride (216 mg, 5.40 mmol, 2.21 equiv, 60%) in portions at 0° C. The mixture was stirred at 0° C. for 10 min and was added by 4-bromo-1-(bromomethyl)-2-methylbenzene (853.6 mg, 3.23 mmol, 1.32 equiv) slowly at 0° C. The reaction mixture was warmed up to room temperature and stirred for 1 h at room temperature. When the reaction was done, it was quenched by the addition of 20 mL sat. NH$_4$Cl solution and the mixture was extracted with ethyl acetate (3×50 mL). The organic layers were combined, dried over sodium sulfate and concentrated under reduced pressure. The residue was purified in a silica gel column eluting with ethyl acetate in petroleum ether (1% to 20% gradient) to afford 4-[(4-bromo-2-methylphenyl)methyl]-8-cyclopropyl-6-fluoro-2,3,4,5-tetrahydro-1,4-benzoxazepin-5-one (900 mg, 90%) as white solid. MS: m/z=404.0 [M+H]$^+$ 8-cyclopropyl-4-[(4-[2-[5-(2,3-dihydroxypropoxy)pyridin-2-yl]-3H-imidazo[4,5-b]pyridin-7-yl]-2-methylphenyl)methyl]-6-fluoro-2,3,4,5-tetrahydro-1,4-benzoxazepin-5-one 8-cyclopropyl-4-[(4-[2-[5-(2,3-dihydroxypropoxy) pyridin-2-yl]-3H-imidazo[4,5-b]pyridin-7-yl]-2-methylphenyl)methyl]-6-fluoro-2,3,4,5-tetrahydro-1,4-benzoxazepin-5-one 20 mg (16% for four steps) was prepared from 4-[(4-bromo-2-methylphenyl)methyl]-8-cyclopropyl-6-fluoro-2,3,4,5-tetrahydro-1,4-benzoxazepin-5-one, 4-chloro-3-nitropyridin-2-amine, 4,4,5,5-tetramethyl-2-(tetramethyl-1,3,2-dioxaborolan-2-yl)-1,3,2-dioxaborolane, 5-(2,3-dihydroxypropoxy)pyridine-2-carbaldehyde using Method 19R, 2J, 1G, 15P. HPLC: 97.6% purity. MS: m/z=610.3 [M+H]$^+$. $^1$H-NMR (400 MHz, DMSO-d$_6$): δ 8.47 (d, J=2.9 Hz, 1H), 8.45-8.30 (m, 2H), 8.31-8.10 (m, 2H), 7.71-7.63 (m, 1H), 7.60-7.52 (m, 1H), 7.49-7.37 (m, 1H), 6.78-6.77 (m, 1H), 6.70 (s, 1H), 4.86 (s, 2H), 4.35-4.02 (m, 4H), 3.79-3.78 (m, 2H), 3.32-3.31 (m, 5H), 2.05-1.99 (m, 1H), 1.08-0.89 (m, 2H), 0.85-0.70 (m, 2H).

Scheme 60

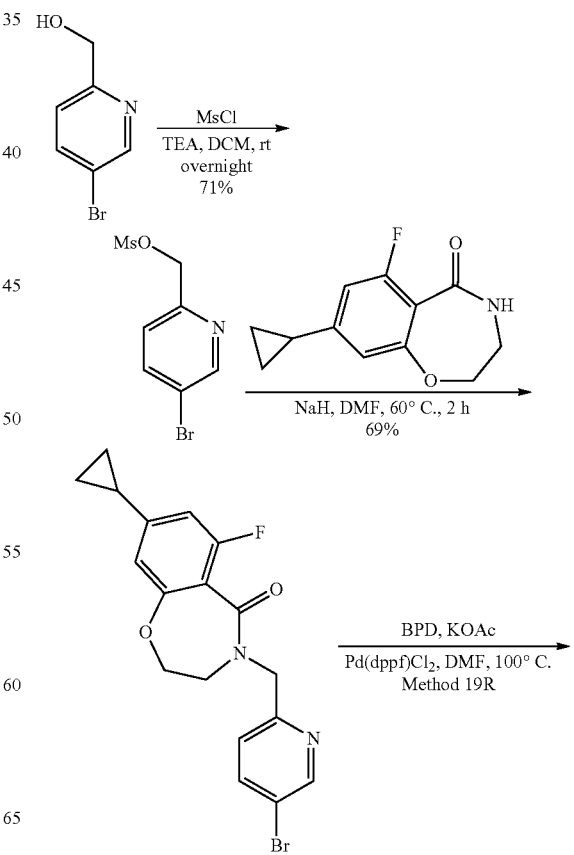

409
-continued

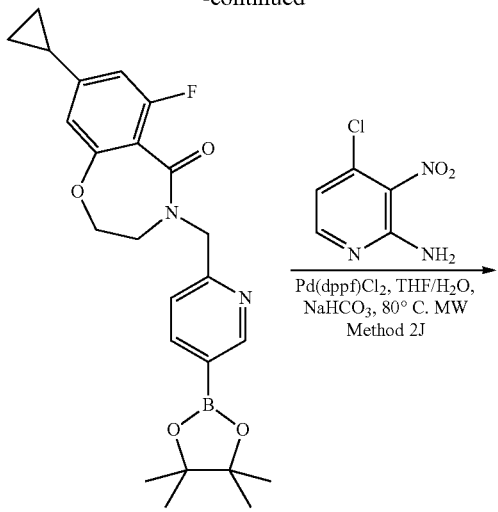

Pd(dppf)Cl₂, THF/H₂O,
NaHCO₃, 80° C. MW
Method 2J

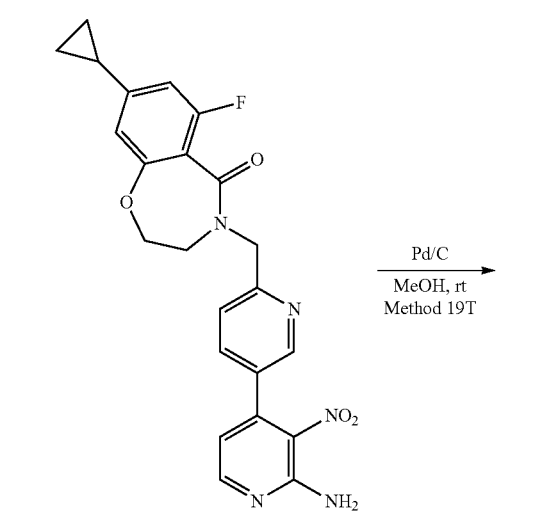

Pd/C
MeOH, rt
Method 19T

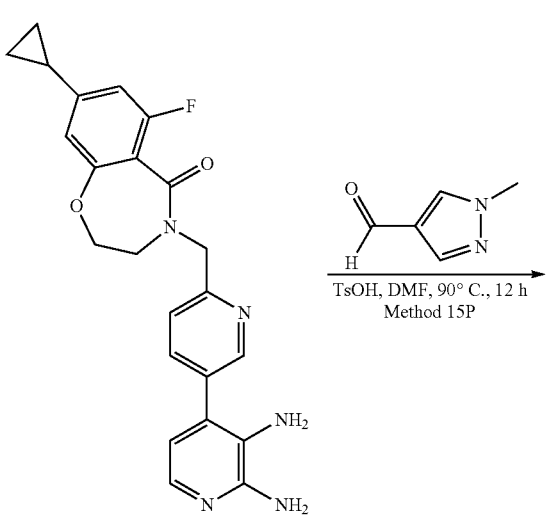

TsOH, DMF, 90° C., 12 h
Method 15P

410
-continued

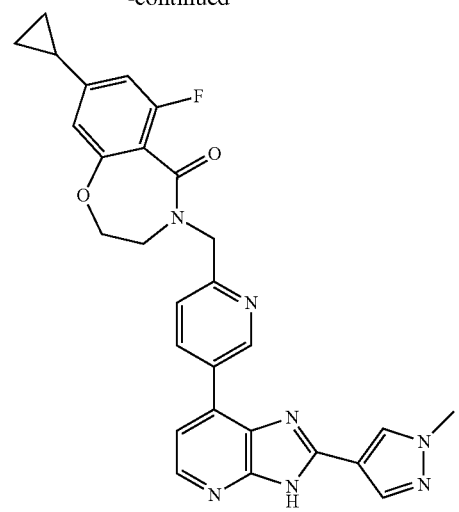

Example 171. 8-cyclopropyl-6-fluoro-4-([5-[2-(1-methyl-1H-pyrazol-4-yl)-3H-imidazo[4,5-b]pyridin-7-yl]pyridin-2-yl]methyl)-2,3,4,5-tetrahydro-1,4-benzoxazepin-5-one

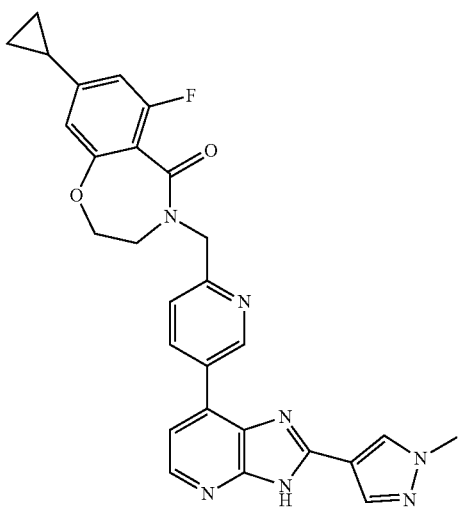 [SMILES: Cn1cc(-c2nc3c(-c4ccc(CN5CCOc6cc(C7CC7)cc(F)c6C5=O)nc4)ccnc3[nH]2)cn1]

(5-bromopyridin-2-yl)methyl methanesulfonate

In a 50-mL round bottom flask, (5-bromopyridin-2-yl) methanol (500 mg, 2.66 mmol, 1.00 equiv) and TEA (210 mg, 2.08 mmol, 1.00 equiv) were dissolved in dichloromethane (10 mL), to which was added methanesulfonyl chloride (300 mg, 2.62 mmol, 1.00 equiv) slowly at 0° C. The resulting solution was then stirred overnight at room temperature. When the reaction was done, it was quenched by 20 mL water and the resulting mixture was extracted with dichloromethane (3×20 mL). The organic layers were combined, dried over sodium sulfate and concentrated under reduced pressure to afford (5-bromopyridin-2-yl) methyl methanesulfonate (500 mg, 71%) as yellow oil.

4-[(5-bromopyridin-2-yl)methyl]-8-cyclopropyl-6-fluoro-2,3,4,5-tetrahydro-1,4-benzoxazepin-5-one In a 50-mL round-bottom flask, 8-cyclopropyl-6-fluoro-2,3,4,5-tetrahydro-1,4-benzoxazepin-5-one (180 mg, 0.81 mmol, 1.00 equiv) was dissolved in tetrahydrofuran (5 mL), to which was added sodium hydride (60% in oil, 72. mg, 1.80 mmol, 2.21 equiv) in portions at 0° C. The resulting mixture was stirred for 1 h at room temperature, and then was cooled to 0° C. and was added by (5-bromopyridin-2-yl)methyl methanesulfonate (360 mg, 1.35 mmol, 1.66 equiv). The reaction mixture was stirred for 2 h at 60° C. When the reaction was done, it was quenched by the addition of 20 mL water and the pH value of the resulting mixture was adjusted to 4 using hydrogen chloride solution (3 M). The mixture was extracted with ethyl acetate (3×20 mL) and the organic layers were combined, dried over sodium sulfate and concentrated under reduced pressure. The residue was purified in a silica gel column eluting with ethyl acetate in petroleum ether (5% to 30% gradient) to afford 4-[(5-bromopyridin-2-yl)methyl]-8-cyclopropyl-6-fluoro-2,3,4,5-tetrahydro-1,4-benzoxazepin-5-one (220 mg, 69%) as white solid. MS: m/z=391.1 [M+H]$^+$

8-cyclopropyl-6-fluoro-4-([5-[2-(1-methyl-1H-pyrazol-4-yl)-3H-imidazo[4,5-b]pyridin-7-yl]pyridin-2-yl]methyl)-2,3,4,5-tetrahydro-1,4-benzoxazepin-5-one 8-cyclopropyl-6-fluoro-4-([5-[2-(1-methyl-1H-pyrazol-4-yl)-3H-imidazo[4,5-b]pyridin-7-yl]pyridin-2-yl]methyl)-2,3,4,5-tetrahydro-1,4-benzoxazepin-5-one 20 mg (17% for four steps) was prepared from 4-[(5-bromopyridin-2-yl)methyl]-8-cyclopropyl-6-fluoro-2,3,4,5-tetrahydro-1,4-benzoxazepin-5-one, 4,4,5,5-tetramethyl-2-(tetramethyl-1,3,2-dioxaborolan-2-yl)-1,3,2-dioxaborolane, 4-chloro-3-nitropyridin-2-amine, 1-methyl-1H-pyrazole-4-carbaldehyde using Method 19R, 2J, 1G and 15P. HPLC: 99.5% purity. MS: m/z=510.2 [M+H]$^+$. $^1$H-NMR (400 MHz, DMSO-d$_6$): δ 13.45 (brs, 1H), 9.52 (d, J=4.8 Hz, 1H), 8.72 (s, 1H), 8.48 (s, 1H), 8.33 (d, J=5.2 Hz, 1H), 8.16 (s, 1H), 7.70-7.35 (m, 2H), 6.83 (dd, J=11.4, 1.6 Hz, 1H), 6.80-6.51 (m, 1H), 4.93 (s, 2H), 4.30 (t, J=5.5 Hz, 2H), 3.95 (s, 3H), 3.69 (t, J=5.4 Hz, 2H).

Example 172. 5-tert-butyl-N-[(4-[2-[5-(dimethylamino)pyridin-2-yl]-3H-imidazo[4,5-b]pyridin-7-yl]-2-fluorophenyl)methyl]-1,3,4-oxadiazole-2-carboxamide

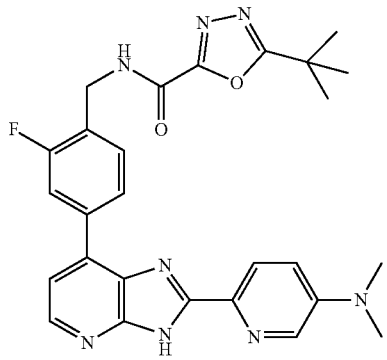 [SMILES: CN(C)c1ccc(-c2nc3c(-c4ccc(CNC(=O)c5nnc(C(C)(C)C)o5)c(F)c4)ccnc3[nH]2)nc1]

5-tert-butyl-N-[(4-[2-[5-(dimethylamino)pyridin-2-yl]-3H-imidazo[4,5-b]pyridin-7-yl]-2-fluorophenyl)methyl]-1,3,4-oxadiazole-2-carboxamide 8 mg (5.5% for three steps) was prepared from tert-butyl N-[[4-(2,3-diaminopyridin-4-yl)-2-fluorophenyl]methyl]carbamate, 5-(dimethylamino)pyridine-2-carbaldehyde and methyl 5-tert-butyl-1,3,4-oxadiazole-2-carboxylate using Method 15P, 19T and 37Y. HPLC: 98.1% purity. MS: m/z=515.1 [M+H]$^+$. $^1$H-NMR (300 MHz, DMSO-d$_6$): δ 9.87 (s, 1H), 8.49-8.25 (m, 2H), 8.25-8.01 (m, 3H), 7.66-7.39 (m, 2H), 7.36-7.06 (m, 1H), 4.59 (d, J=5.0 Hz, 2H), 3.06 (s, 6H), 1.40 (s, 9H).

Example 173. N-(2-fluoro-4-(2-(1-methyl-1H-pyrazol-4-yl)-3H-imidazo[4,5-b]pyridin-7-yl)benzyl)-1-(pyridin-3-yl)methanamine

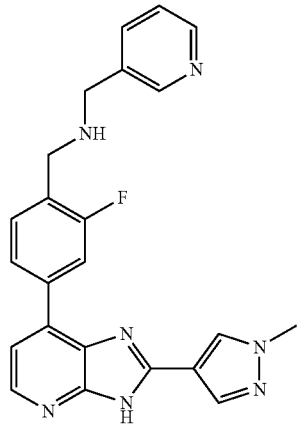 [SMILES: Cn1cc(-c2nc3c(-c4ccc(CNCc5cccnc5)c(F)c4)ccnc3[nH]2)cn1]

To a reaction vial was added 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.), methanol (2 mL), Pyridine-3-carbaldehyde (7.12 μl; 0.08 mmol; 1.00 eq.) and TEA (31.74 μl; 0.23 mmol; 3.00 eq.), The reaction mixture was heated to 60° C. and stirred overnight.

LCMS at 20 hr indicated the reaction was complete. The reaction mixture was poured into saturated NaHCO3 (10 mL) and was extracted with ethyl acetate (2×10 mL). The combined organic phases were concentrated. The crude product was purified by prep HPLC (Interchim P4250; 30×150 mm C-18 column: 0.1% formic acid modified mobile phases (A=water, B=ACN); gradient 10-50% B over 15 min at 60 mL/min). The product fractions were combined and lyophilized to provide 3 mg (10%) of N-(2-fluoro-4-(2-(1-methyl-1H-pyrazol-4-yl)-3H-imidazo[4,5-b]pyridin-7-yl)benzyl)-1-(pyridin-3-yl)methanamine as a white solid. HPLC: 100% purity. MS: 414 [M+H]$^+$. $^1$H NMR (400 MHz, Methanol-d4): δ 8.60 (s, 1H), 8.49 (s, 1H), 8.36 (m, 2H), 8.20 (s, 1H), 7.93 (d, 1H), 7.87 (bs, 1H), 7.65 (t, 1H), 7.49-7.39 (m, 2H), 4.02 (s, 3H), 3.99 (s, 2H), 3.94 (s, 2H).

Example 174. N-(3,4-difluorobenzyl)-1-(2-fluoro-4-(2-(1-methyl-1H-pyrazol-4-yl)-3H-imidazo[4,5-b]pyridin-7-yl)phenyl)methanamine

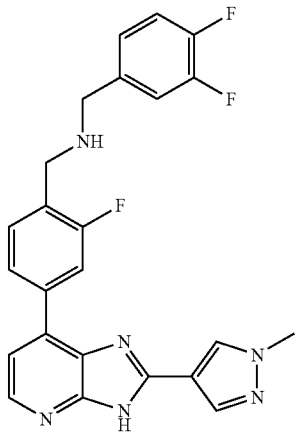 [SMILES: Cn1cc(-c2nc3c(-c4ccc(CNCc5ccc(F)c(F)c5)c(F)c4)ccnc3[nH]2)cn1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in methanol (2 mL) was added 3,4-Difluoro-benzaldehyde (8.39 µl; 0.08 mmol; 1.00 eq.) and TEA (31.74 µl; 0.23 mmol; 3.00 eq.), The reaction mixture was heated to 60° C. and stirred overnight.

LCMS at 20 hr indicated the reaction was complete. The reaction mixture was poured into saturated NaHCO3 (10 mL) and was extracted with ethyl acetate (2×10 mL). The combined organic phases were concentrated. The crude product was purified by prep HPLC (Interchim P4250; 30×150 mm C-18 column; 0.1% formic acid modified mobile phases (A=water, B=ACN); gradient 60% B over 15 min at 60 mL/min). The product fractions were combined and lyophilized to provide 3 mg (9%) of N-(3,4-difluorobenzyl)-1-(2-fluoro-4-(2-(1-methyl-1H-pyrazol-4-yl)-3H-imidazo[4,5-b]pyridin-7-yl)phenyl)methanamine as a white solid. HPLC: 92% purity. MS: 449 [M+H]$^+$. $^1$H NMR (400 MHz, Methanol-d4): δ 8.36 (bs, 2H), 8.21 (s, 1H), 7.89 (bs, 2H), 7.64 (t, 1H), 7.43 (bs, 1H), 7.35 (t, 1H), 7.30-7.16 (m, 2H), 4.03 (s, 3H), 3.93 (s, 2H), 3.83 (s, 2H).

Example 175. N-(2-fluoro-4-(2-(1-methyl-1H-pyrazol-4-yl)-3H-imidazo[4,5-b]pyridin-7-yl)benzyl)-4-methylbenzenesulfonamide

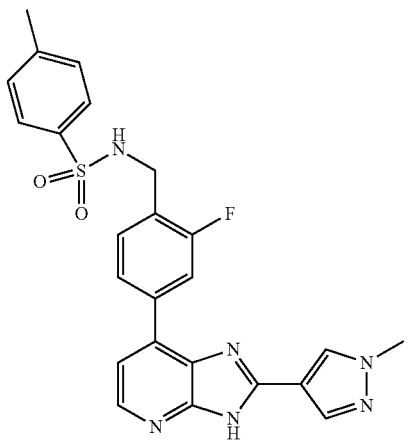 [SMILES: Cc1ccc(S(=O)(=O)NCc2ccc(-c3ccnc4[nH]c(-c5cnn(C)c5)nc34)cc2F)cc1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in ACN (2 mL) was added DIPEA (39.66 µl; 0.23 mmol; 3.00 eq.) and 4-methyl-benzenesulfonyl chloride (15.92 mg; 0.08 mmol; 1.10 eq.), The reaction mixture was stirred at room temperature. The reaction was concentrated and the resulting semi-solid was triturated with ethyl acetate (3.0 mL). Filtration afforded 26 mg of N-(2-fluoro-4-(2-(1-methyl-1H-pyrazol-4-yl)-3H-imidazo[4,5-b]pyridin-7-yl)benzyl)-4-methylbenzenesulfonamide as an off-white solid post high vacuum. HPLC: 90% purity. MS: 477 [M+H]$^+$. $^1$H NMR (400 MHz, DMSO-d$_6$) δ 13.43 (s, 1H), 9.15 (bs, 2H), 8.47 (s, 1H), 8.30 (s, 1H), 8.21 (m, 2H), 8.16 (s, 1H), 8.10 (d, 1H), 7.73 (d, 2H), 7.51 (m, 2H), 7.39 (d, 2H), 4.10 (d, 2H), 3.97 (s, 3H), 2.36 (s, 3H).

Example 176. N-(2-fluoro-4-(2-(1-methyl-1H-pyrazol-4-yl)-3H-imidazo[4,5-b]pyridin-7-yl)benzyl)methanesulfonamide

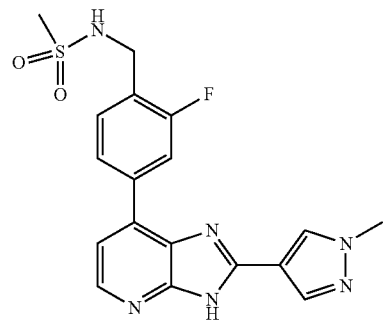 [SMILES: Cn1cc(-c2nc3c(-c4ccc(CNS(C)(=O)=O)c(F)c4)ccnc3[nH]2)cn1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in ACN (2 mL) was added DIPEA (39.66 µl; 0.23 mmol; 3.00 eq.) and methanesulfonyl chloride (8.81 µl; 0.11 mmol; 1.50 eq.), The reaction mixture was stirred at room temperature. LCMS after 16 hr indicated the reaction complete. The reaction was partially concentrated and purified directly via prep HPLC (Interchim P4250; 30×150 mm C-18 column; 0.1% formic acid modified mobile phases (A=water, B=ACN); gradient 10-45% B over 12 min at 60 mL/min). The product fractions were combined and lyophilized to provide 9 mg of N-(2-fluoro-4-(2-(1-methyl-1H-pyrazol-4-yl)-3H-imidazo[4,5-b]pyridin-7-yl)benzyl)methanesulfonamide as a white solid. HPLC: 97% purity. MS: 401 [M+H]$^+$. $^1$H NMR (500 MHz, DMSO-d$_6$) δ 13.39 (s, 1H), 8.46 (s, 1H), 8.32-8.26 (m, 2H), 8.19 (d, 1H), 8.14 (s, 1H), 7.67 (t, 1H), 7.62 (t, 1H), 7.55 (d, 1H), 4.30 (d, 2H), 3.95 (s, 3H), 2.95 (s, 3H).

Example 177. 1-(1-(cyanomethyl)cyclopropyl)-N-(2-fluoro-4-(2-(1-methyl-1H-pyrazol-4-yl)-3H-imidazo[4,5-b]pyridin-7-yl)benzyl)methanesulfonamide

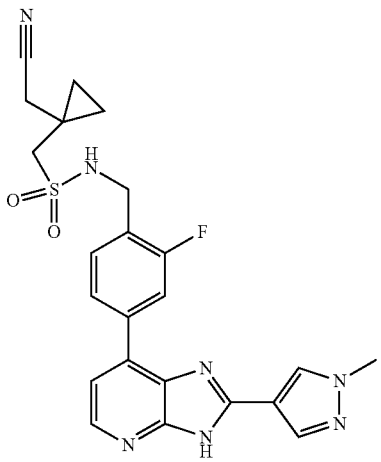 [SMILES: Cn1cc(-c2nc3c(-c4ccc(CNS(=O)(=O)CC5(CC#N)CC5)c(F)c4)ccnc3[nH]2)cn1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in DMF (2 mL) was added DIPEA (39.66 µl; 0.23 mmol; 3.00 eq.) and (1-Cyanomethyl-cyclopropyl)-methanesulfonyl chloride (22.05 mg; 0.11 mmol; 1.50 eq.), The reaction mixture was stirred at room temperature.

LCMS at 2 hr indicated the reaction was complete. The reaction was partially concentrated and purified directly via prep HPLC (Interchim P4250; 30×150 mm C-18 column; 0.1% formic acid modified mobile phases (A=water, B=ACN); gradient 10-50% B over 10 min at 60 mL/min). The product fractions were combined and lyophilized to provide 23 mg (63%) of 1-(1-(cyanomethyl)cyclopropyl)-N-(2-fluoro-4-(2-(1-methyl-1H-pyrazol-4-yl)-3H-imidazo[4,5-b]pyridin-7-yl)benzyl)methanesulfonamide as a white solid. HPLC: 100% purity. MS: 480 [M+H]$^+$. $^1$H NMR (400 MHz, DMSO-d$_6$) δ 13.41 (s, 1H), 8.47 (s, 1H), 8.31 (d, 2H), 8.21 (d, 1H), 8.16 (s, 1H), 7.89 (bs, 1H), 7.64 (t, 1H), 7.57 (bs, 1H), 4.32 (s, 2H), 3.97 (s, 3H), 3.22 (s, 2H), 2.85 (s, 2H), 0.82 (s, 2H), 0.71 (s, 2H).

Example 178. 2-cyclobutyl-N-(2-fluoro-4-(2-(1-methyl-1H-pyrazol-4-yl)-3H-imidazo[4,5-b]pyridin-7-yl)benzyl)ethanesulfonamide

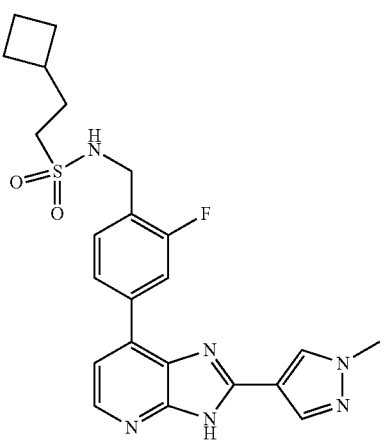 [SMILES: Cn1cc(-c2nc3c(-c4ccc(CNS(=O)(=O)CCC5CCC5)c(F)c4)ccnc3[nH]2)cn1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in DMF (2 mL) was added DIPEA (39.66 µl; 0.23 mmol; 3.00 eq.) and 2-cyclobutyl-ethanesulfonyl chloride (20.80 mg; 0.11 mmol; 1.50 eq.), The reaction mixture was stirred at room temperature.

LCMS at 2 hr indicated the reaction was complete. The reaction was partially concentrated and purified directly via prep HPLC (Interchim P4250; 30×150 mm C-18 column; 0.1% formic acid modified mobile phases (A=water, B=ACN); gradient 10-55% B over 12 min at 60 mL/min). The product fractions were combined and lyophilized to provide 7 mg (20%) of 2-cyclobutyl-N-(2-fluoro-4-(2-(1-methyl-1H-pyrazol-4-yl)-3H-imidazo[4,5-b]pyridin-7-yl)benzyl)ethanesulfonamide as a white solid. HPLC: 100% purity. MS: 469 [M+H]$^+$. $^1$H NMR (400 MHz, DMSO-d$_6$) δ 13.41 (s, 1H), 8.46 (s, 1H), 8.31 (m, 2H), 8.21 (d, 1H), 8.16 (s, 1H), 7.72 (bs, 1H), 7.62 (t, 1H), 7.56 (bs, 1H), 4.30 (s, 2H), 3.97 (s, 3H), 2.90 (t, 2H), 2.30 (m, 1H), 1.99 (bs, 2H), 1.75 (m, 4H), 1.55 (m, 2H).

Example 179. 1-(1,1-dioxidotetrahydro-2H-thiopyran-3-yl)-N-(2-fluoro-4-(2-(1-methyl-1H-pyrazol-4-yl)-3H-imidazo[4,5-b]pyridin-7-yl)benzyl)methanesulfonamide

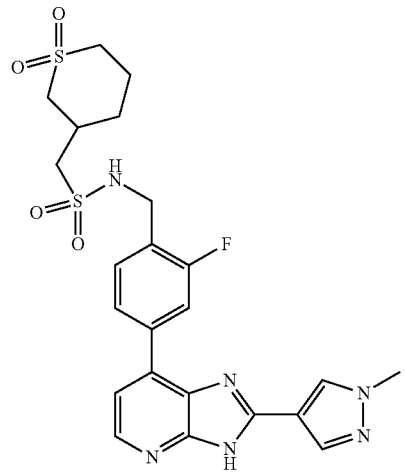 [SMILES: Cn1cc(-c2nc3c(-c4ccc(CNS(=O)(=O)CC5CCCS(=O)(=O)C5)c(F)c4)ccnc3[nH]2)cn1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in DMF (2 mL) was added DIPEA (39.66 µl; 0.23 mmol; 3.00 eq.) and (1,1-Dioxo-hexahydro-1lambda6-thiopyran-3-yl)-methanesulfonyl chloride (28.09 mg; 0.11 mmol; 1.50 eq.), The reaction mixture was stirred at room temperature. LCMS at 2 hr indicated the reaction was complete. The reaction was partially concentrated and purified directly via prep HPLC (Interchim P4250; 30×150 mm C-18 column: 0.1% formic acid modified mobile phases (A=water, B=ACN); gradient 10-55% B over 12 min at 60 mL/min). The product fractions were combined and lyophilized to provide 16 mg (40%) of 1-(1,1-dioxidotetrahydro-2H-thiopyran-3-yl)-N-(2-fluoro-4-(2-(1-methyl-1H-pyrazol-4-yl)-3H-imidazo[4,5-b]pyridin-7-yl)benzyl)methanesulfonamide as a white solid. HPLC: 100% purity. MS: 533 [M+H]+. 1H NMR (400 MHz, DMSO-d6) δ 13.41 (s, 1H), 8.46 (s, 1H), 8.31 (m, 2H), 8.21 (d, 1H), 8.16 (s, 1H), 7.96 (t, 1H), 7.64 (t, 1H), 7.56 (d, 1H), 4.31 (d, 2H), 3.96 (s, 3H), 3.29-2.96 (m, 7H), 2.05 (m, 1H), 1.92 (m, 1H), 1.84 (m, 1H), 1.35 (m, 1H).

Example 180. N-(3-(tert-butyl)benzyl)-1-(2-fluoro-4-(2-(1-methyl-1H-pyrazol-4-yl)-3H-imidazo[4,5-b]pyridin-7-yl)phenyl)methanamine

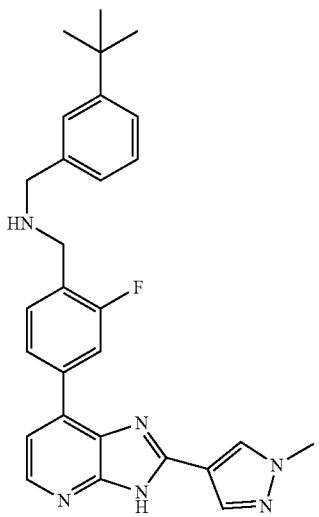 [SMILES: Cn1cc(-c2nc3c(-c4ccc(CNCc5cccc(C(C)(C)C)c5)c(F)c4)ccnc3[nH]2)cn1]

To a solution of 2-Fluoro-4-[2-(1-methyl-1H-pyrazol-4-yl)-3H-imidazo[4,5-b]pyridin-7-yl]-benzylamine hydrochloride (2) (30.00 mg; 0.08 mmol; 1.00 eq.) in DCE (1.5 mL) was added DIPEA (37.73 µl; 0.23 mmol; 3.00 eq.), The stirring solution was then treated with 3-tert-butylbenzaldehyde (12.31 mg; 0.08 mmol; 1.00 eq.) in DCE (0.5 mL) followed by sodium triacetoxyborohydride (24.13 mg; 0.11 mmol; 1.50 eq.), The reaction mixture was stirred at room temperature under N2 atmosphere. After 16 hr the reaction was diluted with DCM (20 mL) and washed with saturated sodium bicarbonate (2×10 mL). The DCM layer was dried (MgSO4), filtered, and concentrated to yield 30 mg of a golden film. The crude was re-dissolved in DMSO (2.0 mL) and purified directly via prep HPLC (Interchim P4250; 30×150 mm C-18 column: 0.1% formic acid modified mobile phases (A=water, B=ACN); gradient 10-55% B over 15 min at 60 mL/min). The product fraction was lyophilized to yield 11 mg (31%) of N-(3-(tert-butyl)benzyl)-1-(2-fluoro-4-(2-(1-methyl-1H-pyrazol-4-yl)-3H-imidazo[4,5-b]pyridin-7-yl)phenyl)methanamine as a white solid. HPLC: 100% purity. MS: 469 [M+H]+. 1H NMR (400 MHz, DMSO-d6) δ 13.40 (s, 1H), 8.46 (s, 1H), 8.28 (m, 2H), 8.18 (m, 2H), 7.70 (t, 1H), 7.55 (bs, 1H), 7.42 (s, 1H), 7.30-7.23 (m, 2H), 7.19 (bs, 1H), 3.97 (s, 3H), 3.83 (s, 2H), 3.77 (s, 2H), 1.30 (s, 9H).

Example 181. N-(4-(tert-butyl)benzyl)-1-(2-fluoro-4-(2-(1-methyl-1H-pyrazol-4-yl)-3H-imidazo[4,5-b]pyridin-7-yl)phenyl)methanamine

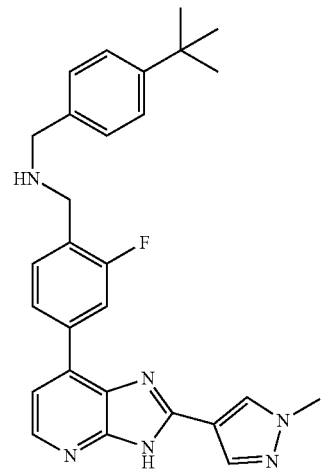 [SMILES: Cn1cc(-c2nc3c(-c4ccc(CNCc5ccc(C(C)(C)C)cc5)c(F)c4)ccnc3[nH]2)cn1]

In an 8 mL reaction vial with magnetic stirbar 2-Fluoro-4-[2-(1-methyl-1H-pyrazol-4-yl)-3H-imidazo[4,5-b]pyridin-7-yl]-benzylamine hydrochloride (2) (50.00 mg; 0.13 mmol; 1.00 eq.) was suspended in DMF (2.0 mL) and treated with DIPEA (88.14 µl; 0.51 mmol; 4.00 eq.). The homogeneous stirring solution was then heated at 75 degrees C. and treated with 4-tert-butylbenzyl bromide (28.73 mg; 0.13 mmol; 1.00 eq.) in DMF (1.0 mL) under nitrogen atmosphere. The reaction mixture was stirred at 75 degrees C. After 3 hr the reaction was partially concentrated and purified directly via prep HPLC (Interchim P4250; 30×150 mm C-18 column; 0.1% formic acid modified mobile phases (A=water, B=ACN); gradient 15-55% B over 15 min at 60 mL/min). The product fraction was lyophilized to yield 10 mg (17%) of N-(4-(tert-butyl)benzyl)-1-(2-fluoro-4-(2-(1-methyl-1H-pyrazol-4-yl)-3H-imidazo[4,5-b]pyridin-7-yl)phenyl)methanamine as a white solid. HPLC: 100% purity. MS: 469 [M+H]+. 1H NMR (400 MHz, DMSO-d6): δ 13.39 (s, 1H), 8.46 (s, 1H), 8.34-8.23 (m, 2H), 8.17 (m, 2H), 7.70 (t, 1H), 7.56 (bs, 1H), 7.40-7.26 (m, 4H), 3.96 (s, 3H), 3.82 (s, 2H), 3.73 (s, 2H), 1.29 (s, 9H).

Example 182. 3-tert-Butyl-[1,2,4]oxadiazole-5-carboxylic acid 2-fluoro-4-(2-trifluoromethyl-3H-imidazo[4,5-b]pyridin-7-yl)-benzylamide

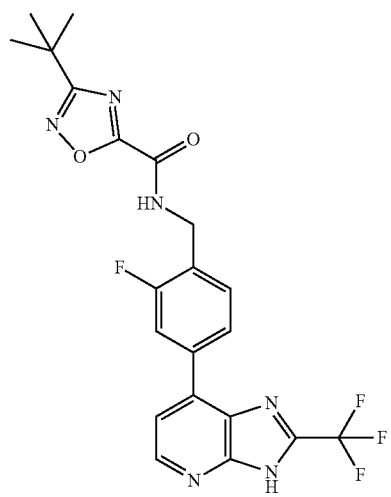 [SMILES: CC(C)(C)c1noc(C(=O)NCc2ccc(-c3ccnc4[nH]c(C(F)(F)F)nc34)cc2F)n1]

Into a 20 mL vial was placed 3-tert-Butyl-[1,2,4]oxadiazole-5-carboxylic acid 4-(2,3-diamino-pyridin-4-yl)-2-fluoro-benzylamide (75.00 mg; 0.20 mmol; 1.00 eq.), trifluoro-acetic acid (16.43 µl; 0.21 mmol; 1.10 eq.), dioxane (7.00 ml), DIPEA (136.30 µl; 0.78 mmol; 4.00 eq.) and 2,4,6-tripropyl-[1,3,5,2,4,6]trioxatriphosphinane 2,4,6-trioxide (232.29 µl; 0.39 mmol; 2.00 eq.), The resulting solution was stirred overnight at 110° C. LCMS at 20 hr indicated the reaction was not complete. Additional trifluoro-acetic acid (16.43 µl: 0.21 mmol; 1.10 eq.) and 2,4,6-tripropyl-[1,3,5,2,4,6]trioxatriphosphinane 2,4,6-trioxide (232.29 µl; 0.39 mmol; 2.00 eq.) were added and the reaction was stirred overnight again at 110° C. LCMS 20 hr later indicated the reaction was complete. The reaction was concentrated dissolved in DMSO and purified via prep HPLC (Interchim P4250; 30×150 mm C-18 column; 0.1% formic acid modified mobile phases (A=water, B=ACN); gradient 15-90% B over 17 min at 60 mL/min). The product fractions were combined and lyophilized to yield 55 mg (61%) of 3-tert-Butyl-[1,2,4]oxadiazole-5-carboxylic acid 2-fluoro-4-(2-trifluoromethyl-3H-imidazo[4,5-b]pyridin-7-yl)-benzylamide as a white solid. HPLC: 92% purity. MS: 463 [M+H]$^+$. $^1$H NMR (400 MHz, DMSO-d$_6$) δ 14.93 (bs, 1H), 9.92 (s, 1H), 8.61 (s, 1H), 8.18 (m, 2H), 7.77 (bs, 1H), 7.64 (t, 1H), 4.62 (d, 2H), 1.38 (s, 9H).

Example 183. 3-tert-Butyl-[1,2,4]oxadiazole-5-carboxylic acid 2-fluoro-4-(2-isobutyl-3H-imidazo[4,5-b]pyridin-7-yl)-benzylamide

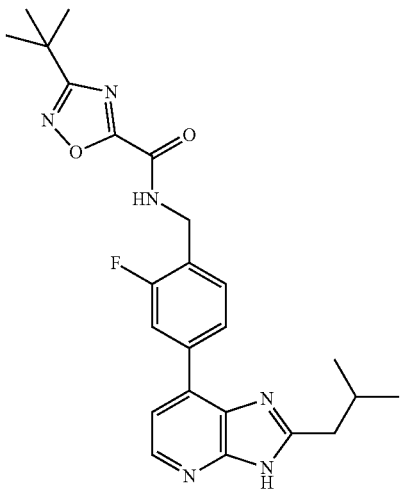 [SMILES: CC(C)Cc1nc2c(-c3ccc(CNC(=O)c4nc(C(C)(C)C)no4)c(F)c3)ccnc2[nH]1]

To a 20-mL reaction vial was added 3-tert-butyl-[1,2,4]oxadiazole-5-carboxylic acid 4-(2,3-diamino-pyridin-4-yl)-2-fluoro-benzylamide (75.00 mg; 0.20 mmol; 1.00 eq.), isovaleraldehyde (0.02 ml; 0.20 mmol; 1.00 eq.), and DMF (2.00 ml; 25.84 mmol; 132.46 eq.). The resulting solution was placed under nitrogen atmosphere and stirred overnight at 130 degrees Celsius. LCMS at 22 hr showed complete conversion of starting material to desired product. The reaction mixture was directly loaded onto SiO$_2$ and purified via flash chromatography (Biotage, SiO$_2$, 80-100% ethyl acetate/hexanes). The product fractions were concentrated, dissolved in DMSO (2 mL), and purified via prep HPLC (Interchim P4250: 30×150 mm C-18 column; 0.1% formic acid modified mobile phases (A=water, B=ACN); gradient 10-60% B over 15 min at 60 mL/min). The product fractions were combined and lyophilized to yield 40.5 mg (46%) of 3-tert-butyl-[1,2,4]oxadiazole-5-carboxylic acid 2-fluoro-4-(2-isobutyl-3H-imidazo[4,5-b]pyridin-7-yl)-benzylamide as a light yellow solid. MS: 452 [M+H]$^+$. HPLC: 97% purity. $^1$H NMR (400 MHz, DMSO-d$_6$) δ 12.97 (s, 1H), 9.90 (t, 1H), 8.29 (d, 1H), 8.26 (dd, 1H), 8.12 (dd, 1H), 7.57 (t, 2H), 7.53 (d, 1H), 4.59 (d, 2H), 2.76 (d, 2H), 1.38 (s, 9H), 0.97 (d, 6H).

Example 184. 3-tert-Butyl-[1,2,4]oxadiazole-5-carboxylic acid 2-fluoro-4-(2-isopropyl-3H-imidazo[4,5-b]pyridine-7-yl)-benzyl

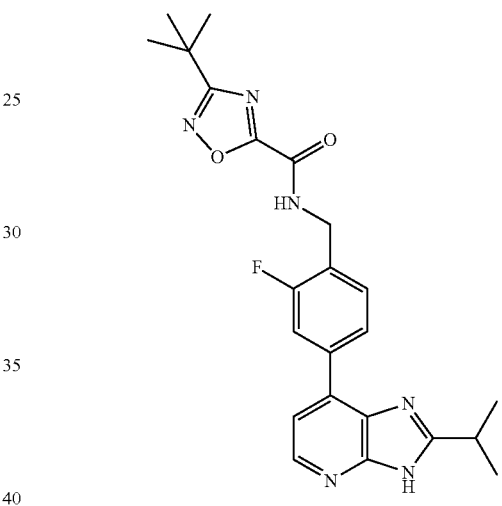

To a 20-mL reaction vial was added 3-tert-Butyl-[1,2,4]oxadiazole-5-carboxylic acid 4-(2,3-diamino-pyridin-4-yl)-2-fluoro-benzylamide (75.00 mg; 0.20 mmol; 1.00 eq.), 2-methyl-propionaldehyde (14.07 mg; 0.20 mmol; 1.00 eq.), and DMF (2.00 ml; 25.84 mmol; 132.46 eq.). The resulting solution was placed under nitrogen atmosphere and stirred overnight at 130 degrees Celsius. LCMS at 22 hr showed minor amounts of starting material. The reaction was cooled to room temperature and then quenched by the addition of water (10 mL). The mixture was extracted with ethyl acetate (3×20 mL) and the combined organic layer was dried over Na$_2$SO$_4$, filtered, and concentrated. The crude material was dissolved in DMSO (2 mL) and purified via prep HPLC (Interchim P4250; 30×150 mm C-18 column; 0.1% formic acid modified mobile phases (A=water, B=ACN); gradient 10-60% B over 15 min at 60 mL/min). The product fractions were combined and lyophilized to yield 17 mg (20%) of 3-tert-butyl-[1,2,4]oxadiazole-5-carboxylic acid 2-fluoro-4-(2-isopropyl-3H-imidazo[4,5-b]pyridine-7-yl)-benzyl as an off white solid. HPLC: 90% purity. MS: 437 [M+H]$^+$. $^1$H NMR (400 MHz, DMSO-d$_6$) δ 12.96 (s, 1H), 8.30 (d, 1H), 8.26 (dd, 1H), 8.15 (dd, 1H), 7.57 (t, 2H), 7.53 (d, 1H), 4.59 (d, 2H), 1.39 (d, 6H), 1.38 (s, 9H), 1.27 (s, 1H).

Example 185. 5-{2-Fluoro-4-[2-(1-methyl-1H-pyrazol-4-yl)-3H-imidazo[4,5-b]pyridin-7-yl]-benzylamino}-2,3-dihydro-pyrido[3,4-b][1,4]oxazine-1-carboxylic acid tert-butyl ester

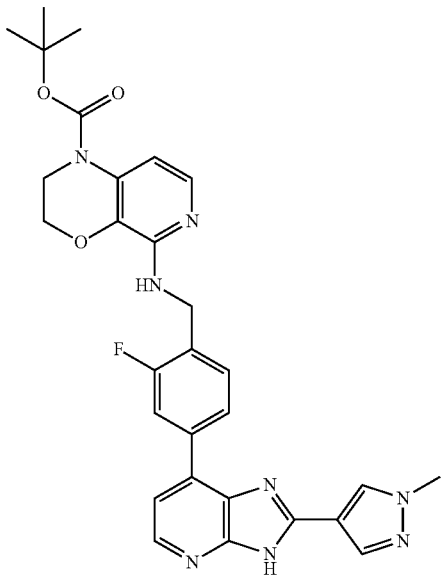 [SMILES: Cn1cc(-c2nc3c(-c4ccc(CNc5nccc6c5OCCN6C(=O)OC(C)(C)C)c(F)c4)ccnc3[nH]2)cn1]

To a microwave vial with stir bar was added 2-Fluoro-4-[2-(1-methyl-1H-pyrazol-4-yl)-3H-imidazo[4,5-b]pyridin-7-yl]-benzylamine (59.81 mg; 0.19 mmol; 1.20 eq.), 5-iodo-2,3-dihydro-pyrido[3,4-b][1,4]oxazine-1-carboxylic acid tert-butyl ester (56.00 mg; 0.15 mmol; 1.00 eq.), sodium tert-butoxide (74.30 mg; 0.77 mmol; 5.00 eq.), racemic-2,2'-bis(diphenylphosphino)-1,1'-binaphthyl (9.63 mg; 0.02 mmol; 0.10 eq.), and bis(dibenzylideneacetone)palladium (0) (5.33 mg: 0.01 mmol; 0.06 eq.), The vial was evacuated and backfilled with nitrogen and dry dioxane (2.00 ml) was added. The reaction was irradiated in the microwave for 1 hr at 120 degrees Celsius and then filtered through celite. The filtrate was concentrated, dissolved in DMSO (2 mL), and reaction was purified via prep HPLC (Interchim P4250; 30×150 mm C-18 column; 0.1% formic acid modified mobile phases (A=water, B=ACN); gradient 10-60% B over 15 min at 60 mL/min). The product fractions were combined and lyophilized to yield 11.5 mg (13%) of 5-{2-fluoro-4-[2-(1-methyl-1H-pyrazol-4-yl)-3H-imidazo[4,5-b]pyridin-7-yl]-benzylamino}-2,3-dihydro-pyrido[3,4-b][1.4]oxazine-1-carboxylic acid tert-butyl ester as a white solid. MS: 558 [M+H]$^+$. HPLC: 92% purity. $^1$H NMR (400 MHz, DMSO-d$_6$) δ 13.37 (s, 1H), 8.45 (s, 1H), 8.28 (m, 1H), 8.23 (d, J=11.8 Hz, 1H), 8.15 (s, 1H), 8.09 (d, J=8.2 Hz, 1H), 7.51 (d, 1H), 7.45 (t, J=6.4 Hz, 2H), 7.11 (m, 1H), 6.57 (m, 2H), 4.68 (d, J=5.3 Hz, 2H), 4.33 (s, 2H), 3.96 (s, 3H), 3.86 (s, 2H), 1.51 (s, 9H).

Example 186. 3-tert-Butyl-[1,2,4]oxadiazole-5-carboxylic acid 2-fluoro-4-[2-((1R,2R)-2-phenyl-cyclopropyl)-3H-imidazo[4,5-b]pyridin-7-yl]-benzylamide

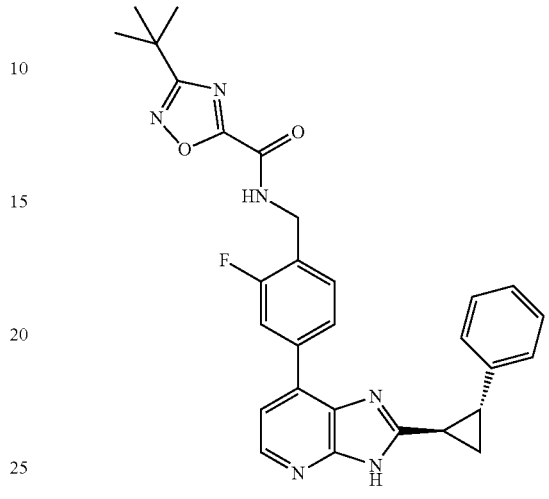

To a 20-mL reaction vial was added 3-tert-Butyl-[1,2,4]oxadiazole-5-carboxylic acid 4-(2,3-diamino-pyridin-4-yl)-2-fluoro-benzylamide (75.00 mg; 0.20 mmol; 1.00 eq.), cyclopropanecarboxaldehyde, 2-phenyl-, (1r,2r)-(28.52 mg; 0.20 mmol; 1.00 eq.), and DMF (2.0 ml). The resulting solution was placed under nitrogen atmosphere and stirred overnight at 130 degrees celsius. LCMS at 22 hr showed complete conversion of starting material to desired product. The reaction mixture was cooled to room temperature, loaded directly onto SiO$_2$ and purified via flash chromatography (Biotage SiO$_2$ column; gradient 50-100% EtOAc/Hex over 10 minutes). The product fractions were combined and concentrated. The material was then dissolved in DMSO (2 mL) and purified via prep HPLC (Interchim P4250; 30×150 mm C-18 column; 0.1% formic acid modified mobile phases (A=water, B=ACN); gradient 10-60% B over 15 min at 60 mL/min). The product fractions were combined and lyophilized to yield 8 mg (8%) of 3-tert-Butyl-[1,2,4]oxadiazole-5-carboxylic acid 2-fluoro-4-[2-((1R,2R)-2-phenyl-cyclopropyl)-3H-imidazo[4,5-b]pyridin-7-yl]-benzylamide as a white solid. MS: 512 [M+H]$^+$. HPLC: 100% purity. $^1$H NMR (400 MHz, DMSO-d$_6$) δ 13.0 (s, 1H), 9.90 (m, 1H), 8.27 (d, 1H), 8.23 (dd, 1H), 8.13 (d, 1H), 7.57 (t, 1H), 7.52 (d, 1H), 7.33 (m, 2H), 7.27 (s, 1H), 7.24 (m, 1H), 7.21 (dt, 1H), 4.59 (d, 2H), 2.63 (m, 2H), 2.45 (s, 1H), 1.91 (m, 1H), 1.69 (m, 1H), 1.38 (s, 9H).

Example 187. 3-tert-Butyl-[1,2,4]oxadiazole-5-carboxylic acid 2-fluoro-4-{2-[1-(2-morpholin-4-yl-ethyl)-1H-pyrazol-4-yl]-3H-imidazo[4,5-b]pyridin-7-yl}-benzylamide

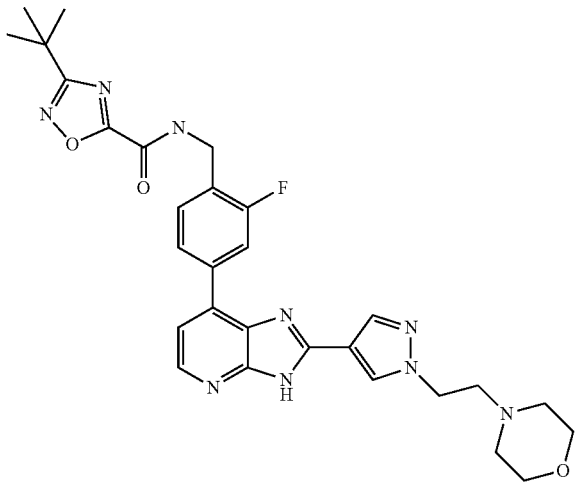 [SMILES: CC(C)(C)c1noc(C(=O)NCc2ccc(-c3ccnc4[nH]c(-c5cnn(CCN6CCOCC6)c5)nc34)cc2F)n1]

2-Fluoro-4-{2-[1-(2-morpholin-4-yl-ethyl)-1H-pyrazol-4-yl]-3H-imidazo[4,5-b]pyridin-7-yl}-benzylamine (66.00 mg; 0.16 mmol; 1.00 eq.), 3-tert-Butyl-[1,2,4]oxadiazole-5-carboxylic acid (34.64 mg; 0.20 mmol; 1.30 eq.), 2,4,6-Tripropyl-[1,3,5,2,4,6]trioxatriphosphinane 2,4,6-trioxide (0.50 ml; 1.12 mmol; 7.12 eq.), DIPEA (0.08 ml; 0.47 mmol; 3.00 eq.), and MeCN (0.50 ml; 9.57 mmol; 61.13 eq.) were combined under N2 (g) and stirred at room temperature overnight. After LCMS indicated completion of reaction, directly loaded onto Interchim HPLC for purification (0-100% 0.1% formic acid (aq)/MeCN). The title compound 3-tert-Butyl-[1,2,4]oxadiazole-5-carboxylic acid 2-fluoro-4-{2-[1-(2-morpholin-4-yl-ethyl)-1H-pyrazol-4-yl]-3H-imidazo[4,5-b]pyridin-7-yl}-benzylamide was isolated as 15 mg of a beige solid (17% yield). LC-MS: 567.2 [M+H]$^+$. HPLC: 100% purity. $^1$H NMR (500 MHz, Methanol-d4): δ 8.41 (br s, 1H), 8.33 (br s, 1H), 7.87 (d, 1H), 7.82 (br m, 1H), 7.66 (br m, 2H), 7.63 (br m, 1H), 7.50 (br s, 1H), 4.76 (s, 2H), 3.95 (br s, 4H), 1.67 (br m, 5H), 1.44 (s, 9H), 1.02 (br m, 4H).

Example 188. 4-[2-(1-Cyclobutyl-1H-pyrazol-4-yl)-3H-imidazo[4,5-b]pyridin-7-yl]-2-fluoro-benzylamine

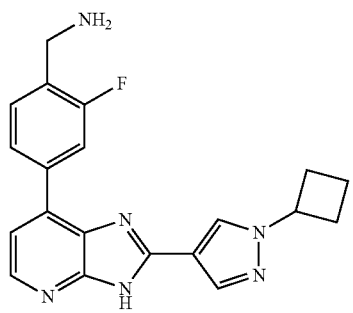 [SMILES: NCc1ccc(-c2ccnc3[nH]c(-c4cnn(C5CCC5)c4)nc23)cc1F]

7-Chloro-2-(1-cyclobutyl-1H-pyrazol-4-yl)-3H-imidazo[4,5-b]pyridine (222.10 mg; 0.81 mmol; 1.00 eq.), [4-(aminomethyl)-3-fluoro-phenyl]boronic acid (274.19 mg; 1.62 mmol; 2.00 eq.), dipotassium carbonate (448.57 mg; 3.25 mmol; 4.00 eq.), and MeCN (4.00 ml; 76.58 mmol; 94.38 eq.) were combined under N2 (g) as cyclopentyl(diphenyl)phosphane; dichloromethane: dichloropalladium; iron (66.26 mg; 0.08 mmol; 0.10 eq.) was added. Capped and degassed with N2 (g) 15 min, then heated to 130° C. in the microwave (Biotage, high absorption) for 2 hours, then cooled to RT. Filtered through Celite, washed with methanol and DCM, and evaporated solvent, then purified by flash column chromatography (Biotage, KPNH silica, 0-20% MeOH/DCM) to afford the desired product 4-[2-(1-Cyclobutyl-1H-pyrazol-4-yl)-3H-imidazo[4,5-b]pyridin-7-yl]-2-fluoro-benzylamine as a white solid (161 mg, 55% yield). LC-MS: 362.1 [MH]. HPLC: 91.1% purity. $^1$H NMR (500 MHz, DMSO-d$_6$): δ 1,3,2 (br m, 1H), 8.81 (s, 1H), 8.55 (s, 1H), 8.49 (s, 1H), 8.23 (s, 1H), 8.15 (br m, 1H), 7.57 (br m, 1H), 7.51 (br m, 1H), 7.45 (br m, 1H), 4.98 (br m, 3H), 4.51 (s, 1H), 4.23 (s, 1H), 2.57 (m, 4H), 2.45 (m, 2H).

Example 189

Assay A: Microfluidic Off-Chip Mobility Shift Assay Protocol for Potency Assessment Against BTK Enzyme The protocol below describes microfluidic, off-chip mobility shift kinase assay to measure inherent potency of compounds against BTK enzyme. The mechanics of the assay platform are best described by the vendor (Caliper Life Sciences, a PerkinElmer Company, Hopkinton, Mass.) on their website at the following URL: http://caliperls.com/ or http://caliperls.com/apps/drug-discovery-and-pre-clinical-development/target-id-validation.htm.

Briefly, 2.5× stocks of full-length human BTK (08-080) from CarnaBio USA, Inc., Natick, Mass., 1.6×ATP and appropriate kinKDR peptide substrate (FITC-AHA-EEP-LYWSFPAKKK-NH$_2$; developed in-house) were prepared in kinase reaction buffer consisting of 25 mM MgCl2, 0.015% Brij-35 (30%), 100 mM HEPES, pH 7.5, and 10 mM DTT. 5 uL of enzyme buffer and 7.5 uL of ATP/kinKDR peptide substrate mix were added to Matrix (#115304) 384-well, sterile, polypropylene plates (Thermo Fisher Scientific, Hudson, N.H.) with 125 nL of serially diluted compounds prepared in 100% DMSO, and incubated for 90 min. at 27° C. Following the incubation period, reactions were stopped by adding 60 uL stop buffer consisting of 100 mM HEPES, pH 7.5, 0.015% Brij-35 (30%), 0.277% Coating Reagent #3 (Caliper Life Sciences, Mountain View, Calif.), 5% DMSO. Stopped reactions were monitored at −2 PSI, −3000 V/−700 V in a LabChip 3000 plate reader from Caliper Life Sciences, a PerkinElmer Company (Hopkinton, Mass.), and the activity was measured by off-chip mobility shift assay measuring the charge/mass difference between substrate and product resulting from peptide phosphorilation. IC50 and efficacy were determined by plotting log [Inhibitor] vs. % Activity in GeneData Screener (Basel. Switzerland).

Assay B: Microfluidic Off-Chip Mobility Shift Assay Protocol for Potency Assessment Against BTK C481S Enzyme The protocol below describes a microfluidic, off-chip mobility shift kinase assay to measure inherent potency of compounds against BTK C481S enzyme. The mechanics of the assay platform are described by the vendor (PerkinElmer, Hopkinton, Mass.) on their website at the following URL: http://caliperls.com.

Briefly, 2.5× stocks of His-TEV-hsBTK(328-659) (C481S) from the Merck Serono Protein Purification Laboratory in Darmstadt, Germany (PCS, Q27/234), 1.6×ATP and appropriate KinKDR peptide substrate (FITC-AHA-EEPLYWSFPAKKK-NH$_2$; Tufts University Core Facility custom synthesis) were prepared in kinase reaction buffer consisting of 25 mM MgCl2, 0.015% Brij-35 (30%), 100 mM HEPES, pH 7.5, and 10 mM DTT.

5 uL of enzyme buffer and 7.5 uL of ATP/KinKDR peptide substrate mix were added to Matrix (#4315) 384-well, sterile, flat-bottom polypropylene plates (Thermo Fisher Scientific, Hudson, N.H.) with 125 nL of serially diluted compounds prepared in 100% DMSO, and incubated for 90 min. at 25° C. Following the incubation period, reactions were terminated by adding 65 uL quench buffer consisting of 100 mM HEPES, pH 7.5, 0.015% Brij-35 (30%), 0.277% Coating Reagent #3 (PerkinElmer, Mountain View, Calif.), 5% DMSO. Terminated reactions were monitored at −2 PSI, −3000 V/−700 Volts in a LabChip 3000 plate reader from Caliper Life Sciences, a PerkinElmer Company (Hopkinton, Mass.), and the activity was quantified by laser-induced fluorescence measuring the charge/mass difference between substrate and product resulting from peptide phosphorylation. IC50 and efficacy were determined by plotting log [Inhibitor] vs. % Activity in GeneData Screener (Basel, Switzerland).

Assay C: PBMC IC50 Assay

Btk is critical for mediating the signalling of B cell antigen receptor (BCR) after anti-IgM stimulation. Based on this principle, a functional cell-based assay was established to determine the potency of compounds at inhibiting anti-IgM-induced expression of CD69, a downstream BCR signaling event, in freshly isolated human peripheral blood mononuclear cells (PBMCs). In the assay, a 90 μl PBMC suspension containing 2.5×10$^5$ cells was pre-treated with 10 μl of test compound at various concentrations for an hour, and then incubated overnight (approximately 16-18 hours) with 5 μl 420 μg/ml affiniPure F(ab')$_2$ fragment goat anti-human IgM Fc fragment per well (Dianova, Cat. No.: 109-006-129). After the incubation, the cells were washed and immunostained with an APC-labeled mouse anti-human CD69 (BD Biosciences; clone: FN50), a PerCP-Cy5.5 labelled mouse anti-human CD19 (BD Biosciences; clone: SJ25C1) and a FITC-labelled mouse anti-human CD3 (BD Biosciences; clone: HIT3a), and fixed for flow cytometric analysis of CD69 expression on CD19 positive cells (B cells). The percentage of CD69 expressing CD19 positive cells was plotted against the concentrations of test compounds to obtain a concentration response curve, and calculate an IC$_{50}$ value as a measure of the potency of test compounds in the assay.

Assay D: THP-1 Cells IL-1β release ELISA Assay

The assay measures IL-1β release by human THP-1 cells after treatment with PMA and LPS in response to BzATP stimulation in order to evaluate the potency of P2X7 inhibitors. THP-1 cells (2×10$^5$ cells/mL) in culture medium (RPMI1640 (Gibco, #22400-089)+10% HI-FBS (Gibco, #10082-147)+1% L-Glutamine (Gibco, #25030)+1% Pen/Strep (Gibco, #15140) complemented with 0.5 μM PMA (Sigma, #P8139) were incubated for 30 min at 37° C. At the end of the incubation time, the cells were titrated and washed gently in PBS. The cells were then re-suspended to a density of 1.5×10$^5$ cell/mL in culture medium complemented with 10 ng/mL LPS (Sigma, #L5293). The cell suspension was dispensed (40 μL/well) into a Corning 384-well plate. After 4 hr of incubation at 37° C., the cells were treated with 20 μL of test compounds at various concentrations. The plate was incubated for 30 min at 37° C. and then the cells were treated with 20 μL of 3.2 mM BzATP (Sigma. #B6396) (0.8 mM final concentration). The plate was incubated for an additional 30 min at 37° C., and then subjected to centrifugation (4 min, 1000 rpm). Supernatant (60 μL) from each well was transferred to a 384-matrix PP plate. The plate was then stored at 4° C. (overnight) or −20° C. for longer term storage. The next day, the IL-10 levels were measured using a human IL-103 ELISA Kit (R & D systems, catalog #DY201) and read using a SpectraMax Plus 384 Microplate Reader.

Assay E: LCK Biochemical Assay

The standard protocol below describes the standard Hot-Spot Kinase Assay run by the Reaction Biology Corporation as a service.

The substrate (poly(EY) (Glu:Tyr (4:1)) and the cofactors were prepared in fresh Reaction Buffer (20 mM Hepes (pH 7.5), 10 mM MgCl$_2$, 2 mM MnCl$_2$, 1 mM EGTA, 0.02% Brij35, 0.02 mg/ml BSA, 0.1 mM Na$_3$VO$_4$, 2 mM DTT, 2% DMSO). To the substrate solution was then added the enzyme (LCK; recombinant human full-length (Genbank Accession #NP_005347); C-terminal His-tagged, expressed in insect cells), and the resulting solution was then gently mixed. The test compounds were dissolved in DMSO and then delivered into the kinase reaction mixture using acoustic liquid handling technology (Echo550; nanoliter range). The reaction mixture was incubated for 20 min at RT and then treated with $^{33}$P-ATP to initiate the reaction. After 2 hours of incubation at RT, kinase activity was detected using Reaction Biology Corporation's proprietary P81 filter-binding method.

The data is interpreted according to the following:

| Example Number | BTK IC$_{50}$ (Assay A) |
| --- | --- |
| 1 | ++++ |
| 2 | ++++ |
| 3 | ++++ |
| 4 | ++++ |
| 5 | ++++ |
| 6 | ++++ |
| 7 | ++++ |
| 8 | ++++ |
| 9 | ++++ |
| 10 | ++++ |
| 11 | ++++ |
| 12 | ++++ |
| 13 | +++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | +++ |
| 23 | +++ |
| 24 | +++ |
| 25 | +++ |
| 26 | ++++ |
| 27 | ++++ |
| 28 | ++++ |
| 29 | ++ |
| 30 | ++ |
| 31 | ++ |
| 32 | ++ |
| 34 | ++++ |
| 35 | ++++ |
| 37 | ++++ |
| 38 | +++ |
| 39 | ++++ |

| Example Number | BTK IC$_{50}$ (Assay A) |
|---|---|
| 40 | ++++ |
| 41 | ++++ |
| 42 | ++++ |
| 43 | +++ |
| 44 | ++ |
| 45 | ++++ |
| 46 | ++ |
| 47 | +++ |
| 48 | +++ |
| 49 | ++++ |
| 50 | ++++ |
| 51 | ++++ |
| 52 | ++++ |
| 53 | ++++ |
| 54 | ++++ |
| 55 | ++++ |
| 56 | ++++ |
| 57 | ++++ |
| 58 | ++++ |
| 59 | ++++ |
| 60 | +++ |
| 61 | ++++ |
| 62 | ++++ |
| 63 | ++++ |
| 64 | ++++ |
| 65 | ++ |
| 66 | ++++ |
| 67 | ++++ |
| 68 | ++++ |
| 69 | ++++ |
| 70 | ++++ |
| 71 | ++++ |
| 72 | ++++ |
| 73 | ++++ |
| 74 | ++++ |
| 75 | ++++ |
| 76 | ++++ |
| 77 | ++++ |
| 78 | ++++ |
| 79 | ++++ |
| 80 | ++++ |
| 81 | ++++ |
| 82 | ++++ |
| 83 | ++++ |
| 84 | ++++ |
| 85 | ++++ |
| 86 | ++++ |
| 87 | ++ |
| 88 | ++ |
| 89 | ++++ |
| 90 | ++++ |
| 91 | ++++ |
| 92 | ++++ |
| 93 | ++++ |
| 95 | ++ |
| 96 | +++ |
| 97 | ++++ |
| 98 | ++++ |
| 99 | ++++ |
| 100 | ++++ |
| 101 | ++ |
| 102 | ++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | ++++ |
| 113 | ++++ |
| 114 | + |
| 115 | ++++ |
| 116 | ++++ |
| 118 | ++++ |
| 119 | ++++ |
| 120 | ++++ |
| 121 | ++++ |
| 122 | +++ |
| 124 | ++++ |
| 125 | ++++ |
| 126 | ++++ |
| 127 | ++++ |
| 129 | ++++ |
| 130 | ++++ |
| 131 | ++++ |
| 132 | ++++ |
| 133 | ++++ |
| 134 | ++++ |
| 135 | ++++ |
| 136 | ++++ |
| 137 | ++++ |
| 138 | ++++ |
| 139 | ++++ |
| 140 | ++++ |
| 141 | ++++ |
| 142 | +++ |
| 143 | ++++ |
| 144 | ++++ |
| 145 | ++++ |
| 146 | ++++ |
| 148 | ++++ |
| 149 | ++++ |
| 150 | ++++ |
| 151 | ++++ |
| 152 | ++++ |
| 153 | ++++ |
| 154 | + |
| 155 | + |
| 156 | +++ |
| 157 | ++++ |
| 158 | ++++ |
| 159 | ++++ |
| 160 | ++++ |
| 161 | ++++ |
| 162 | ++++ |
| 163 | ++++ |
| 164 | ++++ |
| 165 | ++++ |
| 166 | ++++ |
| 167 | ++++ |
| 168 | ++++ |
| 169 | ++++ |
| 170 | ++++ |
| 171 | ++++ |
| 172 | ++++ |
| 173 | + |
| 174 | + |
| 175 | + |
| 176 | + |
| 177 | ++ |
| 178 | ++ |
| 179 | + |
| 180 | + |
| 181 | + |
| 183 | +++ |
| 184 | +++ |
| 185 | + |
| 186 | + |
| 187 | ++++ |
| 188 | ++ |

+ >5 μM;
++ >1-5 μM;
+++ 100 nM-1 μM;
++++ <100 nM.

| Example Number | BTK(C481S) IC50 (Assay B) |
|---|---|
| 2 | ++++ |
| 5 | ++++ |
| 6 | ++++ |
| 10 | ++++ |
| 11 | ++++ |
| 13 | ++++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | +++ |
| 23 | +++ |
| 24 | +++ |
| 25 | +++ |
| 26 | ++++ |
| 27 | ++++ |
| 28 | ++ |
| 29 | +++ |
| 30 | +++ |
| 31 | +++ |
| 32 | +++ |
| 34 | ++++ |
| 35 | ++++ |
| 37 | ++++ |
| 38 | +++ |
| 39 | ++++ |
| 40 | ++++ |
| 41 | ++++ |
| 42 | ++++ |
| 43 | +++ |
| 44 | ++++ |
| 45 | ++++ |
| 46 | ++ |
| 47 | ++++ |
| 48 | ++++ |
| 49 | ++++ |
| 50 | ++++ |
| 52 | ++++ |
| 53 | ++++ |
| 54 | +++ |
| 55 | ++++ |
| 56 | ++++ |
| 57 | ++++ |
| 58 | ++++ |
| 60 | +++ |
| 61 | ++++ |
| 62 | ++++ |
| 63 | ++++ |
| 65 | +++ |
| 66 | ++++ |
| 67 | ++++ |
| 70 | ++++ |
| 71 | ++++ |
| 72 | +++ |
| 74 | ++++ |
| 75 | ++++ |
| 76 | ++++ |
| 77 | ++++ |
| 78 | ++++ |
| 79 | ++++ |
| 80 | ++++ |
| 81 | ++++ |
| 83 | ++++ |
| 84 | ++++ |
| 86 | ++++ |
| 87 | ++++ |
| 88 | + |
| 89 | ++++ |
| 90 | +++ |
| 91 | ++++ |
| 92 | ++++ |
| 93 | ++++ |
| 95 | ++ |
| 98 | ++++ |
| 99 | ++++ |
| 100 | ++++ |
| 101 | ++ |
| 102 | ++ |
| 103 | ++++ |
| 104 | ++++ |
| 105 | ++++ |
| 106 | +++ |
| 107 | ++++ |
| 108 | ++++ |
| 109 | ++ |
| 110 | ++++ |
| 111 | ++++ |
| 113 | ++++ |
| 114 | + |
| 115 | ++++ |
| 116 | ++++ |
| 118 | ++++ |
| 119 | ++++ |
| 120 | ++++ |
| 121 | ++++ |
| 122 | +++ |
| 124 | ++++ |
| 125 | ++++ |
| 126 | ++++ |
| 127 | ++++ |
| 129 | ++++ |
| 130 | ++++ |
| 132 | ++++ |
| 136 | ++++ |
| 139 | ++++ |
| 140 | ++++ |
| 141 | ++++ |
| 142 | +++ |
| 144 | ++++ |
| 145 | ++++ |
| 148 | ++++ |
| 149 | ++++ |
| 150 | ++++ |
| 151 | ++++ |
| 152 | ++++ |
| 153 | ++++ |
| 155 | + |
| 156 | ++ |

| Example Number | PBMC IC$_{50}$ (Assay C) |
|---|---|
| 1 | ++ |
| 2 | ++ |
| 3 | +++ |
| 4 | +++ |
| 5 | ++ |
| 6 | ++ |
| 7 | ++ |
| 8 | +++ |
| 9 | ++ |
| 10 | ++++ |
| 11 | +++ |
| 12 | +++ |
| 14 | ++ |
| 15 | ++ |
| 16 | + |
| 27 | ++ |
| 28 | ++ |
| 34 | +++ |
| 35 | +++ |
| 37 | +++ |
| 39 | ++ |
| 40 | +++ |
| 41 | ++ |
| 42 | +++ |
| 49 | +++ |

-continued

| Example Number | PBMC IC$_{50}$ (Assay C) |
|---|---|
| 50 | +++ |
| 51 | ++++ |
| 52 | +++ |
| 53 | ++++ |
| 54 | +++ |
| 55 | +++ |
| 56 | ++ |
| 57 | ++ |
| 58 | ++ |
| 59 | +++ |
| 61 | ++++ |
| 62 | +++ |
| 63 | ++ |
| 64 | +++ |
| 66 | +++ |
| 67 | ++++ |
| 68 | ++++ |
| 69 | ++++ |
| 70 | +++ |
| 71 | ++++ |
| 72 | +++ |
| 73 | +++ |
| 74 | +++ |
| 75 | +++ |
| 76 | ++++ |
| 77 | ++ |
| 79 | ++++ |
| 80 | +++ |
| 81 | ++++ |
| 82 | ++++ |
| 83 | ++++ |
| 84 | ++++ |
| 85 | +++ |
| 86 | ++++ |
| 89 | ++ |
| 90 | ++ |
| 91 | +++ |
| 92 | +++ |
| 93 | +++ |
| 103 | ++++ |
| 104 | ++ |
| 105 | ++ |
| 106 | +++ |
| 107 | ++++ |
| 108 | ++++ |
| 109 | ++ |
| 110 | +++ |
| 111 | +++ |
| 112 | ++++ |
| 113 | +++ |
| 115 | +++ |
| 116 | ++++ |
| 118 | ++++ |
| 122 | + |
| 130 | +++ |
| 131 | ++++ |
| 132 | +++ |
| 134 | +++ |
| 135 | ++++ |
| 138 | +++ |
| 139 | ++ |
| 140 | ++ |
| 143 | ++++ |
| 144 | ++++ |
| 145 | ++++ |
| 146 | +++ |
| 148 | ++++ |
| 153 | + |
| 160 | ++++ |
| 161 | ++++ |
| 162 | ++++ |
| 163 | ++++ |
| 164 | +++ |
| 165 | +++ |
| 166 | ++++ |

| Example Number | IL-β release IC$_{50}$ (Assay D) |
|---|---|
| 3 | +++ |
| 5 | ++++ |
| 6 | +++ |
| 8 | ++++ |
| 9 | +++ |
| 55 | ++ |
| 95 | ++++ |
| 114 | ++ |
| 115 | ++++ |
| 118 | ++++ |
| 153 | +++ |

| Example Number | LCK IC$_{50}$ (µM) or LCK % inhibition at 1 uM test concentration (Assay E) |
|---|---|
| 81 | 15% |
| 82 | 7.30% |
| 84 | 585 |
| 92 | 29% |
| 108 | 17% |
| 112 | 0.084 |
| 116 | 0.37 |
| 138 | 40% |
| 144 | 49% |
| 146 | 11% |

Example 190. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I,

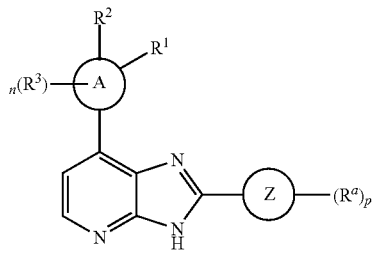

I or a tautomer, or a pharmaceutically acceptable salt thereof, wherein:
Ring A is a phenyl or pyridine;
$R^1$ is H, F, $(C(R^5)(R^5))_m NR_2$, $N(R^4)C(O)R$, $N(R^4)C(O)NR_2$, $N(R^4)(R^4)$, 3-7 membered heterocyclic ring having 1-4 heteroatoms independently selected from nitrogen, oxygen, and sulfur, or 5-6 membered monocyclic heteroaryl ring having 1-4 heteroatoms independently selected from nitrogen, oxygen, and sulfur; or $R^1$ is absent;
$R^2$ is H, $(C(R^5)(R^5))_m OR^4$, $(C(R^5)(R^5))_m N(R^4)COR$, $(C(R^5)(R^5))_m N(R^4)C(O)C(O)NR_2$, or $(C(R^5)(R^5))_m N(R^4)(R^4)$; or $R^2$ is absent;
or $R^1$ and $R^2$ together with the atoms to which they are connected, form a fused 3-7 membered ring which is optionally substituted with $C_1$-$C_6$ alkyl or C(O)R;
wherein $R^1$ and $R^2$ are both not H; and wherein $R^1$ and $R^2$ are both not absent;
each $R^3$ is independently F, Cl, Br, I, methyl, ethyl, ethyl, propyl, i-propyl, butyl, s-butyl, t-butyl, straight or branched pentyl, or straight or branched hexyl; each of which is optionally substituted;
each $R^4$ is independently —R, —$SO_2R$, —SOR, —C(O)R, —$CO_2R$, or —C(O)N(R)$_2$;
each $R^5$ is independently —R, halogen, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each R is independently hydrogen, $C_{1-6}$ aliphatic, $C_{5-10}$ aryl, a 3-8 membered saturated or partially unsaturated carbocyclic ring, a 3-7 membered heterocyclic ring having 1-4 heteroatoms independently selected from nitrogen, oxygen, and sulfur, or a 5-6 membered monocyclic heteroaryl ring having 1-4 heteroatoms independently selected from nitrogen, oxygen, and sulfur; each of which is optionally substituted; or
two R groups on the same atom are taken together with the atom to which they are attached to form a $C_{5-10}$ aryl, a 3-8 membered saturated or partially unsaturated carbocyclic ring, a 3-7 membered heterocyclic ring having 1-4 heteroatoms independently selected from nitrogen, oxygen, and sulfur, a 5-6 membered monocyclic heteroaryl ring having 1-4 heteroatoms independently selected from nitrogen, oxygen, and sulfur; a 10-15 membered fused aryl ring; a 6-15 membered saturated or partially unsaturated fused carbocyclic ring; a 10-15 membered fused heteroaryl ring; or a 6-15 membered saturated or partially unsaturated fused heterocyclic ring; each of which is optionally substituted;
Ring Z is

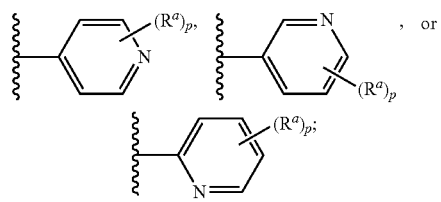

each $R^a$ is independently —R, halogen, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
m is 1, 2, or 3;
n is 0, 1, or 2; and
p is 0, 1, 2, or 3
wherein "optionally substituted" means groups that are substituted or unsubstituted by independent replacement of one, two, or three or more of the hydrogen atoms thereon with —F, —Cl, —Br, —I, deuterium, —OH, protected hydroxy, alkoxy, oxo, thiooxo, —$NO_2$, —CN, $CF_3$, $N_3$, —$NH_2$, protected amino, —NH-alkyl, —NH-alkenyl, —NH-alkynyl, —NH-cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)-heteroaryl, —C(O)-heterocyclyl, —$CONH_2$, —CONH— alkyl, —CONH-alkenyl, —CONH-alkynyl, —CONH-carbocyclyl, —CONH-aryl, —CONH-heteroaryl, —CONH— heterocyclyl, —$OCO_2$-alkyl, —$OCO_2$-alkenyl, —$OCO_2$-alkynyl, —$OCO_2$-carbocyclyl, —$OCO_2$-aryl, —$OCO_2$-heteroaryl, —$OCO_2$-heterocyclyl, —$OCONH_2$, —OCONH-alkyl, —OCONH-alkenyl, —OCONH— alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —$NHCO_2$-alkyl, —$NHCO_2$-alkenyl, —$NHCO_2$-alkynyl, —$NHCO_2$-carbocyclyl, —$NHCO_2$-aryl, —$NHCO_2$-heteroaryl, —$NHCO_2$-heterocyclyl, —NHC(O)$NH_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, NHC(S)NH$_2$, —NHC(S)NH— alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)— heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl, —SO$_2$NH$_2$, —SO$_2$NH-alkyl, —SO$_2$NH-alkenyl, —SO$_2$NH-alkynyl, —SO$_2$NH-carbocyclyl, —SO$_2$NH-aryl, —SO$_2$NH-heteroaryl, —SO$_2$NH-heterocyclyl, —NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl, —CH$_2$NH$_2$, —CH$_2$SO$_2$CH$_3$, -mono-, di-, or tri-alkyl silyl, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, and methylthiomethyl.

2. The compound of claim 1, wherein Ring A is

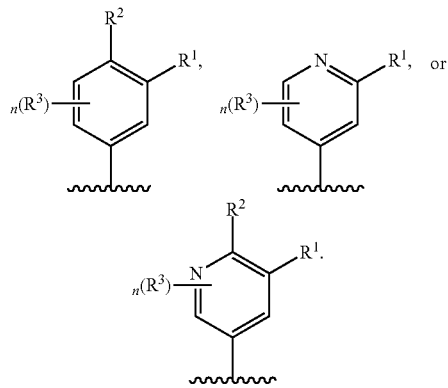

3. The compound of claim 1, wherein R$^1$ is

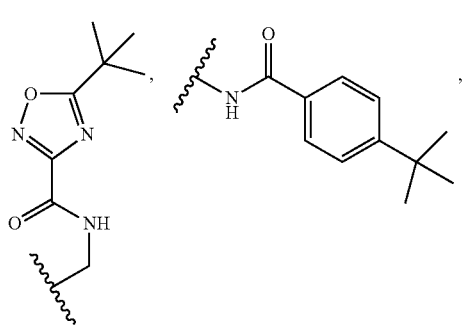

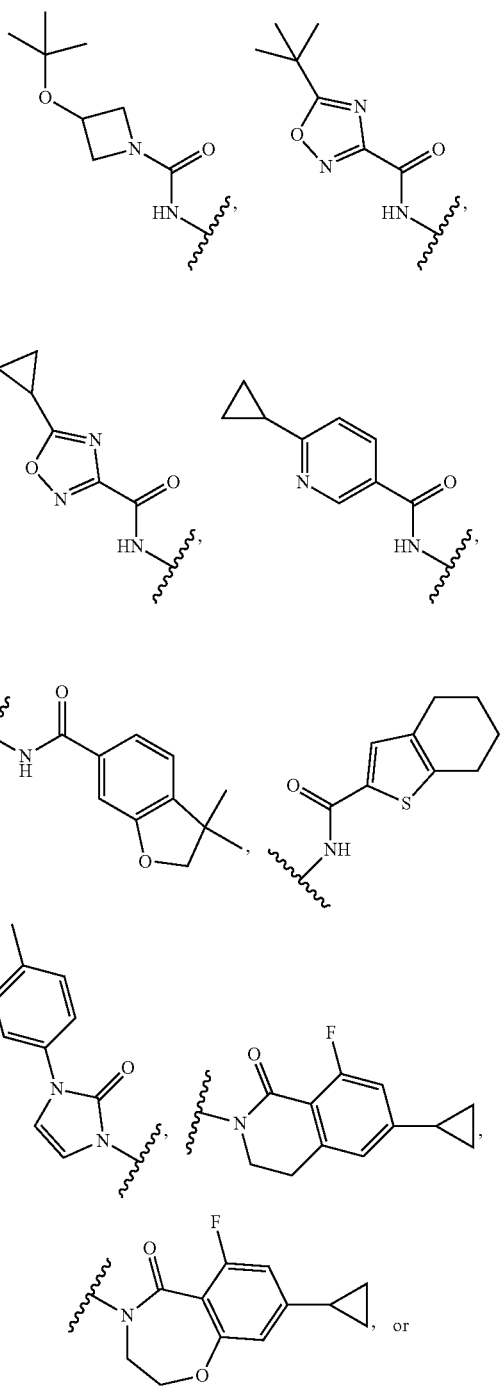

4. The compound of claim 1, wherein R$^1$ is absent.

5. The compound of claim 1, wherein R$^2$ is —CH$_2$OH, —CH$_2$NH$_2$,

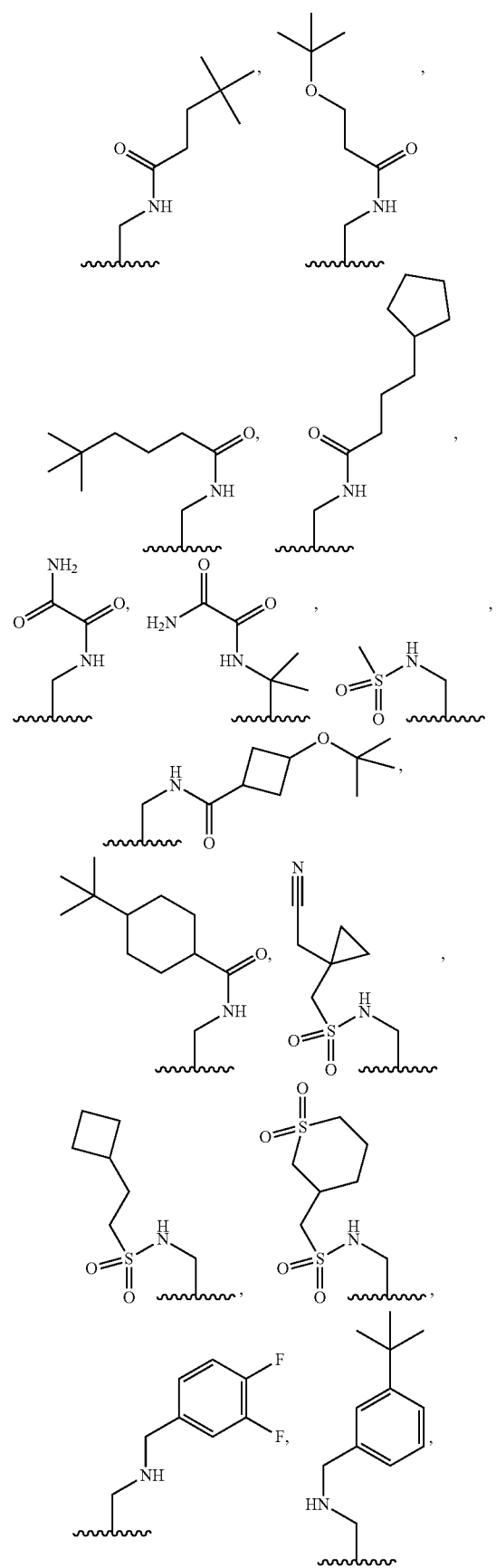
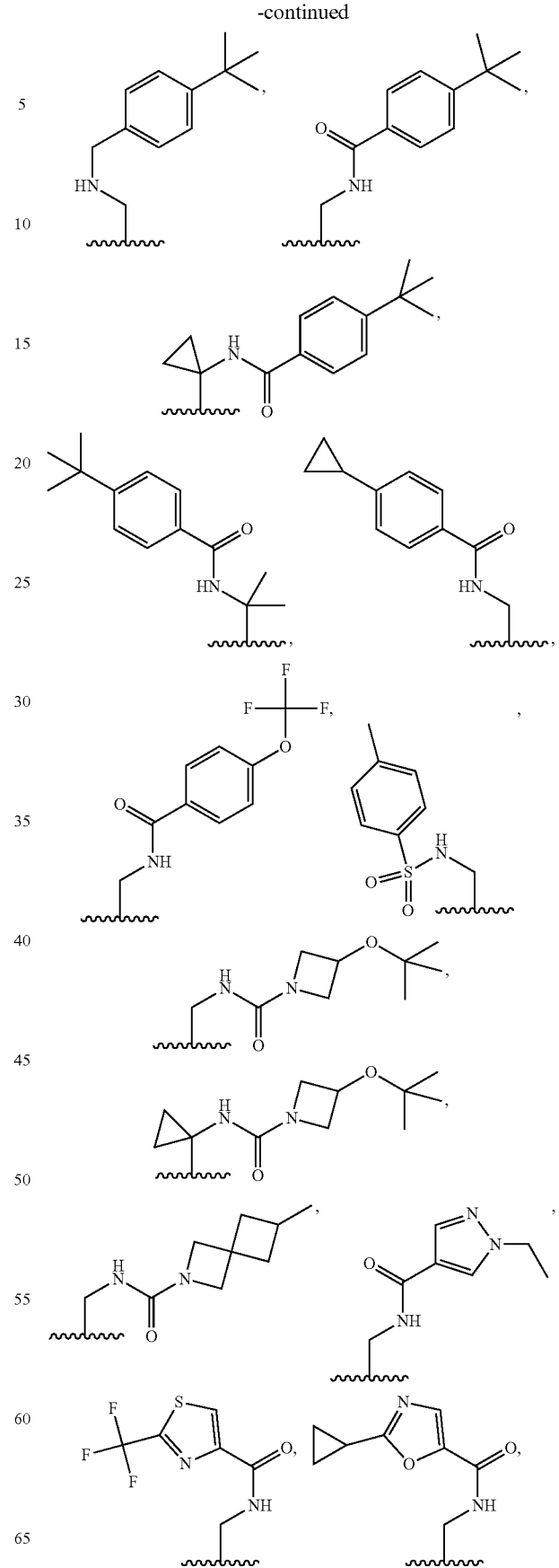

439
-continued
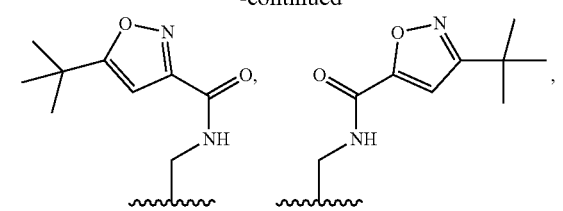
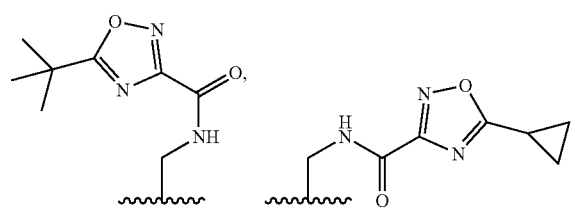
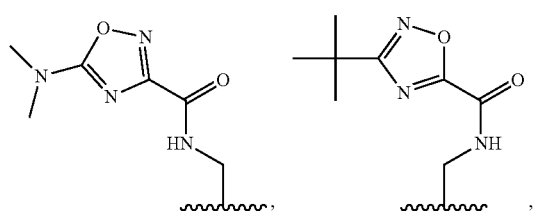
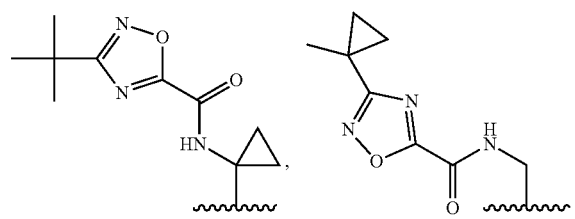
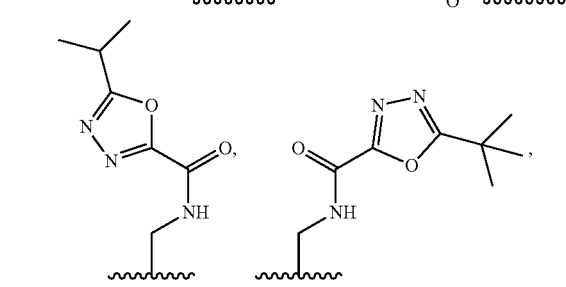
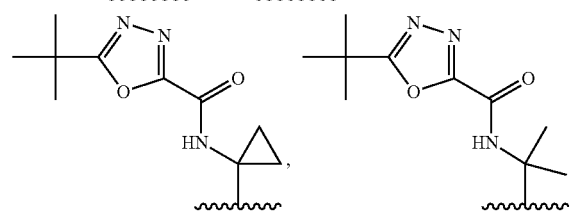
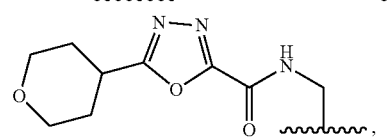
440
-continued
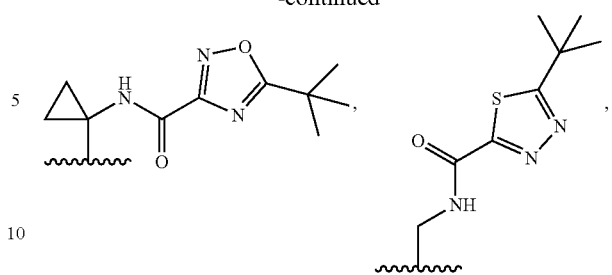
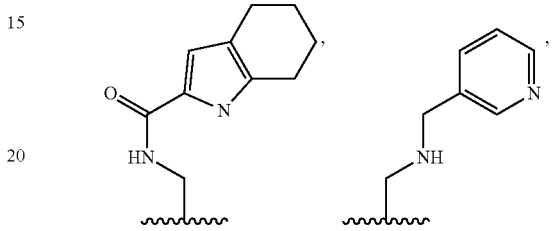
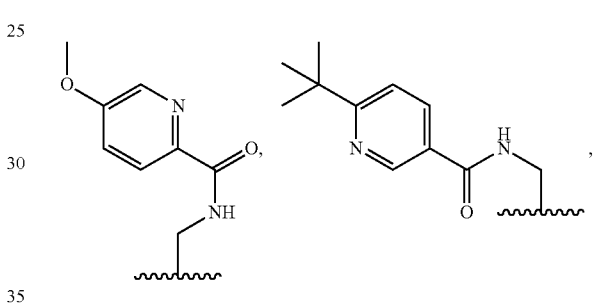
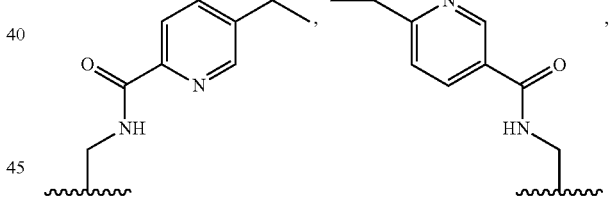
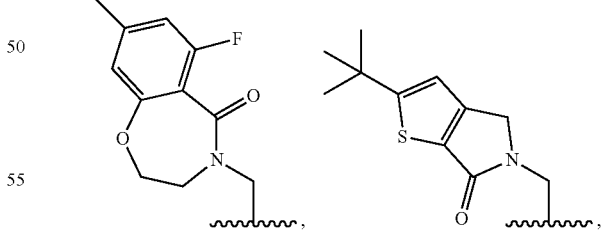
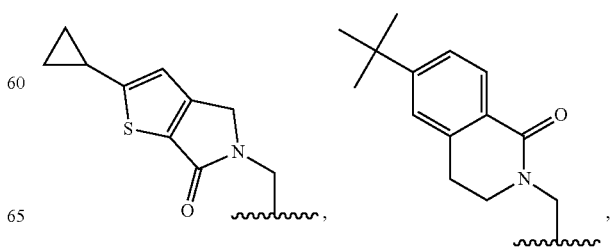

-continued

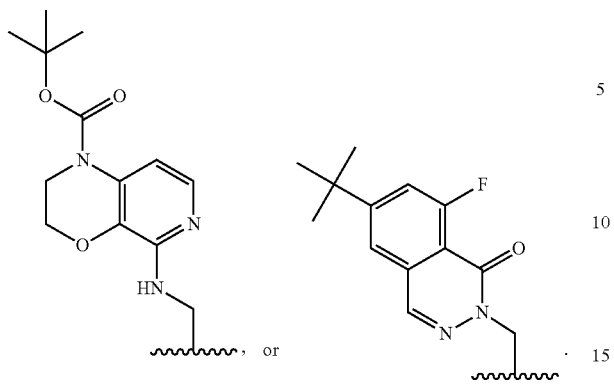

6. The compound of claim 1, wherein $R^1$ and $R^2$ together form

7. The compound of claim 1, wherein each $R^3$ is independently is cyclopropyl, phenyl, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, piperidine-one, pyrimidinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydropyridine, tetrahydropyran, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, or 1,3,4-triazolyl; each of which is optionally substituted.

8. The compound of claim 1, of formula II,

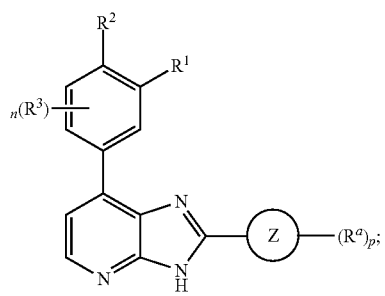

or a tautomer, or a pharmaceutically acceptable salt thereof.

9. The compound of claim 1, selected from the group consisting of:

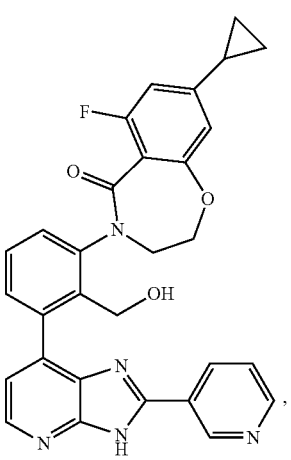

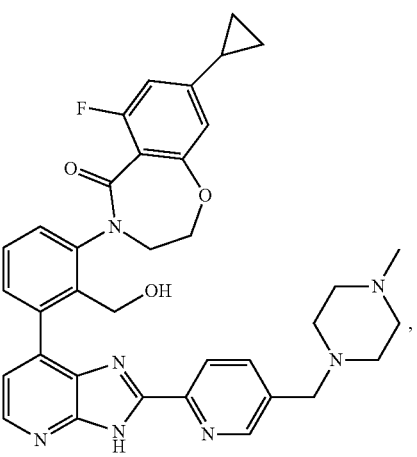

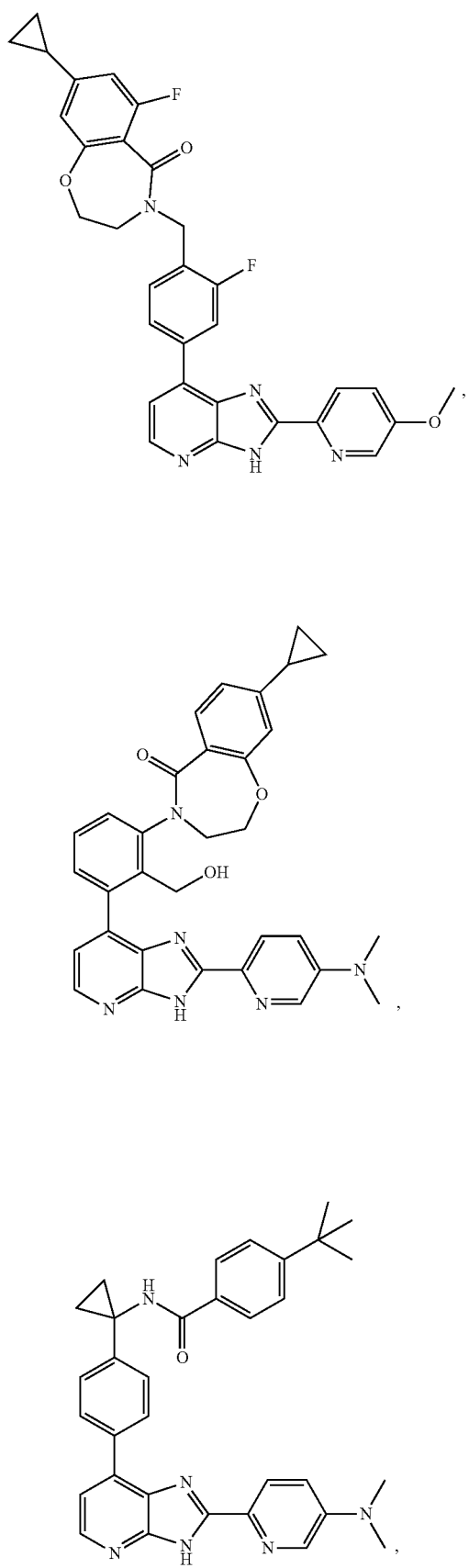
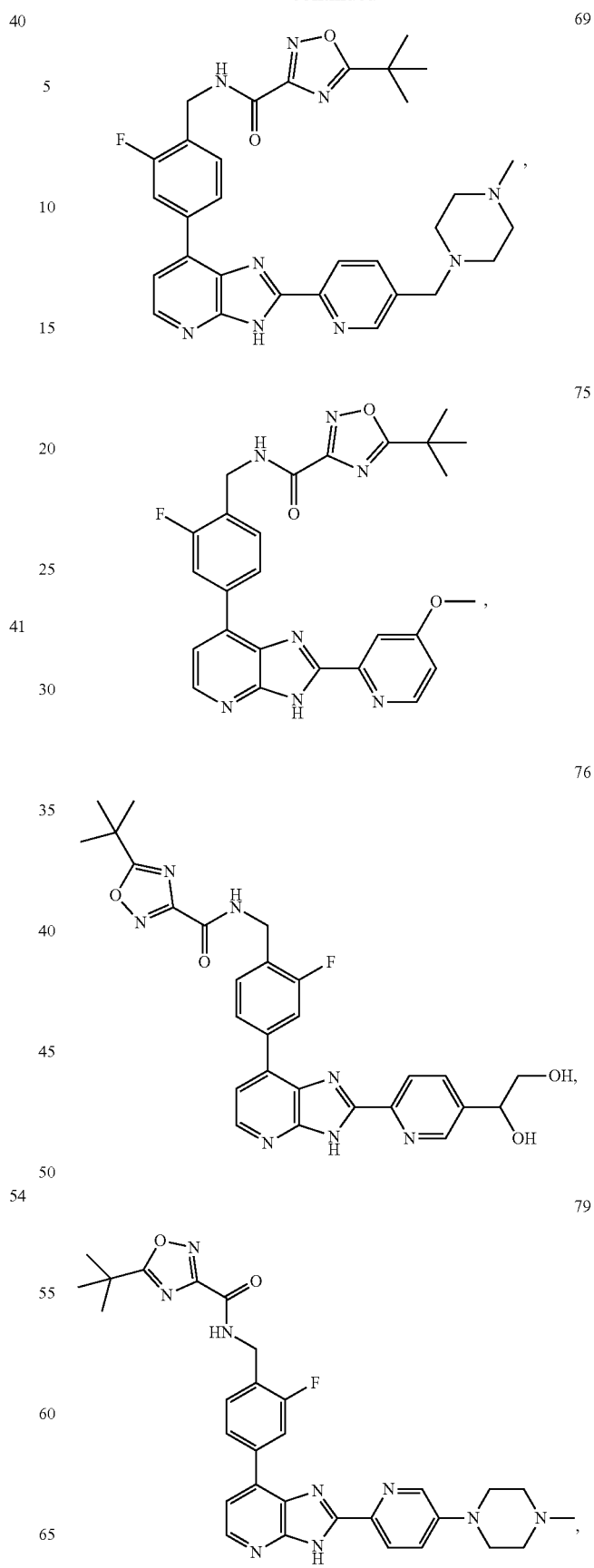

80 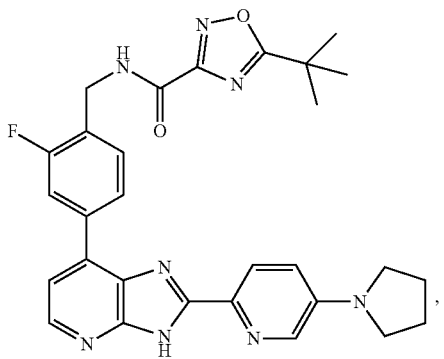
81 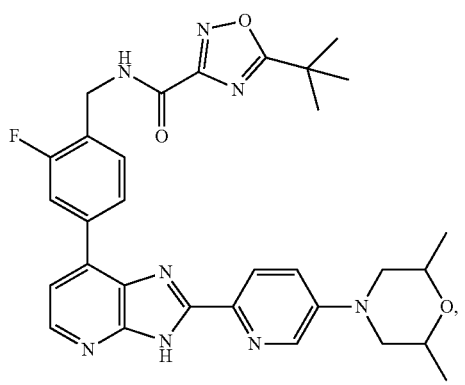
82 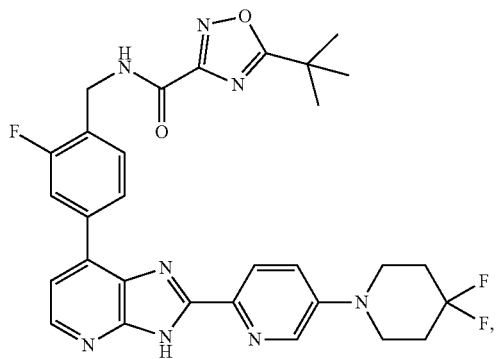
83 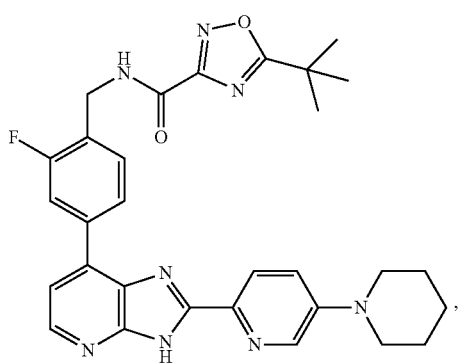
84 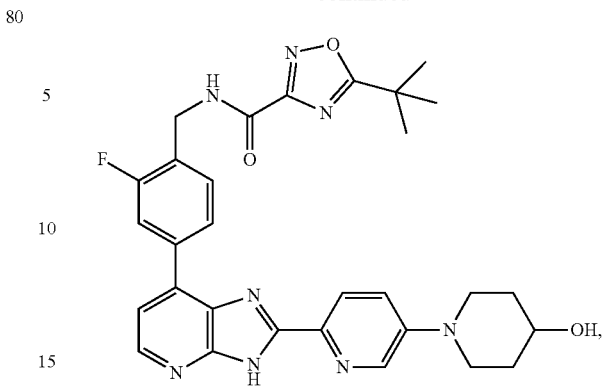
85 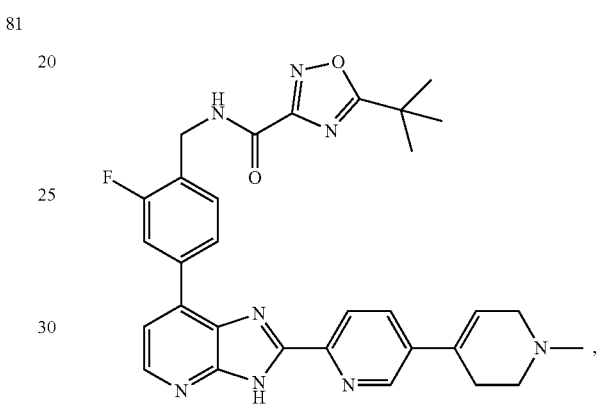
89 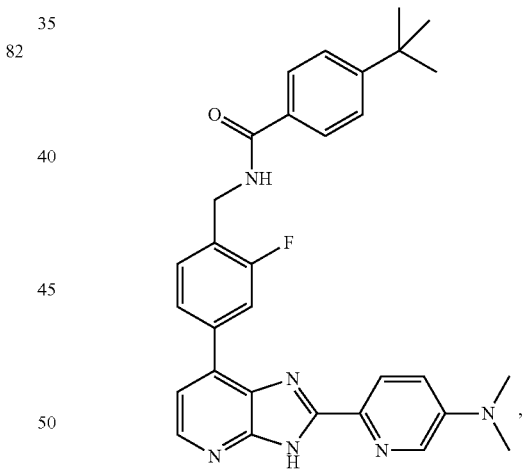
90 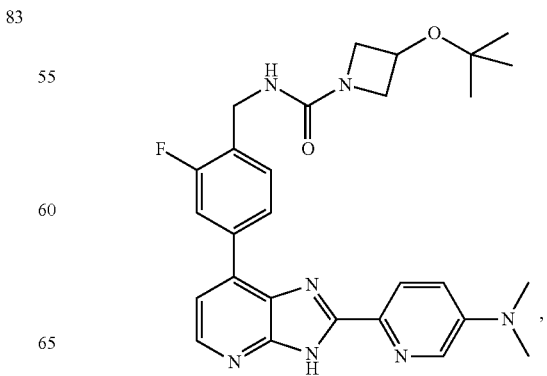

146
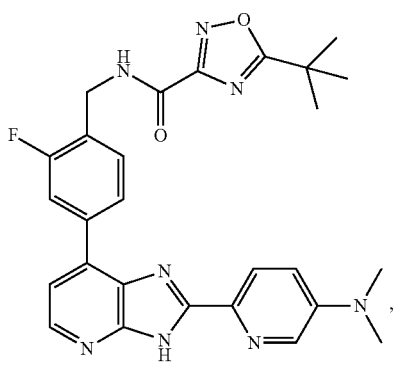
148
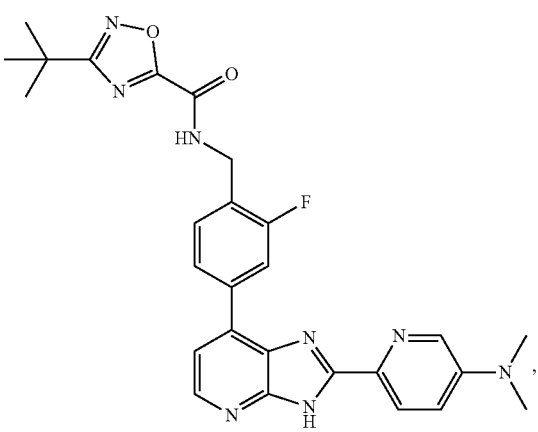
149
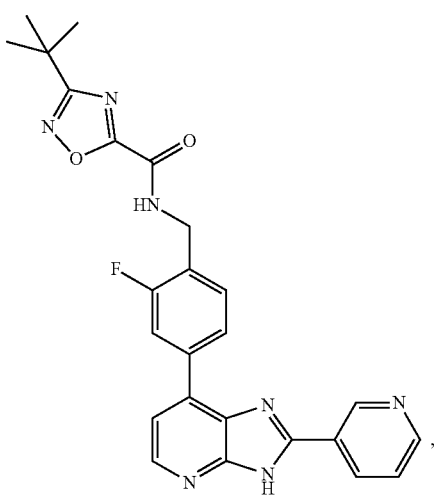
150
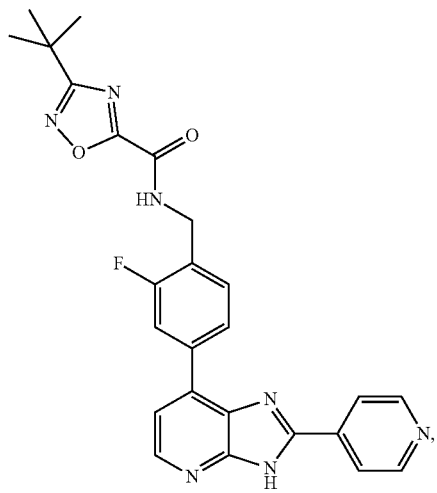
151
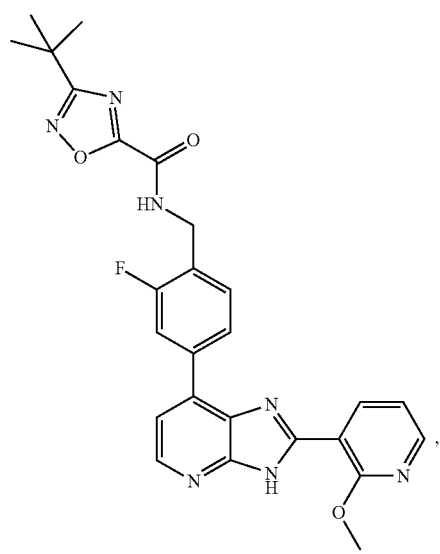
152
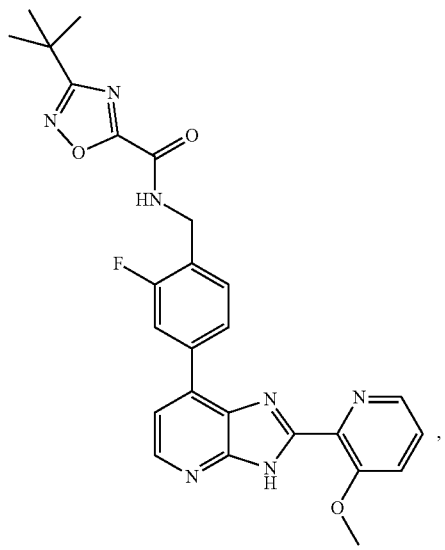

157 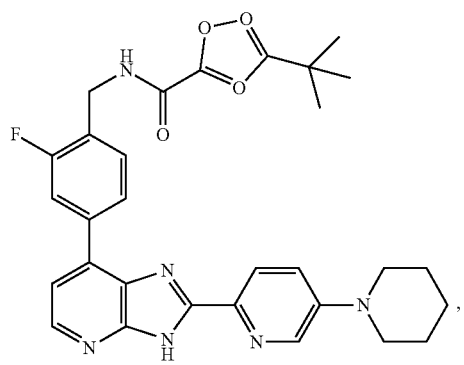
158 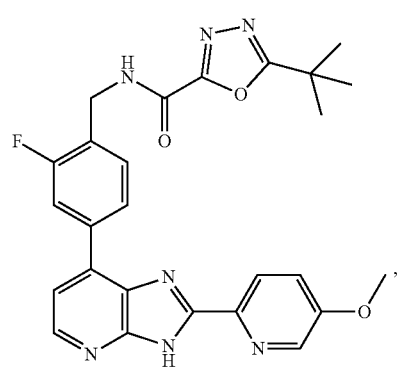
159 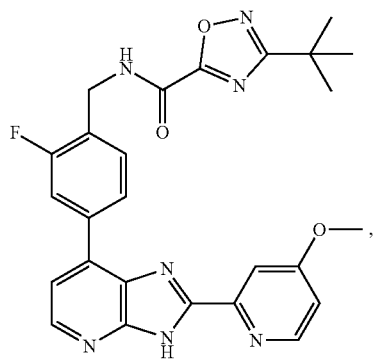
161 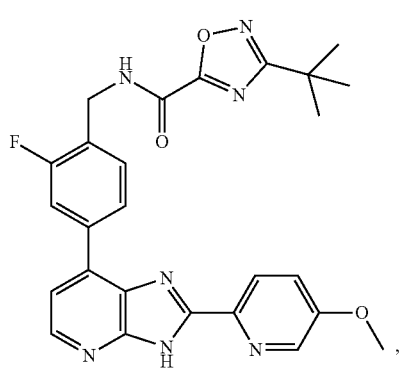
162 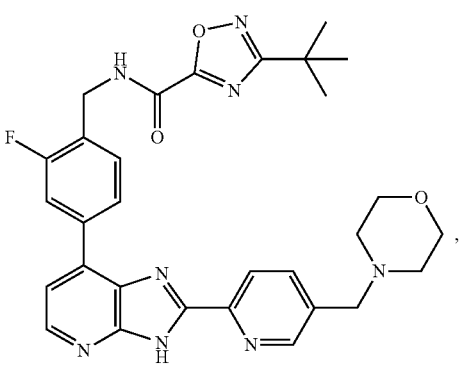
164 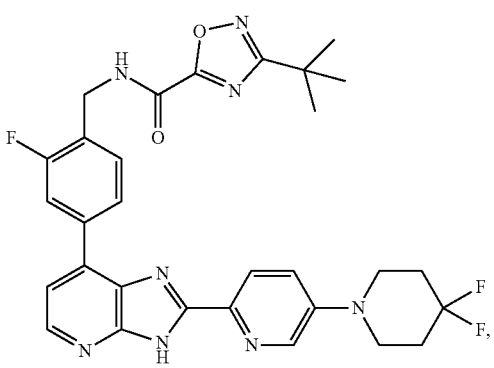
166 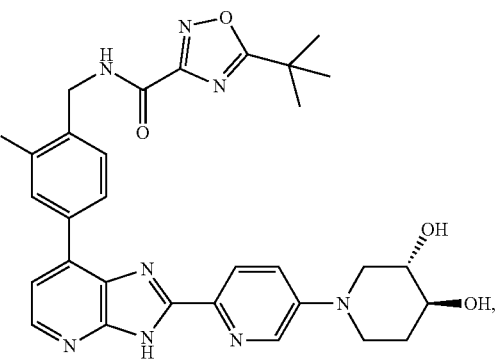

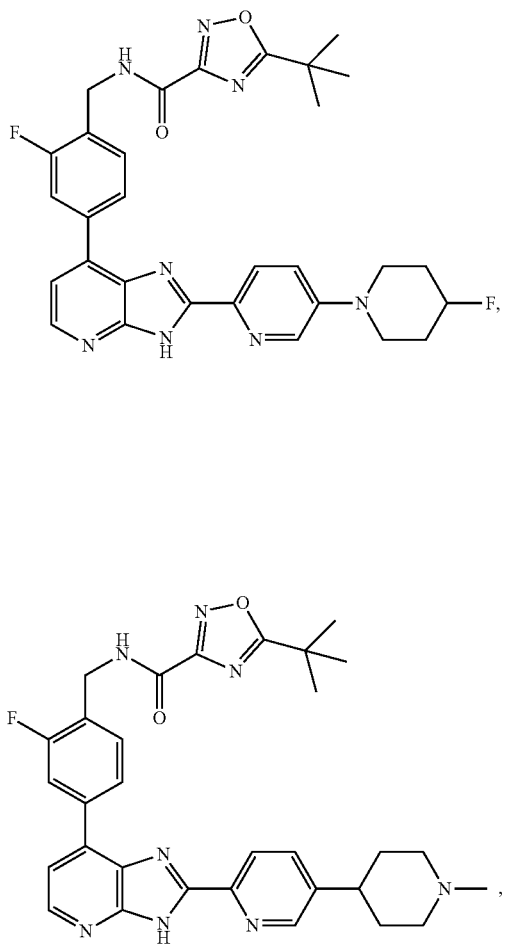
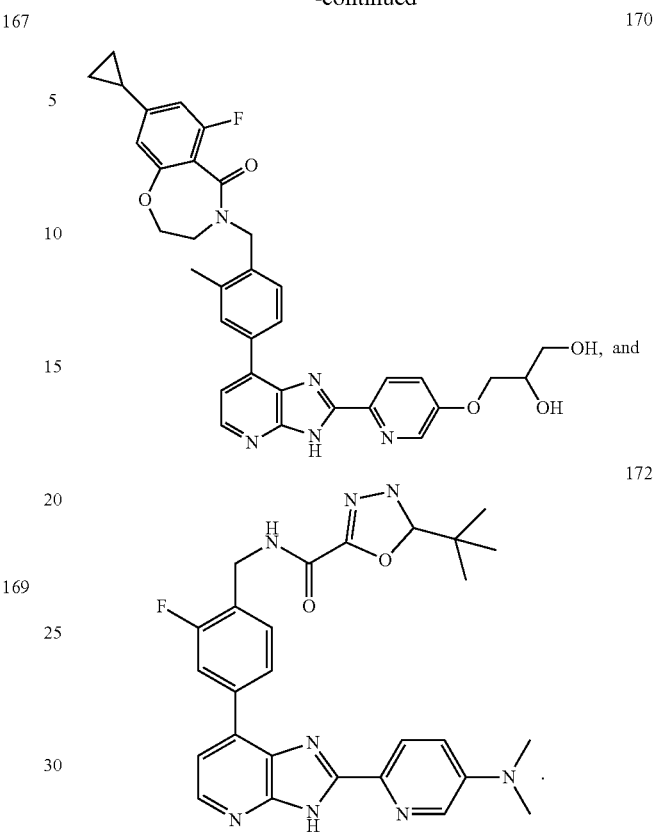
10. A pharmaceutical composition comprising a compound of claim 1, and a pharmaceutically acceptable adjuvant, carrier, or vehicle.
* * * * *